US012286619B2

(12) United States Patent
Misaghi et al.

(10) Patent No.: US 12,286,619 B2
(45) Date of Patent: Apr. 29, 2025

(54) MODULATING LACTOGENIC ACTIVITY IN MAMMALIAN CELLS

(71) Applicant: GENENTECH, INC., South San Francisco, CA (US)

(72) Inventors: Shahram Misaghi, South San Francisco, CA (US); Masaru Ken Shiratori, South San Francisco, CA (US); Bradley Richard Snedecor, South San Francisco, CA (US); Michael W. Laird, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 1079 days.

(21) Appl. No.: 17/036,075

(22) Filed: Sep. 29, 2020

(65) Prior Publication Data

US 2021/0009988 A1 Jan. 14, 2021

Related U.S. Application Data

(63) Continuation of application No. PCT/US2019/024774, filed on Mar. 29, 2019.

(60) Provisional application No. 62/649,963, filed on Mar. 29, 2018.

(51) Int. Cl.

*C12N 15/10* (2006.01)
*C12N 5/071* (2010.01)
*C12N 9/22* (2006.01)
*C12N 15/113* (2010.01)

(52) U.S. Cl.

CPC ......... *C12N 15/102* (2013.01); *C12N 5/0682* (2013.01); *C12N 9/22* (2013.01); *C12N 15/113* (2013.01); *C12N 2310/20* (2017.05)

(58) Field of Classification Search

CPC C12N 15/102; C12N 2310/20; C12N 5/0682; C12N 9/22; C12N 15/113

See application file for complete search history.

(56) References Cited

U.S. PATENT DOCUMENTS

| | | | |
|---|---|---|---|
| 4,560,655 | A | 12/1985 | Baker |
| 4,657,866 | A | 4/1987 | Kumar |
| 4,676,980 | A | 6/1987 | Segal et al. |
| 4,767,704 | A | 8/1988 | Cleveland et al. |
| 4,816,567 | A | 3/1989 | Cabilly et al. |
| 4,927,762 | A | 5/1990 | Darfler |
| 5,122,469 | A | 6/1992 | Mather et al. |
| 5,208,020 | A | 5/1993 | Chari et al. |
| 5,399,346 | A | 3/1995 | Anderson et al. |
| 5,500,362 | A | 3/1996 | Robinson et al. |
| 5,571,894 | A | 11/1996 | Wels et al. |
| 5,587,458 | A | 12/1996 | King et al. |
| 5,624,821 | A | 4/1997 | Winter et al. |
| 5,648,260 | A | 7/1997 | Winter et al. |
| 5,731,168 | A | 3/1998 | Carter et al. |
| 5,770,429 | A | 6/1998 | Lonberg et al. |
| 5,821,337 | A | 10/1998 | Carter et al. |
| 5,869,046 | A | 2/1999 | Presta et al. |
| 6,075,181 | A | 6/2000 | Kucherlapati et al. |
| 6,150,584 | A | 11/2000 | Kucherlapati et al. |
| 6,194,551 | B1 | 2/2001 | Idusogie et al. |
| 6,248,516 | B1 | 6/2001 | Winter et al. |
| 6,737,056 | B1 | 5/2004 | Presta |
| 6,982,321 | B2 | 1/2006 | Winter |
| 7,041,870 | B2 | 5/2006 | Tomizuka et al. |
| 7,087,409 | B2 | 8/2006 | Barbas, III et al. |
| 7,189,826 | B2 | 3/2007 | Rodman |
| 7,332,581 | B2 | 2/2008 | Presta |
| 7,371,826 | B2 | 5/2008 | Presta |
| 7,521,541 | B2 | 4/2009 | Eigenbrot et al. |
| 7,527,791 | B2 | 5/2009 | Adams et al. |
| 7,855,275 | B2 | 12/2010 | Eigenbrot et al. |
| 8,309,300 | B2 | 11/2012 | Junutula et al. |
| 9,000,130 | B2 | 4/2015 | Bhakta et al. |
| 2003/0157108 | A1 | 8/2003 | Presta |

(Continued)

FOREIGN PATENT DOCUMENTS

| | | | | |
|---|---|---|---|---|
| AU | 2016280893 A1 * | 1/2018 | ............. A61P 11/00 |
| EP | 0 307 247 A2 | 3/1989 | |

(Continued)

OTHER PUBLICATIONS

Chiavarina et al (Pyruvate kinase expression (PKM1 and PKM2) in cancer-associated fibroblasts drives stromal nutrient production and tumor growth, Cancer Biology & Therapy 12:12, 1101-1113; Dec. 15, 2011) (Year: 2011).*

Pyruvate kinase M knockdown-induced signaling via AMP activated protein kinase promotes mitochondrial biogenesis, autophagy, and cancer cell survival, J. Biol. Chem. (2017) 292(37) 15561-15576 (Year: 2017).*

Ahn et al., "Towards dynamic metabolic flux analysis in CHO cell cultures," Biotechnol. J. 7(1):61-74 (2012).

Almagro et al., "Humanization of antibodies," Front. Biosci. 13:1619-1633 (2008).

Anderson, "Prospects for Human Gene Therapy," Science 226:401-409 (1984).

(Continued)

*Primary Examiner* — Mark Halvorson
*Assistant Examiner* — Dennis J Sullivan
(74) *Attorney, Agent, or Firm* — Baker Botts L.L.P.

(57) ABSTRACT

The present disclosure relates to methods, cells and compositions for producing a product of interest, e.g., a recombinant protein. In particular, the present disclosure provides improved mammalian cells expressing the product of interests, where the cells (e.g., Chinese Hamster Ovary (CHO) cells) have modulated lactogenic activity. The present disclosure also relates to methods and compositions for modulating pyruvate kinase muscle (PKM) expression (e.g., PKM-1 expression) in a mammalian cell to thereby reduce or eliminate the lactogenic activity of the cell, as well compositions comprising a cell having reduced or eliminated lactogenic activity and methods of using the same.

19 Claims, 26 Drawing Sheets

Figure 1A:
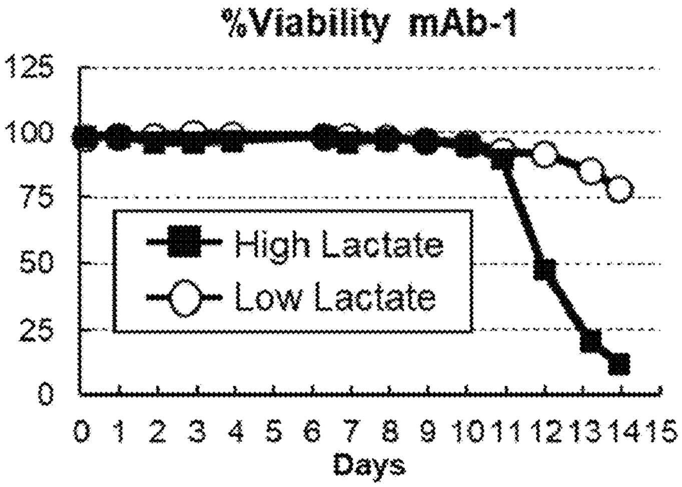

Specification includes a Sequence Listing.

(56) References Cited

U.S. PATENT DOCUMENTS

| | | | |
|---|---|---|---|
| 2004/0093621 A1 | 5/2004 | Shitara et al. | |
| 2004/0110282 A1 | 6/2004 | Kanda et al. | |
| 2004/0132140 A1 | 7/2004 | Satoh et al. | |
| 2004/0259150 A1 | 12/2004 | Nakamura et al. | |
| 2005/0014934 A1 | 1/2005 | Hinton et al. | |
| 2005/0031613 A1 | 2/2005 | Nakamura et al. | |
| 2007/0061900 A1 | 3/2007 | Murphy et al. | |
| 2008/0069820 A1 | 3/2008 | Fuh et al. | |
| 2016/0176954 A1 | 6/2016 | Ruike et al. | |

FOREIGN PATENT DOCUMENTS

| | | | |
|---|---|---|---|
| EP | 0 404 097 A2 | 12/1990 | |
| EP | 2 101 823 B1 | 11/2016 | |
| JP | 2017 075124 A | 4/2017 | |
| WO | WO 87/00195 A1 | 1/1987 | |
| WO | WO 90/03430 A1 | 4/1990 | |
| WO | WO 93/01161 A1 | 1/1993 | |
| WO | WO 93/16185 A2 | 8/1993 | |
| WO | WO 94/11026 A2 | 5/1994 | |
| WO | WO 94/29351 A2 | 12/1994 | |
| WO | WO 97/30087 A1 | 8/1997 | |
| WO | WO 98/50431 A2 | 11/1998 | |
| WO | WO 98/58964 A1 | 12/1998 | |
| WO | WO 99/22764 A1 | 5/1999 | |
| WO | WO 99/51642 A1 | 10/1999 | |
| WO | WO 99/54342 A1 | 10/1999 | |
| WO | WO 01/77342 A1 | 10/2001 | |
| WO | WO 03/011878 A2 | 2/2003 | |
| WO | WO 03/085107 A1 | 10/2003 | |
| WO | WO 2004/009792 A2 | 1/2004 | |
| WO | WO 2004/056312 A2 | 7/2004 | |
| WO | WO 2004/065540 A2 | 8/2004 | |
| WO | WO 2004/106381 A1 | 12/2004 | |
| WO | WO 2005/061547 A2 | 7/2005 | |
| WO | WO 2005/100402 A1 | 10/2005 | |
| WO | WO 2006/029879 A2 | 3/2006 | |
| WO | WO 2006/082515 A2 | 8/2006 | |
| WO | WO 2007/042261 A2 | 4/2007 | |
| WO | WO 2008/024715 A2 | 2/2008 | |
| WO | WO 2008/119567 A2 | 10/2008 | |
| WO | WO 2009/080251 A1 | 7/2009 | |
| WO | WO 2009/080252 A1 | 7/2009 | |
| WO | WO 2009/080253 A1 | 7/2009 | |
| WO | WO 2009/089004 A1 | 7/2009 | |
| WO | WO 2010/112193 A1 | 10/2010 | |
| WO | WO 2010/115589 A1 | 10/2010 | |
| WO | WO 2010/136172 A1 | 12/2010 | |
| WO | WO 2010/145792 A1 | 12/2010 | |
| WO | WO 2011/034605 A2 | 3/2011 | |
| WO | WO 2012/130831 A1 | 10/2012 | |
| WO | WO 2013/026831 A1 | 2/2013 | |
| WO | WO 2013/026833 A1 | 2/2013 | |
| WO | WO 2013/026839 A1 | 2/2013 | |
| WO | WO 2013/120929 A1 | 8/2013 | |
| WO | WO 2014/121712 A1 | 8/2014 | |
| WO | WO 2014/177460 A1 | 11/2014 | |
| WO | WO 2015/095539 A1 | 6/2015 | |
| WO | WO 2015/148806 A1 | 10/2015 | |
| WO | WO 2015/150447 A1 | 10/2015 | |
| WO | WO 2015/153513 A1 | 10/2015 | |
| WO | WO 2016/016299 A1 | 2/2016 | |
| WO | WO 2016/020309 A1 | 2/2016 | |
| WO | WO 2016/040856 A2 | 3/2016 | |
| WO | WO 2016/172485 A2 | 10/2016 | |
| WO | WO 2017/053482 A1 | 3/2017 | |
| WO | WO-2018022511 A1 * | 2/2018 | ............ A61K 38/45 |
| WO | WO 2019/126634 A2 | 6/2019 | |

OTHER PUBLICATIONS

Ashizawa et al., "In Vivo Regulation of Monomer-Tetramer Conversion of Pyruvate Kinase Subtype MP by Glucose Is Mediated via Fructose 1,6-Bisphosphate," J. Biol Chem. 266(25):16842-16846 (1991).

Atwell et al., "Stable Heterodimers from Remodeling the Domain Interface of a Homodimer using a Phage Display Library," J. Mol. Biol. 270:26-35 (1997).

Baca et al., "Antibody Humanization Using Monovalent Phage Display," J. Biol. Chem. 272(16):10678-10684 (1997).

Bacac et al., "CEA TCB: A novel head-to-tail 2:1 T cell bispecific antibody for treatment of CEA-positive solid tumors," OncoImmunology 5(8):e1203498 (2016).

Barnes et al., "Methods for Growth of Cultured Cells in Serum-Free Medium," Anal. Biochem., 102:255-270 (1980).

Barnes et al., "Serum-free Cell Culture: a Unifying Approach," Cell, 22:649-655 (1980).

Blomer et al., "Highly Efficient and Sustained Gene Transfer in Adult Neurons with a Lentivirus Vector," Journal of Virology 71(9):6641-6649 (1997).

Boch et al., "TALEs of genome targeting," Nature Biotechnology 29(2):135-136 (2011).

Boerner et al., "Production of Antigen-Specific Human Monoclonal Antibodies From In Vitro-Primed Human Splenocytes," J. Immunol., 147:86-95 (1991).

Bregni et al., "Human Peripheral Blood Hematopoietic Progenitors Are Optimal Targets of Retroviral-Mediated Gene Transfer," Blood 80:1418-1422 (1992).

Brennan et al., "Preparation of Bispecific Antibodies by Chemical Recombination of Monoclonal Immunoglobulin G1 Fragments," Science 229:81-83 (1985).

Brigham et al., "Rapid Communication: In vivo Transfection of Murine Lungs with a Functioning Prokaryotic Gene Using a Liposome Vehicle," Am. J Med. Sci. 298(4):278-281 (1989).

Brodeur et al., Monoclonal Antibody Production Techniques and Applications, pp. 51-63 (Marcel Dekker, Inc., New York, 1987).

Bruggemann et al., "Comparison of The Effector Functions Of Human Immunoglobulins Using A Matched Set Of Chimeric Antibodies," J. Exp. Med. 166:1351-1361 (1987).

Carter et al., "Humanization of an anti-p185HER2 antibody for human cancer therapy," Proc. Natl. Acad. Sci. USA, 89:4285-4289 (1992).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Chaneton et al., "Rocking cell metabolism: revised functions of the key glycolytic regulator PKM2 in cancer," Trends Biochem Sci. 37(8):309-316 (2012).

Chari et al., "Immunoconjugates Containing Novel Maytansinoids: Promising Anticancer Drugs," Cancer Res. 52:127-131 (1992).

Chothia et al., "Canonical Structures for the Hypervariable Regions of Immunoglobulins," J. Mol. Biol. 196:901-917 (1987).

Chowdhury, "Engineering Hot Spots for Affinity Enhancement of Antibodies," Methods Mol. Biol. 207:179-196 (2008).

Christofk et al., "Pyruvate kinase M2 is a phosphotyrosine-binding protein," Nature 452(7184):181-186 (2008).

Christofk et al., "The M2 splice isoform of pyruvate kinase is important for cancer metabolism and tumour growth," Nature 452(7184):230-233 (2008).

Clackson et al., "Making antibody fragments using phage display libraries," Nature 352:624-628 (1991).

Cleveland et al., "Routine Large-Scale Production of Monoclonal Antibodies in a Protein-Free Culture Medium," J. Immunol. Methods 56:221-234 (1983).

Clynes et al., "Fc receptors are required passive and active immunity to melanoma," Proc. Nat'l Acad. Sci. USA 95:652-656 (1998).

Cornetta et al., "Gene Transfer into Primates and Prospects for Gene Therapy in Humans," Nucleic Acid Research and Molecular Biology 36:311-322 (1987).

Cragg et al., "Antibody specificity controls in vivo effector mechanisms of anti-CD20 reagents," Blood 103:2738-2743 (2004).

Cragg et al., "Complement-mediated lysis by anti-CD20 mAb correlates with segregation into lipid rafts," Blood 101(3):1045-1052 (2003).

(56) References Cited

OTHER PUBLICATIONS

Cunningham et al., "High-Resolution Epitope Mapping of hGH-Receptor Interactions by Alanine-Scanning Mutagenesis," Science 244:1081-1085 (1989).
Dall'Acqua et al., "Properties of Human IgGls Engineered for Enhanced Binding to the Neonatal Fc Receptor (FcRn)," J. Biol. Chem. 281(33):23514-23524 (2006).
Dall'Acqua et al., "Antibody humanization by framework shuffling," Methods 36:43-60 (2005).
Dall'Acqua et al., "Increasing the Affinity of a Human IgG1 for the Neonatal Fc Receptor: Biological Consequences," J. Immunol. 169:5171-5180 (2002).
Danos et al., "Safe and efficient generation of recombinant retroviruses with amphotropic and ecotropic host ranges," Proc. Natl. Acad. Sci. USA 85:6460-6464 (1988).
DeWitt et al., "Genome editing via delivery of Cas9 ribonucleoprotein," Methods 121-122:9-15 (2017).
Dombrauckas et al., "Structural Basis for Tumor Pyruvate Kinase M2 Allosteric Regulation and Catalysis," Biochemistry 44(27):9417-9429 (2005).
Duncan et al., "The binding site for Clq on IgG," Nature 332:738-740 (1988).
Durai et al., "Zinc finger nucleases: custom-designed molecular scissors for genome engineering of plant and mammalian cells," Nucleic Acids Res. 33(18):5978-5990 (2005).
Eglitis et al., "Retroviral Vectors for Introduction of Genes into Mammalian Cells," BioTechniques 6:608-614 (1988).
Felgner et al., "Lipofection: A highly efficient, lipid-mediated DNA-transfection procedure," Proc. Natl. Acad Sci. U.S.A. 84:7413-7417 (1987).
Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II,"Biotechn Bioeng 93:851-861 (2006).
Firan et al., "The MHC class I-related receptor, FcRn, plays an essential role in the maternofetal transfer of γ-globulin in humans," Int. Immunol 13(8):993-1002 (2001).
Friedman, "Progress Toward Human Gene Therapy," Science 244:1275-1281 (1989).
Gagnon et al., "High-End pH-controlled delivery of glucose effectively suppresses lactate accumulation in CHO Fed-batch cultures," Biotechnology and Bioengineering, 108(6):1328-1337 (2011).
Gao et al., "Pyruvate Kinase M2 Regulates Gene Transcription by Acting as a Protein Kinase," Mol. Cell 45:598-609 (2012).
Gazzano-Santoro et al., "A non-radioactive complement-dependent cytotoxicity assay for anti-CD20 monoclonal antibody," J Immunol. Methods 202:163-171 (1997).
Graham et al., "Characteristics of a Human Cell Line Transformed by DNA from Human Adenovirus Type 5," J. Gen Virol., 36:59-72 (1977).
Grevys et al., "Fc Engineering of Human IgG1 for Altered Binding to the Neonatal Fc Receptor Affects Fc Effector Functions," J. Immunol. 194:5497-5508 (2015).
Gruber et al., "Efficient Tumor Cell Lysis Mediated by a Bispecific Single Chain Antibody Expressed in *Escherichia coli*," J. Immunol., 152:5368-5374 (1994).
Guyer et al., "Immunoglobulin Binding By Mouse Intestinal Epithelial Cell Receptors," J. Immunol. 117(2):587-593 (1976).
Ham et al., "Media and Growth Requirements," Methods in Enzymology 58:44-93 (1979).
Harada et al., "Purification Of Four Pyruvate Kinase Isozymes Of Rats By Affinity Elution Chromatography," Biochim Biophys. Acta. 524(2):327-339 (1978).
Hellstrom et al., "Antitumor effects of L6, an IgG2a antibody that reacts with most human carcinomas," Proc. Nat'l Acad. Sci. USA 83:7059-7063 (1986).
Hellstrom et al., "Strong antitumor activities of IgG3 antibodies to a human melanoma-associated ganglioside," Proc. Nat'l Acad. Sci. USA 82:1499-1502 (1985).
Hitosugi et al., "Tyrosine Phosphorylation Inhibits PKM2 to Promote the Warburg Effect and Tumor Growth," Sci. Signal 2(97):ra73 (2009).
Holliger et al., "Engineered antibody fragments and the rise of single domains," Nature Biotechnology 23(9):1126-1136 (2005).
Holliger et al., "Specific killing of lymphoma cells by cytotoxic T-cells mediated by a bispecific diabody," Prot. Eng. 9(3):299-305 (1996).
Hollinger et al., "Diabodies: Small bivalent and bispecific antibody fragments," Proc. Natl. Acad. Sci. USA 90:6444-6448 (1993).
Hoogenboom et al., "Overview of Antibody Phage-Display Technology and Its Applications in Methods in Molecular Biology," 178:1-37 (2001).
Hopp et al., "Development of a High Throughput Protein A Well-Plate Purification Method for Monoclonal Antibodies," Biotechnol. Prog. 25(5):1427-1432 (2009).
Hudson et al., "Engineered antibodies," Nat. Med. 9:129-134 (2003).
Hughes et al., "Retroviral GeneTransferto Primitive Normal and Leukemic Hematopoietic Cells Using Clinically Applicable Procedures," J. Clin. Invest. 89:1817-1824 (1992).
Idusogie et al., "Mapping of the C1q Binding Site on Rituxan, a Chimeric Antibody with a Human IgG1 Fc," J. Immunol. 164:4178-4184 (2000).
International Search Report mailed Jun. 18, 2019 in International Application No. PCT/US2019/024774.
Israelsen et al., "Pyruvate kinase: function, regulation and role in cancer," Semin. Cell Dev. Biol 43:43-51 (2015).
Johnson et al., "Effector Cell Recruitment with Novel Fv-based Dual-affinity Re-targeting Protein Leads to Potent Tumor Cytolysis and in Vivo B-cell Depletion," J Mol Biol 399:436-449 (2010).
Johnson, "Gene Therapy for Cystic Fibrosis," Chest 107:77S-83S (1995).
Kabat et al., Sequences of Proteins of Immunological Interest, 5th Ed. Public Health Service, National Institutes of Health, Bethesda, MD (1991).
Kanda et al., "Comparison of Cell Lines for Stable Production of Fucose-Negative Antibodies With Enhanced ADCC," Biotechnol. Bioeng., 94(4):680-688 (2006).
Kashmiri et al., "SDR grafting a new approach to antibody humanization," Methods 36:25-34 (2005).
Kent et al., "The Human Genome Browser at UCSC," Genome Res. 12:996-1006 (2002).
Kido et al., "Use of a retroviral vector with an internal opsin promoter to direct gene expression to retinal photoreceptor cells," Current Eye Research 15:833-844 (1996).
Kim et al., "Identifying amino acid residues that influence plasma clearance of murine IgG1 fragments by site-directed mutagenesis," Eur. J. Immunol. 24:542-548 (1994).
Kim et al., "Localization of the site of the murine IgG1 molecule that is involved in binding to the murine intestinal Fc receptor," Eur. J. Immunol. 24:2429-2434 (1994).
Kim et al., "Mapping the site on human IgG for binding of the MHC class I-related receptor, FcRn," Eur. J Immunol. 29:2819-2825 (1999).
Kindt et al., Kuby Immunology, 6th ed., W.H. Freeman and Co., p. 91 (2007).
Kipriyanov et al., "Bispecific Tandem Diabody for Tumor Therapy with Improved Antigen Binding and Pharmacokinetics," J. Mol. Biol. 293:41-56 (1999).
Klein et al., "The use of CrossMAb technology for the generation of bi- and multispecific antibodies," mAbs 8(6): 1010-1020 (2016).
Klimka et al., "Human anti-CD30 recombinant antibodies by guided phage antibody selection using cell panning," Br. J. Cancer 83(2):252-260 (2000).
Kostelny et al., "Formation of A Bispecific Antibody By The Use Of Leucine Zippers," J. Immunol., 148(5):1547-1553 (1992).
Kozbor et al., "A Human Hybrid Myeloma for Production Of Human Monoclonal Antibodies," J. Immunol., 133(6):3001-3005 (1984).
Le Gal La Salle et al., "An Adenovirus Vector for Gene Transfer into Neurons and Glia in the Brain," Science 259:988-990 (1993).
Lee et al., "Targeted chromosomal deletions in human cells using zinc finger nucleases," Genome Res. 20:81-89 (2010).

(56) References Cited

OTHER PUBLICATIONS

Lehman et al., "Measurement of lactate production by tracer techniques," Med Sci Sports Exerc. 23(8):935-938 (1991).
Li et al., "Cell culture processes for monoclonal antibody production," mAbs 2(5):466-479 (2010).
Li et al., "Human antibodies for immunotherapy development generated via a human B cell hybridoma technology," Proc. Natl. Acad. Sci. USA, 103(10):3557-3562 (2006).
Li et al., "piggyBac transposase tools for genome engineering," PNAS 110(25):E2279-E2287 (2013).
Lonberg, "Fully human antibodies from transgenic mouse and phage display platforms," Curr. Opinion Immunol. 20:450-459 (2008).
Lonberg, "Human antibodies from transgenic animals," Nat. Biotech 23(9):1117-1125 (2005).
Luo et al., "Comparative Metabolite Analysis to Understand Lactate Metabolism Shift in Chinese Hamster Ovary Cell Culture Process," Biotechnol. Bioeng. 109(1):146-156 (2012).
Lv et al., "Acetylation Targets the M2 Isoform of Pyruvate Kinase for Degradation through Chaperone-Mediated Autophagy and Promotes Tumor Growth," Mol. Cell. 42:719-730 (2011).
MacCallum et al., "Antibody-antigen Interactions: Contact Analysis and Binding Site Topography," J. Mol. Biol. 262:732-745 (1996).
Macintyre et al., "PKM2 and the Tricky Balance of Growth and Energy in Cancer," Mol. Cell 42:713-714 (2011).
Mather et al., "Culture of Testicular Cells In Hormone-Supplemented Serum-Free Medium," Annals N.Y. Acad. Sci., 383:44-68 (1982).
Mather, "Establishment and Characterization of Two Distinct Mouse Testicular Epithelial Cell Lines," Biol. Reprod., 23:243-252 (1980).
Mazurek, "Pyruvate kinase type M2: A key regulator of the metabolic budget system in tumor cells," Int. J. Biochem. Cell Biol 43(7):969-980 (2011).
Medesan et al., "Localization of the site of the IgG molecule that regulates maternofetal transmission in mice," Eur. J. Immunol. 26:2533-2536 (1996).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Improved Retroviral Vectors for Gene Transfer and Expression," Biotechniques 7(9):980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Milstein et al., "Hybrid hybridomas and their use in immunohistochemistry," Nature, 305:537-540 (1983).
Miyoshi et al., "Stable and efficient gene transfer into the retina using an HIV-based lentiviral vector," Proc. Natl. Acad. Sci U.S.A. 94:10319-10323 (1997).
Moen, "Directions in Gene Therapy," Blood Cells 17:407-416 (1991).
Morrison et al., "Chimeric human antibody molecules: Mouse antigen-binding domains with human constant region domains," Proc. Natl. Acad. Sci. USA, 81:6851-6855 (1984).
Mulukutla et al., "Bistability in Glycolysis Pathway as a Physiological Switch in Energy Metabolism," PLoS ONE 9(6):e98756 (2014).
Mulukutla et al., "Glucose metabolism in mammalian cell culture: new insights for tweaking vintage pathways," Trends Biotechnol. 28(9):476-484 (2010).
Nagorsen et al., "Immunomodulatory therapy of cancer with T cell-engaging BiTE antibody blinatumomab," Exp Cell Res 317:1255-1260 (2011).
Naldini et al., "In Vivo Gene Delivery and Stable Transduction of Nondividing Cells by a Lentiviral Vector," Science 272:263-267 (1996).
Ni, "Research progress and future perspectives in antibodomics and antibodomic drugs," Xiandai Mianyixue, 26(4):265-268 (2006).
Noguchi et al., "The L- and R-type Isozymes of Rat Pyruvate Kinase Are Produced from a Single Gene by Use of Different Promoters," J. Biol. Chem. 262(29):14366-14371 (1987).
Noguchi et al., "The MI- and M2-type Isozymes of Rat Pyruvate Kinase Are Produced from the Same Gene by Alternative RNA Splicing," J. Biol. Chem 261(29):13807-13812 (1986).
Ono et al., "Plasmid DNAs directly injected into mouse brain with lipofectin can be incorporated and expressed by brain cells," Neuroscience Letters 117:259-263 (1990).
Osbourn et al., "From rodent reagents to human therapeutics using antibody guided selection," Methods 36:61-68 (2005).
Padlan, "A Possible Procedure For Reducing The Immunogenicity Of Antibody Variable Domains While Preserving Their Ligand-Binding Properties," Mol. Immunol. 28(4/5):489-498 (1991).
Petkova et al., "Enhanced half-life of genetically engineered human IgG1 antibodies in a humanized FcRn mouse model: potential application in humorally mediated autoimmune disease," Int'l. Immunol. 18(12):1759-1769 (2006).
Pluckthun, "Antibodies from *Escherichia coli*," in The Pharmacology of Monoclonal Antibodies, vol. 113, Rosenburg and Moore eds., (Springer-Verlag, New York), pp. 269-315 (1994).
Polakis, "Antibody Drug Conjugates for Cancer Therapy," Pharmacol Reviews 68:3-19 (2016).
Portolano et al., "Lack of Promiscuity in Autoantigen-Specific H and I Chain Combinations as Revealed by Human H and I Chain Roulette" J. Immunol. 150:880-887 (1993).
Presta et al., "Humanization of an Antibody Directed Against IgE," J. Immunol., 151:2623-2632 (1993).
Queen et al., "A humanized antibody that binds to the interleukin 2 receptor," Proc. Nat'l Acad. Sci. USA 86:10029-10033 (1989).
Ravetch et al., "Fc Receptors," Annu. Rev. Immunol. 9:457-492 (1991).
Riechmann et al., "Reshaping human antibodies for therapy," Nature 332:323-329 (1988).
Ripka et al., "Two Chinese Hamster Ovary Glycosylation Mutants Affected in the Conversion of GDP-Mannose to GDP-Fucose," Arch. Biochem. Biophys. 249(2):533-545 (1986).
Rosenberg et al., "Gene Transfer into Humans—Immunotherapy of Patients With Advanced Melanoma, Using Tumor-Infiltrating Lymphocytes Modified By Retroviral Gene Transduction," N. Engl. J. Med 323(9):570-578 (1990).
Rosok et al., "A Combinatorial Library Strategy for the Rapid Humanization of Anticarcinoma BR96 Fab," J. Biol. Chem. 271:22611-22618 (1996).
Sambrook et al., Molecular Cloning: A Laboratory Manual, Table of Contents (Cold Spring Harbor Laboratory Press, 1989).
Schaefer et al., "Immunoglobulin domain crossover as a generic approach for the production of bispecific IgG antibodies," PNAS 108(27):11187-11192 (2011).
Seimetz et al., "Development and approval of the trifunctional antibody catumaxomab (anti-EpCAM x anti-CD3) as a targeted cancer immunotherapy," Cancer Treat. Rev. 36:458-467 (2010).
Sharp, "Gene Therapy," The Lancet 337:1277-1278 (1991).
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem. 276(9):6591-6604 (2001).
Sims et al., "A Humanized CD18 Antibody Can Block Function without Cell Destruction," J. Immunol 151:2296-2308 (1993).
Spiess et al., "Alternative molecular formats and therapeutic applications for bispecific antibodies," Mol. Immunol. 67:95-106 (2015).
Stadler et al., "Elimination of large tumors in mice by mRNA-encoded bispecific antibodies," Nature Medicine 2017, 6 pages.
Straubinger et al., "Liposomes as Carriers for Intracellular Delivery of Nucleic Acids," Methods in Enzymology 101:512-527 (1983).
Tang et al., "Pyruvate Kinase Muscle-1 Expression Appears to Drive Lactogenic Behavior in CHO Cell Lines, Triggering Lower Viability and Productivity: A Case Study," Biotechnology Journal, 14(4):1800332 (2019) 11 pgs.
TeSlaa et al., "Techniques to Monitor Glycolysis," Methods Enzymol 542:91-114 (2014).

(56) References Cited

OTHER PUBLICATIONS

Tolstoshev et al., "Gene expression using retroviral vectors," Current Opinion in Biotechnology 1:55-61 (1990).
Trubitsyna et al., "Use of mariner transposases for one-step delivery and integration of DNA in prokaryotes and eukaryotes by transfection," Nucleic Acids Res. 45(10):e89 (2017).
Tutt et al., "Trispecific F(ab')3 Derivatives That Use Cooperative Signaling Via The TCR/CD3 Complex and CD2 To Activate and Redirect Resting Cytotoxic T Cells," J. Immunol. 147:60-69 (1991).
Umana et al., "Engineered glycoforms of an antineuroblastoma IgG1 with optimized antibody-dependent cellular cytotoxic activity," Nat Biotechnol 17:176-180 (1999).
Urlaub et al., "Isolation of Chinese hamster cell mutants deficient in dihydrofolate reductase activity," Proc. Natl. Acad. Sci. USA, 77(7):4216-4220 (1980).
Van Dijk et al., "Human antibodies as next generation therapeutics," Curr. Opinion Chem Biology 5:368-374 (2001).
Vitetta et al., "Redesigning Nature's Poisons to Create Anti-Tumor Reagents," Science 238:1098-1104 (1987).
Vollmers et al., "Death by Stress: Natural IgM-Induced Apoptosis," Methods and Findings in Experimental and Clinical Pharmacology 27(3):185-191 (2005).
Vollmers et al., "The "early birds": natural IgM antibodies and immune surveillance," Histology and Histopathology 20:927-937 (2005).
Warburg, "On the Origin of Cancer Cells," Science 123(3191):309-314 (1956).
Wolff et al., "Direct Gene Transfer into Mouse Muscle in Vivo," Science 247:1465-1468 (1990).
Wright et al., "Effect of glycosylation on antibody function: implications for genetic engineering," TIBTECH 15:26-32 (1997).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xu et al., "Comparative Proteomic Analysis of Three Chinese Hamster Ovary (CHO) Host Cells," Biochem Eng J. 124:122-129 (2017).
Xu et al., "Correction of the enzyme deficiency in hematopoietic cells of Gaucher patients using a clinically acceptable retroviral supernatant transduction protocol," Exp. Hemat. 22:223-230 (1994).
Xu et al., "Improving lactate metabolism in an intensified CHO culture process: productivity and product quality considerations," Bioprocess Biosyst. Eng. 39(11):1689-1702 (2016).
Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity," Biotech. Bioeng. 87(5):614-622 (2004).
Yeung et al., "Engineering Human IgG1 Affinity to Human Neonatal Fc Receptor: Impact of Affinity Improvement on Pharmacokinetics in Primates," J. Immunol. 182:7663-7671 (2009).
Zhou et al., "Decreasing lactate level and increasing antibody production in Chinese Hamster Ovary cells (CHO) by reducing the expression of lactate dehydrogenase and pyruvate dehydrogenase kinases," Journal of Biotechnology 153:27-34 (2011).

* cited by examiner (WT<PKM-KO<PKM1-KO):

PKM1-KO: accumulation of TCA cycle product (WT<PKM-KO<PKM1-KO):

PKM1-KO: accumulation of TCA cycle product

SEQUENCE LISTING

<160> NUMBER OF SEQ ID NOS: 54

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

Ser Ser Tyr Tyr Met Ala
1               5

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

Asp Ser Tyr Met Ser
1               5

<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 3

Asp Met Tyr Pro Asp Asn Gly Asp Ser Ser Tyr Asn Gln Lys Phe Arg
1               5                   10                  15

Glu

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

Ala Pro Arg Trp Tyr Phe Ser Val
1               5

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

```
Tyr Thr Ser Arg Leu Arg Ser
1               5
```

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

```
Gln Gln Gly His Thr Leu Pro Pro Thr
1               5
```

<210> SEQ ID NO 8
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 9
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105


<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Tyr Leu Ile Glu
1               5


<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Ile Asn Pro Gly Ser Gly Asp Thr Tyr Tyr Ser Glu Lys Phe Lys
1               5                   10                  15

Gly


<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Arg Leu Asp Tyr
1               5


<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

-continued

```
His Ala Ser Gln Asp Ile Ser Ser Tyr Ile Val
1               5                   10


<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

His Gly Thr Asn Leu Glu Asp
1               5


<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Val His Tyr Ala Gln Phe Pro Tyr Thr
1               5


<210> SEQ ID NO 16
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser


<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17
```

-continued

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105


<210> SEQ ID NO 18
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 19
<211> LENGTH: 214
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210
```

<210> SEQ ID NO 20
<211> LENGTH: 694
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

-continued

```
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
        275                 280                 285

Lys Tyr Asn Asn Tyr Ala Thr Tyr Tyr Ala Asp Ser Val Lys Gly Arg
    290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
        355                 360                 365

Phe Ile Phe Pro Pro Ser Asp Glu Gln Leu Lys Ser Gly Thr Ala Ser
    370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445

Val Thr His Gln Gly Leu Ser Ser Pro Val Thr Lys Ser Phe Asn Arg
    450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510
```

Val Ser His Glu Asp Pro Glu Val Lys Phe Asn Trp Tyr Val Asp Gly
515 520 525

Val Glu Val His Asn Ala Lys Thr Lys Pro Arg Glu Glu Gln Tyr Asn
530 535 540

Ser Thr Tyr Arg Val Val Ser Val Leu Thr Val Leu His Gln Asp Trp
545 550 555 560

Leu Asn Gly Lys Glu Tyr Lys Cys Lys Val Ser Asn Lys Ala Leu Gly
565 570 575

Ala Pro Ile Glu Lys Thr Ile Ser Lys Ala Lys Gly Gln Pro Arg Glu
580 585 590

Pro Gln Val Tyr Thr Leu Pro Pro Cys Arg Asp Glu Leu Thr Lys Asn
595 600 605

Gln Val Ser Leu Trp Cys Leu Val Lys Gly Phe Tyr Pro Ser Asp Ile
610 615 620

Ala Val Glu Trp Glu Ser Asn Gly Gln Pro Glu Asn Asn Tyr Lys Thr
625 630 635 640

Thr Pro Pro Val Leu Asp Ser Asp Gly Ser Phe Phe Leu Tyr Ser Lys
645 650 655

Leu Thr Val Asp Lys Ser Arg Trp Gln Gln Gly Asn Val Phe Ser Cys
660 665 670

Ser Val Met His Glu Ala Leu His Asn His Tyr Thr Gln Lys Ser Leu
675 680 685

Ser Leu Ser Pro Gly Lys
690

<210> SEQ ID NO 21
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Glu Phe
20 25 30

Gly Met Asn Trp Val Arg Gln Ala Pro Gly Gln Gly Leu Glu Trp Met
35 40 45

Gly Trp Ile Asn Thr Lys Thr Gly Glu Ala Thr Tyr Val Glu Glu Phe
50 55 60

Lys Gly Arg Val Thr Phe Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Trp Asp Phe Ala Tyr Tyr Val Glu Ala Met Asp Tyr Trp Gly
100 105 110

Gln Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Ala Ala Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Gly Ala Pro Ile
325 330 335

Glu Lys Thr Ile Ser Lys Ala Lys Gly Gln Pro Arg Glu Pro Gln Val
340 345 350

Cys Thr Leu Pro Pro Ser Arg Asp Glu Leu Thr Lys Asn Gln Val Ser
355 360 365

Leu Ser Cys Ala Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Val Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 22
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Asp Phe Thr His Tyr
20 25 30

Gly Met Asn Trp Val Arg Gln Ala Pro Gly Lys Gly Leu Glu Trp Val
35 40 45

Gly Trp Ile Asn Thr Tyr Thr Gly Glu Pro Thr Tyr Ala Ala Asp Phe

-continued

```
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450
```

<210> SEQ ID NO 23

```
<211> LENGTH: 463
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365
```

```
Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460


<210> SEQ ID NO 24
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 25
<211> LENGTH: 213
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 25

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Trp Val Phe Gly Gly Gly Thr Lys Leu Thr Val Leu Ser Ser Ala Ser
100 105 110

Thr Lys Gly Pro Ser Val Phe Pro Leu Ala Pro Ser Ser Lys Ser Thr
115 120 125

Ser Gly Gly Thr Ala Ala Leu Gly Cys Leu Val Lys Asp Tyr Phe Pro
130 135 140

Glu Pro Val Thr Val Ser Trp Asn Ser Gly Ala Leu Thr Ser Gly Val
145 150 155 160

His Thr Phe Pro Ala Val Leu Gln Ser Ser Gly Leu Tyr Ser Leu Ser
165 170 175

Ser Val Val Thr Val Pro Ser Ser Ser Leu Gly Thr Gln Thr Tyr Ile
180 185 190

Cys Asn Val Asn His Lys Pro Ser Asn Thr Lys Val Asp Lys Lys Val
195 200 205

Glu Pro Lys Ser Cys
210

<210> SEQ ID NO 26
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 26

Ala Ile Phe Thr Gly Ser Gly Ala Glu Tyr Lys Ala Glu Trp Ala Lys
1 5 10 15

Gly

<210> SEQ ID NO 27
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

Asp Ala Gly Tyr Asp Tyr Pro Thr His Ala Met His Tyr
1 5 10

```
<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Arg Ala Ser Gln Gly Ile Ser Ser Ser Leu Ala
1               5                   10


<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Ala Ser Glu Thr Glu Ser
1               5


<210> SEQ ID NO 30
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Asn Thr Lys Val Gly Ser Ser Tyr Gly Asn Thr
1               5                   10


<210> SEQ ID NO 31
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
```

115 120

<210> SEQ ID NO 32
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 32

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ser
20 25 30

Leu Ala Trp Tyr Gln Gln Lys Pro Gly Lys Ala Pro Lys Leu Leu Ile
35 40 45

Tyr Gly Ala Ser Glu Thr Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Asn Thr Lys Val Gly Ser Ser
85 90 95

Tyr Gly Asn Thr Phe Gly Gly Gly Thr Lys Val Glu Ile Lys
100 105 110

<210> SEQ ID NO 33
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 33
gtcctttggg cagagacag 19

<210> SEQ ID NO 34
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 34
gaccagagta ctccctcgt 19

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 35
ccagatttgg tgaggacgat 20

<210> SEQ ID NO 36

-continued

<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
gaccagagta ctccctcgt 19

<210> SEQ ID NO 37
<211> LENGTH: 30
<212> TYPE: DNA
<213> ORGANISM: Unknown
<220> FEATURE:
<221> NAME/KEY: source
<223> OTHER INFORMATION: /note="Description of Unknown: Pyruvate kinase muscle WT sequence"

<400> SEQUENCE: 37
gaccagagta ctccctcatg ggcacagtgg 30

<210> SEQ ID NO 38
<211> LENGTH: 29
<212> TYPE: DNA
<213> ORGANISM: Unknown
<220> FEATURE:
<221> NAME/KEY: source
<223> OTHER INFORMATION: /note="Description of Unknown: Pyruvate kinase muscle WT sequence"

<400> SEQUENCE: 38
caccctgcct ctgtctctgc ccaaaggac 29

<210> SEQ ID NO 39
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 39
caccctgcct ctgcatgggc acagtgg 27

<210> SEQ ID NO 40
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 40
caccctgcct ctgcagtgg 19

<210> SEQ ID NO 41
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 41
catgggcaca gtgg 14

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
cccatcacgg cccgcaacac 20

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43
cttcttcaag acgggggatg 20

<210> SEQ ID NO 44
<211> LENGTH: 22960
<212> TYPE: DNA
<213> ORGANISM: Cricetulus griseus

<400> SEQUENCE: 44
gagctgcgga gggattgcgg cgggtcgcag ctgggataac cttgaggccc aagaggcgca 60
gtcccgcaca cccgtgactc gtcctgagac tgcggacgtc cgacttaggc atcgctgcaa 120
gatccggagt acgcccgagg tgagagggga gagcctacgc catctgggcc cagggccgat 180
gcctgcttct gcggagcgca ggcctgcggg cccatgcggg actaaggctc ctggcatcgt 240
gcatcccagt acgggttggg ggaaaagcta cactcgagca caggtcctga gcttccaaag 300
tcagagggcc cagccagccc cttcccacgc ggtagttctg gtccctcttc tttccttctc 360
aatctggttc caccctctta tcttactgct gccgtcctcc ccgccctgtt ctctcccact 420
cttcgatgct catcctcctc agccatttac tagtggttgt tttcccttta ttttaactct 480
gtgccaccat ccccccccacc ttcggtgccc tctttgtaat ctctactcga aataactctc 540
ctgctccccc cttgcgcccc ggcattcatc ccccatccag gtcagtatgc tcttcgcgtg 600
gccctgttgg ctgctccgcc cctccccctc cattccagtc acgtccgcgc cactgcatcc 660
tttcagcatc cggatcctcg cccctccccc tccgcgctgc ttcccccgcc caccgcattc 720
tggtcacgtc cgcggactcc cctcaggccc tcgtggtccg cggcctgtag gtagggtgca 780
gttagtggcc gtccagggag atacagccac cggttacgta acatcatctt cccggtggtg 840
tggcaaggag ggttggcagc tattccttcc tattttgtgc ggccgcagat tcttctggtt 900
gccggcgaag cactcgtgct ccgggctacc cgggccctgt ggggtgcctg caagcgctca 960
cgcggtccat cctgcggtgg cgaggctgcg cgtaccgcag ggctcctgga ccagccagtc 1020
acactgctcc aacgtgctgg cccggggtgg gcgatcaacc aagggcggct tccgaatgta 1080
gctgcagccc gatgcgacca gaacgctcat agcccacaga gttcagtctg attagggaag 1140
caaaatttgt caagtcagtg ctgtgaggaa ggatggggct gcacgagctg gtccgcacac 1200

-continued agggattgag taagcagtag agcacctagt ctgaaggtta cttaaaaata cagtcttgga 1260
aagatgcctc tggatctatc tcctcttcca aacccaggag attgatagga taaatagagc 1320
ctcataatgt gggtccagtc ctgcgtggag gcagcggggg atatacacag gttttaggaa 1380
tcttctgagg tggttcagcc tcttagacat ttgctccaga ctgctggagt tactggcctc 1440
cgtgtctgta cggacatgac taatctcagg tgaaatgacc acgagggcgt gcacatgtac 1500
tttttttttg tcaatggatg aaatacagtt accttgaagg ccgagtctgt cgcccagtta 1560
ttcctctaca cattagtact aagcttgggg aggcagggag gcaatgaaca cccagtatcc 1620
cctaggaaac gaattctctc tggtccgtgt ttacaatgta actaatgtta acaattgcaa 1680
ctcccaagaa agccagctat ctaaagggac aaatgctgca gcttttgtct tcgactgtaa 1740
cggtagaaac aaaggaacag gtacccggat cagtctcttc tgattttctc gtccctgatg 1800
gttcatgtaa gacctttctg ctccctggct tgtaggaagt tggatttgga agctgttgca 1860
gtaagttctg ttgccacaat acttagggtg gggctacttt ctagagtaca gaagggaggg 1920
ccttgggtca ggattcaagg taccattgtt agcaaacaat ttactgtctg gtggcctgag 1980
gatgttgtag gtaaggcagt gaggctgttc tgtgggaaag tgtactgtaa tccaccaccg 2040
ggtctgggca agatgactca tcctttcaca ttagcggcat tcgagaagat tctcatcctt 2100
gggtgagtgg ggaaaacttg gtactcctag gtttagtaag gcccctgttt agtcagtcaa 2160
atactgagct agcgtgcatt tccctaagtt aaacttctat gtgtcactca gactgagtgt 2220
ggtggttcag cacttggagg ccaggatcgc aggttccaga ggggggaagg ggcagcaaaa 2280
tgccggggac caggcccttt gtgctactgg agtgctggaa gtgtgagtgg ttggtcctag 2340
tctataggtc cactcttaat tcttgagtga taggcacagc agcttctcat ggaacaacca 2400
gtatccagaa tgacaatttc tgtgaactca tttgagttac tgcttttaag tggaactata 2460
tggatgataa ttaatcactt tctagtacat agctgactcc aaacaactca gtctcatggg 2520
ggttggatat accatctgtt ttggcaagaa ggtatgatca caggaaagga catcttattt 2580
cttaaagctg ttgatttctt aatattgagt agaagaaacg agccatccat gggcaggaag 2640
gtagaaaaaa aacctattgc attagactca ttacttgggt ttttagtgtc ttttgcttca 2700
gcttttctac aggaagtcaa gatgagttgg ccaagcacta aggtggagat tgaggtagag 2760
gaaaatgact gattcacttt aagtttctga atcatcccaa atacccacag ccaagttaac 2820
tggtaaacta caaaaatgag ttgtcgcctg tgaggttttt tacttcgctg gtaagagtac 2880
ataagtactg agtcatcctt gcaaacttca ctctggtacg gatagaaata aatgacagac 2940
tttttgatta attcctgaca tgatactttc ttgggtattg caatttttcc caagagccag 3000
acttagactg gatatggagt agtcggaaga agtgagccca cgtggtgagc ccacgtgggt 3060
ggtggcctgc aaacctctgc tggcctctta aggcttagtg taacagctca gctcaggact 3120
gggggtggtc ttacagacac caagctgtgc agtgaggcca cgcccctacc gtagtttgtg 3180
cctgtctgca cgtaggaggg aagggggaag gtttgagctg tagtacctct ggtggcctct 3240
gggacacctt cactgaaggg tctggggagc tctgaatctt tcccaaagcc agctaagctc 3300
taaaggaagc tgcatccctt ccaaacattt ttttattttt attttttgtt gttgttgtgt 3360
ttgtttttcg agacagggtt tctctgtggc tttggatgct gtcctgtaga ccaggctggt 3420
cttgaactca cagaaatcca actgcctccc gagtgctgga attaaaggtg tgcactacca 3480
cagcccggct ccttccaaac attttcaatt aacctacagg tcatattttg actttaaact 3540
actggtgttt tccagcaata gtgtaaaaga ttttaaggca tgcccatttt ggaagagtag 3600

-continued

```
ggaagcactg ggtatggtgg tgcacatttt taatctcagc actcaggagg caaaggcagg   3660
cggatcttca attcaaggac agcccagaag aagctggtaa tgtagtgctc gggaaatgtt   3720
tgcctgttgg gcacaaagtc tttccatcac tagcactaca taaaattgac atgcctttaa   3780
ttccaacatt caagatgtgg tggcacgagg attggaagtt tatattcagc ctcagctact   3840
tgatgagctc aaggccagtc ccagatacat gagaacccat atcaaacaag aaaaaaaagc   3900
caacataggg ttcaatatag atatagtgat tgggtatcca aaattcaggg taggggtggg   3960
gacaaaggac agcgggaggg ttagagaagt cagagattgg gagaaggaaa ttatttatgg   4020
attgaataca atcagaatac tttttatttt tggaaagtct aaaaatacaa atcattgttg   4080
aagcagagtt ctaagtggta gaaacacagg gtttggggtc cctctccccc ttgggaagga   4140
atagttgtga tcctataaag gtcactgtag acaggcactc atagtaagta ggtcagtgct   4200
cttggacagc tggtactgcc ttccctattt aacacccccc gcccccccttg gttcaggaca   4260
gaagctgtgc ctccagttgg ggagaccatt gtgcattctg cttacacctg gttggtttcc   4320
tagactccta gccagggtcc agagtgggca tcattcccgg taacactggc agcttaagcc   4380
tgctaaggag ggcaccatgt gccagcagaa cagaaacttt ctcccagatc atcttctggc   4440
tcaaactagt tgcaggagat ccttggtact aaggactgga gagtttcttt gtccctggca   4500
ttctgtcctg aaataaaatg gtctttctgc aggatggtcc tcataattgc atggcaggat   4560
ttacagtagg actgttaaag ttaaggttaa ataaaagatg gtttgtgctt gtttctttaa   4620
ttttttttt gaccccacag aaatgagcca cccaaacagg tgggctcata ttctgaatag   4680
ccttgtaaca ccagactttt ctggtacaga atttgctagg gttaagaagt agacctccct   4740
ctggacaagg tagcaaatgc cttcaatccc agcattcagg aggtagggga gatggatatc   4800
ttgagtttta ggatagccag ggctatgtaa taagaccatg tcttaaagaa taaataagcc   4860
aggcagtggt ggtgcatggc ctgacagtgc cagaattagg gtggcattgg tcagtttttg   4920
ttgttcttat gccctttgtg ccagagatgg gagaaggcag aaccagatga cctgagctga   4980
gcctgtgcat gcctcaacct gcagcccaca ctgaagcctg ggctgctgtc tcctttctca   5040
cagaggggca atggctctga ggaagatact gcttcagggg ctcaggctca agagcagggc   5100
tcctgtccct gagcatggtg tttaccagtg tcattggact tgccaggctt ctgcagctgt   5160
ctggaggttg gctgtgcatg tgggtgcctc ctgaggagga ggatggtggc atgggtgggg   5220
ccgcatgact tggcaggcac tactgtacaa gtagctagcc aatagagcaa gccctaaggg   5280
cctaagaaac tggggctgga actgctttcc tgggccagaa aataacctca gaaagggtat   5340
tctatatgtt atatatagat aggtggttgg tttgagttgt ggggctccat aggggtcatg   5400
ggataggaag aagagtcctg attttgaagg ggggcggtgc tccaggtatc aatagcctgg   5460
gaagagaaac gggttagtga gctgggatcc agattggtag gggacttgaa acacttgaag   5520
ttttgtagga ggtctattta attgtatcga tccattgata catatttcca cttgccactt   5580
tgtatctggt agcaagataa tctgcagact atagtagttc tagatgggga agtgggttat   5640
atttgaagcc aatgaaattt tacctgttaa attgcatttc cccgccctaa gggcagcagc   5700
ccttgtctaa caaggattgt actgtcaacc ctgagaacag gcaaagcagg aaaagaaaat   5760
tactggactc tggcatggaa ctgataagtt tttataatga aaattttcta tgggttatat   5820
tgtacacttt tctttttctt tttggctttg agatcaatgg atcaagttgt tctccaggtc   5880
agtgaagctt ccctgaggtg cacttgtgac tgagggaata ttagcagagt catcctgaag   5940
```

-continued ggctcggctg atatatggaa attcacttta catataattc ctcccatgag ctttatagaa 6000
tgcatagaaa taaatgtgtc attttcagaa actgcgcttt ttttgtttgt tttttggttt 6060
tggtttcttt tttttttttt tttttccgag acagggtttc tctgtggctt tggaggctgt 6120
cctggaacta gctcttgtag accaggctgg tctcaaacac acagagatcc acctgcctct 6180
gcctcctgcg tgctgggatt aaaggcgtgt gccaccactg cccggataaa ggtaaggatt 6240
tttttttttt tttttctcaa gacagggttt ctctgtgtag ctttggagcc tatcctggca 6300
ctcgctctgg agaccaggct gctctcgaac tcacagagat ctgcctgcct ctgcctccca 6360
agtgctggga ttaaaggcgt gcaccaccac accagccact tctggttatt ctttgaacac 6420
tccatcagga tcatacttgc tagattcttg gcattttgca tcaactcttg tttttgagct 6480
ggggtttctt tgtgtaacag tgctcccaag tgctggaatt aaaggtgtgc gccaccacct 6540
ggccacatca acaattttat tgataaagga tatgccactg ggtgcggtga cacagcatta 6600
gaaaggcaga tttcttttgt tttttgtttt tctttcttc tttttttaat agatttattt 6660
atcatgtata cagtgcatgc cagaagaggg cactagatca cattacagat ggttgtgagc 6720
caccatgtgg ttgctgggaa ttgaactcag aacctctgaa agagcagcag tcagtgctct 6780
taactcctga gccatctctc cagccccagg aaggcagatt tctgaattgg agaccaatct 6840
ggtctaagta gcacctccag caggtcaggg atgtatagtg agacactgtc tcagagaagg 6900
aggagggagc attgtagtga atactgccac ccaggtaaca aactgttatt ttgacattta 6960
tcctcttaag ctttttatct taaggtggag accaggtttt tatataaact tagagaatgt 7020
ggtggtgcac atctgtaacc tcaaccttga ggagagaggc aatatgtagt gagttccagg 7080
ccagccagag ctacttagtg agaccctctt aagtaaatag gggttgtagt atattacagg 7140
tttaaagact gtccaggaag gagtcagtcc tagtgactca tgcctgtact cttaacactt 7200
gggaagttga gaccggagga ggatctttgt gagtgaagcc agcctggggt tcattaatat 7260
tgtgtgtgtg tgtgtgtaac atagctgaat ctatctctaa gagcaatttc tacctggtta 7320
aggtgattac cacaaagagc tcagctttcg ccttaatcct tgtacagctc tccaaggcaa 7380
actgtactca gctctgaaca gtctttccaa gtgaggccaa ggagccactc tgagtcaaaa 7440
aaacagcatt atgtcactgg aagcccaggc ccagagaacc aaaggtatga cctgattatc 7500
agtggcctca ggcaggaatt tgcaaggagc tttaatgtct tagttggaga gaagcacctg 7560
gtggctcttc aggaaagtgg gttcggggtc tgtcccactc gtgctgactt catagttcat 7620
agtcctatca tggtcatagc cagacttttg tgtcgtgttg gtttgatgta ccatctattc 7680
ctttagcagc caccaaagca tggctgggag gcatgagagt ttgccagccc tgtttgtttc 7740
aaccatgggt agacaaagga cctgactgcc tgggacttcc tttgtgagga cttctcagat 7800
ttggagaggg gaaacaagca gaactgatct tggcagagag accttaatga gactgagagc 7860
tcatttaaca aatactacaa ggtgccttag caccttgtag accccaaagg agaggttgaa 7920
cagtgttggc caatggcagt agttagaggt ctgattcctc ctttaaaagt tttccgttct 7980
gcagtgaaaa tagtggtgca cccctggaat ccagcaccca gaagcccgga actcgtgggt 8040
ggccagcctt cttttccatt gcatcactag taggttacag gggtccccag gtctcaagaa 8100
gcagagatga attttagtga tcaagaaatc catggttgtt gagtgagggt cctttactag 8160
gagtcagggc agagcaagga tgcagagggg tttattgtag atgagcccct tggcctgaga 8220
actcagatga gaaggacacc cagcttcatt caagcctctc aacttttgta aaacacaaag 8280
cttctacaga gttatgtcct ctaaccagct cagtgagcat ttagttgtga gtcggtaata 8340
aagttaaagc aaaggtcagg cggctgttgg gattgtgacc tgggtggtta attacctgga 8400
acagatgctc aggcttctga gagtgctcta cctacctatc agacatagag agggattcca 8460
gatgcttaga actggggctg ggaaagccat gtctaacgtc agcacgtgga aagatcgaag 8520
agtgagttca aggtcagcct aggttataga gtggattcta ggtcatctga gactagctac 8580
tgtgcaattc tgtttcctag gttacagacg actccttggt gtaatgactt tggagctatt 8640
ccagtgctct tgcgagcaaa atttgctttg tgtgtctttt aattgttgct gttgttttat 8700
tgctaaagca ttctgggatt ttgcttcctg cctagaagaa ctactttttt gccgcctatc 8760
atttggatct tatgctctta tgtctaataa aataagctta ggcaacgagg ccagtgaaaa 8820
cctagaactc tggagctaaa gggggcttgg gacccttgtg tttgtctcct tgatctgtgg 8880
gaccatttga gtttgggtga acatggtaaa gaggctgttg ggtaccaaag cacatacttg 8940
tagattcagt gcctcatcat ggtagacttc ccaaggtacc aggtgtttgt atgatgatag 9000
attagttgta actttggggg aggatagttc ttacaacttt tgcaagtttc ttcaagtatg 9060
taaagtgatg tccttcctag ggtggtgtga aagctatccg tagcagctct tgtgatactc 9120
ctgcttttac tgcccccctgg gacaatatat gctttggatg ggaagttact tttgttcatc 9180
aaggtctttg ctgtttgctc acagtcacat tgagcccttt gcccaatttg aggagcaccc 9240
acagaaccag cacaggccag gcctctgtgt gacttgtgca caaagcaatc gtattaggtt 9300
aatgtgtaat cgggagacag ctgcctacgc caagtggctc attaagcact gcccaatcta 9360
attgcactct tcaactcccc gggacccagg acctcagaaa ccatgccgaa accacacagt 9420
gaagcaggga ctgccttcat tcagacccag cagctccatg cagctatggc tgataccttc 9480
ctggaacata tgtgccgcct ggacattgac tccgcaccca tcacggcccg caacactggc 9540
atcatttgta ccattggtga gtgagtgtgg cgctccccta gatggaggct tcccacctga 9600
tgatctgcta aagagcatag caattacaag gctaacctag gttctgagtg aggcactgta 9660
cacatttctt ggaatggagg tcataagaaa tggccataaa gaattagtat gttttgccgg 9720
gcggaagtgg tggcacacag ctttaatccc agcactcatg acacagaggc aggtggatct 9780
ctgagttcga gctagcttag tctacagagc aagttccagg ccagccaggg ctacacacaa 9840
agcctatttc aaaacaaaaa caaaaaagtg cactttgttt tctgtgatag gtagaattca 9900
ggggttcttc cttagataat cgttgtagga gtatttctga gatctcaggt ctttttcata 9960
tggattgtat caccaacatt cagtagttgg acaacttgag ggcaagggaa actgcttaat 10020
tctaccctcc acttccctga ttatgtgggg gccctaaaga atttagagag tggcagggtt 10080
tccccctcgt atacgtaggt taggaaagtt gactggcata atgctttgtg ttcatttttg 10140
gagttgattt taaaaacaat taaaggatga agaatttgct gagaaaatta cacacgtttt 10200
cttgtatcat gctttttttac ctgtggtttt aaatatttat taataggtcc tgcctcccgg 10260
tctgtggaga tgctgaagga gatgatcaag tctggaatga atgtggctcg tttgaatttc 10320
tctcatggaa ctcatgaggt aggcctcagc tagagcaatt tattggaaac aggaggtgtg 10380
gtgataatta gcgctactcc cggcagatat gaaccccagt tcagtgggac attgtcctag 10440
ccctagccca tcctggattc cctctttccc tcctgtcacc ttcataggcc taaacaaaca 10500
aggccagctt tgtcaaggac cagggctgtc ctacccttaa ccttcacaaa agaaggcagg 10560
aaggatttag ctggtaaccc ctctaggcca tcaactgtct tagctctgca cttgggaaca 10620
atgcctcagg gtttctctag tggctcctgt gagtctggtg accaaaaggt catgcagaag 10680
gttgattccg gcttagttca atcctgagat gattagctag ttccatagat aggggtttcc 10740
acttgagcct gagtcgagtg cccaaagtct gtgatggatc atactcccct ctccattggc 10800
attgtcttcc tagcatcagt tccctccata aggtgaggta ggaatgcatt tgagctgggt 10860
ctgttcatta gaaattccaa ctgatggaga ggcaatatgc aggagccaga tggcagctgt 10920
gagttagaaa aacccatgtg tgccagtgct ctcaagttta gaacaaccca ttctagcagt 10980
cgggcagata aagaaacctt aaaagtttca aatactttca aactggattt tctactggga 11040
tcaatggagg tgggcacaga cctcttccca catcttggtt tctttatgtt ctataaaagt 11100
attaccctgt gctctattct gccctctgac ctttggaagt tgtttagact aaaaatagag 11160
gaggaagagc agtccaagaa aatgaacccc ctccttctca gaacatgaga ctcatcatag 11220
attccatagc ccatattcca taaacagcct ggtggaggct tgcccccaaa tgtcatagta 11280
cctaggatag tctagttgta cctaagcagt atatgacacc tccttgctag atgtggtggt 11340
acagaactgc cttgggatac atagcaggtt ggagacaagc ctcaggaaca taacaagagc 11400
ctattgcaaa ccaaaaagag gaagcttgtt gctttccaag ctctgttgcc gtcggcagga 11460
actgctaaga ataaacacaa gggtaagacc aactcaggca agattggatc cacttgccat 11520
ggtccttgca agtagaatct gcatggtctc cgatttgcag gacagtcaga aaataaattt 11580
ggggacatga cctttcatgg ctcttgaatc ctgtaaaata ataccatgca actctgccat 11640
ggcagtgacc agtgaggttc agacctgctg gacaattggc cagctccagc ttgacttttt 11700
aactataaga agcatttgga gattatctgt acttttccta gattggactt gggctttatt 11760
ttattcattt atttgttctt gtaagtttat ttttaggttt ttagaatgag atgaggttaa 11820
tcccagaagg ttttgggaag ctggtctgtt aatggcatgt cgtgcacaca gtttggccat 11880
gtgttaggtc tcttatttca tgtgctgtct ccatgaggag ctggggtgtt tttgctgggc 11940
ttgatgtgat ggttttaagt tcttccggag acactgggat ggcattccct ccctctgaca 12000
ggaacatcta ccagctgcat ctgatccttt cccatccttg gcagtcttgt aattacacct 12060
cttgctggtc acatgggcaa gatgagtatt cttgctgaac aggcaatgct gtcctgctgt 12120
actgactttt aaatggccta aatttagagc ctctacaagg atggcactca tggattccag 12180
tcttcgttca ccatttggta atgcgccagc aaagccatag ctgtgacaga agacacgatc 12240
taccttccaa aagtgtacca taggttggcc atacaaagaa ttttaataat gggccaccca 12300
gtgttctaac ctttgggatt ataatgcagt tttatataca cggtgccaaa tatgtgtttg 12360
tttagagcac ttgtgaatgg gctgaggtgt gtagctcagc aagaacaaat ccctgggttc 12420
aaacctcaca catacttata aagatacatt aggccagagg gaaggatttt aactcctata 12480
aagtagaaat tattcagctg taattcttct atgggaatta agggcaacct ccaaaaaaaa 12540
actattatga gtacctctct aaaatgaatc aagcagtcag tagttactgt cagaaaagat 12600
tagctctcag gccgcctgtg gatgaaggac agattcaggc ttccaggtgt cttaactggg 12660
cacagtggtt aaaagacaaa gcccttaaaa tgatgaatta tatatatgtc ctgtgatcag 12720
tggcgtcaca cagatctgca ctatccacag attctatagc tgtcttggct ctgactccca 12780
ggtagaaaaa ggaaaaggcc tttgggggta ctattgcaag tgaagtatag tgaacggtag 12840
ttctatcaga gataggccac taatcaccgg ttcctctcct tttctaatca gacctaagaa 12900
agtgattgtg aaaggaggtg tctgcatatg accaagcaat gagctgttta gcttggacca 12960
ttgttacctt aagtcaacaa ctttgggttt gaattgactt tgggatcgat agtggaaaca 13020
gactgccagg gcagacttca aacacaaatc ctgggtcctt tacctgcccc agttgttagg 13080

-continued

```
catctttgag tcctagggat actaggacaa ctgaagggac acatagctgc tttaagagta  13140
gggctttagt gacagtgttt cagaatgttc ttgggatttg ctattggagt tagttctgtg  13200
gtggggagaa tggatgctga tgagattagt gggttgggga tgaggatgga attcagaccc  13260
ttttctttca taagtgattg gtcaactttg gctcacaggt agggaatggg aactgaagtc  13320
aggtgtgggg cacctgtcag tcaatctccc ttctttcccc agtatcacgc agagactatc  13380
aagaatgtgc gaacagccac agaaagcttt gcatctgacc ccatcctcta ccggcctgtt  13440
gctgtggctc tggacacaaa gggacctgag atcaggactg gactcatcaa aggcgtgagt  13500
atcctaggaa gtgctctgag ggcaggcaaa ccctccctcc ctggtagctt tctctagttt  13560
ctgactgggt aagttttaga gtttaagtct accaatgata gtgtttttat taatgcatat  13620
gggtgtgggt ggtttttttg tgtggctatg caccacatgt atgctgtgca ctgcagttat  13680
ggatgtctat gagacccacc atatgggtgc tagatcttct gcatgaacag taagtgctct  13740
aaaccactgc accatctcca gtcccggcat gagaatgttt tttgtcattg ctcttttcat  13800
ctgcatagct aggaaacatg gggttggtc cttaattttt tttaactact taagtctcaa  13860
tggtgaacgg agcttagaat ttcttcaaag gaagaaggtt gcttagtact ccgaaccagg  13920
gtttgagcat ccccattagg ggtgtggctt ctgcagttca cacacccacg ggctgtcttg  13980
aatctacaga gcggcactgc agaagtagag ctgaagaagg gagccaccct gaagatcacc  14040
ctggacaacg cctacatgga gaagtgtgat gagaacatcc tgtggctgga ctataagaac  14100
atctgtaagg tggtggaggt gggcagcaag atctacgtgg atgacgggct catttcactg  14160
caggtgaagg agaaaggtat gcatggcgca tggtccatcg ccaattccca tctccagcgc  14220
tctcaagttg aatctttttt ttaagatttt atttatttat tacgtataca acattctgct  14280
tccatgttta tctgcacatc ggaagagggc accagatctc ataacagatg gttgtgagcc  14340
accatgtggt tgctgggaat tgaactcagg acctttggaa aggagtcagt actcttaacc  14400
tctgagccat ctctccagcc cccaagttga atattttaac tccttttggt atagcactcg  14460
cctgcatgta tagggcctgg gttcaatctc cagaggatca gatttaaaaa aaaaaaaaaa  14520
aaaaactccc caaagggcca ggagggtggg gcgagccttt agtgtttagt cctaacactt  14580
gggagtcaat ggcaggtggg tctctcaata tggcatgtag aatatttcta tgtgcctttc  14640
aagtttttgt tatgttcaca ttgttctgcc tgaatgtcca cctgcatgac ggaagagggc  14700
accaaatctc attacagatg gttgtgagcc accatgtggt tgatggcaat tgaactcagg  14760
atctctgtaa tagcaaccag tcagttctct taacctctga gcaatctctc cagtccctcc  14820
tgtgtgcctt tgaatgccag ttaaatctta cctgtttaaa tggtttatgt gttcgtttca  14880
ttttggtttt atgagagggt ttttttgttg cctgtgctgg gctttactat gtaactgagg  14940
ccaaatgagg ctgattcact agcttagcta tttattttga gacaaggtct cactttgtag  15000
cgctggctga catcactgtg tagatcacct tagtcttgaa cacagatttt tctgcatctg  15060
catcttgagt gttggggtaa ttaacctgtg ctaccacacc caaaattcaa aacatcttag  15120
caacttgtac atgggtattg tttataggtt cggaaactga cagtgtcaaa ttgactcagc  15180
ctgaggtctt gtaatctggc tttcacgtgg ctctagttgc ctcagtgatg tgacctcctg  15240
caagaagagg caggtcctca tcactgatcc ttcacttaca caggtgctga ctacctggtg  15300
acagaggtgg agaacggtgg ctccttgggc agcaagaagg gggtgaacct ccccggagct  15360
gctgtggatc tccctgctgt gtcagaaaag gacattcagg acctgaagtt tggagtggag  15420
```

-continued

```
cagggtgtag acatggtgtt tgcctctttc atccgcaagg cagaagatgt gcatgaggtt  15480
aggaaggtcc tgggagagaa gggccagaac atcaagatca tcagcaaaat cgagaaccat  15540
gaaggcgtcc gcaggtgagt cctgtggccc cttttcatgg tccagccatg gttatgagtc  15600
ctggatccct gcccagcaag tgcagcctgc caagcctggt ttccgtggat gtagcattgt  15660
agtcttcact tggaaaacaa tgattctgat gagtggtcca tttagctcac cataggaaag  15720
aaagcatatg aagcttcgtt aagttggtgt tcataagaat gaggcaaagc agggtgactc  15780
gtttgacgtc tgttctatgt tgataagcca taggtgctat tggaccttgg tgttacgtca  15840
gccctgtagg cactctgggc gggacacctc acctcaaggg tcagcactca gaatcattag  15900
ctaagtgaag ccatgcgcac cttctggcct cactcttgct ttgttggaag cgccaattag  15960
agaagtaaga tacaagaggc tataagagca agacggaaga gaagtcagcc cacgcaacta  16020
aatctcatcc ccctcatctt tcaatgaagt agtcatggtg gtattgaaga agcccagcaa  16080
gcaagattgc tcggttgctt ggatgctttg ttttgttctt tgcttcctat tgaatatcat  16140
ctttctcttc tgaatcaggt ttgatgagat tttggaggcc agtgatggga tcatggtggc  16200
tcgtggtgac ctgggcattg agattcctgc agagaaggtc ttcttggctc agaagatgat  16260
gattggacga tgcaaccgag ctgggaagcc tgtcatctgt gctactcagg catgtactgt  16320
gtactctgtt taggagctgc ccatgtactg tgtactctgt ttaggagaac tttgggtctt  16380
gtcccatggt ccctgttgta cagacatgtt aacctataca tagctgtcct ctggtcctac  16440
aaaatatcca gggagtcatc ttagcaactg cttgtcactg aacgtggccc atagtctcac  16500
acaggtctca ctgaatgctc atctgtcccc tcttagatgc tggagagcat gatcaagaaa  16560
cctcgcccca cccgtgctga gagcagtgat gtggccaatg cagtcctaga tggagctgac  16620
tgcatcatgc tgtcaggaga aacagccaag gggactacc ctctggaagc tgtccgcatg  16680
cagcatctgg tatgttcttc cgagcatggg gtggaaacaa gctctgccac agaggcttct  16740
gcatcctcta catggtctct tcccattctc ctgttgtagt aacagtggcg tagtgtgaaa  16800
gagtgcttct ttattttttt ttttccctgt ggtgctttca ctgcctctac cccagccctc  16860
tttctcctac cctggaggtt gccactttca ttacataggc cacatttgat aaaagattta  16920
agtcatagga tgcagtcaaa ggatgcctta gacctccccc tggacagtcc agaagacctg  16980
gtacctctgc tctattctaa aagagccaag agtttgttcc cagctggtct ttttggtgtt  17040
tggcttccaa tttgatgccc tactagtccc taggacagat gcttgtaccc acactgagct  17100
gttttgagct ggccttgcat ggtgcctgtg tcctgggact gcctcccttg ctgtgccaca  17160
cccaaaccag ggctacaaat agagctgggg gtggagggag agtgttaaac tcagcaggcc  17220
ctgggccagg aatatagagg aactgtgaag actttttctct gggaatatgt tctttaagac  17280
ttctaacttt ggtcagatat ggtgatgagt catgcctgaa gtccagtatt cagaggatgg  17340
ggcaggagga tagctaagag tttgaggcta ggcaggatta caataagact ctatcttata  17400
gggacaatag actccaagca gcaacgtctt ctgctgctta cggatgagga cccagttcat  17460
gagccctgtg ttttgccctg gaacttactg agcttttact tttgactgat gaaagagtat  17520
tagaaattaa cttcttgagc ttttctattc cattttcagc cagcaaagga cccctgtcct  17580
ttttagcccc agtccccaaa tttaagccaa ctgaaaaaag aaagaatagc ccccctctgg  17640
attagtcgtc attcctttct tcccttcatc tgtctgatta ttgagtttgc aaaaattcca  17700
aggtgaactg tattctggct gtgtgaaatt ttctgtggcc ttattatttg tgcctcctat  17760
attgaaactg tcagacaagc cctgttgctg ttctggttgg taatgtgggc tctcatagct  17820
```

gcccatggca ggtagttgct ttttctccca gaaagccatg tgccttcagt caccttcaca 17880
gttgctgcct ttccactttt ataccacata gcccttatct agttacctgc ttagttgtgt 17940
catctggcca cagcgtggtc aggaacaggt taagggcatc tttgaccggg tattctgaac 18000
catgtatcca catagatgta tgtatagctg ggggcaagtt atatgacctc aagaccttgc 18060
cctaagatgg gtttgatgag atattaatta tagccttagc attaaacatt tactgccgtc 18120
attaaatttt agataagcct ctaaacacat tggtgtaatc ttcgtgaccc caatctgtga 18180
atgagtcaca tgatgtgata aatgtgggtt tgagcccagg tttgctttct gtagtgcctg 18240
ccaccggccc atttgcatta tgctggaaca gcagatgtgg acaggtctcc atgtcctact 18300
tccatgccct gttctttcct atggtcagac accttagaac ctcgaggctt gggactgcat 18360
ggcgctgctc agaagatgag gcacagagtc taggttaaac tggctgcctc tccagggggt 18420
acaagccttt ccctctgtta acacctcagc ttctcccctt acctgtcggc tgtttcctcc 18480
cttgtctaac tgatgcagtt catgacctgg aatttagagc taggcaccct agctatggtt 18540
gttggtcctt tgcactgcat gcattccatt cttaacaaaa ggaatacttt tctgcttgtg 18600
aacctgctta tactgtcaaa ttagtgaaat gatttgctgg ttccttctca tccttcccat 18660
actaagatgc cggtgattat ggcattctaa ttttctgaaa cttaaaattt cctttctgat 18720
gcctggtctt acctgaacag gtgtgtctgt aatgtaacac acttgctatc ttgcaacggt 18780
tttaattgct aagttttaat cagtattttg acgtgcatgc atgctttcac gggcatcatt 18840
ctcttcacat ggttgttaag tgagccagag ttttcactat tttctttaga actggtatgc 18900
tgtgggactt tggctctttt gaccccagct ttccagagct gcctcaatgt ttccactgta 18960
aacactgggc tgtgtctatg taagctgggc tggaagccct gttgtagtca gacagccatg 19020
tgaagaggga agggcctatt ctattccttc ctgtaagctg tgttgtgagg cattgtggtc 19080
agatggaagt gatttggcat ccttccatgt caaggtccta gggcctaaca ctttgtccct 19140
ttcttagctt cgatttaaag aaaaagggaa acaaatttat agccagatat tgatggtaca 19200
tgcccattat cccaaagaat tactttgagg gcaatggggg caagttcaca cccagtaagg 19260
gccattatgt aagatcttat ctaaaaaact caaatggggg caggggggag gataaaaaaa 19320
aaataaattg gagggggaaa tcacaagtgg gtaaataaag tctttccaga aaggaaaaaa 19380
ctttccttgt attagaacca aaaaagagca cgtggacttt gaccaccctg cctctgtctc 19440
tgcccaaagg acagatttaa ctgtaccttc ctctctgatt aatcccctct gtcttcccat 19500
gtgttgtctc tcctgttttt tccttcatcc cttctaccct aacccttaca gatagctcgg 19560
gaggctgagg cagccatgtt ccaccgtctg cagtttgaag aacttgtgcg agcctccagt 19620
cactccacag accccatgga ggccatggcc atgggcagcg tggaggcgtc ctataaatgt 19680
ttagcagcag ctttgatagt tctgacgaca tctggcaggt agggccctga gggcaggtat 19740
cgctatagga taaccacttc ttacttcaga aaaaaaaagc cttgtgcctg agcttgggca 19800
cagcttctct ccttcattca ggaaggtagc caaggaggtc atgatagggc aggaccagag 19860
tactccctca tgggcacagt ggaagtcaca ggcaccagtg aggatggttt ctgtggagtt 19920
tttgattttg ctcaatttag aacagttcag tgactgttcc tcctggacct ttttttgccc 19980
aggacatctt cccagttgtc tgtgactcat cctccctctc catttgtgac aaagctctga 20040
caaagccctg tccccccctcc cttcgtccct ctggacggat attgctcccc tagattgccc 20100
gtgaggcaga ggccgccatc taccacttgc agttatttga ggagcttcgc cgtctggcac 20160

-continued

```
ctattaccaa cgaccccaca gaagctgccg ccgtaggtgc cgtggaggcc tctttcaagt  20220
gttgcagtgg ggccattatc gtcctcacca aatctggcag gtaggaggcg gcagtggctc  20280
cctggggatg cccacctcaa ttggcagccc tccttaggga tcccaagagt ggctctgggc  20340
caagttttgc tgccactaaa ggactccagg caccactcac aggtatacca aacaaaccat  20400
gtggttccaa taaagttcag cttgcctcac aatgggaagc aaatacccag ttttgcctag  20460
tttagctacc atgtggtctt gaaaaaggga gcaagctgac tcctgatctc acatgcatgt  20520
cagcagatac actaatagtg ataagcactt taaaattcca cttggactgg gtggtggtag  20580
cgcacatgcc tttactccta gcacttggga ggcaggcagg tggatatcca tgagtttgag  20640
gccagcctag tctacagaga gagttccaga acaggctcca aagctacaca gagaaaccct  20700
gtctcaaaaa taaataagta aataagtaaa taaataaata ttgtgcttgg aggggttgga  20760
gataacatct cagtgagtaa agtatttgtt gcacaaacat gagggtccga attggaatcc  20820
agcacctatg gtaagaatgc atgcagacag gacagtactc ggggcttccc atcaagccag  20880
tcgagtttca gactccataa gagatcctgt ctcaaaaaat tagatgagtg tcttggcctc  20940
tgaggtccct ggcttacaaa ggctcacaac tgtctgtcta gtcctagagg aatccaatgc  21000
ccccttctaa ctccccacag gcagtacatg tatgtggtgc acaaatgcac ttatggaaaa  21060
tacccttaca cataagtaaa aacatccaga tgtgatagcc catatctgta atcccagcac  21120
tcatgaggca gaggaagaaa ggtgggctac agctttgctc ttaggagctc taagatataa  21180
gatcaatgca gggcttttgc ctcagcctct gcactttggc gaggagttcc tgattacagc  21240
aactacccac ttcaaggcct tgtgaatgca ggccagcatg aagaagggta gtctctgctg  21300
tgttttttct ggtttccaca gtacttgtgt gttttcagag cttgttcagt taattcagca  21360
aacctgagac acacctgcta gaagtagaca ttatcacttg tcacaggtag ttttgagaag  21420
ggggggtcac tacattccca aaggttctag atgggctaag cattgctata taatgcctgg  21480
tcactgtccg gattttgtgg caccaagtgt gttttgggct ctagagttag gcttctggga  21540
ctgccatggg aacagcatac tactgcagtc cttaatattg ttggctccca ggagctaggt  21600
gtatgctgct tggttgcaaa tgttgctagc agttgtggat gctggtgaga ttggccaaag  21660
ctgtctccct gctacatgga agggttcatg atatgggagg gattctagcc atgggccctg  21720
agggactgct gctcctattg aaggagcagt taagaaagga cagaggacag gatgtggggg  21780
gtggccagtc cttggaacag agtaagctct cagtgggcaa ggcctgtgcc tcacttgtgt  21840
tagtgagctc ctgctgaagg tgcttcctgt ctcctgggtc ttgtgacacg tttcatagtc  21900
tatcctattt cccatctcag gagtgctcac caggtggcca ggtaccgccc acgtgctccc  21960
atcattgctg tgactcgaaa tccccagaca gctcgtcagg cccatctgta ccgtggcatc  22020
ttccctgtgc tgtgtaagga tgcggtacag gatgcctggg ctgaggatgt agacctccgt  22080
gtgaatttgg ccatgaatgt tggtatgtag ctggaagcaa gaagatgggg tgctgagcaa  22140
tggcttttct gggaattctg aaactgtcat tctctgaaga cttgggctaa gcctttttgt  22200
ccacaccctc ccaatttggg gcccaaggca aaattaaggt gggacacaca gattatgtac  22260
tgctgctata gcctttgttc ctctataagg ttggacattg gggtgggagg aggccgctgg  22320
ctctgtgatc tccaaaggtc cctacagtct tgagttcagc cattgtttgg tctaggaggc  22380
ttgcaccacc ttgtggtaga aagaagaatt ggttcaggca gactggtccc cttatcatag  22440
gcaatgggat tgtaggtagc tctttgggca tttgccctgg aatgcccatg cctgggtggc  22500
ctctgggcta ggagggaagt gccaccttgt ggtaggagag agtaatggtt gttcaatttg  22560
```

gggcagttac cccaagtgtt tacttctatt cacaaccttt ctattctttc aggcaaggcc 22620
cgaggcttct tcaagacggg ggatgtggtc attgtactga ctgggtggcg ccctggctct 22680
ggctacacca acaccatgcg tgtcgtgcct gtgccttgat ggccctctgg agcccctctt 22740
ctagcccctg tcccatcccc tcccccatgc catccattag gccagcaacg cttgtagtgc 22800
tcactctggg ccatactgtg gcgctggtgg gctgggacac ccaggaaaat ttactggctt 22860
tgaaatatgg actagagccc agctgtctca tggccctacc caagctaggg atgaaggagg 22920
aatgcagaat tgtaaaccct ctgcctttat cacaaaaggg 22960

<210> SEQ ID NO 45
<211> LENGTH: 32596
<212> TYPE: DNA
<213> ORGANISM: Homo sapiens

<400> SEQUENCE: 45
aacccataaa tctgggccct gcccaggtag gccgggacag ctggggtggc ctgggccgag 60
agccaagaaa agacacccca tctggcagcc caacttggcg gcaacaggtg gcccggcgcc 120
cgggggtctg ggaggaaagt cgctccgggg gcgggccccg ttgccccgcc gcgtccccat 180
tggtcatcag gtttcttaaa atgtgactct gaatctgtgt ccttccgccg cagaatttag 240
tcccaccgaa agggcaacct gcccgcgcgt tccgccgccg ccgccgcgct tcctcctgaa 300
ggtgactgcg cccgcgggga cgcagggggc ggggcccggg tcgcccggag ccgggattgg 360
gcagagggcg gggcggcgga gggattgcgg cggcccgcag cgggataacc ttgaggctga 420
ggcagtggct ccttgcacag cagctgcacg cgccgtggct ccggatctct tcgtctttgc 480
agcgtagccc gagtcggtca gcgccggagg tgagcggtgc aggaggctac gccatcagtc 540
cccaccaagg gccagtcgcc cggctagtgc ggaatcccgg cgcgccggcc ggccccgggc 600
acgcaggcag ggcggcgcag gatccagggc gtctgggatg cagtggagct cagagagagg 660
agaacggctc ctcacgcctg gggcctgctc ttcagaagtc cccagcgccg ttccttccag 720
atcaggcggg tccgccggct cctttcccgc cccagcccta ccccctcatt ctggtcccat 780
cctcttcctc ctgccccaat cctcaatgcg cctccatcct cgcctgcctt ctctcggtcc 840
ctcgtgattg attccaccct tgcttcccct ttctccgcgc cgcctgttcc gtgctcgttt 900
tcccctcttc ctccttaagt ctggtccttc cacccctcc tcttcaagct gtgcgtgtcc 960
cctgattcta atgctttctg tgtaactcat tgaaactgcg ttctggttcc cctcccgcgt 1020
ccattctcca ttcatgcgcg accgcccttc ccgcgcccca gttccctctc gccgcccctc 1080
cccctgcttg ctggtcacgt ccgctccccc gcatcccctt cctcgcctgg cgtgtccgct 1140
ccctccctcc ctctctgctc tggtcgcgcc cgcccacttg ctccggtctc cgagcgcggt 1200
cccacccccc ttttccatca ccgcctccca gctcccagca ggctcgggcg gtgctgaggc 1260
cccgtgtccg gggcgggcgg gcggagggct gggctgggtg ccccgcgcgg cgggcgggat 1320
gcggcggccc gggggcagct ggagacttac gtaacgttgg cctgccccgc tgccgggagg 1380
cagggcggtt gcccctgcgg cgcggtgccg tcccctgtgg ccgggattag atgggcggcc 1440
tgcgagggcc tgggaatggc tcggggcccg agagctcgac cggcccttgc cgggtggccg 1500
ccagggacca cgctccatct cgccgcggcc gggctgcacg tagcggccgc gcccagggcc 1560 cacccccgctt caccgggcga tggccttggg cctcgtaacg ggcgggataa acctctgcag 1620
gctttgctgg ggcctcctgg ccctcgcccg ttccgcgcct ctccggcacg tttctttctt 1680

```
ttcctttctt ttttctttct tttttttttt tttaattatc cggcacattt tttaacaaat   1740
gcgtcctgat tgtggaacgc ggaggccgcg gggtggggtg gggatctggt tacggagggg   1800
gcaggaaatc tgtcgcgttc actgaacgca aacggtgtgg gtcaagggct gtttgggggt   1860
cagagttaga gaccaggatg actagacgag tcatagccca ccgagctcac aatcttaaaa   1920
tgtatctcct gtaatgctgg gagtggggta cgagcttcct gctgtgggag ggagggggac   1980
aggaagcctc gtaaggtctc accaggtggc aagcacactg gattagaaga tgcaggaaag   2040
caccttccag tctgaagatc atttaaagac tcagtcatgt aagggcatcc cttggcttct   2100
taatctacgt actccagacc cagggcttgg acctttgctg gtacgggtta aagtgaggcc   2160
gacagtgaag gtccacgtgg agagagacat tgggaagttg tcaaaaaggc gtttagaatc   2220
aggtttgact cattaatttc ctgagactct gaaggagttc agcctctaca cctcagtttc   2280
ccctgggaaa actgggagta acattttcct catgatggtt gaaaggattc atgcttacgt   2340
ggatgtggca cactcagtaa gtgtctaatc tctggcgaaa tacccagaag aaaagcctgt   2400
gactgaatat attattttg agcacaatta cttagtccac aattgagcat aagggccttg   2460
atccattgtc ttcctactgt ccccaaacgc ctacagctaa tcgtgaggaa tcaggctctc   2520
tgaataacca cgtgtctcct ggaaaccagt tccccaaggg atctggttta atattgacaa   2580
agtaactgat aatgtaactt tccaactctc tgcttggagc agatgctttt tggtcatctg   2640
agattgggac ctgtagacaa aggcaggcaa ggaggggctg agttaagcct ttggtgttcc   2700
gctgtaagta gaatactacc taccagagga acattccagc ccttgacttg ctctgcctgc   2760
tggtgagatt aggattggag ccagggtcag tagcccccag ttggccgtct tgagggtgtg   2820
gccactccct aggtcacaga ggagatggag gtcaggactc ccctgctgca gcgttgttag   2880
caaataattt gccctttggt ggcctgaggt gctgtggggg caggagtggg ctgtcttgtg   2940
gggaagggaa atgtaacgta tcaccaaatc tgtgggggag tggggctctg tggggaagat   3000
gactcaacct ttcaattatt ctgcttttga gagaattatc ttcgctgggt gagtggggaa   3060
actacattgt ggttcttgca ggcttaaaaa gtcccttctc ccctttcagt gagtcagata   3120
atgaagcatg catttcccct aattaaaaat gcctcaacta cggagcttgc agtgagccga   3180
gatcgcgcca ctgcactcca gcctgggcga cagagcgaga ctccttctca aaaaaaaaaa   3240
aaaaaaaagc cacaactaat taaaaaatga ttggtccggg tcacctggtt ctctgtactg   3300
ccttaagagc ttaagtgtag actggcagag cccggtgccc agctaatgcc gtctgtgcag   3360
cttcattcct ggcccttttg tagcgggcac agccgcctct cctgggactt gattaatgat   3420
gacttaaaga aggttcttga actcatttct cagttactga cttgagccaa aatgtatgga   3480
tgttggtctc ctgtctagca caactgcttt cattttaagc attgcattag aaataatgtt   3540
gtattcatat tttagcaaag agcatcatta gctctttaag aaccgtaccc ccagtgactt   3600
agcaaatttg gtggcggtga ctctaaacag ctagcacttt atgggagttg cttctgtgcc   3660
ttgaatgttg tgacactgat gtggggtcac aggaaaaacc attttatttc ctaaagctgt   3720
ttatttctta atattgaggc aatggaagaa atgaggaaac ggccgtgggc aggaaggtag   3780
aagaaaatgc agcacttaca ttacaaactc actttacttg ggttttagtt tattttgctt   3840
cagtttttg ttttttttt tttttttt ttttttttt gagatagttt tgctcttgtt   3900
gcccagtctg gagtgcaatg gtgtgatctc ggctcactgc aacctccacc tcctgggttc   3960
aagcaattct cctgcctcag cctcccgaag tagctggaat tacaggcact tgcaccacgc   4020
ccagctaata tttttgtatt tttagtagag atggggtttc accatgttgg ccaggctggt   4080
```

-continued cttgaactcc tgacttaggt gatccaccgg cctcggcctc ccaaagtgcc gggattacgg 4140
gcgtgagcca ctgcacctgg cctgcttcag cttttatgaa ggcaagtcag gatgtgttat 4200
cttggccaag agctaagact gagaccggag tagaggaaaa tgactcattt gacattaccc 4260
ttctttctga atcactccaa aagtccacag tcaaatctca attagctggt ataacacaag 4320
aatgcgttga ccctgtgagc agagttttat tgcatcttca agggtcttcg tgagattggt 4380
ttatttggta tgaggtctta aggattttaa gttgtccctt taagcatcag ttctgataca 4440
gatgggaata gagctaaaca accagatata tgaagaccat ttttgatacc accatacttg 4500
cggggagctt gcattttttt accaaggggc agactggata attgagtaat ttaaatactt 4560
gggactttgt taaagaagct gttgggggaa ggtgagcctg ggtgagtggt ggagggtgat 4620
gtgcagcatc tgctgggcct tcctgcctct tggtatgact gctcagctca ggagttgggt 4680
gctttagggc ccctaccatg cagtgcggtg aagccccgcc cctgcagtgg tttgtgcttg 4740
tctgcacgta ggagggaaca agccggctgc agtaccttcg gtggcctctg agactcacct 4800
cccccacttc tgtccataga caaagctcct ggggagccct aagcctcttt cctcatgcca 4860
gcaagcagtc ttggaagcag gctggggctg cagtgggaga gatgccaaga ccagttattc 4920
aagggcagtg aggttgccag tcctagcatt tcacactgtg gaccagcaca gctgctggct 4980
gaatactgca gtcaagattc tctgaaggga gtcctatccc ttccaaacat cttcagttta 5040
cttgcagata atgtttcttc atttttttatt ttattttatt ttatttttatt tttttgagac 5100 ggagtctcgc accatgaccc aggctggagt gcagtggtgc aatctcagct cactgcaagc 5160
tccgcctccc gggttcatgc cattctcctg cctcagcctc ctgagtagct gggactacag 5220
gcaaccgcaa ccacgcctgg ctgatttttt ttgtattttt tagtagagac ggggtttcac 5280
tgtgttagcc aggatggtct cagtctgctg acctcgtgat ccacctgtct tggcctccca 5340
aagtgctggg attacaggca tcagccaccg cgcctggcca tgtttcttca attttaaaca 5400
actgatatct cccttggcca tgaacgaaaa agaactgccc atcagtggag tcagtcaggg 5460
cacataagac acactgtgtc caccatgcca tttcagagga gatttgattg agttaagcag 5520
ggaaatagag atgttgtaaa cgttgaaact atctgggtat ccctctttgg ttattaacat 5580
tagatgagca gaaaaacaaa tgtcaccgat gggcaaacat ttaaaaagtc tggcagtacc 5640
aagtgtggaa aaaggtgtgg aaggcagcaa ctcagcgttc attgatatag ccactttgga 5700
gagcaattca gccttattta gtaaaaatag aaataaacat actccatgac ctaagacttc 5760
aatttctgga tatatagaaa ctcacacagt acagggagac atgtactaca agagtattga 5820
ttaatagaag aaacttagtt taacggggag ggagagtggc caccagtaag acagtccata 5880
aataaaatgg tctgttgtac agtggactag tgtaacagct taaatgaatt agctagatcc 5940
atatacccac tggatggatc ttaaatgtgc tgctgagtga aaaacaagtt actcagtgat 6000
atatacagta taccacttag ggcattaaga aaaccacaat attatagggt tcagtataga 6060
catagataca ctgtacatag acttcagtga actggaagga tatagagttc atgacagtga 6120
ttgggtgtca aaatgcatga tgtggctggg agcagtggct cacacctgta atcccagcac 6180
tttgagaggc tgatgcagga ggatcacttg aggccaggag gtcgagacca gcctgggcaa 6240
catcgcaaga ttcccatctc tatttaaata aataaaatag aaaaaaaagt ttaagatgga 6300
ggtggaaagg gttggaggag cttggggatg gagaaaaaat gaactgtata aaattaaaat 6360
tcttgttttt gtttttagaa agtaaagagg gccgggcaca gtggctcatg cctgtaatcc 6420

```
cagcactttg ggaagctgag gtgggcggat cacgaggtca ggagattgag accatcctgg   6480
ctaacacggt gaaaccccgt ctgtactaaa aatacaaaaa aaaaaaaaaa aaaaaattag   6540
ccgggcctgg tggcgggcgc ctgtagtccc agctactcag gaggctgagg caggagaatg   6600
gcctgaacct gggaggtgga gcttgcagtg agctgagatc gcgccagtgc actccagcct   6660
gggcaacaga gcgagactcc atctcaaaaa aaaaaaaaaa aagaaaaaag aaattaaaga   6720
aaatacagct cagcctttat ttgtgttttt tttttttcc tttttttctg agacagagtt   6780
tttcactctg ttgcccgggc tggagggcag tggtgcgatc tccgttcact gcagcctcca   6840
cttcctggat tcaagcaatt ctgtgtctca gccacccaag tagctgggat tacaggtgcg   6900
cgcctggcta atttttgtat gtttagtagt gatggtgttt caccatatta gccaggctgg   6960
tctcgaactc ttagcctcaa gtgatctgcc cgcctcagcc tttcaaactg ttgggattac   7020
aggcgtgagc caacacagcc agccatggct cagtgttaat ggtcagttct gggtggtaga   7080
gaggcagatg ttaaaacttt tttttcttta attcgtaaca tagaagcaaa cctataaagg   7140
ctgccgtagg aagaccagtc atagtaacta gttcagtgct cttggagagt tggcactgcc   7200
tttcctcctt tatccccccg actagaatgc agggcagccc ttccagtaaa tgttgagcca   7260
gtgcctcact ttgctgaggc catcacccac cttagttgca cttaagagga ccctaaatca   7320
gggtcccagg tcccttgctg attttagagt gtggatatca tacccagaaa caccgcccta   7380
cttttaatcc tagtaaggag gcaccatgtc ccaggacaac taatgcttcc cccaaaccac   7440
ctccttcagg ctgaaaccag ttctctgcac tgagcagctg ggatggaacc aggaaatcct   7500
cggcatctga ggacattgag ggtctctga cttagggctt cttcacctga agttgagtgg   7560
tctttgaggg aagtaggccc atttagcatc agctgctctt ccctattcca cactctagtt   7620
ggaaatagga ccttaggttc ctgttgacaa gtcatttact ttcagccccg aagaaataaa   7680
agagccaaga tttttttttt ttttttaaag ccagggaatt ttactagaac ctacaagtgg   7740
gctcattttg ttctgtgtag cctggtaaca ccatactgct ttctgctgtg gggcctcctg   7800
gggttaaagt gtgggcttaa gacccaggtc tcttagctag aagatatctt atcctctgta   7860
tcctgcaccc atatgcaaat acattattgt cattaccctt aactatagat gaagatgaac   7920
agtgcctatt ccagacctta ctaggttctg ctggcccgtc acccattttg atcatgttgc   7980
tggcctagtt tgattagggc aaatcttaga aactccattt ccattgttga ggaagagaac   8040
tagagagcag gctgacctga atgccagcgt atcatgatgc agactttcta acggatgcag   8100
gtgttcggaa gagttgtgga tcgaaacgcc ttcatgatgg cttggaggtg taggtagcaa   8160
actgacgtca caggaaggaa cacaatcttg ggtacctact ggcaacgttg gagggagaaa   8220
gtgagcatca ggtgccatca ttttatagtt gatctatgtg atgaggttgg tatcggagca   8280
taattggtac aaaggaaaaa tgacttaggc agatgcagac tcacgggcca ggctatttta   8340
ttagggcaga atgatttggt cctttgtgga agaattggtg gagtgaagcg tgaatctttc   8400
ccagcacaac ccaacaacag tcctggccct aagaagtgga gcatgggagt tgggtgtggt   8460
tcgtgcctgt agtcccagct acttgggatg ctgaggctgg aggatcgttt gagggtgcag   8520
tgagctataa tataatataa tcacaccact gcactccagc ctgggtgaca gagtgaaacc   8580
ctgtctgaaa aaaaaaaaaa agaaaaaaaa aaagttggag ggaggagtgt tgggtatttt   8640
ttatgatttt tgtctcctgg tttctgaaga atggccaaaa aattgtgtct gacacaaagg   8700
aaactaatat aaaaagccag gagctgtctg agatgagaaa ggaaagggag aatagggcac   8760
ttggagctga gctgtgattg tgcctgttcc aacctgtcac tccagactaa ggcctcttag   8820
```

agatggtgtc tcctttctca cagaggagac atggctctga ggaagatctt actgcagggg 8880
ctcgggctca agaataaggc tcctggacct gggcatggtg tgtgctgcta tcagtggata 8940
cgccaggctt ccactgctgg ctggaggttg gctctgcatg tctgtgcctt cctaggagga 9000
ggatgcaata gtgagtcaga ctggcatggg tggggccaca tgtcctggca ggcactgtcc 9060
aggcagctgg catgagggag aggagtcttt cccagaagtc cgccctgaga aaccaaggct 9120
gggctgctct cctggagcca ggggagtcca gtgagtgttt tacatacaac tctaggtacg 9180
tggttggtgg gatgggcagt ttgtgctggg aagaggcttg tggaggattt tggagaaggc 9240
aggagagctc tggccctccc tgcaagggag gcttcaggtc agagcctgag gaaagacctg 9300
ggcatgagat atgaggtctc tggctgggta gagagcatga aggacacatg agatctggag 9360
tctggatgaa cttgctgaca agcaagcttt ttttgactgc taatgcgtaa atccactata 9420
gaaattttca tttgtcattt ttgtacttat tggcaaaaaa ttagagctta taggcatcag 9480
atttaatttg agatagttga aatagggttt gtgtttgagg ccaatataat tttatctgct 9540
aatggcatct cgtggacttg gaggcagccc ttctgtacca gaacattgtc aaaagctttt 9600
actgtaaagc ttgagaacaa actagtttgc tggatttggg catgtaacta acaggtttga 9660
ggcatgggat tatcctgtgg actttttttt tttttttttt gctttgaggt tctgaatgta 9720
ttaaggttga ccttcttaag ccgttgaaac tgttctgcag tacatttgtg atgtagggcc 9780
taagacttgt atcgtttttt tttttaatc acaacccagt gtacagaact tgagacatgc 9840
gtcttttctc tgccaccttt taaaagcaga ttattcttga agtgcataga gcagcaattg 9900
attaatggaa ttggtgtctt cacatttcat ttacttcctc ccaacaattt tataggatgc 9960
atataaatat ttccaaaaga ggtacacata atttcttact ataaaagtat ttttatattt 10020
atatcagtaa atttgttaat aaagaggatt ttttttttc tgtaatccta ccaccccaat 10080
gacgtcctat taaaatttca gtatatatcc tcccaggtct tttaggtatg tttaatttgg 10140
tgtcccttcc ccgctcccaa aaggggaggg accaggttct tgtatagaat agtggaatgt 10200
tagtaaatca caggtttaaa gagacataac agtggaatct ctagagcagc tgtcacctgg 10260
atacctggtt attaaggtaa tttttccatt accccaaaga gctttagtta cactcagctt 10320
tttccttaat ccttgtgcag ctctccaggg cacaccgtat tcagctctga gcggtctttg 10380
ctagtgaggc caaggagcca ccctgagcca aaaggggagc attatgtcac cggaagccca 10440
accccagaga accaaaggta tgacctgata ttcagtggcc ccagccaggt ctttacagga 10500
agaccctcat atctcaggtc taagaagagc cagctgatgg tttttaaaaa gagtggaatt 10560
agttactcca acccacttat tcagatctta ttttgttcac aatacagtcc ctagattgta 10620
ggcccattgg aggccacagc aaagcctttg tgttccagtt ggcctgatgt gccatctctc 10680
agtaatgttc ccttaacagc cagacttccc taagcccagc tgggagctct gaaggtatgc 10740
gagccctccc tcaaccatga gtgtagggaa agggaccagg ggccccaggc tttcctgtca 10800
gtaatgcaga agttcctcag atttagggaa gggggagcag aggcataact ttgattctga 10860
caaagaggca ttcagagaga ctgaaaggtc atttaacaaa cactggaatg cttccacata 10920
ctaggtgcta ggagatacaa aaccatatag gtcctggaag ggaggattga ttttttcatt 10980
ttggtacgta gtagatatta ggggcttagg aaatacacat cgaaatgaag agtgcatttg 11040
ccatgttgaa ccgttagccg gtatcttatt tccccatttt aaaagtttta gaatctgtgg 11100
ttgaggactt gtggccatca gttttccata gccaacagac tgttcactac tgccttcaga 11160

-continued gctccttgga cctcagcggg ccttctttgg agatggcaga gatggattta gatgtatact 11220
ctactcgagc cacccagaga gcccacaaag tcagagatgg aacagggtaa aggagtaagg 11280
gtcatatgtg tgagatgcct tgatttggaa ctttgagatt taggatgagg tggggaaggg 11340
ctaaagagga gcttgttcct gagccttgct tggccgaagc atttaggctc aagcgtttta 11400
gaaagagtag cccttggtct gagaactcaa ggaaacagct ttctgatgag acgtgtagca 11460
agcttctggt tcacatcctt acctgatagt tcttcaaaca ctgcctggtc tggttcacat 11520
ccttacctga tagttattca aacactgcct ggaagcttct cctgagtttt tgtctctaat 11580
cagctaacta acaggctgag tgagtttagt tgtaagtcat taatgaagaa agcaaaggtt 11640
ggggccattg tcagggttgt gacctgggct agttaattac ctggaactga tggtctgtgt 11700
tacagagtgg tggtatactt gtcaggctta gaaaagaaat caggatgtgt atcaaaaatc 11760
atttggggaa aagatttgac cagcaacttt aatttctcta tgtttgcaac tatcctgtta 11820
atgtagttgt gataatttca gaattatacc agtgccctta tgttatcctt gctttgcaaa 11880
ttgcaaattg ctttgcgtgt cctgacatcc ttctggccaa cagtagatgt ggttttaggt 11940
ttagactcct gggatggaag cttttgcatt caggggaatg actttgggtt tgggtgagga 12000
ttgtaaagag gcaatatggg tgccccacga caaagcagct atttgtagct ttgtgacagc 12060
ttgacatgca gagatctagg cttatcaagg cactaagcta ggagtcagtt gtttgtatca 12120
ctggaagatt ggttacaact tccttcattg gaagctcctt cagtgcatgt taaatgatgt 12180
tatttataga tagggtggtg agaaagctgt ctaggtagat gtcagtcagc ccagtgtaag 12240
agagacctgc ttactgtggg tgcttgggac tatgtggagt gggtgggagg ttttaacttg 12300
ttcagtaagg tcctttccat tgttcacaat ctggtgaacc ctttttctaa catgaggagc 12360
acccacataa ccagatcatg tctggcttcc ctgtggcttg tgtacaaagc gtgcttattg 12420
agttaatgtg taagcaggag acagccttct gtgctaaatg gtatattaac cacttctcag 12480
tcttaccact ctctttcaat ttgtctcgac ccaggacctc agcagccatg tcgaagcccc 12540
atagtgaagc cgggactgcc ttcattcaga cccagcagct gcacgcagcc atggctgaca 12600
cattcctgga gcacatgtgc cgcctggaca ttgattcacc acccatcaca gcccggaaca 12660
ctggcatcat ctgtaccatt ggtgagtggg tgtgcccctt cccccaaaaa agggcttcat 12720
gggcagtgac ctttctctcc tgaaaagagt aactaaatgt cctaacaaac ctaggtgcta 12780
catgggatac tacacagatt cttatgaaag gactcaggtc ataggaagtt gcagtaaaga 12840
attagtatgt gcataggatg gcaaatacag ttaataagag agtattagac atttcaaaat 12900
tgctaagatg gcgaggtatg gtggctccca gcactttggg aggccaacgt gggaggattg 12960
cctgagcctc gaaatttgag accagcctga gcaacttaga ccctgtctct ccaaaaagtg 13020
aaaaaaaaaa aaaaaaaatt agctgggcat ggtggcatgc acctgtagtt ctggctacat 13080
gggaggctga gacaaagatc acttgagtcc aggagattga agttgcagtg agccatgatc 13140
acaccactgc actccagtct aggcaacaga gcgagatcct gtcttaagaa aaaaaaattg 13200
tccgggcgca gtggcacatg cctgtaatcc agcacttcgg gaggctgagg caggtggatc 13260
acctgaggtc aggagttcga gaccagcctg gccaacatgg tgaaatccca tctctactaa 13320
aaatacaaaa aaattagccg gggtggtggg cgggtaccta taatcccagc tacttgggag 13380
gctgaggcag gagaattgct tgaacctggg aggcggaggt tgcagtgagc tgagatctga 13440
ccattgcact ccagccttgg caacaagaac gaaactctgc ctcaaaaaaa aaaggaagaa 13500
aaaagaaaaa aacatcgcta agagtaaatt tcaaatgttc tcaccacaaa aatgttaagt 13560
atttgaagtc atggatatgt taactaacct gatttaatta ttccacattg tatccaaact 13620
gtatgtattg gattacataa ctttgtaacc caaattataa attaccagtt tataataaaa 13680
aataatttgt tgcaaaaaga atccatatgg tttaggtttt atgctatagg caaaatttag 13740
aagatgtttt ccttagcagg tctttgtagg agcaacttaa agacctagga aagatctttc 13800
taacatgttc tgtgctacca agattctgtg gttggacatc tggctgggtt tcagtgaggg 13860
tggagaaggc tggccaagtc ttaacctagg cttttctgat acagtgggag cctgcagaac 13920
ttgaaggaaa tggtcgaagt gtcccagtag atcaagaaag taagctggca cggtagtagc 13980
cttccatgca ctttttaaag acttttgagc tatttgggag aggaaaagtt ttcagggaaa 14040
aaaattcttt aaacttaagc aaacttaaat gtttttcctt ctttgaataa ttaatacttg 14100
tggctttaaa actttttccta ataggcccag cttcccgatc agtggagacg ttgaaggaga 14160
tgattaagtc tggaatgaat gtggctcgtc tgaacttctc tcatggaact catgaggtga 14220
gctgtggctg gaccctatgg ccattgtgat ggcctgtagg aaacagggag ggggtgcagt 14280
gttcgtttag ccacagtgga ctagacaagg atgagtctga gtttcacagt cagtgtgaag 14340
tttgtcttta ctagcccatc cctactctcc ttccctcttg tcctgacaaa gcaactggct 14400
gagtctcttt tagcaaaaag gaccccccttt gttgctggct gtggttctcc cacacacctc 14460
tcctaccctt agcttttaca aaggaagata tggaaaggtt ctactggaaa accctctaag 14520
ccttaggtgt cctggccaca gcgcttgact ctcctgtccc agggtttctg cttcaccttg 14580
tgttgccatg gtaaaccatc tagcagattg attctagctt agaaccaaaa taactgggca 14640
ggtccatgag aacggtttcc actattctaa gttttgaggg actgagccta atgcataagc 14700
actatctggg gtgtaatacc ccacttcctc agcactgtat tctcagcctg tgccttccca 14760
ggggttctgg tacattaaaa taacaccagt tagcactctt ccccaggagc ctagtaggac 14820
tgtatttgtg ctgggctctt tattagctgg ctttacctat ggacagaggc cttgcccagg 14880
agccaggtag cagctgttgg gatggctcca ttcctgcctc cattgccaga tttagaatta 14940
acccattctg aggagcttgg ggttccctga ggtaccatga cttatttatt tttttatttt 15000
ataaaacaaa attttgctct gtcatccagg ctggactgca gtggtatgat tatggctaac 15060
tggatccttg acctcccagg ttcaagtgat cctcttgcct cagcctcccg agtagctggg 15120
aatacaggca tgcaccacca cacctggcta atttaaaaat ttttttgggg gaaatgaggt 15180
ctcactatat tgccttggct ggtctcaaac tcctgggctc aagtgattct ctcaaatgtt 15240
gggattacag gaatgagcta ccatgctcag cctgggattg tgccttttta aaaccttcag 15300
acttaaccat aggtttccca tagatcatgg gatttcgtaa tggcattgat aagaggaatt 15360
acagaagagg caaactttgc acctgtcttg gcttctgtat ttcctgttga gagtaaagaa 15420
aatgctatcc tgtaaggcca attgccttac agaggttgcc ctctggcatt tggaagttgg 15480
tattaagttt ggactaaaaa taaagcctca ggaaatgcaa tccaagagtg aattcctcct 15540
tttgggaaac acaagactct tcatcataga ttccctaacc tgtgttcata aacagcctat 15600
ggcctggcta gtggctggcc cttaaatgtc atggggacct gaccaagtcc agcagacata 15660
ccatgtaggt taagacatgt ccctgtacct tttggaaaat tctgtagttt tccaaaagca 15720
aggggtcctt agcaggagtc accgagaatt acttgttaga gaattaagtg ttagcttagc 15780
ttagagagag ctgaagacaa tgctggaggt ctgttcgctg ttgatccctg ctgctgtagt 15840
ctgccatggg ctcctgcatt caggggaagg agcagaaata gatttttaag aagttgacct 15900

-continued

```
ttaagtaggc tttatggttc cttcatccag taaaataaca ccacatagct ctaacatggc  15960
aagggcgagt gatacctgcc acacctgctg gatgagagct ggctccgatt ttggtatttt  16020
aaactttaag aggcttttgg agattatctc tactttcact cctattccca gattataatt  16080
aagatttatt ttttattttt tatctattta ttttttaaag atgtccctct tgtgtgttca  16140
ttttgaagtt ttagaccaag atgaggttgt gtgtgggctc agcttggaaa ctgatctgaa  16200
attattctaa tttatataat gtaatgtaaa cagtttcagc cttaccatac gtcagggcta  16260
tcgtttcatg tgcacctttg actaggggct ggggcgtact tttccagttt ctgactattt  16320
taaatgctct tctgagcaga acgttgagat tactgtcttc cctctcactc tgacagaggg  16380
acatcaaatg tctgcatctg atcttttaac agcttttttt ttttgagaca gaatcttgct  16440
ctgttgccca ggctggagtg cactggcaca atctctgctc accacaacct ctgcctccca  16500
ggttcaagca attctcatac ctcagcctcc tgagtagctg ggattacaga cctgtgccac  16560
cacgcccagc taattttttt atatttttag tagagacggg gtttcgccat gttggccagg  16620
ctggtcttga acttgtgacc tcaggtgatc cgactgcctc ggcctcctaa aggcgtgagc  16680
caccacgccc agccctcttt taacagcttt ggcaactagt cttcagccct cacttttggc  16740
agttcacatg ggcaagatgc attcttgctg aacatgtggt tccatatgcc atgttttcca  16800
gatttattta tttatttatt tatttattta gagagggagt ctcgctctgt catccaggct  16860
ggagtgcagt ggcacgatct tggctcactg caacctctgc ctcctgggtt caagagattc  16920
ttctgcctca gcctcctaag tatctgagat tacaggcacc tgccaccaca cccgactaat  16980
ttttgtattt tagtagagac ttggtttcac cttgttggcc aggctgatct cgaattcctg  17040
acctcaagtg atccatccgc cttggcctcc caaattgctg ggattacagg cgtgagccac  17100
cacacctggc ctagaaataa tgacttttaa acaacctaaa tgtagagcct tccacaggac  17160
agcattgatg gatgctttac cacataacat cccaataaag ccacagctga agtggaagac  17220
tcagtacacc tcccagagat gctctaagag attatgatat atgacataga tttgaataat  17280
atacctaata attggtatgt ttataatata tggttttaca tccccaagac caaaaatgca  17340
tgtttgcatg aaacactcat ggttacaaaa atatattagg ccaccaaaaa aaccccccacg  17400
tttcataaag tagaaattat acagacacat tctctgataa aattttttag tggaaattaa  17460
gaacaaagtc aagaaaactg aagtgtgctt actttagaaa gcaaagatct caaggtagat  17520
gaaataaata tttaactcag aacactaggg gaggaaaacc ctaaaaaggg tgaagaaaat  17580
aattttgtaa gattatagct caatgaaatg aaaataaatt tgacagatta agctaagagc  17640
tgattctttg tggggaaaaa atagtaaaat agaaagttct gagaagccag gtgaagaatg  17700
cgaggatgtg caaataagag tatgaataga aaagagaata tttcctacac attggagatt  17760
ttaaaagtca agaaagactt ataacttaat tcctatatag agagatgact ctggctattt  17820
tcaaagaaaa gataaatatc caaaagatag aaaatatgaa tagaccagtg gccataagaa  17880
gttgaaaaag tgggctgggc gtgcggtggc tcacacctgc aatcccagca ctttgggagg  17940
ccaaggcgga gggatcactt gaggtcagga gttcgagacc agcctggcca acatggtgaa  18000
accctgtctc tactaaaaat acaaaaattg gctgggcatg gtggcacatg cctgcagtcc  18060
cagctactcg ggagcctgag gcaggagaat cgcttgaacc tgagaggtgg aggctacagt  18120
gagccaagat cgcgccactg cactccagcc aaaaagttga aaaagtgatt aagatctggt  18180
tcacctcaga acacttaagt ccaaatgatt ttagtggctg aattgtctcc ccttcaaagt  18240
tcagttacat tgttaaactg ttccagagcc tagagaaata tagaaatctt cccactgtgt  18300
```

-continued tctttgaaac caatatacgc tgatactgag atcaaacaag gacagtacca aaaccaggca 18360
ggtactaaca gttagtgtgc tagaccagtc tcacttagat gcagaaaaca aataaaattt 18420
aataatccaa atccagtagt gattgaaagg aatgtcttga tccatgacca agtagatttt 18480
attctaggag aacaaaattc tacatcggga ttaagtagag ttaaggttga catttttttt 18540
tttttcttct gagacggagt ctcgctctgt cacccaggct ggaatgcagt ggcacgatct 18600
cggctcactg caacctctgc cttccgggtt cacaccattc tcttgcctca gcctcccgag 18660
tagctgggac tacaggcgcc tgctaccacg cccggctaat tttgtttttg tacttttagt 18720
agagacgggg tttcaccatg ttagccagga tggtctcgat ctcctgacct tgtgatcccc 18780
cctcctcggc ctcccaaagt gctgggatta caggcgtgag ccactgcgcc tggcctgagt 18840
taaggttgac ttttaaacaa cctaaatata gctaaatata gagccttccg caggacagca 18900
ttgatgtgtg gaactcttat ccacgtgata acatcccaac aaagccacag ctgtagtgga 18960
actcagtaca cctgagtctt atcattataa gatgataata ggtaacattt attagataat 19020
taccatgtac tttgtcctaa tacttcatgt attcttttac tcctcacgtc aactctgaag 19080
gaaaggcacc acctatcccc ttaaaagaaa acaactatta ctattctttt tttttttttt 19140
cttttagaga cggaatctca ctctgtctgt cgcccaggct ggagtgcagt ggcacgatct 19200
cggctcactg caacttctgc ctcctaggtt caagtggttc tcttgcctca gcctcctgaa 19260
tagctgggac tacaggtgca cgccaccacg cccagctaat tttgtattt taagttgaga 19320
cgaggtttca ccatgttggc ctggttgttg tcaatctctt gatctcatga tccacccgcc 19380
ttggccttcc aaagtgttta gatgacaggt gtgagccacc gcgcccagcc tctattctat 19440
tctattttgt tctatttcta ttacaagcca gtaagcaaga aaatatcata atttataagg 19500
aaccctataa aaaacagaca agccaagggt ctgtcattag gaagtatgcc tgaataagaa 19560
gctgaagatt tttagacaca ggtttcaggc aacactgtct ttagaggcta ggctctggct 19620
ccagctccct ccagcctcct gtgaataaca ggcaggctta cttgcaggtg ccactttcct 19680
ggacagtggt ggttaaagga caaggcccag aaagtgctga attaggtgcc cttgttaccg 19740
ctaatgtctt attgatgaca ctatcttaga gctcttttga catcttggct ctgcgtcttt 19800
tttttttttt tttcttgaga tagggtgttg ctttgttatc caggccggag tgcagtggtg 19860
tgatcatggc tcactgtagc cttgacctcc tagacataac ccacctcagc ctcacaagta 19920
gctgggaccc caggcacgca ccatcatgca cagttaattt ttgtgttttt tgtagagacg 19980
aggtttcgcc atgttgccca ggctcatctc aaactcctgg cccaaactgt cctcccacct 20040
tagcctccca aagtgtttgg tttataggca tgagccactg tgcttagcct gagtccctct 20100
tttaaacaaa caaaatggta aatggaaagg aggaaaggct taagaaaaaa gattgaagcc 20160
aggatttgtt gtaagcaagg agtaataaag ggcagttcat ttagagaaag gcatatgacc 20220
acctttcccc ctccaatcag aatctagaaa gtgattgagg ccgggcgcag tggctcacgc 20280
ctgtaatccc agcactttgg gaggccgagg tgggcggatc acgagatcag gagatcgaga 20340
ccatcctggc taacatggtg aaaccccgtc tctactaaaa atcgaagaag ttagccaggc 20400
gtggtggtgg gcgcctgcag tcccagctac tcgggaggct gagaggcagg agaatggcgt 20460
gaacctggga ggtggagctt gcagtgagcc tagatagtgc cactgcactc cagcctgggc 20520
gacagagcaa gactctgtct caaaaaaaaa aaaaacaaag cgattgagaa aatcaggtct 20580
gtgtgacctt agcaatgagt tatttagctt gggccactgt tagcttaagt caataacttc 20640

-continued

```
aagtttgcgt tgtagttgga atcaatagag gaaaagctct cagcattacc acatatatca  20700
gaatgtgaca ttgattgcca gaccagcctt atccaaacac aagtcctagg ctttttgccc  20760
tgtttatgag ctttatatgc tgagggtatt tgatgagtct tagggaaaaa agaacagccc  20820
tggggacaca gctgctttta tgatgagaca tgtttgcacc cataccttaa tgggttttgg  20880
tggcaatatt ctgaaatttg ccacctacat ttcaaagatt tgccctttgg gtgaattagt  20940
gctgtagtag aagtgggtgg aggctgagga ggttggatta agcaggtaga ggatttctca  21000
gtgcatggat cgtgctgagg atggagatag agctctaaga catccacggg cctttcctga  21060
gtgatcagct ttggctcctg ggcaggggaa ttggagctgg attctagtgt gggagcacgc  21120
ttgtcatctt ccttcttttc ccccagtacc atgcggagac catcaagaat gtgcgcacag  21180
ccacggaaag ctttgcttct gaccccatcc tctaccggcc cgttgctgtg gctctagaca  21240
ctaaaggacc tgagatccga actgggctca tcaagggcgt gagtattctg cggagagcga  21300
ggggaaggct cagtaggcaa tatgccccag agacatgtcc tccaaagcgc tgggttgcca  21360
tgtttcttcc cagtactatg aaggactgca gaggagttga ggtctacaaa tgaggattta  21420
ttcatcactg taaacaatgt tgatttgatc tactttgcta ggaaatggta ccacaaagga  21480
accttttttt tttaccctaa aaacctaaac tttaggcttt ctaacttgga gaaccatctc  21540
tttgtatctt tttccccatc attaagtagc ataactgaaa catattcttt tcttggatta  21600
tttccgtgaa gtatacagag ttagagaata agagcaaaaa actgtattac ttttagcagt  21660
gacttgagca ttgttcccgg gaggaaagag cttttccatt ccttctgagg tgatgctgct  21720
actggtgtct ccagtttgga ctcttgctta ctctcttgtc cctagagcgg cactgcagag  21780
gtggagctga agaagggagc cactctcaaa atcacgctgg ataacgccta catggaaaag  21840
tgtgacgaga acatcctgtg gctggactac aagaacatct gcaaggtggt ggaagtgggc  21900
agcaagatct acgtggatga tgggcttatt tctctccagg tgaagcagaa aggtacgtat  21960
gggagctgga gtccagttgt ctaaaacagt cttttgtctc taaacttcct tgacacaagg  22020
aagatgggaa ggttggttgc ctggcagtga gattgagtct gtgtgttctc aggaatccct  22080
tttataactc atttatcctc aaagataggc tttaatccag catagttaca ttcttctggt  22140
tctggagaac acaggaacat acatacatat atatatatat atacatatat atatatatat  22200
atatatatat atatatatat atatatattt gtttcgctgt gttttgtttt gttttcaaga  22260
cagagtctcg ctctgttgcc caggctggag tgcagtggca tgatcttggc tcactgcaac  22320
ctctgcctcc agagttctag ctattctcct acctcagcct cctgagtagc tgggattaca  22380
ggcacccgcc accacacccg gctaattttt ttgtattttt agtagagatg gcgttttgcc  22440
atgttggcca ggctggtctc aaactcctga cctcaggtga tctgcctgcc ttggcctccc  22500
aaagtcagaa cagtcttaat tatccttatt tatgggtgag gaaagtgagg tacagagagg  22560
ttaaatggct tgcccaggat tacacagtgt agtaggtttt caactctggt aaaacagctc  22620
cagcacccat aatgcaccac ttcccagctc actgtccttg cgggaaaggt gcctgcttcc  22680
tgttgacctg tgccctcgtg ctctgcctcc cctacttacc ctttttcata caggtgccga  22740
cttcctggtg acggaggtgg aaaatggtgg ctccttgggc agcaagaagg gtgtgaacct  22800
tcctggggct gctgtggact tgcctgctgt gtcggagaag gacatccagg atctgaagtt  22860
tggggtcgag caggatgttg atatggtgtt tgcgtcattc atccgcaagg catctgatgt  22920
ccatgaagtt aggaaggtcc tgggagagaa gggaaagaac atcaagatta tcagcaaaat  22980
cgagaatcat gagggggttc ggaggcaagt ccccgttgtc cctgctccag tcccagcgca  23040
```

-continued

```
gctctccgaa gggcatggtc catcctgtga atgtctgatt cccagcccct agcccatcag  23100
aatgtagact cccaagccag ttccaaacct gctgaatcag aatatcttag gagagtagaa  23160
ggcattatgt ttttttgttt ttgttttttt gttttttttta aaaaaaagct tcccaggtaa  23220
ttgagatgct ggcagcttga cattgttccc tgggcctggg gaccaacatt tgagagaaca  23280
gggtcactgc tcacaggacc aggggccatg atgttctgtt cctgatcaga aacactacca  23340
gtgtttgctg gaatgggggg accaggggga aagatgacag cagacactta agaaagggct  23400
ctttttggcc cttcctgggg agccatgtgg aatttcaggg cctggtgtcc atgttaaagc  23460
ttatggcctc ctggtcttca cttagaatgc agctggctca gtgatcatgc taactctggt  23520
atggtccatt ccactctcag aggaagatgt gtggttcttc tccagtttca gattgcccca  23580
acttagctta ccccctcccc aatgctcaca aagtagagcc cagtgggcat ggccaccatt  23640
tttggcatcc tgctaggaat acaactcagc acaactaaga tgctagacac actcttgtgg  23700
attagaagtg tgtttgggga gggtggggga gcaaccctgt gcacccactg tagtggcctt  23760
actgtctgag ctttgtgtag atatcctctg taccaggcaa tttggggtcc tccccttttgc  23820
catcctgata agccataggc tagctgaact tggccctagg ccaggcaaag ccacattccc  23880
tcttgccttc agcaggttgg agtgggccac ctcaaagggc agtcctcaag tgtccttgac  23940
tagatgaggc catgggtctt tgtggtggaa gcagtcatca ggcctcaggt tccctgtctt  24000
gaagtgctga ttggaaaatg gaggccctag agagacccct aacatgcatg ggatttggag  24060
aggagacctt gggaatgagc ccatttggat ttgccctctc ccctttcttc cgtcaatgaa  24120
gcatccatat tggtgttgaa gcccagcagg cagaattgtt ggcccactct gggggcctaa  24180
ggtagctgga ctgccttgcc atctgtgtgc acccatgatg atatcatgga tgtctgtcct  24240
ggtacaagga catctaagtt agggaatccc agggaaactt cttgtctact gccatacttg  24300
tggcctctgt tctatataac ctctctcccc ccaactttgt ccatcaggtt tgatgaaatc  24360
ctggaggcca gtgatgggat catggtggct cgtggtgatc taggcattga gattcctgca  24420
gagaaggtct tccttgctca gaagatgatg attggacggt gcaaccgagc tgggaagcct  24480
gtcatctgtg ctactcaggc atgtgcccac ccttccccac attctcatgt gcacactcgc  24540
atgtttgtat gggaaagctc tggaggctgt ctgatctctt cccatggaat tgtcgcacgt  24600
aacacacaga taatcccctt cccccatgta cctacacaaa gccatactct gtgtacctac  24660
tcactatcca gaggatcagc ttgctgtcat ttgtctctga agacagctca agctacatct  24720
cactaatgct ctgtcccctc ccagatgctg gagagcatga tcaagaagcc ccgccccact  24780
cgggctgaag gcagtgatgt ggccaatgca gtcctggatg gagccgactg catcatgctg  24840
tctggagaaa cagccaaagg ggactatcct ctggaggctg tgcgcatgca gcacctggtg  24900
agttctgggg cctgccccat cccccagggc ttcggactgg gcctgggatg gatgcaagct  24960
ctggtgcaga gctttttagg tttctccatc ctcttatgca cagcctttca ttatcctcca  25020
agttacagca gcaagagggt gggggtggaa gtggaggtgg cttttttttt tctcctgttc  25080
tgcattcctg cccacacccc cacccctcca tttccttctg ctctggaggc atcctccttc  25140
attggacacc acacagttta tttcacttct gacttcaagg ttgtgaattc ttcccatggc  25200
ttaagtcctg ggatacttct gcagtgaaag gaggtcttgt acctcttcct cagagtcaga  25260
agttctgagt acctttgccc tattctgaaa agggctaggg gctcctgctc ccagctgccc  25320
tcttcctttg gcttccaatt cagttccctc tgccccgcat cctgcagaca ggcgctcccg  25380
```

-continued

```
caggggggccc ttgtggacct gcactggagt ctgttgcctt cactgagctg cctgtgctgg  25440
ccttgcatgg tgcctgtagg gggatttgct ttgctgtgcc attggggtac agctgctgct  25500
cttactctag accaaaaagt cggggttgagt gactggtggc agggccacag atagagacag  25560
cggggagggt ggctgaccct ggcggccctg gactgagcgt ctggaggagt cgtggaggct  25620
ctttcccttc tttctcctct gagagctcgt tcttcaggct cttccagctt gtcatgtcga  25680
gtgcctggcc actgctcagg gttggaggct cagtcccttt gccctgtctg ttccagctct  25740
ggagctaact cagggatccc tgatcagggt tacataggtt tggtaaaatg agtgctggaa  25800
attaactttc tcccagtagt cttaggtcat gctcagtgaa cttaaacttt atccagatat  25860
ggttttcctt cagcctttct attccctttc tagccagtga aagacccgct gccctttgac  25920
ctcagcccct ccaagccccc aagtttaaaa cgccaccccc tgccaccaga aaaaacagaa  25980
aaaaaaaaaa aaaaaaaaaa ctaaaacacc catctggtct gggcatcttc ctttcctttt  26040
tcactatgta tcctgttact gggcttaaac agctttcaga gaagagatgt catttctatt  26100
aaatgctctt tcagtagcga actgagttca cacttgacta aggatatttt ccggactgtc  26160
tgtcatcagc atccttagtg ggtttcccca tatttaaatt ggtagaggcc agggatggtg  26220
gctcacacct gtaatctcag tactttggga ggccaaggta ggtggattgc ttgagctcag  26280
aagaccagcc tgggcaacct ggtgaaaccc tgtctctact aaaaattcaa gttagctagc  26340
tgggcatggt gatgcacttc tgtagtccca gctacttgga gagggggtga tgctggggca  26400
gcaggatcgc ttgaacccag gaggttgagg ttgcagtgag ccaagatggt accagcctag  26460
gtgacaaagt gacaccctgt ctcaaaaaag aaaccaaaca aacataaaaa aaaaaacaaa  26520
aaaatcggta gagagtgatt tctctcccag gcccacttaa tgtagactgg gcctggctga  26580
cacctcacca ttcgtgtgat gtgattgctg ttctgatgct tagatactct tggcgcagtc  26640
tcacaattgc caccatggta ggaaggtgtc ccaggagacg gtgcaccttg aaccagtcac  26700
cactaaagtg gctgcctttc tgggtctctc cacacatccc ctctctctaa tttccctact  26760
taatcgtgtg acttcatggt ctcaaaggag gaacagaggc tgatcttgac ttagatatac  26820
tgaaccatga aatcactgca tagaatgtgg ggacttgaat gtgtctttgg gcaagtcatt  26880
taacctctta agacctcatc tgtaaaatgg attagatatg tttaattata gccttagcat  26940
taaatattca ttgctgttat tattaagtgt ctgataagtc tctgtgtaca tggatgtaat  27000
cttcctaact cccattacct ccatttatag atgagggtta tatggccaat aaagcctggg  27060
tttgaatcta ggtctactgc ctccaaagcc agtcttctct cctgcaacat catgctctgt  27120
ctagcaggag atgagaacag gtctccattt ggagcctgtc agtggggtca gagactaaga  27180
ttcaggctca gggtctaaat tccatatcct ttcttccata ccctggtgtt tcctatgaac  27240
agatagatac tttagggctg caaggtttgg attgcatggc actgctcaga agataagtta  27300
caggtctggg ctaggctgta gctgcccctc caggtggcta gacctttcct ttctgtgtca  27360
ccagttaaca ctggccaaca gttccttcca ttaactgttc actgctttct cctgtgtcta  27420
actgatgcag tttatgaccc ataactaaga gcagtaccag gtatggctct gtttcctgtt  27480
catgtcccct gtcctctggg ctgcatgcat tccgttctta cagaaagaat acctttaacc  27540
tagtacatcc tgccacacat ctgcttctac tgtgaaattg atgagggggt attaccgatt  27600
cttccctcac ccatcattta ctgagatgct ggtgattgca ttataatcct ctaaagctta  27660
cattgtcttt ctgattcttg gtcttatctg agcaagtgat ctataaataa ctcagtggct  27720
ttctcatgac tgttttaatt attagatttt aatcaagtgt cttattaaat atatctgcat  27780
```

-continued

```
gcttccacag gcatctgtct cttcacatgg ctgttcagtg tgcctctcac aagttagccc  27840
acgttttctg ttctcctgct tcaaactcag ttgagctgcc ttgctttggc tttgatccca  27900
gctttccagc gctgctcaat ctgttgccat ggcaggccat tggaaaggct cagtgcatcc  27960
ccgtgcctga agccaagtga gcgctcactc catgcatgca tggaggctgg gcaggagcct  28020
gcctaatcaa ccagccatgt gaggagggag ggcctgttcc ttcctgtaag ctatgtcatg  28080
aggcagcgtg gtcaagtcct ctgccaggga gtggcctggg cccagcctgg gcatgttttc  28140
atgccagggt gctagagcct actgccagat tgtctccctc cacccccaat gaaaaaatcc  28200
ttccagaagg gaagagccaa tttcccctgt attggagggg aagtggcagc acctcctgaa  28260
gcagttggac tttcatcacc ctacctctgc atctgcctga aggacagatt tagccaatta  28320
acctaaggtt accttcctct ctgataaatt ccccattctg tcttcccatg tgttgtgtct  28380
cgttttttc ctcctccttc cctcttcctt gccccctctt cccctaaacc ttacagatag  28440
ctcgtgaggc tgaggcagcc atgttccacc gcaagctgtt tgaagaactt gtgcgagcct  28500
caagtcactc cacagacctc atggaagcca tggccatggg cagcgtggag gcttcttata  28560
agtgtttagc agcagctttg atagttctga cggagtctgg caggtagggc cctaagggca  28620
ggtaacactg ttaggataac cagcctcttg ctccacctgc tctaggagaa gacagccagg  28680
cccaacctgg catctgggca cagagcctct tctcgtctgt aggaacaccg ccagggaggt  28740
catggcaggg caggaccaaa gggtcctgtg gctcagtagg cacagtagat gtcacaggca  28800
cttggtgaag gactggtttc tgtggagtct tgatcttggc tcagctcaga atctccagtg  28860
attgggctcc tcttggcctt tgttcccagg aacatgttcc tcaccagctg tccggtgact  28920
cttcccctcc ctctcctttt gtgacaaagc tctgacaaag ctctgtcccc ctctcgtccc  28980
tctggacgga tgttgctccc ctagattgcc cgtgaggcag aggctgccat ctaccacttg  29040
caattatttg aggaactccg ccgcctggcg cccattacca gcgaccccac agaagccacc  29100
gccgtgggtg ccgtggaggc ctccttcaag tgctgcagtg gggccataat cgtcctcacc  29160
aagtctggca ggtaggaggc ggcagcggct ccctggaatg ccctgctcag tggtacctca  29220
ccttgggggt cctgggagca gtccattgaa caatgctcag gtggcactga gccaaggtaa  29280
gacccctctg cctgccacct tgggcctgca gggaaggatt gagcagagcc ccttccctgg  29340
gcccaaagga ctctaggtag cactcataag gaatgtcaga acatttggat caaaagcaaa  29400
tttatgctgg agatttatta cataacagtg cacaggctga ctacaaatgg ttatttgata  29460
ttgaaaattt agtcctctaa aattgtaaaa gataaccact tttgcttatt ccagttacta  29520
tgtgctcttt aaaaatttca gttgggaaat gaatttattt aaatgctgtt tactgtgcct  29580
ccatttggca cactagtccc tgctgttttt gagccctaaa gacaaattgg gttccagctc  29640
aggagaggtt gctgtgctat cttggctgac attctgtggg gcctggcagc caggctgagg  29700
actgtgtggc ctatgctggg cctccaactt gggatccctt ccttggccca ggacattgag  29760
ttaatgtcct tcactctcct agttagggag tatgctcctt gtccctgtcc acagggcagc  29820
aagggtttcc tggaagaggg gagcaaacag gcagtgccca tgcactgagg agcagcagat  29880
gggcgtgggc agcccagaga accaggacac aagctctgtg cagatgccct cagcagaggg  29940
ctccagcctc ccactcttgg ctgaacagct ccaacccgta gggttgacct ttcttaaaag  30000
gtccagttct tgctgtttgg ctattttaag ctctagtctt ctggggtttc actcagctgg  30060
tcctggcttc agcaattgct tccctctgaa ggccttgcat agaggccaag cgtgaagtgc  30120
```

-continued

```
agggacttct ctgctgtgat gtggcttaag tttccctgac acctgttgag tgtcctcata  30180
acttcccttc tggtgcccct ccccagctcc tgagacacag ctgcagctac aagtgtgcag  30240
tgtcagtgtt caagaaagtg cctggcagag gggctttaga agggtcccct gccttccaaa  30300
ggagctttgg caggcagagc tgctcctgca gcaacactcc catttcctgt tcttgcctgc  30360
tgagtagcac ctagatttct aagcctcatc tagatactca gatttgattc tgggccttta  30420
tagcccagtt gctgggactg tttcaggagc taggggccat gtggggcagg gagagggcac  30480
aaaagtagag aagcctgatg ttgattccca gggggctggt cagctctgct actgctcctt  30540
gcagatgtca agagtcaggt gctagtcacg tgctgcttgg cttgtcactg tcattggcag  30600
cgagaggaat gggtgctggt gacattgggc cagggctgcc tctctgtgtc agagttcagg  30660
gtgtaggagg ggttctgcca accatgggct gtgtggggta agtgggtgag gctgatcttg  30720
ctgggtcaag gtgatcctga gcccttggcc tgtggaatgg gggtagaggg caaatggtaa  30780
cctagcatgc tgtgggggat ataggatgag gggctgcccg agcctcggga ggggtcctag  30840
ggagcagatg ttgaagaggc cagagccctc agtgagctgg atgagagggt gagctgtttg  30900
aacgccctga gggtacttcc tggggcctcg tgtaatggtc tcttctgtat gtcccccatc  30960
ccatctcagg tctgctcacc aggtggccag ataccgccca cgtgccccca tcattgctgt  31020
gacccggaat ccccagacag ctcgtcaggc ccacctgtac cgtggcatct tccctgtgct  31080
gtgcaaggac ccagtccagg aggcctgggc tgaggacgtg gacctccggg tgaactttgc  31140
catgaatgtt ggtacgtggc tggagcaggg gctagagcct agaggagctt ggggatgctt  31200
gagcattggc ttctgtggga ccccgaaagt ttggggaata gaaaggggaa cacacagacc  31260
ttagtggggc aaaaggccca gcgactgttc ctctccctta ttgggaatgt tcattctgaa  31320
tctctcattc tccgaagtcc taagctgagc caggagggaa aagggtcctt tgagttgtag  31380
ggctgagcaa ttcagttcct cttctcttct agtctggggc tcaaagcaaa attgtccatt  31440
ttttggcatc tgctcattac tgagagtttt ttttgttttt tgtttttttt ttaaataaaa  31500
ttggccacag ctcctgtgct gtggggtggc atacacagat tacgtactga tgtggccatt  31560
gtccctgtat aaggtagggt atcatcagat gacaggaagc agctagctct gaccctgggc  31620
aaggctttgc accctctcca ggatagtgaa tgatgtccaa aggtccctgc caaccctgcc  31680
atctgagtga taaggacatt tcagggcctt cctcctgttt gcctgggctg tgagtttggt  31740
gccaccttgt ggtgtgagga agtagtggtc agccagccta gttcagtact caggctatgg  31800
ggcagctgcc caggtgcaaa cctgcctggc ttggctttta ctcaccaacc tcccttctct  31860
tcctccaggc aaggcccgag gcttcttcaa gaagggagat gtggtcattg tgctgaccgg  31920
atggcgccct ggctccggct tcaccaacac catgcgtgtt gttcctgtgc cgtgatggac  31980
cccagagccc ctcctccagc ccctgtccca ccccccttccc ccagcccatc cattaggcca  32040
gcaacgcttg tagaactcac tctgggctgt aacgtggcac tggtaggttg ggacaccagg  32100
gaagaagatc aacgcctcac tgaaacatgg ctgtgtttgc agcctgctct agtgggacag  32160
cccagagcct ggctgcccat catgtggccc cacccaatca agggaagaag gaggaatgct  32220
ggactggagg cccctggagc cagatggcaa gagggtgaca gcttcctttc ctgtgtgtac  32280
tctgtccagt tcctttagaa aaaatggatg cccagaggac tcccaaccct ggcttggggt  32340
caagaaacag ccagcaagag ttaggggcct tagggcactg ggctgttgtt ccattgaagc  32400
cgactctggc cctggccctt acttgcttct ctagctctct aggcctctcc agtttgcacc  32460
tgtccccacc ctccactcag ctgtcctgca gcaaacactc caccctccac cttccatttt  32520
```

cccccactac tgcagcacct ccaggcctgt tgctatagag cctacctgta tgtcaataaa 32580
caacagctga agcacc 32596

<210> SEQ ID NO 46
<211> LENGTH: 34218
<212> TYPE: DNA
<213> ORGANISM: Macaca mulatta

<400> SEQUENCE: 46
agcatttcct tctcaacaac agctaaagtg accaggaagg cttacagaag aaagtgaaaa 60
atttttatct cacttcaaac agaaatttac ttttaggctg tcactgtctc atcccagctt 120
atctgagcta acaggaagcg aatgaaggcc tgtgattcag ctgcaggcag cgggtaagcc 180
tgagcaggtc acactcattt ggtctctttt gccaggaaaa gaaaaaaaga acctgagaga 240
actgtcttca cattttgaat gcgcaacatt gtatctgtga atgaaggcaa gagttaacag 300
ctgtttaatt gataactgct cgcatcattg gttgctggct aacaattggg aaatcggaaa 360
atgtcttgta gaaaaatgta agaaaagttc caacaatatt gacttaaatt catgacaagg 420
tgaaaacaga aatgctgact cctgcatagg ttatcggctc taatgttctg acttgattat 480
ttccagatgc ccagctctgc gctaatatca acgccgtcta tttgcttttt actctcaggc 540
attcgctctg caggattcca gaccctacta aattattcac atggccccaa cctgtccttc 600
cttgttccgc ggttctaaga caacaaatgg tcctaagagg aaaagggcct cgcgctcccg 660
ctccaggccc acttcgcagt ccctagttct ccctactgcc gctccagtgc cagagcccct 720
ccgaaggcgg tcgagacctc caaccacgca caagtctgca gctctcccca acttcccgtt 780
cagctcagtc tccgagggtg cgccagggca gacacccgga ggagtgggga gtggcagggc 840
ggggccggga gaatgctgcc ccggaaccca taaatctggg ccctgcccag gtaggccggg 900
acagttgggg tggcctgggc cgagagccaa gaagagacct catctggcag cccaacttgg 960
cggcaacagg tggcccggcg cccgggggtc taggagggaa gtcgctctag gggcgggatc 1020
cgctgccccg ccgcgttccc attggccgtc aggttcttta aactgtggct ctgaatctgt 1080
gtccttccgc cgcagaattt agtccccccg aaagggcaac ctgcccgcgc tctctgccgc 1140
cgccaccgcg cttcctcctg aaggtgactg cgcccgcaaa gacgcagggg gcggggcccg 1200
ggtcgccggg agccgagatt ggacagaggg cggggcggcg gagggattgc ggcggcccgc 1260
agcgggataa ccttgaggct gaggtccctg ctactcgcac agcagctgca cgtccctggg 1320
atccacatct cttccaattt gcagcgtagc ccgagtcggt cagcgccaga ggtgagcggt 1380
gcaagaggct gcgccatctg tccccaccaa gggcctgtgc acccggctag tgcggaatcc 1440
cggcgcgccg gccggccccg ggcacgcagg cggggcagcg caggatccgg ggcatgtggg 1500
acgcggtgga gttcagagac tggagaacgg ctcctcagaa gtccccagcg ccgttccttc 1560
cagatcaggc gggtccgccg gctcctttcc cgtcccagcc ctacccccte attctggtcc 1620 catcctcctg ccccaatcct caatgcgcct ccatccttgc ctgccttctc tcggtccctc 1680
gtgattgatt ccacccttgc ctcccctttc tccgcgccct ctgttccgtg ctcgtttgtt 1740
ccacttcctc ctcaagtccg gtccttccac ccactcctct taaacctgtg cttgcctctt 1800
cgttctaatg gcttccgtgt aacttactga aactcggttc tggttcccct cccgggtcca 1860
tgctccattc atgcgcgacc gcccttcctg cgccccagtt ctctcttgcc gcccctcccc 1920
ctgctcgctg gtcacgtccg ctctcccgca tccccctcct cgcctggcat gtcgcctccc 1980

-continued

```
tccctctctg ctctggtcgc gcccgcccac ttgctccggt ctccgagcgc ggtcccgcgc   2040
cccttttcca tcaccgcctc ccaactccca gcaggctcgg gcggtgctgg ggccccgtgt   2100
ccggggcggg cgggcggagg gctgggctgg gtcgcccgcg cggcaggcgg gatgcggcgg   2160
cccgggagca gctggaggct tacgtaacgt tggcctgccc cgctgcctgg aggcagggcg   2220
gctgcccctg cggcgcggtg ctgtcccatg cgaccgggat tagatgggtg gcctgcgagg   2280
gtctgggaat ggctcgggac ccgcgagctc tcccggccct tgccgggtgg ccaccaggga   2340
ccacgctcca tctcgccgcg gccgggctgc acgtagcggc cgcgcccaga gtccaccccg   2400
cttcaccggg cggtggcctt gggccgcgta acgggccgta gaaacgtctg caggcttcgc   2460
tggggcctgc cggccctcgc ccgctccgcg cctctccggc acgttttttt tttttttctt   2520
ttcgtttttt ctttttcttt tctttctttc tttttttttt ttttttatta tccagcaggt   2580
ttttttttaac acatgcgccc tgattgtgga acgcggaggc cgcggggtgg ggtgggggtg   2640
ggctctggtt actgaggggg caggaaatct gtggcgttca ctcaacgcaa acggtgtggg   2700
tcaagggctc tttgggggtc ggagttagag accagaatga ctggacgagt catagcccac   2760
cgagctcaca atcttaaaat gtatacccgg taatgctggg agtggggcac gagcttcctg   2820
ctgtgggagg gaggggggaca ggaagcctcg taaggtctca ccaggtggca agcacactgg   2880
attagaagat gcaggaaagc accttccagt ctgaaggtca tttaaagact agtcatggaa   2940
aggcatccct gggcttctta atctgcatac tccagaccca gggcttggac ctttgctggt   3000
acgggttaaa gtgaggccga cagtgaaggt ccacgtggag agagacatcg ggaagttgtc   3060
agaaaggctt ttagaatcag gtttgactca ttaatttcct gagactgatt gaaggagttc   3120
agccgctaca cctcagtttc ccctgggaaa actgggagta acattttcct catgatggtt   3180
gaaaggattc atgcctacgt ggatgttgca cactcagtta agtgtctaat ctctggcgaa   3240
atacccagaa gaaaagcctg tgaatgaata tattattttc gagcacaatt acttagtcca   3300
gaattgagca taagggcctt gattcattat cttactgctg tccgcaaacg cctgcagcta   3360
atcgtgggga atcaggctct ctaaccacgt gtctcctgga aaccagtccc cccagggatc   3420
tggtttaata ttgacaaagt cactgataat gtaactttcc aactctctgc ttggagcaga   3480
tgctctttga tcatctgaga ttgggacctc tagacaaagg caggcaagga ggggctgagt   3540
taagccttcg gtgttcccct gtaagtggaa tacctcttaa caggggaaca ttccagccct   3600
tgacttgctc tgcctgctgg tgagattagg attggagcca ggatcagtaa cccccagttg   3660
gccatcttga gggcgtggct actcccgagg ccacagagga gatagaggtc aggactcccc   3720
ggctgcagca ttgttagcaa ataatttgcc ctttggtggc ctgaggtgct gtgggggcag   3780
gagtgggctg tcttgtgggg aagggaaatg taacgcatca ccaaatctgt gggggagtgg   3840
ggctctgtgg ggaagatgac tcaacctgtc aattattctg cttttgagag aattatcttc   3900
gctgggtgag tggggaaact acgtagtggt tcttgcaggc ttaaaaagtc ccttctcttt   3960
cagtgagtca aataatgaag catgcatttc ccctaattaa aaatgcctca acttcggagc   4020
ttgcggtgag ccgagatcgc gccactgcac tccagcctgg gcgacagagc tagattccgt   4080
ctcaaaaaaa aaaaaaaaag tgcctcaact aagtgaaaaa tgattggtcc gggtcacctg   4140
gttctctgta ctgccttaag aacttaggtg cagagtggca gagcccggtg cccagctaat   4200
gcagtctgtg cagcttcgtt cctggccctt ttgtagcggg cacagcagcc tctcctggga   4260
catgattaat gatgacttaa agaaggttct tgaactcatt tctcagttac tgacttgaac   4320
caaaatgtat ggatgttggt ctcctgtcta gcacagctgc tttcattgta agcattgcgt   4380
```

-continued

```
tagaaataat gtattcatat tttagcaaag agcatcatta gctctttaag aactgtaccc   4440
ccagtgactt agcaaatttg ttggctgtga ctctaaacag ctagcacttt atgggagttg   4500
cttctgtgcc ttgaatgttg tgacactgat gtggggtcac aggaaaaacc attttatttc   4560
ttaaagcggt ttgtttctta atattgaagc aatggaagaa atgaggaaat ggccatgggc   4620
aggaagatag aaaaaaatac agcagttaca ttacaaactc actttacttg ggttttagtt   4680
cattttaaag cttcagggtt ttttttttt tttttgagac agttttgctc ttgttgctca   4740
gtctggagtg caatggtgcg atcttggctc actgcaacct ccgcctcctg ggttcaagcg   4800
attctcctgc ctcagcctcc tgaagtagct ggaattacag gcacctgcca ccacgcccag   4860
ctaatatttt tgtattttta gtagagatgg ggtttcacca tgttagccag gctggtcttg   4920
aactcctgac ttaggtgatc cactggcctg agcctcccaa agtgctggga ttacgggcat   4980
gagccaccac gcctggcctg cttcagcttt tatgaaggca aatccggatg tgttatcttg   5040
gccaaaagct aagactgaga ccagagtaca ggaaaatgac tcatttgaca ttacccttct   5100
ttctgaatca ctccaaaagc ccacagtcaa atcccaattt aactgatata ccacaagaat   5160
gcattgcccc tgtgagcaga gttttattgc aacttcgagg gtctttgtga gattggttta   5220
tttggtatga ggtcttaagg attttaagtt gtccctttaa gcatcagttc tgatacagat   5280
gggaatagag ctagacaacc agatatatga agaccatttg tgataccacc ttacttttgg   5340
ggagcttgca ttttttacc aaggggcaga ctgaataatt gagtaatttg aatacttggg   5400
gcattgttaa agaagctgtt gggggaaggt gagcctgggt gagtggtgga gggtggcgtg   5460
cagcatctgc tgggctttcc ggcctcttgg tatgactgct cagctcagga gttgggggct   5520
ttagggcccc caccacccag tgcggcgaag ccccgcccct gcagtggttt gtgcttgtct   5580
gcacgtagga gggagcaagc cggctgcagt accttcggtg gcctctgaga ctcacctccc   5640
ccacttctgt ccgtagacaa agctcctggg gagctctaag cctctttcct catgccagca   5700
agcagtcttg gaagcaggct ggggctgcgg tgggagagat gccaagacca gttatacaag   5760
ggcagtgagg ttgccagtcc tagcatttca gactgtggac cagcacagct gctggctgaa   5820
cactgcagtc aagattctct gaagggagtc ctatcccttc caaacatctt cagtttactt   5880
acagataatg tttattcata ttttatttta tttttttgag atagagtctt acactgtaac   5940
ccagggtaga gtgcagtggc acgatctcag ctcactgcaa gctccacctc ccaggttcac   6000
gccattctcc tgcctcagcc tcctgagtag ctgggactat aggcgcccac caccacgcca   6060
ggctaatttt tttgtatttt ttagtagaga cggggtttca ccatgttagc caggatggtc   6120
tcggtctgct gacctcgtga tccgcctgtc ttggcctccc aaagtgctgg gattacaggc   6180
atgagccacc gcgcccagcc atgtttcttc agttttaaac aactgatgtc tcccttggca   6240
atgaataaaa aagaactact catcaatgga atcagtcagg gcacataaga cccactgtgt   6300
ccaccatgcc atttcagagg agattcgatt gagttaagca gggaaataga gatgtcgtaa   6360
acattgaaac tatctcggta tccctctttg gttattaaca ttagatgagc agaaaaacaa   6420
atgtcaccca tcagatgggc aaacatttaa aaagtctggc agtaccaagg gaagaaggtg   6480
tggaatgcag caactcaacg ttgattgata cagccacttt ggagagcaaa tcagccatat   6540
ttagtaaaaa tagaaataaa cataccccat gacctaagac ttcaatttct ggatatatag   6600
aaactcatac agtacaggga gacatgtact acaagagtat tgattaatag agaaaaacta   6660
gtttaatggg gagggggagt ggccaccagt aagggagtcc ataaataaaa ttgtctgttg   6720
```

-continued

```
tacagtggac tagtgtaaca gttcaaatga attagctaga tccatatacc cactggatgg   6780
atcttgaatg tgctgctgag cgaaaaacaa gttactcagt gatatataca gtgtaccact   6840
tagggcatta agaaaaccac aatattatag ggtttcagta tagatataga tatactgtac   6900
atagacttca gtgaactgga aggatacaga gttcatgaca gtgattgggt gtcaaaatgc   6960
atgatgtggc tgggtgcagt ggctcacgcc tgtaatccca gcactttggg aggctgatgc   7020
aggaggatca cttgaggcca ggagatcgag accagcctgg gcaacatcac aagattccca   7080
tctctattta aataaataaa atagaaaaaa gagttcatga tggaggtgga aagggttgga   7140
ggagcttggg gatggggaaa aaatgaactg tataaaatta taattttttt tttttaaga    7200
aagtaaagag ggccaggcac agtggctgac gcctgtaatc ccagcacttt gggaggctga   7260
ggcgggcgga tcacgaggtc aggagattga gaccatcctg gctaacacgg tgaaaccccg   7320
tctgtactaa aaatacacac acacacacaa attagccaga cgtggtggca ggcgccaaaa   7380
cgacgccccg tagacacgcc gatccgatat catccccccc gtggtggaat tcccgattgc   7440
agtgaaccga gatcgcccag cagccccccc gcctgggcaa cagagtgaga ctccatctca   7500
aaaaaaaaaa aaaaaagaag aagaagaaag taaagaaaat acagctcagc ctttatttgt   7560
gttttttttt tttttttcct tttttttctg agacagagtt tttcactctg ttgcacaggc   7620
tggagtgcgg tggtgcgatc tctgttcact gcaatctgca cttcttgaat tcaagcaact   7680
ctgtgcctca gccacccaag tagctgggat tacagatgcg cgccaggcta atttttgtat   7740
gtttagtagt gacagtgttt cgccatatta gccaggctgg tctcgaactc ctagtcccaa   7800
gtgatctgcc cacctcagcc tttcaaactg ttgggattac aggcgtgagc caccacagcc   7860
ggccatggct cagtgttaat ggtcagttct gggtggtaga gatgcagatg ttaaaacttt   7920
tttttcttt aattcataac aaaatagaag caaacctata aaggctattg taggaagacc    7980
agtcatacta actagttcag tgctcttgga gagttggcac tgcctttcct cctttattgc   8040
cccaactaga atgcagggca gcccttccat taaatgctga gccagtgcct cactttgctg   8100
aggccataac ccaccttagt tgcacttaag agtcctaaat caggattcct ggttctagag   8160
tgtggatatc atacccagaa acaccaccct acttttaatc ctagtaagga ggcaccatgt   8220
cccaaggcag ctaacgcttc ccccaaacca cctccttcag gctgaaacca gttgtctgca   8280
ccgagcagct gggatagagc caggaaatac tcggcatctg aggatactga gggttctctg   8340
acttaggact tcttcacctg aagttgagtg gtcttttggg gaagtaggcc tgtttagcat   8400
cagctgctct tccctattcc acactgtagc tggaaatagg accttaggtt cctgttgaca   8460
agtcatttac ttttagccct gaagaaataa aagagccaag tgttttttat ttttattttt   8520
attttttttt aaagcaaggg aattttacta gaacctgtaa gtgggctcat tttgttctgt   8580
gtagcttggt aacaccatac tgctttctgc tgtggggcct gctggggtta aagtgtgggc   8640
ttcagaccca ggtctcttag ctagaagata tctcatcctc tgtgtcctgc acccatatgc   8700
aaatatgcta ttgtcattat ccttaactgt atatgaagac ggacagtgcc tactccagac   8760
cttactaggt tctgctggcc catcacccat tttgatcatg ttgctggcct agtttgatta   8820
gggcaaatct tagaaattcc atttccattg ttgaggaaga gagctagaga gcaggctgac   8880
ccgaatgcca gaatatcatg atgcaaactt tctaatggat gctggtgttc tgaagagttg   8940
agggttgaaa ggccttcatg atggcttgaa gatgtaggta gcaaactgac gtcacagcaa   9000
ggaacgcaat cttgtgtacc tactggcaac gttggagaga gaaagtgagc atcaggtgcc   9060
accattttac agttgatctg tgtgaggctg gtatcggagc ataattggta caaagtaaaa   9120
```

```
atgacttagg cagatgcaga ctcacgggcc aggctggttt attagggcag aatgatttgg   9180
tcctttgtga aagaattggt ggagtgaagc gtgaatcttt cccagcgcaa cccaacaaca   9240
gttctggccc taagaagtgg agcatgggag ctgggtgtgg ttcgtgcctg tagtcccagc   9300
tacttggggt gctgaggctg gaggatcgtt ttgagggtgc agtgagctat aatatataat   9360
gtaatataat ataatataat cataccactg cactccagcc tgagtgacag agtgaaagcc   9420
tgtctcaaaa aaaaaaaggt tggagtgggg agtgttgggt atttttatg attttgtct   9480
cctggtttct gacgaatggc cgaaaaattg tgtctgacac aaaggaaact aatacaaaga   9540
gccaggaact gtctgagatg agaaaggaaa gggagaatag ggcacctaga gctgagctgt   9600
gattgtgcct gttccaacct gtaactccag actaaggcct cttagaggtg gtgtctcctt   9660
tctcacagag gagacatggc tctgaggaag atcttactgc aggggctcgg gctcaagaat   9720
aaggctcctg gacctgggca cggtgtgtgc tgctatcagt ggatacgcca ggcttccact   9780
gctggctgga ggttggctct gcatgtctgt gccttcctag gaggaggatg cagtagtgag   9840
tcagactggc atgggtgggg ccacatgtcc tggcaggtac tgtccgggca actggcatga   9900
gggagaggag tctttcccag aagcctgccc tgagaaacca agactgggct gctttcctgg   9960
cgccaaggga gagtccagtg agtgttgtac atacaactct aggtaggtgg ttggtggtgt  10020
gggcagcttg tgctgggaag aggattttgg agaaagcagg agagctctgg ccctccctgc  10080
aagggaggct tccggtcaga gcctgaggaa agacctgagc ttgaggtatg ggtctctgg  10140
ctcgaagaga gcattaagga tgcatgagat ctgaagtctg gatgaacttg ctgacaggca  10200
agcttttttt tttgactgct agtgtgtaaa tccactatag aaattttcat ttgtcattct  10260
tgtacttatt ggccaaaaat tagagcttat aggcatcaga tttaatttga gatagttgaa  10320
atagggtttg tgtttgaggc caatataatt ttatctgcta atggcatctt ctggacttgg  10380
aggcagccct tctgtaccag aacattgtca caaagctttt actgtaaagc ttgagaacag  10440
actagtttgc tggatttggg catgtaacta acagatttga ggcatgggat tatcctatgg  10500
acttttttt ttttttttgc tttgaggttc tgactatatt aaggttgacc actttaagcc  10560
attgaaactc tcctataata catttgtgat gtagggccta agacatgttt gtttggtttt  10620
ttttttgag acatgtatct ttgctgtctt ttaaaagcag attatttttt atttatttat  10680
ttattttttt gagacggagt ctcgctatgt cgcccagggt ggagtgcagt ggccggatct  10740
cagctcactg caagctccgc ctcccgggtt tttacgccat tctcctgcct cagcctcccg  10800
agtagccggg actacaggcg cccaccacct cgcccggcta gtttttgta tttttagta  10860
gagacggggt ttcaccgtgt tagccaggat ggtctcgaac cctgacctcg tgatccgccc  10920
gtatcggcct cccaaagtgc tgggattaca ggcttgagcc accgcgcccg gccaaaaaag  10980
cagattattc ttgaagtgca tagagcagca accgattaat ggaattggta tcttcacatt  11040
tcatttactt cctcccaaca attttatagg atgcatataa atatttccaa aaaaggtgta  11100
cataatttct tactataaaa gtatttttat tttatatcag taaatttgtt aataaagagg  11160
aatttttgtt gttgttgttg taatcctacc accccaatga catcctatta aaatatcagt  11220
atatatcctc ccaggtcttt taggtatgtt taatttggtg tcccttcccc actcccaaaa  11280
ggggagggac caggttcttg tatagaatag tggaatgtta gtaaatcacg tgtttaaaga  11340
gacataacag ctgaatctgt agagcagctg ccacctggat acctggttat taaggtaatt  11400
tttccattac cccaaagagc tttagttaca ctcagctttt accttaatcc ttgtacagct  11460
```

ctccagggca cactttattc agctctgagc ggtctttgca agtgaggcca aggagccaac 11520
ctgagccaaa aggagagcat tatgtcaccg gaagcccaag cccagagaac caaaggtatg 11580
acctgatatt cagtggcccc agccaggtct ttacaagaag accctgatat ctcaggtcta 11640
agaagagcca gctgatggtt tttaaaaaga gtggaattag ttactctgac ccacttactc 11700
agatcttatt ttgttcacaa tgtagtcccc agattgtagg cccattggag gccacagcaa 11760
ggcctttgtg ttccaactgg cctgctgtgc catctctcag taatgttccc ttaacagcca 11820
gacttcccta agcccagctg ggagctctga aggtatgcca gcccccccct aaccatgagt 11880
gtagggagag ggaccagggc gccccaggct ttcctgtcag taatgtagaa gtttctcaga 11940
tttagggacg tgggagcaga ggcataactt tgattctgac aaagaggcat tcagagagac 12000
tgaaaggtca tttaacaaac actagaatgc ttccacttac taggtgctag gaaatacaaa 12060
accatatagg tcctggaaga gaggatacat agtagatatt agaggcttag gaaatacagt 12120
tgaaatgaag aatggatttg ccacgttgaa tagttagttg gtatcttatt tccccatttt 12180
aaaagtttta gaatctgtgg ttgaggactt gtggccatca gttttccata gccgacagac 12240
tgttcactat tgccttcaga gctctttgga ccttaatagg ccttctttgg agatggcaga 12300
gatgggttta gatgcatact ctgctggagc cacccagaga gcccacaaag tcagggatgg 12360
aacagggtaa aggagtaagg gtcatatgtg tgagatgcct tgatttggaa ctttgagatt 12420
taggaagaga tggagaaggg ctaaagaggg acttgtttct gagccttgct tggctgaagc 12480
atttaggcta aagcgtttta gaaagagtag cccttggtgt gagaactcaa ggaaacaact 12540
ttctgatgag aaatgtagca agcttctggt tcacatcctt acctgatagt tcttcaaaca 12600
ctgcctggaa gcttctcctg agcctttgtc tctaatcagc taactaagag gctgagcgag 12660
tttagttgta agtcattaat gaagaaagca aaggtcgggg ccattgtcag ggttgtgacc 12720
tgggctagtt aattacctgg aactgatggt ctgtgttaca gagtggtggt atacttgtca 12780
ggcttagaaa agaaaacagg atgtgtatca aaaatctttt ggggaaaaga tttgaccagc 12840
aactttaatt tctctatgtt gcagctatcc tgttaatgta gttgtgataa ttttagaatt 12900
ataccagtgc ccttatgtta tccttgcttt gcaaattgct ttacgtgtcc taacgtcctt 12960
ctggccaaca gtagatgtgg ttttaggttt agcctcctag gatggaagct tttgcattca 13020
ggggaatgac tttgggttgg gtgaggattg taaagaggca atgtgggtgc cccacgacaa 13080
agcagctatt tgtagctttg tgacaacttg acatacagat atctaggctt atctaggcac 13140
taagctagga gttagttgtt tgtatcactg gaagattggt tataacttcc ttcgttggaa 13200
gctccttcat tgcatgttaa atgatgttat ttatagatag ggtggtggga aagctgtcta 13260
agtagatgtc agcctagtgt aagagagacc tgcttactgt gggtgcttgg gactgtcagc 13320
agtaggtggg aggttttaac ttgttcagta aggtccattt ccattgttca ccatcttgtg 13380
aaccctttgt ctaacatgag gagcaaccac ataaccacag catgtctggc ttccctgtgg 13440
cttgtgtaca aagcgtgctt attgagttaa tgtataagca ggagacaccc tcctgtgata 13500
aatggtatat taaccacttc tcagtcttac cactctgttt caatttgtct ggacccagga 13560
cctcagcagc catgtcgaag ccccatagtg aagccgggac tgccttcatt cagacccagc 13620
agctgcatgc agccatggct gacacattcc tggagcacat gtgccgcctg gacattgact 13680
caccacccat cacagcccgg aacactggca tcatctgtac cattggtgag tgggtgtgcc 13740
ccttccccaa aaaaagggct tcatggaaag tgaccctttc tctcctgaaa agacttaact 13800
aaatgtccta acaaacctag gtgctacatg ggatgctaca cagattctta taaaaggact 13860
caggtcatag gaagttgcag taacgaatta gtatgtgcac aggatggcaa atacagttaa 13920
taagagagta ttagacattt cgaaattgct aagatggcca ggtatggtgg ctcccagcac 13980
tttgggaggc caaggtggga ggattgtctg aggctagaaa tttgagacca gcctgagcaa 14040
cttagaccct atctctccaa aaagtaaaaa caaaagaaaa aaaaaattag ctgggcatgg 14100
tggcatgcac ctgtagttct gactacatgg gaggctgaga aaaagatcac ctgagtccag 14160
gagattgaag ttgcagtgag tcatgatcac accactgcac tccagtctgg gaaacagagc 14220
gagatcctgt cttaggaaaa aaaaaaaatt gtctgggtgt ggtggcacat gcctgtaatc 14280
ccagcacttt gggaggctga ggtgggcgga tcacctgagg tcaggagaac cagcctggcc 14340
aacatagtga aatcccatct ctactaaaaa taaaaaaaaa tagccgggcg tggtggcagg 14400
tgtctataat cccagctact tgggaggctg aggcaggaga atcgcttgaa cctgggaggt 14460
agaggttgca gtgaaccgag acctgaccat tgcactccag ccttggcaac aagaatgaaa 14520
ctctgtctca aaaaaaaaga aagaaaaaag aaaaaaacat tgctaagagt aaatttcaaa 14580
tgttctcacc acaaaaatgt taagtacttg aagtcatgga tatgttaact aacctgattt 14640
aattattcca cattgtatcc aaactgtatg tattggatta cataactttg taacccaaat 14700
tataaattac cagtttataa taaaaaacaa tttgttgcaa aaagaatcca tatgctttag 14760
gttttacgct ataggcaaaa tttagagggt gttttcctta gcaggtcttt gtaggagcaa 14820
cttacagacc taggaaagat ctttttaata tgttctgtgc aaccaagatt ctgtggttgg 14880
acatctggct gggtttcagt gagggcggag aaggctcgcc aagtcttaac ctaggctttt 14940
ctgatacagt gggagcctgc agaatttgaa ggaaatggtc gaagtgtccc agtaaatcaa 15000
aaaagtaagc tggcacggtg gtagccttcc atacactttt taaagacttt tgagctattt 15060
gggagaggaa aagttttcag ggaaaaaaat tctttaaact taagcaaact taaatgtttt 15120
tccttctttg aataattaat acttgtggct ttaaaacttt tcctaatagg cccagcttcc 15180
cgatcagtgg agacgttgaa ggagatgatt aagtctggaa tgaatgtggc tcgtctgaac 15240
ttctctcatg gaactcatga ggtgagctgt agctggaccc tgtggccatt gtgatggcct 15300
gtaggaaaca gggagggggt gcagtgttca tttagccaca acagattagg cagggatgag 15360
tctgagtttc acagccagtg tgaagtttgt ctttactagc ccatccctac tctccttccc 15420
tcttgtcctg gcgaagaaac tggctaagtc tcttttagca aagaagaccc cttttgtcac 15480
tggccatgtt tctctcacac acctctccta ccgttagctt tcacaaagga agatatggaa 15540
aggttctcct ggaaaaccct ctaagcctta gatgtcctgg ccacagcgct tgactctcct 15600
gtccccaggt ttctgctaca gcctgtattg ccatggtaaa ccatctagca gatcgattct 15660
ggcctatctt agaaccaaaa taactgggca ggtccatgag aagagtttcc attattctaa 15720
gttttgaatg actgagccta atgcacaagc actcgctggc gtataatacc cctcttcctc 15780
agcactatat tcccagcctg taccttccca ggagttctgt acattaaaat aacaccagtt 15840
agcactcttc ctcaggagcc tagtaggact gtatttgtga tgggctcttt attacctggc 15900
tttacctatg gacagaggcc ttgcccagga gccaggtagc agctgtcagg atggctccat 15960
tcctgcttct gttgccagat ttagaataaa cccattctga ggagtttggg gttccctgag 16020
gtaccatgac ttatttattt ttttatttta taagacaaaa ttttgctctg tcatccaggc 16080
tggactacag tggtatgatc atggctcact ggatccttga cctcccaggt tcatgtgatc 16140
ctcttgcctc agcctcccaa gtaactggta atacaggcat ccaccaccgt acctggctaa 16200

-continued tttaaaaaaa aaattttgtg taaatgaggt ctcactatat tgcctaggct ggtctcaaac 16260
tcctgggctc aagtgattct ctcaaatgtt ggaattagag gaatgagcta ctacccccag 16320
cctgggattg tgccttttta aaaccttcag acttaaccat agatttccca tagatcatgg 16380
gatttcgtaa tggcattgat aagaggaatc acagaagagg cagactttgt ccctgtcttg 16440
gcttctgtat ttcctgttga gagtaaagaa aatgctaccc tgtaaggcca agtgccttat 16500
agaggttgcc ctctggcatt tggaagttga tattaagttt ggactaaaaa taaagcctca 16560
ggaaatgcag tccaagagtg aattcctcct tttgggaaac ttgagactct tcatcataga 16620
ttccctaacc tgtgttcata aacagcctat ggcctggcta gtggctggcc cctaaatgtc 16680
atggggacct gaccaagtcc tgcagacata ccacgcaggt taagacatgt ccctgtacct 16740
tttggaaaat tctgtagttt tccaaaagca aggggtcctt agcaggagtc accgagaatt 16800
actacaagtg ttagcttagc ttaaagagag agagctgaag acaatggtgg aggtcagttc 16860
actgttgatc cctgctgctg tagtctgccg tgggctcctg cgttcaggga aaggagcaga 16920
aatagatttt taagaagttg acctttaagt aggctttgtg gttccttcat ccagtaaaat 16980
aacaccacat agctcttaca tggcaagggg gagtgatatc tgctgcacct gctggatgag 17040
agctggctcc gattttggtt ttttaaactt taagaggctt tttggagatt atctctgctt 17100
tcactcctac tcccagatta taattaagat ttttttaaa tttttaatt tattttttaa 17160 agatgtccct cttgtgggtt tattttgaag ttttagacca agatgaggtt gtctctgggc 17220
tcaatttgga aactgatttg aagttattct aatttgtgta atgtaacata aacagtttca 17280
accttaccgt ttgtcagggc tgttgtttca tatgcacctt tgactagggg ctgggatgta 17340
cttttctagt tcctgactat tttaaaggct cttctgagca gaacattgag attactgtct 17400
tccctctcac tctgacagag gaacatcaaa tgtctgcatc tgatctttta acagctttct 17460
ttttttgaga cagagtcttg ctctgttgcc caggctggag tgccctggca cgatctcggc 17520
tcaccacaac ctctgcctcc caggttcaag caattctcat gcttcagcct cctgcatagc 17580
tgggattaca gacctgtgcc accatgccca gctaattttt aaatattttt agtagagaca 17640
gggtttcgcc atgttggcca ggctggtctt gaactcgtga cctcgggtga tccaactgcc 17700
tcggcctccc gaagtgttgg gattacaggc gtgagccaca cgcccagctc tcttttgaca 17760
gctttggcaa ctagtcttca gccctcactt ttggcagttc acatgggcaa ggtgcattct 17820
tgctgaacat gtggttccat atgccgtgtt ttccagattt atttatttat ttagagagag 17880
agtcttgctg tgtcacccag gctggagtgc aatggcacga tcttggctca tcttggctca 17940
ctgcaacctc cacctcctgg gttcaagaga ttcttctgtc tcagcctcct aagtagctga 18000
gattacaggc atctgctacc atgcccggct aatttttgta ttttagtaga gatggggttt 18060
caccttgttg gccaggctga tctcgaattc ctgacctcaa gtgatatgtc tgccttggcc 18120
ttccaaagtg ctgggattac aggtgtgagc cactgtgcct ggcctagaaa aaatgacttt 18180
caaacaacct aaatgtagag ccttccacag gacagcattg atggatgaaa ctctttacca 18240
tgtaacatcc caacaaagcc acagctatag tagaagactc agtacacctc ccagaaatgc 18300
tctaagagat tataatatgt aacatagatt tgaataatac acctaataat tggtatgttt 18360
ataatacata gttttacatc cccaagacca aaaatgcatg tttgtgtgaa acactcatgg 18420
ttacaaatat atattaggcc accaaaaaaa acccccaagt ttcataaagt agaaattata 18480
cagacacatt ctctgctaaa aatttttaa tggaaattaa gaacaaagtc aagaaaactg 18540
aagtgtgctt actttagaaa gcaaagatct caaggtagat ggaataaata tttaactcag 18600
aacactaggg gaggaaaacc ctaaaaaggg tgaagaaaaa taattttgta agattatagc 18660
tcaatgaaat gaaaataaat ttgacaaatt aagctaagag ctgattattt gtgggtaaaa 18720
aatagtaaaa tagaaagttc tgggaagcca ggtgaagaat gcaaggatgt acaaataaga 18780
gtatgaatag aaaagggaat atttcctaca cattggagat tttaaaagtc aagaaagact 18840
tataacttaa ttcctataga gagagatgac actggctatt ttccaagaaa agattaaatg 18900
ccaaaaagat agaaaatatg aatagaccag tggccataag aagttgaaaa agtgggctgg 18960
gctcacacct gcaatcccag cactttggga agccaaggaa gagggatcac ttgaggtcag 19020
gagttcgaga ccagcctggc caacatggtg aaaccctgtc tctactaaaa atacaaaact 19080
ggcggggcat ggtggcacat gcctgcagtc ccagctactc aggagcctga ggcaggagaa 19140
ttgctagaac ctggggaggt ggaggctaca gtgaactgag attgcaccac tgcactccag 19200
ccaaaaagtt gaaaaagtgg ctaagatctg gttcatctca gaacatttaa gtccaaacga 19260
ttttagtggc tgaattgtct ccccttcaaa attcagttac attgttaaac tgttccagag 19320
cctagagaaa tacagaaatc ttcccactgt gttctttgaa accaacatac tctgatactg 19380
agatcagaca aggacagtac caaaaccagg caggtactaa cagcgtgcta gaccagtctc 19440
acttagatgc agaaaacaaa taaaatttaa taatccaaat ccagtagtga ttgaaaggaa 19500
tgtcttgatc catgaccaag tagattttat tctaggagca caaaattcta cattaagatt 19560
aagtagagtt aaggttgact tttttttttt tttttttttt tttttttttt tgagacggag 19620
tcttgctctg tcacccaggc tggagtgcag tggccggatc tcagctcact gcaagctccg 19680
cctcccgggt ttacgccatt ctcctgcctc agcctcccga gtagctggga ctacaggcgc 19740
ccgccacctc gcccggctat ttttttgtat tttttagtag agacggggtt tcaccgtgtt 19800
agccgggatc gtctctcgat ctcctgacct cgtgatccgc ccgtctcggc ctcccaaagt 19860
gctgggatta caggcttgag ccaccgcgcc cggccgactt tttttttttt ttttaagacg 19920
gagtctcact ctgtcaacca ggctggaatg cagtggcacg atctcggctc actgcaagct 19980
gtgcctcccg ggttcacacc attctctgcc tcaggctccc gagtagctgg gactacaggc 20040
acctgccacc aacgcctagc taattttgtt tttgtatttt tagtagagat tgggtttcac 20100
cgtgttagcc aggatggtct cgatctcctg accttgtgat ccccccctacc tcggcctccc 20160
aaagtgctgg gattacaggc gtgagccact gcgcccggcc tgagttaagg atgactttta 20220
aacaacctaa atgtagctaa atatagagcc ttctgcagga cagcattgat gggtggaact 20280
ctttaccaca tgataacatc ccaacaaagc cacagttatg gtggaactca gtccacctga 20340
gtcttaccat tataagatga taataatagg taacatttgt taaataatta ccatgtactt 20400
tgtcctaata cttaatgtat tcctttactg ctcacatcaa ctctgaagga aaggtaccac 20460
atccccttaa aagaaaacaa ctatttctat tctattcttt tatttttttt agagacagaa 20520
tctcactctg tcacccaggc tggagtgcag tggcacgatc taggctcact gcaacttctg 20580
cctcctaggt tcaagtggtt ctcttgcctc agcctcccga gtagctgggt ctacaggtgc 20640
atgccaccat tcccagctaa tttttgtatt ttaagtcaag atggggtttc accatattgg 20700
cctggatggt cttgatctct tgatgtcatg atccacctgc cttggcctcc cgaagtgttg 20760
ggattatagg cgtgagccac cgcacccagc ctctattcaa ttctattttg ttctatttct 20820
attacaagcc agtaaggaag aaaatatcat aatttataag gaaccctata aaaaacaaac 20880
aagccaacgg tccctcatta gggagtatgc ctgaataaga agctgaagat tttcagatac 20940
aggcttcagg caacattgtc tttagaggct aagctctggc tccagctccc tccagcatcc 21000
tgtgaataac aggcaggctt acttgcaggt gccgctttcc tggacagtgg tggttaaagg 21060
acaaggccca gaaagtgctg aattaggtgc ccttgttatc agcaatgtca tattgatcac 21120
gctgtcttag agctctttcg acatcttggc tctgcatctt tttttttttt tttttttaaa 21180 tctttttttct tgagataggg tgttgctttg gatagtaggg tatccaggcc agagtgcagt 21240
ggtatgatca tggctcactg tagccttgac ctcctagaca taagtgatcc tcccacctca 21300
gcctcacaag tagctgggac cccatgcacc caccatcatg cacagttaat ttttgtgttt 21360
tttgtagaga tggggtttcg ccgtgttgcc caggctcatc tcaaactcct gggcccaagc 21420
tgtcctccca ccttagcctc ccaaagtgtt tggtttacag gcatgagcca ctgtgcttag 21480
cctgagtccc tcttttaaac aaacaaaatg gtaaatggaa aggaggaaag gcttaagaaa 21540
aaagattgaa gcacagattt gttgcaagca aggaataata aagggcagtt catttagaga 21600
aaggcatatg accacctttc cctgtctcca gtcagaatct agaaagtgat tgaggctggg 21660
cgcagtggct cacccctgta atcccagcac ttttgggagg ccaaggtggg cggatcacga 21720
ggtcaggaga tcgagaccat cctggataac atggtgaaac ccagtcccta ctaaaaatcc 21780
aaaaaattag ccaggcctgc tggtgggcgc ctgcagtccc agactgaggc aggagaatgg 21840
tgtgaacctg ggaggcggag cttgcagtga gctgagattg tgccattgca ctccagcctg 21900
ggcggcacag tgagactgta ttcccccaaa aaaaaagtga ttgagaaaat caggtctgtg 21960
tgaccttagc aatgagttgt ttagcttggg ccactgttag cttaagtcaa taacttcaag 22020
tttgcgttgt agttggaatc aatagaggaa aagctctcag cattaccaca tatatcagaa 22080
tgtgacattg attgccagat cagccttatc caaacacaag ttctaggctt tttgccctgt 22140
ttatcagctt tatttgctga gggtatttga tgagtcttag ggaaaaaaga acagccctgg 22200
gaacacagct gcttttatga tgagacatgt ttgcacccat accttaatgg gttttggtgg 22260
caatattctg aaatttgcca ccaacgtttc aaagatttgc ccttagggtg aattactgct 22320
gtagtagaag tgggtggagg ctgaggagat tggattaagc aggtagagga gttctcagtg 22380
catggatcgt tctgaggatg gagatagagc tctaagacat ccacaggcct ttcctgagtg 22440
atcagctttg gctcctgggc agggaaattg agctggatcc tagtgtggga gcacgcttgt 22500
catcttcctt ctttttcccc agtaccacgc ggagaccatc aagaatgtgc gcacagccac 22560
ggaaagcttt gcttctgacc ccatcctcta ccggcccgtt gctgtggctc tggacactaa 22620
aggacctgag atccgaactg ggctcatcaa gggcgtgagt attctgtgga gagcgaggga 22680
aagactcagt aggcaatatg ccccagagac atgtcctcca aagcgttgag atgccgtgtt 22740
tcatcccagc actatgaagg actgcagagg agttgaggtc tacaaatgag ggtttattca 22800
tcactgtaaa caacgttgat ttgatttact ttgctaggaa atggtaccac agaggaaccc 22860
tttttttacc ctaaaaacct aaactttagg ctttctaact tggggaacca tctctttgta 22920
tctttttccc catcattaag tagcataact gaaacattat attctatttt cttagattat 22980
ttctgtgaag tgtactgagt tagagaataa gagcaaaaaa ctgtattatt tttagcggtg 23040
acttgagcat tgttccctgg aggaaagagc ttttccattg cttctgcggt gatgctgcta 23100
ctggtgtctc cagtttggac tctggcttac tctcttgctt actccctaga gcggcactgc 23160
agaggtggag ctgaagaagg gagccactct caaaatcacg ctggataacg cctacatgga 23220
aaagtgtgac gagaacatcc tatggctgga ctacaagaac atctgcaagg tggtggaagt 23280
gggcagcaag atctacgtgg atgatgggct tatttctctc caggtgaagc agaaaggtac 23340

```
gtatgggagc tggaatccaa ttgtctaaaa cccatctttt gtctctaaag ttccttgaca   23400
caaggaagat gggaaggttg gttgcctggc agtgagattg agtctgtgtg ttctcaggaa   23460
tccctttat aactcattta tcctcaaaga caggctttaa tccagcatag ttacattctt   23520
ctggttccgg agaacatagg aacatatata tatacacaca tatatttctt ttttgagaca   23580
gagtctcgct ctgttgccca ggctggagtg cagtggcacg atcttggctc actgcaacct   23640
ctgcccccag ggttctagcg attctcctac ctcagcctcc tgagtagctg ggtttacagg   23700
cacccgccac cacgcctggc tagttttttt gtatttttag tagagacggg gtttcaccat   23760
gttggccagg ctggtctcaa actcctgacc tcaagtgatc tgcctgcctt ggcctcccaa   23820
agtcaaaaca atcttaattc ttcctttttta tgggtgtgga aagtgaggta cagagaggtt   23880
aaatggcttg cctaggatta cacagttagt tgtagtaggg tttcaactct ggtaaaacag   23940
ctccagcacc catgatgcac cacttcccag ctcactgtgc ttgggggaaa ggtgcctgct   24000
tcctgttgag ctgtgccctc ggtgctctgc ctcccctgct tacccctttt caaaacacag   24060
gtgctgactt cctggtgacg gaggtggaaa atggtggctc cttgggcagc aagaagggtg   24120
tgaaccttcc tggggctgct gtggacttgc ctgctgtgtc ggaaaaggac atccaggatc   24180
tgaagtttgg ggtcgagcag gatgtcgata tggtgtttgc gtcgttcatc cgcaaggcag   24240
ctgatgtcca tgaagttagg aaggtcctgg gagagaaggg aaagaacatc aagataatca   24300
gcaaaatcga gaatcatgag ggggttcgga ggcaagtccc cattgtccct gctccagtcc   24360
cagcgcagct ctctaaaggg catggtgcat cctgtgaata tctgattccc atcagaatgt   24420
agactcccaa acctgttcca aacctgctga atcacaatat cttagtagag tagaaggcat   24480
tgtgtgtgtg tgggttttgt ttttttgttt tgttttgttt tgtttttaaa aagcttccta   24540
ggtaattgag atgctggcag cttgacattg ttccctgggc ctggggacca acatttgaga   24600
gaacagggtc actgctcata gtaccagggg ccatgatgct ctgttcctga tcagaaacac   24660
taccagtgtt tgctggaatg tggggaccgg gggaaagatg acagcagaca cttaagaagg   24720
ggctcgtttt ggcccttcct ggggagccat gtggaatttc aggggctggt gtccatgcta   24780
aaacatatgg cctcctggtc ttcacttaga acgcagctgg ctcagtgatc atgctaactc   24840
tggtatggtc cattccactc tcagagtaag atgtgtggtt cttctccggg gtcagattgc   24900
ctcaacttag cttaccccct ccacagtgct catgaggtgg agcccagtgg gcatggccac   24960
cattttggc atcctgctag gaatacaact tagcactact aagatgctag acctacgctt   25020
gtggattagg agtgtgtttg gggagggtgg gggaacaacc ctctgcaccc actgtagtgg   25080
ccttactgtc ttagctttgt gtagataccc tctgtaccag gcaatttggg gccctcccct   25140
ttgccatcct gataagctga acttggcgct aggccaggca aagccacatt ccctcttgcc   25200
ttcagcaggt tggagtgggc cacctcacag ggcagtcttc aagtgtcctt gactagataa   25260
ggccatgggg ctttgtggtg gaagcagtca gcaggcttg ggttccctgt cttgaagtgc   25320
tgattggaga atggaggccc tagagagaca cctaacatgc atgggatttg gagaggagac   25380
cttgggaatg agcccatttg gatttgccct ctcccctttc ttctgtcaat gaagcatcca   25440
tattggtgtt gaagcccagc aggcagaatt gttggcccgc tctgggggac taaggtagct   25500
ggactgcctt gccatctgtg tgcatccatg atgatgtcat ggatgtctgt cctggtatga   25560
ggacatctaa gttagggaat cccagggaaa cttcttgtct accggcatac ttgtggcccc   25620
tgtctgtata acctctctcc ccccaacttt gtccatcagg tttgatgaaa tcctggaggc   25680
```

cagtgatggg atcatggtgg ctcgtggtga tctaggcatt gagattcctg cggagaaggt 25740
cttccttgct cagaagatga tgattgggcg gtgcaaccga gctgggaagc ctgtcatctg 25800
tgctactcag gcatgtgacc acccctcccc acattctcct gggcacactc acatgtgtgt 25860
atgggaaagc tctggaggct gtctgatctt ttcccatgga attgtcccat gtaacacaca 25920
gataatcccc ttcccccatg cacctacaca aagccatgct ctgtgcacct actcactatc 25980
cagaggatca gcgtgctgtc atttgtctct gaaaacagcc caagccacat ctcactaatg 26040
ctctgttcct cccagatgct ggagagcatg atcaagaagc cccgccccac ccgggctgaa 26100
ggcagtgatg tggccaatgc agttctggat ggagccgact gcatcatgct gtctggagaa 26160
acagccaaag gggactatcc tctggaggct gtgcgcatgc agcacctggt gagttctggg 26220
gcctgcccca tcccctgggc tgtggactgg gcctgggttg gatgcaagct gtggtgcaga 26280
gctttttagg tttccatatc ctcttaggca cagccgttca ttatcctcca agttacagca 26340
gcaagagggt gggggtggag gtggaggtgg cttttttttt ttttttttt aattctgttt 26400 ttcattcctg ccgacacccc caccccctcca tttccttctg ctctggaagc atcctccttc 26460
actggacacc atacagttca tttcacttct gacttcaagg tggtgaatcc ttcccatggc 26520
ttaagtcctg ggatacttct gcagtgaagg gaggtcttgt acctcttcct cagagtcaga 26580
agttttgagt acctttgccc tattctgaaa agggctcggg gctcctgctc ccaactgccc 26640
tcttcctttg gcttccaatt cagtcccccg acccccacat cccgcagaca ggcgctcccc 26700
cagggagccc ctgtggacct gcactggagt ctgttgcctg cactgagctg cctgtgctgg 26760
ccttgcatgg tgcctatagg aggatttgct ttgctgtgcc attggggtac agctgctgct 26820
cttacaacag accaaaaagt caggttgagt gactggtggc agggccacag atagagacag 26880
cagggagggg ggctgaccct ggtggccctg gactgagcgt ctggaggagt cgtggaggct 26940
ctttcccttc tttctcctct gagagctcct tcttcaggct cttccagctt gtcatgttga 27000
gtgcctggcc actgctcagg gttggagact cagtcccttt gccctgtctg ttccagctct 27060
ggagctaact tggggatccc tgatcagggt tacataggtt tggtaaaatg agtgctggaa 27120
attaactttc tcccagtagt cttaggtcag gctcagtgaa cttcaacttt acccagatat 27180
ggtttttctt cagccattct attccctttc tagccagtga aagacccgct gccctttgac 27240
ctcagcccct ccaagccccc aagtttaaaa cgccaccccc cgccaccaaa aaaaaaaaac 27300
aactaaaaca cccacctcgt ctgggcatct tcctttcctt tttcactatg tgtcctgtta 27360
ctgggcttaa acagctttca gagaagagat gtcatttcta ttaaatgctc tttcagtagc 27420
gaactgagtt cagacttgac taaggatatt ttctgggctg tcatcagcat ccttagtggg 27480
tttccccata ttggaattgg tagaggccgg ggacggtggc tcacacctgt aatctcagta 27540
ctttgggagg ccaaggtagg cggatcgctt gagctcagaa gaccagccta ggcaacatgg 27600
tgaaacccta tctctactaa aaattcaaaa gttagctagc tgggcgtggt gatacacttc 27660
tgtagtccca gctacttgga gagggggtgg tgctggggca gcaggatcac tgaacccagg 27720
aggttgaggt tgcagtgagc caagatggta ccagcctagg tgacaaagtg acaccctctc 27780
tcaaaaaaga aaccaaacaa tcataaaaaa aggaaacaca aaaaatcagt agagagtgat 27840
ttctctccca ggcccactta acgtagcctg ggcctggctg acacctcacc gtttgtgcga 27900
tgtgattgct gttctgatgc tgagatcctc ttggcgcagt ctcacaattg ctccatggta 27960
ggaaggtgtc ccagagacag tgcaccttca accagtcacc actaaagtga ctgcctttct 28020
gggtctctcc acacgtcccc tctgtctaat tcccttactt aattgtgtaa cttcatggcc 28080

-continued

```
tcaaaggtgg gacagaggct gatcttgact tagatttact gaaccatgaa atcactgcat  28140
agaatgtgga gacttgaatg tgtcttttgg caagtcattt aacttctcaa gaccttatct  28200
gtaaaatgga ttagatatgt ttaattatag ccttagcatt aaatattcat tgctcttatt  28260
attaagtgtc tgataagtct ctgtgtatat ggatgtaatc ttcctaactc ccattacctc  28320
catttatagc cgagggttat atggccaata aagcctgggt ttgaatctag gtctgctgac  28380
tccaaagcca gtcttctctc ctgcaacatc atgctcttag gtctagcagg agatgagaac  28440
aggtctccat ttggagcctg tcagtggggt cggagactaa gaatcaggct cagcttctaa  28500
atttcatgtc ctttcctcca taccctagtg tttcctatga acagacagat accttagagc  28560
tgcaaggctt ggattgcatg gcagtgctca gaagataagt tacaggtctg ggccaggctg  28620
tagctgcccc tccaggtggc tagacctttc ctttctgtgt caccagttaa cactggccaa  28680
cagttccttc ccttcactgt tgattgcttt ctctgtgtct aactgatgca gttaatgacg  28740
cataactaag agcagtagca ggtatggctc tgtttcgtgt tcctgttccc tgtcctctgg  28800
gttgcatgca ttccattctg ataaaaagaa tacctttaac ctagtacatc ctgccacaca  28860
tctgcttcta ctgtgaaatt catgaggggc tattaccgat tcctccctca cccatcattt  28920
acttagatgc tggtgattgc attataatcc tctaaagctt acattgtctt tctgattctt  28980
ggtcttatct gagcaagtga tctgtaaata acccagtggc tttctcatga ctgttttaat  29040
cattagattt taatcaagtg tcttattaaa catatctgca tgcttccaca gacatctgtc  29100
tcttcacatg gctgttcagt gtgtctctca cgagttagcc caagttttct gttctcctgc  29160
ttcaaactca gttgagctgc cttgctttgg cttggatccc agctttccag cgctgctcaa  29220
tctgtttcca tggcaggcca ttggaaaggc tcagtgcatc cctgtgcctg aagccaagtg  29280
agcgctcact gcgtgcatgc atggaggctg ggcaggagtc tgcctaacca gacagccatg  29340
tgaggaggga gggcctgttc ctttctgtaa gctatgtcgt gaggcagcgt gatcaagtcc  29400
tctgccaggg agtggtgtgg gcccagcctg ggcatgtttt catgccagag tgctagagcc  29460
tactgccaga ttgtctccct ccatccccaa tcaaatcctt ccagaacgga agagccaatt  29520
tcccctgtgt tggaggggaa gtggcagcac ctcctgaagc agttggactt tcatcaccct  29580
acctccgcat ctgcctgaag gacagattta gccaattaac ctaaggttac cttcctctct  29640
gattaattcc ccattctgtc ttcccatgtg ttgtgtcttg ttttttcct cctccttccc  29700
tcttcctttt cccctcttcc cctaaacctt acagatagct cgtgaggctg aggcagccat  29760
gttccaccgc aagctgtttg aagaacttgt gcgagcctca agtcactcca cagacctcat  29820
ggaagccatg gccatgggca gcgtggaggc ttcttataag tgtttagcag cagctttgat  29880
agttctgacg gagtctggca ggtagggccc taagggcagg taacactgct aggataacca  29940
gcctcttgct tcagctgttc caggagaaga cagccaggcc caacctggca cctgggcaca  30000
gagcctcttc ttgtctatag gaacaccgcc agggaggtca tggcagggca ggaccaaagg  30060
gtcctgtggc tcagtaggca cagcagatgt cacaggcact tggtgaagga ctggtttctg  30120
tggagtcttg aaattggctc agctcagcat ctccagtgac tgggctactc ttggcctttg  30180
tccctaggaa catgttcctc accagctgtc cgggtgactc ttcccctccc tctccttctg  30240
tgacaaagct ctgacaaagc tctgtccccc tctcgtccct ctggacggat gttgctcccc  30300
tagattgccc gtgaggcaga ggccgccatc taccacttgc aattatttga ggaactccgc  30360
cgcctggcgc ccattaccag cgaccccaca gaagccaccg ccgtgggtgc cgtggaggcc  30420
```

-continued tccttcaagt gctgcagtgg ggccataatc gtcctcacca agtctggcag gtaggaggtg 30480
gcagcggctc cctgggatgc cccgctcagt ggcacctctc cttgggggtc ctgggagcag 30540
tgcattgaac aatgctcagg tggcactgag ccaaggtaag acccctctgc ctgccacctt 30600
gggcctgcag agaaggattg agcagagccc cttccctggg cccagaggac tctaggcagc 30660
acacataagg aatgtcagaa catttggatc aaaagcaagt ttatgctgga gatttattac 30720
ataaatagtgc acaggctgac tacaaatggt tatttgatat tgaaaattta gtagccaggc 30780
gctgtggctc actcctgtag gccgggcgcg gtgacttgtg cctgtaatcc cagcattttg 30840
ggaggccgag gtgggcggat cacgaggtca ggagattgag accatcctgg ctaacacggt 30900
gaaaccccat ctctactaac aatacaaaaa attagctggg catggcggcg ggcgcctgta 30960
gtcccagcta ctctggaggc tgaggcagga gaatggcgtg aacccaggag gtggagcttg 31020
cagtgagccg agatcgcacc actgcactcc agcctgggcg acagagtgag attccgtctc 31080
aaaaaaaaaa aaaaaaattt agtcctctaa aatagtaaaa gataaccact tttgcttatt 31140
ccagttacta tgtgctcttt aaaaatttca gttgggaaaa tgaatttatt taaatgctgt 31200
ttactgtgcc tccatttggc gcactagtcc ctgctgtttt cgagccctaa agacaaattg 31260
gtttccagct caggagaggt tgctgtgcta tcttggctga cattctgtgg ggccaggcag 31320
ccaggctgag gactgtgtgg cctatgctga gcctccaact tgggatccct tccttagccc 31380
aggacattga gttaatgtcc ttcactctcc tagttaggga ttatgctcct tgtccctgcc 31440
cacagggcag cgagggtttc ctggagaaga gcaaacaggc agtgcccatg cactgaggag 31500
cagcaggtgg gcatgggcag cccagagaac caggacacaa gctctgtgca gatgccctca 31560
gcagagggct gcagcctccc actcttggct gaacagcttc aaccagtagg gttgaccttt 31620
cttaaaaggt ccagttcttg ctgtttggct attttaagct ctagtcttct ggggtttcac 31680
tcagctggtc ctagcttcag cagttgcttc cctctgatgg ccttgcatat aggccaagcg 31740
tgaagtgcag ggacttctct gctatgatat ggcttaagtt tccctgacac ctgttgagtg 31800
tcctcataac ttcccttctg gtgcccctcc ccagctcctg agacacagct gcacctacaa 31860
gtgtgcagtg tcagtgttca agaaagcgcc tggcacaggg gcttcagaag ggtcccctgc 31920
cttccaaagg agctttggca ggcagagctg ctcctgcacc aacactccca tttcctgttc 31980
ttgcctgctg agtagcactt agatttctaa gcctcaccta gatactcaga tttgactctg 32040
ggcctttata gcccagttgc tggactgttt caggagccag gggccatgtg ggacagggaa 32100
gagggcacaa aagtagagaa gcctgatgtt gattcccatg gggctggtca gctctgctac 32160
tgctctacat gctacttggc ttgtaggtgt caccggcagc gagaggaatg ggtgctggtg 32220
acactgggcc agggctgcct gtctgtgtca gagtgtagga ggggttctgc caaccatggg 32280
ctgtgtgaga taagtgggtg aggctgacct tgggtcaaga taatcctggg tcaggataat 32340
cctgggccct tggcctgtgg agtgggggta gagggcagat ggtagcctag cctgctatgg 32400
aggatatagg atgaggggct gccctagcct tgggaggggt cctagggagc agatgttgaa 32460
gaggccagag ccatcagtga gctgggtgag aggatgagct gtttgaatac cctgaggtac 32520
ttcctggggc cttgtgtgat ggtctcttct gtatgtcccc catcccatct caggtctgct 32580
catcaggtgg ccagataccg cccacgtgcc cccatcattg ctgtgacccg gaatccccag 32640
acagctcgtc aggcccacct gtaccgtggc atcttccctg tgctgtgcaa ggacccagtc 32700
caggaggcct gggctgagga cgtggacctc cgggtgaact ttgccatgaa tgttggtacg 32760
tggctggagc aggggctaga gcctagaggg gtttggggat gcttgagcat tggcttctgt 32820
gggaccctga aagtttgggg aatagaaagg gaaacataga ggggcaaaag gcccagctga 32880
ctgttctctc cctcattggg aatgttcttt ctgaatctgt cattcccgga agtcctaagc 32940
tgagcccagg agagaaaagg gtcctttgag ttgtagggtt gagcagttcc tttcctcttc 33000
tcttctagtc tgggactcaa agcacaattg tccattcttt ggcatctgct cattactgag 33060
ggttttgttt ttgtttttgt tttttaaata aaattggcta cagctcctgt gctgtggggt 33120
ggcatacaca gattatgtac tgatgtggcc attgtccctg tataaggtag ggtatcacca 33180
gatgacagga agcagctagc tcttgaccct gggcaaggct ttgcaccctc tggaggatga 33240
agtgaaagat gtccaaaggt ccctgccaac cctgccaacc ctgccatctg agtgataagg 33300
acatttcagg gcctccctcc tgtttgcctg ggctgtaagt ttggtgccac cttgtggtgt 33360
gaggaagtag tggtcagcca gcctagttca gtgctcaggc tatggggcag ctgcccaggt 33420
gcacacctgc ctggcttggc ttttacttac caatctccct tctcttcctc caggcaaggc 33480
ccgaggcttc ttcaagaagg gagatgtggt cattgtgctg accggatggc gccctggctc 33540
cggcttcacc aacaccatgc gtgttgttcc tgtgccgtga tgaacctgag agcccttcct 33600
ccagcccctg tcccaccccc ttcccccaac ccatccatta ggccagcaac gcttgtagaa 33660
ctcactctgg gctgtaatgt ggcactggtg ggctgggaca ccagggaaga agattagtgc 33720
ctcgctgaaa catggctgtg tttgcagcct gctctagtgc gacagcccag agcctggctg 33780
cccatcatgt ggccccaccc aatcaaggga agaaggagga atgctggact ggaggcccct 33840
ggagccagat ggcaagaggg tgacagcttt ctttcctgtg tatactccgt ccagttcctt 33900
gagaaaaaat ggatgcccag aggactccca accctggcct ggggtcagga aacagctaga 33960
gagttagggg ccttagggca aggggctgtt gtccccttga agctgactct ggccctggcc 34020
cttacttgct tccccagccc cctgggcctc cccagttcgc acctgtcccc gccctccact 34080
cagctgtcct gcagcaaaca ctccaccctc caccctccac cttccatttt cccccactac 34140
tgcagcgact actgcagcgc ctccaggcct gttgctatag agcctacctg tatgtcaata 34200
aacaacagct gaagcacc 34218

<210> SEQ ID NO 47
<211> LENGTH: 31207
<212> TYPE: DNA
<213> ORGANISM: Chlorocebus sabaeus
<220> FEATURE:
<221> NAME/KEY: modified_base
<222> LOCATION: (30235)..(30244)
<223> OTHER INFORMATION: a, c, t, g, unknown or other

<400> SEQUENCE: 47
atgaaggcct gtgattcagc tgcaggcagc gggtaagcct gagcaggtca cactcatttg 60
gtctcttttg ccaggaaaag aaaaaagaac ctaagagaac ggtcttcgca ttttgaatgc 120
gcaacattgt atctgtgaat gaaggcaaga gttaacagct gtttaattga taactgctca 180
catcattggt tgctggctaa caattgggaa atcggaaaat gtcttgtaga aaaatgtaag 240
aaaagttcca acaatattga tttaaattca taacaagggt gaaaacagaa atgctgactc 300
ctgcataggt tatcggctct aatgttctga cttgatattt ccagatgccg agctctgcgc 360
taatatcaac accgtctatt tgctttttac tctcaggcat tcgctctgca ggattccaga 420
ccctactaaa ttattcacat ggccccaacc tgtccttcct tgttccgcgg ttctaagaca 480
acaaatggtc ctaagaggaa aagggcctcg cgctcccgct ccaggttcac gtcgcagtcc 540

-continued

```
ctagttctcc ctactgccgc tccagtgcca gagcccctcc gaaggcggtc gggacctcca    600
accacgcaca agtctgcagc tctcctcaac ttcccgttca gctcagtctc cgagggtgcg    660
ccagggcaga cacccagagg agtggagagt ggcagggcgg ggccgggaga atgctgcccc    720
ggaacccata aatctgggcc ctgcccaggt aggccgggac agttggggtg gcctgggccg    780
agagccaaga aaagagaccc catccggcag cccaacttgg cggcaacagg tggcccggcg    840
cccgggggtc taggagggaa gtcgctctag ggcgggctc cgctgccccg ccgcgttccc    900
attggccgtc aggtttctta aactgtgact ctgaatctgt gtccttccgc cgcagaattt    960
agttcccccg aaagggcaac ctgcccgcgc gttccgccgc cgccaccgcg cttcctcctg   1020
aaggtgactg cgcccgcgaa gacgcagggg gcggggtccg ggtcgccggg agccgggatt   1080
ggacagaggg cggggcggcg gagggattgc ggcggcccgc agcgggataa ccttgaggct   1140
gaggcccctg ctactcgcac tgcagctgca cgtccctggg atccacatct cttccagttt   1200
gcagcgtagc ccgagtcggt cagcgccgga ggtgagcggt gcaagaggct gcgccatctg   1260
tcctcaccaa gggcccgtgc acccggctag tgcggaatcc cggcgtgccg gcgggcccgc   1320
gcaggatccg gggcgtctgg gacgcggtgg agctcagaga cgggagaatg gctcctcaga   1380
agtccccagc gccgttcctt ccagatcagg cgggtccgcc ggctcctttc ccgtcccagc   1440
cctacccccct cattctggtc ccatcctcct gccccagtcc tcaatgcgcc tccatccttg   1500
cctgccttct ctcggtcctt cgtgattgat tccacccttg cctcccctttt ctccgcgccc   1560
tctgctccgt gctcgtttgt tccacttcct caagtcctgt ccttccaccc actcctctta   1620
aacctgtgcg tgccccttca ttctattggc ttccgtgtaa cttactgaaa ctccgttctt   1680
gttcccctcc caggtccatc ctccattcat gcgcgaccgc ccttcccgcg ccccagtccc   1740
ctcttgtcgc ccctccccct gcttgctggt cacgtccgct ctcccgcatc cccctcctcg   1800
cctggcatgt cgcctccctc cctctctgct ctggtcgcgc ccgcccactt gctccggtct   1860
ccgagcgcgg tcccgcgccc cttttccatc accgcctccc agctcccagc aggttcgggc   1920
ggtgctgggg ccccgtgtcc ggggcgggcg ggcggagggc tgggctgggt gccccgcgcg   1980
gcgggcggga tgcggcggcc cgggagcagc tggaggctta cgtaacgttg gcctgccccg   2040
ctgccgggag gcagggcggc tgcccctgcg gcgcggtgct gtcccatgcg accgggatta   2100
gatgggtggc ccgcgagggc ctgggaatgg ctcgggaccc gcgagctcac ccggcccttg   2160
ccgggtggcc accagggacc acgctccatc tcgccgcggc cgggctgcac gtagcggccg   2220
cgcccagggt ccaccccgct tcaccgggcg gtggccttgg gccgcgtaac gggccgtgga   2280
aacgtctgca ggcttcgctg gggcctgccg gccctcgccc gctccgcgcc tctccggcac   2340
gttttttttt ttttcttttc gtttttttctt tttttttttt tattatccag cacgtttttt   2400
taacaaatgc gccctgattg tggaacgcgg aggccgcggg gtggggtggg ggtgggctct   2460
ggttacggag ggggcaggaa atctgtggcg ttcactcaac gcaaacggtg tgggtcaagg   2520
gctgtttggg ggtcggagtt agagaccaga atgactggac gagtcatagc ccaccgagct   2580
cacaatctta aaatgtatac cccgtaatgc tgggagtggg gcacgagctt cctgctgtgg   2640
gagggagggg gacaggaagc ctcgtaaggt ctcaccaggt ggcaagcaca ctggattaga   2700
agatgcagga aagcaccttc cagtctgaag gtcatttaaa gactagtcaa ggaaaggcat   2760
ccctgggctt cttaatctgc atactccaga cccagggctt ggacctttgc tggtacgggt   2820
taaagtgagg cctacagtga aggtccacgt ggagagagac atcgggaagt tgtcagaaag   2880
gcttttagaa tcaggtttga ctcattaatt tcctgagact gattgaagga gttcagctgc   2940
```

tacacctcag tttcccctgg gaaaactggg agtaacattt tcctcatgat ggttgaaagg 3000
gttcatgcct acgtggatgt tgcacactca gttaagtgtc taatctctgg cgaaataccc 3060
agaagaaaag cctgtgaatg aatatattat tttcgagcac aattacttag tccagaattg 3120
agcataaggg ccttgattca ttatcttact gctgtctgca aacgcctgca gctaatcgtg 3180
gggaatcagg ctctctaacc acgtgtctcc tggaaaccag tccccccagg gatctggttt 3240
aatattgaca aagtcactga tgatgtaact ttccaactct ctgcttggag cagatgctct 3300
ttgatcatct gagattggga cctctagagg ggctgagtta agccttcggt gttcccctgt 3360
aagtggaata cctcttaaca ggggaacatt ccagcccttg atttgctctg cctgctggtg 3420
agattaggat tggagcctgg atcagtaacc cccagttggc catcttgagg gcgtggctac 3480
tcccgaggcc acagaggaga taaaggtcag gactccctgg ctgcagcatt gttagcaaat 3540
aatttgccct ttggtggcct gaggtgctgt gggggcagga gtgggctgtc ttgtggggaa 3600
gggaaatgta acgcatcacc aaatctgtgg gggagtgggg ctctgtgggg aagatgactc 3660
aacctgtcaa ttattctgct tttgagagaa ttatcttcgc tgggtgagtg gggaaactac 3720
gtagtggttc ttgcaggctt aaaaagtccc ttctcccctt tcagtgagtc aaataatgaa 3780
gcatgcattt cccctaatta aaaatgcctc agcttcggag cttgcggtga gccgagatcg 3840
cgccactgca ctccagcctg ggcgacagag ctaggttccg tctcaaaaaa aaaaaaaaaa 3900
gtgcctcaac taagtgaaaa atgattggtt cgggtcacct ggttctctgt actgccttaa 3960
gaacttaggt gcagagtggc agagcccggt gcccagctaa tgcagtctgt gcagcttcat 4020
tcctggccct tttgtagcgg gcacagcagc ctctcctggg acatgattaa tgatgactta 4080
aagaaagttc tttttttttt ttttttttga gatggagtct cgctctgtcg cccgggcggg 4140
agtgcagtgg ccagatctcg gctcactgca agctccgcct cccggattca agcgattctc 4200
ctgcctcagc ctcccgtgta gctgggacta caggcgcccg ccactttgcc cggctatttt 4260
tttgtatttt ttagtagaga cggggtttca ccgtgttagc caggatggtc ttgatctcct 4320
gacctcgtga tccgcccgtc tcggcctccc aaagtgctgg gattacaggc ttgagccacc 4380
gcgcccggcc ttaaagaaag ttcttgaact catttctcag ttactgactt gagccaaaat 4440
gtatggatgt tggtctcctg tctagcacag ctgctttcat tgtaagcatt gcgttagaaa 4500
taatgtattc atattttagc aaagagcatc attagctctt taagaactgt acccccagtg 4560
acttagcaaa tttggttgct gtgactctaa acagctagca ctttatggta gttgcttctg 4620
tgccttgaat gttgtgacac tgatgtgggg tcacaggaaa aaccatttta tttcttaaag 4680
ctgtttctta atattgaagc aatggaagaa atgaggaaat ggccatgggc aggaagatag 4740
aaaaaaatgc agcacttaca ttacaaactc actttacttg ggttttagtt tattttaaag 4800
cttcagggtt tttttgtttt gtttttgttt tttttttttt ttttgagaca gttttgctgt 4860
tgttactcag tctggagtgc aatggtacga tcttggctca ctgcaacctc cgcctcctgg 4920
gttcaagcga ttctcctgcc tcaacctcct gaagtagctg gaattacagg cacctgccac 4980
cacgcccagc taatattttt gtatttttag tagagatggg gtttcaccat gttggccagg 5040
ctggtcttga actcctgact taggtgatcc actggcctga gcctcccaaa gtgctgggat 5100
taccggcatg agccaccacg cctggcctgc ttcagctttt atgaaggcaa atccggatgt 5160
gttatcttgg ccaagagcta agactgagac cagagtacag gaaaatgact catttgacat 5220
taccettctt tctgaatcac tccaaaagcc cacagtcaaa tcccaattta actggtatac 5280

-continued

```
cacaagaatg cgttgcccct gtgagcagag ttttattgca acttcgaggg tctttgtgag   5340
attggtttat ttggtatgag gtcttaagga ttttaagttg tccctttaag catcagttct   5400
gatacagatg ggaatagaac tagacaacca gatatatgaa gaccatttgt gataccacct   5460
tacttttggg gagcttgcat ttttttacc aaggggcaga ctgaataatt gagtaatttg   5520
aatacttggg gcattgttaa agaagctgtt gggggaaggt gagcctgggt gagtggtgga   5580
gggtggcgtg cagcatctgc tgggctttcc ggcctcttgg tatgactgct cagctcagga   5640
gttgggggct ttagggcccc caccacccag tgtggcgaag ccccgcccct gcagtggttt   5700
gtgcttgtct gcacgtagaa gggagcaagc ccgctgcagt accttcggtg gcctctgaga   5760
ctcacctccc ccacttctgt ccatagacaa agctcctggg gagctctaag cctctttcct   5820
catgccagca agcagtcttg gaagcaggct ggggctgtgg tgggagagat gccaagacca   5880
gttattcaag ggcagtgagg ttgccagtcc tagcatttca gactgtggac cagcacagct   5940
gccggctgaa cactgcagtc aagattctct gaagggagtc ctatcccttc caaacatctt   6000
cagtttactt acagataatg tttcttcata ttttatttta ttttttgag atagagtctt   6060
gcactgtaac ccagggtaga gtgcagtggc acgatctcag ctcactgcaa gctctgcctc   6120
ccgggttcac gccattctcc tgcctcagcc tcctgagtag ctgggactat aggcgcccac   6180
caccatgcca ggctaatttt tttgtatttt ttagtagaga cagggtttca ccatgttagc   6240
caggatggtc tcggtctgct gaccttgtga tccgcctgtc ttggcctccc aaagtgctgg   6300
gattacaggc ttgagccacc gtatccggcc ttgtttcttc agttttaaac aactgatatc   6360
tcccttggca atgaatgaaa aagaactact catcggtgga atcagtcagg gcacataaga   6420
cccactgtgt ccaccatgcc atttcagggg agattcgatt gagttaagca gggaaataga   6480
gatgtcgtaa acgttgaaac tatctcggta tccctctttg gttattaaca ttagatgagc   6540
agaaaaacaa atgtcaccca tcagatgggc aaacatttaa aaagtctggc agtaccaagt   6600
gtggaaaaag gtgtgcaatg cagcaactca acgttgactg atgcagccac tttggagagc   6660
aattcagcca tatttagtaa aaatagaaat aaacataccc catgacctaa gacttcaatt   6720
tctggatata tagaaactca tacagtacag ggagacatgt actacaagag tagagtgttg   6780
attaatgagg aaaactagtt taatggggag ggggagtggc taccagtaag ggagtccata   6840
aataaaattg tctgttgtac agtggactag tgtaacagtt caaatgaatt agctagatcc   6900
atatacccac tggatggatc ttgaatgtgc tgctgagtga aaaacaagtt actcagtgat   6960
atatacagtg taccacttag ggcattaaga aaaccacaat atttataggg tttcagtata   7020
gatatagata cactgtacat agacttaagt gaactggaag gatacggagt tcatgacagt   7080
gattgggtgt caaaatgcat gatgtggctg ggtgcagtgg ctcacgcctg taatcccagc   7140
actttgggag gctgatgcag gaggatcact tgaggccagg agatcgagac cagcctgggc   7200
aacatcacaa gattcccatc tctatttaaa taaataaaat agaaaaaaaa gttcatgatg   7260
gaggtggaaa gggttggagg agcttgggga tggagaaaaa atgaactgta taaaaatata   7320
atttttttta tttttagaaa gtaaagaggg ccaggcgcag tggctgacgc ctgtaatccc   7380
agcactttgg gaggctgagg cgggcagatc acgaggtcag gagattgaga ccatcctggc   7440
taacacggtg aaactccgtc tttactaaaa atacacacat acacacaaaa attagccagg   7500
catggtggca ggcacctgta gttccagcta cttgagaggc tgaggcagga gaatggcatg   7560
aacctgggag gtggagcttg cagcgagctg aggtcatgcc actgcactcc agcctgggca   7620
acagagtgag actccatctc aacaacaaca acaaaaagga gcagaagaaa gtaaagaaaa   7680
```

-continued

```
tacagctcag cctttattat ttgtgggttt tttttttttc cttttttttc tgagacagag   7740
tttttcactc tgttgcacag gctggagtgc ggtggtgcga tctctgttca ctgcaatctg   7800
cacttcttgg attcaagcaa ctctgtgcct cagccaccca agtagctggg attacaggtg   7860
cgcgccaggc taattttttt atgtttagta gtgacagtgt tttgccatat tagccaggct   7920
ggtctcgaac tcctagtccc aagtgatctg cccacctcag cctttcaaac tgttgggatt   7980
acaggcgtga gccaccacag ccggccatgg cttagtgtta atggtcagtt ctgggtggta   8040
gagatgcaga tgttaaaact tttttttttc tttaattcat aacaaaatag aaggaaacct   8100
ataaaggcta ttgtaggaag accagtcata ctaactagtt cagtgctctt ggagagttgg   8160
cactgccttt cctcctttat tgccccaact agaatgcagg acagcccttc cattaaatgc   8220
tgagccagtg cctcactttg ctgaggccat aacccacctt agttgcactt aaggggaccc   8280
taaatcagga ttcctggttc tagagtgtgg atatcatacc cagaaacacc accctacttt   8340
taatcctagt aaggaggcac catgtcccaa ggcaactaac gcttccccca aaccacctcc   8400
ttcaggctga aaccagttgt ctgcactgag cagctgggat agagccagga aatactcggc   8460
atctgaggat actgagggtt ctctgactta ggacttcttc acctgaagtt gagtggtctt   8520
ttggggaagt aggcccattt agcatcagct gctcttccct attccacact gtagctggaa   8580
ataggacctt aggttcctgt tgacaagtca tttactttta gccctgaaga aataaaagag   8640
ccaagtgttt ttgtttgttt gtttgtttgt tttttaaagc aagggaattt tactagaacc   8700
tgtaagtggg ctcattttgt tctgtgtagc ttggtaacac catactgctt tctgctttgg   8760
ggcctgctgg ggttaaagtg tgggcttcag acccaggtct cttagctaga agatatctca   8820
tcctctgtat cctgcaccca tatgcaaata tgctattgtc attaccctta actgtatatg   8880
aagacagaca gtgcctaccc cagaccttac taggttctgc tggcccatca cccattttga   8940
tcatgttgct ggcctagttt gattagggca aatcttagaa attccatttc cgttgttgag   9000
gaagacagct agagagcagg ctgacccgaa tgccagaata tcatgatgca aactttctaa   9060
tggatgctgg tgttctaaag agttgaggat tgaaaggcct tcatgatggc ttgaagatgt   9120
aggtagcaaa ctgatgtcac agcaaggaac gcaatcttgt gtacttactg gcaacgttgg   9180
agagagaaag tgagcatcag gtgccactat tttacagttg atctgtgtga ggttggtatc   9240
ggagcataat tggtacaaag taaaaatgac ttaggcagat gcagactcac gggccaggct   9300
ggtttattag ggcagaatga tttggtcctt tgtgaaagaa ttggtggagt gaagcgtgaa   9360
tctttcccag cgcaacccaa caacagtcct ggccctaaga agtggagcat gggagctggg   9420
tgtggttcat gcctgtagtc ccagctactt gggatgctga ggctggagga tcatttgagg   9480
gtgcagtgag ctataaaata tactatacta tactatacta tactatacta tactatacta   9540
taatcatacc actgcactcc agcctgggtg acagagtgaa agcctgtctc aaaaaaaaaa   9600
aaggttggag tggggagtgt tgggtatttt ttatgatttt tgtctcctag tttctgaaga   9660
atggccgaaa aattgtgtct gatacaaagg aaactaatac aaagagccag gagctgtctg   9720
agatgagaaa ggaaagggag aatagggcac ctggagctga gctgtgattg tgcctgttcc   9780
aacctgtaac tccagactaa ggcctcttag agatggtgtc tcctttctca cagaggagac   9840
atggctctga ggaagatctt actgcagggg ctcgggctca agaataaggc tcctggacct   9900
gggcacggtg tgtgctgcta tcagtggata cgccaggctt ccactgctgg ctggaggttg   9960
gctctgcatg tctgtgcctt cctaggagga ggatgcaata gtgagtcaga ctggcatggg  10020
```

-continued

```
tggggccaca tgtcctggca ggcactgtcc gggcaactgg catgagggag aggagtcttt  10080
cccagaagcc cgccctgaga aaccaagact gggctgcttt cctggatcca agggagagtc  10140
cagtgagtgt tttacataca actctaggta ggtggttggt gggatgggca gcttgtgctg  10200
ggaagaggat tttggagaga gcaggggagc tctggccctc cctgcaaggg aggcttcagg  10260
tcagagcctg aggaaagacc tgagcttgag gtatggggtc tctggctcaa agagagcatt  10320
aaggatgcat gagatctgaa gtctggatga acttgctgac aggcaagctt tttttttga  10380
ctgctagtgt gtaaatccac tatagaaatt ttcatttgtc attcttgtac ttattggcaa  10440
aaaattagag cttataggca tcagatttaa tttgagatag ttgaaatagg gtttgtgttt  10500
gaggccaata taattttatc tgctaatggc atcttctgga cttggaggca gcccttctgt  10560
accagaacat tgtcacaaag cttttactgt aaagcttgag aacagactag tttgctggat  10620
ttgggcatgt aactaacaga tttgaggcat ggaattatcc tatggacttt tttgtttttt  10680
tgctttgagg ttctgaatat attaaggttg accaccttaa gccattgaaa ctctcctata  10740
atacatttgt gatgtagggc ttaagacatg tttgtttggt tttttttttt tttgacacgt  10800
gtatctttgc taccttttaa aagcagatta ttcttgaagt gcatagagca gcaactgatt  10860
aatggaattg gtatcttcac atttcattta cttccaacaa ttttatagga tgcatataaa  10920
tatttccaaa aaaggtatac ataatttctt actataaaag tatttttatt ttatatcagt  10980
aaatttgtta ataaagagga atttttgttg ttgttgttgt aatcctacca ccccaatgac  11040
atcctattaa aattttagta tatatcctcc caggtctttt aggtatgttt aatttggtgt  11100
cccttcccca ctcccaaaag gggagggacc aggttcttgt atagaatagt ggaatgttag  11160
taaatcatgt gtttaaagag acataacagc tgaatctgta gagcatctgc cacctggata  11220
cctggtaatt aaggtaattt ttccattacc ccaaagagct ttagttacac tcagctttta  11280
ccttaatcct tgtacagctc tccagggcac actttattca gctctgagcg gtctttgcaa  11340
gtgaggccaa ggagccaacc tgagccaaaa ggagagcatt atgtcaccgg aagcccaagc  11400
ccagagaacc aaaggtatga cctgatattc agtggcccca gccaggtctt tacaagaaga  11460
ccctgatatc tcaggtctaa gaagagccag ctgatggttt ttaaaaagag tggaattagt  11520
tactctgacc cacttattca gatcttattt tgttcacaat gtagtcccca gattgtaggc  11580
ccattggagg ccacagcaag gcctttgtgt tccaattggc ctgctgtgcc atctctcagt  11640
aatgttccct taacagccag acttccctaa gcccagctgg gagctctgaa ggtatgcgag  11700
ccctccctaa accatgagtg tagggagagg gaccagggcg ccccaggctt tcctgtcagt  11760
aatgcagaag tttctcagat tgagggacgg gggagcagag gcataacttt gattctgaca  11820
aagaggcatt cagagagact gaaaggtcat ttaacaaaca ctagaatgct tccacttact  11880
aggtgctagg aaatacaaaa ccatataggt cctggaagag aggatacata gtagatatta  11940
gaggcttagg aaatacaatt gaagaatgga tttgccacgt tgaatagtta gttggtatct  12000
tatttcccca ttttaaaagt tttagaatct gtggttgagg acttgtggcc atcagttttc  12060
tgtagccgac agactgttca ctattgcctt cagagctctt tggaccttaa caggccttct  12120
ttggagatgg cagagatggg tttagatgca tactctgctg gagtcaccca gagagcccac  12180
aaagtcaggg atggaacagg gtaaaggagt aagggtcata tgtgtgagat gccttgattt  12240
ggaactttga gatttaggaa gagatgggga agggctaaag agggacttgt ttctgagcct  12300
tgcttggctg aagcatttag gctaaagcgt tttagaaaga gtagcccttg gtctgagaac  12360
tcaaggaaac aactttctga tgagaaatgt agcaagcttc tggttcacat ccttacctga  12420
```

tagttcttca aacactgcct ggaagcttcc cctgagtctt tgtctctaat cagctaacta 12480
agaggctgag cgagtttagt tgtaagtcat taatgaagaa agcaaaggtc ggggccattg 12540
tcaggattgt gacctgggct agttaattac ctggaactga tggtctgtgt tacagagtgg 12600
tggtatactt gtcaggctta gaaaagaaaa caggatgtgt atcaaaaatc ttttggggaa 12660
aagatttgac cagcaacttt aatttctcta tgttgcagct atgctgttaa tgtagttgtg 12720
ataattttag aattatacca gtgcccttat gttatccttg ctttgcaaat tgcaaattgc 12780
tttacatgtc ctaacgtcct tctggccaac ggtagatgtg gttttaggtt tagactcctg 12840
ggatggaagc tttcgcattc aggggaatga ctttgggttg ggtgaggatt gtaaagaggc 12900
aatgtgggtg ccccacgaca aagcagctat ttgtagcttt gtgacaactt gacatacaga 12960
gatctaggtt tatctaggca ctaagctagg agtcagttgt ttgtatcact ggaagattgg 13020
ttataacttc cttcgttgga agctccttca ttgcatgtta aatgatgtta tttatagata 13080
gggtggtggg aaagctgtct aagtagatgt cagcccagtg taagagagac ctgcttactg 13140
tgggtgcttg ggactatcag cagtaggtgg gaggttttaa cttgttcagt aaggtccatt 13200
tccattgttc accatcttgt gaaccctttg tctaacatga ggagcaacca cataaccaca 13260
gcatgtctgg cttccctgtg gcttgtgtac aaagcatact tattgagtta atgtataagc 13320
aggagacacc ctcctgtgat aaatggtata ttaaccactt atcagtctta ccactctctt 13380
tcaatttttc tggacccagg acctcagcag ccatgtcgaa gccccatagt gaagccggga 13440
ctgccttcat tcagacccag cagctgcatg cagccatggc tgacacattc ctggagcaca 13500
tgtgccgcct ggacattgac tcaccaccca tcacagcccg gaacactggc atcatctgta 13560
ccattggtga gtgagtgtgc cccttcccca aaaaaagggc ttcatagaaa gtgacccttt 13620
ctctcctgaa aagactgaac taaatgtcct aacaaaccta ggtgctacat gggatgctac 13680
acagattctt ataaaaggac tcaggtcata ggaagttgca gtaaagaatt agtatgtgca 13740
caggatggca aatacagtta ataagagagt attagacatt tcacaattgc taagatggcc 13800
aggtatggtg gctcctagca ctttgtgagg ccaaggtggg aggattgtct gaggctagaa 13860
atttgagacc agcctgagca acttagaccc tctctctcca aaaagtaaaa acaaaagaaa 13920
aaaaagaatt agttgggcat ggtggcatgc acctgtagtt ctgactacat gggaggctga 13980
gaaaaagatc acctgagtcc aggagattga agttgcagtg agccatgatc acaccactgc 14040
actccagtct gggaaacaga gcgagatcct gtcttaggaa aaaaaaaatt gggtgtggtg 14100
gcacatgcct gtaatcccag cactttggga ggctgaggtg ggcggatcac ctgaggtcag 14160
gagaaccagc ctgaccaaca tagtgaaatc ccgtctctac taaaaataaa aaaaaaatag 14220
ccgggcgtgg tggcgggtgt ctgttatccc agctacttgg gaggctgagg caggagaatt 14280
gcttgaacct gggaggtgga ggttacagtg aaccgagacc tgaccattgc actccagcct 14340
tggcaacaag aacgaaactc tgtctcaaaa aaaaagaaag aaagataaaa gaaaaaaaca 14400
ttgctaagag taaatttcaa atgttctcac cacaaaaatg ttaagtactt gaagtcatgg 14460
atatgttaac taacctgatt taattattcc acattgtatc caaactgtat gtattggatt 14520
acataacttt gtaacccaaa ttataaatta ccagtttata ataaaaaaca atttgttgca 14580
aaaagaatcc atatgcttta ggttttatgc tataggcaaa atctagaggg tgttttcctt 14640
agcaggtctt tgtaggagca acttacagac ctaggaaaga tctttttaat atgttctgtg 14700
caaccaagat tctgtggttg gatatctggc tgggtttcag tgagggcgga gaaggctggc 14760
caagtcttaa cctaggcttt tctgatacag tgggagcctg cagaatttga aggaaatggt 14820
cgaagtgtcc cagtaaatca aaaaagtaag ctggcacagt ggtagccttc catacacttt 14880
ttaaagactt ttgagctatt tgggagagga aaagttttca gggaaaaaaa ttatttaaac 14940
ttaagcaaac ttaaatgttt ttccttcttt gaataattaa tacttgtggc tttaaaactt 15000
ttcctaatag gcccagcttc ccgatcagtg gagacgttga aggagatgat taagtctgga 15060
atgaatgtgg ctcgtctgaa cttctctcat ggaactcatg aggtgagctg tagctggacc 15120
ctttaggaaa cagggagtgg gtgcagtgtt catttagcca caacggatta ggcaaggatg 15180
agtctgagtt tcacagccaa tgtgaagttt gtctttacta gcccatccct actctccttc 15240
cctcttgtca tggcgaagaa actggctaag tctcttttag caaagaagac cccttttgtc 15300
gctggccatg tttctctcat acacctctcc taccattagc tttcacaaag gaagatgtgg 15360
aaaggttctc ctggaaaacc ctctaagcct tagatgtcct ggccacagcg cttgactctc 15420
ctgtccccgg gtttctgcta cagcctgtat tgccatggta aaaccatcta gcagatcgat 15480
tctggcctat cttagaacca aaataactgg gcaggtccat gagaagagtt tccattattc 15540
taagttttga atgactgagc ctaatgcaca agcactcgct ggcgtataat acccctcttc 15600
ctcagcacta tattcccagc ctgtgccttc ccaggagttc tgtacattaa aataacacca 15660
gttagcactc ttcctcagga gcctagtagg actgtatttg tgatgggctc tttattacct 15720
ggctttacct atggacagag gccttgccca ggagccgggt agcagctgtc aggatggctc 15780
cattcctgcc tctgttgcca gatttagaat aaacccattc tgaggagttt ggggttccct 15840
gaggttccat gacttattta ttttttttatt ttataagaca aaattttgct ctgtcatcca 15900
ggctggacta cagtggtatg atcatggctc actggatcct tgacctccca ggttcatgtg 15960
atcctcttgc ctcagcctcc caagtaactg gtaatacagg catccaccac cgtacctggc 16020
taattaaaaa aaattttttt gtgtaaatga ggtcttacta tattgcctag gctggtctca 16080
aactcctggg ctcaagtgat tctctcaaat gttggaatta gaggaatgag ctactacccc 16140
cagcctggga ttgtgccttt ttaaaacctt cagacttaac catagatttc ccatagatca 16200
tgggatttcg taatggcatt gataagagga atcacagaag aggcagactt tgtccctgtc 16260
ttggcttctg tatttcctgt tgagagtaaa gaaaatgcta ccctgtaagg ccaagtgcct 16320
tatagtggtt gccctctggc atttggaagt tggtattaag tttggactaa aaataaagcc 16380
tcaggaaatg cagtccaaga gtgaattcct ccttttggga aacttgagac tcttcatcat 16440
agattcccta acctgtgttc ataaacagcc tatggcctgg ctagtggctg gcccctaaat 16500
gtcatgggga cctgaccaag tccagcagac ataccacgca ggttaagaca tgtccctgta 16560
ccttttggaa aattctgtag ttttccaaaa gcaaggggtc cttagtagga gtcaccgaga 16620
attactacaa gtgttagctt agcttaaaga gagagagctg aagacaatgg tggaggtctg 16680
ttcactgttg atccctgctg ctgtagtctg ccgtgggctc ctgcgttcag ggaaaggagc 16740
agaaatagat ttttaagaag ttgacctttc agtaggcttt gtggttcctt catccagtaa 16800
aataacacca catagctctt acatggcaag ggggagtgat atctgctgca cctgctgcat 16860
gagagctggc tccgattttg gttttttaaa ctttaagagg ctttttggag attatctctg 16920
ctttcactcc tactcccagc ttataattaa gattttttaa aaattttttt atttattttt 16980
taaagatgtc cctcttgtgg gtttattttg aagttttaga ccaagatgag gttgtctctg 17040
ggctcaattt ggaaactgat ttgaagttat tctaatttgt ataatgtaag gtaaacagtt 17100
tcaaccttac cgtttgtcag ggctgttgtt tcatatgcac ctttgactag gggctgggat 17160
gtacttttct agtttctgac tattttaaat gctcttctga gcagaacgtt gagattactg 17220
tcttccctct tactctgaca gaggaacatc aaatgtctgc atctgatctt ttaacagctt 17280
tcttttttttg agacagagtc ttgctctgtt gcctaggctg gagtgcactg gcacgatctc 17340
ggctcaccac aacctctgcc tcccaggttc aagcaattct catgcttcag cctcctgaat 17400
agctgggatt acagacctgt gccaccatgc ccagctaatt tttaaatatt tttagtagag 17460
acagggtttc gccatgttgg ccaggctggt cttgaactcg tgacatcggg tgatccaact 17520
gccttggccc cccaaagtac tgggattaca ggcgtgagcc acacgcccag ctctcttttg 17580
acagctttgg caactagtct tcagccctta cttttggcag ttcacatggg caagatgcat 17640
tcttgctgaa catgtggttc catatgccgt gttttccaga tttatttatt tatttagaga 17700
ggcagtcttg ctgtgtcacc caggctggag tgcagtggca cgatcttggc tcactgcaac 17760
ctccacctcc tgggttcaag agattcttct gtctcagcct cctaagcagc tgagattaca 17820
ggcatctgct accatgcccg gctaattttt gtattttagt agagatgggg tttcaccttg 17880
ttggccaggc tgatctcgaa ttcctgacct caagtgatat gtctaccttg gcctcccaaa 17940
gtgctaggat tacaggtgtg agccactgtg cctggcctag aaaaaatgac tttcaaacaa 18000
cctaaatgta gagccttcca caggacagca ttgatggatg aaactcttta ccatgtaaca 18060
tcccaacaaa gccacagctg tagtagaaga ctcagtacac ctcccagaaa tgctctaaga 18120
gattataata tataacatag atttgaataa tacacctaat aattggtatg tttataaatat 18180
atagttttac atccccaaga ccaaaaatgt atgtttgtgt gaaacactca tggttacaaa 18240
tatatattag gccaccaaaa aaaaccccaa gtttcataaa gtagaaatta tacagacaca 18300
ttctctgata aaaaattttt taatgcaaat taagaacaaa gtcaagaaaa ctgaagtgtg 18360
cttactttag aaagcaaaga tctcaaggta gatggaataa atatttaact cagaacacta 18420
ggggaggaaa accctaaaaa gggtgaagaa aaataatttt gtaagattat agctcaatga 18480
aatgaaaata aatttgacaa attaagctaa gagctgatta tttgtgggta aaaaatagta 18540
aaatagaaag ttctgggaag ccaggtgaag aatgcaagga tgtacaaata agagtatgaa 18600
tagaaaaggg aatattttct acacattgga gattttaaaa gtcaagaaag acttataact 18660
taattcctat agagagagat gacactggct attttccaag aaaagattaa atagccaaaa 18720
agatagaaaa tatgaataga ccagtggcca taagaagttg aaaaagtggg ctgggctcac 18780
acctgcaatc tcagcacttt gggaggccaa ggcggaggga tcacttgagg tcaggagttc 18840
gagaccagcc aacatggtga aaccctgtct ctactaaaaa tacaaaactg gcggggcatg 18900
gtggcacatg cctgcagtcc cagctactca ggagcctgag gcaggagaat cgctagaacc 18960
tggagaggtg gaggctgcag tgaactgaga ttgtaccact gcactccagc caaaaagttg 19020
aaaaagtggc taagatctgg ttcacctcag aacatttaag tccaaatgat tttagtggcc 19080
gaattgtctc cccttcaaaa ttcagttaca ttgttaaact gttccagagc ctagagaaat 19140
acagaaatct tcccactgtg ttctttgaaa ccaacatact ctgatactga gatcagacaa 19200
ggacagtacc aaaaccaggc aggtactaac agcatgttag accagtctca cttagatgca 19260
gaaaacaaat aaaatttaat aatccaaatc cagtagtgat tgaaaggaat gtcttgatcc 19320
atgaccaagt agagtttatt ctaggagcac aaaattctac attaagatta agtagagtta 19380
aggttgactt tttttttttt tttttaaaga cggagtgtca ctctgtcaac caggctggaa 19440
tgcagtggca cgatctcggc tcactgcaag ctgtgcctcc cgggttcaca ccattctctg 19500

-continued

```
cctcaggctc ccgagtagct gggactacag gcgcctgcca ccaacgccta gctaattttg  19560
tttttgtatt tttagtagag attgggtttc accatgttag ccaggatggt ctcgatctcc  19620
tgaccttgtg atccccccta cctcggcctc ccaaagtgct gggattatag gcgtgagcca  19680
ctgcgcctgg cctgagttaa ggatgacttt taaacaacct aaatgtagct aaatatagag  19740
ccttctgcag gacagcattg atgggtggaa ctctttacca catgataaca tcccaacaaa  19800
gccacagcta tggtggaact cagtccacct gagtcttacc gttataagat aataataggt  19860
aacatttatt aaataattac catgtacttt gtcctaatac ttaatatatt cttttactgc  19920
tcacatcaac tctgaaggaa aggtaccaca tccccttaaa agaaaacaac tatttctatt  19980
ctattctttt attttttttt agagacagaa tctcactctg tcttccaggc tggagtgcag  20040
tggcacgatc tcggctcact gcaacttctg cctcctaggt tcaagtggtt ctcttgcctc  20100
agcctcccga gtagctgggt ctacaggtgc acgccaccat tcccagctaa tttttgtatt  20160
ttaagtcaag atggggtttc accatattgg cctggatggt ctcgatctct tgatgtcgtg  20220
atccgcccgc ctcagcctcc cgaagtgttg ggattacagg cgtgagccac cgcgcccagc  20280
ctctattcaa ttctattttg ttctatttct attacaagcc agtaagcaag aaaatatcat  20340
aatttataag gaaccctata aaaaacaaac aagccaacgg tccctcatta gggagtatgt  20400
ctgaataaga agctgaagat tttcagatac aggcttcagg caacattgtc tttagaggct  20460
aagctctgtc tccagctccc tccagcatcc tgtgaataac cggcagactt acttgcaggt  20520
gccgctttcc tggacagtgg tggttaaagg acaaggccca gaaagtgctg aattaggtgc  20580
ccttgttatc agcaatgtca tattgatcat gctgtcttag agctcttttg acatcttggc  20640
tctgcatctt tttttttttt ttttttttta aatctttttt cttgagatag ggtgttgctt  20700
tggatagtag ggtatctagg ccagagtgca gtggtatgat catggctcac tgtagccttg  20760
acctcctaga caaaagtgat cctcccacct cagcctcaca agtagctggg accccatgca  20820
cacaccatca tgcacagtta atttttgtgt tttttgtaga gatggggttt cgccatgttg  20880
cccaggctca tctcaaactc ctgggcccaa gctatcctcc caccttagcc tcccaaagtg  20940
tttggtttac aggcatgagc cattgtgctt agcctgagtc cctcttttaa acaaacaaaa  21000
tagtaaatga aaaggaggaa aggcttaaga aaaaagattg aagcacagat ttgttgcaag  21060
caaggaataa taaagggcag ttcatttaga gaaaggcata tgaccacctt tccccctctc  21120
cagtcagaat ctagaaagtg attgaggctg ggcgcagtgg ctcacccctg taatcccagc  21180
actttttggg aggccaaggt gggcggatca ccaggtcagg agatcgagac catcctggat  21240
aacatggtga aacccagtcc ccactaaaaa tccaaaaaat tagccaggcc tgctggtggg  21300
cgcctgcagt ccccgactga ggcaggagaa tggtgtgaac ctgggaggcg gagcttgcag  21360
tgagctggga tagtgccatt gcactccagc ctgggcggcc agtgagacta tctcaaaaaa  21420
aaaaagtgat tgagaaaatc aggtctgtgt gaccttagca atgagttgtt tagcttgggc  21480
cactgttagc ttaagtcaat aacttcaagt ttgcgttgta gttggaatca atagaggaaa  21540
agctctcagc attaccacat atatcagaat gtgacattga ttgccagatc agccttatcc  21600
aaacacaagt tctaggcttt ttgccctgtt tatcagcttt atttgctgag ggtatttgat  21660
gagtcttagg gaaaaaagaa cagccctggg gacacagctg cttttatgat gagacatgtt  21720
tgcacccata ccttaatggg ttttggtggc aatattctga aatttgccac caacgtttca  21780
aagatttgcc cttagggtga attactgctg tagtagaagt gggtggaggc tgaggagatt  21840
ggattaagca ggtagaggag ttctcagtgc atggatcgtt ctgaggatgg agatagagct  21900
```

-continued

```
ctaagacatc cacaggcctt tcctgagtga tcagctttgg ctcctgggca gggaaattga  21960
gctggatcct agtgtgggag cacgcttgtc atcttccttc tttttcccca gtaccacgcg  22020
gagaccatca agaatgtgcg cacagccacg gaaagctttg cttctgaccc catcctctac  22080
cggcccgttg ctgtggctct ggacactaaa ggacctgaga tccgaactgg gctcatcaag  22140
ggcgtgagta ttctgtggag agcgagggaa agactcagta ggcattatgc cccagagaca  22200
tgtcctccaa agcgttgaga tgccatgttt catcccagca ctatgaagga ctgcagagga  22260
gttgaggtct acaaatgagg atttattcat cactgtaaac aatgttgatt tgatttactt  22320
tgctaggaaa tggtaccaca gaggaaccct ttttttaccc taaaaaccta aactttaggc  22380
tttctaactt ggggaaccat ctctttgtat ctttttcccc atcattaagt agcctaactg  22440
aaacattata ttctattttc ttagattatt tctgtgaagt gtactgagtt agagaataag  22500
agcaaaaaac tgtattattt ttagcggtga cttgagcatt gttccctgga ggaaagggct  22560
tttccattgc ttctgaggtg atgctgctac tggtgtcttc agtttggact ctggcttact  22620
ctcttgctta ctccctagag cggcactgca gaggtggagc tgaagaaggg agccactctc  22680
aaaatcacgc tggataacgc ctacatggaa aagtgtgatg agaacatcct atggctggac  22740
tacaagaaca tctgcaaggt ggtggaagtg ggcagcaaga tctacgtgga tgatgggctt  22800
atttctctcc aggtgaagca gaaaggtacg tatgggtgct ggaatccaat tgtctaaaac  22860
catcttttgt ctctaaagtt ccttgacaca aggaagatgg gaaggttggt tgcctggcag  22920
tgagattgag tctgtgtgtt ctcaagaatc ccttaatatt tttttttttt ttttttttga  22980
gacggagtct cgctctgtgg cccagactgg agtgcagtgg ccggatctca gctcactgca  23040
agctccgcct cccgggttta cgccattctc ctgcctcagc ctcccgagta gctgggacta  23100
caggtgcccg ccacctcgcc tggctagttt tttgtatttt ttagtagaga cggggtttca  23160
ccgtgttagc cagaatagtc tcgatctcct gacctcgtga tccgcctgtc ttggcctccc  23220
aaagtgctgg gattacaggc ttgagccacc gcgcccggcc aggaatccct tttataactc  23280
atttatcctc aaagacaggc tttaatccag catatttaca ttcttctggt tccggagaac  23340
ataggaacat atatatatat acacacatat atttcttttt tgagtgagag tctcgctctg  23400
ttgcccaggc tggagtgcag tggcacgatc ttggctcact gcaacctctg cccccagggt  23460
tctagcgatt ctcctacctc agcctcctga gtagctgggt ttacaggcac ccgccaccat  23520
gcctggctag ttttttgta tttttagtag agacggggtt tcaccatgtt ggccaggctg  23580
gtctcaaact cctgacctca agtgatctgc ctgcctcggc ctcccaaagt caaaacaatc  23640
ttaattctcc ttttttatgg gtgtggaaag tgaggtacag agaggttaaa tggcttgcct  23700
aggattacac agttacttgt agtagggttt caactctggt aaaacagctc cagcacccat  23760
aatgcaccac ttcccagctc actgtacttg ggggaaaggt gcctgcttcc tgttgagctg  23820
tgccctcggt gctctgcctc ccctgcttac cccttttcaa aacacaggtg ctgacttcct  23880
ggtgacggag gtggaaaatg gtggctcctt gggcagcaag aagggtgtga accttcctgg  23940
ggctgctgtg gacttgcctg ctgtgtcgga aaaggacatc caggatctga agtttggggt  24000
cgagcaggat gttgatatgg tgtttgcgtc gttcatccgc aaggcagctg atgtccatga  24060
agttaggaag gtcctgggag agaagggaaa gaacatcaag ataatcagca aaattgagaa  24120
tcatgagggg gttcggaggc aagtccccat tgtccctgct ccagtcccag cacaactctc  24180
taaagggcat ggtgcatcct gtgaatatct gattcccagc cccctagccc atcagaatgt  24240
```

-continued agactcccaa acctgttcca aacctgctga atcacaatat cttagtagag tagaaggcat 24300
tgtgtgtgtg tgggttttgt ttttttgttt tgttttgttt tgtttttaaa aagcttccta 24360
ggtaattgag atgctggcag cttgacattg ttccctgggc ctggggacca acatttgagg 24420
aacagggtca ctgctcatag taccaggggc catgatgctc tgttcctgat cagaaacact 24480
accagtgttt gctggaatgt ggggaccagg gggaaagatg acagcagaca cttaagaagg 24540
ggctcgtttt ggcccttcct ggggagccat gtggaatttc aggggctggt gtccatgcta 24600
aaacttatgg ccttctggtc ttcacttaga acgcagctgg ctcagtgatc atgctaactc 24660
tggtatggtc cattccactc tcagagtaag atgtgtggtt cttctccagg ttcagattgc 24720
ctcaacttag cttacccct gcgcagtgct cacgaggtag agcccagtgg gcatggccac 24780
catttttggc atcctgctag gaatacaact tagcactact aagatgctag acctacgctt 24840
gtggattagg actgtgtttg gggagggtgg gggaacaacc ctctgcaccc actgtagtgg 24900
ccttactgtc ttagctttgt gtagatatcc tctgtaccag gcaatttggg gccctcccct 24960
ttgccatcct gataagctga acttggcgct aggccaggca aagccacatt ccctcttgcc 25020
ttcagcaggt tggagtgggc cacctcacag ggcagtcttc aagtgtcctt gactagataa 25080
ggccatgggt ctttgtggtg gaagcagtca gcaggcctcg ggttccctgt cttgaagtgc 25140
tgattggaga atggaggccc tagagagaca cctaacatgc atgggatttg gagaggagac 25200
cttgagaatg agcccatttg gatttgccct ctccccttc ttctgtcaat gaagcatcca 25260
tattggtgtt gaagcccagc aggcagaatt gttggcccgc tctgggggac taagctagct 25320
ggactgcctt gccatctgtg tgcatccatg atgatatcat ggatgtctgt cctggtacga 25380
ggacatctaa gttagggaat cccagggaaa cttcttgtct tccggcatac ttgtggcccc 25440
tgtctgtata acctctctcc ccccaacttt gtccatcagg tttgatgaaa tcctggaggc 25500
cagtgatggg atcatggtgg ctcgtggtga tctaggcatt gagattcctg cggagaaggt 25560
cttccttgcc cagaagatga tgattgggcg gtgcaaccga gctgggaagc ctgtcatttg 25620
tgctactcag gcatgtgacc acccttcccc acattctcct gggcacactc acatgtgtgt 25680
atgggaaagc tctggaggct gtctgatctc ttcccatgga attgtcccat gtaacacaca 25740
gataatcccc ttccaccatg cacctacaca aagccatgct ctgtgcacct actcactatc 25800
cagaggatca gcgtgctgtc atttgtctct gaaaacagcc caagccacat ctcactaatg 25860
ctctgttcct cccagatgct ggagagcatg atcaagaagc cccgccccac ccgggctgaa 25920
ggcagtgatg tggccaatgc agttctggat ggagccgact gcatcatgct gtctggagaa 25980
acagccaaag ggactatcc tctggaggct gtgcgcatgc agcacctggt gagttctggg 26040
gcctgccccc atcccctggg ctttggactg ggcctgggat ggatgcaagc tctggtgcag 26100
agctttttaa gtttccatat cctcttaggc acagccattc attatcctcc aagttacagc 26160
agcaagaggg tgggggtgga ggtggaggtg gctttttttt ttttttaatt ctcctgtttt 26220
tcattcctgc cgacaccccc acccctccat ttccttctgc tctggaggca tcctccttca 26280
ctggaatcat acagttcatt tcacttctga cttcaaggtg gtaaatcctt cccatggctt 26340
aagtcctggg atacttccgc agtgaaggga ggtctcgtac ctcttcctca gagtcagaag 26400
ttttgagtac ctttgcccta ttctgaaaag ggctcggggc tcctgctccc aactgccctc 26460
ttcctttggc ttccaattca gtcccccgac ccccccatcc cgcagacagg cgctccccca 26520
gggagcccct gtggacctgc actggagtct gttgcctgta ctgagctgcc tgtgctggcc 26580
ttgcatggtg cctataggag gatttgcttt gctgtgccat tggggtacag ctgctgctct 26640
tacaacagac caaaaagtca ggttgagtga ctggtggcag ggccacagat agagacagca 26700
gggagggtgg ctgaccctgg tggccctgga ctgagcgtct ggaggagtcg tggaggccct 26760
ttcccttctt tctcctctga gagctcattc ttcaggctct tccagcttgt catgttgagt 26820
gcctggccac tgctcagggt tggagactca gtccctttgc cctgtctgtt ccagctctgg 26880
agctaacttg gggatccctg atcagggtta cataggtttg gtaaaatgag tgctggaaat 26940
taactttctc ccagtagtct taggtcaggc tcagtgaact tcaactttat ccagatatgg 27000
tttttcttca gccattctat tccctttcta gccagtgaaa gacccgctgc cctttgacct 27060
cagcccctcc aagcccccaa gtttaaaacg ccaccccccg ccaccaaaaa aaaaacaaca 27120
aacaactaaa acacccacct cgtctgggca tcttcctttc ctttttcact atgtgtcctg 27180
ttactgggct taaacagctt tcagagaaga gatgtcattt ctattaaatg ctctttcagt 27240
agcgaactga gttcataatt tgactaagga tattttctgg gctgtcatca gcatccttag 27300
tgggtttccc tatattggaa ttggtagagg ccagggacgg tgccttacac ctgtaatctc 27360
agtactttgg gaggccaagg taggcagatt gcttgagctc agaagaccag cctaggcaac 27420
atggcgaaac cctatctcta ctaaaaattc aaaagttagc tagctgggcg tggtgataca 27480
cttctctagt cccagctact tggagagggg gtggtgctgg ggcaggagga tcactgaacc 27540
caggaggttg aggttgcagt gagccaagat ggtaccagcc taggtgacaa agtgacaccc 27600
tctctcaaaa aagaaaccac acaatcataa aaaaaggaaa cacaaaaaaa tcagtagaga 27660
gtgatttctc tcccaggccc acttaacgta gcctgggcct ggctgacacc tcaccgtttg 27720
tgcgacgtga ttgctgttct gatgctgaga tcctcttggc gcagtctcac aattgccccc 27780
atggtaggaa ggtgtcccag gagacagtgc aatttcaacc agtcaccact aaagtgactg 27840
cctttctggg tctctccaca cgtcccctct ctctaattcc cttacttaat tgtgtaactt 27900
catggcctca aaggtgggac agaggctgat cttgacttag atttactgaa ccatgaaatc 27960
actgcataga atatggagac ttgaatgtgt cttttggcaa gtcatttaac ttctcaagac 28020
cttatctgta aaatggatta gatatgttta tagccttagc attaaatatt cattgctctt 28080
attattaagt gtctgataag tctctgtgta tatggatgta atcttcctaa ctcccattac 28140
ctccatttat agataagggt tatatggcca ataaagcctg ggtttgaatc taggtctgct 28200
gactccaaag ccagtcttct ctcctgcaac atcatgctct taggtctagc aggagatgag 28260
aacaggtctc catttggagt ctgtcagtgg ggtcagagac taagaatcag gctcaacttc 28320
taaatttcat gtcctttcct ccatacccta gtgtttccta tgaacagaca gataccttag 28380
agctgcaagg cttggattgc atggcagtgc tcagaagata agttacaggt ctgggccagg 28440
ctgtagctgc ccctccaggt ggctagacct ttcctttctg tgtcaccagt taacactggc 28500
caacagttcc ttcccttcac tgttgattgc tttctcctgt gtctaactga tgcagttaat 28560
gacgcataac taagagcagt agcaggtatg gctctgtttc ctgttcctgt tccctgtcct 28620
ctgggttgca tgcattccat tctgataaaa agaatacctt taacttagta catcctgcca 28680
cacatctgct tctactgtga aattcatgag gggctattac cgattcctcc ctcacccatc 28740
atttacttag atgctggtga ttgcattata atcctctaaa gcttacattg tctttctgat 28800
tcttggtctt atctgagcaa gtgatctgta aataactcag tggctttctc atgactgttt 28860
taatcattag attttaatca agtgtcttat taaacatatc tgcatgcttc cacagacatc 28920
tgtctcttca catggctgtt cagtgtgtct ctcacaagtt agcccaagtt ttctgttctc 28980

-continued

```
ctgcttcaaa ctcagttgag ctgccttgct ttggcttgga tcccagcttt ccagcgctgc  29040
tcaatctgtt tccatggcag gccattggaa aggctcagtg catccctgtg cctgaagcca  29100
agtgagcgct cactccgtgc atgcatggag gctgggcagg agtctgccta accagacagc  29160
catgtgagga gggagggcct gttcctttct gtaagctatg tcgtgaggca gcgtgatcaa  29220
gtcctctgcc agggagtggt gtgggcccag cctgggcatg ttttcatgcc agagtgctag  29280
agcctactgc cagattgtct ccctccatcc ccaatcaaat ccttccagaa cggaagagcc  29340
aatttgccct gtattggagg ggaagtggca gcacctcctg aagcagttgg actttcatca  29400
ccctacctcc gcatctgcct gaaggacaga tttagccaat taacctaagg ttaccttcct  29460
ctctgattaa ttccccattc tgtcttccca tgtgttgtgt cttgtttttt tcctcctcct  29520
tccctcttcc ttgtcccctc ttcccctaaa ccttacagat agctcgtgag gctgaggcag  29580
ccatgttcca ccgcaagctg tttgaagaac ttgtgcgagc ctcaagtcac tccacagacc  29640
tcatggaagc catggccatg ggcagcgtgg aggcttctta taagtgttta gcagcagctt  29700
tgatagttct gacggagtct ggcaggtagg gccctaaggg caggtaacac tgctaggata  29760
accagcctct tgcttcagct gttctaggag aagacagcca ggcccaacct ggcacctggg  29820
cacagagcct cctcttgtct ataggaacac cgccagggag gtcatggcag ggcaggacca  29880
aagggtcctg tggctcagta ggcacagcag atgtcacagg cacttggtga aggactggtt  29940
tctgtggagt cttgaaattg gctcagctca gcatctccag tgactgggct actcttggcc  30000
tttgtcccta ggaacatgtt cctcaccagc tgtctgggtg actcttcccc tccctctcct  30060
tctgtgacaa agctctgaca aggctctgtc ctcctctcgt ccctctggac ggatgttgct  30120
cccctagatt gcccgtgagg cagaggccgc catctaccac ttgcaattat ttgaggaact  30180
ccgccgcctg gcgcccatta ccagcgaccc cacagaagcc accgccgtgg gtgcnnnnnn  30240
nnnnggatga agcaaaagat gtccaaaagt ccctgccaac cctgccatgt gagtgataag  30300
gacatttcag ggcctcaatc ctttttgcct tggctgtaag tctggtgcca cattgtggtg  30360
tcaggaagga gtgttcagtc agcctagttc agtgctcggg ctatggggca gctgcccagg  30420
tgcacacctg cctggcttgg cttttactta ccaatctccc ttctcttcct ccaggcaagg  30480
cccgaggctt cttcaagaag ggagatgtgg tcattgtgct gaccggatgg cgccctggct  30540
ccggcttcac caacaccatg cgtgttgttc ctgtgccgtg atgaacctga gagcccttcc  30600
tccagcctct gtcccacctc cttcccccaa cccatccatt aggccagcaa cgcttgtaga  30660
actcactctg ggctgtaatg tggcactggt gggctgggac accagggaag aagattagtg  30720
cctcgctgaa acatggctgt gtttgcagcc tgctctagtg ggacagccca gagcctggct  30780
gcccatcatg tggccccacc caatcaaggg aagaaggagg aatgctggac tggaggtccc  30840
tggagccaga tggcaagagg gtgacagctt cctttcctgt gtatactccg tccagttcct  30900
tgagaaaaaa atggatgccc agaggactcc caaccctggc ctggggtaaa cagctagaga  30960
gttaggggcc ttagggcacg gggctgttgt tcccttgaag ctgactctgg ccctggccct  31020
tacttgcttc cccagccccc tgggcctccc cagttcacac ctgtccccgc cctccactca  31080
gctggcctgc agcaaacact ccaccctcca ccttccattt tcccccactt ctgcagcgac  31140
tactgcagcg ccttcaggcc tgttgctata gagcctacct gtatgtcaat aaacaacagc  31200
tgaagca                                                            31207
```

<210> SEQ ID NO 48
<211> LENGTH: 24791

<212> TYPE: DNA
<213> ORGANISM: Canis lupus

<400> SEQUENCE: 48
gaaatgcagt ggggctgtcc tgaggggaag ggtatgtagc ccatcaccag gtttgtggat 60
gagtggggag gcctctgggg gaagatgact caacctttca acctctctgc ttttgagaga 120
attctctttg ttgggtgagt gggaaactgc attgtggtct tcacaggttt aaaaagtccc 180
ttctcttcat ttagtgagtc aaatagtgaa acacgcattt tccccagtta agtgaaaagt 240
ggttgtccag gttgtcccgg ctctctgtac tcccctaaga gcttaggtgc agcgtgacac 300
aggcctgtgc ccaagtaacg tagtctatgc acctgcattc ctgagacttc cccaggggac 360
acggcagtcc tttgtgggag gggggcctgt tatggttatg aataatgatg actgaaagaa 420
tgtccttgaa ctcacctctg acttgagtca aaatagatgg acattagtct cttccagtct 480
tagtttagct gctctcattc taagcactgc gttaggagta aataattttg atgttgaatt 540
catagtttaa cagcattttt gggtgtctaa taatttgcca gtgacctggc caatttggta 600
ggggggactc cagacagaac tgggaccttg tacaagttgt ttctgtgcct tggatgttgt 660
gacattaatg gggtgggggg tgtcacggga aaagccattt tatttcttaa agctgtgtgt 720
ttcttaatgt tgaggcagtg gaagaaatga ggaaatgact gtgagctagg aaaaacccaa 780
ctcttgcatt atcaactcac actaccctgg ttctaattta tgttgcttca gcttgtatga 840
aggcatgtca ggatgtgtta ttttggccaa gagctaagac tgagctcaag gtaggggaaa 900
atgactcatt tgacatttta tttctgaatc attccaaacg tctacagtca aatctcagtt 960
aggtggtacc ccacaaggat gagtcgcccg tttgagcaaa gttttcttgc agccttgttg 1020
aggacgttgg gaaatgtaga agtggtttac tcggtgggag atcctgtagg aggggagcct 1080
ggctggctca gccagtagaa agggcgactc ttgatcttgg ggtcgggagt ttcagcctca 1140
tgttgggtac agagattact ttaaaaaaga aacatttttt aaaagttctc caggactgtg 1200
agtcatcact ttaaacctca gttctggtcc agctaggact agagctaaag gaagagcgtt 1260
cttaatgcga gcatgctctg ggaacttggg tttttcacca cgagcccgtc tcagactaga 1320
ccaatgaata gtctgcttgt ttggggcttt gttaaggaag ctgtttgggg gaaggtgagc 1380
cagggtggct agtggatggg ggtgtgcaac atctggtggg cctctctctc ggcctcccgg 1440
tgtgactgct cagctcaggg gagggggtgt tggcagagcc accgagtggt gtggcgcccg 1500
cccctgcagc ggtctgtgca gttctgcacg taggaaggag ggcctgcagg aaggagggcc 1560
agccgggctg cagtacctcc ggcggcctct gagacttacc tcccccactt ctgtccatag 1620
caaagcttct ggggagctct aagcctctct tccctgacgc cagcaagcta tgtttggaag 1680
ttaggcaggg gccgtggtgg gggagatgcc aagccaagct gtgacagtgc cagcttagct 1740
gatatagttc gaaaaggtct ctggaaaggc gcccattcct tccgagcctt tgaagtcgac 1800
ctacagctag tacttcttta acttcaggta attagtgtct tccgtgtttc cagcgacgag 1860
ggcaaaagaa ttaacccggt cagtgaatca gtcacggtat aggagacaaa accacgggca 1920
acttgaagga gccctgggag ttttaatctc gttagaggta gggaagtaga ggcttttgat 1980
aactggtatc tctcttttgt tatgacatta gaaaacaggt taatgtcccc tatccagagg 2040
gtctacattt taaagctctg acaatattga atgctggcag aagtgttaga gggcaagaac 2100
tcacattgct ggatggttgt aaatggatat aacctcgtta gggcccttca gcaatattta 2160
gcaaaataga aaataaacat accctgtgac ttaggaattt catttctgga tatatataga 2220

-continued

```
agctcacact tgcacataga gccgtgtacc aggagaattg ttgattgcat tgaataatag   2280
ggggaaaatt gattgggttg ccaaccagta agggaatgcg taaataaccg atgtagtcgt   2340
gcagcggatc ggcatagtcg ttcgtatgaa ttaactagat ctgtgtaccc gcaggataga   2400
tcttacatgt gctgaaaaaa agcaagatgt ttatttgtac agtattgtac tgagggcatt   2460
ttagaaaacc ggtgtcatag gaatcagtat agatatagat gcttaaatgg attagaagga   2520
tacaaaattc ctgacagtgg ctgggtgtca aagttcgtcg aaaggttgga gggccctggg   2580
gatggaggga aaataaacta caaaattgta atggttaaga aaaaaaagtc tacaggaatt   2640
ctggctaaat gttagtagtc agttctgggc ggtagaaata cggatgttaa tattcctttt   2700
tttttttctt caattaaaaa taaagcaaaa tagaagcaga tctgtgaaag tcactttagg   2760
aagaccagtt gtactaacta ggtcagtgtt cttggagagc tgggactgcc cttcctcctt   2820
tcatcctccc cttctctccc tccagctatg gtgcaggaca acccctcctt taaatgctga   2880
gctagaacac ctcactttgc ggaggctgtc acccatcctg gttgtgtatc ggactttgaa   2940
gggccctaac ctagagtccc aggtcccttg ctacttccaa actatgcata tcatgcccta   3000
aaacactgcc tcactatttt aggcctagta aggaggcgtg gtaacacagg acaacaacag   3060
tttcctccaa acttccttct tcaggctgaa accacttctc tgctttgagc ttctgtggtc   3120
aaacaaggac atctgaggtt tctctgactt gggacttcct gctctggagt ggagtggttc   3180
tttggaggct gggcccgtgt tgtatctact tttgtgccct aatcccactt tgaaatatga   3240
cttgagactc ctgcttgtaa agccacgtcc ctgaataaat aaaagcaagg gaattttact   3300
tgaacctgca agtgggctca ttttgtttcc tgtaagcagg tgagctagac tttgctgtct   3360
gctagggagc atgctgaggg ttggaacctc agctccctcc tccgtatctc gctccatata   3420
taaatgcaca atatcattac tctaactgtt tatcagggca aacagtcatt cggtgcagac   3480
cttactaggt tctgtgggtg gcctggcacc tgttttgatc gtgttgtcag attggggtca   3540
gtcttgggaa ttgggaattc tattgctcca tcatctagga actctctaga gagcacactg   3600
gcccgaacgc cttgtctgtt ctgaagatta gaggcctgaa aggccttcat catgctagct   3660
tggagacttg gaggtgtagg tagcatattg atgacagagc caggaccaca gttgtgggca   3720
tcaggtgcca tcatcgttgg gttactctgt gtggcgaggt cagcgtcaga ggaaacttgg   3780
tgcggagagc cctggctggt taaaaattgg cttgtgtgca tacagctcac gggccaggct   3840
ggtttactag ggcagaatga tttgggcctt tgtgaaagaa tcagtggagt gaagcgtgaa   3900
tctttcccgg cacaaacttg ccaacagtac tggccctaag aagtggcacg tcgtatcttt   3960
tatgtgattc cctcccactg tggtttctgg agcgtggccg aagacctgtg tctggcacaa   4020
aggaaactat agttttggag aaccaggagc tgcttaagat gagaaaggaa aggtgggccg   4080
gggacctggg gagctcaggt gtgaccgtgc ccacccccatc cccttggcct ggtagggctt   4140
ctcacggtgt ctcctttctc acagaggaga aatggctctg aggaagatgt tactgcaggg   4200
gctcaggctc aagaataagg ttgccgtacc tgggcatggc atttgccacc atcagtggat   4260
acgccgggct tctactgtag gctggaggtt ggctctgcat gtctgtgcct cccgggagga   4320
gggtgcaaga gtgagtcagc ggggcacccg ctggctgcgt gtcccggcag gcgctgtcca   4380
gacggccagc atgagggagg gagctcttcg cagaggcccg cgggaaacca gggctttggc   4440
tgctgccctg gggccagggg agagtcctgg ggggttttgg caagaacttg aggtagtggt   4500
ggttggcagg acgggaaact ggtgctcagg aggacctgag aggcaggcag cagagccctg   4560
acttccagca agggggctc agaggctggg agctgagtgc tctggtttgg tagacgtgtc   4620
```

-continued

```
taagggcact ttgagatctt gtaggagttt ggacaagcaa gcttttttt ctttttttt   4680
cttttttct gattactggt gtggaaatcc actcaaatgc cagataagtg ttcattatta   4740
ttattatttt ttacatttca taggctgggt gagcagaaaa tcagcttgca aaacctcaga   4800
tttaaattga gatggtaaaa tagggttgtt gtttgagcgc aatataattg tatttgctaa   4860
tggcatctcc tggccttgga gacagccctt ctgtaccaga atatccttgt cacaaagatt   4920
atgctgagaa gtttgaggac agactaaaca ggcaaagaag tttgctggat ttggatgcat   4980
aactaacagg cttggagcat agaattgtcc tgtggtctat gtcaactttt ttttttttt   5040
tccttttctt tcttttttt ttttttttta atttttattt atttatgata gtcacagaga   5100
gagagagaga gagaggcaga gacacaggca gagggagaag caggctccat gcaccgggag   5160
cctgacgtgg gattcgatcc cgggtctcca ggatcgcgcc ctgggccaaa ggcaggcgcc   5220
aaaccactgc gccacccagg gatccctttt ttttcctttt ctttctttgg ggttctaagt   5280
ggatcagagt tggccttctt aagccagtgg aatggtctgg caatgctttt gtgatctggg   5340
gcctgagacg tgttatctcg cctctgccac atttaagcag agtattcctg aagtgcatag   5400
agaggcggtt gattaatgaa accagaagtt aagcttcatt tttgttttga ttccaacatt   5460
tttaccagga aacttataaa tgtatcattt ttggaagaag tacatttgtg atttttctta   5520
atacaaaaat atttccatta gtaaatttat tagtaaagcg aagaaaacat tttgctgtaa   5580
tcctaccacc taggtgacct gccattactt tatgggtaaa tagacttcca ggcctattat   5640
gcatgtttag tttagtagcc cttctccctc aaaaactggg aattgaccag gttcttgtat   5700
agaatagtga aatgttaatt aaccacatat ttaaagggaa tttagagcga aaataatctg   5760
ggtattcagg aggagataaa gcatcataga gctagcaaga atttccttta cctgcaaatt   5820
ttctgttacc attttcttgg tatttccttg gaggtatctg tgtgtgtgtg tgtgtgtgtg   5880
tgtgtgtgtg ttttaagatt ttatttattt attcgagaga gagagagagg cagagggaga   5940
agcaggctcc atgcagggag tctgatgtgg gacttgatcc cgggcccctg ggatcatgcc   6000
ctgagctgaa cgcaggcgct taaccgctga gccacccagg agtcccatat ctatgttttt   6060
ctctgtaaca tagcagagtc tccgggagca gctaccatct ggttacctag ttactaaggt   6120
catatttcca ttgccccaaa gaacttcagt tacactcagc ttctaccttg atccttgtac   6180
agctctgcag agcaaacctt actcagctct gagcggtctt tgcaagtggg gccaaggagc   6240
caccctgagc cacaaaaagg acattatgtc accggaagcc caagccccga gaacacaagg   6300
tatgacccaa caacctgtgg ccccggccag gtctttgttt gcaaggaaac actcttgtct   6360
cgggtctaga gaagagatag ctgactatgt ttttgtgttt tttatgtttc tgtttttggt   6420
ttttgtcagg tgtttttttt ttttttttt tattttaaat tttatttatt caggacagac   6480
acagacagac agagagaggc agagacacag gcagagggag aagcaggctc catgcaggga   6540
gcccgatgtg agactcgatc tcgggtctcc aggatcacgc cctgggctgg aggcggtgcc   6600
aaaccgctgg gctatcaggg ctgctccagc tggtgatttt taagaagatg caggttaatt   6660
attccaatcc actttttgag atcttgtttt attcatgatg acagtcctca gactggatga   6720
tgattccact tggaggccac agctaggcct ttgtgttcca gttggctggg tgtgccacct   6780
ggtgccatct cttcagtcat gttctcttaa caggcagact tacctcagcc ctgccatgtg   6840
ctccgaaggc acaggagccc tgactccacg cgagtgccaa taaagaaacc ctggctgccg   6900
aggcaggccc tctagtaatt cataaattct tcagatttgg ggaaggaggg aagagaggta   6960
```

-continued

```
taactttggt tttgacaaag aagctttgag gtacacggaa aggtcgttca gcaaacactg   7020
gaacactccc cagtactagg tgctaacaga gaacaggtag gtcacagagg agaggacctc   7080
caaacatttt cgttttggtg cctggtgtgt attagggagt tacgaaacac acgttgaaag   7140
gagcagcgca tttgccgtgt ggaatagtta gccaacatct tatttcccca tttttgaagt   7200
atcagcctct gtagctgagc atgggtagcc atccgttttc actagctgac aagttttgct   7260
cacaactggt cacggaactt cttgggcgtg tatcagaatt cttgaaggta gcagatatgg   7320
gctgagatgc aagctacccc gagaggcccc aaagtcaagg gcgggggag gaggaagtaa   7380
aagtggcatg tatggcgtgc ctggattcag agccctgaga gttaggagga gctgggacag   7440
gcctgaggag aggcttgttc aggagcctgg gctgaagcct tgaagctccc agggtgttag   7500
gagtaaccct tggtccaaga acttgaagaa gggacagcct tgtgatgagg agggtcgagc   7560
ttctgactca catccttacc tgatggtcct tcagaccagc ctggaagctt cttaggtctc   7620
tataatcagc aaactaaccg gctgagtgag tttagctgtc agtagtgaag gaagcaaagg   7680
tcgggacagt tgtcaggatt gtgaccgggt ctgtttaatt acctgtaaca ggtggtcttt   7740
gcggtgtgct tgtcagaaag ggaatcggga tggtgtatca gaaaatcagg tgggggagag   7800
ggtttggcca gcagtctgga tggatttcct caggtgtaac tgtcctgtta aagtaggtgt   7860
aatacgtcta gaacctgacc agtgccattg ggttatctg gttttatgca aattgctttg   7920
cacgtcccta aagtcctgct gaccacaagt agctgtggtt ttcaggtgca gactcctggg   7980
gtgaaagtgc gctcgggatt ttgggtcagc tctgcttcct gtccaaggag tggttcttac   8040
tatctgtcag tgaactggga tcggctctcc tgccagagca agccaaggaa tgaacttaca   8100
tgttgctctg gcttagagaa aatctaggat tccagaggtc aaaggactgc ctggatgatg   8160
attgtcttta caaccaggaa aatcactttg agtttgggtg gggattatta aaaaccacta   8220
tggatgcccc accccatagc ggacgtttat agcttgagat agcttttcat acaaagattt   8280
atatttgcca agatactaaa ctagcagtta gtgctttctg tcgctggaag gttggtcacg   8340
ccttcctttg gaggtagctt ccttcgatgc ctgtgagatg ttgtttggag gaggacgagg   8400
aaagctgtca aagcggatac tagcccgttg taagggagat ctgcttacag cggatgcttg   8460
ggaagcacgt gtgttgggga cgaggtttta aattggtctt tgaggtcctt tccacttgct   8520
catggtcacg tgaacccttt gcccgacttg aggagtgccc acgccaccag agcatggtgg   8580
ggctccctgt ggctcgtgca gagtgtgcct attgagttaa tgtgtaagca ggaaacagcc   8640
tcttgtgcta agagatctat taaccacctg ggcttctcag actgatgact ctctcttcaa   8700
ttcccctgga tccaggacct cagcagccat gtcaaagccc catagtgacg tcgggaccgc   8760
cttcattcag acccagcagc tgcacgcggc catggctgac acgttcttgg aacacatgtg   8820
ccgcctggac atcgactccc cacccatcac ggcccggaac actggcatca tctgtaccat   8880
tggtgcgtgg gtgtgtcccc cgctgcgccc cccccccccc caaaaaaaaa acaggggctt   8940
catatgaccg tgatcttccc tgaaaagaca aaagaaatgt agcaaacctg ggtgctgagc   9000
gagatgctac acaggttctt tgggaactct ggactccggt cctaggaagt tgcaataagg   9060
aattttgcgt gctctgtgtt tgctgctaaa ggcagaatat agacagtgtg ttgttccata   9120
gcacatcttt taggagcatc tcagaaatct agggaagatc cttttttttt tttttttttt   9180
aagattttat ttattcatga gagacacaga gggaggcagt gacacaggca gagggagaag   9240
caggctccat gcagggagcc cagtgtggga ctcaatcctg ggaccccagg atcacgccct   9300
gagcctaagg ccgacgctca accactgagc cacccgggga tccctaggga agatcttttt   9360
```

-continued

```
gacttgctgt gtgcaaccaa gattctgtgg ttggacatct ggctaggctt cagggccaag   9420
tcttacttag gccttcttag ttagatgggg gcctgtagga tttcaagggc atagcaaaag   9480
catcccctta gctcagggaa gtgggtaaac ataatattag tcatgtatat gcttttgaaa   9540
gaattttgag ctgtttctgg gaggaaaatt taagggaaaa ggatatcaag agttcttcaa   9600
acttgaaagt gttattccac ctttgaatat ttaacacttt ggctttaaaa cttttttttcc   9660
ccctccacta ggaccagctt cccgatcggt ggagacgttg aaggagatga ttaagtctgg   9720
aatgaatgtg gctcgtctga acttctctca tggaactcac gaggtaagcc tcagctggac   9780
agcctggcca taggggcagc ctgtaggaaa ttgggtggca gtgtggttca tttagtcata   9840
gtgaattagg caagaggaag tctggggttt acagccagcg ggacgagtgt cttcactggc   9900
ctatcctatc atcctttccc catctcctgc catcccagtt ggccaagtct tcttacccaa   9960
agatgaccta tttggttatt ggccatggtt ttctcacact cgtgtactga ctaaagtgtg  10020
gaaggtttgg ggcacctggc tggctgaggc agaggagcgt gcaactcttg atctcagagg  10080
tgaacatttg gggcccacac tgagtgtaga gcttgctggg aaaataactt taaaaaaaga  10140
gtgtggaagg gttctactgg aaaaccctgt aagccgttag gtagcatggc ctcagtgctt  10200
gacacctcct accccctgggt ttctatagct gttcatattg cagtgatgaa ccaaaaagtc  10260
accctgcaga ttgatttctg gccgaatgta gacccaagat aactgagcag gtccaagaga  10320
agagtttcta taccattgca agttaaggac cgagtccgat gtaatcacac tatccagcat  10380
acagtacccc acttcatcaa cactgttcct agcctctctc ttcccatggg ttctagcatg  10440
ttaaaataga gtcagcacac tccccagcag cctggtagga aaggatctgt actgaggctg  10500
agtatgagct gacttgacct gtggacagag acttgaccca gggaccaggt ggcaactctt  10560
gggacatgct ccatccccccc tcctgttccc aaactaattt tgagggagga gtggaggttc  10620
cctgagggac aattcctttt aaaacccatc gggttccatc ataagctgtg ggatttcaaa  10680
gtggtatcga taaagaatga aggcgccaga cttagttcct tctttcgact tctgatactt  10740
tctgttcaga ataaagaaaa agctgccctg taaggacaag tggtgagggg ttgccctctg  10800
gcatttggaa gctgctgttt agactaaaaa taaagcctca ggaagtacag cccaagaggt  10860
gaacttctcc ttctggaaac gtgagactct ccagcatggg ttccctaacc cagtttcata  10920
aacagcctat ggcctggcag gcagctggcc tccaaatgtc atgggggcct gactgagttc  10980
agaggagctg ggctcagccg gcacttcagg caggttaaga cacgttcgtg gtgacattct  11040
gcaattttcc aaagtcgggg tccttggcaa gagtccccag gaattcttgc aagggttagc  11100
tcagcccaga gagagagcta aagatatcag tggggatcag ttcaccattg atccctgctg  11160
ccggaccatg ccagggtctg ctgggtgcag cagaagcagc agaaatagat gtgaagaagt  11220
tgacctttaa caaggcttga tatggcctct cccatccagt aaattaacac cacagcagct  11280
ccaaaatggc aaggctgtgt ggtgtccgct acacgtgctg gacagggggg ctggcttggg  11340
gatttggact ttttaaaaca agagccattt ggagataatc tctgcttaaa tacttattcc  11400
cagattagaa ttgggatttg gggaaaaaaa acaaaaacac ccaagttcct gttgtttgag  11460
gtttttgact agaataaagt tgtctctggg atcaagggtt taaaaactcc tctgaaattg  11520
ttctgatatc ctataatgtc acataagcag tttgaccgca tatccgagct cttacttaat  11580
acccaccttt ggttagtggc tacaatctgc tttcccagct cttgacaatt tttaaatact  11640
cttctaaaca gagcattgaa atagttttct ctccctcaca ctgaagggac gtctattgtc  11700
```

-continued

```
tgcatctgat cttttctgac agctttgcct gccacactgt ccctaacccc cttgggcagt  11760
tcatatgtgc aagaggtatt cttactcaat gtgtggtccc agagacacag accttttct  11820
ttttaagatt ttatttattc atgagagaga ctgacaggca gagaaacagg cagagggagg  11880
aacaggctcc atgcagggag cccagtgcga gacttgatcc cggaactctg agatcacggc  11940
ctgagccaaa ggcaaacgct caactgctga gccacccagg cgtccggaga cactgacttt  12000
taaacagcct aaatttagaa ccttccacag ggacagtatt gatggatgga actctttacc  12060
atttggtaac atccaacaaa accacagcca tagtggaaga ctcagtacac ttcccagaaa  12120
tgcaccaaaa gatgacagta tagaggatct gaatgatgta agacctaata atctcatttg  12180
tttatacata gccgatgatt ttatgccccc cccaagaaca aaaacacgtg ttgatttaga  12240
atgtttatga ttaagtaagt tattaggcca ccaaaacccc tcaagttcca taaaatggaa  12300
attatataga ccatattttc tgggatatct ttttatgcaa attttcagtc tccggaaaac  12360
tttcaggggc atgggcacac agtaggttaa tcatcttact cttgatttca gctcaggtca  12420
tgacctcagg gttgtgagat caagccccac atcagactcc gtgctgggca tggagttttc  12480
ttaggatcct ccctttccct cagtcactcc cctacttcat ccacaaacaa aacttacagg  12540
cttaaatgta ctttttggaa aacaaaagtc ttaatgaaag ttaatgaaat acttaaaata  12600
ctaggagcca aataatctaa aagggataaa agaaaagcac tgatcttcaa gcataacttg  12660
ataaaacaaa atgaatttga caaaccgaaa ataacttcct gtgaaacaaa cttctggaaa  12720
gtctggtcaa gaatgaggat gcataaaaag accatgaaaa gggactattt cccatatatt  12780
aggagagagt ttgaaagtca taaaaagact tctctaattt ctgtaagttg agatgaagtt  12840
gactatcctc caagaaaagg taagtccaag aggtagaaag tgtagattaa cagcctgaag  12900
aaatcggaaa ggtgggcagc ccaggtggct cagcggtttg gcaccgcctt cagcccaggg  12960
tgtgatcctg gagacccggg atcgagtcct acgttgggct ctctgcatgg agcctgcttc  13020
tccctctgcc tgtgtctctg cctctctctc tctctctctg tgtgtctctc tcatgaataa  13080
ataaaaaaaa aaaaaaagaa aaaaagaact cgaaaaggtg actgtgggct ctagctccat  13140
cccaggtcaa gaggacttga tggcttactt ctgtctcccc tcaaaggaac tttgtcatgc  13200
tgttccagag cctagaagtc ttcccaatat gttctttgaa gccaacacac accctgatag  13260
tgaagtgaga tgaggacagt accgcaacca gacaggttag ctcttggggc ctgtctctca  13320
cttagaagca gaaagcaagg gtaaaattca acagtccaca tccactcatc tgttaaagga  13380
atttcttccc ccgtgaccat gtgaatttta ttctaggaac ataaagtcca cactgggatg  13440
aaatagagtg gccagcatga ggtgatggtg ataactaggt gctcacctct gttctaagga  13500
cttcgtggat tcttttactt ttcacatcag ctctgaggaa aaggcatctg acaacaacga  13560
aacacctact cctttaaaat aaattacctc tatattctgt tctatacaga atatttttat  13620
tctgtttcac aagctagcaa tagaaagaca tattttcata actcctagta cggacatctg  13680
cccccagaga acaagccatg gtcctcatca gagactataa tagaagctga agattctcag  13740
acacagcttc aggcagcacc atccttggag atgagactct ggttccagct cccccctcag  13800
ctgccttatg ggtgctgctc tcccgggcag gctgaaggac agacaaggcc tgtcaagtgc  13860
tgaactgggt gcccctgtta ccagcaatgt cctggtggct acactaagaa cttggtgacg  13920
tcttggcttt gagtcccttt ttcagtcgtc agtcgtggcg agtggaaagg gaaaaggctg  13980
gaagccaggg cgcgtggttc agagagaggc gcattttcct gttccctaga ccactccaga  14040
aagtgattgt gaaaaccagg tctgtgggcc cctaggcgat ggcttattta gcttgagcta  14100
```

-continued ttgtaagctt aagtaaataa ctctggagtt tgaattgtag ttggaatcaa taggggaaaa 14160
gctcagaact gccaactctc ccaccggact ctgacactga ttgcccggcc agtatcaccc 14220
acacacacgt tagtgcaagg tctttttctc ccgcggtctg ctttatttgc caagggagca 14280
tgagcgtaag ggagacagac ttctttcatg ctgacaccgt gtttacatca tccctgtagt 14340
gggctttggt ggccgtattc tcgggtttct aagctttggc cttgagtgag tgagtgagtg 14400
agtgccacgg aaggagtggg tggcaacgag gcgattgaaa tgagcaagtg gggggtgctc 14460
agtgagtgga tgaccctgac gccagacaca ggagggtaga ggtctggaac atcacaggcc 14520
tttgcggagt gatctgcttc agccgcggct ccagatcttg ggtgggagca cagctgtcct 14580
cttccttccc ccagtaccac gcagagacca tcaagaacgt gcgtgcagcc acagaaagct 14640
tcgcttctga ccccatcctc taccggccag tggctgtggc cctggacacc aaaggccctg 14700
agatccgaac tggcctcatc aaaggcgtga gtatcagggg ccagtgggag ggaaggtgca 14760
ggaggcagtg ggccctagag agccgtcctc ggtggcgtgt gtcccggttg gaggccgtgt 14820
tcctcacagt gcagatctgg aaattctatt catcatggct aaaaaagttg atttggtgta 14880
ctttgctaaa aaatggtaca aagaagaatc tttttttac tttactctga gaacctcctt 14940
ccaagtctgt ccgttgcttt tcctctatcg ttacatagcg agacgatgat gttgtaggac 15000
gttgtaagtc tttcttgggt cacttccttg agaaaagatt gtttatttcc aaagccagaa 15060
gctttattgt tcctcatggc tgggattgga gcatgttccc tggaggaaag agcttttctt 15120
ttccttcgga gcgggcccgg ctcctgtggt ttggactcgt ggcttattct cttgtctgta 15180
gagcgggact gcagaggtag agctgaagaa aggagccact ctcaagatca ccctggacaa 15240
tgcctacatg gaaaaatgtg acgagaacat cctgtggctg gactacaaga acatctgcaa 15300
ggtggtggaa gtgggcagca agatctacgt ggacgatggg cttatttctc tgcaggtgaa 15360
gcagaaaggt atgtactgga ggcaatgtct cggtgtctag aaccagccct aaatttcctt 15420
tgacccaagg aaagtgggaa gtttggctga cagcaaggtt aaggctggtt tttctcagga 15480
tttctttctg taattccttg tcctttacaa tagactttgg ctcaacttaa tcaccttctt 15540
ggggagcata ggagaagatt tctttttccc catcctgttt gtgtctttgt ggttttcttc 15600
cttccatcgc tcagtgtgat acgtgtcagg cactatccca agtattttac atggtaattt 15660
gttcacgttt tataacaacc ttatgagtgg gtattatgat ctctgacagg tggggaaaca 15720
ggcacagaga ggttagttga cctttcccag actttacgat tagtgagtta ggatctgagt 15780
tctggacata gtggctccag cacccacaat gtgctgcttt ccagttcacc ctgctgggga 15840
gagcctgctt cctgttggac attgtgcttc catccctcca tccccatttc gcacaggtgc 15900
tgacttcctg gtgacggagg tggagaacgg tggctccttg gggagcaaga agggtgtgaa 15960
cctccccggg gctgctgtgg acctgcctgc tgtgtcagag aaggacatcc aggatctgaa 16020
attcggggtg gagcaggacg tagatatggt gtttgcgtct ttcatccgca aggcagctga 16080
tgtccatgag gtcaggaagg tcctgggaga gaaagggaag aacatcaaga taatcagcaa 16140
aattgagaat catgagggag ttcggaggtg ggtgtcctga ccgccccctg cccctcagcc 16200
ccagcccggc attccagaaa gcagactgta tcccgtggat acccaggtcc caaacctggc 16260
gacctaccca tcagagtgca aactcccaag cttaggctag acccactggg gaggagaagg 16320
cattggcatt tttaattatt tacataaggg ttttttttt ttttttaatt tgatgtattt 16380
attcatgaga gacacaggca gaaggagaag caggctccat gcagggagcc caatgtggga 16440

-continued

```
cttgatcctg ggattccagg atctcgccct gagtcaaagg cagatgctca accactgagc  16500
cacgcaggtg cccctattta cttagttttt tgttgaattt tatttaagta atctctatac  16560
ccgatgtggg gcttgaaccc acaatcctga gatgaagagt cacatgttct ttcaagtggg  16620
ccagccaggg gccccaagga atgggtattt ttaagaaaat acatatatca tatatatctt  16680
cccaggtgat tggcatggcg atgcacccca gaagtgactg acattgttct gtaggcccag  16740
gcccagtgtt gggagtggat ggggagggtc actgctcaca ggggccctca tgctgtcctc  16800
ctgatgagcg ctacctgtgt ttgctggaat aagaggacgt ttccccccat cctacacctc  16860
caccccattt ttcccagtgg aaggaagaag atggcaggct gttaggaagg tgctcttgtt  16920
tggcccctca cttgggagat aggtggaagc tcatggtgtc cttgtcttca cttaaaaggc  16980
agttggcctg ctgactgggc cggttctggc atgttcccag cttcctggag gaaagcatgt  17040
ggtcctagct gtacttcacc tccttcccag tatccccaag tagagctaaa agagtatggc  17100
cagcttggtg acatctgttc ctctgcagct ccctgctagg aacataagtc accagaacta  17160
aaaccccaga cctacttggg tggattaggc ctgtgcttgg agagggcaga ggggcagccc  17220
tacttgatct tgccatcctt agctttgtgc gggtggcctt tgtaccaggc aatatggagt  17280
ctaccttctg tcctgataaa ccatgggtga tagctgtcct tggccatagg ccaggccaag  17340
ccacatgtcc tcatgccttc agcaggttgg aggggccccc ctcaaggaac agccctcagg  17400
tgtccttggc tggaaggcca cagacctttg tgtcaggagc agtcagctaa ccttggaagt  17460
gctggcggca gtgggggtgg tagagaggtg ccttaggcgg ggcctcatga cctgcagggg  17520
gagaggaaac aaacccaggg ggcttcggag gaaaccttgt cttttccctt acccccttggt  17580
ggaacctcca tacgagtgct aaagcagccc agcaagcagt actgttagcc caccttggga  17640
gaccaggtag ctggaacacc ccatcccctt tgtgcccacg gcgaggtcct ggacagctgt  17700
cctggtgaag ggctgctgag tcagagtcca ggagaacctc tgtgcgtcac tgcacttgcg  17760
gccttgttcc atagaacctc tctctccctg ccctctttgt caggtttgat gagatcctgg  17820
aagccagcga tggcatcatg gtggctcgag gtgatctagg cattgagatt cctgcagaga  17880
aggtcttcct tgctcagaag atgatgattg ggcggtgcaa ccgagcgggc aagcctgtca  17940
tctgtgcgac acaggcatgt gcctctcccc acactcacac actcacaggc gggtgctgct  18000
tggtctcttc ccaggaccct gccccacgcc tctcaaacac acgtgcaccc tcccttcccc  18060
tcgtgcatgc acacaaagcc ttactctgtg cacgaacaca ggatccaggg aatcagcctg  18120
tagtccttcc tttctggaga ccgcccaggc cacatctcac taatgctctg tccccgcgca  18180
gatgctggag agcatgatca agaagcctcg tcccacccgg gctgagggca gtgatgtggc  18240
caatgcagtg ctggatggag ctgactgcat catgctgtct ggagagaccg ccaaagggga  18300
ttaccccctg gaggctgttc gcatgcagca cctggtgagt tcctcgggcc tccccgccga  18360
tgtctgtagg ctcgggctgg gtggaagcag gctctggtac gaggcaacac ctttcaggct  18420
tctgtgccca caacctttta tgatcctcta ataagtcaca gcaagactgc ggaggtgtgt  18480
gctggggagg agagggtgtc ttggttttcg ttctcttctg tcttcactgt ccacgctcca  18540
tctcctgtct cctcctgtcc tggaggcatc ctccttcatc agcctacacg gttcacttct  18600
ggcctcgagg ttgtgaatct gtcccatgat tcaagtactg aggtacttgt ccctcttcct  18660
ctggacagcc cagaggaccc agaagaggcc gtgggctcct gctccctgcc agcctgtctg  18720
gcttccgttt gcatccccac ctggccacat caggtgtctc cccccgcccc caggggcccc  18780
gggcctgcac tggagactgt cgtgtgtgtg aggggaccga gctggccttg catggcgcct  18840
```

gcagcggggc ctgcttcgct gagctgctga acggtggggt ttagtgactg gcagcaagtc 18900
cacaagtaga ggcaggtgga aggcgactga gcctgctggg gcgtggaggg agagcctccg 18960
gaagagtcct ggaggcagct ttttcccacc ctggcagcta gctagctctg acgctcttgg 19020
gcttgtccac gtgcccctgc ctggctcctt ctcagttcct tggccctgtc tggtcctgct 19080
ctagacacac ggaagacttc acccagggtt cacttaccag ggctcctgag gcctgggagg 19140
cagaggcctg cacattcact ttcttaacag tagtccagtg tcagcactta acgtgtgtgg 19200
agctctgcaa acttgcctct gatcctgaag tggtttttcc ttgacctatt ccttttccca 19260
tcagcagagg gaccctgtgc cctttgcgtg atgccgcctc ccccgaactc tcccagatgt 19320
aaccccccaa tacacaaagt ctcttccttt cctcgttcac tttttgtgtg tccagttatt 19380
agcctgtgta gattgatgta atctttgtat atcccctgtg tgatagatgt caccccaatt 19440
tacggatgag gattacgtga tgataaagcc ttagtttgaa cccagaactg ctggctgcag 19500
ggccagtgtt gtcctgtatg tagtgttctg tctagcaggc gataaggcca cgtctccatc 19560
aggggcctgt actgggctca gagattaaga ctctccctct ggcctctgaa ttccagctat 19620
ttttccataa ccagtttctc ctctggacag acagacacac cttagagaga accccagggc 19680
ttggatggca ctgctcagaa gataagtgat gaggtgtagg tgaggtggcc tctcctcacg 19740
tccccagtta acgccgagct tctcttaacc gttcactgct ttctctcgtg tgttgtgtaa 19800
atgaggcaat taaccaccca taactcaggg ctaggccgtc tcaggtacgt cccgtttcct 19860
gctcggtctc ctgtcctttg gattgcatgc actccgttct tagagaagaa agaaaacctt 19920
taacctagtg aatcctgtac ctgcctttac cgtcaaatta atggaacgtt ctgatttttc 19980
tcgcacccat cattctctaa gattccaatc ttccgaagct taaattttct ttctacttcc 20040
tgatgttatc cgagcaggta gtctgtgact ataacggaac ggctttctca tgactgtgat 20100
aatccttaat gttgtaatca agcgtctctg ttaaactcac ccgtgtgctt ccacaggctt 20160
ctgtcccttc acatggctgt tgagtgtgcc cctcgcaagt ttgccatctc cccacctttg 20220
tgcttggacc tcggttaagc tgtgtggctt tggcttcatc tgaccccagc tttccagcgc 20280
tgctccgcgc gtttccatgg caggccatcg gaaaggctcc tagcagccgc atgcggaggc 20340
caagcaagtg ctccatgtgt gcatggaagc caggcaagac gccccgtggt aaccagacag 20400
ccatgtgagg agggagggcc tgttccttcc tgtaagctgt gtcttgaggc agcatggtca 20460
ggtcctgcca gggagcggcg tgggcccagc ctgggcatgt ttctatgcca aggcgccggt 20520
gcctgccgcc atcttgtctc cctctacccc cccaccccca atcagaaaat ccttccagaa 20580
tggaaaaccc catttttcct cttttggaga ggaaacagca gcagttgatg ctggaaattc 20640
tccagccatc cctgagcagt tgggctttca tcatgctgcc tcttcgcatc tgcatgaagg 20700
acagatttag ccaattaacc taaggttacc ttcctctgat taattcccca ttctgtcttt 20760
ccatgtgttg tctctcgttt ttctccctcc tccttccctc ttcttgcttc tcctccccc 20820
tccaaacctt acagatagct cgtgaggctg aggcagccat gttccaccgc aagctgtttg 20880
aagaacttgt gcgaggctca agccactcca cagacctcat ggaagccatg gccatgggca 20940
gcgtggaggc ttcttataag tgtttagcag cagctttgat agttctgacg gagtctggca 21000
ggtagggccc caagggcagg taactccgta ggataaccag cctcttgctc cagctgatct 21060
agaagacggc tggggcgcag ccctgcagct ggggcccggc tccagtcctc tcctcgtctg 21120
caggaagcca gccagggagt cagggcaggg caggaccgca agggcctccg gctcggtagg 21180

-continued

```
cacagtggct gccacaggca cctggtgatg ggccagttcc catgaacctt ggtcttgcgc  21240
gggtctgcgg ctccagttgt ccgccgcctc ttggcctcct gtccggggac acgtccctca  21300
ccagctgtct gtgagcctct tcccctccgt ctcccgtgcg acaccgctct gacagtcctg  21360
tcccccctcct gtccctctgg acggatgttg ctcccctaga ttgcccgtga ggcagaggcc  21420
gccatctacc acttgcaatt atttgaggaa ctccgccgcc tggcgcccat taccagcgac  21480
cccacagaag ccgccgccgt gggcgccgtg gaggcctcct tcaagtgttg cagcggggcc  21540
ataatcgtgc tcaccaagtc tggcaggtag gaggtggcag cggctcccag ggcacgccct  21600
gctcggggca ccttccctgg gcgtcccgag agccgtgcgt tgatcggggc tcagatggcc  21660
ctgagcccag gtaagcccct ctgcctgcca cctgggcctg aggacccgag gttagactag  21720
agacttcgtt gccgaacgac agactgcaca tgctcacttg agtatgtgaa agttcatctt  21780
ttaagaaagt aattgatgac cagttttgtt cattccagcc actacatgcc ctttaaaagt  21840
tcagtttggg agattagtgc tgttcactga cgtgctgttg ggttggtgca cctgtctctg  21900
tctgtctttg agccccaaag gcaagcagat tcaggcctag gaaaggtcac cacgtcatct  21960
tgctggcacc ctagtgtcgg gccgccgagc tgaggctgct gattggcctt ggcttgggat  22020
ctcctcctca tctggacatg gagtcagcct ctgtcattgc cccagtctgg gagtgtgctc  22080
ctcatccctg cctgcagggc cacaggaatt cctggaaggg gaagggatgg ggtcaggctg  22140
gtggtccccg agcatggagg tgcggcaggt ggggttgcgt gtagaaccgg gacatgagat  22200
ctgtgcagat tacctcagca gagggctccg gataaacagc tccaaccatc agggttgacc  22260
tttgtggaaa ggtccagcct ttgctctttg gctattttta gctccagtct tctgggattt  22320
cactctaacc agtcccgact tcagcacttg cttccctctg aagccttgta tgggggccag  22380
gcctttagca gggcagcctc tgctgtgaca tggcttaagt ttccctgaca cctgtcggtg  22440
tccttagggc ttgccttccg acgcccagtg cctcctgcaa gcaagcccct ccccagctcc  22500
tgagacccgt ctacagccac aagtgtacaa tgttcaagga agcatgtggc actggggccc  22560
agggggggccc tctaccctcc aggggactct gcacagacag agcctcccac attaaccttc  22620
ccatctcctg gtctagcctc ctgggtaata cccaggtttg gctctagagc tgggttgcta  22680
ggactgtttt agggacttgg gggccatgta ggctggggga gagggcacag cagtagaggg  22740
ctggctttgt aggttccctg gggggctggt gagctctgct gctgttcttt gcagatgcca  22800
agagtcaggt gctattcaca tgctgcttgg cttgtagctg ctgctggcag caggaggaat  22860
gggtgctggt gaggttgggc agggctgtat ctgtgccagg atgggaaagt tcagaggagg  22920
ggcttctgcc aactgagtcg tgtggggtga gtgggtgaga ctgaccgggc cgggtcggtg  22980
tgatcctggg gccctgggct gtggggaggg gggtaagaag ccaagtggac agatagcata  23040
ggaagaagag tcggattctg ttcctcggaa ggtggaggac gaggggcagc cctggcatgg  23100
ggagcagatg ctaaagtggc cagagtctga tgctggcaga atgagttgga ttagaggctg  23160
agttgttgct gaaggccctg tggggggctc tgggaggctc tggaacactg tttaatggtc  23220
tcttctgctt ggccgtcatc ctgtcgcagg tccgctcacc aggtggctag ataccgcccc  23280
cgcgccccca tcatcgctgt gacccggaac caccagactg ctcgccaggc ccacctgtac  23340
cgcggcatct tccctgtggt gtgtaaggac ccagtgcagg aggcctgggc tgaggacgtg  23400
gacctccggg tgaacttggc catgaatgtt ggtgcgtggc tgggagcaaa gggctagcac  23460
ctgcctggag gggtggggac ggtgcttggg cactgatctc cctgggatcc tagagaaagg  23520
ggaacatgct gaccttggag tgtgcaagag tcctagctgt cttcccaggg aacgttctct  23580
```

-continued

```
gactcctcct tcccattccc tgaagttctg ggctaagccc aggagggagg aggagccttg  23640
gagttctggg gctgagctgc ccacttctct gtcttcccat ccggggccca aagcaaagga  23700
tcctggatag tcaggaatgt cccttcttgg gcatctgctc cttgttgagg gttaagaaaa  23760
gattagagcg ttacatcatg gggtgtccta cacacagatc acgtactcat ggcctttgtc  23820
cctaataaaa gtaggatgtc cgtgcatgag agggactact ccaccctcta gagtataaaa  23880
tgatgtccaa aggtccccgg cagctgccat ttcaattgat gaggaagagt cggggcctcc  23940
ctggtccctg ggctgggcgg cttgcgccac cttgtggtgg gaggcagtaa gggtcaccca  24000
gtctggctac ctcggcgggc gggtcagaca ggtgctctcc tgcctggctt gctttttctc  24060
accgaccttt cttctcttct ttcaggcaag gcccgaggct tcttcaagaa gggagatgtg  24120
gtcattgtgc tgaccgggtg gcgccctggc tccggcttca ccaataccat gcgtgtggtg  24180
cctgtgccgt gacgggcccc agagtccctc ctccagcccc tgtcccaccc ccttccccaa  24240
cccatccatt aggccagcaa tgcttgtagt gctcactcgg gggttgtcat gtggcactgg  24300
tgggctggga tgccagggaa gatgaacgcc tctgtaaaac atgacttttt taggaccctg  24360
ttcagtgcag gtggcccaga gctgggctgc acatcaggtg acctcaccgc agcaacggac  24420
gagggaaggg tgcaggactg gaagccccag agctttaaca cggagggcaa cagctcctgc  24480
ttctcctcct ctgtgtactc cattcggttc ctatagaaaa tggatacgca gagaactccc  24540
aaccctggcc tggctgggtc tagagaccac cgcaagaatc gcagcccagg gcagtggttc  24600
cagttacact ggctcaggcc cttactcgct tctccacccc cctgtctccc ccactcccac  24660
ctgcccttct gttcctaggc tcagctgcag gcaaacactc caccctccat ttcccccact  24720
cctgcagctg cctccaggcc tgttgctata gagcctacct gtgtgtcaat aaacaacaat  24780
tgaagcaccc a                                                       24791
```

<210> SEQ ID NO 49
<211> LENGTH: 23008
<212> TYPE: DNA
<213> ORGANISM: Mus musculus

<400> SEQUENCE: 49

```
cgatgtcctt ccgccacgga aggtagtcct cctcaaaagg gcaacctgct tgtcccgcct     60
accctgagct tctctcagga ggtgcgggcg ccccgttgag aggcggggcg ccgccggccg    120
cagcccggat tgggcgaggg gcggggctgc ggagggattg cggcggcccg cagctgtgat    180
aaccttgagg cccagtcggc gcagccccgc acagcagcga ctcgtcttca cttgactgac    240
gtccgctcta ggtatcgcag caggaaccga agtacgcccg aggtgagcgg ggagaaccta    300
agccatctgt ccccagagcc gatgcccact ggtgtgtaac gcaggcctgc ctgcccacgc    360
gggactcagg cgccaggcat cgagcatccc actccgggtt ggggaggagc cacacttgag    420
tccaagtctt aatcctccaa attgagggtg gccggctagc tcctttccca cggtctcatt    480
ctgctctctc ttccatctca atctggttcc agcctcttat cttactattg ctatcctcgc    540
caccctgttc tcgccctgct ccgatgctcg tcctcctaca tccactacga cttacgacct    600
tcctcttagc tctgtgccct cataattcgg tgccctcctc ttaatctcta cttgaaataa    660
ttcccctact caccccaccc ccacccccca ttcagcctcc gcgttcatcc tcctttcagg    720
tcagcgttct cttcccgcgc cagtgttcgc agctcttcgt cgcccctccc ccctccgatc    780
cggtcacgtc cgcgccgcag catcctttca acctccatat cctcgcccct ccccctcgca    840
```

-continued

```
gcttttcccc tccccccgca ttctagtcac gtccgcggac tcctcgtggt ccggtgcatg    900
gaggtaggat gcagtcacta gcggtccttg gtaatgcagc tacaagttac gtaacttttg    960
tattcccggt ggcctggcaa gaaaggttgg ccgctattgc tgcctgtttt gtgtgcccgc   1020
agatttttgg tggtgggcac gggccctcat tgctctcgcg ctccatcctg cggcggaggg   1080
gcggcacgta ctgcgatgcg tctgattaat cggtcatgct gctcccacgt gctggcgagg   1140
gggagggtgg gcgatcaacc catacccgtt cccgacagaa actggagccc gacgctacca   1200
gaacacacat agcccacaga gctcggtcta attagggaag cagattttgt caagtcagtg   1260
ctatgaggaa gatggggctg catgcacaag gtggccggca tactggtttt gaaaaagccg   1320
ggcatcttct agtctgaagg ctataaagac ccagtaaata cccagtcata gtaagataag   1380
agctcgacca ctttttccaa atccaggaca ctggtagttt ggaaaaagtg aaccttatag   1440
tgaaaatcca gtcgtgcatg gaggcagcta ggttttggaa tccggtgtga tctattaata   1500
ttcttaggtt tggcctctgg tcctgtgtca ctccaggctg ctaaattact ggtctccttg   1560
taagtacggg ccatcctcga tgtagtgact aacctcgggt gaaatatcca gaagggcatg   1620
cattatatcc ttttggtcaa tgaatgaagt agttaccttg aaggctacca acttgattct   1680
gtctccttac tatttttatg cacattaggg gtaagcttgg ggaggcaggt aggctctgaa   1740
tacccagtat gcccatggaa acaaattctc tctggaatcc cgtcagtgtt tacaaagtaa   1800
ttaatgttac attgcagctc tcctgagaaa gagctatcta aagggagaaa tctgtgcagc   1860
ctttgtcttt ggctgtgagg gtagaaacaa agaaacaggt acccagatag aagccttccg   1920
gtcctctttg ttcaagtaag ccttttatgc cttctggctt gtaggaagtt tggtactgtt   1980
gccccaacag tggggtgggg gggctcagat caagactcaa ggaagcattg ttagcaaata   2040
atttgccctc tgatggcctg attatgctgt aggaaaggca gtgagggtgt tctttgggaa   2100
agtagtgtaa accatcaccg ggtctgggca agatgactca acctttcaac tttgcggctt   2160
ttgagaaaat tttcttcctt gggtgagtga ggggaccaca cttgttctct gaagtgttgt   2220
aaggttccct ctttttagt gagtcaaata gcgtgcattt tccctgaatt aaacatgtct   2280
cactcagact gagtgtggtg gttcagcttt aatcccagta cttgggagga aggcctgtga   2340
gcttgagaac atggagcggg tgataccctg tttccagagg tggcgggtat cacctaaatg   2400
aaggtgacca taagagtgga aatgtggagt ggctgcttct agacggcata ttttcattct   2460
tgaatgattg gcacagcagc ttttcataga acaaccagta tccagattgg cagtttctct   2520
cgaggcattt ctgaattatt gcttaagcca aactatatga atactaatca cttatttagt   2580
acatagctat tttcatttta agcattatat tttaaattat ttaatttgta gggaaatttg   2640
ttaagaactg tttgccagca ctcaggaggc agaggcatgc agatctgagt ttgaggccag   2700
cctactctac aaagtaccaa gacatccaga gctacacaga aaccctattt tgggagtggg   2760
ctttggtgga aatgtatctc aaccaggtat aatggccctt gatcccttta ttcccggtgt   2820
tctggaggca aactggcaaa tgactttgag tttagtccag ccagtgagtg acttggcaca   2880
tttcatagct gactccaaac agatttatgg gggctgggta tgccatctgt gttatatgaa   2940
cgtgttggtc acaggaaacg ctattttatt tcttaaagct gttaattgct taatattgag   3000
tggaagggat gaggaagcgg ctatggacag aaaggtagaa aaagcgtttc ttgccttaaa   3060
ctcacattgg gtttttagca tctttagctt ttttgcagca agtcgacacg agttgggcaa   3120
gaactaagct ggagattgag gtagaggaaa atgactcatt tgtctttcag tttctcaatc   3180
atctcaaata cccacaggca agttaactgg tgagtttttt tttttttttt ttttttact   3240
```

-continued gcttctggta aaggaccgag tcatctctgt aaactgcact catggagact ataataggag 3300
tagatgactg tatgacgaag aacattcttc ctgccctgga actttcgtgc gtcttgaaat 3360
ttttaaccaa gagccagact tactttggct atgtagtaat caggagaggt gagccccacg 3420
tgcatcgtgg cctgcaaaac tgctggatct taaggcctag tgtagctact caggtttgga 3480
ggtggtccca gggcaccacc agctgtgctg tgaggccaca cccctactgt ggtttgtgcc 3540
tgtctgcacg taggagagag gtctgggctg cagtacctta agtggcctct agggagctct 3600
gagcatctcc tgaggcctgc ctccaaagga agctgtattc cttctaaatg tgtgaataac 3660
ctttaggcca tattttggcc ttaaagtact ggtgtctcca gtgtaaaaga ctttaccctt 3720
tgccatgccc actttggagg agtcaaaggt ttgatttgat gtagagaagg gctgggtgtg 3780
gtggaatgta tttttaatct cagagagaca ggacagtcag gatttgtaga gtccttgtct 3840
caaaaaaaca aagtagggaa ggggctggca atgtagatct gatacaaagc catggtccat 3900
ccctactact acataaaatg cacatagtag cacgtgtctg taatcatact gagcaaagga 3960
cagtgggatt ggagaagttg tgagttggaa aaaacaaaat ggactatgaa ctgaataaag 4020
tcagaatgct atttaattaa gttttggaaa ctataaagat aaaaagtcag tgttgatgct 4080
aagttctggg tgggagaaat ggagtcttta gatcccactc cttggggaaa aggcggtcgt 4140
gcaagcctgc gggcagaagt agtaagtagg tcagtgctct tggacagctg gtgctgcctt 4200
ccttccgact ttaatcaccc tgcccccaac tgtggctccg ggctgagccg gtgcctcctg 4260
ttgctgagac cattgtgcat tctgcttaca cctggttctc tgggcttctg agccagggtc 4320
cagagcatgg gcagcattcc cggaaacact ggccttgcta aggaagaccg catgtgccaa 4380
ccggacagaa acttctgcaa agtcacctcc ttcctgctct ggctagttct ccgctctgca 4440
cagctgagct agaagccagg aaatcccttg ctttgaggaa agtaagacct tgtcttaaaa 4500
atcaaataag ctgggccgtg aggcaggcag atctctcagt ttgaggccag cctggtctat 4560
tgagttccag gacagccagg gctacacaga gaaaccctgt ctggaatctg actctcaacc 4620
cccaaaatct ctgctcaagt gatctgtacc cttgataccg cacatttaat tttgttgtat 4680
gctgggtact gtgctccagg ccttaccact ttctggggat agaactgtca cctgctttga 4740
ccctggtgtt ggcttctcat tagggtcact gatagctgga cagcagcctt tctgatggat 4800
gaagtgagat gatcttgggt actggggaaa gtaggcttgg ggtgacatca gagaaaggtt 4860
gctacaaagc cctgttccta ggccaggctg ctttattagg gcagcaatga tttggaccta 4920
cgtgacgatg tcattggtgg ggtgaggcat gaccttccaa gagtgttggc tctaagaagc 4980
agggtggcac caggcatttt tggtttgggg attttttttt tttaatgacc tttgttcctg 5040
acacgaggga gatgaatgtg aagggccgag gagaactgcc tgagacagga aagggcagaa 5100
ccaggtaatc agagccaagc tgggcctgtg catgctccaa cctacagccc aactgaggcc 5160
tgggctggtg tctcctttct cacagagggg caatggctct gaagaacatc ctgcttcagg 5220
ggctcaggtt caagagtaag gcttctgccc cagggcatgg tatctactgc tgtcgtggga 5280
cacaccgggt ttctgctgcc ggctggaggt tggctgtgca tgtgggtgcc tcctgaggag 5340
gaggatgctg tagtgagttg gctggcatgg gtggggccgc atgtcctggc agtcactgct 5400
atctatacaa gtatttggcc aataaggcaa gtcctgccca ggggcccacc ttaccctaag 5460
gaacaaggct ggagctgctg tcctgggcca gaaaagactt ctaaaagggt gttctattta 5520
tactatacta tagataggtg gttggctgga gttgtggggc tctggaggcc atgcaatggg 5580
cagaagagct gtgggaggga gggaggggct ccaggtcaga gccttgggag tgaaaatagc 5640
tgggttctaa ggatgaggtt ggtaggggac ttgaaacccc tgtaaggttt gttagaagtc 5700
tgtttaattg tgtccatcca ttggaacaca tgtattttca tttgtcactt tgtatatggt 5760
agcaaggtaa gtctactctg cagactttag gtttaattct agatagagaa atgggttgtg 5820
tgtgaaattt tacctgctaa attgcatcct gagccctgga gggcagcagt gcttgtctgt 5880
tggaacatcc ttgttgcaca acaaagttct gtcaagcctg agaccggtca aaacaggaga 5940
agaaaattgc atggaactga taggttgtgg tcatgaaatt tttccatgga ttagccacac 6000
acttttggga aggtgacttt taaagtcagt ggattaagtt gcccttcctg ggtcagtgaa 6060
gctgccctgc tgagcacttt tgagggcata gagaacacac atctatcact atattttagc 6120
agggtaattc tgaaggacac ggctgatgtc acagtgagct ttatagggtg catagagata 6180
aatgtgtcat tttcaaagac tacttaatta acagttttat taataaagga cacgctgggc 6240
agacagaagt gtagtaagat gctgtctcag aagagtaggg cagtaacgtg atacaggcta 6300
tcatccaagg tggagcagcg agggtcagtg agatagcttg gaaacacaca caggagcttg 6360
cttctgatgg ctccagtgct tctgtcccca gaacctgagt ggtaggaggg gagagcacag 6420
ttgtggtcct ctgatccctg caaggtgccc accaggtacc ccctaaaact aaatagtgaa 6480
atttgtgtat tgggggaata aagtacttca agggatccag taaagggtca cttttaccac 6540
tgggtttttt tatttatatc ttctccactg tatatctgtt ttaatgtagt taacagcaac 6600
tttttgcctt gttattaagg tcgttaccac aaagagctta gtcatattca gctttcacct 6660
taatccttgt agctcttcag ggcaaagcat actccactct gagcgatctt tccaagtgag 6720
gccaccaagc cacactgagt caacaaaaca gcaatatgcc atcagaagcc cagacccaga 6780
gaaccaaagg tatgacctga tcactgggcc tcactcaggc agggatttgc gagggcacac 6840
tcgtgtctca gatgggaaga acggcctggt ggctggcttt ttcagtagtt ttcagacact 6900
gtcctggtgt ctgtcccgct cacttgtccc atctcggaca cagcaaggcc tttgtgtctc 6960
attggcttgg tgtaccatct gtactgtccc ttagcggcca cttatcctaa gcctggctgg 7020
gagccgtgag tttgccagtt gtgtttgttt cggccatgag tagaccaagg acctggctgc 7080
ctagggactt ctcacatttg gggagaggga aaaccaggca gaattgatct tggcagagac 7140
ccggagctca tttaacaaac aaggtgctgg gaggcaagga gctaagactc tggagaagtt 7200
gacatcttgg tgtctgatgt gtcttgtaga gttaggaatg aacaatgttg gccactggtt 7260
tcttccttcc tttaaaggtt ctcaattctg caaagaatgt agtggttgca cccctgtaat 7320
cccagcaccc aagagctgga acatgagact gtcatcagtt caagaccagc ctgtgctaca 7380
tatgataact ttgtcttaaa gtttttcata tctgcatttg aagacttaca ggtgtctggt 7440
acttggtcac tagtgggtgg ctgaagtctc aggttgcaga gacagactta ggtacatact 7500
ctccaggcgt ccagaaaagc cagagttccg ggaagagtgg gggtcctcag ctgaggagac 7560
aggggagagc aaggatatgg agatactgtg gagcacaggc tgaagacttt atgttcagga 7620
gtttgagagg agccttgtgg cctgaaaact cagatgagaa agaatgtcag cttcattcaa 7680
gtctcagata gtctgcgagc tatagcccag agctctcccg agagttctgt cctctaatca 7740
gctgactatc cagctcagtg agcacttagt tgtaatgaag taaaagcaaa ggtcaggaca 7800
gctgttggaa ttgtgacctg ggtggttaat tacctggaac agatgttcag actactgggt 7860
gctataccta tcagacagag aaagaggctc caaatagcca gacctcgggc tggggaagct 7920
aggtctaatg tcagcccttg gaaagattaa agatggtaac ttcaaggtca gcctaggttg 7980

-continued cacagtggat ttcaggccag tgtagagtag ctgctgtgat tccatctcct aggttacaga 8040
agactccttg gtgaggttat aatgactttg gggccatttc aatgcccttg tgcaaaattt 8100
gctttgtatg tcttgtaggt ggtactgtgt ttttgttttt gcttttgttt attttttgct 8160
aaagaattat ggacttttgc ttcctgccca gaagaactgt tttgttccct gtaatttgga 8220
ccttactctt gtgtctgata aaagctaaag aatacattta gatagacctg ggactttggg 8280
agtaaaagaa aggctttggg acagggtttc tcttgtttgc aggaccactt taggtttggg 8340
tgaatgagag agtgagacca tgctgagtgc ctaccaaagc caatactgga gattggacat 8400
catgataggc ttcccaagat gtttgtgtgc tgacatacta gttagaacat gcgctggggg 8460
gtgtttctta ctgtaacttt ggaggtttcc ttgtgtgggg aaagtgatgt tctttctagg 8520
gttgatgaga aagctcttaa gacaaggtga cagcccatgt gagaagcctg cttaaactgg 8580
ctcccagggt gtgtgcagtg ggtagggagt tactcttgtt caccaaggtc tttgctgttt 8640
gccaatagtc acaagagccc tttgcccaat ttgagtagca cccacataac cagcacgtgc 8700
caggctttta tgctgcttgt gcacaaagca atcttattgg gttaatgtgt aagcaggaga 8760
cagcttccta tgccaagtgc ctcattaagc agtgcctaat ctaattgcac tcttcaaatc 8820
tccgggaccc aggacttcag gaaccatgcc gaagccacac agtgaagcag ggactgcctt 8880
cattcagacc cagcagctcc atgcagccat ggctgacacc ttcctggaac acatgtgccg 8940
cctggacatt gactctgccc ccatcacggc ccgcaacact ggcatcattt gtaccattgg 9000
tgagtgtggc cctccttcct ctaaatggag gcttctacct gatttgaaag gcatagtaac 9060
cattgcagag ctagcctagg ttctgagtga ggcacggtcc acatttctag ggagtagag 9120
gtcttgggaa ttggccatca agaagaatta gtgtgctttt tctgtagttg gtgaggttca 9180
ggggtggtct ttttcatgtg ctgtcaccaa cagcattcgg tagacagaca tcttgaaggc 9240
agagaaaact gttgccctcc acttttctgg ctgaatgagg ccctgcagaa tttgtagaga 9300
atgttagtgt tcccacataa ttaagaaagt gactagtaca atagtctttt ctgtactttg 9360
gaaagacctt tctcttaatt tgtgaaggta attaaaagca aaggatgaag agttgtttaa 9420
atgttgagca aatttcagac attttcctac ctgagtcatg attttcttcc tgtggatcta 9480
aatgtttctt gatagggcct gcttcccgat ctgtggagat gctgaaggag atgattaagt 9540
ctggaatgaa tgtggctcgg ctgaatttct ctcatggaac ccatgaggtg agcgtcaacg 9600
agatccagga gactcagcga ttccttaaca gtcgtactgc aggcaggtgt gagtccaggg 9660
gtcccagtga acggaacatt gccgtttctc tcttctaact tcactggaat agaaacctgg 9720
cctgctttgt cacccaccga ccagggttag ccctaccgtc aacctttatg aaagaaggca 9780
cgtaagggtt tagctggaaa ccctaggcca tcagatgtct tggcccccat gcttcagggt 9840
ttttacagtg gttcctgtgt gtgaaccaaa aggttctgag cagatggata gctggagtca 9900
ttttaagatc taccttttaa atacttctct ctccccctcc ctccctctcg acagggtttc 9960
tctgtatagc cctggctgtc ctggaactca ctttgtagac caggctggcc tcgaattcag 10020
aaatctacct gcctctgcct cccgagtgct gggattaaag gcttgtgcca ccaccgccca 10080
gctttttaaa tactttctaa cttgactgtg gatttcctac tggtattggt gaaggaggga 10140
aggagactcc tctctgcctc ttggtttctg tgtcctattt agagtaaaag cattaaccct 10200
gtgctgtttt gccctctgac ctttggaagt tgtttggact aaaaatagat ggagaagaat 10260
ggtccaagaa gtgaacccca gaacatgaga atcttcatag attccctaac ccatattcca 10320

-continued

```
taaatagctt ggaggctagt gcccaaatgt catggaacct gagatagttc ctcaggcacc  10380
taagcaatat ttgacacatt cttgctgggt gtggtggtac aagattgtgg ttttgaggcc  10440
agaatgggga ctatcctcag taacatagta agatcttatt gcaaaccagg agaggtcctt  10500
attttccaaa ctctggcttt ccacaggagc tcccaggaag aaggtgagcc tagttcagag  10560
acagaactag ggccacttgc catggtcctt gcgagtagtg tgtttagtca ggcaaaaata  10620
gatttggagg tgctgacctt tagggctctt gagtccagta aaataacacc atgcagcagg  10680
tctaagaggg caggggacag tgagactgtc cagaccactg ggcaggccag ctctgccttg  10740
atttcagact aaggcattag agattggctg tactttgaac ctttttatat cacaatataa  10800
agcttcacaa gtcagggctc ttattccatg tgcaccttca gtgaggctct gggtgatggt  10860
ggtgctggtc ttggtgattc cctggagacc gtggaaacca agctccttcc ctctgacagg  10920
aacatcagcc acctagctgc acctgatctt gacagctttg gctgtgtctc taattcccat  10980
ctcttgcttt tcacatattc aagatgtgtc attcttgctg aacaggcagt actgtactcc  11040
cacactggct tttaaacagc ctaaatttag agcctctaca aggatagcac tgatggctgc  11100
cagtcttccc catttggtta catgccagaa aaaccacagc tgtgataatg gatagcacga  11160
cccagctccc agcagtgtta ccatgcagag aaggctaatt caccaccaga tactccaatc  11220
acaatgcagc tttatatata cgaagctgaa gagtgtttat tatgctcgtg aatgtgctga  11280
ggtgtgtaac tcagtgtgta cagccataat tcttcagtgg aaattaaggg agaaatccaa  11340
acttctagag gatctctaaa gcaaatgaag gcagtcggta gtcaatattt tgggatatct  11400
ggagctgggt taccgggtgg tggtcagcct ttgggcagct tcggtccttg tggatgaatg  11460
gtggttccag ctctgcccta acaaacaggc ttgcaggtgt tttgctgtgc tcagtggttc  11520
aaggaccaga ctcataaagt gctgaattga atggtccatt gtcaccagtg tcacaaggat  11580
atgcactggc aacaaactat tttgctatct tggctctgag tcccagatag gaaagggaaa  11640
aggtttgggg aaactttatt acaagtgaag aaagcaatgg cggttgcacc ggggcaggct  11700
cctggtcgga ggaagtggtt atgaaagcag ggtctgcgtg actagagctg tttagctcgg  11760
ccattgctca ctaagtcaac agctttgagt ttgaattgca gttgggatcg atagtgaaaa  11820
cagatagagg ctgccagggc agaaatcttc aaacacaaat cctgggtctt tgcttgtcct  11880
gattagcatc ccttggtgag tcctagggac actgggacaa cagaagggtc ccacaggatg  11940
ggtttatagt cttccccttta attgattttg gtggcagtat tctggaactg tatgagagtt  12000
ggagttgatg ctgttgtgta gagggaagaa tggatattgc taaggttagg agatgggtga  12060
aggtcaggag tcagacatac tttttttttt ttatttgcta attgatcatc tttagctcca  12120
gggtggggat tggaaactgg acagggacac ctcacctgcc aatctgcctt tctttctcca  12180
gtaccatgca gagaccatca agaatgtccg tgaagccaca gaaagctttg catctgatcc  12240
cattctctac cgtcctgttg cggtggctct ggatacaaag ggacctgaga tccggactgg  12300
actcatcaag ggcgtgagta tctagaatag cctggtaggg ggtcacactt ttgctatgta  12360
aataacctat ttagtctcac tctgggaaac gggtattttg tttgttttat ttcttcctca  12420
atatacaaat tcaggcttta tagaaaggtg agaggtttct ttggactttg agccagagtt  12480
gagcgccccc atcaggggca ttggcttctt cagttcacac tcccatttcc tgctttaatc  12540
catagagcgg caccgctgag gtggagctga agaagggagc cactctgaag atcaccctgg  12600
acaacgctta catggagaag tgtgacgaga acatcctgtg gctggactac aagaacatct  12660
gcaaggtggt ggaggtgggc agcaagatct acgtggacga tgggctcatc tcactgcagg  12720
```

```
tgaaggagaa aggtatgtct ggtacacagt ccgtggccaa tgccaactcc aatccccaga  12780
gctctggcaa gcacagacct cgaatgtatg aagatctggg tttaatctcc agaggatcaa  12840
aagtctaagg ttattgttgg tctgcgtccc tgacctgtct gaaatactgt ctcagaaaaa  12900
aggcagatgg ggctggagag atggctcagt actgactgat cttccgaaga tcctgagttc  12960
aaatatccca gtaaccacat ggttgctcac aaccatctat aatggttgtg atgccctctt  13020
ctggtgtcta aagagagcta cagcgtgtat aaaaggtctt tgggccggag caagtggggg  13080
atcctaaatt caattcccag tagccacatg atggctcaca aaccatctct acagatacag  13140
tgtacagata aaacacatta agtaaataaa taaataaata aataaatata aaaggtcttt  13200
gggccggagc aagtggggga tcctaaattc aattcccagt agccacatga tggctcacaa  13260
accatctcta cagatacagt gtacagataa aatacattaa gtaagtaaat aaataaataa  13320
ataaataaat aaataaattt ttttaaaaaa gaaaagggca aataacccac aaaggtccag  13380
gtacctttag tcctccgtcc tagcgttcgg gaatcaggaa ggtggagatg tctcggtgca  13440
gcatatgtta gactactatt atatgcctta gaatgagagt taaagttact tattctaaat  13500
actttgtgac agtttgagag ggtttcctat agctagcctt gaactcttga ttcttctgtt  13560
tccacctccc aaatgctcac attaagaata tacaccacca gctgggcatg gtggcgcacg  13620
cctttagtcc cagtactcgg gaggcagaga caggcagatt tctgagttcg aggccagcct  13680
ggtctacaaa gtgagttaca ggacagccag ggctatacag agaaaccctg tctcgaaaac  13740
caaaaaagaa tgtacaccac ctcgtgtggc tatttatttg tttattcatt aatttgaggc  13800
aaggtttccc tttgtagccc tgcctgactt ggaattaact gtgtgtgtag accaggctgg  13860
tcttgaactc aaaggtctgt ttgcatttgc ctcttgtgct accataccta aaactcaaat  13920
tttcttagca gtttgtaagt aagtatttat aggtgagaaa actgacttgg ctttcctgaa  13980
gtgttttgtt tggtttggtt tttgttttgt gtgtgttgga gtcttaatta tggctttaga  14040
gtcctcctcc ctctgcttct tgtaaattga ggtggtcttc tgtgatccct ttcacacagg  14100
cgctgacttc ctggtgacgg aggtggagaa tggtggctcc ttgggcagca agaagggcgt  14160
gaacctgccg ggcgctgctg tggatctccc cgctgtgtcg gaaaaggaca tccaggacct  14220
gaagtttggg gtggagcagg atgtggacat ggtgtttgca tctttcatcc gcaaggcagc  14280
cgacgtgcat gaagtcagga aggtgctggg agagaagggc aagaacatca agatcatcag  14340
caaaatcgag aaccatgaag gcgtccgcag gtgagtcctg agacccttcc attgcccagc  14400
ccttgagagg ggtgtggcca tggtgtgtcc tggatacctg ctcagcaaaa tacagcctgc  14460
tgggattggt ccaggcggac atctgaatca gcattaggga ggccaagtat ttttagtcat  14520
cattttggga cccggctgga tactcaaggg cctcagatgt ccatgctaaa gcttgaagcc  14580
ttagaaatct tctggtctga taatggtgct gatgaggagt ggcccattca gcttcccata  14640
gagaagcatg atgcctacgt aaatggaaat taattaaggt ggcattcata aggatgagtg  14700
gtttattgac aaatgttcat acttggcttt ctccctactg cttcccctag aactgcttct  14760
gtgggttaca gtgggcttgg ctctgtgtcc tttgtactgg gcaactggga gtctctttct  14820
atcttgataa gccataggtg ctgatggcct tggtatttgg ggctggggag tgggtcagct  14880
caaagggcag cagtcagtgc ccttagctaa atgatgatcc actttgtaga agatccactg  14940
gcctcattct gtctttgaag tgtcgattag ggaagtacaa aacggggtgg ggggtgagat  15000
gcagaccaaa acctccctga aatatttatt atggtgttta agaagtccag ccagtaaaat  15060
```

-continued

```
tgttgtgctg tgagtattat catactgtgc tgtggatgcc ccctcgcctg tgtgcccctg  15120
ggtgtgacct ttgaaagcat ctctgtcggg atcccaggta ctttggttgt gcttcctgtc  15180
ctctattatc tttctcttct ttaccaggtt tgatgagatc ttggaggcca gtgatgggat  15240
catggtggct cgtggtgacc tgggcattga gattcctgca gagaaggtct tcctggctca  15300
gaagatgatg atcgggcgat gcaaccgagc tgggaagcct gtcatctgtg ccacacaggc  15360
atgtgctatt tcattccttc tgcattctcc acctaggaga cctggccttg tcctgtcctt  15420
tgggcacaca tagctgtgat ctgtgcacct gcacaatctt aagggaatta tcttggcaat  15480
tatcactgaa gatggcctag gatctcattt agtgatggtc ttttaccgag agcccttgtc  15540
tgtcccctcc tagatgctgg agagcatgat caagaagcca cgccccaccc gtgctgaagg  15600
cagtgatgtg gccaatgcag tcctggatgg agcagactgc atcatgctgt ctggagaaac  15660
agccaagggg gactaccctc tggaggctgt tcgcatgcag cacctggtaa gtcctccaag  15720
cctaccacca aggcctctgc atcacccagt cttttacctc cctccgacca cggccagaag  15780
agtgaggtgt gtggagcatg ctctgcttct tgattttcac gttgtgctct cgctgcctgc  15840
gccccaccac gttgtcctgc tctggcgatt accttttcca ttacgtaggc cacatctggc  15900
taaaatatta aagtcctagg acttagtcaa gggatacctt cctccctcct gaacacccag  15960
acggcggggc ggcctctatt ctaaaggagc caagagtgtg tattcttggc tgttcgcctg  16020
gtttggcttc taatttgatc tcttgatggt cccatgagca gatgcttctc tgcactgcag  16080
gctgtagcca tactaagctg ctttgagctg gccttgcatg gtgcctgtca catgggacgt  16140
ctcttgctat gccaaaccca atgtagggct agaaatagct ctgggcgtgg ggaatgggtg  16200
ctgaatttag caggttctgg actggagatt ataaagactt tctctgggca aatctatgct  16260
ctttttgact aagtcttctg gtttcagtaa gatagggtct ggaggtccag cattcagagc  16320
ctgaggcagg aagatagctt gaggctaggc tgggctagaa taaggcatta tcttacagaa  16380
acaacagact tccagctgac ctgactcctg ctgactgtga tgggtgagga cccagaactt  16440
cctgagcaga gcagttagct agggcgccag ttaggacctt tccttgcctc atgaaagcat  16500
tgttggctaa ctttcttgga gcttttctat tccctttttcg gccagcaaag aaccactgtt  16560
ctttttgtgt ctccagtttc caataagccc ccaaactgaa agaaaaaaaa gccccccttca  16620
ggattagaca tcttaccttg cttcatttgt gtacagctgt taagtagatt ccatgatcta  16680
cccatggttt atctgaattg tagctgtagc cagatgtgtg cctatattga aacagaccag  16740
ccgttttgta gaagcttgaa ctcagcttgt ctcagctggt cacctcctga tctgattggt  16800
attgggagct gatcttcaca gcttctcagt agctagcatg cagacattcc ttctccagca  16860
gtctgtgtgc cttcctgatc tacaccaaac ccccttcttt tctagtcacc tgcttagttg  16920
tcttatcacc tcagagtggt caggaacaag accaggtagt ctaaaccatg cagtcacata  16980
catggattta tctttgtata gctctgggtg acttatatga ccgcaagacc ttgcccaagg  17040
tggcatttga tgagattaat tataattaat tagtcataac attaaacaat ttactgccat  17100
aatgaaatgt tagataaccc tctgggctca ttgatgtaat ctttgcattc tcattttctt  17160
tttaaaggga atcacatgtg atagtgtgtt tgagcacaga tttgctatcc tcatagggcc  17220
agccagctgt ctgtttgcac cctgctgtag caggtgtggg cagagtagga gttagttctc  17280
atgtcctgcc ctctctcatg ccctgccctt tcctatgaac agacacctta gaacctcgag  17340
gctgggattg catggccctg ctcagaagat gagtcacaga gtccgggtta gactgtggct  17400
gccccttcag gggtgcaag cttctctctc atcagttaac actcaggata gcttctcccc  17460
```

-continued ttcatctgtt cgctgcctcc tcctctgtct aactgatata gttcatgacc tgtaattaag 17520
agctagacat cccagctatg gtcgtttcct gttcatgtcc tttgggctgc atgcattcca 17580
tttatttgta actaaaagaa tactttccac ttgcaaatct gctaatacta ccaataaatg 17640
tgagttattg gttttacatc ttctctatac taaaatactt gggattgcac tctctaaaac 17700
ttagatttc attctaatgc ctggttttac ttgaacagat agtctatata taacacattt 17760
gctgttttgt aacagtttta attgctaagt tttaattggt gtcttaaggc atgcatgctt 17820
tctcaggcat ctgcctcttc acacggctgt ccactgtgtt caagtgagcc agagttggcc 17880
actgttctgt ttagaactgg cgcaccatgt aactttggct cttttgacct ttgaccccag 17940
ctttcagagc tgcccagatg tttctattat aaaccaggtg caaggactcg ctcttgtatg 18000
taggctaagc tagatgtctt gtaaccacac agccgtgtgt ggaggggagg cctagttctt 18060
cctgtaagct gtgtcatgag gcagtgtggt caagtggaag tgtggttggc tccaccttgg 18120
catctttcca tgccaaggtc ctagggccta acaatatgtc cctgtcttag cttcaatcaa 18180
aaacaaaaga aattgatggt gcctgcctgt tatcctagca cttgggaggc tgaggcaaag 18240
aaaatagtga tttttgagga taactgtggc aagttcaagg ctgatagggg ctatggtaag 18300
atcccatctc aaacacatgg gggtgagtcc catctcataa acacatgggg atggggtttt 18360
ttttaagaaa caaaggggaa agtcccaaaa ggataatatc tttctagaac ggaaggaact 18420
ttccttgtat ttgaacagta aggggaaaag gagcagccca aaatcccacg caaccattcc 18480
aggagcatat gggctttgac caccctgcct ctgcatctgc ctctgcatga agaaaagatt 18540
aaacctaaac ctaagggtgc cttccttcct ctctgatgta gttccctgtc tttccatgtg 18600
ttgtctctct tgtttttgcc tttatccctc ttccttatcc ctcctaccct aaaccttaca 18660
gatagctcgg gaggctgagg cagccatgtt ccaccgtctg ctgtttgaag agcttgtgcg 18720
agcctccagt cactccacag acctcatgga ggccatggcc atgggcagcg tggaggcctc 18780
ttataagtgt ttagcagcag ctttgatagt tctcacggag tctggcaggt agggccctaa 18840
gggcaggtat cattatagga taaccagctt ctcgcgcaac taggtccgct atgtgcctga 18900
gcctaggcac agcctctctc cttcaggaag acagccaagg tcaccatagg gcaggaccaa 18960
aggattccct tgggcacagt ggaagtcaca gcacctggtg caggatggtt cctgtggagt 19020
ttctaatctt gctcagttca gaacatggag tggctcacct tctcctggcc atttttgtgc 19080
ccagggacat gttccttccc agttgtctgt gactcctttc ctccctctcc atttgtgaca 19140
aagctctgac aaagccctgt cccccgtcct cgtccctctg gacggatgtt gctcccctag 19200
attgcccgag aggcagaggc tgccatctac cacttgcagc tattcgagga actccgccgc 19260
ctggcgccca ttaccagcga ccccacagaa gctgccgccg tgggtgccgt ggaggcctcc 19320
ttcaagtgct gcagtggggc cattatcgtg ctcaccaagt ctggcaggta ggaggcggca 19380
gtggctccct ggggatgccc acgctcagtt gacacctctc cttgaggatg ccaagagtga 19440
gtggctctgg gccagtttaa ggcccctggc tgccactaga ggattccagg cagcactcac 19500
agatagacca aaccaactgg ctggctccag tgcacgttca aagcctgcct cacagagagc 19560
tggaacaaac acccagtttc accgtgatta gtactgtggg gccttttgac agaacactgc 19620
gtggcagctg ggcatggcgg agcatgcctc taatctcagc acttgggcca aagaggtagg 19680
cgaatgtctg gatttgtagc ctgtctagtc tacaaagtga gttccatcca ggacagagcc 19740
ctactcacaa aatagctcag ctggtaaagt tgcttgctac acaagcttga cccatatttg 19800
gtccccagaa accatggagg acggagaagg ctggccctgg gtatgcgcaa gggtacacac 19860
ttggaggggt cttggtggat aaaggatttg cacaatcatg actatctgaa tttgaatctg 19920
gcaccttaaa ggttttttat tattactttt tatttttttta aagtgcacac agaggtcacc 19980
aggaaaggtg gtctggcctt taggagcact gtcagttctt tcagaggccc aacacctgcc 20040
tatatatggc agctcacaac tgtctgactc cagtcctggg gaaatctaat gcatgtggtc 20100
agaataccca ggcagctgta gtgaatgtac ggtggaggga gagagtgagg tgcccagtgt 20160
ctatctatct atatagcaca atagatagat aaaaaatacc caagtgtggt ggtgtgtgcc 20220
tgtagcccca gtgctcatgg tgcagaggaa gaaagagcaa gttgtatcac agcctagcta 20280
cagaaagcca aacacatgta aaatcagtgt ggaggactag gcactggtct gtctccctaa 20340
ggcagtgttc atgaactaag tagcagaaag ctacttaggc ctgggctgag gatggtggcc 20400
tctgtgtaag cttggccatg aatgttggta tgtagctgga agccagggat gatggggtac 20460
tgagaaatgg ggacactaaa actatcattt ttagtcctgg agttttgaaa gctctaaaat 20520
acaaggtcta tgctaattct ggggtttctc tgaagagttc ctggttccag cagctacctc 20580
cttccttcaa agcctatgta tgcaggctag catgaagctc tgctgtggaa ttcctcagtc 20640
ccccgtgcct agctaattga gtaatctgat agagatagac actatcattt gttacaggtt 20700
gagaataggg gttccctaca ttcccagggg atcttgaatg gccagatatt cctcttacca 20760
cacctgatca ccacccagat ttcttttttct ttcttttttt tttaaattta tttatttata 20820
tgagtacacg tacttcagac ataccagaag aggacattgg tatcggatcc cattacagat 20880
ggttgctggg atcccatgtg gttgctggga attgaactca ggccctctgg aagagcaatc 20940
agtgctctta actgctgagc tatctctcca gcccccagat ttcttttttct ttcttttttt 21000
ttttaaagat tgatttatta ttatatctaa gtacactgta gctgtctgca gatgcaccag 21060
aagagggtgt cagatttctt tatggatagt tgtgagccac catgtggttg ccgggacctg 21120
aactcaggac cttctgaaga gcagtcagtg ctcccaacca ctgagctatc tctccagccc 21180
taccacccag atttctaaaa ccatagaaat tctgaggttt cttttaacat tagctgctag 21240
gactcccata ggagaacagt atagtgttat ggtgaacatt gttggcttcc agggcctggt 21300
aactctgctg ctgttctttg cagaagaagt caggagctag gcacatggta cttggattgt 21360
aaaagttgct ggcagctaca ggagtgggtt ctgctgagat tgggccaaag ctgcctcact 21420
gccagatgga agggttcatt tgtgggaaga attctaccag ccatgctcct ataggactgc 21480
ccatactgag agcaggataa tcatcttaga aaagacagga caggtctgag gggcaggcca 21540
gaccttgaaa cagttgtcag tgggcaaagc ctgtggtcca gagttgaatt agagggtatt 21600
acttttggct taggcttact gaaagggtct tatgacatgt ttaacggtca gtctttccaa 21660
cctgtttcca tctcaggagt gctcaccaag tggccaggta ccgccctcgg gctcctatca 21720
ttgccgtgac tcgaaatccc cagactgctc gccaggccca tctgtaccgt ggcatcttcc 21780
ctgtgctgtg taaggatgcc gtgctgaatg cctgggctga ggatgtcgac cttcgtgtaa 21840
acttggccat ggatgttggt atgtagctgg aaacaaggga atgatgaagt gctaataaat 21900
ggggacccta aaactaccac ttcctgaagt catgggctgg gcctatctgt tttatcaccc 21960
agttgtaaga ttagctggag ctactgtcct gagcagggtg gggttagagg gtggggaaca 22020
caagcttttg tggccttatt cctatataga gacaaggagg cagctgaccc tgactctcta 22080
gagtataaac tgaatggtgt ccaaaggtct ctgcattctg agttcagcct cagcccttgt 22140
ttaggctagg aggcttgcac catcttgtgg tgagaagaag taactgtcaa cctgctcccc 22200

-continued

```
tacccagacg aggattatta gggcagttat ctgcacctgc cttgttggat ttgtgtctgg  22260

gttgggaaaa gtgccacttt gtgtgatcaa ttaggactgt ggggctttgc agttttcctc  22320

aagtgtatac ctctactcac caacctcctt ttccccccag gcaaggcccg aggcttcttc  22380

aagaagggag atgtggtcat tgtgctgacc gggtggcgcc ctggctctgg attcaccaac  22440

accatgcgtg tagtgcctgt accttgatgg ccctctggag cccctcttct agcccctgtc  22500

ccttcccctc ccctatcctt tccattaggc cagcaacgct tgtagtgctc actctgggcc  22560

atagtgtggc gctggtgggc tgggacacca gggaaaatta atgcctctaa aacatgcaat  22620

agagaccagc tattattcag ggccctacct gagccagggg tggaggagga atgcaggact  22680

ggaaaccctg actttatcac agaagggcgg cagcatctct gggctttgct tctgtagaaa  22740

gttgtcagaa ttcccagccc tagcctggag tcaggagaca gcaaaagagt aggggctgag  22800

ggtgtggggc ccagggtccc agtgtagatg acgacttctg gccctggccc tgacctgctt  22860

tcccaacagc tttggcctcc ccacttcttg tgcactccac ttctgtcact gcagacactc  22920

cactctccac cttgtattct gcagagtctc caggcctgtt gctatagtgc ccacctgaat  22980

gtcaataaac agcagctgaa gcacctgt                                      23008
```

<210> SEQ ID NO 50
<211> LENGTH: 21995
<212> TYPE: DNA
<213> ORGANISM: Rattus norvegicus
<220> FEATURE:
<221> NAME/KEY: modified_base
<222> LOCATION: (20158)..(20161)
<223> OTHER INFORMATION: a, c, t, g, unknown or other

<400> SEQUENCE: 50

```
aatgtccttc cgccacggaa ggtagtcccc ctcaaaaggg caacctgctt gtcccgccta     60

ccctgcgact ctctcagaag gtgcgggtgc ctgttgagag gcggggctct gctagctgct    120

gcccggattg ggcgaggggc ggggctgcgg agggattgcg gcggcccgca gcagtgataa    180

ccttgaggcc cagtctgcgc agccccgcac agcagcgacc cgtcctaagt cgacagacgt    240

cctctttagg tattgcaaca ggatctgaag tacgcccgag gtgagcgggg agaacctttg    300

ccatctgtgc ccagagccaa tgcccactag tgcgcaacgc aggccttctt gcttgcccac    360

gctggaccca ggcgcctggc atcgagcatc ccattccggg ttgggggaga agctacactt    420

gagtctaagt actaatcttc caaattgagg cgcggggtgg ggggcggcta gctcctttcc    480

cacgtactcg ttctgctctc ctttctcaat ctggttccaa cttcttattt tattattgct    540

atcctcgcca ccttgttcca atgctcatcc tcctacattc actagtactt tcgaccttca    600

tcttagctct gtgcccttat cattcggtgc tctccttgta atctctcctt gaaataactc    660

ccctgctcac ccccctcccg cttcagcacc gacgttcatc ctcctttcag gtcagcgtgc    720

tcttcccgcg cctgggttag cagctccttg tcgcccctcc cccactcctt tctggtcacg    780

tccgcgccat agcatccttt cagcctccct atcctcgccc ctccccacag cttttcccct    840

ccccctcatt ctagtcacgt ccgcgaactc ccctctggcc ctcgtggtcc gttgcatgta    900

ggaagaatgc aatcactagc aatcctaggt gatgcagcta caaattatgt aatttttgta    960

attccggtgg ccaggcaaga aaggttggcc ctattgctgc ctattttgtg cgcccgcaga   1020

tttctgtggt cgtgggctag gctcctcgcg caccggggtc ctgcgtgctc ccgtgctcca   1080

tcctgcggcg gcgggcctgc acgtactgcg gggcgtcggc tcccacgtgc tggagagggg   1140
```

-continued

```
aaggtgggcg gtcaactcat acctgctccc tacagaagct ggagccggac gcgacccgaa   1200
cgcacacagc ccgcagagct cagtctaatt agggaagcag aatttgtcaa gtcagtgcta   1260
tgaggaagat ggagctgcat gcacaaggtg gccggcatac taggtttgaa ggagccgggc   1320
atcttctagt ctggaggcta tataaagacc cattcatagt aagatatctc tcgatcacct   1380
tttccaaatc caggacattg gtagttcgga aaaagtgaac ctaatagtga aaattcattt   1440
gtatgtggcg gcagctgcgt tttagaatcc gctgtcattt attaatatct gaggtttttg   1500
gtcctgtgtc atgagtggaa acatttactc caggctgcta aattacttgt ctccttgtgt   1560
gtacgacatc ctcgacctac tttctggtga aatgcccaaa agggaatgca tatatccttt   1620
ttgtcaatga agtagttaca ttgaagacca ccaacttcag tctgtctctg ctatttttac   1680
gcaggttaag gttatgcttg gggaagcccg taggctccga atacttattc acatggaaac   1740
aaaatctctc tggaacccca tcggtgttta caaagtaact aatgttacat tgcaactctc   1800
ctgagacaac catctaaaag gagaaatctg tgcagccttt gtctttggct gtgagggtag   1860
aaacaaagaa acaggtatcc agatagcctt ccgagtctgg tctctgttca tgtaagactt   1920
tcatgctttc tggcttgcag gaagttacat ttggtactac tgttgcagta ctgttgcctc   1980
caaattcagg gtgtggctac attctagggt acagaggga ggccttaggt caacactgaa   2040
ggtagcattg ttagcaaata atttgccctc tgctggcttg agtatgttgt agggaaggca   2100
atgagaatgt tctgtgggaa agtgtaaacc atcaccgggt ctgggcaaga tgactcaacc   2160
tttcaactta gaggcttttg agagaatttt cttccttggg tgagtgggga aaccacactt   2220
gttctccaag gtgttgtaag atcccctctt aagtgagtca aatactatag ttcatttccc   2280
taaattaaac atgtctcacc gggactgagt gtggtgtgca tttggcttta atcccagcac   2340
tgaggaagaa gggctagacc tgtgagcttg agaccatgta ggtggtgggt atcaagtaaa   2400
tgaaggtgac ctttgtgctg ccataagagt ggaagtgtgg agtggctgct tttagtctgc   2460
atatcttcat ttttgagtga cacagcagct tctcagaacc accagtatcc agaatggcag   2520
tttctgggaa tgcgtttctg agttattgcc taagccaaac tctgaatgct agtcacttat   2580
ttagtacata gctattttca ttttaagcct tatattttaa attagttgta gggaaatttg   2640
ttctataatg aggagatctt tgccagcaat caggacgtag aggcatgcag atctgagttt   2700
aaggccagcc tagtctacac agccagagct acacaggaac cttgttaaag ctgttgattg   2760
cttaatattg agtggaagaa atgaggaagc agctatggac agaggggtag aaaaactttt   2820
tttttttag catctttagc ttttctgcag caagtcgaga tgagttgggc aagaactaag   2880
ctggagattg gggtagagga aaatgactca tgtctttcag tctctgaatc attccaaata   2940
cccagagcca agttaacttg ttgtcccccc ccccctacca cttctggtaa aagaccgagt   3000
catctctgta aactgcgctc atagaaacta taataggagt aaatgacaga ctatatgaca   3060
aagaacattc ttcctgctgt ggaactctcg tgagtcttga aatttttacc aagaggcaga   3120
cttagtagtg ggagagggga gcctacatgg tcatggcctg caaacctctg cctgatctta   3180
aggcctggtg taacagctga ggattgggga gtggtcttag ggccaccact agctatgcag   3240
tgaggccaca cccctgctgt ggtttgtgcc tgtctgcacg taggagggag gtctgggctg   3300
cagtaccttc agtggcctct cgggagctct gagcatctcc tgaggcctcc aaaggaagca   3360
gtattccaaa tgtgtgacta acctgcagtc atattttggc tttaaactac tggtgtctcc   3420
agcaatgagt gtaaaagatt ttaccccata ccatgcccat tttggaggag tcaaagtttt   3480
gaccttaagt aaagaagggc tgagcttggt ggcatgtgtt tttaatctca gagacaggag   3540
```

gaactgagtt cgaggacagt ccgggctatg tagagagtcc ttgtctcaaa aaaaaagtag 3600
ggaaggagct ggtaatctct atggaattcc attctgatgg aatgtttgcc tatggtgcat 3660
aaagccttgc tccatcccta gtactacata gtatgctcat agtagcacgt gtctgtaatc 3720
aagctgaggg tgggagcaaa ggacaatggg attggagaag ttatgagttg gaaaaaaaca 3780
aatttgtgtg tgaatttatt aaaatcagaa tcctttttcg tttttggaaa atgtaaaaac 3840
aaatctgtga taatgctaag ttctaggtgg gagaaatagg ttttggattc cactcctcct 3900
tgggaaaaag gcaaccctgt aggcagaagt agtaagtagg tcagtgctct tggacagctg 3960
gtgctgtctt ctttaatcac ccccaccccc aactgtggct cagggcattt taaatgctga 4020
accagtgcct cctgttgctg aggccattgt gcattctgct tacacctggt cctccagggt 4080
ctggaggagc acaggcatca ttcccagaaa cactggtcct tctaactgct aaggaagaca 4140
gcatgtgcca acagaacaga gacttctgca aatcccctcc ttcctgctct agctagttct 4200
ctgctctgca cagctgagct agaagccagg aaatccctct ctttgaggaa agagtttaaa 4260
gtagaactgt tcaggttaag gttaaataaa agttggtttt tgcttatttt tctctctagt 4320
tgttttgacc acaggagttt aacttgactt caccaggtgg tagctagcct agtaagccag 4380
gcctttctga gagaatatac tcttctttgg acatggtagc atatgccttt aatcacagca 4440
ctcaggaggc agaggctaac cagggctaga tagtaagacc tggtcttaaa aaatcataat 4500
ctgggccgta gtgacacacg cctggaatcc cagcacctag cagatctctg agttaaaggc 4560
cagccttgtc tattgaattc caggacaacc aaggctacac agagaaaccc tgtctagaat 4620
ctgaccccca acctaatctc tgcttaagtg atctgtaccc ccaataccat atatgactta 4680
attttgttgt attctgggta ctgtgttcca gaccatacca atttctgggg gtggaattgt 4740
cagctgcttg gaccctggtg tagcctgtgg gttagggtca cttctgtaga tctgtgctcc 4800
agaggaagct cctagagagc agggtgacca gcatgttgcg tgtcatcttg cagcctttct 4860
gatggatgaa actaggtgat cttgggtact ggaaaaagta ggcttcagat gatatcaaaa 4920
aaatggtggc tacaaagccc cgtccctagg cagcagtggt tcggggcccg tccctaggca 4980
gcagcagttc gggccccatt cgtccctagg cagcagtggt tcgggccccg tccgtcccta 5040
ggcagcagcg gttcgggccc acatgaagat gtagttgttg tcggagtgag gcatgacctt 5100
acaagagttg gctctataaa aagcagggtg gcactgggca tttggggttt taagtgacct 5160
ttgttcctga cacgagggaa atgaatgtga agggccaagg aactgcctga gacaggaaag 5220
ggcagaacca ggtaatcagc caagccaggc ctgtgcatgc tccaacctgc agcctgcact 5280
gaggcctggg ctggtgtctc ctttctcaca gaggggcaat ggctctgagg aacatcctgc 5340
tgcagggcct caggttcaag agtaaggctc ctgcctctgg gcatggtgtc tgctgctgcc 5400
gtgggacaca ccgggcttct gctgctggtt ggaggttggc tgtgcatgtg ggtgcctcct 5460
aaggaggagg atgctgtagt gagttgcgct ggcatgggtg gggccgcatg tcctggcagt 5520
cacagctatc aatctatgca ggtaattagc cgatagtgcg agccctgccc agagggcccc 5580
ctactctaag agacaagggt ggaccaggaa aagacaccaa gagtagggtg ttctattttt 5640
atactatact ataggtaagt gattggctgg agttggggct ctggaggcca tgggacaggc 5700
agaagagcta tgggtgggtg agagtggggg gtcagagcct tgagtgaaaa gaactgggtt 5760
ctagggataa ggttagtagg agagttggaa cgcttgtgag ttttgttaga ggtctatttt 5820
gtatcagtcc attgaaacac atgtatttcc atttgtcact ttttatctgg tagcaggata 5880

-continued

```
agtccactct gcagacttca ggtttaattc tagagagaga aatgggttgt atatttgaga   5940
ttttacctgc tagattgtgc cctgagccct ggaggcagca gtgcttgtct atcagaacat   6000
tcttgtcagc acaacaaaga ttgttctgtc aagcctgaga ccagtcaaaa caggaaaaga   6060
aaattgctgg actctggcat ggaactgata ggttgtggtc atgaaatttt tccatggatt   6120
agacacactt tggggaaggt ggctttttaa atcaatggat taagttgccc ttcccaggtg   6180
aatgaagctg cccagcttga gcacttggga gggcaaagag aacacatctg ttactgaatc   6240
ttagggtagt ttcgaaagac acagggctga tgtgtggaac ttcgcaatga gtttatagga   6300
tgcatggaaa taaatgtgca tttccaaaga ctgttcttaa tttcacatca acagtttctt   6360
tattaataag gatatgctgg ttggattttg ctggagacca ctctggccta tgttgtacct   6420
tacataataa gaaacagtct caggggggttg gggatttagc tcagtggtag agcacttgcc   6480
taagaagcgc aaggccctgg gttcagtccc cagctccgaa aaaaagaacc aaaaaaaaaa   6540
aaaagaaaca gtctcagaag gggggaggga atgtcataat acatgctacc actcaggtaa   6600
tgaagaaggg ggaaacaaag caacgagggt cagtgagaca gatggctggg aggacacgga   6660
aacttgcttc tgatgactca ggtacttcta tccccagaac ctgagagata gaaggaatga   6720
gaagacttgt ggtcctctga tctctatacg gcgtccacca tgtacccccct aaaactaaat   6780
agtaaatttt aggtgttggg aataaagtac ttcaggggat ccagtgaggg gtcacttacc   6840
accgggtttt tgtcttctcc agtatacatc tattttaatg tagttgaatc tctaaaagca   6900
acttttacct tgtcattaag gtcattttca caaagagctt agtcacattc agcttttccc   6960
ttaatccttg tagctcttca gggcagagca tactcagctc tgagctgtct ttccaagtgg   7020
ggccatcaag ccaatctggg tcaaaaaaac ggcaatatgt caacagaagc ccagacccag   7080
agatccaaag gtatgacctg atcacctggc cctgagcagg aatttgcaag gatacacttg   7140
tctccggtgg agagaagggc ctagtggctg gcttttcagt acttttcaga cactcttcta   7200
atgtctgtcc cactcatttg gacttcatag ttcatagtcc catcgtggtc acagcaaggc   7260
ctttgtgtct ctttggcttt gtgtaccatc tgtactgtcc cttagtggcc acttaaccta   7320
agcctggctg ggagccatga gggtttgcca accatgagtt tgtttcaacc atgagtagac   7380
caaggacctg gctgcctagg atatcctgtt gtatacagga cttcctcaga tttggggaga   7440
gggaaaacta gtagaccctg gagaagaggt tgacttgacg tcttggtacc taatgtgtct   7500
tgtagagtta ggaatgacca atgttggccg ctggtttctt cttcctttaa aagttctcaa   7560
ttctgcaagg aatgtagtgg tgtacctcta atcccagcac ccaagagctg gaatatcagg   7620
actgtcatga gttcaaggcc agcctgggtt gtatatgaga acttgcctca aagtttttca   7680
tctccaggcc tctgattttt gatcactagt gggtggctgc aatgtcaggt ggcagagcca   7740
ggcttgggtg catgttcttt aggtatccag aaaagccgat gtccagggta gagtgcgggt   7800
ctttgggaag gcagggaaga gcaaggagat gtggagtgca ggctgtgtgc tcaggagttt   7860
gaaaggagcc tcgtggcctg aaaattgatt caagtctctg gtattctgtg aggtacatcc   7920
caggttctcg cttactcagc caactatcca gctcagtgag tgcttagctg taagtcgtaa   7980
taaagtaaaa gcaaaggtca ggacagctgt tgggattgtg acctgggtga ttaattgcct   8040
ggaacagatg ttcagactac tgtgtgtggt ccctatcaga cagagaagga gactctagat   8100
agccagaact ggggctggga aagctgggtc taatgtcagc ccttgggaag agtagtgact   8160
ttcaaggtca acctcggttg cacagtggat ttcaggccag catagactag ctactgtgtg   8220
tgattccatc tcctaggtta ctgaagactc cttggtgagg ttgtaatgac tttggagcca   8280
```

tttcaatgtc cttgtgcaaa atttgctttg tgtgtcttgt acatggtgct gttttttgct 8340
tcttgtccag aaaaaaactt gttgcctgta atttggacct tattcctgtg tcggatagag 8400
gctaaggaat acatttaggt gatacctcaa acctaggact ttaaaaagaa aggacttggg 8460
acagggttcg tctcttggca gcaggatcgc tttaggtcat ggcgaacatg ataaagaggc 8520
tatgtcagtg ccaaagcagg tttgacattg tcgtgatagg cttcccagat gttcgtgtgc 8580
tgacacatta gctacgtgct ctgcaggagt ggggaggttt ccttgtgtgg gaaggtgatg 8640
ttctctctag ggttggtgtg aaagctcttc aaatagatgg cagccgttgt aagaagcctg 8700
cttaaactgg cttccagggt gtgtatgtgc actgggaagg aagctacttt tgttcaccaa 8760
ggtctttgct gttcgttcat agtcacagga gccctttgcc caatttgagt agtacccaca 8820
taaccagcac gtgccaggcc tctgagtgac ttgtgcacaa agcagtctta ttgggttaat 8880
gtgtaagcgg gagacagtct cctatgccaa atggttcatt aagcactgcc tagtctaatt 8940
gaactcttca aatctccggg atccaggatc tcagaaacca tgcccaagcc agacagcgaa 9000
gcagggactg ccttcattca gacccagcag ctccatgcag ccatggctga caccttcctg 9060
gaacacatgt gccgcctgga cattgactcc gcacccatca cggcccgcaa cactgggatc 9120
atctgtacca ttggtgagtg agtgtggccc ccttcgcagg gcttctgcct ggtttgaaag 9180
gcgtaataac cattgcaggg ctaacctagg ttctgagaga cactgtccac acttttagag 9240
gaagtattgg tgtacttctt ctgcagttgg cgaggttcag ggtggtctta gtgggccttt 9300
gcaggagtag ttcagggact tcagatcttt ttcctgtgct gtcactccac tttctgcaga 9360
atttatagaa aatgatagtg tccttcctta catataaatt aagagagtcc ttccttacat 9420
ataaatcaag agagttgact agcacagtag tctttctgga ctttggaaag acctttctct 9480
aaatttgtgg aggtgattaa aaacaaagga caaggagttg ctttgatagt gagcagattt 9540
catatacttt cctacctgag aatcatgatt ttcttcctgt ggctctaaat gtttcttggt 9600
aggccctgct tcccgatctg tggagatgct gaaggagatg attaagtctg ggatgaatgt 9660
ggctcggctg aatttctctc atggaaccca tgaggtgagt ggcagcttga tccaggaggt 9720
tcgggacttg ctgctgctgt gctccaggct tctcagtgaa tggagcgttg ctctagctag 9780
catttacatc cctctctccc tcttcccctc tggccaactt cattggcatc aacaacctgg 9840
cctgctttgt cgccggccag ggttatccct accatcaagc tttgtgaagg aaacccttta 9900
tgtaagggtt tggctggaaa ctctaggcca tcatgtgtct tgactgcact tggcacccac 9960
gcctcgggct ttctacagtg gctcctgtga gtccggtgaa ccaaaaggtc atgcagaaga 10020
cttagttcag gccccagatg gctaggtagg tgcagatggt tttcccgtga gaccgagtct 10080
aacgcacaaa tgcagtgcgg tctggggata tcccacttac tcctgctgca ctgtctgccc 10140
atcatcagtg cccctcccta ggagtgaggt agggatgacc tgggctgttt attattaggt 10200
ggccccactg atggagaggc tgtgcctagg aagcaggtgg cagctgttag aagggtccat 10260
tcctgcccct gctcactttg agaacaaccc gctctgagca gatgggtagg tgggggcgtc 10320
caacgatccg ccttctgact ttctaacttg acagcctttc ctactggcac tgatgaagga 10380
gggagagact ccttcctgcc tcttggtttc tctgtctatt tagagtataa gtattaaccc 10440
tgtgctattt tgccttctga cctttgaagt tgttttgact aaaaatagat ggagaagaac 10500
agtccaagaa gcgaaccctt ccttcccaga acataaggat cttcatagat tccctaaccc 10560
atattctata aatagcttgt agactagccc ccaaatgtca tgggagtgca atggtccctc 10620

-continued

```
aggcacctaa gcagtacttg atacattctt gcttgggtgt ggtgctacag aatgtgggtt  10680
caaggccagc gtgaggtaac ataccaagat cctattgcaa accaagagag gtcgttgctt  10740
tccgggctct gttgctctcc atcagagctc ccaggactaa acgcaaaggt aagcatagct  10800
cagagtcaga actagatcca tttgccatgg tcctcaggtc tgttcagcca ggcaaaaata  10860
gatttggaga cactgacctt tagggctctt agatccagta aaataacacc gtgcagcagc  10920
ccggacatga caggggacag tgagacagtt cagaccactg ggcagctcag ctctgccttg  10980
attctaactc taaggcatta gagattagct gtcctttgaa ccttttttatg tcacataatt  11040
aaagcttcac cagggctttc ttattctatg tgcaccttcg atgaggggct gtggctgtct  11100
gtcttggatg aggggctgtg gctgtctgtc ttggttttaa ccattcctgg agacggtgga  11160
atgaatcgag ctccttcgag ctccttccct ctgacgggac catcaattag tcagctgcac  11220
ctgatccctg ggcagttttg gcagtgtctc tagttcccgt ctcctgcttt tcacatggtc  11280
aggatgtgtc ccttttgctg aacaggcagt gctgcactcc cacactgact tttaagcagc  11340
ctaaatttag agcctctaca aggacagcac cgatggctac ccgtcttcac catttggttg  11400
tgtgccagga aaaccattgc tgtgatagtg gaaagcacgg tctacctccc agaagtgttc  11460
ccgtgtagag aaggttgctg gaccatcaga cactcgaatc tttttttttt ttaaagattt  11520
attcatttat tatatataag tacactgtag ttgtcttcag atacactaga agagggcatc  11580
agatctctct acagatggtt gtgagccacc atgtggttgc tgggaattga actcatgacc  11640
tctggaagag cagccgggtg ctcttaacca ctgagccatc tctccagccc cagacactcg  11700
aatcttaatg cagttttaca tacatgcggt agaaagtttg tcattgctga attgaatggt  11760
ctgctgtcag ctgtgtcact tggaggcaca ttggcaacag actattttgc catcgtggct  11820
ctgtgtccca aagaggaaag ggaaaaggtt ttgtttgggg gaactttatt gcaagtgaag  11880
aatagcaaag gcagttccac tggggcacgc tactggtcag agaaagtgat tgtgaaagca  11940
atgtttgcac gaccagagca atgggctctt cagctccggc cattgttcaa agtcaacagc  12000
tttgagtttg aattgaggtt gggatcgata gtgaaaacag atacagacag ccagggcgca  12060
aatcttcaaa cacaagtcct aggtctttgc ctgtcctggt tgttagcatt ctttggtgag  12120
tcctagggac actagaacaa cagaagacac acagtaggac aggcttaata ctcttcgagt  12180
tggagttgat gctgttatgt ggaggggaga atggataagg tgaggttcag gacttggaca  12240
tacttttctt ggctaattga tcatctttgg ctccagggtg gctcagggca tgggaactgg  12300
acttgggtgt ggagaacacc tacctgtcaa tctccccttc tttctctcca gtaccatgca  12360
gagactatca agaatgtccg tgcagccaca gaaagctttg catctgatcc cattctctac  12420
cgacctgttg cggtggctct ggatacaaag ggacctgaga tccggactgg actcatcaag  12480
ggcgtgagta tccaggagtt taggtcttta aatgagaata tttttcatct gcctggtagg  12540
aattattata gatgcacatt tttggtatgt gaataacata cttaagtctc actctgggga  12600
cctggtttgt tgtttgtttt gtttgtttcc ctcaataaac aaattcagga tttacagaaa  12660
ggtgatcggt ttcttggggc tttgagccag agtttgagcg ccgccatcag ggtgttggcg  12720
tccacagtca cacgcctctg ctgtctttaa tctagagcgg caccgcagag gtggagctga  12780
agaagggagc cacactgaag atcaccctgg acaacgccta catggagaag tgcgacgaga  12840
acatcctgtg gctggactat aagaacatct gcaaggtggt ggaggtgggc agcaagatct  12900
acgtggacga tgggctcatc tccctgcagg tgaaggagaa aggtatgtgt ggtgtacagt  12960
ccacggccca atgccactcc catccccaga actctggtaa gcacttaacc tagcatgtat  13020
```

-continued

```
gaattggtct cccaaggatc aaaagtttaa ggtggttgtt ggtctgcatc cctggcctgt  13080
ctgaaacact gcctgagaaa aaaaagacaa ataacctaca aaggcctatg tgtacacctc  13140
taccctttag ttccagcact cgggaatcag caggtgtgtg agttctcatg tgtaagacta  13200
ctcctgtatg ccttagaatg atagttaaaa tttaccgaat ctaaacactt tgatagtcta  13260
agacagcgtt ttcagtagct agccttggac tcctgcttct ccggtttcca cctctcaaat  13320
gctagcatta aaaatacaca tcaccattca tggctgtttg tttattcatt tattttgagg  13380
caaggtttca ctcttttgac ttggaattaa ctgtgtgggc caagctggtt ttgaacttga  13440
tctgtttgcg tgtgcctctt gtgctaccac cccaaaaact cagattttct tagcagcctg  13500
tgggcagggg tttataagtg aggaaactga tttattggct tgcttaatca tggctctaga  13560
gttctcttgg cttctcacaa actgagatag atggtcttga tccctttcac acaggtgctg  13620
actacctggt gacagaagtg gaaaatggtg gctccttggg cagcaagaag ggcgtgaacc  13680
tgcctggtgc tgctgtggac ctccctgctg tgtcagaaaa ggacatccag gacctgaagt  13740
ttggggtgga gcaggacgtg gacatggtgt ttgcgtcttt catccgcaag gcggctgacg  13800
tgcatgaggt taggaaggtc ctgggagaga agggcaagaa catcaagatc atcagcaaaa  13860
tcgagaacca tgaaggtgtc cgcaggtgag tcctggtgga gaccttttc acattaccca  13920
gccatcgaga gagagagaaa ggtgtgtctg tgctgtgtcc tcagcaaaat aaagcctgcc  13980
aggactggtc cagaatatct gggtcagcat cggaaaggca aagtagtgtt agtcattatt  14040
ttggaaactc gggcctggtg tccacctaga tagagccttg gaagtcgtct ggcctgacaa  14100
tggtgctgag gaagactggc ccattcagct tcccataggg acgcatgctt tagttaagat  14160
gtcattcata aggatgagtg gtttagtgat acatacttgg cattctctca cttcccctag  14220
acctacttct gtgggttacg agtgggcttg gaagagttag ggcggtaatt gttaacacac  14280
acacacactt gtccttggct ctgtgtcctt ttatactggg caatttttcc ctcttgataa  14340
gccataggtg ctggtggcct tggtatttgt tcagccctgg aggaggtggg gagtggaaca  14400
gctcaaagga cagcactaag gaccctagta aggaccctta gctaaatgga gcatgggcct  14460
ttgtaggtct gtgggcctca atttgtcttt gaagtgctga ttagggaagt atgatacaag  14520
gggttgtgag atgtagaccg aagaacccat ggaactgaac ctcatcccct tgacgtatcc  14580
ccgcaagtaa aatggttatt gtgctgtggg tatcatcaag gtggtgggtg cccactccct  14640
caccgtgtgc ctgggggtgt ggccttggag ggcacctctg tcagggcccc aggaaagctc  14700
tgtccattct ttggttgtac ttcctgttct atagcatctt tctttttatc aggtttgatg  14760
agattttgga ggccagcgat ggaatcatgg tagctcgtgg tgacctgggc attgagattc  14820
cggcagagaa ggtcttccta gctcagaaga tgatgattgg acgatgcaac cgagctggga  14880
agccagtcat ctgcgccacc caggcatgtg ctatcccttc cttctgtgtt ctccacctag  14940
gagacctggt cttgacctgg cctttaggta cacgtacccg cacatagcta tgacctgcgt  15000
acctgtgcaa gcttcgggga attgccctgg caatcatcac tgaagatgtc ctgctcttcc  15060
attatttagt gactttcatt tagcggtggt ctcttactta ataaaaaccc ttgtttgtcc  15120
cctcctagat gctggagagc atgatcaaga agccacgccc cacccgtgct gaaggcagtg  15180
acgtggccaa tgcagtccta gatggagctg actgcatcat gctgtccgga gaaacagcca  15240
aaggggacta ccctctggag gctgttcgca tgcagcacct ggtgagtaag tcctcagagc  15300
ctggggtaga agcagctctg ctggagaggc ctctgtccag tcttgttaca ttgctcccgt  15360
```

-continued

```
cacagcaagg agagtgaggt ttgtggaggt gtgcttgagt ttcattgtgc tttcactgcc  15420
tgcacctgcc cctttgtcct gctctgggga ttacataggc cacatctggc taaaatatca  15480
aggtcctagg atgcagtcaa gggatgcctt ccttgtggac acccagaggg cctgggtacc  15540
tctattctaa aggagccaag agtttgttca gctattctcc ttgtttagct tctcatttgg  15600
tctcctggtg gtctgtccca tgggcagatg cttctctcca ctgcaggctg tagccatact  15660
gagctgcttt aagctggcct tgcatggtgc ctgtgacatg ggacttcctc ccttgctgtg  15720
ccagacccaa ctcggggcta caaatagctc tgggggtggg gaatgggtgc tgaatttagc  15780
aggttctgtc tggtctagga attataaaga cttctcaggc atattatgtg ctcttttgat  15840
taagtcttct ggtttcagta agatagggtc tggcgcaagc ttgtaattcc aacaatcaaa  15900
tcagcctgcg gcaggaagat ggcttgagat taggctggac tagaatgaga catcttgtag  15960
aagcaacagg cgtcagctga cctgtccctg cggactttcc acccaggcct ccgtcttctg  16020
tgttctgctc cagaacttct tccggagcag aacaattatc tggggcatca gttagggacc  16080
gttgcctgat aaaggcatgg tggattagct ttttgggggt tttctattcc cttttcagcc  16140
aacaaagaac cacagtatct tttgtggctc cagtttccca caagcccccc caaacttaag  16200
acaagtgaaa gaaaagaagg aagccccttc tgggttaggc atcttacctt gctttatatg  16260
tatatgagag ttgagtagat tccatgatct ttccatggtt tatctgaatt atagctgtag  16320
ccagatgttt gcctatattg aaacagacca gcgctttgac tcggctggtc atgacctgtt  16380
ctgattggaa ttgtgagctg gtcctcatag cttctcatag catgcaggca ttctctccca  16440
gaagactttt cccttccttc aatctccccc acagtagctg ccttcctggt ttacaccaaa  16500
acccctttc tacttacctg gcctcacagt ggtcaggaac aggactttga ccaggtattc  16560
taaagcatgt agtcacataa atgtattttt ggatagctca agaagacctt gcccaaagtg  16620
gcggttgatg agattaatta caattaatta tatgtgtatg agttagtttt ggtgtcctgt  16680
ccttttctca tgccctggtc tttcctatga acagacacct tagaacctcg aggctgggat  16740
tgcatggccc tgctcagaag atgagtcaca gagtccgggt tagactgtgg ctaccccctc  16800
aggggataca aatttctcta tcagttaaca cttaggacag cttctcccct ttctttatct  16860
gtttgctgtt tcctcctgtg tctaactgat tcagttcaaa acctgtaatt aaaagctaga  16920
catcccagct gtggttgctt cctgtccatg cctcttgtcc tttgggcttg cctgcattcc  16980
atgcttaacc aaaagattac tttccacttg caaatctgct aatgctacca ataaaatcga  17040
gtgctggttt catatcattc ctggaattgc actctctaaa actttatttc tttatttcta  17100
atgcttggtt ttacttgaac aggtggtctg tatataacac atttgctatc ctgtaaccgt  17160
tttaattatt gagtttgaat ctgtgtcttg aaaggcctgt gtgctttccc aggcgtctgc  17220
ctcctcacat ggctgttcag tgtaccgtgt tcaagtgagc cagtcgacca ctgttctgtt  17280
tagaacttgt gcactgcaac tttggctctt ttgaccctca cccccagctt tcagagctgc  17340
ccgagtgttt ccactgtaag ccaagtgcaa gcgctcactc ttgtgtgtag gcggagttgg  17400
atgccttgta accacatagc catgtgagga ggggacgcct ttttcttcct gtaagctgtg  17460
tcaggaggca gtgtggtcaa gcggaagtgt agttggctcc accttggcat ctttccatgc  17520
cagggtccct ttctcagctt taatcaaaaa caaaagaaat gatggatggt gcatgcctag  17580
cacttgggag gctgaggcaa agaaaatagt ggtgttttga ggctgaccat ggcaagttca  17640
aggccagtag gtgctatggt aagatcctat ctcaaacctg tgtggggttg agaattggct  17700
ttttttgttt gtttgttttt agaaacagga aaatcccaaa aggatactat ctttccagaa  17760
```

```
gggaaggaag gatctttcct tgtgtttgaa cagaaaagag agccacccaa aatcccacat  17820
ataataccat tccaggcttt gaccaccctg cctctgtatc tgcatggaga agaaaagatt  17880
aacctaagag ttccttcctc tcattagttc cctgtctttc catgtgttgt ctcttgtttt  17940
tgccttcatc cttcttcctt atccttccta ccctaaacct tacagatagc tcgagaggct  18000
gaggcagccg tgttccaccg cctgctgttt gaagagcttg cgcgagcctc cagtcaatcc  18060
acagaccccc tggaggccat ggccatgggc agcgtggagg cctcttataa atgtttagca  18120
gcagctttga tagttctgac ggagtccggc aggtagggcc ctgagggcag gtatcattat  18180
aagataacca gcttctcaca caactagggc ccactgtgtg cctgagcctg ggcatagccc  18240
tctctcctgc aggaaggcag ccaaggaggt cacgataggg caggaccaaa ggattcccta  18300
gtgggtacag tggaagtcac aggcactggt tcaggatggt tcctgtggag tttctaatct  18360
tgctcagttc agaacgtgta gtgactcatc ttctcctggc tttttgtgcc cagggacatg  18420
ttccttccca gttgcctgtg actcctttcc tccctctcca tttgtgacaa agctctgaca  18480
aagccctgtc ccccttcctc gtccctctgg acggatgttg ctcccctaga ttgcccgaga  18540
ggcagaggct gccatctacc acttgcagtt attcgaggaa ctccgccgcc tggcgcccat  18600
taccagcgac cccacagaag ctgccgccgt gggtgccgtg gaggcctcct tcaagtgctg  18660
cagtggggcc attatcgtgc tcaccaagtc tggcaggtag gaggcggcag tggctccctg  18720
gggatcccca gagcaactct gggctgattt aagacccctg gctgccacca aaggactcca  18780
ggcagcactc ccaggtacac cagattaggt ggctccagtg ccagtcagtg cacggcctgc  18840
ctcagggcct gaagcatata tacagttttg cttagttacg gtgtggaagc tgggcatggg  18900
tacatgcctt taatcctccc agcattcggg cagaagaggt gggcaaatgt ctgcattcgt  18960
ggacagtctg gtctacaaag caagttccag gacagagccc tagctcacaa aaataactca  19020
gctggtaaat actacttgct acacaagtta gaccatggag gagggagaaa ggtaacttac  19080
aagcgtgccc aaggacatat acagtaacac tttttctcat cccacttgga gggagctcaa  19140
tggataaagt gttggcaatc tggatttgga tctggcacct gtgggttttt gttgttgttt  19200
gggtttttgt tttttttttt ttttttaagt cacctggaga agtagttagg cctttaggag  19260
cactggggtt ttggttttta agatttattt attatatatg aatacactgt ccctatcttc  19320
agtcgcacca gaagagggtg attacagatg attgtgtaag ccaccatgtg gttgctggga  19380
gttgaactca ggacctctgg aagagcagtt agtgctctta accactgagc catctctcca  19440
gccagcactg ttctttcaga agcccaacac atacatgaca gctcacacta tctaactgca  19500
gtcctggggg gaatctaatg ccctcttcta acttccagcc gtacatgttt atatgatgca  19560
tgtggtcagg atacccagac agctggaggg aaaggaaggt gcccaacaca cctgtgtgcc  19620
tgtaatccca gcactcatgg tacagaggta gaaagatcac aagataggtc taatctgagc  19680
aaattctgca acagcctaga tacagaaagc caaacacata aaaatcagtg tgggctgagg  19740
atgttgacct ttgtgtgaac ttggccatga acattgtatg cagctggaag caagggatgg  19800
ggtgctgaaa aatggggacc ttaaaactaa ttttctgaag tcctgaagtt tcgagagctc  19860
caagatacaa gttctatgct aatcctggac tttctctgaa gagttcctgg ttccttcaaa  19920
gcccatgtag gccagcatga agcagggtat tttctgctgt ggaatgccac atcccctaat  19980
accttgtgtg tcctcaagat gcctagttaa ttcagtaagc ctgaaacaga tctgatagaa  20040
gtaaacatat catttgctat cggttgagga gagaggggct ccctacattc ccaaaggatc  20100
```

ttgattggcc agatattaac catgcctggt cacacctaga tttccaaaaa ccataggnnn 20160
nagatttcca aaaaccatag aaattcagag gtttctttta gcaccaagtt cagctgataa 20220
gactcccaaa ggagcagtat agtactgctc tggcaaatac tgtccactcc agggtctctg 20280
cagataccag aagtcaggag ctaggcacat ggtgcttgga ttgtaaaagt tgctggcagc 20340
tacaggatgg ttctggtgag attaggccag agctgcctca ctgcctgatg gaagggttca 20400
cagtgtggga gggatcctgc cagccgtggt cctatgggac tgcccacact gagatcagga 20460
caatgagtta aaaaggacag gacaggtctg agggggtggc caggcactga aacagtaagt 20520
tgtaagtggg caaagcctgt ggcctagagg tgaattagag ggtgctgcct ttggctgact 20580
gaaagggtct cgtgacacaa tggccattct tcccaccttc tcaggagtgc tcaccaagtg 20640
gcccggtacc gcccaagggc tcctatcatt gctgtgacac gcaatcccca gacagcccgc 20700
caggcccatc tgtaccgtgg catcttccct gtgctgtgta aggatgccgt actggatgcc 20760
tgggctgagg acgttgatct tcgtgtgaac ttggccatga atgttggtat gtagctggaa 20820
gcaagggatg gggtgctggg aaatggggag cctaaaacta ccatttcctg aagccctcac 20880
ccaattttgg gcccaaggca aaattaattg cctcattagg ctcttgtaag attaattgga 20940
gctactgccc tgtggggtgg ggcacacaag ctgttgtggt ctttgttcct atataaggtt 21000
ggatatcaag agacaaggaa gcagctgacc ctgaacttgg gcaaggctgg ccactctaga 21060
gtctaaactg aatggtgtcc aaaggtccct gcagtctgag ttttgcctca gcccttgttt 21120
aagctaggag acttgcacca ccttgtggta aaaagaagta actggcaacc tgctctccta 21180
cctgaattag aagcaatagg gcatttgtac ctgcctggtt aggcttgtgt ctgggctggg 21240
agaaagcacc accttgtggt aggagagagt actggttgct cagttaggac tgggtagggc 21300
tttgcagtta tccccaagtg ttgtatatac ctctactcac caacctcctt ctcccctcag 21360
gcaaggcccg aggcttcttc aagaagggag atgtggtcat tgtgctgact ggatggcgcc 21420
ctggctctgg cttcaccaac accatgcgtg tagtgcctgt accatgatga tcctctggag 21480
cttctcttct agcccctgtc ccttcccctc ccctatccta tccattaggc cagcaacgct 21540
tgtagtgctc actctgggcc atagtgtggc gctggtgggc tgggacacca ggaaaaatta 21600
atgcctctga aacatgcaat agagcccagc tatttttcat ggccctactt gagccagggg 21660
tgaaggagga atgcaggatt ggaaaccctc tgactttatc acagaagggc agcattatct 21720
ctgtgttctt tgctcctgta gaaagttttc cagagaattc ccagccctgg cctggaatca 21780
ggagacagca agaacagagg ctgggggccc agggttccca tgtagatgac ttttggccct 21840
gtccctgact tgctttccca acagctttgg cctctctcct cgtgcactcc actgctgtcc 21900
ctgcagatgt tccactctcc acctcgtact ctgcagcgtc tccaggcctg ttgctatagt 21960
gcccacctga atgtcaataa acagcagcgg aagca 21995

<210> SEQ ID NO 51
<211> LENGTH: 13748
<212> TYPE: DNA
<213> ORGANISM: Oryctolagus cuniculus
<220> FEATURE:
<221> NAME/KEY: modified_base
<222> LOCATION: (6934)..(7189)
<223> OTHER INFORMATION: a, c, t, g, unknown or other

<400> SEQUENCE: 51
atgtcgaagt cccacagtga agccgggtct gccttcatcc agacgcagca gctgcacgca 60
gccatggcgg acacattcct ggagcacatg tgccggctgg acatcgactc cgcgcccatc 120

-continued

```
acggcccgca acacgggcat catctgtacc atcggtgagc ctcggggacc gagtccggga    180
aggagcgcgc attgtgcgtt ctgctggggg tgagcgtccc cagctcagag gcctaggcct    240
atgccaccaa gatgggcaga gggctggcca agctcttaac ctgggctttc ctgactgtag    300
ggggctacag acctgtgcag ggcgtgggga gaggtgttcc cctaaatcaa gaaagcaggc    360
tagcacatcg acggccgtga gtgtgctctc tgaaagactt gcgttatttg gggaggaaa    420
ccgaggaagc gtttctttga gtcactgacg ctgtgccgca atatgtaaca ggccctgcct    480
cccgatcggt ggagacgctg aaggagatga tcaagtctgg gatgaacgtg gcgcgcatga    540
acttctccca cggaactcac gaggtgagcc tcggctgcac attggccgcg ggggcggctg    600
taggcgacag ggaggagtgc cttgttcact tagggtgggc tccacagatt ccagtctggg    660
tgtcccagcc ctaggctcct gccctgagct ctctgcagct tggttctggc ccagttcagg    720
ctgcagagag ctgggcaggc gcccagaggt ttccactctg gcaggcgagt gccccgcccg    780
tcagcactgt gcccccagcc tcgccctctc cagaggttct gctgcacgga cagaaaacca    840
gccggcgagt gtttgcgctg gagctgttgg ccgtggcagg aagcggcgct ctgagggtgc    900
tggggttccc tgaggggccg cagtcgtggg gcttcatttc ggcattggta gaggagtaat    960
gggcaggctg acgttgccct ctcttgccct ctgtcctttc ctcctctgag gtcagtggtg   1020
agggtcactc tctggcattt ggaagctggt gttaagtttg gactaaaaat aagccctcgg   1080
gcagtgcaaa ccgcggggtg aattcttgct ttctggaaac atgagacttg actctccatg   1140
gtaaatgctg cagcccctaa ctctggggcc cagccagggc cagcaggcac ctcgggcagc   1200
ctgaggcgca tcctgggctc tcaccaggaa ttgctgcgtg tgtcaccctg cccagagggc   1260
caaggcagca gtgaggatca gttcaccttt gacccctgct gccggagtct gccgtgggcc   1320
ctgcgtgcgg gtgaggagca gaaatagatt tggaggcgct gacctttcag ccgctgcgcg   1380
ctccctccac cagtaaaaca acaccgcccc gctcggaaat ggcaagggct gcacctgtcg   1440
cacgagggcg tgggtctgtg cttctgattc tcattcccag attaaaagtg ggatgaaaaa   1500
ggaaagaagc gcagtgcctc tggtggttta gggtcaggcc caggtgagct tccagggtca   1560
gcatctggga agcgggcctg aggtgctgag gtgtggactg acgtgaccgc cttccccctc   1620
ctcacctgac agaggcacgg ctgcttctgt gtctgggctt ttgtgttgtt ttttgttttt   1680
gttttgtttt gttttttttt ttttttttaa tttatttaat tctatttgaa aaacaaacag   1740
attttcccac tgatttattc tccaaatgcc tgcagcagcc aggaggcagg actcggttca   1800
ggtctcccgc atgggtggca ggggcccgca cacttgagcc ccgtcacctg ctgccatcca   1860
agcgtgacga gaaccaggac tcaaccccag gccctccggt atgggatgca cacatcccag   1920
gtgctgtctc cagtgctcag tcctacacct tgtctctggc agctctgacc gtgtccctag   1980
cccccgccct ggcagctcat gtggaccatc tgtgcttgct gaacatgcag ttccacaacg   2040
ccaggctggc cagaactgac tctgacataa tctaaattta gagccttcca cagggcagca   2100
gtaatggtgg ggtgggcacc actccgcaga taataagcag cccagcccca ccccagccag   2160
caccctgtca accatttaga atgtttatga cataagattt tacatcccca agaccaaaaa   2220
tggcatgttt atatactttg agttgcaaaa agtattttct gtcactcacc aaaaaacttc   2280
aagttccata aaagtagaaa ttttacagac acatgacctg acataatttt ttagaattgt   2340
ttgaaaggta gaggcagagc gacatctctg atcttcccaa atgtccatag cagctggagc   2400
tgaaccaggc cagagctggg agtccggaac tcactctggg tctctgtaca aggcaggcag   2460
```

-continued

```
ggacccaggc acttgaacca tcacctgctc tgtccatgca ctgtgttgtc aggaggctgg   2520
atcggaagtg cacctgggac tcaggcgtgt cttcagtgga ttcttgactg ctgtgccaca   2580
ctcagccctg acttttttc atggaaatca agatcagtat agagtgtgat gatcaggaga   2640
gcttcaaaac tcgttctaga accagaagcc gtggcaccgg caataaataa atctttaaaa   2700
aaaagttaaa gaaaaagaat ttgtaagacc atggcttgat gaaatagaag attgaaaaat   2760
taagctgaga tctgattctt tgtgggaaac agtaaatcag aaatctcagg aaggcctggt   2820
caagaatacg aggatggggg ccggcgctgc ggctcactgg gctaatcctc caccttgcgg   2880
tggcggcaca ccgggttcta gtcccggttg gggcgccgga tcctgtcccg gttgcccctc   2940
ttccaggcca gctctctgct gtggccaggg agtgcagtgg aggatggccc aaatgcttgg   3000
gccctgcacc tgcatgggag accaggagaa gcacctggct cctgccatcg gatcagcgcg   3060
gtgcgctggc cacagcgcat cggccgcggc ggccattgga gggtgaacca acggcaaagg   3120
aagacctttc tctctctctc tctctcactg tccgctctgc ctgtcaagaa aaaaaaaaaa   3180
aaaagaatac gaggatgggg agggaattgt ggcgcagagg cttaagcctc cactgggacc   3240
cagacacctc atatcagagc actggtttgg gtctcactgg ctctactttt ttctttattt   3300
atttttaaag atttatttta tttgtttgaa agagttacag agagaggtag aggcagaaga   3360
agagaggagt ctttcatctg ctggttcact ctccagatgg ccacagtggc tggagctgag   3420
ctgatcccaa gctgggagcc aggagcttcc gggtctccca cgtgggtgca ggggcccaag   3480
cacttgggcc atcttcactg ctttcccaga tgcaccagca gagagctgga tctgaagtag   3540
agcagctggg actcgaacca gtgcccatag ggattctaa cactgcaggc cagaaattta   3600
acccactgca ccgcagcgcc agcccctggc cccacttctg atccagtttc ctgctggtgt   3660
gcctgggagt aatggcctca gtacttgggt cctggtcacc cacatagaga cccaggatag   3720
agtgaggttc ctggcttcag cctggaccag ccctagccat tggagccact tggggagtga   3780
accaatgatg aaagatctcc cactccctct cctctgttaa aggaatttct tgactggtgg   3840
ccaagtaaat tttattgtgg gaacatagag ttattaaata attcctgtgt gcttgactct   3900
tctgagtttc atgttatttt agtcctcaga acaaaaggta tttggtaata ttcagcaccc   3960
ctccctccct ccctgcctct ctctctttct ttctttaccg gcagagttag agagagagac   4020
agagaaaggt ctttcttttc cattggttca cctccaaatt ggctgctgtg gctggcgtgc   4080
tgccccaatc tgaagccagg agccaggtgc ttctcctggt ctcccatgcg ggtacagggc   4140
ccaagaactt gggccatcct ccactgccct cctgggccac agcagagagc tggacaggaa   4200
gaggagcaac caggactaga actcggcgcc ccaaccggga ctagaactca gggtgccggt   4260
gccacaggca gaggattagc ctagtgagct gtggcgccgg ccaatccgtt cctttttac   4320
atactgcagg atcaaaaaac accacaccag aactatctcc agactgggtg tctggtcaga   4380
ggttaagttg ctccttggaa tgtccacatc tcatatctaa gtgcattgtt caagtcccag   4440
cttctctgct tccaactgtt tattgttagt gcatatcctg ggaggcgacc catgcgggag   4500
acctggatgg agttgtaggc tcctgacaat tgcaggcatt tggggagtga acccagcagc   4560
tgcaagataa tctctctctc tgcctttgaa ataaaaagtg aaaataaatt aattataagt   4620
aaatgatttc tattgcaaac cagcaatacg aagaatgtag aacctctgtg gaatagaaag   4680
tggagccagt ggtcgctcct tgcagagagt gcctgagtta gaagctcatg gtggtcagac   4740
agctttgggc agtgtcgtcc ctggagacgg ctctggctcc tggtaccttc cagcgtccca   4800
ggcctgctgg cagctgctgt tgcccagaca gtggtggtta aaggccaagc ccatgaagtg   4860
```

```
ctgagcgagg tgcgctgtta tcagcagtgc cgtattgatt accctatctg ggagcccttt   4920
tgacatctta tctcggcttt gactgccttt ttgattgaac agtactggca agtgagggag   4980
aaagggcttt ggagagagac gggagccagg atgtgctgcc agggcagttg gtgcggagag   5040
gggcctgaga gcaccttggc ctgctcctct cctctcaggc cacaccctgg gaagggaggg   5100
tgcagccagc tctcatgacc tacctgagct ttcaggtgaa gtccacaacc tggtgttgga   5160
actgtggttg gaatccgtgg gagagggccc tcgcctggcc acctctgtca ggctctgcgc   5220
tgattgcccg gcggtctcac ccacacctgc cctggttctt ctgccccagt cgtcttgccc   5280
tgttagttgt cttaggggaa agagcacagc ccgaaggtgc tgctgcttgt gtggttctgg   5340
acggcagtgg cctctgctga gtgcgtgccg tggtggaggt gcggagaggc tgcgggtgct   5400
cgggcggacg gcggccgagg tgggcgatgc agctttggct cccagcccca gggatgccag   5460
ctggcccgag cgtgggagga cacttgtcct cttctccctc ccccagtacc atgcggagac   5520
catcaagaac gtgcgcacag ccacggaaag ctttgcctca gaccccatcc tctaccggcc   5580
cgtcgcggtg gctctggaca ctaagggacc cgagatccga acggggctca tcaagggcgt   5640
gagtatcctt gggacacggg gagcccaggg cgtgtctgtg gtgtttgcct gggtgctgcc   5700
atgttttaga attcaggtca agtgtaaatg tggattccat ggtaccacaa aaggatcttt   5760
tttttttag tctaaaaact gacttctggc tttgagaagc agtttctttg tgtgtcttgg   5820
ccgtctttaa gtaacgcaac agaacgtgtt ggcctttgtc tttggctgtt tcctcggatg   5880
tgctaagtta gagaagggca tctgttcacc aagggccaag ctttgtgatt cctctgagat   5940
tcagacattg tgctggggag gcgggggcgc tggctgccag ctggactctc gctcactctc   6000
ctgtccagag cggcacggcg gaggtggagc tgaagaaggg agccacgctc aagatcacgc   6060
tggacaacgc ctacatggag aagtgcgacg agaacatcct gtggctggac tacaagaaca   6120
tttgcaaggt ggtggacgtg ggcagcaagg tctacgtgga cgatggcctc atctccctgc   6180
aggtgaagca gaaaggtgtg tatcgccagc ctgagcagca ccccggcctc aggacagcaa   6240
aggcagagag ctcctccggc ctcccgactt gcggggctcg tggaaggtag ggaggtagga   6300
agcttggttg tctggcggag agatggtggt atggtgagct ctgtttattt gagaggtaga   6360
ttgacagaaa ggggaagaca gattttctgt ctgctagttc actccccggg tgcccacggc   6420
atccaggacc aaaggcagga gccaggtctc cttcgtggat gggccatcag ctgtgcctcc   6480
agctgtgtca gcagggagcc ggatcagcag ctgaacgagg cgctccacta tgggatgtag   6540
gcgtcccaag tggcggccta acctgcacca cggcactcac ccaaacgagt gagggagcgc   6600
tggcagacag gctgtgggcg gcggttgggc ttgtttgcgt ggccccggcc cccaggtgtg   6660
cttccctggt cctccgcggg agggaggcac ctgctgcttg ctgctcccct gtcccctggg   6720
gatgggccct ggcggctctg catcccctgc tcgctgtgcc cacaggtcct gacttcctgg   6780
tgacggaggt ggagaacggt ggcttcttgg gcagcaagaa gggcgtgaac ctccccgggc   6840
tgcggtggac ctgcctgccg tgtccgagaa ggacatccag gatctgaagt tcggcgtgga   6900
gcaggacgtg acatggtgtt tgcctctttc atcnnnnnnn nnnnnnnnnn nnnnnnnnnn   6960
nnnnnnnnnn nnnnnnnnnn nnnnnnnnnn nnnnnnnnnn nnnnnnnnnn nnnnnnnnnn   7020
nnnnnnnnnn nnnnnnnnnn nnnnnnnnnn nnnnnnnnnn nnnnnnnnnn nnnnnnnnnn   7080
nnnnnnnnnn nnnnnnnnnn nnnnnnnnnn nnnnnnnnnn nnnnnnnnnn nnnnnnnnnn   7140
nnnnnnnnnn nnnnnnnnnn nnnnnnnnnn nnnnnnnnnn nnnnnnnnna ccgggggacc   7200
```

-continued

```
cacaccagag agagcaggcc tccggccaca ggaagggggg ctgcccccgt tcctgaccgg   7260
cgacccatgg ggaagcgcga gggtcggggt cttggtcttc cctcagaagg gctggcccgg   7320
gcgatgagcc actcgccccc agagggaagc ctggggggtc ttcttcaggt ccccagggct   7380
gccccagccc agcctgacca cctccgccgt ctcagtgtgg ccagctggcc cctcctagag   7440
cagtagctcg tgaggggcag ggcggcagca gccctggggc cccacagcct ggtgttctgg   7500
ccgtctccgg ctctgcctgg gcgtccttcc taccacatga gctcggctct ctgcctttgc   7560
tgtcctgatg ggccgggctg ctggctcggg ccggtgatgc gcgtgccctc ttgcctcccc   7620
ggggcatgcc tgtggtgtcc ttggctagat gaggccgccg accttggggt gggaagcagc   7680
cagcagcgtc ggtgcccttc ctgggaaatg ctgactggag cacttgaggg cctcacaggg   7740
tcaggtggag aggcggggcg gggcatccca gaaggtgtcg aggcccagga gccgggagcc   7800
tggccacgtg cacgcatctg tgctgtgtcg ggccctccga gttaggggtc gtggccgggg   7860
cttcctgtct gtcaccatac ttgggacccc tgtggaatat gacttctgtt tcgtccctgc   7920
cccctctgtc aggtttgatg agatcctgga ggccagcgac gggatcatgg tggctcgtgg   7980
tgatcttggc attgagattc ctgcagagaa ggtcttcctt gcccagaaga tgataattgg   8040
gcgatgcaac cgtgctggga agcctgtcat ctgtgccacg caggcatgtg gccctccctg   8100
gggaccccgt ccctgtgcac ccccagtcca gcagggtctc acccgtgctc tgcccctccc   8160
agatgctgga gagcatgatc aagaagcccc gccccacccg cgccgagggc agtgacgtgg   8220
ccaacgcggt cctggatgga gccgactgca tcatgctgtc tggagagacg gccaagggcg   8280
actacccgct ggaggccgtc cgcatgcagc acctggtgag tgcccagggc cccgcttccg   8340
cggagcctca ctgcacgagt gaggcatgtg ctgggcgtgg ggcgcccctt ctgccccgcc   8400
tcccagctcc tgtccggaga agtcacccca gcttccgagt ccttcgcctg agtcctgggg   8460
tactgctgcc ctcagcagat gcctgtcgcc ctcctcagag gtccaggggc ttcagcacct   8520
ttggcctgat ctggaagaca ccagggctcc tgcccccagc tgctctgttt ggctttgact   8580
ggactccctg cggggcctgt gtgcacccag caagctgcct gtgagccggc cttgcatggt   8640
gcctgcagcg ggaccggctt ctgtgctgtg ggggtgcagc tgcctcactt agtccagacg   8700
acccagaggg gcttgggaag gtggccagcc ccggtggtcc tcacactgga gtcatctgca   8760
ggagtctggg gctgggccat agccgcctga cctcttctgt aggtgggagc ccagggctgg   8820
ttgtcaaggc cgctcgggct tggtgcacct tgagccccag tcacctggag agtggctccc   8880
tgtggtctct gacgcccctc tgtctgtgtg ctgtggtaag ctcaagcggg agggtgatga   8940
ccttgtctga agcacacgga ctacagaaag tgtctctggg cgaagtctcc gctctctcag   9000
gacctcgtct gtaagctgga ttagatgaga tctacgactg ctggctttag ttctgataag   9060
tccctggtac actgatgtaa tcctgacagc tcccagcatc accagggctg tgggacaaga   9120
actcccagga cactgaccca aagccggcct tctccctgcg gttcccctgc ccagtaggac   9180
ttagaacgag gctctgggtc ccagagttgg ttctgggttc tgaattctgt gcctctttcc   9240
cttaactggt ctttcccatg gacagacagc ttagggcgtt gcaggctctg ggccaggatg   9300
tggctgccct gcaggtggtg caggccacta gccggcagcc gcctctcagt gtccgtgctc   9360
ggactgatgc actgacccgt aactcagggc taggccgcac caggtatggc cctggctcct   9420
gtccctgtcc ctgtccctcg ggctgcatgc actcattcca tcgttaactc ggcggtgctc   9480
cccgcgtctg cttccgctcg gagatgaaat gaatggggcg gtgctgctga cccttcctcg   9540
cccgttgatg actaagccac tgggaactgc attgtaatct cgaacgcttc cactcgcttt   9600
```

-continued ctgattctca gtctcacctg agctggtggt ctgtggtaac tcagctctct cgcgcctgtt 9660
ttaatcagta gctgttaatc aagcgtcctg tgacgtcccc gcatgctccc atgggtgtct 9720
cttcacatgg ctgttcaggg cggccctcgc gagctggcct gtgctgccag ctctcctgcg 9780
tggccttggc tgctgacgcc tgcctcccag ccctgttgtc tgtttccacg gcgggcactg 9840
gggagagcac ccttgtgcct caagccaagc agcctccatg tggcacaaac acccagacag 9900
ccaagtgagg aggggcctgc tccttcccga aatctgtgtc acgaggcagc gtggtcaggt 9960
ccagcctggg caggtcccca tgccacggcg ctagagcccg cggccatact ggcttccctc 10020
cactcccagc cccggtatcg gagggtgagg tgtgaaattc tccatgcccc acagctggct 10080
ggacctggac cctctgcctc tgcctgacga cccgattaac ccggggtgcc ttcctccctg 10140
attaatcccc cgttctgtct ttccgtgtct tgtcttccct gtctcctcct cctcctctct 10200
tccttgccct ctcccctaac ccttacagat agctcgcgag gctgaggcag ccatgttcca 10260
ccgcaagctg ttcgaagaac ttgcgcgagc ctccagtcac tccacagacc tcatggaggc 10320
catggccatg ggcagcgtgg aggcttccta taagtgttta gcggcagctt tgatagttct 10380
gacggagtct ggcaggtagg gcccgaggcc aggtaacgct gcaggggacc ctgcctcttg 10440
cgccagctgc tccaggatgc gcggcctggg cccagagcct ctgctcagct gcaggaagac 10500
agccagggtg gtcaggacag ggcaggaccg gaggctctgc ctcggtaggc agcggcgtct 10560
cgggcagccg gtggaggaac gccctcgggg agtctggctc tgctgctccc gggctgcagc 10620
cctcaggctc gtgttggcct tgctgggccg tgtcccccac ccgctgtctg tagactcatc 10680
ccctcccctc tgacgaagct ctgacgaagc tctgtcccct ctcgtccccc tggacggatg 10740
ttgctcccct agattgcccg tgaggcagag gctgccatct accacttgca attatttgag 10800
gagctccgcc gcctggcgcc cattaccagc gaccccacag aagccgccgc cgtgggtgcc 10860
gtggaggcct ccttcaagtg ctgcagtggg gccataatcg tgctgaccaa gtctggcagg 10920
taggaggcgc cagcgagcgc ctggcagtgc cctgctgcgg gacacccctg caggaggggc 10980
ctgggagcgg tcctggcgca gtgcgcagat ggtgctgagc caaggtaagc ccctctgccc 11040
accacctgca ccctggcagg gaaggatgct cccaggcccc cgggccagga ccagcagtga 11100
gcggagccgg gttgtggact cgctgcgtaa ggggtagggc tgacgacaca tacttgttct 11160
ttaaaagctg ctccttggaa acagaagcag ggttgccttt tctggttctt aggacctctt 11220
tgcaaactta gtctggaaaa tctgaatgct gttcccatct ctgccagaca caccagtggg 11280
ttctgggccc aggaaggtca cccccccttt cccctcattt tgtggggctg tggtgccggg 11340
gttggacttg gcctgagtta ccctccctcc cctgtggccc tgggagacag cgggtgggga 11400
ggaggggctg tagctgggct gccgtgtgcg accaggagag gtctgcgacg cccactcttg 11460
ggctttcggg ctgacctttg tagaacggcc ggcttagctc tgcactattc ttagcggcag 11520
tcttctgaga tttcacagct ctgaccccag cagctgcctc ccctgaaggc caagcctgtt 11580
cctggcacct gttctgtctt cgcagcttgc tcccggggcc tgctccttcg cgggcccctc 11640
cccagctcct gcagggcccc tggcacaggg ctcagcagag tccccacctc cagggtcccc 11700
tgacaggcgg agctgccccc atgcccacct ttctctcatc acgaagccct tacctgaatc 11760
tacacaatct taggagttaa tctttggtta aaaaatcttt tttacttatt tgaaaggcag 11820
agttggagaa agggagacag gtcttccccg gttcacgccc cgaatggctg cagcggccag 11880
ggctgggcca ggctgaagcc gtgcccgtgt gggatgccca tgtccctatg ccacaatgct 11940

-continued ggccccccccg ggaattttt ttttttttt taagatttat ttatttattt gaaagagtta 12000
cacagagaaa gaagcagaga gagagaggtc ttccatcggc tggttcactc cccaattggc 12060
cacaatggcc agagctgtgc cagttcaaag ccaggagctt ctgggtctcc cacgtgggtg 12120
caggggccca aggacttggg gcgtcttcca ctgcttcccc aggccacagc agagagctgg 12180
atcggaagtg gagcagccga gactcaggca gtacccttat gggatgtcgg cactgtatgt 12240
ggcggcttca cctgctatgc cacagcactg gccctttggg aattcttaag atgcctccgg 12300
atcttcaagt ttgtctgaga tctggagccc agttgctggg gccgcttggg tggacgagcc 12360
cggcagtgga gggtccgtgt gttgctgggc ccagggtctg gcagctgtgc tgcggctctg 12420
cagtcaggct gtgggccaca cgctgctccg ctgtgcttct gccggcccca agacgaggcc 12480
ctgcactagg gctgccaggt ggagggagca ggactccctc tgccatagtg gaaaagtcca 12540
gggtgtggca aggcagctgc cagccctggc cacgtggggt cagtggatga gatggggcgg 12600
ctccctgccc tcagaggcac cagagagcag gtgtggaagt ggccagagct tcaggctggc 12660
gtagtgagtt ggattagggg gtgagctatt gccaaaggcc cgggggggg gggggctcc 12720 agggacactg cttaatggtc gtcctgcttg tctcctgtcc caggtctgct caccaagtgg 12780
cccggtaccg cccgcgcgcc cccatcattg ccgtgacacg gaaccaccag accgcccgcc 12840
aggcccacct gtaccgtggg atcttcccgg tggtgtgtaa ggatccggtc caggaggcct 12900
gggctgagga tgtcgacctc cgggtgaact tggccatgaa tgtcggtgcg tgctgggagc 12960
aagactagag acctgagggg caggatacct ggctactggc ttctgggacc ctgaagcctg 13020
gggaacataa cgggggggaac cccaagacca gagaggccaa gagacctagc tgagcacccc 13080
tggtccccac tggggatgtt ccctgaatcc cactgcttgc cagtcctgag cagcgcccgg 13140
gaggggaggg gtgccatagc tcgcagccac agtaaaacgc ctcgttctgt ggcagtgctc 13200
tgggggttaa ggtttatgtc atttatttga agggcagagt gcctgagggg gagggaggga 13260
ggcaaagatc ttgcatccac tggttcagtc ctcaaatagg cgcaacagcc agaaggccag 13320
agtcgggccc agagctccat ccgggtcccc cccatggatg gcagaggcaa aggcatttgg 13380
gccaccttag gatgccttcc ctggctcgtt ggtaggaagc aggagcagcc tggacagggg 13440
atgccggcgt ggagtggcag cttaccctgc tgcaccacgc tgttggcccc gctgcccggg 13500
tgttgggaga ggagaggagc agctggctct gaccttaggc agtcttaggt cgtgtccaag 13560
tccctgccca ctttgtcccc gctgtgaggc tggcgccacc ttgtggaggg tggaagtccc 13620
tcaccagctt ctctcctgca ggcaaggccc gcggtttctt caagaaggga gatgtggtca 13680
ttgtgctcac cggatggcgc cctggctctg gcttcaccaa caccatgcgc gtggtgcccg 13740
tgccgtga 13748

<210> SEQ ID NO 52
<211> LENGTH: 17257
<212> TYPE: DNA
<213> ORGANISM: Gallus gallus

<400> SEQUENCE: 52
agcggcggcg gcgctcgggc aggacaggct ttgggcacgg cggcggaagc agcagcagga 60
ggtaacggcg gcctccggcc ccgcataggg agggcgttga aggagggcgg cgagcgggca 120
gccgaggccg ccgtcgtcat cgccggaccc gacgttcagg cgggagtgtt acgttcagga 180
cagggcgctg agggggcgct gaggggaggg ggcggctcca cgcggttggg gtaacggcgg 240
cgctggcgga gggatggatg atggatggat gatgggtggg tgggcagatg ggtgcccgca 300

-continued gcgctccgcc cgcccgggct gagtcagccg tcggcgccac ggccacgtgc tggggccccg 360
ctcggctctt cccgaggctc ccggctctcc cagccccgag gtcccattca tccccgcgtg 420
gccgcccacc ccctccccccc gccccgccgc gggccctgaa gcgctcgggg tgcgtgaatg 480
gggcttttgt tggcgcacgg cggccgcccg tcggggcggc gaggcggcgt gcagagcccg 540
cttcgtgccg ctccgggtcg cacagcgctc tgtggggagc gggtggtgcg cggggccggg 600
ttccggcacc ctcctcctcc agggacggct ccagagcacg cgctggcacc gggccgttgt 660
gtgtgtgtgg gggggtaacc ggagaaccgc accccaacgc ggggccgaaa tcgccgccgt 720
cagtacgcgg ctccaccccg ttcccggagc aacgctcgga cagctgcgag ccgtggagga 780
gcggccgcgc ccgcgcacct cgccgtgccc cggggctgag cgccgcgacc acgtgctgcc 840
ctgcgcgggg tgggggcggg gcggggcgcc gcgctgtgcg gtcccgcacg tacggcatgg 900
actgctgcgg gggcttcctg gggtacggct ccagagcgcc gagctctgat tgctgccgtt 960
gtgcagcgaa gctgtctgac ctgtgccggc gcagcccgca gcgcggtgag gctggaaggt 1020
gtgcacgctt caactgtact ctctcgataa gtttgccgtc tgttctttaa tcgaagcctg 1080
ctccgtgccc ttgtcctccg agaagggcag acgcagcata gcaacacgta gtgaaggtgc 1140
ccaacgctca tcctccgcct gcaggctcag tggcccatcc cggccggccc cacgagggct 1200
gacgttggga ggccatcttg cagttgcata aggctgcggc gcaacctccc tcccgcagta 1260
ggagtcatcc ttcccccccc cccctccacc cccctctctg caagggggt tgccgtgttg 1320
gcagcctgcc gtgcgcccag ctccatggct gtggggtggg gatggcggtg gggctgtgcc 1380
tctttcctgc cccggggtac agctggaatg cctcagctag aggttccgta ctgcaactca 1440
cactgagtca ccccgctgcc ctgcaacggt cctgcctttc tggaacgttc agcggccaag 1500
ggaggaaccg gccatcttga gcgtgccctg cctgaaatgg ggtgatacct tggggggatt 1560
taagagttac gccccgagaa aggaaagcag ctttgtgcag ggaatcaggc tttgcaaggt 1620
attactcccc gccccccttcc tggctcagct cagagtgcct tcaggtgttc ctgagaagct 1680
gatttaaaaa acaaaaagtg ggaaatgcca gacattcctc ttagggttat aaaaccgccc 1740
tttgagcatc actccttgca gatgggatgc aggaggaagc acaggaatgt agggctccct 1800
gcagcccagc agacggtggc tggggtttct ttcttctgct gctgcgtttc ttctctcccc 1860
ctcgggcaag gtcacagcat cgcggcgcct ctcatctcct tgaatttgct gaaaaatctc 1920
aggggattct gactcaaagc agttttaact ctccttcctt tttatacaat cgtaaagcct 1980
ttggggcttg aaaatcacac ttacaaatga cttgagtggg tggggagttt ccacggggag 2040
gaagctgcct ccaaagcagg gaggctgagt tgctgcccat ctttctggga acatatgagt 2100
cgcactcagt gcttgtccct ccccacaccc cattccccac agccacgcgg gccctttttgc 2160
tgctgtttgc agaggcagtt tcccagcaga ggccttttgc actgtccagc aggtgctcca 2220
ggatgcgcca gcagatgtta gagggctgaa acaccgtgtt caggtctgag cagcgggcat 2280
ccccgtaata aggcgccttt gttgaggctt ttatgtgggc aggctttctt gtactgactc 2340
gagtgaatca gcagcttctg gcagggctga ggtgaaggac gcctgccagg acaaattatg 2400
gtttctgctg gcccgtcttt gcgctccatt tcgcgcggcg atgaggcgat ggtgagtcag 2460
ggctgcctgc gagaggattg gcacgtaggt gggggggagcg gccggcgggg gacctccgtg 2520
ctcatgctgt tcccttctgc tcagcccggc tttagtggag ctgctggttt attaatgccc 2580
tgtgcagctg gaggtgcagc gtgcgcggtg agctccattt ttgcgacaga tggagtgcat 2640

-continued

```
ccctgcatgg ctcagtgtgc cgatggcgtt ctgagcgtga gcggccccca tccaaccgtg   2700
gggagcaatg cactcgaggt ggtggcagca gcacagcaag aagctgagcc ttgcacaggc   2760
acaaagtcct gcctcacctg ggtgtaaatg cagaaggaag gtgtgcaggg aggggaacat   2820
gggcagcttt gagctgtatt gctgcttgag gacaaaattc ctcaattccc ccccctcagg   2880
gagggggagg agggggggga ttctcccatt gcagcacacg tctgtgggtt tcactcagct   2940
ttcttatagg gtcgggacct tccctgctgt tctggggatg ctttcatctc gtggaggcaa   3000
gcacggagtt tcttactccc agaatcagcc agtcttgagc cctgtggagg cttcctgccc   3060
cctgcaaatg caggggctgc agtagactgc atggtgtctt cgtttggaag agggcacttg   3120
aggacattca aggattcttt agccttattc gcgtttgtct gccccggtgt tgtgttcaat   3180
caactcaagt ctgattatct gtgcaggctt aaaggccggg ttaagcctag gtgcacttgg   3240
tgtgctgagg tgtgtccccg cgtgcagcac gcctgcagtc acgctagcag ccggctgccc   3300
ggtccccagg ctgctggcag agatgggctg agagcgggca gggagcgggc agcgcgctgc   3360
ctgtgcactg aagcgcttga attttgttgc gttgtgtagc tgcaggggaa gactggcaat   3420
gaagagaagc tatgaaggga acttctgcat agaaggcagg tgagctttgg gtggcatccg   3480
tggggaatga catttaaata gaagtgtgtc ttgcctgtat ctaagactct caagtaggaa   3540
cataacgata gtctgaccca gtagcagctt tcttgttacc tccatattca tcacgtgggt   3600
gtgttggtgt ctctgcatgg tgagcgagca ggggcaatcc ctaaacccgg caccgttttc   3660
ttctcttgca gacaccgaac tccagtaacc atgtcgaagc accacgatgc agggaccgct   3720
ttcatccaga cccagcagct gcacgctgcc atggcagaca cctttctgga gcacatgtgc   3780
cgcctggaca tcgactccga gccaaccatt gccagaaaca ccggcatcat ctgcaccatc   3840
ggtacgtggc tcccagatcc caggaactgt ggctcacgtt aggctgtgaa cgcctgcgtt   3900
ggtgaaactc attgtgggaa tgtgggatgg cttcagcctt catccgttgc cagggttgtg   3960
tcttgtctgt tgaaacaaca caactttccc atgcctgcct gcccagtttt attgctaggg   4020
gtaaatcgag cgatgtctga actggttggg ttcagatgtg ctccctaaga caaggcaaag   4080
gagctgcttt cgtgttgagc aagtctgtat ccactgtgct tcacttatcc cctccatgtg   4140
aaacagcctg acgtttgtgg gttatctcat tatttatatg aagttaatat tcaaactgtt   4200
tcctcctttt ttaggcccag cctcccgctc tgtggacaag ctgaaggaaa tgattaaatc   4260
tggaatgaat gttgcccgcc tcaacttctc gcacggcacc cacgaggtaa gggtggggat   4320
ggggctgacg ctgccctgaa cctgtaactg ctcatccctt ccttcccttc tgtaagagga   4380
gaccaaggga aatcgagctt gctgcagagc agctgtggta gtgtaggaag acagaacttt   4440
agctttatgt gtgggggaag tgtgccagct gtaaatacca agcctgcaag actgctgata   4500
agatttcagt gctttctggt agcagcttga gttgtttcca caccccttctc tgtacctacc   4560
tctaccttgg gagtcaggta gctgatatct gaggcccttc acttctttcc cccctcatgg   4620
gggagtgaac ttgcatttcc tttacaggac tgctgctcct gagttacttg tgcacccctg   4680
caggagtaca caactatcag ttgttcaccc tgcttcactg ttggaggctt tgcaagcggt   4740
cagtgaatga ccttgtctca aaatataaat catttgaagt aattactgtg tgcatttgaa   4800
agaattgagc ttctggactt gcctggctag ccagccgctc aggttatgtt cccagtagtc   4860
atgaggctgg ttgcttgtca cttggggggc aataaacctc taagactaag gtcagaagaa   4920
atcaacactg cttgtggtgg acgagccctt tttgatataa atagatgaga tcctcagcaa   4980
tgctgcagga gcaaaggatc ccattccagg gttgcccaga atgtcatcct tagcgttgag   5040
```

gctgagttct tacgctggct gtcctccagc tttcaaaatg tcaaactgta accaaatgac 5100
agctgtcggt ggctttactt actgaactgt gagccctgag gtgcgtaaca gctcgacctc 5160
tcaccctcat ggcctttaaa ggccacaggg cactgcagaa atcaaaaggt ctagtgttta 5220
gctgcgcaca gccgttggac catgactgta ttagcctgtg gtagcagcag tgtgcaggct 5280
acagctgacc aaaattccaa tgcagaaagg gccgtatgga ccaacttcac ccctcagtgg 5340
tcatgtgctg ctacacagcc agcaggctca gcaaagagtt ggtggccaag cttgaacctt 5400
cttagctgtc ttagcacagt gctgtggttg gtgtgcttgt tagctgaggt gaagggcacg 5460
gaatgtggct tggctttggg tgtagtgcag ctcaattgcg tatttggttt agatggaggt 5520
taggtgatgg cagttggtca tgctgcaatc tcctgcctgg tttgactgcc agctgtaacc 5580
aggcaagtct gagttccctt ctggttcctc aagcactccg ttgtccgcga cggttgcctg 5640
gggttttcat gtgctgcgct tgtttcagtt ccagtgttca tcctaaagca catcatgggg 5700
ctcgagttag caactgcaaa tagatgctag accttgaagc tctttcatgg aggaagtctg 5760
ctttacttaa gcccctgtca gcattcctgt cacatacgta attctcaagg aagtcacact 5820
ccctaggagc cggtcattga tctgtatcaa gtcacaaaat gccccaggtg actgggagca 5880
gataagcccc atgactctgc tcagatatgt ttcctgtgct gcccctgtta cagctgtgat 5940
gtgtggaagg gccaggtgcc tcttcagtct ccggttgtgc ccttgatcag taaacttaat 6000
tttttctgct cttgagagtt aactgtggtg tatttctggc tgagggcatg cgcactgacc 6060
tgagcacagc ttgctgcagc tgcaccttcc tgatcccagg gcaggtgatg tgagggcagc 6120
caggtgatcc aggctgcatg ctgtcagccc gtgccacaga gaggggaaag ggcatttctt 6180
atcttgagga gcctgccaag tattgcataa ctctgtcaag cttatctcta gtgttgttta 6240
aactagatag caacctgact tgatgatcat ctgaagcttg tttgagatga ttgggttggg 6300
aatttccttg tgaaactgtc ctgaaattgg cagcgctaac aaaatgctct tgcacatgtg 6360
gaagggtttt ggactgtggt gtgcagtgac agagccttgg acttccggct gcagttgctt 6420
tagctctcaa aataaaatgc aaatacgtaa agggataata tcctctgaga agatccctta 6480
tccctagggg agatttgagc cagagttgta aaagtgtcca cccgtatgcc tgacagcaga 6540
gtccttgttt tggtcatgcc tgtaggactg acagaggggg atgaggtcga aaggctttgg 6600
ggcagtgtgg caccttcact tttaagctct gaggggaaga ggacagcagc cgtgtgcaac 6660
tgtcacttag ctgtgatgct ttctcagtgt tcagcccttc cacacatgtc agtcctccag 6720
ctgctgatgt tttatcatgc ttgagtagtg tttgggctat gtagcacaag cagtggagta 6780
gaagtgggct gaaagtttcc ctttcttttc cagtatcatg agggcacaat taagaacgtg 6840
cgagaggcca cagagagctt tgcctctgac ccgatcacct acagacctgt ggctattgca 6900
ctggacacca agggacctga aatccgaact ggactcatca agggagtaag ttgctctttt 6960
tatttacccc cacccccagt gcctgagact agatagtgtt gttcccatgg cctgcttttc 7020
ccaaacaagg attatcttat gagaacaaaa taactgtttg ctgtgtctgg catttgtagc 7080
aagagtctgc acagactgct gcaagctggg ggacagctgg gtgcttggtt ttttttctga 7140
aatccttgtt ttgacatgca gagtggcaca gcagaggtgg agctcaagaa gggcgcagct 7200
ctcaaagtga cgctggacaa tgccttcatg gagaactgcg atgagaatgt gctgtgggtg 7260
gactacaaga acctcatcaa agttatagat gtgggcagca aaatctatgt ggatgacggt 7320
ctcatttcct tgctggttaa ggagaaaggt gtgtagcaac cctcacagga tttgctagct 7380

-continued

```
ctgcctgttc attcttccct aagaatcttt gtgggttttt ttttcacctc cagaatggtt   7440
cattaagttc tgtattaaag aaattagcac tgagatctaa gacttactac tgctgtaaaa   7500
tgttgaaagt ttggagaaaa aaaaagttgc tcagtttggg gtaattagct tgagctgaca   7560
ttcactagtc atccaaaacc ccctcttaca ggtgaatatg tgggggacac gcttatgctt   7620
atttaactat gttaattcat acttccttct cagagttgag caaattttac aacattaaaa   7680
cccagtgttt tatggttaga agctgaacta gctttactgg taatgcaagg gaaagttaat   7740
tccccagtgt ttccttcatg gtggttcaaa aatctgctct agcctggagg tatctcctgt   7800
aaccccagag cgtgcaggtg aggtgctggg atattatggg atgctcatgt gcagaaatgc   7860
aacctgctag ttcttggagg gaggcagccc ccgtctcctg catgggggga aaagaggcat   7920
ctttcccaaa agcagcacag tgggtttgtg ctgtgctgcc atgggtacat tacaagctca   7980
catgttatgg gagtccaagg agagcagtgt tgtgcttctg ttgtgattgc tgtaaacact   8040
gtggttctca ggcagctttg gcaggagggg gtgtgggagc tggtggtggg gagctcgccc   8100
tgttatgctc tgactgtggg aatacatctg tttcaggcaa ggactttgtc atgactgagg   8160
ttgagaacgg tggcatgctt ggtagtaaga agggagtgaa cctcccaggt gctgcggtcg   8220
acctgcctgc agtctcagag aaggacattc aggacctgaa atttggcgtg gagcagaatg   8280
tggacatggt gttcgcttcc ttcatccgca aagctgctga tgtccatgct gtcaggaagg   8340
tgctagggga aaagggaaag cacatcaaga ttatcagcaa gattgagaat cacgagggtg   8400
tgcgcaggtg agctctgcac gagtggcact gcaagtcctt cactctgtag cagcagaagg   8460
acacagccct ttaatgctgt agatttctga ggagctacgt cactctttgt aatgagtgtg   8520
agttcagact tcagcgttct ggatgcggac tggtgagcta atgcatggaa tcaccaaatc   8580
tgtgacaaac tattagactg aaatgtctca gatgaactct tgctcctctt aatctgttta   8640
tatatagctt aagaaactgt cctatggctt gaccttgttt tcctacctcc tactgtggta   8700
ttacagggta ccaaaatggc acttggaagg tcagtgtgcc gatagggtgt ctgcgcatca   8760
ggctctagag tggtgcttcc tttcagaaaa gggggacag agcagagggt ccaccctaag   8820
aacaaaggga gtaatgaatc tctcctcttg ttgtcaggtt tgatgagatc atggaggcca   8880
gcgatggcat tatggtggcc cgtggtgacc tgggtattga gatccctgct gaaaaagtct   8940
tcctcgcaca gaagatgatg attgggcgct gcaacagggc tggcaaaccc atcatttgtg   9000
ccactcaggt gctcagaaca tgaagctagc ttgtataacg gctgggtgtt tgtgggtctg   9060
gcagggtgtg agtgtcagca gctgtccttg cacgctgagg agattctggg ggcaggtcct   9120
tgatggcact tgctattggg tgagaagcaa gagccaggag gtgttgcggt ggctgaacaa   9180
ctcatcttca ggcaattcag ggatttagga tcttcctctt taaggtttgg ctgctgaagg   9240
ctctaccctt tgaaaccttg tactatgcga gccttttgag ctgtgaccaa acacattttg   9300
gggaaaaata acttgcactt tgcatctcag agcagcacat ctgtgcctaa caaaatgatt   9360
gctctgagtt gctgtgtccc aggtcttttg aaagttgcac ccacgctgct gcattagaag   9420
gaactgaaaa aacaatataa tcttaccttg ggagctgcaa gtgaggggag gaagctgatg   9480
ctctgcagct ttagtacaga tcacaaacag gcagtcctta ggcactggca gggctgactt   9540
tctagaagta cttgctctgg gcacaggctg tgggaatgtg tgcttctggt agggtagtgc   9600
agactgactc caggcagtca ttagttgaga ttctggatgt accagccaca tgttcccaac   9660
cagaacagca cgttagtagc aacctcagaa agggacggga acatgcactg caatgcatct   9720
ccaagttgag ttccttggac caagccctgg tgttgggaat ttgaatcaga aagtgagaat   9780
```

```
acagtatctg tggtgctgtg atttaaatcc cttcagaaaa ggagtaagtg tagagtgggg   9840
agaaaatgtt ggcttttctt gctttaattc agaggttgtt agggagcagg cccctcttgg   9900
ccctgtaact acaggagaat gctaccagag gtcaggttat atcctgactt ctaccttatg   9960
tgtgtattga ggggccttag tggaaaatca gccacttctt cctgctgtat cctgactctt  10020
ggacttgttt atctgcagat gttggaaagc atgatcaaga aacctcgccc gacccgcgct  10080
gagggcagtg atgttgccaa tgcagttctg gatggagcag actgcatcat gctgtctggg  10140
gagaccgcca agggagacta cccactggag gctgtgcgca tgcagcacgc tgtgagtagc  10200
catcctggtg caagtggcag tgctctgcct tccatctgag tccacacata aagatgtaaa  10260
tacctggtgc taggtggcag cacctagtag cataaagcag cagttcttta gttcaagctc  10320
tcagcatgag gtttacttca cctagtgtgg aaccttggac tgaatgctgt gtgctactgt  10380
caggtggagc tgagagctgc tttgcagtgc tcagagacct aaaacctcaa ttataccaca  10440
ttcattttga tttaaggcca cggtaaaggc tttttggctg ctaccttggt atgaatttct  10500
ttgagtgcct tgtgcatttt agtgttttaa atgctttaaa cttgcccaag gtcaggacgc  10560
tgcttgttaa gcagtgtatc tctagataaa aagtgttagc tgactcctct gggttagggg  10620
ggggaggggg tgttgggggt tgggagaggg tgaggagaag gcttgaggtg ttgcatccag  10680
cagctgatgc atttggtggt gggaatgttt gttgcacgaa tgctgacagc accatgtttt  10740
tacatgcctg aactgccaga aagctctgct ctgcttcatg ttaacccagc ttgtgtttca  10800
gttcatcaaa aatcctgatg caaggcatct agaagtactg gatttcccca cttgctaggg  10860
ctgtgaatca cgttagtttc acctgcagct caggtgatac atctgaaggc actgagctag  10920
cgtttctgtt tgcagtgcat tatctaaaca tcttttacct ggtcagtatg gagtgctgtt  10980
ttctcatgtg gcaaataaag catgacctta actactgggc agtgactgct ggcttacaag  11040
ctgaattcta actgtggact caaaatgttc ttccttagtc tttcagtcct acattgaggg  11100
ctgaatcttc ctaccaaggt ttggaaactt agtgccatga atattgcaat tttggcctga  11160
aagcttagtt aagtacagca caacctgtct gagtttgtgg ctctgtaccc cccctgcatc  11220
tgcaaggaac ttttcctgca gggctgggga taatggtgtt ccttctttca ggccccccaga  11280
gatgaactgt aagtttttac ctgctgtgca gaggagcaaa tccagattta tcttgtttaa  11340
tgtacatagg cacaggcagc aaggtcatca gcagcactga aaatgagcag ggcctgcacc  11400
tttgcaccac tgaaactctc ccagggtttt gctgggttgc tgcgtggttt cacaaagcaa  11460
tcactttcca gtgagctttg cagcaatgag ctttctgttt cctgactggc atctctgcag  11520
caaaagaaag tgcttggagt tcggcagcaa gtttccaaat gttgggcagg ctgattccta  11580
cttcttggag tgggcttcct tccacttcca gctgacgatc tgcagttgtc aaatgctgac  11640
atggcccttc tgtctaacag gactatgatg tgcatagctc ttccacttcc tttcctctcc  11700
cttccaccct ccagtctctt acctgcatgc caactacaaa cacttaaact atttccatgc  11760
aagtgaatcc agctgtgatg tgcagcgagt aattgctatg ccctcctgaa gtcattgtca  11820
gagcaggcac ttgggcacac acactgtgac tctttacagt ggggaagtag ccttccccact  11880
aaactcatgt tcactctgca tgtagtgcag agctacctgc ctctggcctg agcgctgaag  11940
gtgtgctgcc tgcctgctgg tgcctgcaga gtttttaggt agagaagtat actccatatt  12000
ccatttgacc taacagtaag tgtgaagcca gcagaaacaa aactgtgtgc tttaggacca  12060
gtgtgttggc tctggactcg tgttcctgtc tgtcacgtgt cctgttatat ttagacataa  12120
```

gacacttaac tactttggct taaactgata tcagtggaag agggataatt ccagcatcac 12180
aaaaaataat ctattagcac cagagtagca aaatttctat tggaagaggg atccaagtac 12240
agaaattcca tgacaatggc actgcagtct ttgctttaac atcagcttgt tgtgcagtgt 12300
gtggcggctg ttcaactttg ggagtaaggg gatgaagtgt ccttgagaag atcggccttt 12360
gcatgctttt ctagtctctg caagccttct ttatcaggtt gtcaaggacg agtgcagccc 12420
tttgagatgg gaattgtctt ttaatgtgag tgattctcat gctactggga tgaataaatc 12480
atgaagcttg ttgcacatgc taaggctgtg accaggaggc ctttaattgt gcacctctgg 12540
cctgtttgag cctggcataa attcttcact gtacgtggtg agacagccct gtaaggaagg 12600
cttgcttctg cttctttcct ctgttactga aagagaagtt ggtactgcac ttggaggtga 12660
aacttctttg gctcttagtt gaactagatg aaacctggaa gggagcacat ctccctttcc 12720
agggaagaac taccaagaag tgaaataagc agccacaaga aagtgcagtc tgaggggcta 12780
tgctgtaagc cctgaaaagc gagctgtgtt tggttgatct gagaagagtc caaaatacag 12840
caagagtgct gccattaaaa cacctgccgg ctggatggtg cggggcggcc agtgcagctg 12900
tgctgtgaca tgcagcattg cacctgggag ccaaagagtg ttttgcaccc tgaccttgag 12960
tatcctcttg catgcattac tatgacaatt aagcaaatta acgtgatctc atgttactct 13020
ggtctacctt tccttctttt ctttcctctt ttcttctctg cccttcttcc tcgggcctgc 13080
agattgctcg tgaggctgag gccgcaatgt tccatcgtca gcagtttgaa gaaatcttac 13140
gccacagtgt acaccacagg gagcctgctg atgccatggc agcaggcgcg gtggaggcct 13200
cctttaagtg cttagcagca gctctgatag ttatgaccga gtctggcagg tagggctcag 13260
agaagggaga ggcttaggct gcgtacggta accgatgctc gctcccagca tgcgggttag 13320
atatgtgctg cttgccagtc actgcgtgaa tgagaccacg cttaacattg caggcattca 13380
gcaagcagcg tgcagctctg gtatctgcag ggcagggccg caggtgggta ggagcagagc 13440
aagagtgcct ggcagttggg catgaatggc aattgagtgt gggctcagca gggtgaggtg 13500
ccgccaactg ggggaagaaa aacttggagg atcaaattgc ttgttcatta aggtggtgct 13560
gaagccaatt ttggctcatt ggcaactctt ctgaaagcct gaagctggca gcagctgtgt 13620
gacacctctg tgacagagca cctcaccctg ccctgtgctg agtgactgac acgagtgttg 13680
tcttcccgaa tgcgtgtcgc tcttctagat tgcccgtgag gcggaggccg ccatctttca 13740
caggcagctg tttgaggagc tgcgtcgcct gacctccctg aactgtgatc ccaccgaggc 13800
cgctgctgtt ggcgctgtgg aagcgtcctt caagtgctgc agcggggcca ttattgtcct 13860
caccaagtct ggaaggtagg aggccgcagg ctccctcggg tcacgctggc tccgtgaccg 13920
agttggggga aggagaccca cacagagtgc cttgaaataa agctgtagca gcggagcccg 13980
ggttctggca gcgacgattc cttgggaggt gacagacatg tcaaacatct gcgcatacgc 14040
agcaccgggt tcccgagcct gccagcgtgg catcggcacc aggccctgcc tcttcctgtt 14100
ctgcacagca cctctgccag cagcgctggc tggaagagtt ggaggggaaa agtaaactgc 14160
tgcaacttcc aacttcttag caagaagtcc tcaagttagc agtagagtta aaagttcagc 14220
agatgcagaa tcttttcctt tcaatcaagg ctttgtcctc ttgaaggagc tgtagtttgg 14280
ctgctaccct gctgaaccta ttgggtgcca gcccagctcc cctaagcaca agaggggtga 14340
agagaaaatg cttaactaga actgtcaggc agggggagtg aatgcgttgc aagttcttac 14400
gggcttcctg aggccttccc gtgagtagtc ctgcagaaga agcaggcatc cagcttctgc 14460
actgccagct gagcccagca ctgtggtttc aggtgaggtg gtgatgcaga ctgagactat 14520
gtagggaggg atttctgacc agccgtgctg gtaatgctgc tcttcctgtt gagtgggagc 14580
gaagcacagg gctgcagcct ggctgtgagc agcttttcca tctagagaag ccatgctcaa 14640
agcgtgttgg accataagtc tcaagctact ttctggaaga gaagctgagt atcttacctg 14700
gagctggcaa cagaattagt gctgcaacgg aaacacgacc gtgtgcgtgc tgggcatggc 14760
ctacctcaag agcccttgag tgaaccctta acctaaactt acagcttaga atgatttgaa 14820
gcagccactt tgtgcagaga tgaggaacga ctacatgagc actgagttgt ggataccctt 14880
ctaaagtttc tttgtgaaag gttccagtct tacacttgac ctttttggaa agatttgaac 14940
tctggtattt gaatattttt agctgtggat tctgttacag ccttggagta cctgtgtctg 15000
ttagagctgc tgggaggttt ggggaggatt gtctgagagc tggcacgtgt gactgggggc 15060
ttctgaacca ggttcttgct gagcttggct ccagaaagca aggtttgcaa aagttggcga 15120
ggctgctggc atgcgtgtca gaacgacgga gctgtaaatg gcatggctgt gcagcttcta 15180
ttcatttatt tatttttgct tctacaagca gagcccaagg gaggggaggc tgtagttgcc 15240
acccagcgca tgctgcctgc tgtatggagg cactggtgtc tctggtcact gcatgtgggt 15300
ggcagcctcc ttcagagcaa cccggtactc cctgctctaa gaccaaatga aggcacttgc 15360
ttcagtgttg ctttcagcag tgcttctgct tctggggagg tgggaggatg agcacgtggg 15420
attaaatgtt ggctgctcct ctgggactta aacccattgg tgagctgtgg tcagacccat 15480
ttttgggggt gactgccttt ccctgacatg gattctgccc tctggaagca tcctcctcac 15540
agtgctgctg acacaggctt gttccacctc acaaagtggg ggttgacaag aatggtggaa 15600
acttgcaggg accctgctga gattccaagg agagcttgca gaggacagaa taaatggcag 15660
ctagccacct tcacatagca acagagacaa ataaatgctt gtgtttgggg ccaaagcatg 15720
ccaatggcac tcaggggtgt gacagtctcc cccacaagac tggttagagt ctgttgcctt 15780
ctgctcttgc tcagccccat tgctaaatag agaaatgagc gttgagctct gctggtggga 15840
ctcggctctt gcaaaatact gtgccagcat cccctggtcc caacctggca cacttccaga 15900
agtggcagag ctctccggga tgacgggctg agcctcgtgc tgcaggcagg ggtgcccctc 15960
tggttgtgcc tgcgctgcag tgccgtgcct caccctgtgc ctgttgtcct tcttgcaggt 16020
ctgcacacct ggtgtcccgg taccgcccgc gggctcccat catcgccgtc acccgcaatg 16080
accaaacagc acgccaggca cacctgtacc gcggcgtctt ccccgtgctg tgcaagcagc 16140
cggcccacga tgcctgggca gaggatgtgg atctccgtgt gaacctgggc atgaatgtcg 16200
gtgagtgctg cgctcctgcc ttgctctggg ggctgcggtg gggccgcagc aggacctgca 16260
gcacggtgtt ggcgctgctg ttgggatgcg ggggaccgag gttgcataag cgcaccgcat 16320
ctaaggggga aatgggacgg tggttttgtc acagcagcct tgaaatagct gcctgcagaa 16380
aaccaggttt gctttaataa gcgagagaag gggggtgtga ggagacctga gtgctgacgc 16440
tttttcctcc ttttccccag gcaaagcccg tggattcttc aagaccgggg acctggtgat 16500
cgtgctgacg ggctggcgcc ccggctccgg ctacaccaac accatgcggg tggtgcccgt 16560
gccatgagct gccggcgccc ccgcctcttc cacccccgcg ccccttcccc atgcattagg 16620
ccagcagtcg cttgcgatgt tctcctcgtc cctagcgtgg atttaggttg ctcaacacca 16680
ccgagtgcag cagcggggga agagacctta aatcactcag aatacttgaa gtgtgtagtt 16740
gtttccagac ctctctccct gtagttagcc atgtcagagc ggggccctgt gctccccacg 16800
tcccccctagc ttagcactgc cctcagggtg tggctgtgcc tctccttgcc ccggctgtgg 16860
ggtgatgggg aaggagtggg cgcttatggt aacggttctg ctgctgcaca ccgcagctcc 16920
cccaggttgg tgccctctgt ccatgagggg ttataggttg tcccctctgg gcttacactc 16980
caaaggtgtg ctccacggtt cctacaagaa tcccaaacca gggtgctgct cgttgtcccc 17040
ctgggtgcag gtggagtcct gcgggttgtt ggggtgcagg atgggtgggg gacgcacgct 17100
tcatctccat gcagccacct gcccttctat ggtgtctgtc tgtgttgtcg cctttcctga 17160
gagcgttcct tttgtctggg cgccctgttt gctccggtgg gtgtattggg ttgtggagca 17220
ccactgtgca cgtcaataaa gagctgagca cccctgc 17257

<210> SEQ ID NO 53
<211> LENGTH: 60974
<212> TYPE: DNA
<213> ORGANISM: Sus scrofa

<400> SEQUENCE: 53
cagagtggct cagcgcggcc gtgacggaac gacgaggcgt gcgggtgcgc gacctctccc 60
gcccggcccc ggcccccgcc ccttggcctg ccgctccgcc cccgcggggc gtcccgggcc 120
gctcgtcccc tcagcggcgg ccgcgcgcgg cccggggtcg ccgtgagtac tcgcgaggcc 180
agcttgtggg gcggccgcca cggggacggg gcggggcggc cgagccgcgg gaagggtgcg 240
gggccagggt ggaggaagtg aagggtttgg acccggtggc tctgagaggc cttctgagtt 300
taacaggctt cgcttatggc cgggcggctg gcgacacaga tcgggctcag agcttcttcc 360
ccgggaggca ggtgttgggt gtcttcgggg tctccggggg aaaccggaga agagctctaa 420
gtgcttcccc aagggaggcc tcagtgaggg cctgttctgg aagcacgagt ggcggccaat 480
gttgggggct caccccggcc tcttcttccg ccgggtacac gagatagcgc tgggaagcgg 540
gcatcgccgg gcggtgggtt ctcccccgca ctctttgttc catggcctag gctttttgaa 600
aggagcactt cgctgcagag cggagtcacc ttctttccca ggaccgccaa gccgggatca 660
aacgttgaga tcggaggctt ctttgactag atgcaaagtt gtcacgcgga gaagcgcttt 720
tggacctagg ccaggacatt tgtgatccgg acttgatgct tatttacttt tggcctattc 780
ttatgcaaat tttttgttag ctgctctcta gcgctgacac ccttctctgg gcattcttca 840
tacagtcagt atttgacttg gcttttcttg aaagggttcc cttgattacc tcgtttagat 900
aaatcaaata ggtctttctt actagttcat taacagctcc cttaattggg ttgtaatctc 960
atcactggaa gagtggatgt cattagaatc tgacaaatgt gctatagtcc ccagttccac 1020
tgtacgctat tatacttctg accctaagca agttgcttga cgtccctgca cctgcatact 1080
ctatctgtag tgtgaaaagt ttaaaatagg ttatatacag cctagtttga aaaagatggt 1140
agtctctaaa ttgtttcttc actggacagg aaaaattctc tctgaactac tttttctcc 1200 ttgtggtaac agcagaaacc aagcagcaac agcccttgga gagagactaa gctttcttga 1260
cctctacagt ggcacagtgg caaagagctt gagaaagttg gcacttctgg gctacaccat 1320
tgtcatccag gacattaatg cctccctctt tgttcctctg agaccgtcca gatcagcacc 1380
tgtttatttt caaatctcac aaaccccacc ccagatcttc atagtttggt tctcagctgc 1440
tcttgaaggt gaatggagtc ttgcttttta aaatcatttt tgtatggttt tgtctatgtg 1500
tagatgtgtt taggttcttg tatttatctc ccctttggct taggtcacag ttcattcatt 1560
cattcactca ttcaattagc tatgttatga gggactgaca gtacagacag tgaaaatgct 1620
caaagcctct gccaccgtag agcttacatt ctgatgggag gtaaatacaa taaacaaaca 1680
ttttgtcata gagtggtaag tgctgtagga aaaaataaag caaggaaagg gtttggagag 1740

```
tgctagtgtg ttgtgtattg tgattttact gttttatgta ggatagtcaa ggtgatcttc   1800
aagcagagat ctgaaagagt aaaggagcaa gcccagtgaa tatgggtgaa aagcattcca   1860
agaagagtgg caagcaggca caaagaccct gtggtgggaa tatgcttgat atgttggaag   1920
aacagcaagt tagagagttt cagtgatact cttcatttca catttagagt tgataggaga   1980
ctccttaaaa agtatgaaag tagcctctgg gtttgtttgt ttttcttttt agaatgaaaa   2040
tttccaacta tatacaaaag tagagagttt acaaaccctt gtgtacttat cactcagctt   2100
cgtttgtaat caacatttta tgattttcat ctgaacattt catctgttcc ccattttatt   2160
tgtgctggaa tagtatttta aagcaaatct tggcgttccc atcgtggtgc agtggaaacg   2220
aatccgacta ggaaccatga ggttgtgggt tctatccctg cccttgctca gtgggttaag   2280
gatctggtgt tgccgtgagc tgtggtgtag ttcgaagaca tggctcggat ctggcgtggc   2340
tgtggctgtg gtgtaggcca gtggttacag ctccaattgg acccctagcc tgggaacctc   2400
aatatgctgc aggtgtggcc ttaaaaagac aataaaaaag gaaatattta aattaagatt   2460
tgaatattta aagatatcaa gcatttcatc tctaagaact tcagctgcag tttccttgtg   2520
cattttgttt gtaatgggtc aggcagcact gttggctgaa ggactgctat gttgtttgcc   2580
ctggcattgt gctttaggtc cccattctgg gtcagttacc aggtttaaat tggtatccga   2640
ggaacagacc acaagccctt ggaacacaca aggatttaga acagtggtct cagattttat   2700
cattcatcag aataacttgg agggcttgtt aaaacatccc atctctgaag tttctagttc   2760
agtaggtttc agtatgaggt ctgagaattt actctttttt tttttttttt ttgcctttta   2820
ggaacacacc tggagcccat ggaagctccc tggctagggg tcgaattgga gctccagctt   2880
ctggcctatg ccactgccac agcaacatgg gatcccagcc atgtctgcaa cctacactgc   2940
ggctcatggc aacaccagat ccttaattta ctgagcgtgg ccaggaattg aacccacatc   3000
ctcatggata ctagttgggt ttgtttctgc tgagccacaa aaggaactcc atgaatttac   3060
atttttaaca agttcccagg tgatattgat tctgcagatc cacagaacca aggatctagt   3120
aacctaagat tcaatagaac catgttacag accaagaaca tctctcttta aggttgggat   3180
ggatgaaact gagataaatg tagagccaag aaggccaagg acagtggttt ttagttttgt   3240
gaaagggcta ggagttagtg tttttctgag catttctttg gatcattatt acattaattg   3300
gggagtgggt tccaagatga gtccatggct ttattttgac tatgacaact cagactatga   3360
gtaccagaga atggtcagtg ttgttgagga ctttttaact tggctctgat tgttatatga   3420
tgtctttgag ggatgctagt gttaaataag agattatgac taaatcacca ggggtaaaga   3480
ctccaaaaga gtctgcttct gatgggcgtt ggtactatga agaatattct aaaatgaact   3540
gactagactg agtagcataa gcgtctggtt ctgccaccat cacttgtggc gtcagaggtt   3600
tgatgcagca ttgtgaacta gagcaaggac gtgattcaat cccagccttc cagcttaatt   3660
ggaacagtag tatcttatgt ttgtatagtg ctttcatatt tcattatctt taaagaactg   3720
tgcgtacatg cattcaagta tgtcttctta tgtgcaggtg cctacatgtg tataataaaa   3780
atatatgcta acgtgtacct gtgtatatgc cccctagctg ttaagtgagg atgaaatcag   3840
ttgttttcta ctttccatag gacagcgagt gacttattac caccaccaca acagagcctg   3900
ccttctccag cagatctcca gtcagctccc gacatcatcc ccaccccctt ctcccttgtg   3960
gcctcctaaa tgcccatctc gttagcctgg gttcatccgg tggtatggag gggtgctgcc   4020
tagcactgac ctggaagtgt gtgtgaccct ctgacccaat ggtgagaact gattgcccac   4080
```

-continued

```
ttcttcaact gatcactggg ggcagatgga acagactgca gaccaccttt tcctagtatt   4140
ttccttccca ccctttggga aagtagagtg gctatttgaa gttagagaga aggggcatgg   4200
gaacagtctt acttggtgtc tacagaggga gttttcttgg gaaggaaggg gagagttaaa   4260
tacttaaggg ataaaaaaag ggaattatga gacgaaagag tttaggtagg ctggggagct   4320
gccttaggta atgaccctag aagtggccag tatgtacttg aacctagata tcctagaaat   4380
taactctgac atcaaagtgc tcctcaccct cagtcatcat accagtattt aaagaaggcc   4440
aaaattccct gttgttttct tccatgccac caagtcagtg atgggccatg gatgtgacca   4500
gatttaggaa gagactgaga cccttccaaa agataaggtg aagggaacaa ggggattagg   4560
gcttcagtta ttctgttcca agagacctcc cgttctttgt ggaaatctgt ttcccatctt   4620
aatttgactg tgttccctgg aataacacgg acccagcaaa gcattgtacc cttatttctt   4680
attaggacat caaaggccag ttctggaatg atgatgattc ggagggagat aatgaatcag   4740
aggaatttct ctatggagtt caggtgaggt cctagccccc aaaacccatg ttgcatgatc   4800
taaatgtgtg tttctctctt gatacattgg aagtgaaaaa gattgttttg gagcagagat   4860
aagatgaaga cctaatgttg gtgtggtctg aggattgtca tgttagagct aatttcatat   4920
ctttgctctt gcctgggact catacttttc ccagggtaaa ctgcatcctc tgtatgtgga   4980
gcttactcat atgtttagtt ggaaataatt attttctgac tatttcctcg ctagccagtg   5040
ggagtaattt tattcattag catcagaatt ttaacagatt attctgccag tgattggtta   5100
atgctgtcac tgtccagtgc atgatcctga acaggaatgt tggacttttta aagtcagaac   5160
caatctgatt taaattctgt actcttcagc atgttctgag ttctcataga aaagatacct   5220
aagtatcctg gtcaaggtct gagagaagag ttgagactta tggatgtgag ctccttaagc   5280
aaagccctca gttggtctac tgaaaattct tagagtggtg atggagatcc ccatcacctg   5340
tctctcagat ccccagcaag agccaccacc aagagcacct tcatataagc agctcttgct   5400
tatatgtatt gctgtagttt gattttcctg ttcctgatgt ttcttcatgt tctattttca   5460
tctatttcct tctccctgta tctttcctct ctccactgtt tttgctgctg actcagggga   5520
gctgtgcagc tgacctctat cgacacccac agcttgatgc agacattgaa gccgtgaagg   5580
agatctacag tgagaactct gtattcatca ggtgggactt gactttctgg gatggcaagg   5640
gaatcaacca catctttcca agttgttaaa atgactagag gttttcttct ttatggtgtg   5700
atgagttggg tgcggtctgt ggatattgat gagctacgag cttaatgata gtgggagtgg   5760
ctcagaatat ttaaggttgg ctgacaggaa taaataggga agtgcagcca cttttcctag   5820
aagttccctc ttatcctaga ctcctctagg ctgtttcccc tttaagataa gaagggcttc   5880
tggcctggag aagaccttga tcataaaagt gggatgaggc tatagctaag agcctaaata   5940
cagagttgcc ttccaccctt ccctttccct tgtccccagg ctcagttctc tctccacttc   6000
agtctctgtt cccttctttc tcccttaatg agtctcacct atggtcacct gtatctctat   6060
agagaatatg gaactatcga tgacgtggac attgacctcc acatcaacat cagcttcctc   6120
gatgtaagtg gtgctagtag ctgccaacaa catgtctgtt gggcttgtgg attggagttt   6180
gacttgtagg cttagaatct tgtttctgag tactgtattc agagcacatc ctcttcatcc   6240
ttgtctttcc ttgaccatca gcagacagtg gtgtgtgcat gtgtgtcata tagggaaaat   6300
gtcaagtcca ttcctctctg ttgccacact ggaaactgtt tcccttactc ttttaggagg   6360
aagtttctac agcctggaag gtcctccgga cagaacctat tgtgttgagg ctgcgatttt   6420
ctctctccca gtacctcgat ggaccaggta aaggcagtga cttcaggcaa gtgggtgctt   6480
```

tgaatgtggt ctagtccaaa atcttaagtt aactgaggta gagaacatcc cttaaaggcc 6540 cttttttatta atgaaattgt tttctctagt ccctggatat tatttattcc ttctttcccc 6600
tcaacttctc taaggaaata tttgaaattg gtcagttagt tcccagattc taccttctgc 6660
ctcgatgttt tccttctcca tcattggtgt ttagagcatc cttagaatct gaggaagcta 6720
atccactgaa ctggagctgt ggactcccaa gaggatagac acgcatatgt aggagctttc 6780
tcttctcttt gcagaaccat cgattgaagt tttccagcca tcgaataagg aaggatttgg 6840
gttgggtctt cagttgaaga agtaagaact tttttttttt tttttttttt tttaatcttg 6900
ttttaggggt gcacccacag catatggaga ttcccagtct aagggtcaaa ttggagctgt 6960
agccgccagc ctctgccaca ggcacagcaa cctgggatcc gagcacatct gtgacctata 7020
ccacagcaca cggtaacact ggatccttaa ggcactgatc aaggccaggg attgaacctg 7080
tatcttcatg gatactagtt ggttttgtta actgctaagc catgatggga actccaggaa 7140
aagtaggaac tttgatcttt ctggttatga actttttttt tgcttttcag ggccacactt 7200
tcgacatatg gaagtttcca ggctaggggt tgaattggag ctacaggtat tggcctatgc 7260
tacagccaca gcagcatggg atctgagctc tgtctgtaac ctgcaccaca gctcatggca 7320
atgccagatc cttaacccca ctgagcaagg ccagggattg aacaggtgtc ttatagatac 7380
tggttgagtt tgtttctgct gagccacaac agaaacccct tggttatgaa catttgaggg 7440
gaagagatgt ggatatgtgg atggacagac agaaatctca aatagattat ttctttccaa 7500
aaatgtattt ctgagatatg cccaagaaag agtaaaatta atttgggcca aatttctggt 7560
tgtgtgggga agcttatgtt tttggggtat ctgcccttca gacttcttgg aggtgagaag 7620
ataggcttga ggaaaagcac aaccctggaa tttgagtcat gctgatcaca tttcctgtgt 7680
ggtttactca gagtagggct ctaggagctc agagagtttt agctattgaa tgtgtggggc 7740
accttactaa gtatttggta tacaaagaga agtgaattat agattctccc ctcagtcacg 7800
ttccaaatag agtccagtgg atacatgttc taatacaagt gaatatgtaa ggtttagaaa 7860
ggacacagag gaagttataa ctcagtctgg tggcaggtga atgaatgaaa gatgaaagga 7920
ggtaattaat ggttttcaag aatgggtaag agttgcccat gaagacagtt tctgagggta 7980
acatttgcaa gggcacagtc atgtgtagga agcttaaagt agttatatat tgctggtaaa 8040
atgcaaaggg agtaggatct aaagctaaag aagtactaat gagtccaaat cagagaggat 8100
cttgaaattt tattttgtag gcagtgggaa gattgaaggg ttttaggcaa gaaaaggact 8160
tgatcagttt tagttttaaa aaaatcattt tggtagcatt gtgcaaagat agaaaggatg 8220
agacaagaga ccaaaactat ttttgtaggc gacatttgtt ggagtccatc catgagatga 8280
tgtaaacctg agctaggtat gactctaggt aagaagaaag gctagagaga ttatttgcag 8340
ggtataaaat tcataagact tgatgactga gttgggtata ttatacatga caagagccaa 8400
ggagtagtgg aatattactc atgcgtttcc agcctggatg tatattgtaa taccagtaat 8460
ctaaataggg gcttaagaag agtaagttca taggatgaag attaataatt agttccattt 8520
taaacatgta gtttaaaggt aactttgggt tattcaagtg gagaagctca gtagagagat 8580
atatagattt gatacttaaa ggagaggttc aggttgaaga ttcgtattag ttataagggt 8640
cagaattgca gctatcatag aatatggtgc tcagagattg ctaagggaga gcatgataga 8700
atgagaagaa aatagaatca agggcaaaac accctttaac atccagacag aatgccaaaa 8760
gtaggtagag ggagagaaac actcaaggta ggacagagaa gttggaaaag aacgggaaga 8820

-continued gaatagtgtc attgaaggca aggaggagtg tttctacaag gagggccaaa atttctgttt 8880
gatttaacat caaagtgaga gcaattgtag cgcagtggtg aaggtagaaa ccagactgta 8940
ctaagtaaaa attcgtcatt ggcaataaaa gagaaacagt aagtatgggt tgagaaattt 9000
ggttgcagat aggagaggaa aagagaggta gctaggctga ggtgccaaaa gttgaaactt 9060
tttatagact tgggtaaagg aactgacagg aaagggggat ggttgacaga tcaaggtccc 9120
tatagagggt ctgagatcta gggtacaaat agagcaattt gtccttaata ggagggtcac 9180
cttgtcttcg gagaatggag ggatcaaggt aagggtagaa atggattttg tggtagggtt 9240
gcaaaatttt cagttttctt tactgagaag aaaggtcatt agttgtaggg ttgtaggtga 9300
agttaggagc ttaaaggaga tgataggatt tagaataaca gtgtagaatg atatgagaga 9360
gaactgatca aagagaagtg aaaggattga caagaccagc tgagggccca gctcaagttg 9420
gaaaccataa atttagggat gtaatttttt gcccaacaaa gtcagtaccc ctcgtgtccc 9480
ttgtcttttt cttcactgtt cacaaggcag tgggtggtac tcactatccc accacttttg 9540
ttccactctc agtatagtta ttcttggcaa taaattgcca ggttcacagc cctggaagac 9600
acacctctaa aggcagagga tctgagaatt tctctggtcc attagatgag gcctgctagc 9660
tagtgggtat atacccactg aggtaaagag gtactttagg acagtacatt tccatgtgct 9720
aaggttttaa caggggggtt ctttagatcc acattccctt gtaacaacta gcttagtggt 9780
ccctgggtct gaattttaga ttagttgcct tttgtgatcc tggtccccca acccccagat 9840
cgggaaacat gtaagatgaa gacaggattt cattaccatc ttactgcaat tttcttttct 9900
ttctttcttt ttttttttt tttttttgt ctttttgcct tttctagggc tgctccagca 9960
gcatatggag gttcccaggt taggggtcga atcggagcca tagccctagg cctatgccag 10020
agccacagca acgggggatc tgagctgcat ctgcaaccta caccacagct cactgcgatg 10080
ctgaatcctt agcccactga gcaaggccag ggatcgaacc tgtaaccttg tggttcctag 10140
tcagatttgt taaccactga gccacgacgg gaactcctta ctgcaatttt cttatgtgtt 10200
actagcctac atacctcatg ttttctgtaa tcacgcagat atgaatagaa gtttgaatga 10260
ttaaataaat gaaaagttca tttactgcag agaatcattt cacaaggcat cacagtccta 10320
tgtcttgatc acttccctgc ctgggcttcc ttaagcctgt tcctctttga ttccttagga 10380
tcctgggtat gtttacatcc caacaatgga aacatctcag caatgatttc ctcaagaccc 10440
agcaggaaaa gaggcatagc tggttcaagg caagtggtac catcaagaag ttccgagctg 10500
gcctcagcat cttctcaccc atccccaagt aagtgttcct ccataagctg attatctctt 10560
atcaccttaa tctcctctaa gcccctacct caccttgatt atgtaaactt acatattctt 10620
tcctctcctc aggtcctctg aattctgtgt ctttaattat taacaccatc cacatggtcc 10680
tgtcccctat gtgtctttac ccttttactc ctggcccagt agtcatacct tgtcctttat 10740
gtaaaaccca gtacctagct catggtatgt atttggagaa atgtatgcta atctctccac 10800
ctatcctgtc tttgaccctc atccttattc cctatgctaa ggaggcagag tcagagcacc 10860
aaatccttgc ttttctggaa ggatacactg ttttattatc taggttctag aaataaattc 10920
tgctccattc tttgacccca ggtctacatt ttcccctccc tggtgccttc tgatcttttc 10980
agaggcaaaa acaaacccag attgtagttt tccttacaca attattgtca gtcaaacatt 11040
aggctctttg gggtccagct gcctcttgcc tagtttaatc acatatatac aaatgcatgc 11100
gtgtgtgcac acacacacac agtaggtgaa ctaggcatcc tctccttacc tggcctagat 11160
gccgtagaga ttgacctagg ctttgcctct gcctgcaact tcatgttcta atcttaagaa 11220

```
cacacagata atgacataag atgtctggtg atctccttgt tttgacaatt tgatccaatg  11280
aaactttcct cagatatgag ttgctctttg acttagcttg tttggtactt tcttatctcc  11340
aggcctcttc cagactcata ctgaatcccc agtttcatca cttctcttta ctttctcttc  11400
aggtctccca gcttccctat catacaggac tccatgctga aaggcaaact gggtgtacca  11460
gagcttcggg ttggacgcct catgaaccgt tccatctcct gcaccatgaa gaaccccaaa  11520
gtggaggtgt ttggctaccc tcccagcccc caggcaggtc tcctctgccc ccagcacgca  11580
ggcctccctc ccccagcacg gacctctcct ttggtacatg ggctgagtta gggtttgact  11640
tgggtatcag aggatgggag gggaaatgtg ggaatatgat ttctcaagat gaggtgggga  11700
tctggttgtc aggtatcaaa aaccatgaca tgaatcatga gggagtagaa tgaagcacat  11760
ttagtggttg tgaactcata tttaaacagt ctggcaagct tctctgatgg taggcaaaga  11820
gtctggggtt gggcagctca gggaaatgtc atgtgtaata ttattaggtt gtggttagga  11880
cttggtagtc agctgctata gagacctatt ccacgtactt tggagagggt taaggacagg  11940
tgagcctttt tcaagagcct ttggccaaaa tgtctgaagg tcttctctcc agcttgggga  12000
ctacttagac tgatcagagc tagggcatag ctactttagg agaattttag gtaatgggta  12060
tgagtgaggt ctttctaggc accagcttca taggaggctc atgggatttg tctttttaat  12120
ctcatcaggt cagtggtcac tgcaagaaca tccccactct ggaatatgga ttccttgttc  12180
aggtaatcaa gtctaaagct tcatgcataa gcctttcccg ttttctgacc catctaattc  12240
cccaatacct cccagctttt cagtcagtta gcacacattt cctgaattgc tctatttcta  12300
gaactaagta actgttgttc agataggaaa aaagaaggca cagttcccat cttcaagaag  12360
cttgtagcat tactgggaag acaacactca cagactactt acaatctaac gtcaaatgag  12420
gcactgcaaa ttttaagtgc acaggtgcca agatgagagt taaaaatgaa gctaattttc  12480
ttagattccc acacatcctt gctcatgtga tctttacatt tcctcacaaa ctttccctgc  12540
ttgaccacca ctggtcgctt gcttcttttt aaaacctttt tactttctgg acacagtttc  12600
acttttgcat ctgcaattcc tttgttcatg tcattccctc cagtggcctt cttccctgtg  12660
tctgcctgtt gcaatcaaag tctctgatgc cacctttttct ataaaatctt cccttttacc  12720
tgaaatatat tagctggaaa tatgtctcct ctcactgaac tcacataaca ctttttgttt  12780
tatatggcac tgatgtgtca tgtgccacat gctgccttgg attgtagtta atttgtgtac  12840
ataccacatc tctcctgttg gactatagtg tctgagaaaa cttttgttac tgagtaatca  12900
aggagacctt tcaccaagtt aggtacatag taggcattca gtaaatccac attaaaggaa  12960
tgagtaaaag cccttgtatg tccatttact ataccaaaag tttgtgaaat ggaaacagtt  13020
tgatttatac acaaagtata tacgtggttg gaatagccat gttaagacag tgtgtaaaaa  13080
aatacgttag aatattgctg catgagctct ggatttgtgc tgtctgccca gcatagggtt  13140
ttatctatga tattgatcag tttacaggca gattgttctt ggtagtaaaa atggctcttc  13200
tggccccctg acatctaatc atggactgaa tactcgtttg ccacacagac acagtcttta  13260
atgactacag ttaaggttaa tagtttgatt agtacctgta aatgtttatg aagtatttca  13320
agattcatct cattactctt gatacctctt tgaagtgaat aatgtgcact ttgtaaatga  13380
ggaaaccaag gctcaggtta actaaattgc ccaaagttat atatgatatt aagtagcgga  13440
ggaggggagt tcccattgtg gctcagagga aatgaatctg actagtatcc atgaggatgc  13500
aggttcaatc cctggccttg ctcaagtagg ttaaggatcc agtgttgctg tgagctgtgg  13560
```

tgtaggtcgc agatgctgct cgaatctggc attgctgtgg ctgtggtgta ggccagcggc 13620
tacacctccg attctacctc tagcctggga acctccatat gccacgagta tggccctaaa 13680
aagaaaatag atcgatagat tgatagataa agatcagtca aaaaatccca tactaaagaa 13740
aaaatagtag aggagggatc ttaaccaaag tcatctacca tgtctggtct tgtttttact 13800
ataacattca gtcttagctc tagagtcagg ccatcagttt aactaagtgt agaacctaag 13860
aatagattct accttactta catgtctggg aggtaggaga gtaacagaaa gaagtttaaa 13920
ttatttcctg tatttgggtc tgtacttctg aaagacttaa tagaatctct tctccctcca 13980
gatcatgaaa tatgcagagc agaggattcc aacattgaat gagtactgtg tagtgtgtga 14040
tgagcagcat gtctttcaga atgggtcaat gctcaaggta aatgcctcaa atgtgaccct 14100
cttccttaga cccatggcta agaccgcttc agacctcatc tctattttcc tttcttcctg 14160
ggtctgtggt aaaggtagaa ttctgtctct actccttgag actttagaaa tctcatcaat 14220
gctacttgga aagataagga ttatcattct agagttgtct gaggtcaaga ttgtccctca 14280
ctccttacct tcttattgca cacctcttac caccaccatc tcttaatatt tccattcagc 14340
cagctgtttg tactcgcgaa ctgtgtgttt tctccttcta cacattggga gtcatgtctg 14400
gagctgcaga ggaggtggcc actggagcag aggtatgggg gagagaaaag ctgctgggga 14460
cccaggatca agaaagacca atgaacctag cagtttcacc gcttggaatt taatgtccag 14520
aaatgctttc ctatgtcagg atattgactg taggattgtt tataacagct tttttaaaaa 14580
tggatacagg cccatctgaa tgaagtccat ttaagttatg gtattttctt acactggaaa 14640
tactatacag ctgttattta tggatagaaa attacatata aaagaaaata caaccgtatg 14700
tatagcacag ttctttttg ttgtatttcc tatataataa ctatttctct aggaaaacta 14760
tctggaagag tatatatcaa acttagctgt agttacctgt gaggaatgga atttggggat 14820
gaggggatgg tttctatctt tttaaaatca ctcttttaaa tattattctt attaggagtt 14880
tatattttct aatgagaaaa tgatacacat atttgctttt gaaaaaaatg ctgagagcct 14940
ccataaggta gacctatgct ggctactgtg tgactcccag cactgggaaa tcatttcgct 15000
tctcatctct ttctctcctt ttccctaagg tggtggatct gctggtggcc atgtgtaggg 15060
cagctctgga gtcccctaga aagagcatca tctttgagcc ttatccttct gtggtggacc 15120
ccactgatcc caagactctg gcctttaacc ctaaggtata gttgcttggg aagaaagtca 15180
ggacaaagga acagaaatgc taaagataat gggagactat gggctatcat tctagtgtac 15240
acaacaggtt ggaataaggg gaactcttaa accctaaact ttggttgttt tagtgaataa 15300
ataagtaaac ataacttgca atataacaga aacaataacg tctgagtttg tcagaagaaa 15360
gggagaagag ttaatattag ttttgtcgtt ataggaaaga atatagactt tgattcaaga 15420
cacactatga ttccgtttag gttccgttgc atcctagctt aatggtgtta ggcaaatcac 15480
tgaatatgtc tgaacctcag tttccttata atgcctatta taaaaataag agataacata 15540
aaatactata ttagtaaggg ttctctagac aaacagaacc agtagttaat atatggagat 15600
atttattgta agaaattggc ttatgtgatt atgaagactg agaataccaa gatctgtggt 15660
gggcaagctg gagattcaga agagctgacg gtatagggtc caacccaaaa gccagcaggt 15720
tcaacatcta agaagagctc atttttctgt ttcagtttga aagcagggaa aaaaaaaacc 15780
aatgtctcag ctctaggcag tcaggcaaga ggagttcctt cttactcagc tgttgtgttc 15840
tattcaggcc ttcagctgat ttagatgagg cccatctgaa gagggagggg tatccgcttt 15900
cctcagtcta ccctcaaacg tttatcccat ctagaaatgc cttaacagac acacccagaa 15960

-continued

```
taatgtttga gcaaatgttt gggcagtcca tggcccagtc aaattagcac aattaacagt  16020
tgacaaaatt aaccatcatg tgttcccagc agagtgcttc actattactc attgctgtgt  16080
atcaggcact ataccaggtt ctttacatat gttaatcttc agaacatctc tatgagaata  16140
gtgggatttt gtgttttcac ttacacagag atactgaggt cctaagaggc atataactta  16200
ccctattatg ctcatttggt aaaagagaac atacatacta ttctagaact tcctgacact  16260
aaatatatgt tctttccatg aaatatgctg tttcccaagg gcctagtctt cttttgtaca  16320
tgtcaccctc ctttacatca catctcactc tcttcctctt ttcttcacct ggttcttctc  16380
ttcccattga ttccttgcag aagaagaatt atgagcgact tcaaaaagct ctggatagtg  16440
tgatgtccat ccgggagatg acccaggtat tctgcccttt gcctgtcccc tgtgttatgc  16500
ctgccggctc atgtgcccta ttctgcttgg aattcatggg agtggaatga agatttagaa  16560
atgttactca aatctctcac tgtattttct ttagtcttcc ctttttagcc ttcccagtct  16620
ttgttctctg ttttgttagc tctgttacac ctctttctct ctcctatgtc tctcttaacc  16680
tttaccttta ttgctgattt attcgcaagt tgttcatatt taatgttttt cccataattc  16740
ttagggcatc agagaggtga gggaaagccc tttgcccagg gttgggaggg tgaggagggg  16800
ggcttggagg taaggaacta gatccagggg cctacatctt ctatccttct aggggtgggg  16860
cagccacatg gagcagtgat catcctttga ctcaaggctg tccctcacca gacttcccca  16920
cccctcgtct gcaatctctg catgaataga cattcatttg tactcacatt gacaggtggg  16980
cctcttctca gcaaatccta tatatcacaa ttcagattaa cacataagat acacctagga  17040
gggataattt acttgtcgga agaattcttt gctttatgtc aagttttacc acaggattcc  17100
ttagcctaat ctttctgcga cattgatttt gtttattttt ttgatttata gtaaactttt  17160
tagggctgta ggaattgcat aaaatgaggg agacccacct gcatgttgtt ttgtaagcat  17220
cttcagtcat tttcatattt atttatttat tagtctttgc aacctgactg gggtccttga  17280
gggtgggaac cccatctcct cttgccttgg tgtggccttc agtgcctacc ttgccctggg  17340
ctgatagtct ttggaaaatg ggagggctcc cacctctcct gggagataac cttatggctg  17400
ttgtcttaca gggctcatat ctggaaatca agaagcagat ggacaagctg gatcccctgg  17460
cccatcctct cctgcagtgg tacgagtaga atggttcatc cctcagcggg tgggggagta  17520
gggcatagta ccagatgtgg agccttctct tcttggcatc tttctcttag aggtggtttc  17580
agcatccttc ccaaggttat atattttatg gctgcttttt cttggggctt tattgataca  17640
cctggacttg acaagaactc agatcctgac aaagagccca caggttctga catgatgcct  17700
caagttttct gtgggtgttt cctgtttcct agtaggcttt tgagtgctgc ttacatgtag  17760
gaattaatgc tgttgaattc aattcttttt ttatgcatgc agagagatct gtctccctat  17820
ttctactccc tttccctatt tcaagccctt ccctgttgtt gactggttga ctggccagag  17880
ccttttgaag cactatcatt acccccgctt ccttgcaagg ttctggccct tctctacttt  17940
cctctacccc cctgctctct ccctgatttt gattccgttc tctattcctg acagagcttt  18000
ccccttctag actactctct gtctggttag cctttgacat tagtactttc tcagtgcaac  18060
atgctctttc ttagcatgag gaatggccag gcatagacca tccaggatgg catcacaggt  18120
actggcatga agcaccaaaa accaaaccat atccatagga gataatgctc ccttgctgag  18180
ccattaatgg tttactcctt tgttctctcc tgtcatctga gttcagccta catacagctg  18240
agtctgtccc tgaatcctca ggaaatttgg gctaatttct tctgtttctt tttccagccc  18300
```

```
aaagagtaac ttttcatctt ccccatctcg gaggcttcag gcttcctctc aggataaccc  18360
tgagccctag ttctaaattt ctaaatccca agtgtcagtt gtcacatcgt aatacagacc  18420
ccacctttct agtttctttt tttttggtag cttacctctt gttcatttct ttttttgttt  18480
ttactttta cgactgtacc tatggcatat ggaagttcct gagccaggga tcaaatctga  18540
gctgcagctg gggactgtgc cataactata gcaacaccag atccgagctg catatgcaac  18600
atatgccaca gcttgtgaca atgctggacc tgtaacccac aaagtgatgc cagggatcaa  18660
acttatatcc tcattcagac aatgtttggt ccttaaccca ttgagccaca gtggaaactc  18720
tttgttcact tcctttcatt gtattcttta gtctccctag atataggcag cccatttccc  18780
acctctctct ttcttttatc catttttaa actaccttgt aactagctag tctctggtca  18840
gtaacttcac ttttttaag tttttataca caaacactac ccgtaggaat atccgtatag  18900
tgacctggac ttaattcaca cagccctgga atctttgctt gttctcgcag aggcagagca  18960
agctgctact ttgttcagag tggcctaacc acacacttat tctatccttt ttgtttttac  19020
tctgttttgt cttaggatca tctctagcaa caggtcacac attgtcaaac tacctctcag  19080
cagggtaagt gactgttctc ccgctaaact ctttaaattt ctggtgagag gcagggaggg  19140
gctccaaacc agctaaccac attagtccta gacctgcctg gttgtcttgt ccatcagtaa  19200
tagtctatgc gcctaagtat atatccttta tttggggtca gtacaagcct gatttgctcc  19260
ctttccccag cccttccctc cctgatctcg atttctgttc tgttttcctg accaccccc  19320
caccctgggc agcagctgaa gttcatgcac acctcacacc agttcctcct gctgagcagc  19380
cctcctgcta aggaggctcg gttccggacc gccaagaagc tctatggcag cacctttgcc  19440
ttccagtgag gagtggggg gggctgggca tgggtgctgg atgaggcaaa aataatatag  19500
ggggatggga gggtaggttc tcttgaggaa tacgagttta tgttacacta tgtccatcaa  19560
ccagtcagtg aacaaatact tattaaatgc tattgtgata ggtgttgtag agaatagaga  19620
tacataagat aaagtcatta ctctcaagct acttacagtg ttgttgagga gaaatgatat  19680
ttacatataa aaagatgtgg ttgaaagaac agattggcag gggtagattt gaaagctact  19740
ttggaggaaa tcactttatg cctaattgta ggaggagaga gaggggaaa aaaagagaga  19800
ttaaagataa tttcaagggg agtcagtggt acccttcctt aggatagatg tgaagtcatg  19860
actggaagcc atatttggaa tcagtgataa gcttgttgaa ttcaagatga ttttgtttaa  19920
tttgaaatag caggataata gacaaatgaa aatattgaac cagcagttga ggatttagga  19980
tgggactagc caaagcacag aaaagagggt gggactgaat attagccaca cacacacaca  20040
tcttgcatgc ctgtgatgac acccatgtgc atgtccattg ctaggtgtat ctgtgtccat  20100
cttcatgtcc tgcgtgggtg agaatgggtg ggagtggcag tcttggaagt gtttttgaga  20160
acctcatacc atgaggagac atatattcta ccctgccttg cagtgggtcc cacattgaga  20220
actggcattc gatcctgcgc aatgggctgg tcaatgcatc ctacaccaaa ctgcaggtga  20280
ggctgtgccc cttttccctt tccactccct gccccctgcc ccactcagtt ttggggaagt  20340
ctgccctaga gtacccagct gtttttgct tcagcatcct caaacctagc ctcccgtgag  20400
gcttccctag ggaggaagtt gcagccacgt agaatgaatg tgactgttgt atatttgacc  20460
ttaagctgtg ctttttggtg ttgtaggaat gggaatgtag ctctaggcag gaatcagctg  20520
taggctgatt gcagccactg tgatcaatta acctgttaga acttttctat ttatttaact  20580
gttcattcag agagttgata taggagacat atttctttgc tctgcaagac tctaaagaat  20640
ggttattgtc cctcatcctg gctgctgtcc tatattcctt tttgggggt ggtaatctgc  20700
```

```
atatgtccca aggcctaggg acaggagcat ggattctgag ggaatggatt caacggctct  20760
ataactcctc tccaaggcat cagtatctag tgtttcatag gcaaagggtt aacctgcatc  20820
cacttttcag ccaagcagct tttcaagagt aggtgcctaa gattatctga atgagtgaga  20880
agataaaatg gggggacaga gggctggata agccttgtgg ctgcctaata tacagccatg  20940
ggagggccca ggctcatatt gctcatcctg gtgtttccct gcaagctgca tggagcagcc  21000
tatggcaaag gcatctacct gagccccatc tccagtattt cctttggata ctcaggtaag  21060
aaataatctc tggccacgtt gactctattt acattgcatc cattttgtga atacataatc  21120
ctatgctgtc tcctccatca tggatacttg gtctatgtca gttctctccc cagtcatgga  21180
tacataatct tctctacttt ctctccttag aaatttagat tctttgcaaa gtgaggccat  21240
gtctcccttt ctcttagata gtcctcttct tcatggggat ggttttattc actggagagg  21300
cttggctctg agaatgggtt atggaataac tggtagatga aactaggctc ttttggagaa  21360
cacatttttg gtagtagcct gtcattacag gttgtgtgtg tgtacacatg cgtatcggtt  21420
tatatatgaa agcttgagtc ccttccattg gcttatatct ctggagacat tgttcttctc  21480
cctgtcaacc accttttaca atttaaactg tctgtaatta cacactattg tattagtcac  21540
tttaaatata agagaaagca ttttatttca aagataggca tgaacaagtt tcatagttta  21600
gttaggagat gagttaagct ttgtccagtt cagaaaatgt atctgactta gagctctgtc  21660
tttgttccag gtttatgtct gagttccttt tcagtcttct tttgttctta ttctgtatcg  21720
tctgtgtata aaagatagcc accacgtagc tgcatgtcta ccgtatgaag gggacagtgc  21780
tagatccttt atagattact atttagtatt ctccagtaat tataactgtt acaaagataa  21840
ggaaacttgg gtccagaaac gcaaaaccag aaaattccct aataatagga taaaccaaac  21900
agtagaagaa aggagataat acaggtaaga gccaaaatca gtgaaataaa aacaggtatc  21960
aataggagtt cccactgtgg cagagtggga ttgacagtgt ctctgtggtg ccaggatgca  22020
ggtttgatcc tctgcctggc acagtgggtt gaaggatccg gcattactgt agctctggcg  22080
taggtcacag ctgcagttca gatctgatcc ctggcccagg aactccacat gcctcggggt  22140
ggtgaaaaaa gaaaagccag atatattaga taggtccaaa aaagccaaaa gatgattctt  22200
ttaaagaact aaccagacag ataaacctgg ttagactgat taagaagaaa aagcacaatt  22260
aataaaaagt acgattaaat aatgaagaaa ggaacataac tatcgatgta gcagaatttt  22320
aaaagttaat ggtggaaatc catcagcttt atgccagtga tttgaaacct ttgtcaaaat  22380
ggatgaatcc ctagaaaaat ataacaacaa aactgattca agaagaaata gtctgaatag  22440
ctctaaaatt ataaaagaca ttgaaatagt agtttaaaat tttctacaac aaaacagaaa  22500
aagttaccaa cccctgataa ttttacctag tgagtcttaa gtcaaacttt caaagaacat  22560
attatcccaa tcttaaacaa aatcatccag agaatagaaa gaaatggaat tgcaaatcat  22620
aataaattga taaatttaac tttattaaca ctaaaatctt catcagaaga caccttaaga  22680
aagtaaaaag ttaagttaca gagcaggaga aaacatttgc aacacatata accgcaaaag  22740
attagtagta aaaatgtgtt aaaaaaaaat tctttcagga gttcccattg tggctcaacg  22800
aaaatgaatg tgactagtat ccacgaggat gcaggttcga ttcctggcct ctcagtgggt  22860
taaggatctg gcattgccat gagctgtggt gtaggtcgca gacacatttg gcgtggctgt  22920
ggctgtggct atggctatgg cttaggccaa tggttacagc tgcgatgaga cccctagcct  22980
ggggacctct atatgccatg ggttaggccc taaaaagacc ccccccccca aaaaaaaaat  23040
```

```
cacaaataat aaaaagacaa ctcagttaaa aaataggcaa acaacatgaa cagacatttc  23100
actgaagatg tgaccaagga aacatgagca gctgctcagc ttctattaat caagtaagta  23160
aaacaaaacc aaaatgactt accatttagc atgtaagtgg attggcaaaa tttgagaatc  23220
tgatgccttt gattgtagca gaggtgtaga tcagcatgat ctcttttatt gcatatggga  23280
atataaattg gtacaaccac tttggaaata atttggtggt aaatttcata aaagtgagaa  23340
aattttaccc ctgcaatcca gcattttcat ttctgcatat gtccacccaa aggtgtatac  23400
atgtatgttc agagtaatac tgtttgcgac agcaaatctt agaaacaatg caaattctca  23460
tcatcaggag aatggataga gtttccgtta tggctcagtg gtgacgaacc taactagtat  23520
ctatgaggat actggttcag tccttggtct cgctcagtgg attaaggatc cagtgtttcc  23580
atgaactatg gtgtaggttg cagatgcagt ttggatctgg cattgctatg gatgtggtag  23640
ctacagctcc gatttgaccc ctagcctggg aacttcaata tgctgcaggt acggccctaa  23700
aaagtcaaaa agagagagag aatgggtaga tacattttaa tatattcttg catcgggctg  23760
tcattcagca gtgaaaatga gccaacaatg gcattcaaca acttgggaga aattagctta  23820
ggcctgtagg tattcattgt gctattaaat aaaagtgtgt aatgaaccaa aggtcatgag  23880
tgatccatga agggtaagtg ctcagtgaat atttattgaa tgtgtgaatg agtcttactc  23940
catgtgctta gggtccaaag tgtgggtggg gttggaatag tcttttggct ttgtctaggt  24000
tcttagtttt tatctttgtc cctgcctgag cttccctcta attaagctct tgttctaagt  24060
agtgaggttc ctctgcctcc cgctacccac agagtttctt tttgtctatt ttctccctat  24120
tctctctctc tcttctctcc cattggcctt tatttattac tgagtgcctg aatgacttta  24180
gttatcattt gaagccagaa atctctattg actttttaat tttcttcttt atttactgct  24240
tatgtaaaat atcatatggc accattcttc atcctctcca aaggtcaatt tgattatata  24300
tacaaaatga catatgcttt tgctgttgga gttacaggtc atcttgttca atctcttatt  24360
actttacaga taagaaagca gatacacaga aaaaaatgac tttgtcgggg tcatacggct  24420
tgaagtagca gagctagaac ccagatccag ttctcttaac ctctaggcca gttacaggac  24480
tgacagggta ggctttgctt gaatgactga gtttccgagg gccccataga tatgtgagag  24540
tctctaccac tgggtgggat gtttggtaat gtccagactt attttagtca ctctagcatt  24600
tggccagctc tgtctttgtt gtatgtttcc ttctgctcct ttctgctctg attttcttta  24660
ttcttcctca gggtatctgt aggttagtgt caccgggtac cctctggaca tcattataaa  24720
tagagagcat ccatttaact agcggaaact gatgacttgg ccgtagttgc aggttaaaat  24780
gaggcacagt gggagatggt aaactttgtc tgtttattta gtcatgtgta gaaacttctc  24840
acaagtatat actctggaca ccaagtcttt agggactgtc tttgcctcca ggttctcagt  24900
gtgcattgga aaactcacag aagatgattg ggtcactgcg gacaggacag tgtgcaacag  24960
gattgaaatg ggacaagatt tagattatat cataaggacc atctctaaga ctagtcgtag  25020
aaatcagagt gttctctggg gtagaaccta agtgggaatt tcacttagga ccgtgcactg  25080
aaatactcaa atctaaaaat gtcgtaacgt ttggacacag agctaaacct agtcaagact  25140
aatggagaag ttggaaacag gggtggtagg tatcctgtag gaggaaattg gaaattcaag  25200
tcttgaggct ctcattgccc tgaattttgt cagggacttc agtatgagtg catgatgaat  25260
tgacagcctg agcagtgaag aatgtcagtc cagtggttat catttctacc tctataccat  25320
gactatcaca aaaccaagac ttgcagcaga agttagttgg agttagaacg ttccagggtg  25380
ggctgatcag ataagggccc ctgcttatga cctgcaatga tggcatcatt ttccatcctc  25440
```

```
acttatcttc ctttcagtgt catggtctca tatgcacata cacagactca tcccaactgt  25500
cataaggctg tgcctgtgat gaagctgaat acagagactg aagtcctaat cataggccag  25560
aaagagttgg cactctttca tatctaaaca ggaagaattg gaatgagtct atagttataa  25620
acagggctat tcagtgaggg gtaaggaggg tggaggattt atggatctag atagggcgaa  25680
aatgagtgaa ttggcacctc tcccttaagt ctgggaagac tttctgcagg aagcaggact  25740
cttcaaggta gttactgtta tggttacctg tggaaaattt ttcatctctt aatgttgtgc  25800
tttatccctt taccctgaat gactcttgtc agagcttttt atgtaacttt gaaactagag  25860
tagttctgat ttgctctgct tgcttcctct ccactcattt cactcagcct ggcatttgac  25920
atgaggcatt gatgtcacca ttctcctggg ccgctcattc ctggctcatt tcacgtgtta  25980
cttcctatct tagaatcctt cagtgatgcc ctgatgttct taggataaag tccagttgcc  26040
ttaacatggc ctacaaggtc tgcttgattt tatcctagcc tacctcttcc acatcatctt  26100
tcaccacttc tctaccattg actatacccc atacaaacta aggcacaagg ctttgctttt  26160
cctccaggcc attcatgtca tattacctct gcttagaaca cttccctacc ttcatttaac  26220
taattaagtc ttcctaatcc tatacttctc agcctagctg tcaccaggaa gccttcttca  26280
aacccctagg ctaggctggt tcccctcctc tgactccaca cagtgttctg tatccttccc  26340
atcataacct ttagcatgct gtgttgtaat tatttgttcc tttcctgtaa tctctataaa  26400
actaaagtct gtgagggcag atacattgtt ttcttcgctg ttgtattacc atgtatctct  26460
agcttagtgc ctgacacata gtaggcactt cagtaaatat ttgattaagg aatgggtgac  26520
tgaactggtt tgttgttctg tgacaggaat gggaaaagga cagcacagga tgccctccaa  26580
ggatgagctg gtccagagat ataacagaat gaataccatc ccccaggtat tattcgttag  26640
ttgcccttgg tccactgagg cagaaccctt cctctgggat aagtttaggc tacaggggtg  26700
gatgggggaaa cagtggtagt ggtgggatgg gtggtttaaa gatcattttg aaggaatcag  26760
atatgtttta agatgaacac atttccagag tcatttgtgg cctcagtcat aagtatgaag  26820
gcagagactg agtttaaatg cagtgacatg aaactgtaaa gatggaagcc tggactcatc  26880
tagactgatt atgggaaagc aaaaattttg ggggggtgac tgggagccca ggatatccca  26940
atacccatcc ccaaccatta cctactaacc agcctctcta gggaaagtgt aacagtctac  27000
ctggctctgc tttcctcttc cagacccgat ccattcagtc aaggttcctg cagagtcgga  27060
atctaaactg tatagcactt tgtgaaggta tgtagcttac ccagcccctg tttttctggg  27120
ccctctgtct ttatttctgg tgcccctttg gcacatggat ccaaccaagg ataatgatga  27180
tgccatttct tccctgccta aacattatat ctgtaacctc tggccctctt cttcccagtg  27240
attacatcca aggacctcca gaagcatggg aacatctggg tgtgccctgt ctctgaccat  27300
gtctgcacac ggttcttctt tgtgtaagtc taggaggtta ccttggggac tccttggagg  27360
agtgagggtg catgatggga ctgggagcat gacgacgtgt gactatgggg aaagtctctt  27420
tctgttatca gagacttgtc cctggctacc tgagtggtgc tagcactggg acttgcccct  27480
tggaggacag ggatgggtat agatcagggt ctgtttagag gaaaccagat aagctgaatc  27540
ttttccacac taaagagtaa caagaaaggg tttgacttac ggggtggtgt ggccacactt  27600
ctgaatgcag ttccattggt tgacattatt ctggtattgt tctccctctt gcgctcacac  27660
ttgccctatc tttggcagat atgaggatgg tcaggtgggc gatgccaaca ttaatactca  27720
ggaccccaag atacagaagg aaatcatgcg tgtgatcgga actcaggttt acacaaactg  27780
```

-continued

```
agggggcccc agccctcgta ccacccccat tcccccggga tccatccacc ctaacaaaaa  27840
gggctcagga gcagcagaca gggctgccct gaggacaagg ggccattatc aaggggcagg  27900
aaaagaataa aagcggcggc cttcatggtg gaaattgacc caggaactac tccacatttg  27960
gatggcccag attgactccc tactcctgat tgtcccagtt gacttcaccc tgtttgtaaa  28020
taaaacaata aaatggaagg tgctgtggac tggatatgat cactgtggtc tgactagcct  28080
tggcccagca cctgccccaa gccccaatgg aggtgggggt ggggagagtg gaacatcacg  28140
agggttggga ctgtttatgt tgtgggaatc agagctgaat ctgtctagta tagtatacta  28200
cagatctgtc aacattttaa ccaacaaatt agataaagga aacttatcag ttatgcagat  28260
gacataaact gaggatatag aataccactg atgactgttc ttcacgattt aaaaggacta  28320
atggaggcca aaacccctca gatttcctat ccttagaacc tctactttct gcataaaacc  28380
tctcccctct cctttgctgt atatatcagg agctgatccc tacttgcctc ctccttccag  28440
ctgtttcttt ttgataggga gatgagggga gagctggcag gtacaggaag tgggttggtc  28500
tctaattcaa aatctataaa gaaatcctaa ggaatcagct tcccttagtg aaatgaaatc  28560
caaattctcc aaggctagca atgggaggga agacagctgt tcctaggaga cctaattgtt  28620
tcagtgaaag ccatctccct gatgaaattc ccactgccag ccttctgctg gcctttaggc  28680
tatgctccat gtacctaaaa tcctaaatta gttacaagag accagttgga cattacaaaa  28740
tattttatga attattaatg aaaaatagga acataagcat agagacaaca aaaagcactg  28800
aacaagcctg gtttttaagt atagattttt aattctgtta taacatcttg atgttggact  28860
acctgtttct tttcattatc ttcaccctac ttcggaaata accttctttg cctgggtgcc  28920
ttacctgctt tgtagttatg actacaaggc ctgaacttaa catggaagta ccattcttaa  28980
ggtccatctc ctaggagctg tttcttaaac tgctttactc cttgaatgag actgctgcca  29040
ttctgactct acatgtctcc taaggctctc tcccccaatc tggtttcagg tctaggagaa  29100
tagctcttct ctaagtaaat gaccccatca ggtgacccac cctaactgaa aatcctgcct  29160
cctgggaaga cccttgcagc tcatctgtgt agtatcagag atagctacta acatttttta  29220
gttcttaggt agatcattaa gtttataaca ctttggcttt cttaccaagt gcttggtatt  29280
gttgtaagct ctctacttgt attgactaat acaattctca aaacaagcct gcgaagtaga  29340
tgtcattatt cacattttgc agatgagaaa acaggcacag aggatgagtg atttgctcag  29400
attccacggc tagtgactga tggggcaacc tgactccaga attgctattc tggttctatg  29460
ctatatatcc tttcaaactt cacaattttt gttttttca tttaatcctg acaacaaaga  29520
tggaagatag gtgtttttag agatcataag taatatgtgc aaggtctcac agttggttag  29580
tggccattgc tgggttttta accagatttg ctcaactcca ggacttgagc tcttaaccat  29640
tcttttactt ccccagcggt tctcaaactg ttggcactgg tgttccaaca gttgaaccta  29700
cgtgcttggc tactcaaatg gtataacatt tttgctcagt tttcagaaat tattaataga  29760
tttttctcag ttgtaaccat ttcttagttt ttctgtatca gtaacatctg acagagcaag  29820
tactagcaaa cggtggaatg agaagtaatg aacaggagtt cccgttgtgg ctcagtggtt  29880
aacgaatctg actaggaacc acgaggttgt gggttcgatc cctggccttg ctcagtgggt  29940
tggggatccg gtgttgccgt gagctgtggt gtgggttgca gacgtggctt ggatcccatg  30000
ttgctatggc tctggcgtag gccagtgact acagctccaa ttagacccct agcctgggaa  30060
cctccatgtg ctgcggaagt ggcccaagaa atggcaaaaa gataaaaaaa agaagtaatg  30120
aacagatagt gtatgtttcc agaaaaactc aaaatacctg agctgacctc atggaagtca  30180
```

```
cttttttaat aggatataca caagtctttt agtgccaata aaattataat gaaattaaat  30240
gtaccatttt atagtgttct gcataacagc aacaggagtt ttttaatctg aaaagttaga  30300
aagctgtaca tgaaaaaatt caggaattcc ctggtggctc agtgggttat agtctagcat  30360
tgtcactgct gtggcacaag ttcagtcctt agcctcagaa cttccacatg ccgcaggcat  30420
ggaaaaaaaa aattcaaaac atgtatggta taaaacaaat ctaattaaaa cccgcagcat  30480
tcctataaca agaatgcttg cattgcccag aaagttgcac agggccctga atttctggag  30540
aggagtcctc ccacagcctg gagtggaaat taaaggacca ttgccccttt ctcccaccca  30600
gggctggctg ccttagaggt gggaggtgaa acctgtgaaa gccaagtctg tgccagagat  30660
tgtccttcac caaagccaag attgttgcaa atcctacaca cagaggttca cctactcctg  30720
gttcaccctt tcagacctgg acaggctttg ttagtactag gtctgggaaa ataactattt  30780
tcttcaatta gttctagggg gagagtaaat agctatgatt tctggattga gaacttaaaa  30840
ctcctggagt ttaaacttcc ccatccctct tatggtaatt ttccatccag gcagggtgtg  30900
gccatgattc agtttgtggt gaggatgtgg ccatccagag aggaggagcc ttctgttaga  30960
ttctgccttt catcttggcc agtggggaga gggagggaag aggctggtgc tgagtcatga  31020
ctgggtaact taccaggttc tcacaagatg gattctgaga tggaggtttg ggtgctgtct  31080
cagtttctgg aatcaatttg ggagtggcag ggaggaagct tcaggggtca cacaattcct  31140
tcagagccct cttcccccag aaagggtggg aataaagtgg ttcatctgaa gtgacatcag  31200
tctctggagt ataggaattt tcccaagtgt ttcagagcca ccctgcagtg ggcccaaaga  31260
tgttaccttt aagttaaagc attgcctaca aaaattgttt tatgtagaaa agagatcaaa  31320
atttcctttg tcctagctct ccttcctggg acaagtagat caggctagct ggtagccagt  31380
gagcatggag tggagactag aaatatggtg ctaaggacaa tgtgactttg atggaactac  31440
agcaggagga catcctgggg aaggaggcat ttgatctctt gtttgctgat gcctttcttg  31500
gtcttccaga tcttaattac tttggggtaa caaggcctgc atacaattcc acttgcatct  31560
tagggagcct gagctctggc tgtacttgta gggaaaaagg agagagcacc gcagtgggaa  31620
aaggtagagg cttggtggat aggacaaacc caccctaagg aggctttgtc ctgtaagcac  31680
tagcagttct gggctataga aaaattgctg gaggtcttgt tggctggggt aggacttcac  31740
tggaatgaac aaggacttct caaaaatctt ctctccatct aagtgctgat gaggcatctc  31800
cttaggaggg ggacctagat acacagtttg atccagaaaa cttttttttt ttccactctt  31860
cctttcctct gaaagggtct ttccatacat acattcatgt ctccttccct tttcctcaca  31920
acctcttccc tcactaccct taactccaaa aggccaactt tctctttctt ccaggatttg  31980
tctggaatta agatttttct gccaccccttc cacctacccc tggtgggcct gaagagatct  32040
tgggaatctg aaggaaagca aagaagaaat taaaaaggct acttgttctg gctctggaaa  32100
gggcatataa agtccaaagt gaggagttcc tgtcatggct cagtggaaat gaacctgact  32160
agtatccatg aggatgcaga ttcaatctct ggcctcactc agtgggttaa ggatccggtg  32220
ttgccgtgag ctgtggtgta ggtcgcagac gtggatcgga tctggccttg ctgtggctgt  32280
ggtgtagacc agcgactaca gctccaatta gacccctagc ctgggaacct ccacaggcca  32340
tgggtgcggc tctgggaaaa aaaaaaaaaa attccaaagt gataagcatt tctaaacctg  32400
acattcaggc caatgggttg tcctgggaat ttatattggc ctgagaaaac taactgctgt  32460
ttcaggcaga agccaagagt taacataacg gtaaataaaa cttgtaatct tgccctcttt  32520
```

gtcagggcca aagtttttct gttggctcca gagttgggtc agatattgtt tgcttacaca 32580
cctaccttgc cagtgactcc aaatgaccat caagagttaa atcaggagtt cccgtcgtgg 32640
cgcagtggtt aacgaatccg actaggaacc atgaggttgc gggttcggtc cctgcccttg 32700
ctcagtgggt taccgatccg gcgttgccgt gagctgtggt gtaggttgca gacgcggctc 32760
ggatcccgcg ttgctgtggc tctggcgtag gccggtggct acagctccga ttcaacccct 32820
agcctgggaa cctccatatg ccgtgggagc ggcccaagaa atagcaacaa caacaacaac 32880
aaaaaagaca aaagacaaaa aaaaaaataa aataaaaaaa aaaaaaaaag acttaaatca 32940
ttaaggagtt cctgctgtgg cgcagcagaa acaaatccaa actagtaacc atgaggtggt 33000
gggtttgatc cctggcctca ctcagtgggt taaggatcca gcgttaacat gagctgtggt 33060
gtaggtcgca gacatggctt ggatcctgtg ttgttgtggc tgtggctgtg gcctgcagct 33120
gtagctctga ttcaacccct agcctgggaa cttccatatg ctgagggcac agccctaaaa 33180
ggggaaaaaa caaaacaaaa caaacaaaaa aatcattaag ctccagagtc tgatttcctg 33240
gttaagaatc caaacaggta acagcaatct ataccctcac tcacacctct gtccagtgaa 33300
cctagcagct ccccctccta tctgccaggt ctgtgagcat agtaggaggg ctggcttatg 33360
gaggaggagc ctagcttcta gttgagtctg tgtccttcct tagtttccct agtttcatgc 33420
agtcctaggg ttacctgttg ctgagtctaa ggaataaagg ttcaagagga tggatcagag 33480
aatggcagag ttacttgaat tgagaaagat gttctggtac aagtcacaag gaaaaacctc 33540
taggactagt caattctcaa agaggatgcc tgctgggcac tggtttttat actcattcac 33600
ataatcatct aaccaaaccc cacccaacaa gtatgacttt ccttcagttt acctttaatg 33660
aactggactc acgttcaatt acaagatacg gtcatagggc tagtgagtgg aattgtaact 33720
aaacaccaca gatcccaagc ttgcttctgt actctgctcc ttctcatcaa aataatgaca 33780
accaccttaa actctgtgac agattttcac catgcatcta atgtgagcaa aattatgatg 33840
gattggagga gtaggtcaca actaggaact aacccctagt ctgggaattc catatgccac 33900
agggtggcca ggggggaaaa aaaaatccaa aaaactggat tagggtctgc cagtttcatg 33960
gacagcattt taaaaaaata actgttggat gatcagtatc tgtaactgaa gggcaatagt 34020
ttgccatcag ctctctaact taatgcatat gcttttccat cctgggaata tacctagttt 34080
agatctttaa agtgcaacat agtctagcat tagccagatt tttgccactc cattgtggtc 34140
caccactgtt cttagttcat cattagctca ggggccacag ctggtcattt ataccattcc 34200
tttctctgga tagggaggga tctgattgtc cctggtggga catgtggctt ttttcccctc 34260
tcaacttcat gtgctctcac catctcaata accaagcatt tacttcctat ctgcaaacta 34320
aggggatggg aaaagattac agaagaaatt ataaagtatt ttatctcaaa tttaagttgt 34380
cactttctcc tcgaagctta tctgagctaa caggaaggca taatgaacgc ctgtgattca 34440
gctacagcgt gtctgcctga gcgagcaggt cacacccatt ggtctcattt tccaggaaga 34500
ggaaagaatc taagagaata gcattcacga tttttaacga ggcaacactg tatctgcttt 34560
taaaacttgg ctgaaagtag gcaagagtta taggtgtttc gttgataact gcagccatca 34620
cttgttgcct aattactggg aaatcagaaa atgctttaga gaaaaatgta aaaaacctcc 34680
aacaatattg atttaaatgc acaaaattga aaacagaagt gcttattcca gcagagatta 34740
cgggatctaa gtctaactgt atttcctgtt ggttgagttc tgcacgaaaa ctttgtattc 34800
actttctact gtctgctgga ctccagtccc caccaaagca tttgcctggc ccaacttgtc 34860
ctttgttcta gccctaagaa caaaagggcc tcgtgctcct gtgctcccgc tccacgcaaa 34920
ctccgccctc tctatttctc cctaccccag ttccagtgtc ggagcccttt cgaaggcggc 34980
ccattgtctc cgtcccttcc cacctctgat accctctcag gctcctcaac ctgcagctcg 35040
gcttggtctc cagggtgcgc gctggggcgg gcacccgggc ggagtggggg gcggggagtc 35100
gcaggacagg acttggggaa tgctgtccag ggacccataa atttgggtag accagggtag 35160
ctcagctggg gtggcctggg ccaaaggtca agcgaagagc gctggtccag gatcccaaat 35220
tggcggcaac aggtggcctt gggcgccggg aggtctggga gggaggtctt cggcactccg 35280
agggcgggtc ctgctcctcg ccgcttcccc attggtctct acggaatgtc aatgctcagt 35340
attttatgta atgtgtcctt ccgccacgga atgtagtcct ccccaaaagg gcaacctgcc 35400
tgcctgttct gcctcagcgg cacttcctgc agaaggtgac tgtgccccgc gaggacgcag 35460
aggggcgggg cactgcgaga ggggagccag gattgggtgt ggggcggggc ggcggaggga 35520
ttgcggcggc cctgcagtgg agataacctt gaggctgagg cagccgattc ccgcattgga 35580
gcgacgcgtc gtgagcctcc agaggtctct gcgagcatcg catcctaagc cggaccacgt 35640
cggaggtgag caggggggaga cactgggcca tctgtcccca ctagggctcc atctgcccgg 35700
ccagtgcgga atcttggcct gcctacgcac acagggcacc catatcggag acagcgcagg 35760
aacttgggca tcttggagtc acccggttgg ggtcggaaga gaggaaaaaa gctgcttgcg 35820
cctagggcct ctttttcaaa accctccagc tcctgctttt tcggaaagca gatgggttgg 35880
ccagctcctt tcctgccgca gtccttcatc ttcccccacc cccattctgg ttccaacctc 35940
tcctcctttt ccttcccttc tgtttctggt cccatcctca tcttcttccc cttattctca 36000
cctaatttgg tcctttcctt tcgaccctcc tcgtttctcc tttctctact ctgctcccat 36060
gttcgcctcc tccccttccc ccttaatact cgcatctcgt cttcaacctg actgtgcccc 36120
cttcattctg atgctttcct tgaaactcct ctagctccac tccctggtcc ctcctccgtt 36180
caggttcggt cccctccaca tgcctacccg cattcatgcc tggttcctgc ccctccccct 36240
cctctctggt cacgtcctct cctccgcatc cctctcctcc gcaccctcct tcgcgccacc 36300
cgcgtcctcg cccctcctct tctgttctag tcacgtccgc ctgctttccc gcccccgccc 36360
cttggcctca catctagttc tgtctcctcc atcgcggttc ctcactcagt cttgggcact 36420
cctgcagcca cggacctgcg tcccggggtc actgtgcgaa gtacagtggt ttgcgggata 36480
ggctcccgtg tgcggccacg ggatgcagaa gcggcgcccg gcaccgctaa agggttacat 36540
aacccttggc cttctccact gcacaggaag aaagggtggc tgccctgtgg cgtgttcctg 36600
ttttgtgcgg tccttaataa gatggggcga cagcagcgct gcactagctc caagagggtt 36660
acaagactcc atcccgccgc ggcggggttg cacgtagcgg cccaggaccc gccccgcccc 36720
gcgggatcac caactactga ccttccggcc cgttactggc caggcatcac ccctggcctg 36780
ataagactgt gcatgctgct cgggggcctc ttaacattgg aggcagtcac ctggctcctg 36840
gcctctgctt cacgttaaca gatactcccg attgtagaac atggaggcca cggggtgggg 36900
ccaggagcag gttatgggga gaggaggaat ttgtcaagag tttggtgccc agtactgcat 36960
ccactcagta tgtaaagtgt gcaaagggct gtttggggaa ggggtgtgga aaccaggatg 37020
gctagaatgg tcatagccca gggaagtcac aatctaatta ggggacacag tgctaaagtc 37080
tgtgaggaag gtacacactc cctgtggggt tgaggggggga gggcggccgg aggccttata 37140
aggtggtatc acattgggtt tgaagaagca ggaaagcacc ttccaatctg aaggttatgt 37200
aaagacccag taatggaaag gtatgccttg gcttcatatc tgtgttcttc aaacccagaa 37260

-continued

```
cattgattct accccccacc ccccagccct tgcacaagca gtgcctgata gttaaggtcc  37320
agacatgata gtggcattgg gaacttggaa ataggctttt agagtcagat ctaactcatt  37380
aacatactgc tatgggtaat ggagggaatt cagcctcagc accacagttt cccacatata  37440
aattgtagca ttttcctcct gatgaaagga ttgctttgta cacaactaca tggaaatatg  37500
ttgactactc agtgcagtat ctaatctctt gtgggatggc tctaaatgta tacttttctt  37560
ttcttttttt ttgcttttta tactcctgtg cccggggtaa atggaggttc ccaggctagg  37620
ggtcaaatca gagctgtagc tgctgaccta ggccacagcc acaccagacc cgagctgtgt  37680
ctgcgaccta caccatggct catggcaatg ctggatcctt aacccactga gtgaagctag  37740
gaatcgaacc tgcagcctca aggatactaa tcagattcgt ttccactgag ccacgatggg  37800
aactcctaaa tgtattcttt tggtcactga gtgcaattgc ttaatccata actgagcatg  37860
agggttcttc ttctccctgc catccccaaa ccctcagagt taatctttga gagtcaggct  37920
ctctaaatac cagacatctc ctggaaacca gtcccctcag ggatcctggt acagtgttta  37980
caaagtaact aataatgtta cattgcaact ccgcttgcaa cagcggctct ttggtctcct  38040
gaaaatgggg acctctggac aaagaaaggc aaggaggggg atgattttag cctttgatgt  38100
ttggctacaa gagtagaatc aaatttgcaa ctggggatgg taatctatct tcaccttcca  38160
ctcccaccta ctccaggtag ggttctagga cctgcttagc cagctggtga gtgtgagatt  38220
aggattggag gcaaaggaca gtagctcctt gttggctgtg caagggtgtg gccacttcct  38280
gaggcacaga ggacagttta ggtcaggact ctgcagcatt gttagcaaat aatttgccct  38340
caggctgcct gaggatgctg ctgggaatgc agtggggctg ttctgagggg aagagtgtaa  38400
cccatcacct ggtctgtggg ggagagggga aggctttggg gacaatggct caacctttga  38460
atatatctgc ttttaagaga actgtcttca ttgggtgagt ggggaaactg cactataggc  38520
ttccacaggc ttaaaaactc ccctctcccc tttcagtgag tcaaaaaatg aagcatgaat  38580
ttccctcagt taagtatctc gactaagtgg aaaaatgatt agtgcaggtc cccaggcgct  38640
ataccgccct aatgcttagg tgcagcacgg cagagcccca tgcccaggta atataatctg  38700
tgcacctgaa ttcctgagcc ttatgcagtg ggcatggtaa ccctttgggg aataaaagtt  38760
gtagtggata tgaataacaa tgactttaag aatgtccttt aactcacttc tgaattactg  38820
gacttgagcc aaaatatatg gacattagtc ttctttctag gacactgctc tcttgttaag  38880
cactgcatta aaagcagatg attttagtgt tgaattcaca gtttaaccaa gagcactatt  38940
gggtctttaa gaattgcacc ctcagtgatt tggcaagtga ctccaagcag aactagcacc  39000
ttttgggagg tgcttctttg ccctgagtat tgtgacataa tgcgggggtc acaggaaaag  39060
ccatttttatg tcttaaaact gtttatttct taatattgag gcagtgggag aaatgaggaa  39120
atggttggga gcaggaaggt agaaaagatg taactcttgc attacgaact tgcactgcag  39180
tggttttaac ttgcttcagc ttttatgaag gcaagctagg gtgtgttatt ttggctaaga  39240
gttgagactt aggtgaaggt agtgggaaat gactcatctg acattatctt tatttctgaa  39300
tcattcaaaa tatccacagt ccaatcccag ttaactggta caccacaaga atgagtcatc  39360
ccatgctaga agcaatagtt ttcttgtaac tttgttgagg atcttgtgag ataatataag  39420
tgatttattt cataaaagtt ctcataagac cttgagtcct cactttagca tcaattctgg  39480
tatgaagagg agcagagcta aatgaagact actaccatac tttctgggaa cttttttttt  39540
ctttctttct ttctttcttt tttcttttaa ccatgagcca gccttagacg ataaacaaat  39600
aggctgatta tctggggctt tgttagagaa actgctttgg gaaggtgatc cagagtgggt  39660
```

-continued

```
ggtgagtgca atgtgcagcc tctgtcagac tttttggcct cctggtatga ctgctcagct  39720
taggagggga ggttggcagg gccaccaagt ggttcagctc cgccccttgc agccattttt  39780
cctacattgg tttgtgccag tctgcacgta ggagggaggc caggctgcag tacttctggt  39840
ggcctctggg actcacctcc cccactctgt ccataggcag aactcctggg gagctgtaag  39900
cctctctttc ctgacgccag caagctgtat ttggaagtca gacaaggatt ctggtggggg  39960
agatgccaag agccgctatg atagagcatt gagcttgctg gtcatagcat ttcaaagtaa  40020
ggaccagctc agctgatcca gggggaaaaa aaattctctg aagggagccc cagcccttcc  40080
aaacacttaa tcaactggta gataatattt gtttaacttt agacaactgg tatctcctct  40140
gtcttgggtg atgagtttaa aataattagt ccgctgagtc aggcttagta taggagacaa  40200
agaaaattgc gcattttgga ggaatcatgg agttttgatc tagttaagag gcagaagagt  40260
aaaaacttgg taaacaaaac catcctggta atctagtatc cctcttctgt ttttacatta  40320
gagagcagat taacacatgg cacccatcag atgggcaaat gttttaaaag tctgacagtg  40380
tcaagtgttg gcaaaggtgt agggaggcaa gagctccctt tactggttga ttgtaagtgg  40440
atataaccac tttggagagc agttcggcaa tatttagtaa agtagaaagt aaacttaccc  40500
tgtgacccag gaattcattt ctggatgtat agaaactcac gtctggacta ggacacatgt  40560
actaggagag tattgattaa tgaggaaaat tttggtttaa tgggggaaat gaccaactag  40620
taagggaatg catagatgaa tggactagtc atacaatgga ctagtatagc agttcgtaca  40680
agttaactag atctgtatac caactggata gatcttaaat gtgctggaaa ggcaagttgt  40740
aggatggtac cttataatac actacttagg gtattttata taatataatg gagttcagta  40800
tagatacaga caccctcaaa tgaactggaa aaatacgaag ttcatgacag tggttggtta  40860
tcacagttta tgctggggtg tggaaggact ggagggacct ggggatggag gaaaatgaac  40920
ttatttttaa gagtctagag aaaatttggc taaatgttaa tggtcagttc tgggtggtag  40980
aaatacagat gttaatattt ctttagttca aagcaaaaca aaatagaagc aaacctacga  41040
cagtcactat agggaacacc aggcttacta actaggtcag tgctctcaga gctggcactg  41100
ctctttcttc cttccatccc cccttctccc aacagctgtg atgccgagca gttcctcctt  41160
taaatgctga gccagtgcct cccttttgct gaggccctca ggcatcctgg tgttgtacct  41220
gacttggaag ggctctaaat cagggttgca gatccccttgc tgcttccaga gtgtaaatat  41280
cttgccctca gacaccgcct tataatttta agcctcataa ggggcacaac acagcaaaaa  41340
tttcatctaa acttcctcct ttagactgaa accagttctc tgctcttagt gtctgtgatc  41400
aaaccaggaa atctttgata cctgaggaca gcaagatttc tgtgacttgg gacttcctgc  41460
cctggagttg agtggtcctg ttgggggtgg gcccatttag tatcagcttt tatgacttat  41520
tcaacctcag atttgaaata gggccttggg ctcctgctta taaagtttaa gtcgacttct  41580
agccctgaat aaaagagcaa gggaatttta cttgaaccta taggtgggct cattttatgt  41640
aacctagtaa caccagactt tgctttttgg tatggggcct gctgagggta gaatggactt  41700
aatagtctca tttcttaggc taaaaactgc atgtcctggc cccactccat atgcaaatat  41760
actgtcatca ttactctaac tgtatgtgag gatgaacagc cattcactca agaccttact  41820
aggttctgtg gctggcgcag cacccatgtt gatcttagtg ctgctgttgt cagattgggg  41880
ccagtcttgg gaattatgtt ctgctccatc atctaggaac agagtccggc acattctgat  41940
gcaaactttc tagtgaatgc tgcagttctg aaggtgtgga aatcgggcct tcatgctggc  42000
```

-continued

```
ttggagacat ggagctgtgg gtagcaaatt gatgttgcaa caaggaacag ctgtggacat  42060
caggtgccgt catcattggg ttagtctctg tggtgagatg ggcaacaaag cagaattggt  42120
acacagagcc ctggctagtg gaagattggc ttaagtagat gcgggctcct aggccatgct  42180
ggtttactag ggcggaatga tttgggcccc tataaaggaa agaattggtt gagtgaagca  42240
tgacttttcc cagcacaacc tgccaacagt actggctcta agtgacatgc tgggtatttt  42300
taattaatta atttatttaa aaaaaaattt tttttggctg cacctgtggc atctggaagt  42360
ttcaggccag ggattgaatc tgagcctcag ctgtgaccta tgctgcagct gtggtaatgc  42420
tggatcccct gctctgggcc agggattgaa cccgagcctc cgaagcaacc cgagtcactg  42480
ccgtcggatt cttaatccac tgcaccgtgg caggaatgct gggcattttt tcttatatgg  42540
ttttcaccct ttggtttctg aaaagtgacc aaaggattgt gtctgacaac aaaactagtt  42600
tttgagaacc agcagccact taagatgaaa ggtgggaata ggggccgctg gagctgagct  42660
ggctgcctgc tctatcgttt tggcccccac caaggcctct gatggtgtct catttctcac  42720
agaggagaaa tggctctaag gaagatccta ctgcaggggc tcaggctcaa gaataaggct  42780
ccctggacag ggcacagcat gtgctgccat cagtggatat gcccggcttc cactgcgggc  42840
ttgaggttgg ctctgcatgt ctgtgcctcc tgaggaggat gaaggaatga gtcagcctgg  42900
cgcgggctgg gccttgggtg ctggcaggca ctgtcctgac agctgatgtt ggggagggga  42960
gctctttgca gagacctgcc ttgagaaacc agggccaagg ctgctgtcct ggggctgggg  43020
gagaccccag agggtggtgt aggtggagga ccttggagac aagcaggaga gccctgactc  43080
tccctgtaag ggagactctg gggtggagtc tgaggggagg gagacctgtg atgacctggg  43140
catgagtcat gaggtctctg gtttggtctg ggttttaagg acatgttgag atcttgtagg  43200
agtttggact gacttgctga caagccaggt ttttttgatt gctggtgtgt aaatccactc  43260
aaaggccaaa caaaatttca tttgttgttt ttgtccttaa tagcctgggt gagcaaaaga  43320
tgagagcttt tagacctcag atttaattca agatgacgaa atagggttag tgtttgagtg  43380
cagtatagtt gtatctgctc tatgtccttg agacggccct tctgtaccag aacattcttt  43440
tttttttttt ttggtctttt tgtctttttg tattttctag ggccgcacct gcagcatatg  43500
gaggttccca ggctaggggt caaataagag ctgtagctgc cggcctttgc cagagccaca  43560
gcaacgcggg atccaagcca catctgcaac ctacaccaca gctcacagca acaccagatc  43620
cttaacccac tgagcaaggc caaggatcga acccgcaacc tcatggttcc tcgtcggatt  43680
cgttaaccac tgcgccatga caggaactcc taccagaaca ttcttatcac aaatattttc  43740
ctctgatgct tgaggacaga ctacgtaaga aaggaagttt gctgggtttg ggcacataac  43800
aggctttttg gcagagaact gtcctatgga ctgtattaat tgtcccccaa cccccccacc  43860
cctttgaggt tctgaaaggg atcaaggttg accttcttaa gtcagtgaaa ttatcctgca  43920
gtgcctttgt gacctagggc ttaaggtgca ttattccacc aaggccatgt ttaaacggta  43980
ttcctgaagt gcatagagca gcgatggact aatggaactg ggaacttctc attgctttcg  44040
cttccaacac ttttaccagg atgcttgtaa atctatcatt tttggaagag gtacatttgt  44100
aatttatctt attatgaaag tatttcacat tagtaagctt tttttaataa gagaagaaaa  44160
atttgcaatt tacagtgatc ctaccaccca gataacatgc tgatagtaat ttggtaacta  44220
tccttccagt cctgttctgt atgtttaatt tagtgaccct tcccctactc tcccccaaag  44280
gggagggacc aggttcttct gagatttttt tttttttttg tctttttttcg ggccacaccc  44340
acagcatatg gaggttccca ggctaggggt caaatcagag ctgtagctgc tggcatacac  44400
```

-continued

```
cacagccaca gcaacgccag atctgagcta cgtctgtgac ctacatacac cacagctcac  44460
ggcaacgccg ggtccttaac ccactaagca aggccaggga tcaaacccaa gtcctcatgg  44520
atactagtct ggttcgttac tgctgagcca caatgggaag tcctaaagag actttaaagg  44580
agagcagtct ttggagtatt aggggagtga taagcctaat accaaagaga tggtcccaca  44640
gaaggaccaa taagaactca gttttgcctg caaattttct gttaatcagt ttcttggtat  44700
tttcttggga ggcttctgtg ttttacttta taacatggct gaatctctag aagcagctat  44760
tgccaactac tacctggata cctggttatt aaggtaattt ctctattacc ccagagagcc  44820
ttagttgcac tcagctttta ccttgatcct tgtacagctc tgcagggcaa acctttctca  44880
gatctgagca gtctttgcaa gtggggccaa ggagccaccc tgaaccaaca aaagagcatt  44940
atatcaccgg aagcccaagc cctgagaaca caaggtatga acagtaatca gtagccccag  45000
ccaggtcttt gcaagagacc ctaatgtctc aggtagagcg aagatccaac cgatgagttt  45060
taagaagagt ggggttggtt actttagcct actcattgag gtcacaatac agcccccagg  45120
ctggatggct tctcccactg ggaggccaca ccaaggcttg tgtgtctgta gttgaggact  45180
tgtagccact ggctttcact agcttgcagg agattcactc acaactggtc tcaaaacttc  45240
ttgggcttta cctgacttct aggaagtggc agagatcgac ttagatgcag gctctgctca  45300
agccacccaa agaggctaca aagttaggga tggaggagga gaaaaaggcg gggttaaatg  45360
taggggtgcc ttgatttgga gccctgagat ttaggaggag gtgggacagg gcagaagaag  45420
ggcttggctt gtttttctga gcctgggtga agcacccagg cacggggatt tgagaaggag  45480
tagcccttgg tctgagggtt tgaggagaga gatggtctgc tgacgaggcg tgtcaagctt  45540
ctggctcaca tccttgcctg atggttcttc aaatgctgcc cagaagcttc tcaggtctct  45600
gtctataatc agctagctaa ccggctgagt gagtttagtt gtaagtaatg aagaaaagca  45660
aaggttgggg cagttgtcag gagggtgacc tgtgctgatt aattacctgg aacagatggt  45720
ctttgttact cggggtggtg tgcttgtcag acttagaaag gcaatcgggt tggtgcatca  45780
gaagatctgc tgtggagagg atttaacaag caaccttcac ttcctcgtgt tgcaactgtc  45840
ctgttaatgt aactgtagta attttagaat cagatagtgc cactgtggtt atcgttggct  45900
tgatgcaaac tgcttcgcat gtcctaaagt cctgaccaaa agttacagga tggggttggg  45960
tacagattcc tgggactggt tttattgcc tgtccgtggc ctgggacctc ctctccagcc  46020
tagggtgaat tgaggaatgt gcttatgtag tcctgtgggt tagtgaaaac cttggactcc  46080
agaactagga agaatgcctg gatggtggtt atctccatga ttaagaaagt cactttgggt  46140
ttgggtgtag attgttaaga ggcagtgtgg gtgccctatc ctgtagcagg tatttgtagc  46200
tttgagacag ctttttgtac aaagatctag tttgaccaag gtactaaact aggggtgagt  46260
tgttgatatc actgggagat tggttgcagc ttccttcagt gcatttaaaa tgatatttat  46320
aggattagcc cagggtgagg gtggtatgct tacagtggat gcctgggaag tcccctgtgt  46380
tggccatgct ttttaacttg tttctttgtg gtcttttcca cttgctcacg gtgacaagcc  46440
tggggaccta cctgaggagc acccacacag ccagagcgtg gcagggctcc ctgtggcctg  46500
tgcacagagc gtgcttgttg agttaatgtg taagcaggaa acggcttcct gtgccaagct  46560
gtatattagc catcccaggc ctctcagact gatccctctc tctcttcagt tcctctggac  46620
ccaagacctc agaagccatg ccgaagcccc acagtgatgc cgggaccgcc ttcattcaga  46680
cccagcagct gcacgcggcc atggctgaca cgttcctgga gcacatgtgc cgcctggaca  46740
```

-continued

```
ttgactcgcc acccatcacg gcccggaaca ccggcatcat ctgtaccatc ggtgagtggg  46800
ggtgcccccc tcccctggaa acaagggctt catgagacag ggatcttttc tctcctggaa  46860
agactaaata aatgtagcaa acctgggtgc tgagtgagat gctaaaaaga tccttatggg  46920
tactgaggtc ataggaattt acagtgaggt actggtatgc tctacgcatg ctctatgctt  46980
tatgataaag gtgaaattta gagggtatct tccttagtgg atctttgtag gaacatctca  47040
gaaacctacc tgggaaagat cttgacatgc tgtgtacaac tgagactctg tagctggaca  47100
tctgggtggg cttcagggag tgcagagagc gctggtctag tcttagctag gctttcctaa  47160
aagaattagg agttatttgg gggaggaaaa gtttaagggg agggaaaaaa attttttttt  47220
gcttcttata ctgaagcaaa cttaaagtgt tattcttatt ttgaataatt aatacttaat  47280
cactttaatt ttttttaact taggcccagc ttcccgatca gtggagacac tgaaggagat  47340
gattaagtct ggaatgaacg tggctcgttt gaacttctct cacggaactc atgaggtgag  47400
cctctgccgg acagtttggc cactggggca ccttgtgggc aacagggcgg gagatgccat  47460
gttcatttag ccacggtgga ccaggcaaga aagattggtt tacagccagt gggaaggttg  47520
tcttcaccag cccatcctca cgctcctttc ccctctcctc ctcctgccct ctcaagtggc  47580
caagtctcct ctagcaaaca agacctgctt tgtcattggc catggttctc ccccacagct  47640
gagctccatt agccctcagt aaggaacgtg tgggagagtt tctctggaaa cccctctaag  47700
ccatggggct tgacattccc accccagcat ttctctaaca gcttgtgttg cagtgatgaa  47760
ccaatggctc accttgcagg ttgattctgg ccaagtttag acccaagaca aactgggcag  47820
gtccaggaga agggtttcca ctgttgccag tgaaggactg agtctaatgc tctaacaccg  47880
tctggtgtat cctaccccac ttcatctgca ttgtgttgcc agcctttccc ttcccaggga  47940
ttctggtaca ttgaaataaa gaagccagca tgtttcccta ggagcctggt aggaatatct  48000
tagctggggc tgtttatgag cagacttgac ctgtgggacc ttacctgggg tcgaggtaga  48060
agctattggg aagcactccc tcatgcttct gttcccaagt tcagaacaaa tttattttga  48120
ggagtgtggg agctccctga gggacagtgc cttttaaaaa gaccttcagt ttcaaccaca  48180
gaccatgggc tgatgagagg gtaatggatg agataaattt ttctcactct taatctctgt  48240
atttcctatt caggataaag aaaatgctac cccataaggt caagtggtga ggggttgccc  48300
tctggcattt ggcagttggt gttaagttta aactaaaaat aaaggcttag aaggtgcaat  48360
ccaagagctg aattcctcct ttctggaaac atgaggctct tcattggagg ttccctaacc  48420
catatttcat aagcagccta tggtctggca ggtatccagc ctccaaatgt cagaagggcc  48480
tgaccaagtg cagaggaacc gtgctcagca ggcccctcgg gcaggttgat acgtctgtgg  48540
tggcattctg taattttcca aaggcaggga gtcctcagca ggaagtcact gggcattcct  48600
gcaagtatta gcttagtcca cggagagagc tgaagacatc agtgaaggtc agttcactat  48660
tgattgctcc tgctggcctg tgtgcagggg aaggagcaga aatagatttt aagaagttga  48720
cctttagcta ggctttatgg cttcttccat ccagtaaaat aacaccacac agctctgaaa  48780
tggcaagggc cagtggtatc tggtgcacct gctggaaggg ggctggctca gggattttgg  48840
cttttttaa ctccaagagg cttttgtagg ttctctgtgc tttaactctc attccaagat  48900
gagacgggat ttaaacaaaa acccatgcct gccttgtgga tttattttga gatttttgac  48960
caggatgaag tgggttgtcc ctgggatcgg cattttagaa actgatctga aattgttcta  49020
atattaatta tataacgtaa gcagtcttat tttgacaagc agttggaaca tccttttcca  49080
gctcatgaca gttttcagta ttcttctaag cagaacattg gaatggcttt ctctccctca  49140
```

-continued

```
ctgtgacaat gggacctcca gtgtctgcat ctgatctttt tgtggggttg ttgttgctac  49200
agcatctgat cttttgacag ctttgccata gcacctctaa accccacttt tggcaagatg  49260
tgttcctact gattgtgtgg tcccattgtg ccatgtgggc cagaaataca gacttctgaa  49320
caaactaaat gtagaacctt ccataaggac agtgttggtt tgatggaatt cactgccacc  49380
ccgccccagt cccctcctcg tgcgtgccac tctcctggac ggtggtggtt aaatgacaag  49440
gcccataaag tgctgagttg ggagactttt atcagcagtg tcatttcaat aactcttatc  49500
taagagcttt tgacttcttg cctctgagtc cctttttagt caagtagttg tggcaaatgg  49560
aaaaagaaaa aggaatggga gaaaaaatta tgtattcatg tatgtgtaac tgggtcccca  49620
ttctgtatag tgggggaaaa aaagtgtgtt gagggaaata acaataaaaa aagaaaaaga  49680
gaaagggctt cacaggtgag attaaaacca ggatttgttg caagtgagaa tagcaagggt  49740
tagttagttc agagaaaggt gtgttcccac cgttgccttt tgcactttga gactcgagga  49800
agtgattatc agaaccaggt ctgtaggacc tctgcaatga gttatttagc ttggaccact  49860
gttagcttga gtaaataact gagtttgaag tgcggtcata atcaatagag gaacagctca  49920
gaattaccaa atctgtcagt ctgaccctga tggccaccag actggtattt tccaaacata  49980
agtcctaggt cttttagccc aagtgtctgc tttatttgct gagggtttag gtggcagtct  50040
aaaagttcct aagattggcc ctgagagcgg gggagtgctg tggtagaggt gggtggaagg  50100
tgcttggtga gtgggcggcg ctgagactag ccgatggcga caggggtcca gagcgtccgt  50160
ccacagctct ttcctgagtg ctcagcttca gctctggtgc tccaccctgg ggcagggaag  50220
gtggcttatc cttctccctc ctttccccca gtaccatgca gagaccatca agaacgtgcg  50280
tgcggctaca gaaagctttg cttcagatcc cattctctac cggccagtgg ctgtggccct  50340
ggacactaaa ggacctgaga tccgaaccgg gctcatcaag ggcgtgagta tcctggggga  50400
ggggggaagg agctggggcc ccagagacat cctctgcagc ctatcccacc cggaagcctt  50460
gtttctcaga gctgaggtct atacatgagt tttatccatc actgcaaaaa actttgatct  50520
actttgatta gaaacaatac ccagaaggaa tgattttttt tactctcaaa acttgcttcc  50580
aagactctcc taacctttgg gatcaacttg tctcttttcc cctatcatga aatagtatca  50640
ctaaaacctt gtgggttttt cttgggtcat ttccttgaaa tatactgagt tagacaatgg  50700
gatcatttct ttccaaagaa aaaagcttta ttgttacttc cagctgagat ttgagccttg  50760
ctccctggag gaaagctttt cttctcctgc caggagggcc tggcttctct ggacctgtgg  50820
cttcctcttg tctgcagagc ggcactgctg aggtggagct caagaaagga gccacgctca  50880
agatcaccct ggataatgcc tacatggaaa agtgtgacga gaatgtcctg tggctggact  50940
ataagaacat ctgcaaggtg gtggatgtgg gcagcaaggt ctacgtggat gatggactta  51000
tttctttgct ggtgaagcag aaaggtatat atgggagcca gggtctaact gtctagaggc  51060
agctcccatc tcttttcttt ggcagaagat aggaaggtgg tgggttggct ggcagcaaga  51120
ttgaatccat gcatcctcag gaattccttt tataataaac tccttatcct caaaagcagc  51180
tctgtcgtac ctcttgggaa gcagatgaga ggatttcttt tctccctgtc cgcactactt  51240
gaggttttct gcttttctcc tccatctccc cagtgtggca tgtctgggac tccagtatgc  51300
ctgtgattga tagctcacac ttcagtgcca ggtactactc taagcattta acatattaat  51360
ttgtttaaat tttaaaacaa cacgaattcc ttggtggcac agcagattaa ggatctgtca  51420
tcgtggctca ggtcgctcct gtggcacagg tttgattcct ggtcccagaa ctttggcatg  51480
```

tctcaggtgc agccaaaagc aagcaaacaa acaccttatg agtagatatt gttattatct 51540
ctatttaact gaggtatgga gaggttaact gacttaaccc caggttacac agctagtgga 51600
gtgtggatgt gaaccctgca atgtggctcc agcacccacc acgtgctgtc acccagttct 51660
gtctcctgga gagagcctgc ttcctgggga agacgtggcc cccatggccc tgccacccca 51720
cctactccat tcccacaggt cctgacttcc tggtgacgga ggtggagaac ggcggcttcc 51780
tgggcagcaa gaaaggtgtg aaccttcctg gagctgctgt ggacctgcct gccgtgtccg 51840
agaaggacat ccaggatctg aagtttgggg tggagcagga cgtggatatg gtgttcgcat 51900
ctttcatccg taaggcggcc gacgtccatg aagtcaggaa ggtcctggga gagaaaggaa 51960
agaacatcaa gataatcagc aaaatcgaga atcacgaggg agttcggagg ttagtcctcc 52020
tgcctctccc ctgcctcctt cagcccccgg cccagctctt tgaagagcaa gatgtccctg 52080
taaatacctg cctccctgcc catcaactta gaggctctca agcttatttc agagccactg 52140
aatcagaaca tcctaagagg gggagtggaa agtgttggtt ttttcaaggg ggaaaaacaa 52200
accaataact taggtgattg ggatgctggt atcttttttt ttttttttta gtgattttta 52260
tttttttcca tcatagctgg tttacagtgt tctgtcagtt gtctacatac agcatggtga 52320
cccagtcaca catacattct tttctcacat tatcgtatgc tccatcacaa gtgactagac 52380
atagatccca gtgctataca gcaggatctc attgctcatc cattccaaag gcaatagttt 52440
gcatctatga accccaaatt cccagtccat cccactccca cctctccccc ttggagccac 52500
aagcctgttc tccatgtcca tgattttctc ttctgtggaa gggttcattt atgaggatgc 52560
tggtatcttg acattgttcc taggccccag gaccagcacc ggagagccca gggccactgc 52620
ttcccagttt gggagccatc acgctgtgct cctaacacag cctgtgtttg ctagaattgg 52680
gccacccaca gggaaggcag cagactctta ggggtgctcc ctcccctggg agccacgtgg 52740
aagctcaggg cctggggttg acaccaaagc atgtggcctc ctagtcttca ctggccgtgg 52800
cttgggatgg gccagttctg gcatggtatc agcttcctag ggggaagcat gccattctcc 52860
tccaggtcca ggttgtccca gctcatctcc tccacctccc cattgctcac caggtagagc 52920
cccatgagca tagccagctt ggtggcatca cttcctcttt ggttcctttc tagaaacaca 52980
gctcagtgct gtgacccccct gacctgcttg tgtgggttca gtatgtgtgt ttgcccacct 53040
tagctttgtg tagatgtcct tagtactggg aaatttgggg tcctccctct gccatccaga 53100
aaagccatgg gtacttgctg accttgtctc caggccaagc aaagccatat ccccttgcct 53160
tcagaaagct ggaggtgccc cctgaaggag cagccctcag gtgtccttgg gtggaagagg 53220
ccatgaacct ttgtgtcagg agcagtcaac caccttgggt tccctttgct ccaaaagcgg 53280
ggactggact ggaggtggta gagaaacacc ttaagagggg cctcataaga aggagatgga 53340
gaggaaatgg gaccctggga ctttggaata gacctcactc ccttccattt cccccagtaa 53400
agtgtccaca ctggtgccga cgaatcccag aaagcagaac tgtcgaccct ctttgaggta 53460
ctgaggtagc tggaagaccc accacctcca tgtacccatg atgacttcat gcatgggtgt 53520
ttgtcttggt gcaaggacgg ctgagtcaga gaatcccagg aaaacgtcct ttgtatcacc 53580
attcttctgg cccctattcc atataacttc tctctctttc caacttacct gtcagatttg 53640
atgagatcct agaagccagc gatggtatca tggtggctcg tggtgatcta ggcattgaga 53700
ttcctgcaga gaaggtcttc cttgcccaga agatgatgat tgggcggtgc aaccgagctg 53760
ggaagcctgt catctgtgcc acgcaggcat gtgcctctcc tggagcttac aaccttgcac 53820
ggggaagcat tggcggctac cgggtctctc ccatctcttc cctgctccac gtctcacata 53880

-continued

```
acacacacac ataccccctt tcccccacat ccctacacaa agccattctg tctgcacata  53940
catgctctct aggggggtta gcctgcagtc gtttgtgtcc ggagacagtc caggccacgt  54000
ctcacgagta ctctgtcccc tcccagatgc tggagagcat gatcaagaag ccccgtccca  54060
cccgggctga gggcagtgat gtggccaatg cagtcttgga tggagctgac tgcatcatgc  54120
tgtctggaga gacggccaaa ggggactacc ccctggaggc tgttcgcatg cagcacctgg  54180
tgagttctca gcctgccatc ttcccgctca gctcagcttg ggcttgggct gggatggagg  54240
tgtgctctgg cactgagcaa taccttttag gcttctatgc ctacagggtt ttatctgtca  54300
agtcacaagc cagagtgagg agatgtgtgc tgggggcatg gagatgtctt attttttttc  54360
tgttctacct tcctgcccac acccctctcc cagttccttc tgttctggag gtggcctcct  54420
tcagcagacg tagcacaatt cactcctgtc ttcagggttg tgaattcttc ctttggctcc  54480
agtactgggc tatctatctg tccctggaca gcccagagga cctgagtacc tctgccctat  54540
tctggaaaag gccacaggct cctgctccca gctgttcttt gtttggcttc tgttttgact  54600
cgacacctgt cccaagccag ctgcctccgc ctgcaggagg agcctgggcc tgcggcctgc  54660
actggagtct gttgcccacg ctgagtcgac tgagctggct ttgcatggtg cctgcagcag  54720
cgcctgcttt gctgagctgt tgcactcgcc tcagactaca aagtggggtt taagtggtgg  54780
gtgacagggc cacaaataga gacagttgga gggatgactg attctggctg gctctggggt  54840
gagagcatct ggaggagccc tgagggccac tcgtcctttt cccctaggac ctagcttttc  54900
agggctctcc cactaagctg tgtcccacag cctggctgct tctcagggct tgaggctggg  54960
ttcctgtgtc tgctcctgct ctagagctta ctgaagagtt agtgcaggga tcagctatca  55020
gagctgagaa agcaagtgaa ctttcagagc agtcccaggt cactgtcgat atagctcagt  55080
gaatgaactt gcctgttaac ctgaaatggt gtttctttaa gcttttattt gcttttcagc  55140
caacaaaaga ccctgtgccc tttgtgtgac accctctccc ctgcattcca cccaaattta  55200
ccccccacac acatacccca taggaacccc tggactagat aggatccttt tttccttcac  55260
tttctgtgta attattaggc tttggtagct tccaaagaag atatgactaa atcatttttt  55320
acactaaatc gctttttcag tggtgaaaca agacatcttg actaaagagg ctctctgggc  55380
tgtccttggc ctcctgggtg ggtttgccca taacaaaatt gatagagacc aatccctgtc  55440
cctgggatgc gagatatgtt tagttagaac cttagagtta aattttgctg ccaaaatttt  55500
cctgtgtaga ttgatgtaat cttcataact tcagtgagat agaagtcacc ccttgttata  55560
gaggagggtc cctgatgata ggacttgagt ctgaacccag atcatctggc tctaaaaccc  55620
gtgttctcct ctgcaatatg gtgcttcgtc tagcaggaga tcaggacagg tttccatgtg  55680
ggggctgtgc agaggccaga gacgaggcat caggctctgg gctttgaatc catgtatgtt  55740
tttccatatc cctgtctttc ctttgaacag acaccttaga actgcaaggc tgggactgaa  55800
tagcactgct caggagataa gttatggagt ctgggccagg cagtgcaggc ctctcctgtc  55860
catgtcacca gttaacactg gccagcagct tcccctctta actgtccact gctttctcct  55920
atatctaacc gaggcagtca atatcccata actaagggtt aggcaatacc aggtatggtt  55980
ctctttcctg tcacatcccc tgtcctgtgg gctgcatgcc ttccattctt gcagggagaa  56040
aacctttaat aaccgagcaa attctgccac tcatctgctt atcctatctg attaatgaga  56100
tggcattacc aattgtccct tgtccatcat tctctaaggt gctggtaatt gcattataac  56160
ctctaagctt acattttctt tctatttctt ggtctgagca ggtctgtgaa taactcagtg  56220
```

gctttctcct gggtgtttta atcacttgat tttaatgaaa tgtcttgtta cacttacctg 56280
catgcttcca caggcacctg tctcttcaca tggctgttca gtgtgtcccc tcacagctca 56340
ccgattttcc acctgcctgt ttagaacgtg gtcaagccac gtggccttgg ctttgtctga 56400
cccagcttcc cagcgcagct ctgtgtgctt ccatggcagg ccattgcaaa ggctcgtagc 56460
gtccctgtgc ctgaagccaa gcaagtgctc catgaatgca tggaggccgg caggaagccc 56520
ggttggtaac cagacagcca tgtgaggaag gaggcctgtt ccttcctgtg agctgtgtca 56580
tgaggcagcg tggtcaagtc ctaccaggga gccatgcagg cccagcctat gtatgtttcc 56640
atgccaaggc gctagggtct gctgccatac tgtctcccac cgccagtcaa aaagtccttc 56700
caaaatcaaa aggcccaatt tcccttctgt tggaagggaa gcagcagcag tcagtgcttg 56760
gaccacacct ccctgagtgg gcttccatca ccctgcctct ttgcatctgc ctaaaggaca 56820
gacttagcca attaacctaa ggtaccttcc tctctgatta attccccatt ctgtctttcc 56880
atgttgttgt ctctcgtttt ttttttcccc ctcctccttc cctcttcctt gcctcccctc 56940
ctccttaaac cttacagata gctcgtgagg ctgaggcagc catgttccac cgcaagctgt 57000
ttgaagaact tgtgcgagcc tccagtcact ccacagacct catggaagcc atggccatgg 57060
gcagcgtgga ggcttcttat aagtgtttag cggcagcttt gatagttctg acggagtctg 57120
gcaggtaggg ccccgagagc aggtaactct gtaggataac cagcctcttg ctccagctgc 57180
tctagaagac agccagggcc tagccctctg ctcaggacct cttctctcat ctgcaggaag 57240
ccagccaggg aggtcagggc acgacaggac tgcagggtcc ttgagccccg tagggacata 57300
atgtcacagg cacctggtga agggctggtt cctggggagc cttgatctca cttagcccca 57360
caccccaatg tttgggctcc tcttggcctc tgcacccagg gacatgttcc tcaccagctg 57420
tctgtgcgac tcttcccctc cctctcccgt gtgacatggc tctgataaag ctctgtcccc 57480
ctctcgtcca tccggacgga tgttgccccc ctagattgcc cgtgaggcag aggccgccat 57540
ctaccatttg caattatttg aggagctccg ccgcctggcg cccattacca gcgaccctac 57600
cgaagctgcc gccgtgggcg ccgtggaggc ctccttcaag tgctgcagtg gggccataat 57660
cgtcctcacc aagtctggca ggtaggaggt ggcagcggct ccccaggaac gccccgctca 57720
gtggcaccct tccttggggg tcctgggagc agtgcactga atggtgctca gatggcactg 57780
agccaaggta agacccctct gcctgcgccc cggaccctgc agggaaggag ctcccccagc 57840
cccactggcc aggctctggg agcgagccta gcccttgccc tgggcctgaa ggatgggacc 57900
ccaggcagca cgcataggat gaccgtttgg gtccaaatca agtttatatc ttcatgatga 57960
atcagagact taattgcata actacagata gatagagtga tgacaaatgg ttattcaaca 58020
ttaaaagctg ttctcaaaaa gtaggagata atcagctacc acttttgctt attctagtta 58080
ctacatgctc tttaaaaagt tcagtttgga aagttagtgc tgcttgctta catgctttgg 58140
ttggtgcact catcccatct gtctttgagt cccaaagaca agtaattggg tgctgcccag 58200
gaaaggtcac cgtgctgtct tgctggcact gtgggactgg gcagccacgc cgaggcctct 58260
gcttgacctc agactcgggg tcccttccaa attcgggaca ttgacttatc aactttgctc 58320
tggggcctgg cgatatgctc ctcccagggc agctagggtt tcctggaaga ggagggtgga 58380
gaggaaggaa caccgaggag cagcagatgg ggctgctgtg ggaccatgac acaagatgca 58440
gatttcctca gcagagggct cagaataaac agttccaacc attagggttg acctttgtga 58500
aaaggtccaa cctttgctac ttggctattt ttaactccag tcttctggga tttcactcag 58560
tgggtcctga cttcagcact tgcttccctc cgaaagcctt gtatggaggc cagcccttaa 58620
gcagggcatt ctctgctgtg acatggctta agtttccctg acacctgttg agtgccctca 58680
tagcttgcct tctggggccc agttccccct gcaagccctt ccaaccccta agacacatct 58740
gcagctacaa gtgcatagtg tcagtgttga aagaagtgcc ggcattaggg ttttaagggg 58800
gggggccctc acccctccag aggagcctcc acaggcaaag ccttccctgc taagcactcc 58860
aatctcctgg tcttgactcc tgggtagcac ctatatttct aaacctcgct tgggttttac 58920
ttgagctcta cagcccagtt gctgggactg tttcaggggt catgtgaggt cgggagaggg 58980
cacagcagaa gggaaggctt gcgttataaa gtctcagggg gactggtggg ctctgctcct 59040
gttttatgta gatgtcaaga gtcaggtgct attcacatgc tgcttggctt gtatgtagtg 59100
ttgctggcag caaaagaaat gggtgtggtg aggttgggca gggctgcctc cctgtgccag 59160
aatggaaaaa ttcagggaag gggggttctg ccaactatgg gccctgtggg taagtgggtg 59220
agcctgacca ggctgggtca gcatgatccc caggcccagg cctgtgggga ggggtgcagc 59280
atagatggag agcacagctg tgaagaagag ctatatgctg tggaagataa aggatgaggg 59340
gctgcccagc cttgggagca gatactgaac tggtcagagc cttaggctgg catggtgagt 59400
tggattagag ggtgagctct tgctaaaggc cctgaggggc ttcctgggac actgtttaat 59460
ggtcttgcct gtccctcatc tcaggtctgc acatcaggtg gctaggtacc gcccccgagc 59520
ccccatcatt gctgtgaccc ggaatcacca gacagctcgc caggcccacc tgtaccgcgg 59580
catcttcccc gtggtgtgta aggacccagt gcaggaggcc tgggccgagg acgtggacct 59640
ccgggtgaac ttggccatga atgttggtgc gtggctggga agcaagggct agaggtgggg 59700
gttggggaag gtgtccctct ctaatgctga atgttctctc tgaatcctcc atcccattcc 59760
ctgaagcctc tgggctgaga ccaggagggt ctgatccacc cattttctct cctcactctc 59820
ttctagtctg gggtccaaag caagggatcc tggagagcta gggttgttca ttctttagca 59880
tctgctcatt attgagattt ttcataaatt tagccagagc tcctgcattg tggggcagcc 59940
cacatatggc ttctgtccag tataagagca gagtgttgtg ggatcagagg aagcagctat 60000
agctgtgacc ttgagctggg ctctccaccc tctagagtag aaaatgaatg ttgtccaaag 60060
gtccctgcca gctctgctct gaatgataag gaaatatcag ggctgtgggg ctggcgccac 60120
cttgtgggta taaggaagta aaggcctgcc tgtccttctt gctatttttg attgtggggc 60180
cgtcttgcag gtgcatacct tcctggcatg atttttactc acccgcctct ctcctctttt 60240
tccccaggca aagcccgagg cttcttcaag aagggagatg tggtcattgt gctgaccggg 60300
tggcgccctg gttccggctt caccaacacc atgcgcgtag tgcctgtgcc gtgatgcacc 60360
ctgcagcccc tactccagcc ccatcccatc cccctccctc aatccatcca ttaggccaga 60420
aatgcttgta gtgctcactt ggggccgtgt gtggcactgg tgggctggga cccagggaca 60480
cctctgtgaa acatggctgt ttttaagacc ctgcttgggt ggggtagttc agagctggac 60540
ctcccatcaa gtatccccat ccaagcaagg gatgaaggaa gggtgcaggc aggactggag 60600
tccccagagg gcaacagctc ctgcttctct tcctttgtgt actcctgtag ttctgtagaa 60660
aatggatacc cagagaactc ccagccctgg cctggaatca gcaaagagca ggggccttag 60720
ggcatggggc atgaagcagt ggttccagtt taagcagact ctggccctgg cccttactta 60780
cttctccaac ccccttagcc tccctcactc cccctttgtt gtgcactgtg cacttctgtt 60840
ccttcactcc atttagctgc cgctgcagac aaacactcca ccctccacct cccatttccc 60900
cgactactgc agccgcctcc aggcctgttg ctatagagtc tacctgtatg tcaataaaca 60960
acagctgaag cacc 60974

<210> SEQ ID NO 54
<211> LENGTH: 26664
<212> TYPE: DNA
<213> ORGANISM: Bos taurus

<400> SEQUENCE: 54
ggcacttcct actgaaggtg actgtgcccg gcgaggacgc ggaggggcgg ggccccgaga 60
gccgggagcc aggattggat gggaggcggg gcggcggagg gattgcggcg acccacagtc 120
gggataacct tgaggctaag gcagcggatc cccgcattgg agcgacgcgt cgcgagcccc 180
aggacctgtg tgcagtagcc gcgcatcccg agccggacca cgtcggaggt gagcgtgggg 240
agagactggg ccatccgtcc ccaccggggc tccgtctccc ggggcagtgc ggaatgctgg 300
cccgcctgcg cactcaggat ggcgcaggat ccgcggcatc gtgggctcac ccggttggga 360
tcagaaaaga ggagaaaggc tgcttgtgcc tagggtctcc ttcaaatccc ccagctcccg 420
cttcttccga aggcagatgg gtcagccagc ccctttcttt ccccagtccc tgatctccca 480
tccccattct ggtcccattc tcacctccct attcctccct cctctatctg gtctcgctct 540
cgtcttcctc cctttattct cctaatttga tagtttcctt tcatgcgtca gtctccccca 600
tttccactct gctcctatgc ccgtcccttt cccatcatcc ttaatactcg cttcttgttt 660
tcaacctgtc catgtccccc tcattctgat gctttctgta acttctcctt gaaagtcccc 720
aagctccgct cccctgtttc tcctccattc agctgctgtc cccttcttgt acctaccctc 780
attcacgccc tggctcccgc ccctcccccg cctctctggt cacgtcgctc cagcgcatcc 840
ctctcctgcg caccttcctt cgcgccacca gcctcctcgc ccctcccctt ctgttctagt 900
cacgtccgcc tgcactcacg tccccgcccc tcggcctcgc atctcctgcc cccctctcc 960 atcatagttc cccagccctg ggctggagtt ccggggtcag ctcccgaagt gcagcggtct 1020
gcggatgggc aggctggctc ccaggcgacc cggagatgga tgcagtggcg gccggaggag 1080
cagttaggtt acataaccct tgatctaacc caatgcaaag gaagaaaggg tggctgccca 1140
gtggcgcgtt cctgttttgt gctgcccaga atacgatagt gcgaccgctg cgctccgctt 1200
gctccagggg gccttggggg cggggggggg gggtggaggg cggtgcgcgg tgtcccgggc 1260
tccatcccgc cgaggcgggg ctgcacgtag cggcgccgga cccgccctgc cgcgcccgct 1320
cctcggcatc acgaaacact gaccttcggg cccgttaccg accaagcatc atctccggcc 1380
cgccaagcct ctggatgctg ctcagaggcc tcctcgagtt cgaggcactc acctggctcc 1440
ctgcctctgc ttcacgttac ttaacagcgt tgcttaacag atgcgcccga ttgtagagcg 1500
cggaggccgc gggttggagg agagtagaaa tatatcaaga gcttggtgcc acgtacatgc 1560
gctcattcaa taaaaactcg tataaagagt tgtttggggg agggctgtgg agaccagacc 1620
aggatgacta aaatcgtcct agcctacgga actcagtctg attagcaaac gaatgtaaaa 1680
gttaccactg taagtgccgt gaaaaggtac acacgtgctt ccacacgtgg agggtacgca 1740
cttcctgtcc gggtttagga ggcctcacca ggtgtcatca cacggggttt gatgaagcgg 1800
aaacgcacct tccagtctga agattatttg aagacccagt aatgggttgg catcccttgg 1860
cttcttatct gtgttcttca aacccagaac actgatcctt ccccgtacaa atgagcctga 1920
taactgaggt ccgtgacgga cagaggcagt gggaagatga aaacaggctt tcagaatcag 1980
gtttaactca ttacatactg atatgaataa tagagggaat tcagactcag gacctcagtt 2040
tcccatgtga aaattgtaac ttttttcatc ttggttgtta aaagggtggg tcgctatata 2100
cacacttaca tagatacata ttgagtactg ggtgcagtgt ttaatctctg gtgagatgcc 2160
cccagatgta ttcttttggt cacagtgagc ccaatgactt catccataat tgaactcaag 2220
cactcctctt cttgctgcca tcccaaaaca cagactcagt tcatctttgg gagtcaggct 2280
ctgtgtaaat accagagatc tcctagaaac cagtccgctc agggatcctg ctgcagtgtt 2340
ggcaaagtaa ctaacaatgt tactttgctg ctctccattt gcaacagggg ctctttggtc 2400
ctctagccaa aggaaggcaa gaagagagat ggctttcagc ctcctgtatt atagattttg 2460
gctattaaga ttagaaacaa acttgcaaac ctaagaccaa aatcttcagg ttctattggc 2520
acctgctcca ggtagcattc tgggatttgc tcaaccagct ggtgtgagat taagataaga 2580
ggcaaaggac agtagctcct tgttggctgt atgcagggtg tggccactcc ctgggatata 2640
gagaaggccc taggtcagga ctctagtcat tgttagcaaa taattcaccc tcaggttgcc 2700
tgaggatgct gttgggaatg caggggggcc tgttctgagg ggaggagtat gtaacacctc 2760
accagatctc tggggggggt ggggtggggg aggatgtagg gaagatgact caacctttga 2820
atttttctgc ttttaagaga actgtcttcg ttgggtgagt ggggaaactg cactgtggtc 2880
tttgcaggct taaaaatctc ctctcccttt tcagtgagtc aaataatgaa gtatgcattc 2940
ttcccaatta aaagtgcctc agctaggtga caaatggatg gtggaggtcc ccaggctctc 3000
tggacaatgc ttaaatgcca cgtggcagag cctcaggccc cagagatagt ctgcacacct 3060
gtcctgagcc ttgtgcgatg gatgtggcaa cccttttggg aataagcatt gtagggaaga 3120
tgaataatga tgacttaaag attatgtcct tgaactcatt tctgcattac tagaatggag 3180
ccaaaatgta gggacattag tcatatatag gacagctgct ctcattttaa gcactgcatt 3240
agaagtaaat aatttcagtg ttcacagttt aaccaaaagc attattgggt ctttaggaat 3300
tgcagcccca gtgacttggc aagtttggta gctgttactc caaacagagc taacacctaa 3360
ggggaggtgc ttatgtgccc tgagtgttgt gacattaatg ttgggtcacg ggaaatgcca 3420
ttttatttct taaaactgct tatttcttaa tgttgaggca gtgaaagaaa tggagaagtg 3480
tttgagagca ggaacgttga aaaacatgca actcttacgt tacagacttg taatgcaagt 3540
ctacaggagt ttttaaatat ttatcttcag gttttatgaa ggcaagtaag ggtgtgttat 3600
tttggctaaa agctaagact gaggtgaagg tggggggaaa tgactcattt gacattaact 3660
ttatttctga atcatttgga atgtccacag tcaaatccca gttaactggt gcaccacagg 3720
aatgaggcat ccatgggagc agagttgttt tgcaacacta ttgagtgagg gtcttgtgag 3780
atatgtaagt gatttatttc gtgaccagtc ctatgggacc ttgaatcatc actttaagct 3840
tcagttctga tacagataga actaaatgaa gactactctt tgcgggggtg ggggggggtgt 3900
tgctttgtgt cacagcttgt gggtccttag tttccccacc aggggtcgaa cgtgggccct 3960
cagcattgaa agtgcaatgt cttaaccatt ggaccactgg ggaattccca atgaagacca 4020
ttcttaattc taccatactt tttgaaaact tgctttttct ctctctctct ctttaaccac 4080
aaactagcca aggactagat aaacgaatag gctgattatt tggggctttg ttaaagaagc 4140
tgttttgggg gaggtgagcc aggatgggtg gtgagtggca gtgtgtgcag actctgctga 4200
acctttggac ctcctcctat gactgctccg cttaggaggg gaggtgggca gggccaccaa 4260
gtggtgcaac cccacccctg cagccgtttt tcctatattg gtttgtgctg gtccgcacgt 4320
aggagggaga gccaggcttc agtacttctg gtggcctctg tgactcccct cccccacttc 4380
tccctatagg caaaactcct ggggacccgt aagccgctct ttcctgacgc cagcaagctg 4440

-continued

```
tttggaagtc agacaagggc tttagtcggg gagataccaa gactagctat gacagggttg   4500
ttgttcgtgg catttcagag tatggaccag ctcggctgat ggcagtttat attaaaaaaa   4560
aaaaattttt ttttccttat aaaaattatc tgaaaggagc cccagccctt ccaaacattt   4620
aatcagccaa caggtaatat ttaactgtag gtgactggtg tcacatcacc cctttctcag   4680
gtgatgagtg cagtcatggc atatgagacc aagccataca acgttttgga ggagcactga   4740
agttttagtc tggttaagag tcaggaaagt aaagactcaa aagaaaacta tcctgatatc   4800
tgatatccct cttgttattt cgtcaaagag cagattaaca catcaccaat cagttgggca   4860
aacgttgtaa gagtctgaca gtgtcaagtg ttggcaaagg tgtgggaagg caagaactca   4920
cttgactggt tggttgtaaa ttaatgtaac cactttggag agcaattaag cactattttg   4980
taaaacagaa agcaagcata ccctgtggcc caggaataca cctctggtat agaagccaca   5040
cctgcacaaa gagacatgta ctaggagaaa tattatagta ttgattaatg aggaaaaatt   5100
gggtttagtg ggaaaatggt caaccagtga gggaatacat aaatagtcta gtcacacact   5160
gggctagtat agcagttcat atgaattaac tagagctgtg tgccaactgg atagatctta   5220
aatatgctgc gaaagcaagt tgtttgataa tgcctttcag tgtattactt agcatattat   5280
agaagcagca gtatcatagt gttgaataga gatacagaca cccttagatg aactataagg   5340
atagaaaatt catgaccttg gttgggtatt aggatgtgat gtgaaagggt tggaggaacc   5400
acctggggat ggaggacaaa tgaattggat acaatggtaa ttttaagtct aaaaatctgg   5460
attaagaaca attttttttct ggccatatct cacagcatct tagttcccca accaggtttg   5520
aacccagccc ttggtagtga aagtgtggag tcctaaccat tggactgcca gggaattcct   5580
tggataatat taatggtcag ttctgggtgg cagaaatata gatgttaatg tttcttcctt   5640
cagttcaaaa cagaagcaaa cctatggtgg tcactgtagg gagaccaggc atactaagta   5700
ggtcagtgct cgggagatct ggcatgcctt tctcctccca tcccctcctc ttctccctgc   5760
agctatgatt gattcagggc agctcctcct ctaagtactg agccaaggcc tccctttttct   5820
gaggctatcc ctcccctggt gttgtacctg acttggaagg atcctgaatc agggtcccag   5880
gtcccttggt gcttccagag tgtcagtctt acgccctgaa gcactgtctc ataattttaa   5940
gtttagtaag gagcacaact cagcaaaagc tttgtctcca cttcctcctt cagactgaaa   6000
ccaggtctct tctctgggca tctgatcgaa ccaggaaatc ctcagctttt gaaatggtag   6060
cagtttctct gactcaggac ttcctgccct ggagttgagt ggtccttata ggagtgggct   6120
ctttagcatc agcttttgtg ccctattgca cactcagatt tgaaatagga ccttgggctc   6180
ctaggtataa tatttaagtc acttagttct aaccctgaat aaaagagcaa gggaatttta   6240
cttaaaccta cagtgggctc attttgtttt gtgtaacatg gtaacatcag gctttgcttt   6300
ctgttatggg acctgttgag agaatggact taatattccc atctcttagc taagaactgc   6360
ttgtcctggc cccactccat acttgagaga atggacttaa tattcccatc tcttagctaa   6420
gaactgcttg tcctggcccc actccatacg cgtatatact gttatcatta ctctaactgt   6480
gtaggaggat gaagggcttc tcaggtggct cagtgtaagg gacccatctg ccagttcagg   6540
agacaatccc gactccttgg agtaggaagt tgcaacgact ctagtattct tgcctggaga   6600
attgaatgga cagaggagcc tggtgggcta cagtccatgg ggtcgcaaaa gagtaagatg   6660
cgaccgaccc acaacaacaa ataggatgaa cagctgagat tcattccgga ccttactagg   6720
ttttgtggct ggcctggcac ccattttgat tttgtcgctg cctttgtcag ataagggcca   6780
gtcttgggaa ttatattttt ctgctccatc gtctactaac agagctccta gaaagcagac   6840
```

-continued

```
tgacctgaat gccttgtcca gcattttttt aatatttatt tatttcaccg ggtcaggtct   6900
tagttacggt acatgggatc tagttccctg accaaggatc aaacctgggc cctctgcatt   6960
gggagctcgg agtcttagcc actgggctag caggaaagtc cctgtccaac atactgtgat   7020
gaaaactttc taatggttgt tagtgtgcca aagatttggg aatcagacct ccatgctggc   7080
ttggaaacgt ggagatgtag atcgcaaatt ggtgtcacaa ttgtgggcag caggtgccat   7140
catcattgag tcagcctgtg tagtgagatt ggcatcagag cacacatagg ttaaaggttg   7200
gcttatgcag atgtgggctc acaggccaag ctggctttct agggcagaat gatgtgggct   7260
tttgggaaac tcgaatcggt ggagtgaagc gtgagtcctt cagcacaccc tgccagcagt   7320
actggctctc agtgacgtgt tgggtagttt ttcttttatg gtttctaccc cctggtttct   7380
gaggagtgat ccaagacttg tgtctggcat gaacagaact gtggcttcag aagaccagga   7440
gccacttgga aaggagaggt cggagctggg gcccgtggag ctgagctgcc acttgtgcct   7500
gctctcagtc ctttcaactg ctctcaggcc tctgatggtg tcttgtttct cacagaggag   7560
aaatgtctct gaggaggatg ctacaacagg ggctcgggct caagattcag gttcccgtac   7620
ccgggcatgg catttgctgc catcagtgga gatgcccagc ttccactgct ggctggaggt   7680
tggctctgca tgtctgtgcc tcctgaggag gaggatgtag gaatgagcca gactggcatg   7740
agctggacaa cgtgtgctgg caggcactgt cccagtggct agcctgaggg tgggggagct   7800
cttcccagaa gctggccctg agaaaccagg gctgaggctg ggggagagtc caggggggtgt  7860
tttaggtggg gatgggcagc ttgtgctctg gagaagaggc tcatgggagg cttcagggca   7920
aagcttgagg gaatggaaac ccagctgggg acctgggcag gtgacaaggt ctctggtttg   7980
ctagtggact ttaaggacat ggtgagatct catagggaatc tggacagatt tgctgacaaa   8040
ccagcttttt tggattgctg gtgggtacac acactcaaat agcaagtaaa atttcacttg   8100
ttatttttgt acttagtagc ctgggtgagc aaaagatcag agcttgtaga cctcaggctt   8160
aatctgagat aatgaaatag ggctagtggt tgagccgagt gtattaattg tatctgctga   8220
tagcatctcc tgttgttgag gcagcccttc tgtaccagga tatccttgtc acaaagattt   8280
tgctctgatg cttgaaggca gactaaacag gaagataagt ttgttggatt tgggcatgta   8340
actcagattt ggggcacaga gttgtcctat ggaccatatt agctttcctc cccaccaact   8400
tggaagttct ggatgaatca aggttttacc tgcccattgc ttctgcacca tcagtacaaa   8460
taccagcaca ttaaagaagg caaataatgt ctttgaaagc tctgctctca cggaccatcc   8520
tttggtaacc gctagagtta ctcagttaga gtgactcagg tttctttttt cctcactgtg   8580
tcatgtggct tgtgggatct tagtttgcca accagggatt gaacctgggc ccagggagtg   8640
aaagcgctga gtcctaaaca ctgaaccacc agagaattcc taaggttgat cgtcttagtc   8700
agtgaaacta tcctgctgtg agtttatgat ctagggccca agatgcatta ttctacctct   8760
accatgttta gaatattcct gaggtacata gagtggcagt tgaataatgg tacaaggacc   8820
ttcacttttg ttttaattcc aacattttta ccaggacgct tgtaagtgtg tcatttttga   8880
aagaggtaca tttagaattt ttcttatgaa agtagtatca gtaaactttt tagtaaagag   8940
aagaaagaaa tttgcttgta atcctaccac acagataata tgctgataat attttggtag   9000
gtatccttcc agtccagtta tgtatgttta atttagtgcc tcccctccca aagaaggggt   9060
ggggggtaat agtgaaatat tagtaaacga aggtttaaag agacgttata gggcagggga   9120
taaagcattg caaaggagcc actgacaact cttttacctg agaattttct tgggtgactt   9180
```

```
ctgtgtatta atttataacg tagctgaacc tctaggaact accactgcct ggatacctgg   9240
ttattaaggt gatttctcca ttacccccaa gagctttagt tgcactcagc ttttacctta   9300
atccttgtac agctctgcag ggcaaacctt tctcagctcc gagcagtctt ttcaagtggg   9360
gccaaggagc caccctgagt caaaaaaaga gcattatgtc accggaagcc caagcccaga   9420
gaacacaagg tacggcacga taatcagtgg ccccactcgg gggtctttgc aaggagaccc   9480
taatgtctca ggtctagagc cgatccaact aatgcctctt ttgggggcca cacacagcag   9540
tgggatctta ctttcccagc tgaggatcag actcatggtc cttgcagtgg aagtgtggag   9600
tcttaaccac tggactgcca gtgaggtccc caactgatga tttttaagaa gagttacttt   9660
aacccactca ttgaggtcac actggatgac tccatttgcc tggaggcctc agtgagacct   9720
gtgtgttccc gtggccttgg cgtgccacca agggaaccat ctcttcagtg gtgttccctt   9780
tacagccaga cgcaccgcag taatagtggg tgctactgtg taagcccagc ttccaccctg   9840
agtgcacggt gggaccttgg ctgcccaggc catcctgtca gtgattcaga agttctcaga   9900
tttggtgggg gagggggcat agctataact gcgatttgtc acagaggcat taataggtgc   9960
tctgaaacat catttggcaa acaccggact acctccaagg tcatggtgct aagagatatg  10020
aaaccactat gtcgtggagg aaaggatgtt gttttttggt ggagaggatg ttgttttcat  10080
ctcggtacct ggtatgttgt ggggagttaa gagatacata tcgaaaggaa cagtgtatat  10140
gccacgttgg atagttggct ggtcttagtt tcttgttttt aaaggtgtag ttggggatct  10200
atagctactg gttttcagca gcgtgtagga gcctcactta atacctggtc acagagcttc  10260
ttgaagttca ccagactttt tgaaagtgtc aggcgggttt agatgtgtgc tatgccccag  10320
ccacctggag aggccactca gtcaaggatg caggaggga aagagtaagg gttacatgga  10380
tggggtgcct tggtttggag ccctgagatt ttggaggagg tgggacaggg caaaagaaag  10440
gcttgttctt gtgcctcggc tgcagcactt aggcacagga tttgagaagg agcagccctt  10500
ggtctgaaaa cctgcaaaaa ggtttctgat gaggactgca agtttctggc tcacgtgctt  10560
acctgatgag tcttcagaca ctgcctggaa gcttctcaag tctcttgtct ataatcagct  10620
aactaactga ctgagtttag ttgtaaagtc agcaatgagg aaaaataaag gtctgaacca  10680
ttgtgccctg ggtcaggctt gtgacctggg ctgattaatt acctggaaca gatggtcttt  10740
gttactgtga gtggtgtgct ttccagactt agatagggaa tgggtggagg gtcagaagat  10800
cagcctggaa aggatttgac aagcagtgtt aatttcttca tagtgcaata attttagagc  10860
caggctagga ctattgtggt tatccttggt ttgacgcaaa ttgctttgaa tgtgcctaag  10920
tccttctgac tgaaagtacc agatgtagtt aattcctggg gaaaaaaata ttttgcattc  10980
ttggttctgg ttggacttaa cctgtccagg gatgggtttt tttgcctctc agtgggctgg  11040
ggcatactgt ccagcttatg gtgaatcgag gaatggactt atgtgtccct gtgggttagt  11100
gaaacctagg actccaggac taggaggcta cctgaatagt ggtctccacg accaggaaag  11160
tcactttggg tttgggtggg gactgtgaag agagagtatg ggtaccacac cccatagcag  11220
atgtttatag ctttgagaca gcttttcaca aaaagatcta gattgaccat ggtactaagc  11280
taggggtgag ttgtctgtat ccctggaaga ttggcaagag attttgacaa aacttccttt  11340
tgaggaaact cctgcagtgc atgtaaatgg tgccatttac aggattagta ggggagttgt  11400
caagatagac attatcccag tgtgagggag gtgtgtgctt aacatgtgcc tgggaagtac  11460
attcattggg aatgtggttt tgacttattc tttggggtct ttcctacttg ctcatgataa  11520
tgtgagccca tggcccgact tgagcaccca cgtagccaga gtgtggcggg gctgcctgtg  11580
```

-continued gcttgtgcac agagcatgct tgttgagtta atgtgtaagc aggaagcagc ttctgtgcca 11640
agctatatat tagccattca ggcagatcac actctctcca gttcctctgg acccaagaca 11700
tcagaagcca tgtcgaagca ccacagcgac gccgggacgg ccttcattca gactcagcag 11760
ctgcacgcag ccatggccga cacattcctg gagcacatgt gccgcctgga catcgactca 11820
ccgcccatta cggcccgaaa caccggcatc atctgtacca tcggtgagcg cgggtgccca 11880
ctccccctga aacaagggct tcctgagaca gtgatctttt ctccccccaa aagactaaat 11940
gtagcaaacc tgggttctga gcaagatgct acagagagat tctcagggga aatgacgtca 12000
tggacttggt cgctcagacc tgtccaactc tgtgacccat ggactgtagc ccatgaggcc 12060
cctctgtcca tgggatttgt cagacaggaa tactggagtg ggttgccatt tccttcttca 12120
aactgagttc ataggaattt gcaggaagga attcatatgc tttatgtgtt ctgctaaagg 12180
taaaatttag agggtgtttt ccatggcagt tcttactgtc tctgagcatc tcagagacct 12240
aggaaagatc ttgtggactt gctctgttca accaaaatgc tgtagttgga catctgactg 12300
ggcttcaggg ctggctacat tttactttgg ttattaagag ttctttaaac tgaagcacac 12360
ttgaagtgtt aatcctcttt tggataatga acatttaatg actttcaaac ttttgttttg 12420
tttttctgga actaggccca gcttcacgag cagtggagac attgaaggag atgattaagt 12480
ctggaatgaa tgtggctcgt ttgaacttct ctcatggaac ccacgaggtg agccttgatg 12540
gtgtggcccc ttgggcagct tgtaggaaac agggtgggca tgctgtgttt atttagccac 12600
agtggaccag gcaggaagaa gtggggaatc aatgggaagg ttgtcttcac cagcccatcc 12660
ctaccgttct tccccccaga tccctgacat ctcaagtggc caagtctcct taagcaaaga 12720
tgacctgctt tgtcattggc catggttctc cccaacacct gtgctccgtt agcctttgat 12780
aaggaaagca tggaagggtt ttcctggaat cccctctaag ccatggggct tgacacttct 12840
gcaccagggt ttctataaca gctcataatt gcaatgatga accagtaagt caccctgcag 12900
gttattctgc ctattttcat tttagaccca tgataaatgg ggcaggtccc agagaagggt 12960
ttccactatt gcaagtgaag gactgggtcc tggtttgtag taccccactt catcaacatt 13020
gtgttcccag cctgtccctt cccaggagtt ctgggacatt aaaataaagt cagcacactt 13080
gtctagtgat ctgggaggag tatgttagca ctggggctgt ttatgagctg acttggcccc 13140
tgggaccagg tgacagctat tggaaagtgc tccactgtgc tgctattccc aagatcggaa 13200
caagctcatt ttgaggagtg tgtgggctgc ctgaggaaca gtgccatggg atttcatact 13260
ggcatcaata gaagactagt ggaggaggca agctcttgat cctcttggac tctgtatttc 13320
ctgttcagaa taaagaaaat gctgccctgt aaggtcacgg ggttaagggg ttgccctctg 13380
gcatttggaa gttggtgata agtttaaact aaaaataaag cctcagtaaa tgcagtccaa 13440
gaactgtatg cctcctttct ggaaacatga gagtgttcct cgtaggttcc ctaccccatg 13500
ttccataaac agcttatagc cttcaaatgt cacagggacc tgaccaagtt cagaggaact 13560
gcgctcagca ggcaccctgg ggcaggttaa gaagcccaca gatggcattc ttaattcccc 13620
aaaggtgaag agtcctccgc aacagtcact aggcattcct gcaggcctgt gcttagccca 13680
gagagagagc tagagacacc agtgaaggtc cattcacaat tgatccctcc tgctgacttg 13740
tgccagggtc tgctgtgtgc aggggaagga gcagaaataa gaaatagctt ttaggaagtt 13800
gacctttaac caggctttat ggcctcttcc atctggtaaa ataataccac ccagctctga 13860
aatggcaggg ggagagggtg gtatctgcac ctgttggagg gggctggctc aggggagttg 13920

-continued

```
gtgttttaaa ctacaagaag catttggtga ttatctgtgc tttgactctt attcccagag  13980
ttggaatttg ttttcttttt ccacactgta tggcaggatc ttagttcccc aaccagggat  14040
caaacaaacc cagggcccct gccttggagg cacagaatct taaccactgg accacctggg  14100
aagtcccttg tgggtttaat ttgaagtttt tgaccaggat gaagttatgt tgcccctgga  14160
atcagttttg gaaactgatc tgaaatatta gttatataat gtaaacagtt atagtttgac  14220
aaacttccac cttttggccg tttttaatac tctactaagc agaacattgg gtttgctttc  14280
tgtccttcac tcagacagag gaacatctac catctgatct cttttttttgg ttttgtttat  14340
ttggtttatt gcatctggcc ttttgacagc tttgccacag tgtctccagc cccgcttttt  14400
ggcagctctt gtgggcaaga cgtgtcgtat tctccggtgc cactcacccg gatggtggtg  14460
gttgaaggat gaggcctaca tcctgtgtta tcagcagtgt cacactgata gcactaggaa  14520
cttttgccat cttggctccg agtccctttt tagtcaaaca gtaatggcta atgggaaaga  14580
gaaagggctt ccagggtgag actgaagccg ggatttgttg caagtgagaa atagcaaagg  14640
tcagttagtt cagagaagcg tattcctacc tctccgtgtt ccgtttcctt ttctaatcag  14700
actggaggaa gtgattgtca gaaccaggcc tgcatgactt gagcaacata tttaacttgg  14760
gctgcgtcag cttaagtaaa taactgagtt tgaattgcgg ttgtaatcga tagagaagag  14820
ctcagaattg tcagatctgt cattctaact ctggtggcca gagcattatt atccagatac  14880
aaggtctttt accccagttg tctgctttgt ttgctgagaa tgtttgttga atcctagagg  14940
ctggaggggg aggaaacaag cctcttttat gttgacatgt gttgccacca aaaaccatta  15000
aagatatggg tgtaaatatt ctaaagttcc taagatttgc ccttagagtg gatgatggcg  15060
gtggagaagt gggtgaagag ctggtaggaa tctgctgtat agcacaggga gctcaacttg  15120
gtgctcgggg atgacaagaa gtgagtagag gcgaggaggt tgatgtaagc aggtagagga  15180
tgctcggtga tggaggcagt ggtctagaat cctggtgacc agcttcagcg ctaatcctag  15240
atcccgttgt gtgagatgac agatgtggag cttatcgtct cccctctttt cccctagtac  15300
cacgcagaga ccatcaagaa tgtacgtgaa gccacggaga gctttgcttc agaccccatt  15360
ctctatcggc cagtggcagt ggccctggac actaaaggac ctgagatccg aactgggctc  15420
atcaagggcg tgagtatctt ggggagaagc aggagagaag gcatagggga ccagaaagcc  15480
cagaagccac gtttctcaaa gtttaggtct ataaaggaga gttttatcca tcagtgtaga  15540
aagtcttcct ttgacctgct ttgctaagaa acagtaccag aaagaaacct cttttacact  15600
caaaatctac ttccaagtct tttagggagc agcttatctc ttcctcttta gtataactga  15660
aacactgcag gttattcttg ggttatttcc ttgaaatata ctaagttaga aaaggcttta  15720
ttgttccttc caactgaaat ttaatcctgg ttccctagag gaaaaagctg ttctcctgcc  15780
aggaaggccc agctttggac ttgtggctta ctctcttgtc tgctgcagag cggcaccgct  15840
gaggtggagc tgaagaaggg agccacactg aagatcaccc tggacaatgc ctacatggaa  15900
aagtgtgacg agaacatcct gtggctggac tacaagaaca tttgcaaggt ggtggatgtg  15960
ggcagcaaga tctacgtgga tgatgggctt atttctctgc tggtgaagca gaaaggtagg  16020
gacagaagtc ggtctgattg tttaaaacca gctcccatct ctaatttcct tgccagaaga  16080
taggaaggtt gtttggttgg cagagagact gaatctatat agtctcagga cttcctttct  16140
tttttcaaat aatctgttta tttatttata tttattttgg ctgcgttggg tcttagttgt  16200
agcacatggg gtctttagtt gcaacactgg actctgtggc acatgggctc attttttttat  16260
ggctcgaggg cttagtggct gtgcagcctg tgggatctta gttcccccac cagggatcaa  16320
```

actcacttcc tatgcattgc aaagtggatt cttaaacact ggaccaccag ggaagtccca 16380
ggagttcctt ttataatgaa ctcctatcct caaaaacaga tttcactcca gttcagttgt 16440
actcctggag agcaggtgag aagcgctttt acccatcctc actatttaaa gatttgcttc 16500
cctccttcat ccacttaaca tggtgtctat aggactccag tgtgcctggg aatgatggct 16560
aacctttaag tgatctgcag tgttctaagc tctttcttta catgtagatt tgtttaaatt 16620
ttgaaacaac ctaatgagta gatactatca tccctgtgga gctgagacac tgagaggctg 16680
atggacttgc tcacagttga attggagtgt gaaccctggc atgtggctcc accacccacc 16740
acgtgcccct tcccagttct ctcgactggg gagagcctgc ctcctggtgg ggacacctgc 16800
acccagggct cggcctcccc aacctgttcc attccataca ggtcctgact tcctggtgac 16860
ggaggtggag aacggtggct ccttgggcag caagaagggt gtgaacctcc ctggggctgc 16920
cgtggacctg cctgctgtgt cagaaaagga catccaggat ctaaagtttg gggtggagca 16980
gaacgtggat atggtgtttg cgtctttcat ccgcaaggct tctgatgtcc atgaagtcag 17040
gaaggtcctg ggagagaaag gaaagaacat caagataatc agcaaaatcg agaatcatga 17100
gggagttcgg aggtaagtcc cctgcctcct tcagccccaa ccaagctttc tgcagagcaa 17160
tatgtagcct gccacctgcc cattagaaat aacgtctcaa acttatttca gacccactga 17220
ctcagaatat cctatgacat tggtgggctt gccagatggc cctagtggta aagaccccac 17280
ctgccagtgt aggagttgtg agttctgtcc ttggactgag aagatcccct ggtgaaggga 17340
atggcaaccc actctagtat tcttgtctgg agtatcccat ggacagagga gcctggtggg 17400
caaccatcca tggcgtcgca aaagcagaca aaactgaagt gacttagtgc acacgcctga 17460
tactggtatt ggtatttcag gggggagaaa aaaggcttca cagatgattg gggtgccagc 17520
accttgacat tgttccaggg agcagcactg gagagggaca gggtcaccac cactcccggg 17580
ctcaagaacc gtgtgtagtg ttcctacact ggctacgttt gctggaattg gggggccacca 17640 aggggaaaga cagcaggctc tcaggaggag ggggctcctt ctcttggcaa gcagtgggat 17700
tgttggttgg ggcagctctg gcgtggcatc cacctccctg gggaaaacat gccgtcttcc 17760
tctggttctg cgtggtccca atcctgctcc actgcttccc cagtgctcac caggcagagc 17820
cacacgagtg aggccagctg ggtgacatct actcctgctt ggcctcccta ctgacagccc 17880
aggcttacat gaggggtcag gtgtgtgcat gggaagagtg ggaggagccg tgccgcccac 17940
tgttgcagcc ttgccatcct tagctttgtg tctgtgtccg ttgtacgggg aaattcaggg 18000
ccctccctct gccatcctga tgagccatgg gcacctgctg actttggctt caggccaggc 18060
aaggccatgt tcttgtgcct tcaacacact ggggagggac ctctgaagga gcagccttcc 18120
agtgtccttg actggaagag gccacggacc tttgtgtcaa gagcagtcag ccaccttggg 18180
ttccatttct gccccagcgg tgatgactga aatgcagatg gtagagacac ctcaagaggg 18240
acctcataag atgcaggtgg acactgagaa tggacttagg gttaccagag gggaacgatg 18300
ggaggaagga atggtcaggg agtttgggat ggacctgtac acgcttctgt atttaaaatg 18360
gatgacccac aaggactact gtagagcaca gggaactctg ctcggtgtta catggcaacc 18420
tgggtgggag gagggtctag gggagagtgg gtgcacatat gtgtatggct gagtcgctct 18480
gctgtgcatc tgaaaccatc aagacatggt taatagctat acctcagtat aaaataaaaa 18540
gttaagggaa aaaagacaga tggagaggaa gtgaacccat gggattttgg aggagacccc 18600
cctggcccct ccccttcccc tcagtgaagt gtccatcctg gtgctgaagg agtccagcga 18660

-continued

```
gcagaactgt tggcccettt gggggactga gacagctgga acacccctgt gatgatgtca  18720
tgggtacttg tcctggtgca agaatggcca agtcagagaa tcccgggaaa ctttgtgcca  18780
ccgtacgcga ggcccctgtt tgtataacct ctgtctctgc aacttgcctg tcaggtttga  18840
cgagatcctg gaagccagtg atgggatcat ggtggctcgt ggtgatctgg gcattgagat  18900
ccctgcagag aaggtcttcc ttgcccagaa gatgatgatt ggtcggtgca accgagctgg  18960
gaagcccgtc atctgtgcca cacaggtgtg tgcctctccc tgagcgtgca tccttgtaca  19020
aggaagctct ggaggctacc tggtctcttc ccatggaccc tgccccacat catacacaaa  19080
cctattcccc ccacctgccc ccacacacct acacaaagct ggattctgta catacatgct  19140
ctccaggggg tcaccttgtg tccaaagccc tcccaggcca catctcacaa atactgtgtc  19200
ccctcccaga tgctggagag catgatcaag aagcctcgcc ctacccgggc ggagggcagt  19260
gacgtggcca atgccgtctt ggatggagcc gactgcatca tgctgtccgg agagacggcc  19320
aaaggggact accccctgga agctgtccgc atgcagcacc tggtaagttc tcccgctgcg  19380
ggtggaggca aactccagca tatgggggca ccttgtagtg tcaccctctg tgccctcgat  19440
cttttattgt cctccaagtc acacgcagag tgaggaggtg tgtgctggag tcatgggggt  19500
gtcttttttg atgggttttt ttttttgctc ttctgccttc ctgcccacac ccatctccta  19560
gtcccttctg ttctggaggc ggcctccttc atcacacgta gcacagttca ctcccatctt  19620
cggggtgtga atccttcctt tgcttgagtc ctgggatatc tgtactgctt cccccctggac  19680
agtctagagg acctgagccc ttcttccctg ttctggaaaa gtccaagagc tcctgctccc  19740
agctggcctg tgtttggctt ccattttgat tccccacctg tcccagccag tgcctccccg  19800
acggggtcct ctgggcctgc actgatttgg ctgtgagctg gccttgcatg gtacctgcag  19860
cagcgcctgc tttgctgagc tgttgcactc accctagcag tggggtttaa gggaggggtg  19920
acaggcccac aaatagaagc aggtggaagg ctggctgatc ccagctggcc ctggggtgag  19980
agtgtctgga ggagccctag tggccgctcc tcattctcct gtgggagcta gcttttccag  20040
ggtcttctgc tggaccatgt cccacagcct ggctgcctct gctctaaagc atcctaaaga  20100
ggaacacagg cctggggaaa cgagcgctac agatggactt tcacaagggt cctaggtggc  20160
tgttgataat gtatagctca gcaaactgtt tctttaaccc tcctgttcat tttccagcca  20220
gcaaaggacc ccaggccctt tgtgtgacat ccctccaatg catcctcccc caaaaaaacct  20280
ctggactaga taccatcctt tccttcttca ctttctaagt gattaggctc aagtggcttc  20340
caaagaagac atgacagtca cagtggatac tttctcaggg gtgaaacaag acatcttgac  20400
tacagatgtt ttctggtctg tccttggtgt tctgggtgga tttgccccta atgaaatcag  20460
tagagaccag tgtctgccct tgggacagct gtgtttttct ggctgatggc cacccccctgt  20520
gtgacatgac tgctgtcctg atgctcatgc actgcaggct cacggttctt ctcacctgtc  20580
ccagtgagta cttcctctct cctgggagat agtgaccttg aaccagtccc ctctagagtg  20640
gttgatgtta gtgtttatgg gtttccatat agaattatat acatatactg taacgataac  20700
tgctttgctt agtcatgtgg ccccacggcc tctgagacct tgacacgtta gactttaggg  20760
actttgtgtc tttgggcaca tcattggacc tctcaaggcc ttatctaaga agtgaattag  20820
atgggatatg tttaattaca ccctttgcgt taaattgcac tgctgttata aaatgtctgc  20880
taagaacctc atgcaggttc ttaacctcag tgaggtcaat gtcaacccac ttctaatgga  20940
tgagggcaca tgataatcga gcttgagttt ggacccaggt cagctgactc tgaagccagc  21000
attccctctt agaacacatc tagcagatca ggacaggtgt cctgtggggc ctgtcctggg  21060
```

gtcagagact aaaccagact ccgggctctg caagcatgtc tgtttttcca aacccaatct 21120
tttctttgaa caaacacctt agaactgtga gactgggatt gcatggccct attcaggagg 21180
tgagttctcc tggccgtgtc accagttaac actggccaat agcttcccct cttaactgtc 21240
cactgctttc tcctgtaact gacgcaattg acgttcttaa ctatgggcta ggtagtacca 21300
gctgtggttc tctttcctgt tcatgtgccc tgtcctcctg ggctgcatgc attccattct 21360
tgcaggaaga aaccctttaa cctagcaaat tcagccactc attggctcat cctgtcagat 21420
taatgagatg gcgttactga ttcttccctc acccatcatt gtctaagacg ctcataactg 21480
cattataacc ctctaaagct taagttttct aattcttggt gttacctgag caagatggtc 21540
tgaataacac agtggctttc tcatgggtgt tttaatcatt caattttaat caaatgcctt 21600
ggtaagctta cctgtgtgct tccacaggca cctgactctt cacatggctg ttcgttgtgc 21660
cccttacaag cttgccagtt tccagctgcc cgcttagaat gtggtcaagc tgcgtgtcct 21720
tggctttgac cccagctttc tagcgctgct caatgtgctt ctgccgcagg ccactggaga 21780
ggcaggcagc atctctgtgt ctgaagccaa gcaagcactc catgtgtgca tggaggaggc 21840
caggcacgaa gccctgtggt aactaggcag ccatgtgagg aggggggcct attccttcct 21900
gcgagctatg tcatgaggca gtgtggtcga gtcctgccag ggagccgtgg aggggcccca 21960
gcctccgcat gtttctatgc tgaggcgtta gagcctgccg tcatattgtc tccctcaccc 22020
ccaccgccag tcatggagac ctaccaaaat caagagatcc ttccagaatg gaagaaccag 22080
tttcctctct gatggaggag gaacagtagc cattgacgct tgaacttccc tgagcaggct 22140
ttcaccaccc tgcctctttg catctgcctg aaggagagac ttagccaatt aacctacagt 22200
accttcctct cattaattcc ccgttctgtc tttccatgtt gttgtctctt gtttgtttcc 22260
ccccaccctc cttcttccct cttccttgcc tcccctcctc taaaccttac agatagctcg 22320
tgaggctgag gcagccatgt tccaccgcaa gctgtttgaa gaacttgcgc gagcctcaag 22380
tcactccaca gacctcatgg aagccatggc catgggcagc gtggaggctt catataagtg 22440
tttagcagca gctttgatag ttctcacgga gtctggcagg tagggccccg agggcaggta 22500
actctgtagg ataaacagcc ttttgctcca gccactctag acgacagcca gggcccagcc 22560
ctgagcctag gacgctcctc tcgtctgcag gaagccagcc agggaggtca gggcaggaca 22620
gggccacagg atcctccggc tcagaaggca cagccatgtc acaggcacct ggtgaggggc 22680
tggttcctgc aagtctcgat ctcactcagc tcagaacctc cagtgatcgg gctgttcttg 22740
gccactgtac ccagggactt gctcctcccc agctgtctgt gcgactcttc ccctccccgt 22800
cccgtgtgac acggctctga cagctctgtc cccctcgtcc ctctggacgg atgttgcccc 22860
tagattgccc gtgaggcaga ggctgccatc taccatttgc aattgttcga ggagctccgt 22920
cgcctgtcac ccattaccag cgaccccacc gaagctgccg ctgtgggggc cgtggaggcg 22980
tccttcaagt gctgcagtgg ggccataatc gtcctcacca agtctggcag gtaggaggtg 23040
gcagcaggtc cctgggaatg ccccgctcag cggcccccttt ccttgggggt cctgggagcg 23100
tgtactgcac ggtgctcaga tggcattgag ccaaggtaag acccctctgc ctgcaccccg 23160
gaccctgcag ggaaggagcc ccctccccct cccccaccca gccccccagg cggcacttag 23220
tgggtccaaa gcgagtttta ttaaccctca caacgagcta gacttaatca gataactaca 23280
ggtagcctga ggacaagtgg ttatttgata ttgaaaagct gttcttaaaa aggaaaggac 23340
caccagtttt acttctagct aagtgctctt taaaaaagtc cagtttgcaa aatgagtttg 23400

-continued

```
caaaaaaagt ccagtttgct gacagtgcta tttggttggt gtgcctgtcc catctgtctt  23460
tgagtcccac agataagtgg gtgctgccta ggaaaggtca ctgtgctatc ttgctggcac  23520
tcgggccagg caaccagtct gagacctcta cttggcctct ggcttgagtc ccttccaaat  23580
ccaggatctc aagttaatac cccttgctcc ctgggtctgg gggtatgctg ctcctccctg  23640
gggcagctag ggtttcctgg aggagggagg tggagaggag cagacaggca cccccgtacg  23700
ccaaggagca gcagctggga ctgcctttag gaccaggaca caagatgtgt gccgagtccc  23760
gcagtagagg gcttagggta aaaagctcca gccgttaggg ttgacctttg tgaaaaggtc  23820
caacctttgc tacttggcta tttttagtcc agtcttctgg ggtttcactc tcagtgagtc  23880
ctgacttcag cacttgcttc cctcagaaaa ccttgtatgg aggccaggcc ttaagcaggg  23940
catcctctgc tgtgacatgg cttaagtttc cctgacagct gttgcgtgtc ctcacagctt  24000
gccttctgag cctcgggtcc cctgccagca gccccctcca actcctgaga caccagctcc  24060
taccagtgta cagtgtcagt gttgaaggaa gcatccagcc tttgagttta aaggggccca  24120
gtcccctcca ggggatcctt cataggcaga gcctcccccg ctgacactcc atcccctagt  24180
actgccttct gggtagcact tatatttcta atcctcagcc tcgcttagat actcaggttt  24240
gactctgggg ctctacagcc cagttgctgg gactatttca ggggcctggg ggtcatgtgg  24300
agtcaggaga gggcacagca gtaggcaagg cttgtcttgt agatttccca ggcaggctgg  24360
tggtctctgc tcctggtttg ggtttttttt tttttttttt tgcagatgtc aagtgtcagg  24420
tggtcttcac atgctgcttg gcttgtagct gttgctggca gcaagagaaa aggatgtggt  24480
gggcttggac agggctgctt ccctgtgcca gaatgggaaa gttcagggaa tggtgggggg  24540
tctgccaagt atgggccatg tggagtaagt gggtaagact gaccatgctg ggtcagtatg  24600
atcctgcggc cctggcctgt aggaggggtt tagggtagca tagctctaaa gaatatgcta  24660
tggcagatac agggtgatgg gacacctcag tcttgggagc aaatgttgaa atggtcagag  24720
cctcaggctg gcagagttgg attccagggt gagttgttgc tgaaggccct gaggggactg  24780
tttaaccatc ttgtctgcct accccatctc aggtctgcac atcaggtggc cagataccgc  24840
ccccgggccc ccatcattgc tgtgactcgg aatcaccaga cagctcgcca ggcccaccta  24900
taccgcggca tcttccctgt ggtgtgtaag gacccagtgc aggaggcctg ggctgaggac  24960
gtggatctcc gggtgaactt ggccatgaat gttggtgcgt gtctgggaga gaaagctccc  25020
ggtggagggc tggggaaggt gctagagcac tggcttctct gagaccctat tgaaagagga  25080
acatgccagc ctttgtgggc aagagctggc ctcactagga atgttctctg gttccttccc  25140
agtccctgga gtcctgggct acgctcaggg cagggagagg acctttgacg tgtggggctg  25200
agcagcccag gttctcacct cacgttcttt gggagtggga tccaaagcaa aggatcctgg  25260
ataatcacct ttgtccattc tttggcactt gctcattatt gaggtttttt ttttcttccc  25320
tataaaatta accagatctc ctacacttgg ggccagtaca catttagatt atgtactcaa  25380
atggcctttg tcacagtata aaagtaggat gtcacaggat gagaggaaac agcgagctgt  25440
gaccttgggc tgggctctcc accttcttga gtagaaaata aatgatgtcc aaaggtccct  25500
gctacctctg ccatctgagt gataaggaaa taataccaag gcctccctca ttccctttgc  25560
ctgggctgtg agcctggcgc caccttgtgg tgtaagaaag taaaggcctg tcagcccttc  25620
ctcagttgtg gggcactcca atactttggc cacctcatgt gaagagttga ctcattggaa  25680
aagactctga tgctgggagg gattgggggc aggaggagaa ggggatgaca gaggatgaga  25740
tggctggatg gcatcgactc gatggacatg agtttgagtg aactccagga gttggtgatg  25800
```

-continued

```
gacagggagg cctggcgtgc tgcgattcat gaggtcgcaa agagtcggac acgactgagt  25860
gactgaactg aactcccaag tgtatacctt cttggcttaa tttttcattt accagctctc  25920
ttctcttctt ccaggaaagg cccgaggctt cttcaagaag ggagacgtgg tcattgtgct  25980
gaccgggtgg cgccctggtt ccggcttcac caacaccatg cgtgtagttc ctgtgccatg  26040
atggactccg aagcccctcc tccagcccct gtcccacccc tcttccccaa accatccgtt  26100
aggccagcat tgcttgtagt gctcacttgg ggctgtaatg tggcactggt gggctgggac  26160
accagggaag aagatgaata cctctgtgaa acctggctgg ttttaagact ttgcttgggt  26220
cgggtagttc agagctgggc cactcatcac gtggctgcat ccaagcaggg gatgcaggag  26280
ggatgcaggc aggactggag gctccagagc ttcacacaca gggcaacagc tcctgcttcc  26340
cttcctttgt atacccgatt cagctcctgc agaaaatgga tatccagaga attcccagcc  26400
ctggcccgtg atcaagagta ggggccttag ggcatggggc agtggttcca gtttaagtag  26460
actctggccc tggcccttac ttgcttctcc aaccccctca gcctccctcc ccttgtgcac  26520
cgtatacttc tcttccttca ctccacccag ccgatgctgc aaacactcca ccccccatct  26580
tccatttccc ccactactgc agctgcctcc aggcttgttg ctatagagcc tacctgtatg  26640
tcaataaaca acagctgaag cacc                                          26664
```

MODULATING LACTOGENIC ACTIVITY IN MAMMALIAN CELLS

CROSS REFERENCE TO RELATED APPLICATIONS

This application is a continuation of International Patent Application No. PCT/US2019/024774, filed Mar. 29, 2019, which claims priority to U.S. Provisional Application No. 62/649,963, filed Mar. 29, 2018, the contents of each of which are hereby incorporated by reference in their entireties.

SEQUENCE LISTING

The present application contains a Sequence Listing which has been submitted in ASCII format via EFS-Web and is hereby incorporated by reference in its entirety. Said ASCII copy, created on Sep. 29, 2020, is named 00B206_0953_SL.txt and is 444,572 bytes in size.

1. FIELD OF INVENTION

The present disclosure relates to methods and compositions for producing a product of interest, e.g., a recombinant protein. In particular, the present disclosure is directed to mammalian cells expressing a product of interest, where the cells (e.g., Chinese Hamster Ovary (CHO) cells) have modulated lactogenic activity. The present disclosure is also directed to methods and compositions for modulating pyruvate kinase muscle (PKM) expression (e.g., PKM-1 expression) in a mammalian cell to reduce or eliminate the lactogenic activity of the cell, as well compositions comprising one or more cells that have reduced or eliminated lactogenic activity and methods of using the same.

2. BACKGROUND

Chinese hamster ovary (CHO) cells have been widely used in the production of therapeutic proteins for clinical applications because of their capacity for proper protein folding, assembly and post translational application. Normally, CHO cells, like other immortalized cell lines, tend to consume glucose and generate lactate through aerobic glycolysis, a process known as the Warburg effect (Warburg, 1956, Science 123(3191):309-14). Accumulation of lactate in the production culture can adversely affect cell growth, viability and productivity. Such lactogenic behavior (i.e., lactate generating behavior) of CHO cells during manufacturing processes can cause a decline in viability and productivity and can alter the quality of the produced therapeutic proteins.

Several approaches targeting the process conditions have been developed to mitigate lactate generation in lactogenic CHO cell lines. For example, optimizing copper levels has been shown to be effective in preventing lactogenic behavior in some CHO cell lines (Luo et al., 2012, Biotechnol. Bioeng. 109(1):146-56; Xu et al., 2016, Bioprocess Biosyst. Eng. 39(11):1689-702). Another approach involving controlled nutrient feeding triggered by rising pH in culture (High-end pH-controlled Delivery of Glucose, or HIPDOG) has also been shown to be effective in reducing or eliminating lactate accumulation in large scale CHO cultures (Gagnon et al., 2011, Biotechnol. Bioeng. 108(6):1328-37). However, these approaches have their limitations as the former approach cannot apply to all lactogenic CHO cell lines, and the latter can complicate the process of large-scale manufacturing. Furthermore, these approaches do not target the underlying mechanisms of lactogenic behavior in CHO cells.

Therefore, there is a need in the art for techniques for reducing lactate production in cell cultures.

3. SUMMARY

The present disclosure relates to methods, cells and compositions for producing a product of interest, e.g., a recombinant protein. In particular, the methods, cells and compositions described herein include improved mammalian cells expressing the product of interest, where the cells (e.g., Chinese Hamster Ovary (CHO) cells) have modulated lactogenic activity. The methods and compositions described herein modulate the lactogenic activity of mammalian cells, and thus reduce or eliminate the undesired effects associated with the lactogenic activity, e.g., reduced viability and productivity of the mammalian cells and altered quality of the produced products of interest.

This disclosure is further directed to methods and compositions for modulating pyruvate kinase muscle (PKM) expression (e.g., PKM-1 expression) in a mammalian cell to thereby reduce or eliminate the lactogenic activity of the cell, as well cells having reduced or eliminated lactogenic activity and methods of using the same.

In one aspect, the present disclosure relates to a mammalian cell having reduced or eliminated lactogenic activity, in which the expression of a pyruvate kinase muscle (PKM) polypeptide isoform, or isoforms, is knocked down or knocked out. In certain embodiments, the PKM polypeptide isoform knocked out or knocked down is the PKM-1 polypeptide isoform. In certain embodiments, the PKM polypeptide isoforms that are knocked out or knocked down are both the PKM-1 polypeptide isoform and the PKM-2 polypeptide isoform. In certain embodiments, the lactogenic activity of the mammalian cell is less than about 50%, e.g., less than about 20%, of the lactogenic activity of a reference cell. In certain embodiments, the reference cell is a cell that comprises one or more wild-type alleles of the PKM gene, e.g., both alleles of the PKM gene are wild-type or unmodified. In certain embodiments, the lactogenic activity of the mammalian cell is determined at day 14 or day 15 of a production phase. In certain embodiments, the mammalian cell produces less than about 1.0 g/L or less than about 2.0 g/L of lactate during a production phase, e.g., produces less than about 1.0 g/L or less than about 2.0 g/L of lactate during a production phase in a shake flask. In certain embodiments, the mammalian cell produces less than about 2.0 g/L of lactate during a production phase in a bioreactor. The present disclosure provides a mammalian cell comprising an allele of a PKM gene that comprises a nucleotide sequence selected from the group consisting of SEQ ID NOs: 39-41, or comprises the nucleotide sequences set forth in SEQ ID NOs: 37 and 38. The present disclosure further provides compositions comprising one or more cells, e.g., mammalian cells, disclosed herein.

In certain embodiments, the mammalian cell comprises a nucleic acid sequence encoding a product of interest. In certain embodiments, the nucleic acid sequence is integrated in the cellular genome of the mammalian cell at a targeted location. Alternatively and/or additionally, the nucleic acid encoding the product of interest is randomly integrated into the cellular genome of the mammalian cell. In certain embodiments, the mammalian cell is a CHO cell.

In certain embodiments, the product of interest comprises a protein, e.g., a recombinant protein. In certain embodiments, the product of interest comprises an antibody or an antigen-binding fragment thereof. For example, but not by way of limitation, the antibody is a multispecific antibody or an antigen-binding fragment thereof. In certain embodiments, the antibody consists of a single heavy chain sequence and a single light chain sequence or antigen-binding fragments thereof. In certain embodiments, the antibody is a chimeric antibody, a human antibody or a humanized antibody and/or a monoclonal antibody.

In another aspect, the present disclosure relates to a method for reducing or eliminating the lactogenic activity in a cell. In certain embodiments, the method includes knocking down or knocking out the expression of a pyruvate kinase muscle (PKM) polypeptide isoform. In certain embodiments, the method includes administering to the cell a genetic engineering system, in which the genetic engineering system knocks down or knocks out the expression of a pyruvate kinase muscle (PKM) polypeptide isoform. In certain embodiments, the genetic engineering system is selected from the group consisting of a CRISPR/Cas system, a zinc-finger nuclease (ZFN) system, a transcription activator-like effector nuclease (TALEN) system and a combination thereof. In certain embodiments, the method results in the cell having a lactogenic activity that is less than about 50%, e.g., less than about 20%, of the lactogenic activity of a reference cell. In certain embodiments, the reference cell is a cell that comprises one or more wild-type alleles of the PKM gene, e.g., both alleles of the PKM gene are wild-type or unmodified. In certain embodiments, the lactogenic activity of the cell is determined at day 14 or day 15 of a production phase. In certain embodiments, the cell produces less than about 1.0 g/L or less than about 2.0 g/L of lactate during a production phase, e.g., produces less than about 1.0 g/L or less than about 2.0 g/L of lactate during a production phase in a shake flask. In certain embodiments, the cell produces less than about 2.0 g/L of lactate during a production phase in a bioreactor.

In certain non-limiting embodiments, a genetic engineering system for use in the present disclosure is a CRISPR/Cas9 system that includes a Cas9 molecule, and one or more guide RNAs (gRNAs) comprising a targeting domain that is complementary to a target sequence of the PKM gene. In certain embodiments, the target sequence is selected from the group consisting of: a portion of the PKM gene, a 5' intron region flanking exon 9 of the PKM gene, a 3' intron region flanking exon 9 of the PKM gene, a 3' intron region flanking exon 10 of the PKM gene, a region within exon 1 of the PKM gene, a region within exon 2 of the PKM gene, a region within exon 12 of the PKM gene and combinations thereof. In certain embodiments, the one or more gRNAs comprise a first gRNA comprising a target sequence that is complementary to a 5' intron region flanking exon 9 of the PKM gene and a second gRNA comprising a target domain that is complementary to a 3' intron region flanking exon 9 of the PKM gene. In certain embodiments, the one or more gRNAs comprise a first gRNA comprising a target sequence that is complementary to a region within exon 2 of the PKM gene and a second gRNA comprising a target domain that is complementary to a region within exon 12 of the PKM gene. For example, but not by way of limitation, the one or more gRNAs comprise a sequence selected from the group consisting of SEQ ID NOs: 33-34 and 42-43, and a combination thereof. In certain embodiments, the expression of the PKM polypeptide isoform is knocked out or knocked down, and the lactogenic activity in the cell is eliminated. In certain embodiments, the PKM polypeptide isoform is a PKM-1 polypeptide isoform or a combination of the PKM-1 and PKM-2 polypeptide isoforms.

In certain embodiments, a genetic engineering system for use in the present disclosure is a zinc-finger nuclease (ZFN) system or a transcription activator-like effector nuclease (TALEN) system. In certain non-limiting embodiments, the genetic engineering system includes an RNA selected from the group consisting of a short hairpin RNA (shRNA), a small interference RNA (siRNA) and a micro RNA (miRNA) and the RNA is complementary to an mRNA expressed by the PKM gene. In certain embodiments, the mRNA expressed by the PKM gene encodes a PKM-1 polypeptide isoform. In certain embodiments, the expression of PKM-1 polypeptide isoform is knocked down, and the lactogenic activity of the cell is reduced. In certain embodiments, the genetic engineering system further comprises a second RNA selected from the group consisting of a shRNA, an siRNA and a microRNA miRNA, wherein the second RNA is complementary to a portion of an mRNA expressed by the PKM gene that encodes the PKM-2 polypeptide isoform. In certain embodiments, the expression of PKM-1 and PKM-2 polypeptide isoforms are knocked out or knocked down, and the lactogenic activity of the cell is reduced.

In a further aspect, the present disclosure provides methods for producing a product of interest, e.g., from the cells disclosed herein. For example, a method of producing a product of interest comprises culturing mammalian cells to produce the product of interest, wherein the mammalian cells have reduced or eliminated lactogenic activity. In certain embodiments, the present disclosure provides a method of culturing a population of mammalian cells expressing a product of interest, wherein the mammalian cells have reduced or eliminated lactogenic activity. In certain embodiments, the reduction or elimination of lactogenic activity results from knocking down or knocking out the expression of a pyruvate kinase muscle (PKM) polypeptide isoform in the mammalian cells. In certain embodiments, the PKM polypeptide isoform is the PKM-1 polypeptide isoform. In certain embodiments, expression of the PKM-2 polypeptide isoform is also knocked down or knocked out. In certain embodiments, the method can further comprise isolating the product of interest from the cell culture.

4. BRIEF DESCRIPTION OF THE DRAWINGS

FIGS. 1A-1F. Lactate levels of mAb-1 cell line directly correlate with the PKM-1 levels. Percent cell viability (FIG. 1A), day 14 titer (FIG. 1B), and lactate levels (FIG. 1C) in mAb-1 cell line under low and high lactate processes. (FIG. 1D) PKM-1 and PKM-2 western blot analysis of mAb-1 cell lysates at different days during production under the low and high lactate processes. Actin was used as the loading control. Quantification of relative PKM-1 (FIG. 1E) and PKM-2 (FIG. 1F) levels, normalized against Actin.

FIGS. 2A-2F. Lactate levels of mAb-2 cell line directly correlate with the PKM-1 levels. Percent cell viability (FIG. 2A), day 14 titer (FIG. 2B), and lactate levels (FIG. 2C) in mAb-2 cell line under low and high lactate processes. (FIG. 2D) PKM-1 and PKM-2 western blot analysis of mAb-2 cell lysates at different days during production under the low and high lactate processes. Actin was used as the loading control. Quantification of relative PKM-1 (FIG. 2E) and PKM-2 (FIG. 2F) levels, normalized against Actin.

FIGS. 3A-3E. CHO cells do express PKL/R enzymes, but levels of these enzymes do not correlate with lactate levels in production culture. (FIG. 3A) Western blot analysis of intracellular expression of PKL/R proteins in two different CHO host cell lines (K1 and DHFR−/−) as well as human 293 cells. Actin is used as loading control. (FIGS. 3B and 3C) Intracellular protein levels of PKL/R at different days during the low and high lactate production processes of mAb-1 (FIG. 3B) and mAb-2 (FIG. 3C) cell lines. (FIGS. 3D and 3E) Quantification of relative PKL/R levels normalized against Actin in mAb-1 (FIG. 3D) and mAb-2 (FIG. 3E) cell lines.

Figure 4A:
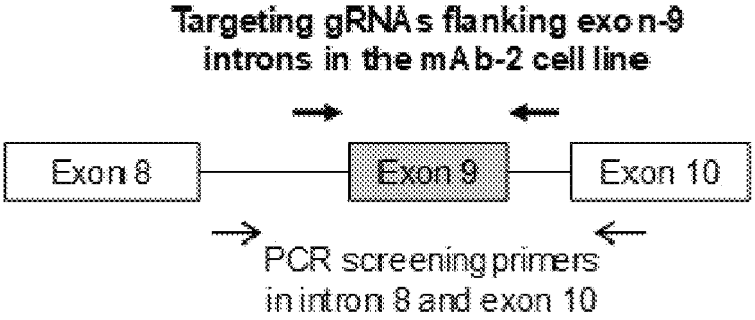
Figure 4B:
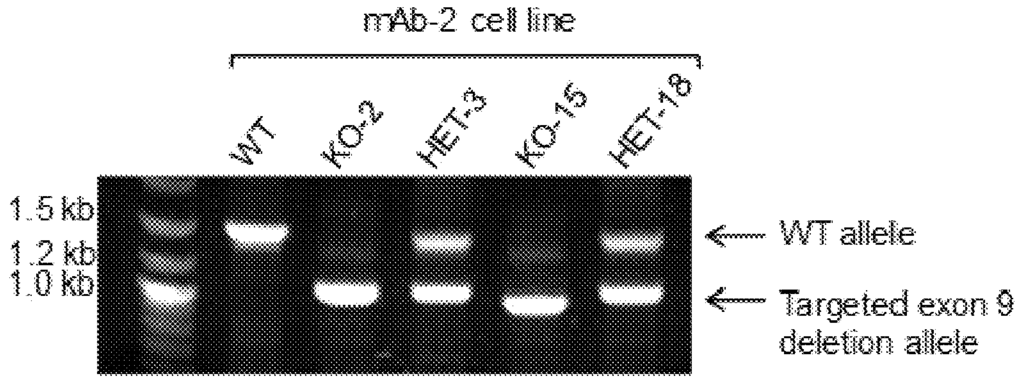
Figure 4C:
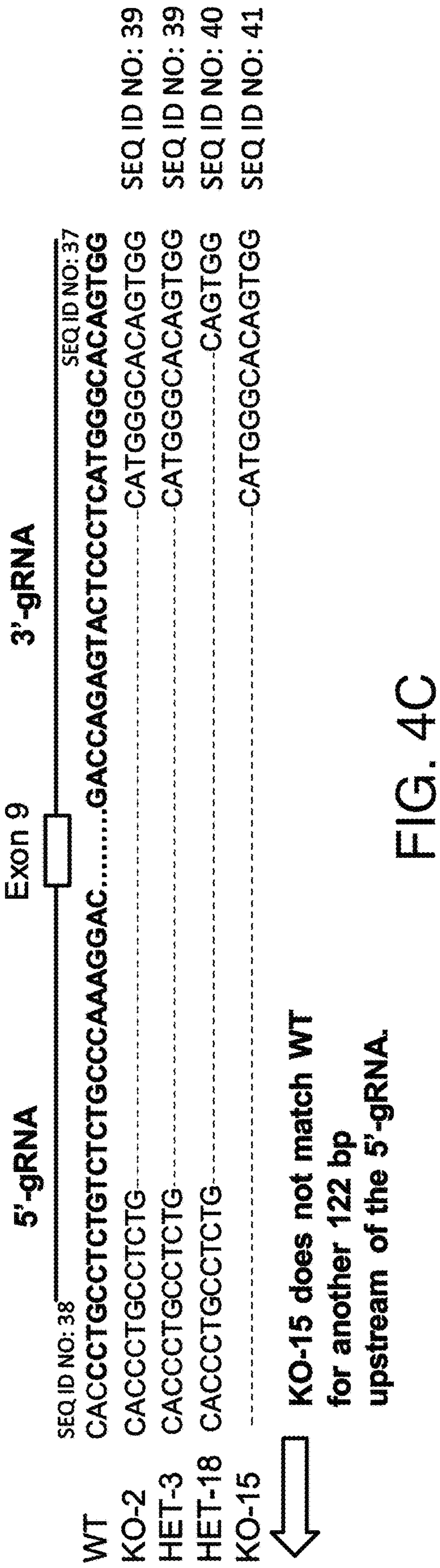

FIGS. 4A-4C. Generation of PKM-1 knock out cell lines. (FIG. 4A) Schematic of exons 8-10 of PKM gene and gRNA and screening primers used to evaluate deletion of exon-9 in mAb-2 cell line. Two gRNAs flanking the exon 9 of PKM gene were co-transfected with Cas9 transgene to induce exon 9 deletion. Transfected cells were single cell cloned. PCR primers flanking the deletion region were used to screen cell lines with successful deletion of exon-9 in PKM allele(s). (FIG. 4B) Wild type (WT) mAb-2 cells and cell lines with targeted deletion of exon-9 via gRNAs and Cas9 transgene were analyzed by screening PCR primers. Upper band represents WT PKM allele(s) while lower band represents PKM allele(s) with exon 9 deletions. KO: knock out cell lines, HET: heterozygous cell lines. (FIG. 4C) Sequence comparison of PKM WT allele in contrast with exon-9 KO allele(s) in targeted cell lines. Note that KO-15 cell line bears larger than intended (by 122 bp) deletions in 5' region of exon-9 in targeted PKM allele(s).

FIGS. 5A-5H. Abolishing or reducing PKM-1 expression averted lactogenic behaviors in mAb-2 cell line even under high-lactate process. Viable cell count (FIG. 5A), Percent cell viability (FIG. 5B), day 14 titer (FIG. 5C), day 14 specific productivity (FIG. 5D), and lactate levels (FIG. 5E) of WT, and PKM-1 HET and KO mAb-2 cell lines during a 14-day fed-batch production assay using AMBR15 bioreactors. Process control was the same as the high lactate process in FIG. 2. (FIG. 5F) Western blot analysis of cell lysates of indicated cell lines for PKM-1 and PKM-2 proteins. Actin is used as a loading control. (FIGS. 5G and 5H) Antibody product qualities including percent aggregation (FIG. 5G) and percent charge variant (FIG. 5H) of mAb-2 from indicated cell lines.

FIGS. 6A-6G. Lactogenic behavior is averted or reduced in PKM-1 KO or HET mAb-2 cell lines, using the high-lactate process, irrespective of cell age or post thaw. Viable cell count (FIG. 6A), percent cell viability (FIG. 6B), day 14 titer (FIG. 6C), day 14 specific productivity (FIG. 6D), and lactate levels (FIG. 6E) of indicated cell lines, at a young cell age, in a 14-day fed-batch production assay using AMBR15 bioreactors. (FIGS. 6F and 6G) Antibody product qualities including percent aggregation (FIG. 6F) and percent charge variant (FIG. 6G) of mAb-2 from indicated cell lines. Process control was the same as in FIG. 5. Error bars represent standard error from four individual experiments.

Figure 7:
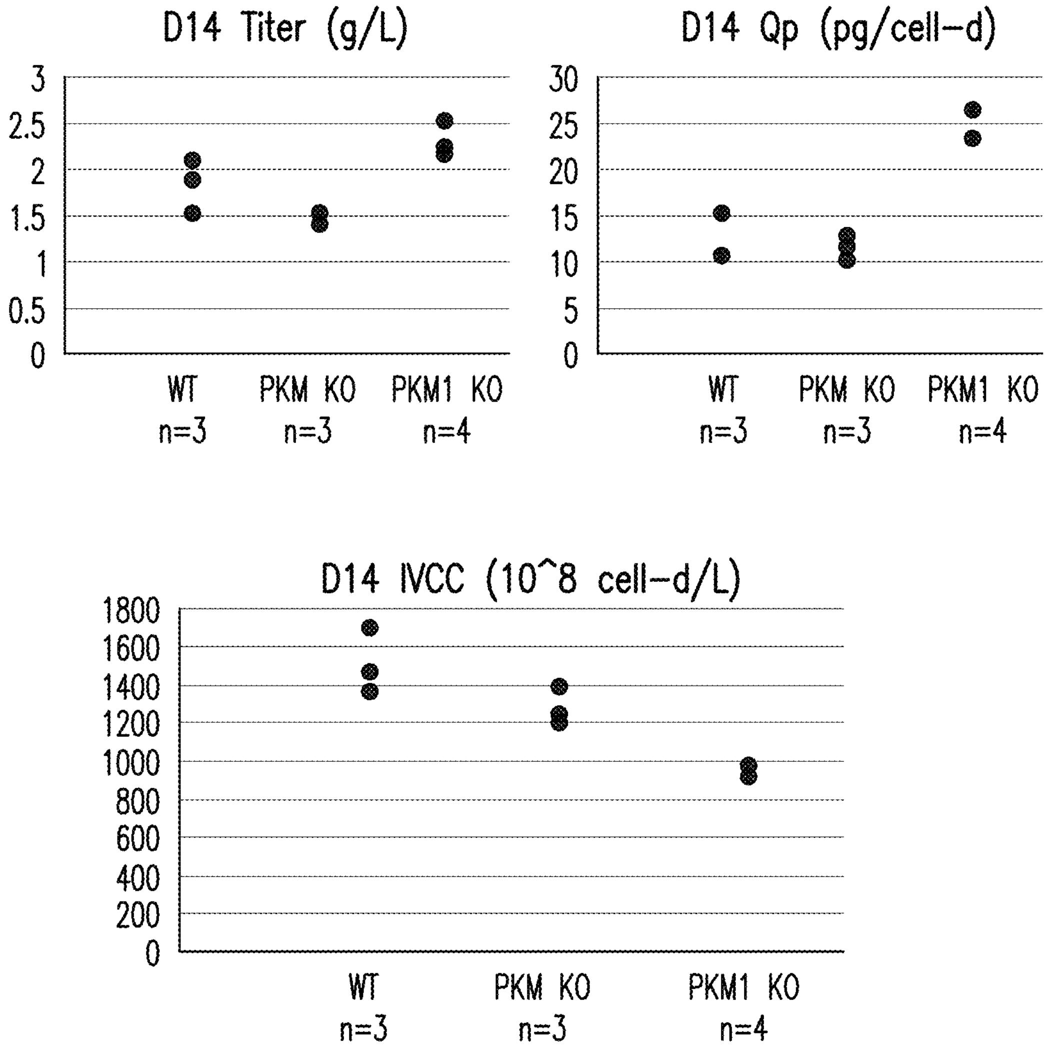

FIG. 7. MAb-3 producing pools derived from PKM and PKM-1 KO host cell lines had comparable or higher Qp and titer, but lower growth (in shake flask production).

Figure 8A:
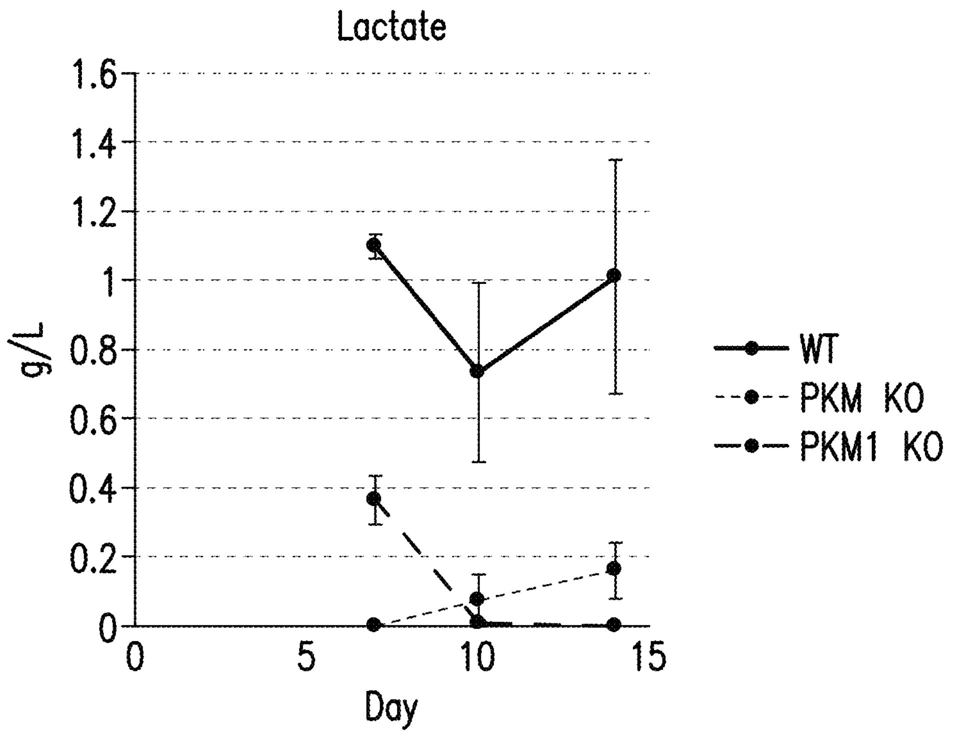
Figure 8B:
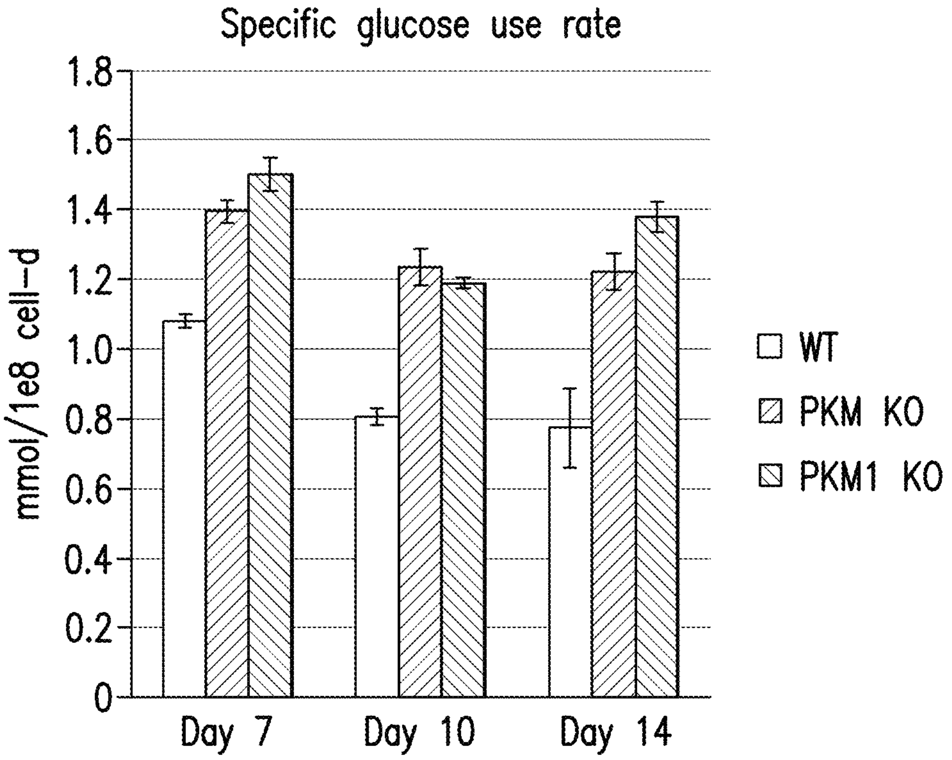

FIGS. 8A-8B. MAb-3 producing pools derived from PKM and PKM-1 KO host cell lines generated lower lactate (FIG. 8A), but consumed more glucose (FIG. 8B) in shake flask production.

Figure 9A:
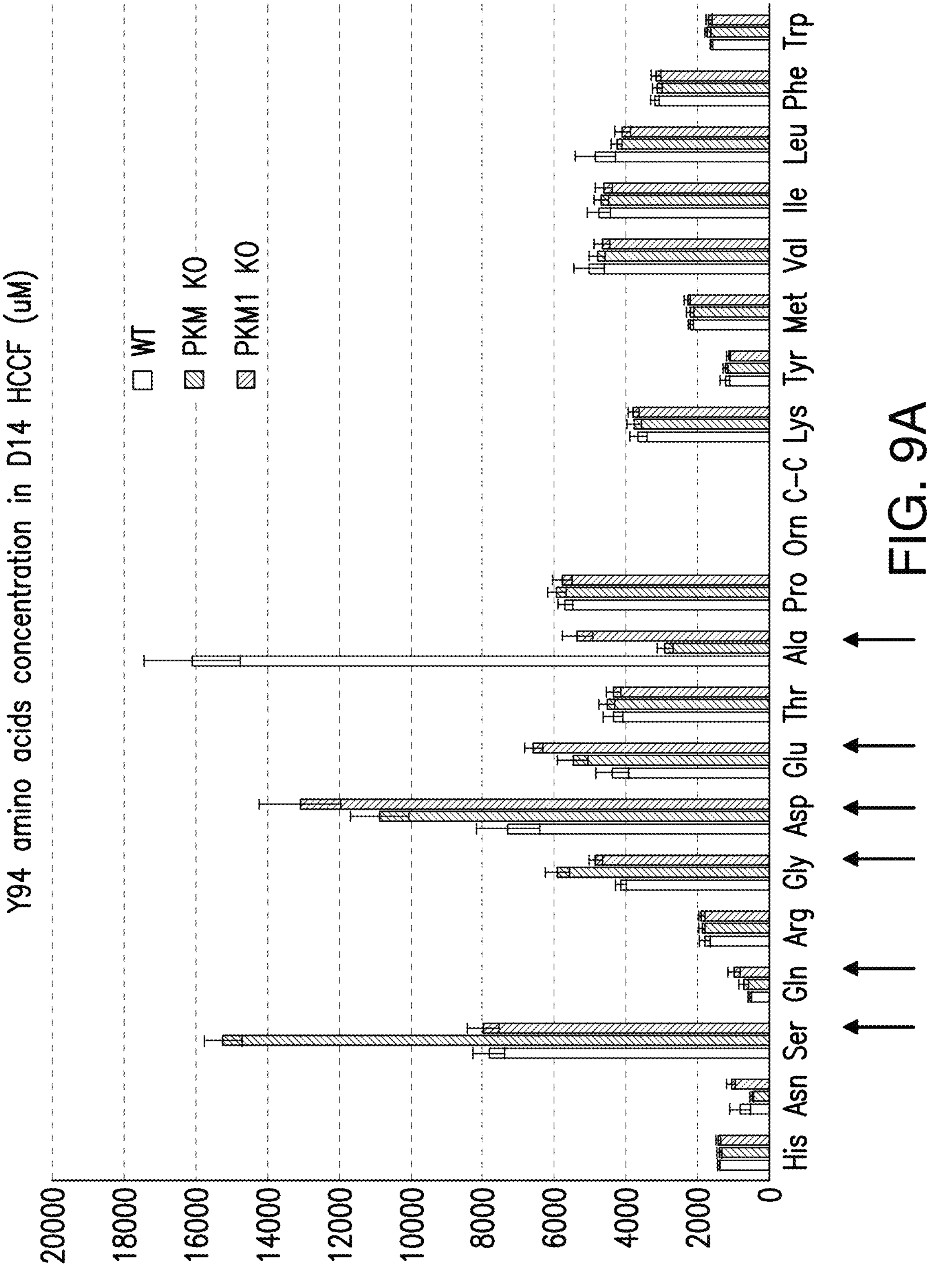

FIG. 9A. MAb-3 producing pools derived from PKM and PKM-1 KO host cell lines exhibited different amino acid synthesis/consumption rates in shake flask production.

Figure 9B:
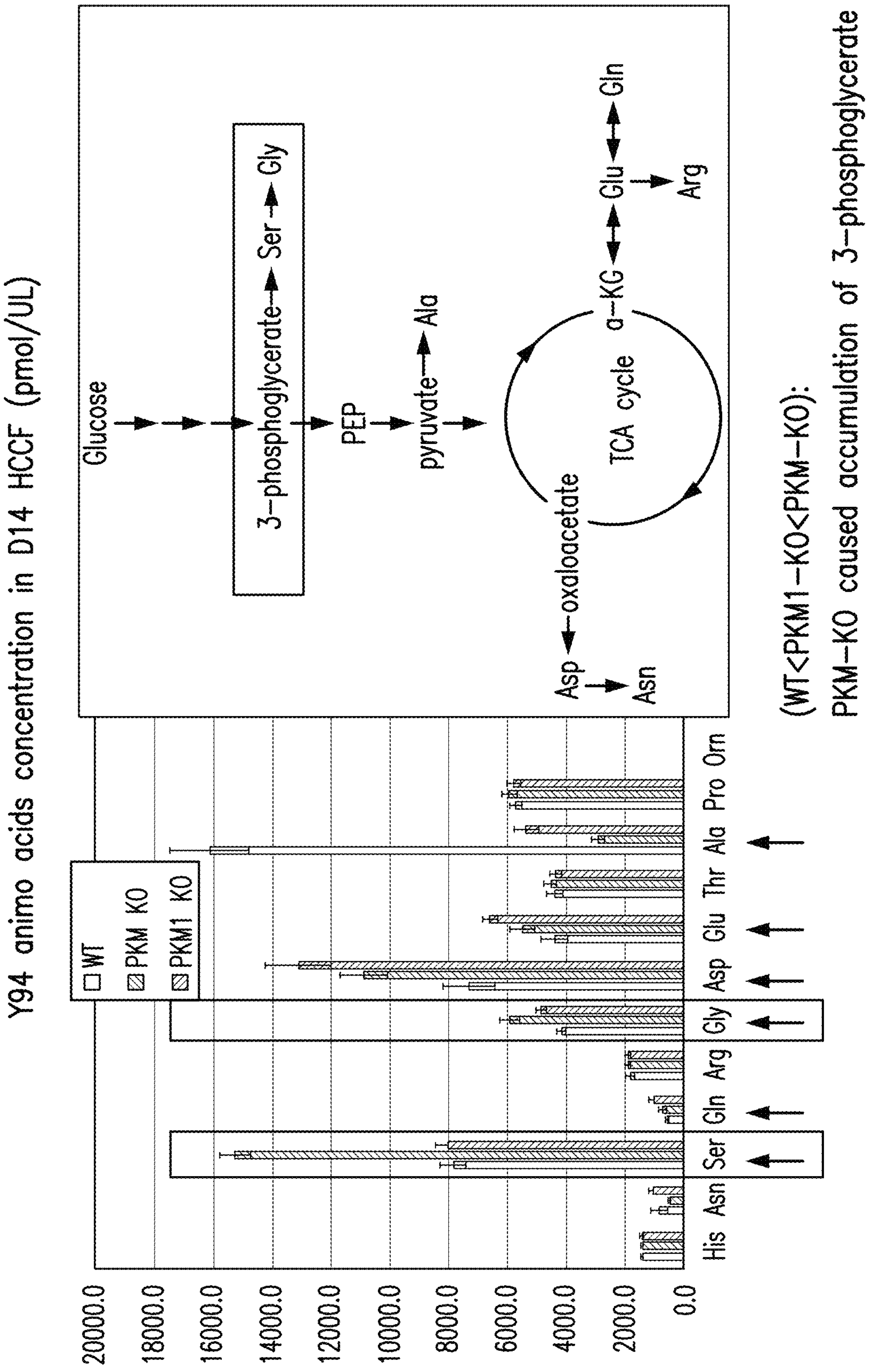

FIG. 9B. Bars and pathways enclosed in rectangles show that PKM KO host cell lines accumulated 3-phosphoglycerate.

Figure 9C:
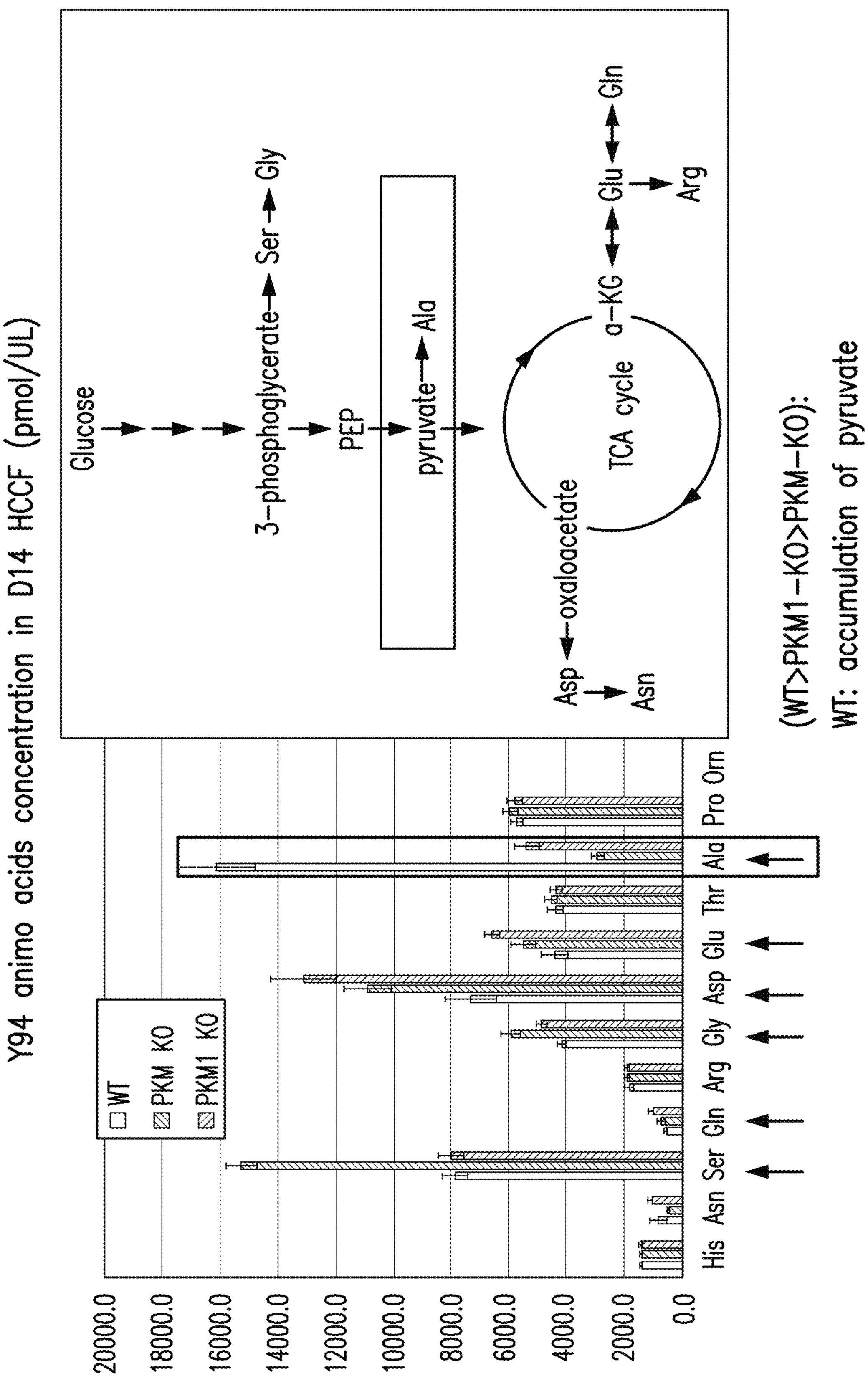

FIG. 9C. Bars and pathways enclosed in rectangles show that WT host cell lines accumulated pyruvate.

Figure 9D:
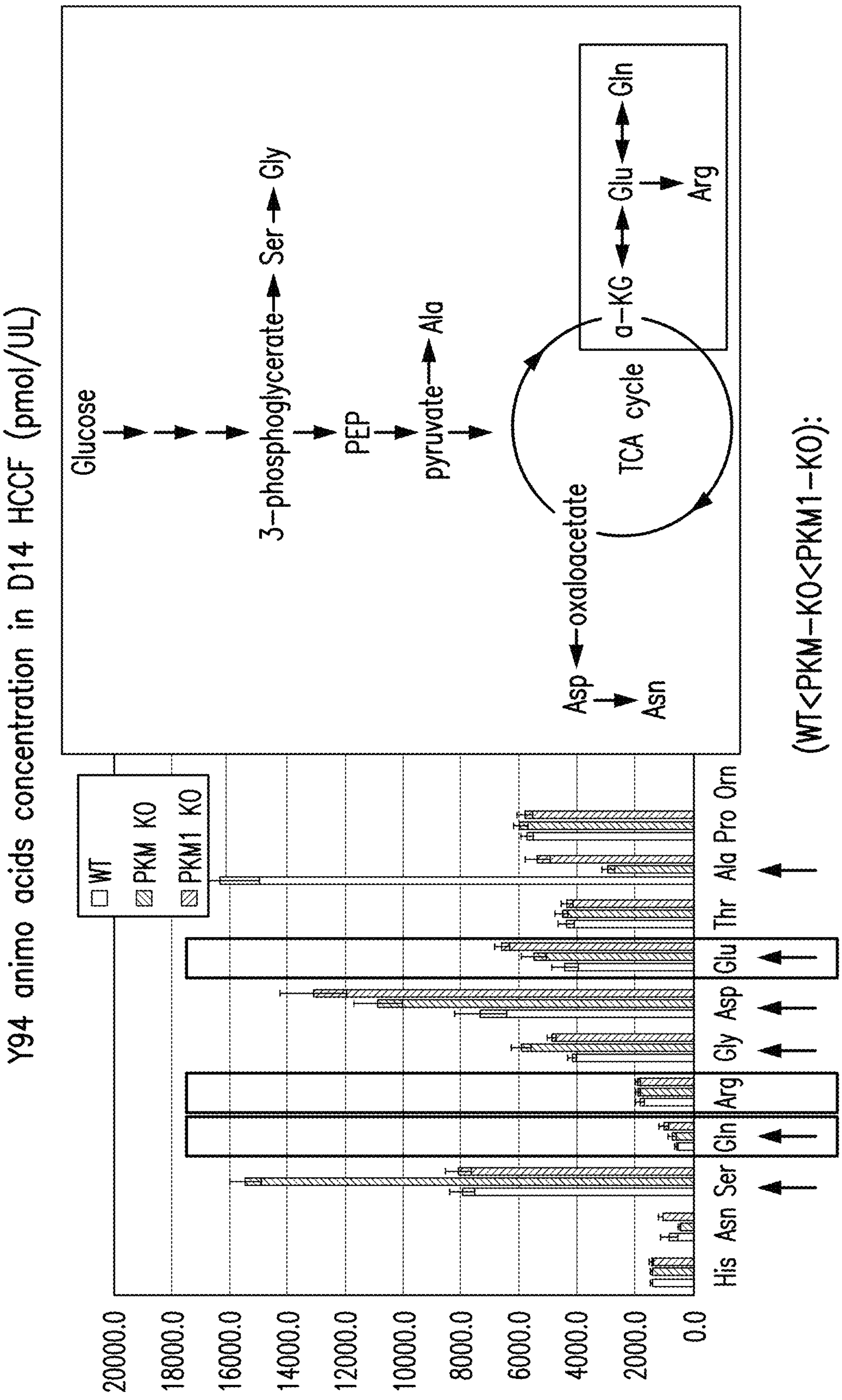

FIG. 9D. Bars and pathways enclosed in rectangles show that PKM-1 KO host cell lines accumulated the TCA cycle product, alpha-ketoglutarate (a-KG).

Figure 9E:
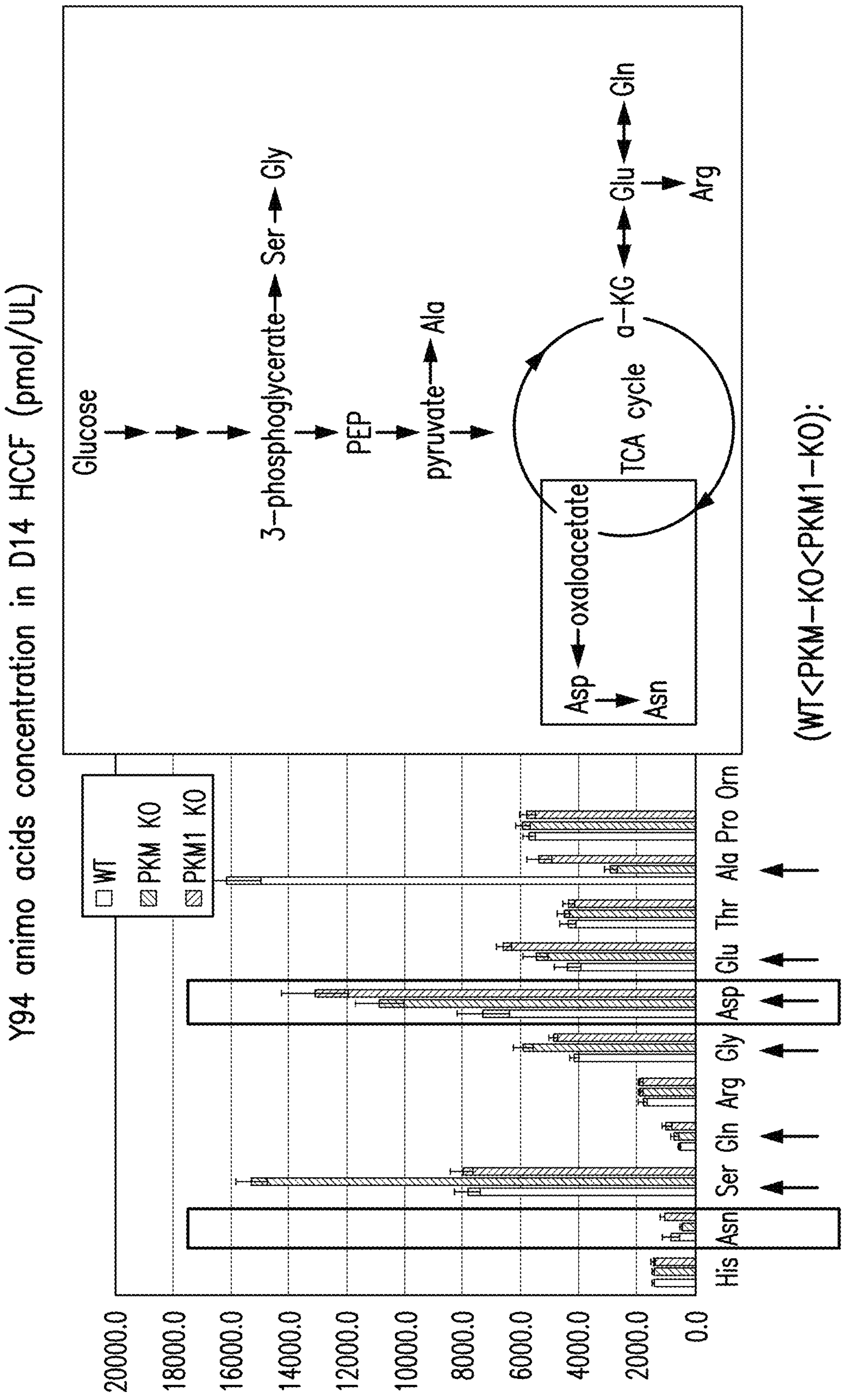

FIG. 9E. Bars and pathways enclosed in rectangles show that PKM-1 KO host cell lines accumulated the TCA cycle product, oxaloacetate.

Figure 10:
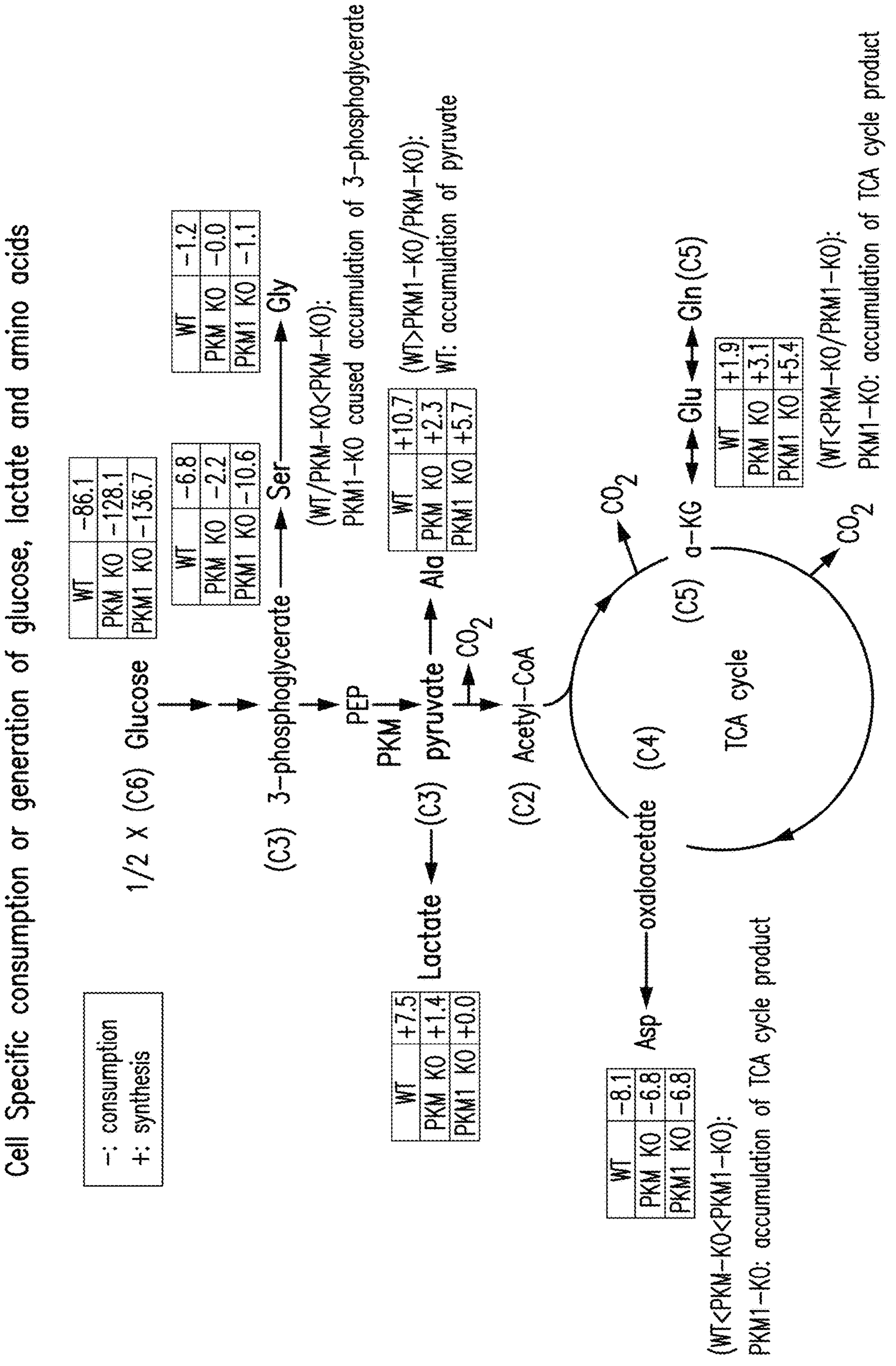

FIG. 10. Host cell specific consumption or generation of glucose, lactate and amino acids.

Figure 11:
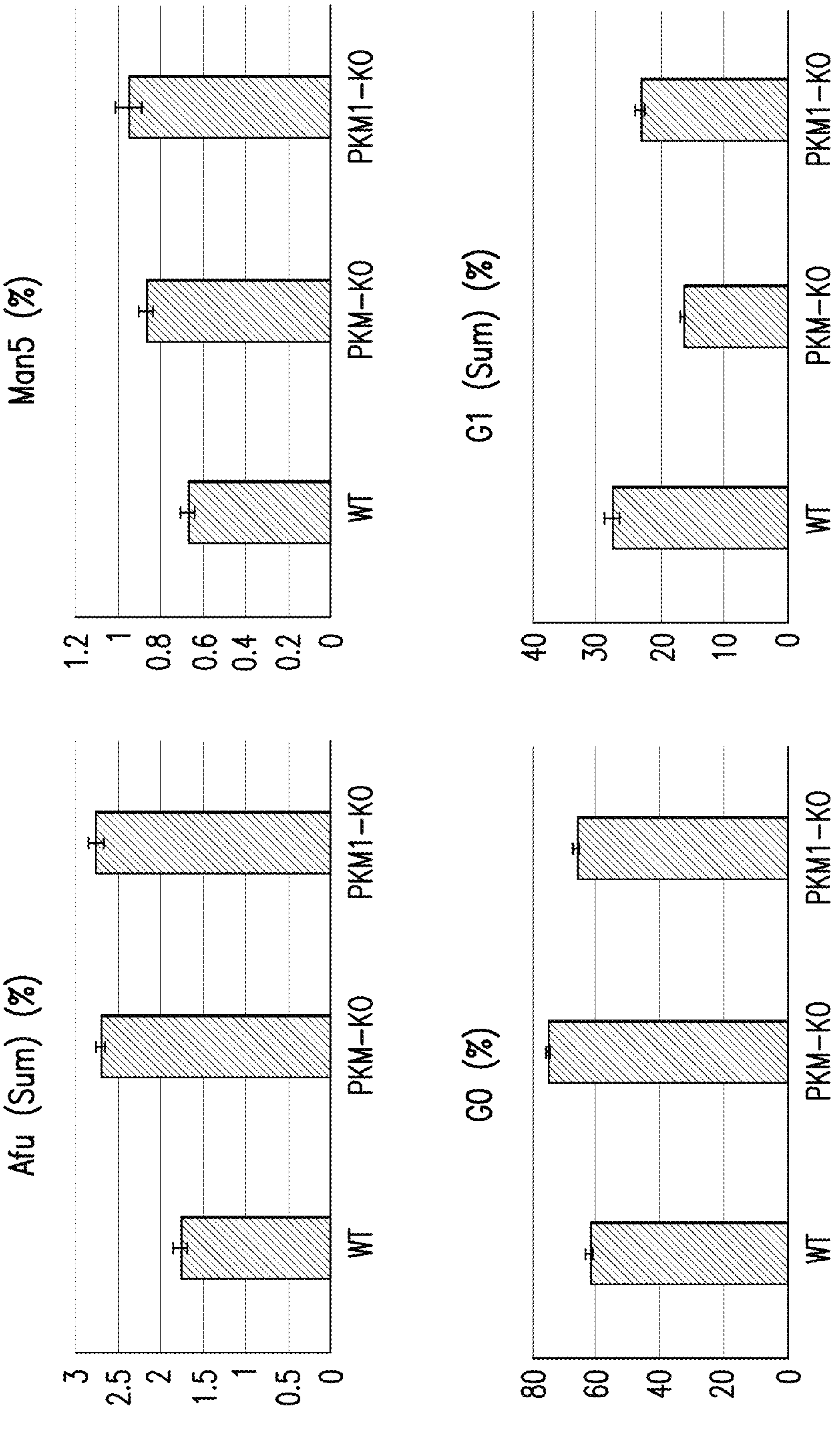

FIG. 11. MAb-3 producing pools derived from PKM and PKM-1 KO host cell lines exhibited different glycosylation profiles in shake flask production. PKM KO host had decreased galactosylation, and PKM KO and PKM-1 KO host cell lines had slightly decreased fucosylation.

5. DETAILED DESCRIPTION

For clarity, but not by way of limitation, the detailed description of the presently disclosed subject matter is divided into the following subsections:

5.1 Definitions;
5.2 Modulating PKM expression;
5.3 Cells with reduced or eliminated lactogenic activity;
5.4 Cell culture methods;
5.5 Products; and
5.6 Exemplary embodiments.

5.1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification can mean "one," but it is also consistent with the meaning of "one or more," "at least one" and "one or more than one."

The terms "comprise(s)," "include(s)," "having," "has," "can," "contain(s)" and variants thereof, as used herein, are intended to be open-ended transitional phrases, terms or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "lactogenic behavior" or "lactogenic activity" refers to the lactate producing activity of a cell, for example, by consuming glucose and generating lactate through aerobic glycolysis. In certain embodiments, the lactogenic activity of a cell can be measured by the level of accumulated lactate in the cell culture medium.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The terms "cell culture medium" and "culture medium" refer to a nutrient solution used for growing mammalian cells that typically provides at least one component from one or more of the following categories:

1) an energy source, usually in the form of a carbohydrate such as glucose;
2) all essential amino acids, and usually the basic set of twenty amino acids plus cysteine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient solution can optionally be supplemented with one or more components from any of the following categories:

1) hormones and other growth factors as, for example, insulin, transferrin, and epidermal growth factor;
2) salts and buffers as, for example, calcium, magnesium, and phosphate;
3) nucleosides and bases such as, for example, adenosine, thymidine, and hypoxanthine; and
4) protein and tissue hydrolysates.

"Culturing" a cell refers to contacting a cell with a cell culture medium under conditions suitable to the survival and/or growth and/or proliferation of the cell.

"Batch culture" refers to a culture in which all components for cell culturing (including the cells and all culture nutrients) are supplied to the culturing bioreactor at the start of the culturing process.

"Fed-batch cell culture," as used herein refers to a batch culture wherein the cells and culture medium are supplied to the culturing bioreactor initially, and additional culture nutrients are fed, continuously or in discrete increments, to the culture during the culturing process, with or without periodic cell and/or product harvest before termination of culture.

"Perfusion culture," sometimes referred to as continuous culture, is a culture by which the cells are restrained in the culture by, e.g., filtration, encapsulation, anchoring to micro-carriers, etc., and the culture medium is continuously, step-wise or intermittently introduced (or any combination of these) and removed from the culturing bioreactor.

As used herein, the term "cell," refers to animal cells, mammalian cells, cultured cells, host cells, recombinant cells and recombinant host cells. Such cells are generally cell lines obtained or derived from mammalian tissues which are able to grow and survive when placed in media containing appropriate nutrients and/or growth factors.

The terms "host cell," "host cell line" and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny does not need to be completely identical in nucleic acid content to a parent cell, but can contain mutations. Mutant progeny that have the same function or biological activity as screened or selected for in the originally transformed cell are included herein.

The term "mammalian host cell" or "mammalian cell" refers to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described for example in Mammalian Cell Culture (Mather, J. P. ed., Plenum Press, N.Y. 1984), and Barnes and Sato, (1980) Cell, 22:649. Typically, the cells are capable of expressing and secreting large quantities of a particular protein, e.g., glycoprotein, of interest into the culture medium. Examples of suitable mammalian host cells within the context of the present disclosure can include Chinese hamster ovary cells/–DHFR (CHO, Urlaub and Chasin, Proc. Natl. Acad. Sci. USA, 77:4216 1980); dp12.CHO cells (EP 307,247 published 15 Mar. 1989); CHO-K1 (ATCC, CCL-61); monkey kidney CV1 line transformed by SV40 (COS-7, ATCC CRL 1651); human embryonic kidney line (293 or 293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2). In certain embodiments, the mammalian cells include Chinese hamster ovary cells/-DHFR (CHO, Urlaub and Chasin, Proc. Natl. Acad. Sci. USA, 77:4216 1980); dp12.CHO cells (EP 307,247 published 15 Mar. 1989).

The term "peptone" within the context of the present disclosure is meant to refer to a media supplement that is essentially hydrolyzed animal protein. The source of this protein can be animal by-products from slaughter houses, purified gelatin, or plant material. The protein is typically hydrolyzed using acid, heat or various enzyme preparations.

"Growth phase" of the cell culture refers to the period of exponential cell growth (the log phase) where cells are generally rapidly dividing. The duration of time for which the cells are maintained at growth phase can vary based on the cell-type, the rate of growth of cells and/or the culture conditions, for example. In certain embodiments, during this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. In certain embodiments, during the growth phase, cells are cultured in nutrient medium containing the necessary additives generally at about 30°-40° C. in a humidified, controlled atmosphere, such that optimal growth is achieved for the particular cell line. In certain embodiments, cells are maintained in the growth phase for a period of about between one and four days, usually between two to three days.

"Transition phase" of the cell culture refers to the period of time during which culture conditions for the production phase are engaged. During the transition phase environmental factors such as temperature of the cell culture, medium osmolality and the like are shifted from growth conditions to production conditions.

"Production phase" of the cell culture refers to the period of time during which cell growth is/has plateaued. The logarithmic cell growth typically decreases before or during this phase and protein production takes over. During the production phase, logarithmic cell growth has ended, and protein production is primary. During this period of time the medium is generally supplemented to support continued protein production and to achieve the desired glycoprotein product. Fed-batch and/or perfusion cell culture processes supplement the cell culture medium or provide fresh medium during this phase to achieve and/or maintain desired cell density, viability and/or recombinant protein product titer. A production phase can be conducted at large scale.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

As used herein, "polypeptide" refers generally to peptides and proteins having more than about ten amino acids. The polypeptides can be homologous to the host cell, or preferably, can be exogenous, meaning that they are heterologous, i.e., foreign, to the host cell being utilized, such as a human protein produced by a Chinese hamster ovary cell, or a yeast polypeptide produced by a mammalian cell. In certain embodiments, mammalian polypeptides (polypeptides that were originally derived from a mammalian organism) are used, more preferably those which are directly secreted into the medium.

The term "protein" is meant to refer to a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD. Examples of proteins encompassed within the definition herein include all mammalian proteins, in particular, therapeutic and diagnostic proteins, such as therapeutic and diagnostic antibodies, and, in general proteins that contain one or more disulfide bonds, including multi-chain polypeptides comprising one or more inter- and/or intrachain disulfide bonds.

The term "antibody" is used herein in the broadest sense and encompasses various antibody structures including, but not limited to, monoclonal antibodies, polyclonal antibodies, monospecific antibodies (e.g., antibodies consisting of a single heavy chain sequence and a single light chain sequence, including multimers of such pairings), multispecific antibodies (e.g., bispecific antibodies) and antibody fragments so long as they exhibit the desired antigen-binding activity.

An "antibody fragment," "antigen-binding portion" of an antibody (or simply "antibody portion") or "antigen-binding fragment" of an antibody, as used herein, refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')2; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG and IgM, and several of these can be further divided into subclasses (isotypes), e.g., $IgG_1$, $IgG_2$, $IgG_3$, $IgG_4$, $IgA_1$, and $IgA_2$. In certain embodiments, the antibody is of the $IgG_1$ isotype. In certain embodiments, the antibody is of the $IgG_2$ isotype. The heavy chain constant domains that correspond to the different classes of immunoglobulins are called α, δ, ε, γ and μ, respectively. The light chain of an antibody can be assigned to one of two types, called kappa (κ) and lambda (λ), based on the amino acid sequence of its constant domain.

The term "titer" as used herein refers to the total amount of recombinantly expressed antibody produced by a cell culture divided by a given amount of medium volume. Titer is typically expressed in units of milligrams of antibody per milliliter or liter of medium (mg/ml or mg/L). In certain embodiments, titer is expressed in grams of antibody per liter of medium (g/L). Titer can be expressed or assessed in terms of a relative measurement, such as a percentage increase in titer as compared obtaining the protein product under different culture conditions.

The term "nucleic acid," "nucleic acid molecule" or "polynucleotide" includes any compound and/or substance that comprises a polymer of nucleotides. Each nucleotide is composed of a base, specifically a purine- or pyrimidine base (i.e., cytosine (C), guanine (G), adenine (A), thymine (T) or uracil (U)), a sugar (i.e., deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including, e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule can be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the disclosure in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see, e.g., Stadler et al, Nature Medicine 2017, published online 12 Jun. 2017, doi:10.1038/nm.4356 or EP 2 101 823 B1).

As used herein, the term "vector" refers to a nucleic acid molecule capable of transporting another nucleic acid to which it has been linked.

The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., Nature, 537:3053 (1983).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally can comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and which determine antigen binding specificity, for example "complementarity determining regions" ("CDRs").

Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

An "immunoconjugate" is an antibody conjugated to one or more heterologous molecule(s), including but not limited to a cytotoxic agent.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the presently disclosed subject matter can be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. *Kuby Immunology, $6^{th}$* ed., W.H. Freeman and Co., page 91 (2007).) A single VH or VL domain can be sufficient to confer antigen-binding specificity. Furthermore, antibodies that bind a particular antigen can be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

As used herein, the term "cell density" refers to the number of cells in a given volume of medium. In certain embodiments, a high cell density is desirable in that it can lead to higher protein productivity. Cell density can be monitored by any technique known in the art, including, but not limited to, extracting samples from a culture and analyzing the cells under a microscope, using a commercially available cell counting device or by using a commercially available suitable probe introduced into the bioreactor itself (or into a loop through which the medium and suspended cells are passed and then returned to the bioreactor).

As used herein, the term "seeding" refers to the addition or inoculation of growing cells into a culture medium at the beginning of the production phase. Further, as used herein, the term "seed train" refers to a continual passaging of cells in volumes of culture medium of about 20 L or less for the maintenance of the cell line.

As used herein, the term "recombinant cell" refers to cells which have some genetic modification from the original parent cells from which they are derived. Such genetic modification can be the result of an introduction of a heterologous gene for expression of the gene product, e.g., a recombinant protein.

As used herein, the term "recombinant protein" refers generally to peptides and proteins, including antibodies. Such recombinant proteins are "heterologous," i.e., foreign to the host cell being utilized, such as an antibody produced by CHO cells.

As used herein, a "PKM polypeptide" refers to a polypeptide that is encoded by the PKM gene. A PKM polypeptide includes the PKM-1 polypeptide isoform and/or the PKM-2 polypeptide isoform.

5.2. Modulating PKM Expression

Glycolysis is the process of glucose metabolism used by mammalian cells, e.g., CHO cells, to generate energy. Glycolysis can occur at high or low flux states. The cell response to glucose levels and the switch between these flux states can vary depending on the cell lines and the levels and the combinations of isozymes present in the glycolytic pathway (Mulukutla et al., 2014, PLoS One 9(6):e98756). Under normal culture conditions, CHO cells, like other immortalized cell lines, tend to consume glucose and generate lactate through aerobic glycolysis, a process known as the Warburg effect (Warburg, 1956, Science 123(3191):309-14). Accumulation of lactate in production cultures can adversely affect cellular growth, viability and productivity. Therefore, regulation of cellular energy flux and metabolism can be leveraged to avoid undesirable outcomes caused by lactate accumulation during the cell culture production phase (Mulukutla et al., 2010, Trends Biotechnol. 28(9):476-84; Luo et al., 2012, Biotechnol. Bioeng. 109(1):146-56; Ahn and Antoniewicz, 2012, Biotechnol. J. 7(1):61-74).

The final step of the glycolysis process involves conversion of phosphoenolpyruvate (PEP) to pyruvate, which is mediated by the pyruvate kinase (PK) enzymes. Four different isoforms of PK have been identified: PK liver (PKL), PK red blood cells (PKR), PK muscle 1 (PKM-1) and PK muscle 2 (PKM-2). The PK enzymes are expressed by two different genes, PKLR and PKM. Alternative exon splicing gives rise to different PK isoforms. The presence of both exons 1 and 2 in an mRNA transcript from the PKLR gene results in expression of PKR protein, whereas an mRNA transcript that starts with exon 2 results in the expression of PKL protein. Alternative splicing of exon 9 or 10 in the PKM gene transcript gives rise to PKM-1 or PKM-2, respectively. Specifically, PKM-1 includes exon 9 and excludes exon 10 of the PKM gene, and PKM-2 includes exon 10 and excludes exon 9 of the PKM gene. Tissue specific promoters, transcription factors, and alternative splicing regulate expression of these isoforms in different tissues and cell lines (Chaneton and Gottlieb, 2012, Trends. Biochem. Sci. 37(8):309-16; Israelsen and Vander Heiden, 2015, Semin Cell Dev Biol 43:43-51; Mazurek, 2011, Int. J. Biochem. Cell Biol 43(7):969-80; Harada et al., 1978, Biochim. Biophys. Acta. 524(2):327-39; Noguchi et al., 1986, J. Biol. Chem. 261(29):13807-12; Noguchi et al., 1987, J. Biol. Chem. 262(29):14366-71).

PKM-2 has been extensively studied due to its central role in cancer cell metabolism and tumor growth, hallmarked by high glucose consumption and lactate production. While the PKM-1 enzyme is constitutively active, PKM-2 activity is regulated by oligomerization, substrate binding and post-translational modifications (Christofk et al., 2008, Nature 452(7184):230-3; Chaneton and Gottlieb, 2012, Trends Biochem. Sci. 37(8):309-16; Israelsen and Vander Heiden, 2015, Semin. Cell Dev. Biol 43:43-51). For example, fructose 1,6-bisphosphate (FBP) reversibly binds to PKM-2, promoting its tetramerization and hence activation (Ashizawa et al., 1991, J. Biol. Chem. 266(25):16842-6; Dombrauckas et al., 2005, Biochemistry 44(27):9417-29). Phosphorylation of PKM-2 at tyrosine 105 or its binding to other phosphotyrosine proteins inactivates PKM-2 by blocking FBP binding and preventing PKM-2 tetramerization (Christofk et al., 2008, Nature 452(7184):181-6; Hitosugi et al., 2009, Sci. Signal 2(97):ra73). Increased levels of glycolysis, however, promote acetylation of PKM-2 at lysine 305 as part of a metabolic feedback loop, which targets PKM-2 for its degradation via chaperone-mediated autophagy (Lv et al., 2011, Mol. Cell 42(6):719-30) (Macintyre and Rathmell, 2011, Mol. Cell 42(6):713-4). Additionally, PKM-2 dimers have been shown to localize to the cell nucleus acting as protein kinases, utilizing PEP as a phosphate donor, to promote cell proliferation through phosphorylation of STAT3 and activation of MEK5 (Gao et al., 2012, Mol. Cell 45(5):598-609).

In accordance with one aspect, the present disclosure relates to methods for modulating lactogenic activity of a mammalian cell by modulating PKM expression, e.g., PKM polypeptide expression, in the cell. For example, but not by way of limitation, methods for modulating lactogenic activity of a mammalian cell include knocking out or knocking down PKM polypeptide expression in the cell. In certain embodiments, the expression of PKM-1 is knocked down or knocked out. In certain embodiments, the expression of PKM-2 is knocked down or knocked out. In certain embodiments, the expression of both PKM-1 and PKM-2 are knocked down or knocked out. As used herein, knocked out expression refers to the elimination of the expression of a PKM polypeptide, e.g., a PKM-1 polypeptide and/or a PKM-2 polypeptide, in the cell as compared to a reference cell. As used herein, knocked down expression refers to a reduction in the expression of a PKM polypeptide, e.g., a PKM-1 polypeptide and/or a PKM-2 polypeptide, in the cell as compared to a reference cell.

In certain embodiments, the reference cells are cells where the expression of a PKM polypeptide, e.g., PKM-1 and/or PKM-2, is not modulated, e.g., reduced. In certain embodiments, a reference cell is a cell that comprises at least one or both wild-type alleles of the PKM gene. For example, but not by way of limitation, a reference cell is a cell that has both wild-type PKM alleles. In certain embodiments, the reference cells are WT CHO cells.

In certain embodiments, the expression of a PKM polypeptide, e.g., PKM-1 and/or PKM-2, in a cell that has been modified to knock down expression of the PKM polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2% or less than about 1% of the PKM polypeptide expression of a reference cell, e.g., a WT CHO cell. In certain embodiments, the expression of a PKM-1 polypeptide in a cell that has been modified to knock down expression of the PKM-1 polypeptide is less than about 90%, less than about 80%, less than about 70%, less than about 60%, less than about 50%, less than about 40%, less than about 30%, less than about 20%, less than about 10%, less than about 5%, less than about 4%, less than about 3%, less than about 2%, or less than about 1% of the PKM-1 polypeptide expression of a reference cell, e.g., a WT CHO cell.

In certain embodiments, the expression of a PKM polypeptide, e.g., PKM-1 and/or PKM-2, in a cell that has been modified to knock down expression of the PKM polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2% or at least about 1% of the PKM polypeptide expression of a reference cell, e.g., a WT CHO cell. In certain embodiments, the expression of a PKM-1 polypeptide in a cell that has been modified to knock down expression of the PKM-1 polypeptide is at least about 90%, at least about 80%, at least about 70%, at least about 60%, at least about 50%, at least about 40%, at least about 30%, at least about 20%, at least about 10%, at least about 5%, at least about 4%, at least about 3%, at least about 2%, or at least about 1% of the PKM-1 polypeptide expression of a reference cell, e.g., a WT CHO cell.

In certain embodiments, the expression of a PKM polypeptide, e.g., PKM-1 and/or PKM-2, in a cell that has been modified to knock down expression of the PKM polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the PKM polypeptide expression of a reference cell, e.g., a WT CHO cell. In certain embodiments, the expression of a PKM polypeptide, e.g., PKM-1 and/or PKM-2, in a cell that has been modified to knock down expression of the PKM polypeptide is no more than about 40% of the PKM polypeptide expression of a reference cell, e.g., a WT CHO cell. In certain embodiments, the expression of a PKM-1 polypeptide in a cell that has been modified to knock down expression of the PKM-1 polypeptide is no more than about 90%, no more than about 80%, no more than about 70%, no more than about 60%, no more than about 50%, no more than about 40%, no more than about 30%, no more than about 20%, no more than about 10%, no more than about 5%, no more than about 4%, no more than about 3%, no more than about 2% or no more than about 1% of the PKM-1 polypeptide expression of a reference cell, e.g., a WT CHO cell.

In certain embodiments, the expression of a PKM polypeptide, e.g., PKM-1 and/or PKM-2, in a cell that has been modified to knock down expression of the PKM polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the PKM-1 polypeptide expression of a reference cell, e.g., a WT CHO cell. In certain embodiments, the expression of a PKM-1 polypeptide in a cell that has been modified to knock down expression of the PKM-1 polypeptide is between about 1% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 1% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 1% and about 70%, between about 10% and about 70%, between about 20% and about 70%, between about 30% and about 70%, between about 40% and about 70%, between about 50% and about 70%, between about 60% and about 70%, between about 65% and about 70%, between about 1% and about 60%, between about 10% and about 60%, between about 20% and about 60%, between about 30% and about 60%, between about 40% and about 60%, between about 50% and about 60%, between about 55% and about 60%, between about 1% and about 50%, between about 10% and about 50%, between about 20% and about 50%, between about 30% and about 50%, between about 40% and about 50%, between about 45% and about 50%, between about 1% and about 40%, between about 10% and about 40%, between about 20% and about 40%, between about 30% and about 40%, between about 35% and about 40%, between about 1% and about 30%, between about 10% and about 30%, between about 20% and about 30%, between about 25% and about 30%, between about 1% and about 20%, between about 5% and about 20%, between about 10% and about 20%, between about 15% and about 20%, between about 1% and about 10%, between about 5% and about 10%, between about 5% and about 20%, between about 5% and about 30%, between about 5% and about 40% of the PKM-1 polypeptide expression of a reference cell, e.g., a WT CHO cell.

In certain embodiments, the expression of a PKM polypeptide, e.g., PKM-1 and/or PKM-2, in a cell that has been modified to knock down expression of the PKM polypeptide is between about 5% and about 40% of the PKM polypeptide expression of a reference cell, e.g., a WT CHO cell. In certain embodiments, the expression of a PKM-1 polypeptide in a cell that has been modified to knock down expression of the PKM-1 polypeptide is between about 5% and about 40% of the PKM-1 polypeptide expression of a reference cell, e.g., a WT CHO cell. The expression level of the PKM polypeptide, e.g., PKM-1 and/or PKM-2, in different reference cells (e.g., cells that comprise at least one or both wild-type alleles of the PKM gene) can vary. For example, seed train cells or low-lactate producing cells may produce low levels of PKM-1, whereas high-lactate producing cells may produce high levels of PKM-1.

Alternative splicing of exon 9 or 10 in the PKM gene transcript gives rise to PKM-1 or PKM-2, respectively. The PKM gene that is knocked down or knocked out can be a PKM gene from a human. In certain embodiments, the PKM gene can be from a non-human, e.g., a Rhesus Monkey, canine, green monkey, chicken, cattle, pig, mouse, Chinese hamster, rat or rabbit.

In certain embodiments, the PKM gene that is knocked down or knocked out is a Chinese hamster PKM gene. In certain embodiments, the Chinese hamster PKM gene sequence has a NCBI Reference Sequence ID NW_003613709.1 (range: 200602 . . . 223561) (SEQ ID NO: 44). In certain embodiments, the PKM gene sequence differs by 1, 2, 3, 4, 5, 6, 7, 8, 9, 10, 11, 12, 13, 14, 15, 16, 17, 18, 19, 20 or more nucleotides from the NW_003613709.1 sequence. In certain embodiments, the PKM gene sequence differs by 1%, 2%, 3%, 4%, 5%, 6%, 7%, 8%, 9%, 10%, 11%, 12%, 13%, 14%, 15%, 16%, 17%, 18%, 19%, 20% or more from the sequence set forth in SEQ ID NO: 44.

Additional non-limiting examples of PKM genes include the human PKM gene (e.g., NC_000015.10 (range 72199029 . . . 72231624) (SEQ ID NO: 45)), the Rhesus monkey PKM gene (e.g., NC_027899.1 (range 49211766 . . . 49245983) (SEQ ID NO: 46)), the green monkey PKM gene (e.g., NC_023667.1 (range 11224332 . . . 11255538) (SEQ ID NO: 47)), the canine PKM gene (e.g., NC_006612.3 (range 35712853 . . . 35737643) (SEQ ID NO: 48)), the mouse PKM gene (e.g., NC_000075.6 (range 59656368 . . . 59679375) (SEQ ID NO: 49)), the rat PKM gene (e.g., NC_005107.4 (range 64480963 . . . 64502957) (SEQ ID NO: 50)), the rabbit PKM gene (e.g., NC_013685.1 (range 304096 . . . 317843) (SEQ ID NO: 51)), the chicken PKM gene (e.g., NC_006097.4 (range 1506428 . . . 1523684) (SEQ ID NO: 52)), the pig PKM gene (e.g., NC_010449.5 (range 60971807 . . . 61032780) (SEQ ID NO: 53)) and the cattle PKM gene (e.g., AC 000167.1 (range 18965981 . . . 18992644) (SEQ ID NO: 54)). In certain embodiments, the PKM gene sequence differs by 1, 2, 3, 4, 5, 6, 7, 8, 9, 10, 11, 12, 13, 14, 15, 16, 17, 18, 19, 20 or more nucleotides from any one of the sequences set forth in SEQ ID NOs: 45-54. In certain embodiments, the PKM gene sequence differs by 1%, 2%, 3%, 4%, 5%, 6%, 7%, 8%, 9%, 10%, 11%, 12%, 13%, 14%, 15%, 16%, 17%, 18%, 19%, 20% or more from any one of the sequences set forth in SEQ ID NOs: 45-54.

One skilled in the art would know that different mammalian cell lines, even those from the same species, e.g., two CHO distinct host cell lines, may not share identical PKM gene sequences. Small differences in the sequences of PKM gene, e.g., differences of 1, 2, 3, 4, 5, 6, 7, 8, 9, 10, 11, 12, 13, 14, 15, 16, 17, 18, 19 or 20 nucleotides, can exist between two mammalian cell lines from the same species.

5.2.1 Methods for Modulating PKM Expression

In certain embodiments, a genetic engineering system is employed to modulate (e.g., knock down or knock out) the expression of a PKM polypeptide (e.g., PKM-1 expression). Various genetic engineering systems known in the art can be used for the methods disclosed herein. Non-limiting examples of such systems include the CRISPR/Cas system, the zinc-finger nuclease (ZFN) system, the transcription activator-like effector nuclease (TALEN) system and the use of other tools for protein knockdown by gene silencing, such as small interfering RNAs (siRNAs), short hairpin RNA (shRNA), and microRNA (miRNA). Any CRISPR/Cas systems known in the art, including traditional, enhanced or modified Cas systems, as well as other bacterial based genome excising tools such as Cpf-1 can be used with the methods disclosed herein.

Any PKM inhibitors known in the art can also be used with the methods disclosed herein to modulate PKM activity, and thus modulate lactogenic activity of the cells disclosed herein. Non-limiting examples of PKM inhibitors include sodium monofluorophosphate, L-phenylalanine, creatine phosphate, $Ca^{2+}$, flurophosphate and pyridoxal 5'-phosphate.

In certain embodiments, a portion of the PKM gene is deleted to modulate, e.g., knock down or knock out, expression of a PKM polypeptide. In certain embodiments, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or at least about 90% of the PKM gene is deleted. In certain embodiments, no more than about 2%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85% or no more than about 90% of the PKM gene is deleted. In certain embodiments, between about 2% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 2% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 2% and about 70%, between about 10% and about 70%, between about 20% and about 70%, between about 30% and about 70%, between about 40% and about 70%, between about 50% and about 70%, between about 60% and about 70%, between about 65% and about 70%, between about 2% and about 60%, between about 10% and about 60%, between about 20% and about 60%, between about 30% and about 60%, between about 40% and about 60%, between about 50% and about 60%, between about 55% and about 60%, between about 2% and about 50%, between about 10% and about 50%, between about 20% and about 50%, between about 30% and about 50%, between about 40% and about 50%, between about 45% and about 50%, between about 2% and about 40%, between about 10% and about 40%, between about 20% and about 40%, between about 30% and about 40%, between about 35% and about 40%, between about 2% and about 30%, between about 10% and about 30%, between about 20% and about 30%, between about 25% and about 30%, between about 2% and about 20%, between about 5% and about 20%, between about 10% and about 20%, between about 15% and about 20%, between about 2% and about 10%, between about 5% and about 10%, or between about 2% and about 5% of the PKM gene is deleted.

In certain embodiments, at least one exon of the PKM gene is at least partially deleted. "Partially deleted," as used herein, refers to at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, no more than about 2%, no more than about 5%, no more than about 10%, no more than about 15%, no more than about 20%, no more than about 25%, no more than about 30%, no more than about 35%, no more than about 40%, no more than about 45%, no more than about 50%, no more than about 55%, no more than about 60%, no more than about 65%, no more than about 70%, no more than about 75%, no more than about 80%, no more than about 85%, no more than about 90%, no more than about 95%, between about 2% and about 90%, between about 10% and about 90%, between about 20% and about 90%, between about 25% and about 90%, between about 30% and about 90%, between about 40% and about 90%, between about 50% and about 90%, between about 60% and about 90%, between about 70% and about 90%, between about 80% and about 90%, between about 85% and about 90%, between about 2% and about 80%, between about 10% and about 80%, between about 20% and about 80%, between about 30% and about 80%, between about 40% and about 80%, between about 50% and about 80%, between about 60% and about 80%, between about 70% and about 80%, between about 75% and about 80%, between about 2% and about 70%, between about 10% and about 70%, between about 20% and about 70%, between about 30% and about 70%, between about 40% and about 70%, between about 50% and about 70%, between about 60% and about 70%, between about 65% and about 70%, between about 2% and about 60%, between about 10% and about 60%, between about 20% and about 60%, between about 30% and about 60%, between about 40% and about 60%, between about 50% and about 60%, between about 55% and about 60%, between about 2% and about 50%, between about 10% and about 50%, between about 20% and about 50%, between about 30% and about 50%, between about 40% and about 50%, between about 45% and about 50%, between about 2% and about 40%, between about 10% and about 40%, between about 20% and about 40%, between about 30% and about 40%, between about 35% and about 40%, between about 2% and about 30%, between about 10% and about 30%, between about 20% and about 30%, between about 25% and about 30%, between about 2% and about 20%, between about 5% and about 20%, between about 10% and about 20%, between about 15% and about 20%, between about 2% and about 10%, between about 5% and about 10%, or between about 2% and about 5% of a region, e.g., of the exon, is deleted. For example, but not by way of limitation, exon 9 of the PKM gene can be at least partially deleted or completely deleted. In certain embodiments, exon 10 of the PKM gene can be at least partially deleted or completely deleted. In certain embodiments, exons 9 and 10 of the PKM gene can be at least partially deleted or completely deleted. In certain embodiments, the region that encompasses exons 1-12 is at least partially deleted or completed deleted.

In certain non-limiting embodiments, a CRISPR/Cas9 system is employed to modulate the expression of a PKM polypeptide. A clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), and trans-activating crRNA (tracrRNA, binds to crRNA and forms an active complex with Cas9). The terms "guide RNA" and "gRNA" refer to any nucleic acid that promotes the specific association (or "targeting") of an RNA-guided nuclease such as a Cas9 to a target sequence such as a genomic or episomal sequence in a cell. gRNAs can be unimolecular (comprising a single RNA molecule, and referred to alternatively as chimeric) or modular (comprising more than one, and typically two, separate RNA molecules, such as a crRNA and a tracrRNA, which are usually associated with one another, for instance by duplexing). CRISPR/Cas9 strategies can employ a vector to transfect the mammalian cell. The guide RNA (gRNA) can be designed for each application as this is the sequence that Cas9 uses to identify and directly bind to the target DNA in a cell. Multiple crRNAs and the tracrRNA can be packaged together to form a single-guide RNA (sgRNA). The sgRNA can be joined together with the Cas9 gene and made into a vector in order to be transfected into cells.

In certain embodiments, the CRISPR/Cas9 system for use in modulating expression of one or more PKM polypeptides comprises a Cas9 molecule and one or more gRNAs comprising a targeting domain that is complementary to a target sequence of the PKM gene. In certain embodiments, the target gene is a region of the PKM gene. The target sequence can be any exon or intron region within the PKM gene, e.g., the targeting of which eliminates or reduces the expression of PKM1 and/or PKM2 polypeptides. In certain embodiments, the target sequence can be a 5' region flanking exon 1, a region within exon 1, a 5' region flanking exon 2, a region within exon 2, a 5' region flanking exon 9, a 3' region flanking exon 9, a 3' region flanking exon 10, a region within exon 12 and/or a 3' region flanking exon 12 of the PKM gene. For example, but not by way of limitation, the target sequence is selected from the group consisting of a 5' intron region flanking exon 9 of PKM gene, a 3' intron region flanking exon 9 of PKM gene, a 3' intron region flanking exon 10 of PKM gene and a combination thereof.

In certain embodiments, a 5' intron region flanking exon 9 of the PKM gene and a 3' intron region flanking exon 9 of the PKM gene are both targeted using a CRISPR/Cas9 system disclosed herein. For example, but not by way of limitation, the CRISPR/Cas9 system comprises a Cas9 molecule, a gRNA targeting a 5' intron region flanking exon 9 of PKM gene and a gRNA targeting a 3' intron region flanking exon 9 of the PKM gene, e.g., for generating cells that have PKM-1 knocked down or knocked out. In certain embodiments, the gRNA targeting a 5' intron region flanking exon 9 of PKM gene comprises the sequence set forth in SEQ ID NO: 33. In certain embodiments, the gRNA targeting a 3' intron region flanking exon 9 of PKM gene comprises the sequence set forth in SEQ ID NO: 34.

In certain embodiments, the target sequence can be a 5' region flanking exon 1, a region within exon 1, a 5' region flanking exon 2, a region within exon 2, a region within exon 12, a 3' region flanking exon 12 or a combination thereof. For example, and not by way for limitation, a CRISPR/Cas9 system of the present disclosure can comprise a Cas9 molecule, a gRNA targeting a region within exon 1 of the PKM gene and a gRNA targeting a region within exon 12 of the PKM gene, e.g., for generating cells that have both PKM-1 and PKM-2 knocked down or knocked out. In certain embodiments, the CRISPR/Cas9 system of the present disclosure can comprise a Cas9 molecule, a gRNA targeting a region within exon 2 of the PKM gene and a gRNA targeting a region within exon 12 of the PKM gene, e.g., for generating cells that have both PKM-1 and PKM-2 knocked down or knocked out. In certain embodiments, the gRNA targeting a region within exon 2 of the PKM gene comprises the sequence set forth in SEQ ID NO: 42. In certain embodiments, the gRNA targeting a region within exon 12 of the PKM gene comprises the sequence set forth in SEQ ID NO: 43.

In certain embodiments, the gRNAs are administered to the cell in a single vector and the Cas9 molecule is administered to the cell in a second vector. In certain embodiments, the gRNAs and the Cas9 molecule are administered to the cell in a single vector. Alternatively, each of the gRNAs and Cas9 molecule can be administered by separate vectors. In certain embodiments, the CRISPR/Cas9 system can be delivered to the cell as a ribonucleoprotein complex (RNP) that comprises a Cas9 protein complexed with one or more gRNAs, e.g., delivered by electroporation (see, e.g., DeWitt et al., Methods 121-122:9-15 (2017) for additional methods of delivering RNPs to a cell). In certain embodiments, administering the CRISPR/Cas9 system to the cell results in the knock out or knock down of the expression of the PKM-1 polypeptide. In certain embodiments, administering the CRISPR/Cas9 system to the cell results in the knock out or knock down of the expression of both the PKM-1 and PKM-2 polypeptides.

In certain embodiments, the genetic engineering system is a ZFN system for modulating the expression of a PKM polypeptide in a mammalian cell. The ZFN can act as restriction enzyme, which is generated by combining a zinc finger DNA-binding domain with a DNA-cleavage domain. A zinc finger domain can be engineered to target specific DNA sequences which allows the zinc-finger nuclease to target desired sequences within genomes. The DNA-binding domains of individual ZFNs typically contain a plurality of individual zinc finger repeats and can each recognize a plurality of base pairs. The most common method to generate a new zinc-finger domain is to combine smaller zinc-finger "modules" of known specificity. The most common cleavage domain in ZFNs is the non-specific cleavage domain from the type IIs restriction endonuclease FokI. ZFN modulates the expression of proteins by producing double-strand breaks (DSBs) in the target DNA sequence, which will, in the absence of a homologous template, be repaired by non-homologous end-joining (NHEJ). Such repair can result in deletion or insertion of base-pairs, producing frame-shift and preventing the production of the harmful protein (Durai et al., *Nucleic Acids Res.;* 33 (18): 5978-90 (2005)). Multiple pairs of ZFNs can also be used to completely remove entire large segments of genomic sequence (Lee et al., *Genome Res.;* 20 (1): 81-9 (2010)). In certain embodiments, the target gene is part of the PKM gene. In certain embodiments, the target sequence is exon 9 of PKM gene. In certain embodiments, the target sequence is exon 9 and exon 10 of PKM gene.

In certain embodiments, the genetic engineering system is a TALEN system for modulating the expression of a PKM polypeptide in a mammalian cell. TALENs are restriction enzymes that can be engineered to cut specific sequences of DNA. TALEN systems operate on a similar principle as ZFNs. TALENs are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome (Boch et al., Nature Biotechnology; 29(2):135-6 (2011)). In certain embodiments, the target gene is part of the PKM gene. In certain embodiments, the target sequence is exon 9 of PKM gene. In certain embodiments, the target sequence is exon 9 and exon 10 of PKM gene.

In certain embodiments, the expression of PKM polypeptide can be knocked down using oligonucleotides that have complementary sequences to PKM nucleic acids (e.g., PKM mRNA, PKM-1 mRNA or PKM-2 mRNA). Non-limiting examples of such oligonucleotides include small interference RNA (siRNA), short hairpin RNA (shRNA), and micro RNA (miRNA). In certain embodiments, such oligonucleotides can be homologous to at least a portion of a PKM nucleic acid sequence, e.g., a PKM, a PKM-1 or a PKM-2 nucleic acid sequence, wherein the homology of the portion relative to the PKM nucleic acid sequence is at least about 75 or at least about 80 or at least about 85 or at least about 90 or at least about 95 or at least about 98 percent. In certain non-limiting embodiments, the complementary portion can constitute at least 10 nucleotides or at least 15 nucleotides or at least 20 nucleotides or at least 25 nucleotides or at least 30 nucleotides and the antisense nucleic acid, shRNA, mRNA or siRNA molecules can be up to 15 or up to 20 or up to 25 or up to 30 or up to 35 or up to 40 or up to 45 or up to 50 or up to 75 or up to 100 nucleotides in length. Antisense nucleic acid, shRNA, mRNA or siRNA molecules can comprise DNA or atypical or non-naturally occurring residues, for example, but not limited to, phosphorothioate residues.

The genetic engineering system disclosed herein can be delivered into the mammalian cell using a viral vector, e.g., retroviral vectors such as gamma-retroviral vectors, and lentiviral vectors. Combinations of retroviral vector and an appropriate packaging line are suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art. Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to modify the mammalian cell disclosed herein. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic engineering of the mammalian cell disclosed herein. For example, a nucleic acid molecule can be introduced into the mammalian cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation and protoplast fusion. Liposomes can also be potentially beneficial for delivery of nucleic acid molecules into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically.

5.3 Cells with Reduced or Eliminated Lactogenic Activity

In one aspect, the present disclosure relates to cells or compositions comprising one or more cells, e.g., mammalian cells, having reduced or eliminated lactogenic activity and methods of using the same. The expression of a PKM polypeptide (e.g., PKM-1 expression) is knocked down or knocked out in the cell, which results in reduced or eliminated lactogenic activity of the cell. Non-limiting examples of the cells include CHO cells (e.g., DHFR CHO cells), dp12.CHO cells, CHO-K1 (ATCC, CCL-61), monkey kidney CV1 line transformed by SV40 (e.g., COS-7 ATCC CRL-1651), human embryonic kidney line (e.g., 293 or 293 cells subcloned for growth in suspension culture), baby hamster kidney cells (e.g., BHK, ATCC CCL 10), mouse sertoli cells (e.g. TM4), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor (e.g., MMT 060562, ATCC CCL51), TRI cells, MRC 5 cells, FS4 cells, human hepatoma line (e.g., Hep G2), myeloma cell lines (e.g., Y0, NS0 and Sp2/0). In certain embodiments, the cells are CHO cells. Additional non-limiting examples of CHO host cells include CHO K1SV cells, CHO DG44 cells, a CHO DUKXB-11 cells, CHOK1S cells and CHO KIM cells. In certain embodiments, only one allele of the PKM gene is modified in a cell of the present disclosure. In certain embodiments, both alleles of the PKM gene are modified. In certain embodiments, a cell of the present disclosure comprises at least one allele of the PKM gene that comprises a sequence selected from the group consisting of SEQ ID NOs: 39-41, or comprises the nucleotide sequences set forth in SEQ ID NOs: 37 and 38 (see FIG. 4C). For example, but not by way of limitation, a cell of the present disclosure comprises an allele of a PKM gene that comprises a nucleotide sequence selected from the group consisting of SEQ ID NOs: 39-41, or comprises the nucleotide sequences set forth in SEQ ID NOs: 37 and 38. In certain embodiments, a cell of the present disclosure comprises at least one allele of the PKM gene that comprises a sequence selected from the group consisting of SEQ ID NOs: 39-41. In certain embodiments, the cell is a CHO cell. Non-limiting examples of the cell having reduced or eliminated lactogenic activity include HET-3, HET-18, KO-2 and KO-15, disclosed herein.

In certain embodiments, the expression of a PKM polypeptide (e.g., PKM-1 and/or PKM-2) is knocked out, which results in eliminating the lactogenic activity of the cell as compared to a reference cell. In certain embodiments, the expression of a PKM polypeptide is knocked down in the cell, which results in reduced lactogenic activity of the cell as compared to a reference cell. In certain embodiments, the reference cells are cells where the expression of a PKM polypeptide is not modulated. In certain embodiments, the reference cells are cells that have at least one wild-type PKM allele. In certain embodiments, the reference cells are cells having both wild-type PKM alleles. In certain embodiments, the reference cells are WT CHO cells.

In certain embodiments, the lactogenic activity of cells is indicated by the lactate concentration in the cell culture media during the culturing period of the cells. In certain embodiments, the lactogenic activity of cells is indicated by the lactate concentration in the cell culture media on day 2, day 3, day 4, day 5, day 6, day 7, day 8, day 9, day 10, day 11, day 12, day 13, day 14, day 15, day 16, day 17, day 18, day 19, day 20, day 25, day 30, day 35, day 40, day 45, day 50, day 55, day 60, day 65, day 70 or day 80 of the culturing period. In certain embodiments, the lactogenic activity of cells is indicated by the lactate concentration in the cell culture media more than 80 days after the start of the culturing. In certain embodiments, the lactogenic activity of the presently disclosed cells is indicated by the lactate concentration in the cell culture media during the production phase, e.g., on day 2, day 3, day 4, day 5, day 6, day 7, day 8, day 9, day 10, day 11, day 12, day 13, day 14, day 15, day 16, day 17, day 18, day 19 or day 20 of the production phase of a cell culture process. In certain embodiments, the lactate concentration is determined on day 6, day 7, day 10, day 11, day 14 and/or day 15 of the production phase. In certain embodiments, the lactate concentration is determined on day 7, day 10 and/or day 14 of the production phase.

Any methods known in the art for measuring lactogenic activity of a cell and/or for measuring lactate production by cells in culture can be used with the subject matter disclosed herein. Non-limiting exemplary methods include those disclosed in TeSlaa and Teitell, *Methods Enzymol* (2014) 542: 91-114 and in Lehman et al., *Med Sci Sports Exerc.* (1991) 23(8):935-8, which are incorporated for reference in their entireties herein. For example, but not by way of limitation, such techniques include using commercial extracellular lactate kits, use of an extracellular bioanalyzer, measuring the extracellular acidification rate (ECAR), e.g., by using a Seahorse XF analyzer, measuring the activity of rate-limiting glycolytic enzymes and measuring lactate production by using tracers.

In certain embodiments, the lactogenic activity of the cells having reduced lactogenic activity (e.g., because of the modulation of the PKM gene in the cells to knock down or knock out a PKM polypeptide) is about 80%, about 70%, about 60%, about 50%, about 40%, about 30%, about 20%, about 10%, about 5%, about 4%, about 3%, about 2% or about 1% of the lactogenic activity of a reference cell. In certain embodiments, lactogenic activity of the cells having reduced lactogenic activity (e.g., because of the modulation of the PKM gene in the cells to knock down or knock out a PKM Polypeptide) is less than about 80%, about 70%, about 60%, about 50%, about 40%, about 30%, about 20%, about 10%, about 5%, about 4%, about 3%, about 2% or about 1% of the lactogenic activity of the reference cell. In certain embodiments, the lactogenic activity of the cell is less than about 50% of the lactogenic activity of a reference cell, e.g., as observed at day 14 or day 15 of the production phase of the cell culture. In certain embodiments, the lactogenic activity of the cell is less than about 20% of the lactogenic activity of a reference cell, e.g., as observed at day 14 or day 15 of the production phase of the cell culture. In certain embodiments, the lactogenic activity of the cell is less than about 10% of the lactogenic activity of a reference cell, e.g., as observed at day 14 or day 15 of the production phase of the cell culture. In certain embodiments, the reference cell is a cell that comprises at least one or both wild-type alleles of the PAM gene.

In certain embodiments, the lactate concentration in the cell culture media produced by cells of the present disclosure is less than about 15 g/L, less than about 14 g/L, less than about 13 g/L, less than about 12 g/L, less than about 101 g/L, less than about 10 g/L, less than about 9 g/L, less than about 8 g/L, less than about 7 g/L, less than about 6 g/L, less than about 5 g/L, less than about 4 g/L, less than about 3 g/L, less than about 2 g/L, less than about 1 g/L or about less than about 0.5 g/L, e.g., in the production phase of the cell culture (e.g., on day 2, day 3, day 4, day 5, day 6, day 7, day 8, day 9, day 10, day 11, day 12, day 13, day 14, day 15, day 16, day 17, day 18, day 19 or day 20 of the production phase). In certain embodiments, the lactate concentration in the cell culture media produced by cells of the present disclosure is less than about 5 g/L, less than about 2 g/L, or less than about 1 g/L. In certain embodiments, the lactate concentration in the cell culture media produced by cells of the present disclosure is less than about 5 g/L, less than about 2 g/L, or less than about 1 g/L on day 7, day 10, day 14 or day 15 of the production phase of the cell culture. In certain embodiments, the lactate concentration in the cell culture media produced by cells of the present disclosure is less than about 1 g/L, or less than about 2 g/L during the production phase of a shake flask culture. In certain embodiments, the lactate concentration in the cell culture media produced by cells of the present disclosure is less than about 2 g/L during the production phase of a cell culture in a bioreactor.

In certain embodiments, the cells with reduced or eliminated lactogenic activity as disclosed herein (e.g., cells generated by knocking out or knocking down of the expression of a PKM polypeptide) have comparable titer and/or specific productivity as cells with regular lactogenic activity (e.g., wildtype cells). In certain embodiments, the difference in titer and/or specific productivity between the cells with reduced or eliminated lactogenic activity and the cells with regular lactogenic activity is less than about 1%, less than about 5%, less than about 10%, less than about 15%, less than about 20%, less than about 25%, or less than about 30% of the cells with regular lactogenic activity (e.g., a reference cell). In certain embodiments, the cells with reduced or eliminated lactogenic activity have higher titer and/or specific productivity than the cells with regular lactogenic activity. In certain embodiments, the titer of the cells with reduced or eliminated lactogenic activity is about 1%, about 5%, about 10%, about 15%, about 20%, about 25%, about 30%, about 35%, about 40%, about 45%, or about 50% higher than the titer of the cells with regular lactogenic activity. In certain embodiments, the titer of the cells with reduced or eliminated lactogenic activity is more than about 50% higher than the titer of the cell with regular lactogenic activity. In certain embodiments, the specific productivity (Qp) of the cells with reduced or eliminated lactogenic activity is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% higher than the specific productivity of the cells with regular lactogenic activity. In certain embodiments, the specific productivity of the cell with reduced or eliminated lactogenic activity is more than about 90% higher than the specific productivity of the cell with regular lactogenic activity.

The lactate concentration in the cell culture media can be measured by a chemistry analyzer or a lactate assay kit. Non-limiting examples of chemistry analyzer include Bioprofile 400 (Nova Biomedical), Piccolo Xpress Chemistry Analyzer, Excel—Semi-automated Chemistry Analyzer, Indiko Clinical and Specialty Chemistry System, and ACE Axcel® Clinical Chemistry System. Non-limiting examples of lactate assay kit include L-Lactate Assay Kit (Colorimetric) (ab65331, Abcam), BioVision Lactate Colorimetric/Fluorometric Assay Kit, PicoProbe™ Lactate Fluorometric Assay Kit, Lactate Colorimetric Assay Kit II, Cell Biolabs Lactate Assay Kits.

In certain embodiments, the cells disclosed herein express a product of interest. In certain embodiments, the product of interest is a recombinant protein. In certain embodiments, the product of interest is a monoclonal antibody. Additional non-limiting examples of products of interest are provided in Section 5.5. In certain embodiments, the cells disclosed herein can be used for production of commercially useful amounts of the product of interest.

In certain embodiments, the cells disclosed herein can comprise a nucleic acid that encodes a product of interest. In certain embodiments, the nucleic acid can be present in one or more vectors, e.g., expression vectors. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). Additional non-limiting examples of expression vectors for use in the present disclosure include viral vectors (e.g., replication defective retroviruses, adenoviruses and adeno-associated viruses) that serve equivalent functions.

In certain embodiments, the nucleic acid encoding a product of interest can be introduced into a host cell, disclosed herein. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, the host cell is eukaryotic, e.g., a Chinese Hamster Ovary (CHO) cell or lymphoid cell (e.g., Y0, NS0, Sp20 cell).

In certain embodiments, the nucleic acid encoding a product of interest can be randomly integrated into a host cell genome ("Random Integration" or "RI"). For example, but not by way of limitation, a nucleic acid encoding a product of interest can be randomly integrated into the genome of a cell that has been modulated to have knocked down or knocked out expression of a PKM polypeptide, e.g., PKM-1.

In certain embodiments, the nucleic acid encoding a product of interest can be integrated into a host cell genome in a targeted manner ("Targeted Integration" or "TI"). For example, but not by way of limitation, a nucleic acid encoding a product of interest can be integrated into the genome of a cell that has been modulated to have knocked down or knocked out expression of a PKM polypeptide, e.g., PKM-1, in a targeted manner. An "integration site" comprises a nucleic acid sequence within a host cell genome into which an exogenous nucleotide sequence is inserted. In certain embodiments, an integration site is between two adjacent nucleotides on the host cell genome. In certain embodiments, an integration site includes a stretch of nucleotide sequences. In certain embodiments, the integration site is located within a specific locus of the genome of the TI host cell. In certain embodiments, the integration site is within an endogenous gene of the TI host cell. Any integration site known in the art can be regulated and used with the subject matter disclosed herein. The targeted integration can be mediated by methods and systems known in the art. For example, but not by way of limitation, methods and systems disclosed in International Application No. PCT/US18/067070, filed Dec. 21, 2018, the content of which is incorporated herein by its entirely, can be used for targeted integration.

In certain embodiments, the nucleic acid encoding a product of interest can be integrated into a host cell genome using transposase-based integration. Transposase-based integration techniques are disclosed, for example, in Trubitsyna et al., Nucleic Acids Res. 45(10):e89 (2017), Li et al., PNAS 110(25):E2279-E2287 (2013) and WO 2004/009792, which are incorporated by reference herein in their entireties.

In certain embodiments, the nucleic acid encoding a product of interest can be randomly integrated into a host cell genome ("Random Integration" or "RI"). In certain embodiments, the random integration can be mediated by any method or systems known in the art. In certain embodiments, the random integration is mediated by MaxCyte STX® electroporation system.

In certain embodiments, targeted integration can be combined with random integration. In certain embodiments, the targeted integration can be followed by random integration. In certain embodiments, random integration can be followed by targeted integration. For example, but not by way of limitation, a nucleic acid encoding a product of interest can be randomly integrated into the genome of a cell that has been modulated to have knocked down or knocked out expression of a PKM polypeptide, e.g., PKM-1, and a nucleic acid encoding the same product of interest can be integrated in the genome of the cell in a targeted manner.

In certain embodiments, the host cell is a RI host cell. In certain embodiments, the host cell is a TI host cell.

5.4. Cell Culturing Methods

In one aspect, the present disclosure provides a method for producing a product of interest comprising culturing a cell disclosed herein. Suitable culture conditions for mammalian cells known in the art can be used for culturing the cells herein (J. Immunol. Methods (1983) 56:221-234) or can be easily determined by the skilled artisan (see, for example, Animal Cell Culture: A Practical Approach 2nd Ed., Rickwood, D. and Hames, B. D., eds. Oxford University Press, New York (1992)).

Mammalian cell culture can be prepared in a medium suitable for the particular cell being cultured. Commercially available media such as Ham's F10 (Sigma), Minimal Essential Medium (MEM, Sigma), RPMI-1640 (Sigma) and Dulbecco's Modified Eagle's Medium (DMEM, Sigma) are exemplary nutrient solutions. In addition, any of the media described in Ham and Wallace, (1979) Meth. Enz., 58:44; Barnes and Sato, (1980) Anal. Biochem., 102:255; U.S. Pat. Nos. 4,767,704; 4,657,866; 4,927,762; 5,122,469 or U.S. Pat. No. 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements can also be included at appropriate concentrations that would be known to those skilled in the art.

In certain embodiments, the mammalian cell that has been modified to reduce and/or eliminate the expression of a PKM polypeptide is a CHO cell. Any suitable medium can be used to culture the CHO cell. In certain embodiments, a suitable medium for culturing the CHO cell can contain a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) (the formulation of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

In certain embodiments, the mammalian cell that has been modified to reduce and/or eliminate the expression of a PKM polypeptide is a cell that expresses a recombinant protein. The recombinant protein can be produced by growing cells which express the products of interest under a variety of cell culture conditions. For instance, cell culture procedures for the large or small-scale production of proteins are potentially useful within the context of the present disclosure. Procedures including, but not limited to, a fluidized bed bioreactor, hollow fiber bioreactor, roller bottle culture, shake flask culture, or stirred tank bioreactor system can be used, in the latter two systems, with or without microcarriers, and operated alternatively in a batch, fed-batch, or continuous mode.

In certain embodiments, the cell culture of the present disclosure is performed in a stirred tank bioreactor system and a fed batch culture procedure is employed. In the fed batch culture, the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel).

In certain embodiments, the cells of the culture can be propagated according to any scheme or routine that can be suitable for the specific host cell and the specific production plan contemplated. Therefore, the present disclosure contemplates a single step or multiple step culture procedure. In a single step culture, the host cells are inoculated into a culture environment and the processes of the instant disclosure are employed during a single production phase of the cell culture. Alternatively, a multi-stage culture is envisioned. In the multi-stage culture cells can be cultivated in a number of steps or phases. For instance, cells can be grown in a first step or growth phase culture wherein cells, possibly removed from storage, are inoculated into a medium suitable for promoting growth and high viability. The cells can be maintained in the growth phase for a suitable period of time by the addition of fresh medium to the host cell culture.

In certain embodiments, fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30° to 38° C. and a suitable $dO_2$ is between 5-90% of air saturation.

At a particular stage the cells can be used to inoculate a production phase or step of the cell culture. Alternatively, as described above the production phase or step can be continuous with the inoculation or growth phase or step.

In certain embodiments, the culturing methods described in the present disclosure can further include harvesting the product from the cell culture, e.g., from the production phase of the cell culture. In certain embodiments, the product produced by the cell culture methods of the present disclosure can be harvested from the third bioreactor, e.g., production bioreactor. For example, but not by way of limitation, the disclosed methods can include harvesting the product at the completion of the production phase of the cell culture. Alternatively or additionally, the product can be harvested prior to the completion of the production phase. In certain embodiments, the product can be harvested from the cell culture once a particular cell density has been achieved. For example, but not by way of limitation, the cell density can be from about $2.0\times10^7$ cells/mL to about $5.0\times10^7$ cells/mL prior to harvesting.

In certain embodiments, harvesting the product from the cell culture can include one or more of centrifugation, filtration, acoustic wave separation, flocculation and cell removal technologies.

In certain embodiments, the product of interest can be secreted from the host cells or can be a membrane-bound, cytosolic or nuclear protein. In certain embodiments, soluble forms of the polypeptide can be purified from the conditioned cell culture media and membrane-bound forms of the polypeptide can be purified by preparing a total membrane fraction from the expressing cells and extracting the membranes with a nonionic detergent such as TRITON® X-100 (EMD Biosciences, San Diego, Calif.). In certain embodiments, cytosolic or nuclear proteins can be prepared by lysing the host cells (e.g., by mechanical force, sonication and/or detergent), removing the cell membrane fraction by centrifugation and retaining the supernatant.

5.5 Products

The cells and/or methods of the present disclosure can be used to produce any product of interest that can be expressed by the cells disclosed herein. In certain embodiments, the cells and/or methods of the present disclosure can be used for the production of polypeptides, e.g., mammalian polypeptides. Non-limiting examples of such polypeptides include hormones, receptors, fusion proteins, regulatory factors, growth factors, complement system factors, enzymes, clotting factors, anti-clotting factors, kinases, cytokines, CD proteins, interleukins, therapeutic proteins, diagnostic proteins and antibodies. The cells and/or methods of the present disclosure are not specific to the molecule, e.g., antibody, that is being produced.

In certain embodiments, the methods of the present disclosure can be used for the production of antibodies, including therapeutic and diagnostic antibodies or antigen-binding fragments thereof. In certain embodiments, the antibody produced by cell and methods of the present disclosure can be, but are not limited to, monospecific antibodies (e.g., antibodies consisting of a single heavy chain sequence and a single light chain sequence, including multimers of such pairings), multispecific antibodies and antigen-binding fragments thereof. For example, but not by way of limitation, the multispecific antibody can be a bispecific antibody, a biepitopic antibody, a T-cell-dependent bispecific antibody (TDB), a Dual Acting FAb (DAF) or antigen-binding fragments thereof.

5.5.1 Multispecific Antibodies

In certain aspects, an antibody produced by cells and methods provided herein is a multispecific antibody, e.g., a bispecific antibody. "Multispecific antibodies" are monoclonal antibodies that have binding specificities for at least two different sites, i.e., different epitopes on different antigens (i.e., bispecific) or different epitopes on the same antigen (i.e., biepitopic). In certain aspects, the multispecific antibody has three or more binding specificities. Multispecific antibodies can be prepared as full length antibodies or antibody fragments as described herein.

Techniques for making multispecific antibodies include, but are not limited to, recombinant co-expression of two immunoglobulin heavy chain-light chain pairs having different specificities (see Milstein and Cuello, Nature 305: 537 (1983)) and "knob-in-hole" engineering (see, e.g., U.S. Pat. No. 5,731,168, and Atwell et al., J. Mol. Biol. 270:26 (1997)). Multispecific antibodies can also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992) and WO 2011/034605); using the common light chain technology for circumventing the light chain mispairing problem (see, e.g., WO 98/50431); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g., WO 2001/77342 and WO 2008/024715). Other non-limiting examples of multispecific antibodies with three or more antigen binding sites can be found in WO 2010/115589, WO 2010/112193, WO 2010/136172, WO 2010/145792 and WO 2013/026831. The bispecific antibody or antigen binding fragment thereof also includes a "Dual Acting FAb" or "DAF" (see, e.g., US 2008/0069820 and WO 2015/095539).

Multispecific antibodies can also be provided in an asymmetric form with a domain crossover in one or more binding arms of the same antigen specificity, i.e., by exchanging the VH/VL domains (see, e.g., WO 2009/080252 and WO 2015/150447), the CH1/CL domains (see, e.g., WO 2009/080253) or the complete Fab arms (see, e.g., WO 2009/080251, WO 2016/016299, also see Schaefer et al, PNAS, 108 (2011) 1187-1191, and Klein at al., MAbs 8 (2016) 1010-20). In certain embodiments, the multispecific antibody comprises a cross-Fab fragment. The term "cross-Fab fragment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See, e.g., WO 2016/172485.

Various further molecular formats for multispecific antibodies are known in the art and are included herein (see, e.g., Spiess et al., Mol. Immunol. 67 (2015) 95-106).

In certain embodiments, particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells.

Additional non-limiting examples of bispecific antibody formats that can be useful for this purpose include, but are not limited to, the so-called "BITE" (bispecific T cell engager) molecules wherein two scFv molecules are fused by a flexible linker (see, e.g., WO 2004/106381, WO 2005/061547, WO 2007/042261, and WO 2008/119567, Nagorsen and Bauerle, Exp Cell Res 317, 1255-1260 (2011)); diabodies (Holliger et al., Prot. Eng. 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat. Rev. 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

5.5.2 Antibody Fragments

In certain aspects, an antibody produced by the cells and methods provided herein is an antibody fragment. For example, but not by way of limitation, the antibody fragment is a Fab, Fab', Fab'-SH or F(ab')2 fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an $F(ab')_2$ fragment that has two antigen-binding sites (two Fab fragments) and a part of the Fc region. For discussion of Fab and $F(ab')_2$ fragments comprising salvage receptor binding epitope residues and having increased in vivo half-life, see U.S. Pat. No. 5,869,046.

In certain embodiments, the antibody fragment is a diabody, a triabody or a tetrabody. "Diabodies" are antibody fragments with two antigen-binding sites that can be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction:

a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., PlUckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody.

5.5.3 Chimeric and Humanized Antibodies

In certain aspects, an antibody produced by the cells and methods provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In certain embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that can be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. *Proc. Natl. Acad. Sci*. USA, 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5.5.4 Human Antibodies

In certain aspects, an antibody produced by the cells and methods provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals can be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

5.5.5 Target Molecules

Non-limiting examples of molecules that can be targeted by an antibody produced by the cells and methods disclosed herein include soluble serum proteins and their receptors and other membrane bound proteins (e.g., adhesins). In certain embodiments, an antibody produced by the cells and methods disclosed herein is capable of binding to one, two or more cytokines, cytokine-related proteins, and cytokine receptors selected from the group consisting of 8MPI, 8MP2, 8MP38 (GDFIO), 8MP4, 8MP6, 8MP8, CSFI (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFN81, IFNG, IFNWI, FEL1, FEL1 (EPSELON), FEL1 (ZETA), IL 1A, IL 1B, IL2, IL3, IL4, IL5, IL6, IL7, IL8, IL9, IL1 0, IL 11, IL 12A, IL 12B, IL 13, IL 14, IL 15, IL 16, IL 17, IL 17B, IL 18, IL 19, IL20, IL22, IL23, IL24, IL25, IL26, IL27, IL28A, IL28B, IL29, IL30, PDGFA, PDGFB, TGFA, TGFB1, TGFB2, TGFBb3, LTA (TNF-β), LTB, TNF (TNF-α), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNF SF10 (TRAIL), TNF SF 11 (TRANCE), TNF SF12 (APO3L), TNF SF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL 11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.k In certain embodiments, an antibody produced by cells and methods disclosed herein is capable of binding to a chemokine, chemokine receptor, or a chemokine-related protein selected from the group consisting of CCLI (1-309), CCL2 (MCP-1/MCAF), CCL3 (MIP)-Iα), CCL4 (MIP-Iβ), CCL5 (RANTES), CCL7 (MCP-3), CCL8 (mcp-2), CCL11 (eotaxin), CCL 13 (MCP-4), CCL 15 (MIP-Iδ), CCL 16 (HCC-4), CCL 17 (TARC), CCL 18 (PARC), CCL 19 (MDP-3b), CCL20 (MIP-3α), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GROI), CXCL2 (GR02), CXCL3 (GR03), CXCL5 (ENA-78), CXCL6 (GCP-2), CXCL9 (MIG), CXCL 10 (IP 10), CXCL 11 (1-TAC), CXCL 12 (SDFI), CXCL 13, CXCL 14, CXCL 16, PF4 (CXCL4), PPBP (CXCL7), CX3CL 1 (SCYDI), SCYEI, XCLI (lymphotactin), XCL2 (SCM-I β), BLRI (MDR15), CCBP2 (D6/JAB61), CCRI (CKRI/HM145), CCR2 (mcp-IRB IRA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Rα), IL8RB (IL8Rβ), LTB4R (GPR16), TCP10, CKLFSF2, CKLFSF3, CKLFSF4, CKLFSF5, CKLFSF6, CKLFSF7, CKLFSF8, BDNF, C5, C5R1, CSF3, GRCC10 (C10), EPO, FY (DARC), GDFS, HDF1, HDF1α, DL8, PRL, RGS3, RGS13, SDF2, SLIT2, TLR2, TLR4, TREM1, TREM2, and VHL.

In certain embodiments, an antibody produced by methods disclosed herein (e.g., a multispecific antibody such as a bispecific antibody) is capable of binding to one or more target molecules selected from the following: 0772P (CA125, MUC16) (i.e., ovarian cancer antigen), ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; amyloid beta; ANGPTL; ANGPT2; ANGPTL3; ANGPTL4; ANPEP; APC; APOC1; AR; ASLG659; ASPHD1 (aspartate beta-hydroxylase domain containing 1; LOC253982); AZGP1 (zinc-a-glycoprotein); B7.1; B7.2; BAD; BAFF-R (B cell-activating factor receptor, BLyS receptor 3, BR3; BAG1; BAI1; BCL2; BCL6; BDNF; BLNK; BLRI (MDR15); BMP1; BMP2; BMP3B (GDF10); BMP4; BMP6; BMP8; BMPR1A; BMPR1B (bone morphogenic protein receptor-type IB); BMPR2; BPAG1 (plectin); BRCA1; Brevican; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP1δ); CCL16 (HCC-4); CCL17 (TARC); CCL18 (PARC); CCL19 (MIP-3β); CCL2 (MCP-1); MCAF; CCL20 (MIP-3α); CCL21 (MTP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Iα); CCL4 (MDP-Iβ); CCL5(RANTES); CCL7 (MCP-3); CCL8 (mcp-2); CCNA1; CCNA2; CCND1; CCNE1; CCNE2; CCR1 (CKRI/HM145); CCR2 (mcp-IRβ/RA); CCR3 (CKR/CMKBR3); CCR4; CCR5 (CMKBR5/ChemR13); CCR6 (CMKBR6/CKR-L3/STRL22/DRY6); CCR7 (CKBR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD22 (B-cell receptor CD22-B isoform); CD24; CD28; CD3; CD37; CD38; CD3E; CD3G; CD3Z; CD4; CD40; CD40L; CD44; CD45RB; CD52; CD69; CD72; CD74; CD79A (CD79a, immunoglobulin-associated alpha, a B cell-specific protein); CD79B; CDS; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21/WAF1/Cip1); CDKN1B (p27/Kip1); CDKN1C; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLL-1 (CLEC12A, MICL, and DCAL2); CLN3; CLU (clusterin); CMKLR1; CMKOR1 (RDC1); CNR1; COL 18A1; COL1A1; COL4A3; COL6A1; complement factor D; CR2; CRP; CRIPTO (CR, CR1, CRGF, CRIPTO, TDGF1, teratocarcinoma-derived growth factor); CSFI (M-CSF); CSF2 (GM-CSF); CSF3 (GCSF); CTLA4; CTNNB1 (b-catenin); CTSB (cathepsin B); CX3CL1 (SCYDI); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR5 (Burkitt's lymphoma receptor 1, a G protein-coupled receptor); CXCR6 (TYMSTR/STRL33/Bonzo); CYB5; CYC1; CYSLTR1; DAB2IP; DES; DKFZp451J0118; DNCLI; DPP4; E16 (LAT1, SLC7A5);

E2F1; ECGF1; EDG1; EFNA1; EFNA3; EFNB2; EGF; EGFR; ELAC2; ENG; ENO1; ENO2; ENO3; EPHB4; EphB2R; EPO; ERBB2 (Her-2); EREG; ERK8; ESR1; ESR2; ETBR (Endothelin type B receptor); F3 (TF); FADD; FasL; FASN; FCER1A; FCER2; FCGR3A; FcRH1 (Fc receptor-like protein 1); FcRH2 (IFGP4, IRTA4, SPAP1A (SH2 domain containing phosphatase anchor protein 1a), SPAP1B, SPAP1C); FGF; FGF1 (αFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR; FGFR3; FIGF (VEGFD); FEL1 (EPSILON); FIL1 (ZETA); F1112584; F1125530; FLRTI (fibronectin); FLT1; FOS; FOSL1 (FRA-1); FY (DARC); GABRP (GABAa); GAGEB1; GAGEC1; GALNAC4S-6ST; GATA3; GDFS; GDNF-Ral (GDNF family receptor alpha 1; GFRA1; GDNFR; GDNFRA; RETL1; TRNR1; RET1L; GDNFR-alpha1; GFR-ALPHA-1); GEDA; GFI1; GGT1; GM-CSF; GNASI; GNRHI; GPR2 (CCR10); GPR19 (G protein-coupled receptor 19; Mm.4787); GPR31; GPR44; GPR54 (KISS1 receptor; KISS1R; GPR54; HOT7T175; AXOR12); GPR81 (FKSG80); GPR172A (G protein-coupled receptor 172A; GPCR41; FLJ11856; D15Ertd747e); GRCCIO (C10); GRP; GSN (Gelsolin); GSTP1; HAVCR2; HDAC4; HDAC5; HDAC7A; HDAC9; HGF; HIF1A; HOP1; histamine and histamine receptors; HLA-A; HLA-DOB (Beta subunit of MHC class II molecule (Ia antigen); HLA-DRA; HM74; HMOXI; HUMCYT2A; ICEBERG; ICOSL; 1D2; IFN-α; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; ILIA; IL1B; ILIF10; IL1F5; IL1F6; IL1F7; IL1F8; IL1F9; IL1HY1; IL1R1; IL1R2; IL1RAP; IL1RAPL1; IL1RAPL2; IL1RL1; IL1RL2, IL1RN; IL2; IL20; IL20Rα; IL21 R; IL22; IL-22c; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); influenza A; influenza B; EL7; EL7R; EL8; IL8RA; DL8RB; IL8RB; DL9; DL9R; DLK; INHA; INHBA; INSL3; INSL4; IRAK1; IRTA2 (Immunoglobulin superfamily receptor translocation associated 2); ERAK2; ITGA1; ITGA2; ITGA3; ITGA6 (a6 integrin); ITGAV; ITGB3; ITGB4 (b4 integrin); α4β7 and αEβ7 integrin heterodimers; JAG1; JAK1; JAK3; JUN; K6HF; KAI1; KDR; KITLG; KLFS (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); LGR5 (leucine-rich repeat-containing G protein-coupled receptor 5; GPR49, GPR67); Lingo-p75; Lingo-Troy; LPS; LTA (TNF-b); LTB; LTB4R (GPR16); LTB4R2; LTBR; LY64 (Lymphocyte antigen 64 (RP105), type I membrane protein of the leucine rich repeat (LRR) family); Ly6E (lymphocyte antigen 6 complex, locus E; Ly67,RIG-E, SCA-2, TSA-1); Ly6G6D (lymphocyte antigen 6 complex, locus G6D; Ly6-D, MEGT1); LY6K (lymphocyte antigen 6 complex, locus K; LY6K; HSJ001348; FLJ35226); MACMARCKS; MAG or OMgp; MAP2K7 (c-Jun); MDK; MDP; MIB1; midkine; MEF; MIP-2; MKI67; (Ki-67); MMP2; MMP9; MPF (MPF, MSLN, SMR, megakaryocyte potentiating factor, mesothelin); MS4A1; MSG783 (RNF124, hypothetical protein FLJ20315); MSMB; MT3 (metallothionectin-111); MTSS1; MUC1 (mucin); MYC; MY088; Napi3b (also known as NaPi2b) (NAPI-3B, NPTIIb, SLC34A2, solute carrier family 34 (sodium phosphate), member 2, type II sodium-dependent phosphate transporter 3b); NCA; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR112; NR113; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZI; OPRD1; OX40; P2RX7; P2X5 (Purinergic receptor P2X ligand-gated ion channel 5); PAP; PART1; PATE; PAWR; PCA3; PCNA; PD-L1; PD-L2; PD-1; POGFA; POGFB; PECAM1; PF4 (CXCL4); PGF; PGR; phosphacan; PIAS2; PIK3CG; PLAU (uPA); PLG; PLXDC1; PMEL17 (silver homolog; SILV; D12S53E; PMEL17; SI; SIL); PPBP (CXCL7); PPID; PM; PRKCQ; PRKDI; PRL; PROC; PROK2; PSAP; PSCA hlg (2700050C12Rik, C530008O16Rik, RIKEN cDNA 2700050C12, RIKEN cDNA 2700050C12 gene); PTAFR; PTEN; PTGS2 (COX-2); PTN; RAC2 (p21 Rac2); RARE; RET (ret proto-oncogene; MEN2A; HSCR1; MEN2B; MTC1; PTC; CDHF12; Hs.168114; RET51; RET-ELE1); RGSI; RGS13; RGS3; RNF110 (ZNF144); ROBO2; S100A2; SCGB1D2 (lipophilin B); SCGB2A1 (mammaglobin2); SCGB2A2 (mammaglobin 1); SCYEI (endothelial Monocyte-activating cytokine); SDF2; Sema 5b (F1110372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B); SERPINA1; SERPINA3; SERP1NB5 (maspin); SERPINE1(PAI-1); SERPDMF1; SHBG; SLA2; SLC2A2; SLC33A1; SLC43A1; SLIT2; SPPI; SPRR1B (Sprl); ST6GAL1; STABI; STATE; STEAP (six transmembrane epithelial antigen of prostate); STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein); TB4R2; TBX21; TCPIO; TOGFI; TEK; TENB2 (putative transmembrane proteoglycan); TGFA; TGFBI; TGFB1II; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLR1; TLR2; TLR3; TLR4; TLR5; TLR6; TLR7; TLR8; TLR9; TLR10; TMEFF1 (transmembrane protein with EGF-like and two follistatin-like domains 1; Tomoregulin-1); TMEM46 (shisa homolog 2); TNF; TNF-a; TNFAEP2 (B94); TNFAIP3; TNFRSFIIA; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSFS (CD30 ligand); TNFSF9 (4-1 BB ligand); TOLLIP; Toll-like receptors; TOP2A (topoisomerase Ea); TP53; TPM1; TPM2; TRADD; TMEM118 (ring finger protein, transmembrane 2; RNFT2; FLJ14627); TRAF1; TRAF2; TRAF3; TRAF4; TRAF5; TRAF6; TREM1; TREM2; TrpM4 (BR22450, FLJ20041, TRPM4, TRPM4B, transient receptor potential cation channel, subfamily M, member 4); TRPC6; TSLP; TWEAK; Tyrosinase (TYR; OCAIA; OCA1A; tyrosinase; SHEP3); VEGF; VEGFB; VEGFC; versican; VHL C5; VLA-4; XCL1 (lymphotactin); XCL2 (SCM-1b); XCRI(GPR5/CCXCRI); YY1; and ZFPM2.

In certain embodiments, an antibody produced by the cells and methods disclosed herein is capable of binding to CD proteins such as CD3, CD4, CD5, CD16, CD19, CD20, CD21 (CR2 (Complement receptor 2) or C3DR (C3d/Epstein Barr virus receptor) or Hs.73792); CD33; CD34; CD64; CD72 (B-cell differentiation antigen CD72, Lyb-2); CD79b (CD79B, CD79(3, IGb (immunoglobulin-associated beta), B29); CD200 members of the ErbB receptor family such as the EGF receptor, HER2, HER3, or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18, or anti-CD11b antibodies); growth factors such as VEGF-A, VEGF-C; tissue factor (TF); alpha interferon (alphaIFN); TNFalpha, an interleukin, such as IL-1 beta, IL-3, IL-4, IL-5, IL-6, IL-8, IL-9, IL-13, IL 17 AF, IL-1S, IL-13R alpha1, IL13R alpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In certain embodiments, the cells and methods provided herein can be used to produce an antibody (or a multispecific antibody, such as a bispecific antibody) that specifically binds to complement protein C5 (e.g., an anti-CS agonist antibody that specifically binds to human C5). In certain embodiments, the anti-CS antibody comprises 1, 2, 3, 4, 5 or 6 CDRs selected from (a) a heavy chain variable region CDR1 comprising the amino acid sequence of SSYYMA (SEQ ID NO:1); (b) a heavy chain variable region CDR2 comprising the amino acid sequence of AIFTGSGAEYKAEWAKG (SEQ ID NO:26); (c) a heavy chain variable region CDR3 comprising the amino acid sequence of DAGYDYPTHAIVIHY (SEQ ID NO: 27); (d) a light chain variable region CDR1 comprising the amino acid sequence of RASQGISSSLA (SEQ ID NO: 28); (e) a light chain variable region CDR2 comprising the amino acid sequence of GASETES (SEQ ID NO: 29); and (f) a light chain variable region CDR3 comprising the amino acid sequence of QNTKVGSSYGNT (SEQ ID NO: 30). For example, in certain embodiments, the anti-05 antibody comprises a heavy chain variable domain (VH) sequence comprising one, two or three CDRs selected from: (a) a heavy chain variable region CDR1 comprising the amino acid sequence of (SSYYMA (SEQ ID NO: 1); (b) a heavy chain variable region CDR2 comprising the amino acid sequence of AIFTGSGAEYKAEWAKG (SEQ ID NO: 26); (c) a heavy chain variable region CDR3 comprising the amino acid sequence of DAGYDYPTHAMHY (SEQ ID NO: 27); and/or a light chain variable domain (VL) sequence comprising one, two or three CDRs selected from (d) a light chain variable region CDR1 comprising the amino acid sequence of RASQGISSSLA (SEQ ID NO: 28); (e) a light chain variable region CDR2 comprising the amino acid sequence of GASETES (SEQ ID NO: 29); and (f) a light chain variable region CDR3 comprising the amino acid sequence of QNTKVGSSYGNT (SEQ ID NO: 30). The sequences of CDR1, CDR2 and CDR3 of the heavy chain variable region and CDR1, CDR2 and CDR3 of the light chain variable region above are disclosed in US 2016/0176954 as SEQ ID NO: 117, SEQ ID NO: 118, SEQ ID NO: 121, SEQ ID NO: 122, SEQ ID NO: 123, and SEQ ID NO: 125, respectively. (See Tables 7 and 8 in US 2016/0176954.)

In certain embodiments, the anti-C5 antibody comprises the VH and VL sequences QVQLVESGGG LVQPGRSLRL SCAASGFTVH SSYYMAWVRQ APGKGLEWVG AIFTGSGAEY KAEWAKGRVT ISKDTSKNQV VLTMTNMDPV DTATYYCASD AGYDYPTHAM HYWGQGTLVT VSS (SEQ ID NO: 31) and DIQMTQSPSS LSASVGDRVT ITCRASQGIS SSLAWYQQKP GKAPKLLIYG ASETESGVPS RFSGSGSGTD FTLTISSLQP EDFATYYCQN TKVGSSYGNT FGGGTKVEIK (SEQ ID NO: 32), respectively, including post-translational modifications of those sequences. The VH and VL sequences above are disclosed in US 2016/0176954 as SEQ ID NO: 106 and SEQ ID NO: 111, respectively. (See Tables 7 and 8 in US 2016/0176954.) In certain embodiments, the anti-C5 antibody is 305L015 (see US 2016/0176954).

In certain embodiments, an antibody produced by methods disclosed herein is capable of binding to OX40 (e.g., an anti-OX40 agonist antibody that specifically binds to human OX40). In certain embodiments, the anti-OX40 antibody comprises 1, 2, 3, 4, 5 or 6 CDRs selected from (a) a heavy chain variable region CDR1 comprising the amino acid sequence of DSYMS (SEQ ID NO: 2); (b) a heavy chain variable region CDR2 comprising the amino acid sequence of DMYPDNGDSSYNQKFRE (SEQ ID NO: 3); (c) a heavy chain variable region CDR3 comprising the amino acid sequence of APRWYFSV (SEQ ID NO: 4); (d) a light chain variable region CDR1 comprising the amino acid sequence of RASQDISNYLN (SEQ ID NO: 5); (e) a light chain variable region CDR2 comprising the amino acid sequence of YTSRLRS (SEQ ID NO: 6); and (f) a light chain variable region CDR3 comprising the amino acid sequence of QQGHTLPPT (SEQ ID NO: 7). For example, in certain embodiments, the anti-OX40 antibody comprises a heavy chain variable domain (VH) sequence comprising one, two or three CDRs selected from: (a) a heavy chain variable region CDR1 comprising the amino acid sequence of DSYMS (SEQ ID NO: 2); (b) a heavy chain variable region CDR2 comprising the amino acid sequence of DMYPDNGDSSYNQKFRE (SEQ ID NO: 3); and (c) a heavy chain variable region CDR3 comprising the amino acid sequence of APRWYFSV (SEQ ID NO: 4) and/or a light chain variable domain (VL) sequence comprising one, two or three CDRs selected from (a) a light chain variable region CDR1 comprising the amino acid sequence of RASQDISNYLN (SEQ ID NO: 5); (b) a light chain variable region CDR2 comprising the amino acid sequence of YTSRLRS (SEQ ID NO: 6); and (c) a light chain variable region CDR3 comprising the amino acid sequence of QQGHTLPPT (SEQ ID NO: 7). In certain embodiments, the anti-OX40 antibody comprises the VH and VL sequences EVQLVQSGAE VKKPGASVKV SCKASGYTFT DSYMSWVRQA PGQGLEWIGD MYPDNGDSSY NQKFRERVTI TRDTSTSTAY LELSSLRSED TAVYYCVLAP RWYFSVWGQG TLVTVSS (SEQ ID NO: 8) and DIQMTQSPSS LSASVGDRVT ITCRASQDIS NYLNWYQQKP GKAPKLLIYY TSRLRSGVPS RFSGSGSGTD FTLTISSLQP EDFATYYCQQ GHTLPPTFGQ GTKVEIK (SEQ ID NO: 9), respectively, including post-translational modifications of those sequences.

In certain embodiments, the anti-OX40 antibody comprises 1, 2, 3, 4, 5 or 6 CDRs selected from (a) a heavy chain variable region CDR1 comprising the amino acid sequence of NYLIE (SEQ ID NO: 10); (b) a heavy chain variable region CDR2 comprising the amino acid sequence of VINPGSGDTYYSEKFKG (SEQ ID NO: 11); (c) a heavy chain variable region CDR3 comprising the amino acid sequence of DRLDY (SEQ ID NO: 12); (d) a light chain variable region CDR1 comprising the amino acid sequence of HASQDISSYIV (SEQ ID NO: 13); (e) a light chain variable region CDR2 comprising the amino acid sequence of HGTNLED (SEQ ID NO: 14); and (f) a light chain variable region CDR3 comprising the amino acid sequence of VHYAQFPYT (SEQ ID NO: 15). For example, in certain embodiments, the anti-OX40 antibody comprises a heavy chain variable domain (VH) sequence comprising one, two or three CDRs selected from: (a) a heavy chain variable region CDR1 comprising the amino acid sequence of NYLIE (SEQ ID NO: 10); (b) a heavy chain variable region CDR2 comprising the amino acid sequence of VINPGSGDTYYSEKFKG (SEQ ID NO: 11); and (c) a heavy chain variable region CDR3 comprising the amino acid sequence of DRLDY (SEQ ID NO: 12) and/or a light chain variable domain (VL) sequence comprising one, two or three CDRs selected from (a) a light chain variable region CDR1 comprising the amino acid sequence of HASQDISSYIV (SEQ ID NO: 13); (b) a light chain variable region CDR2 comprising the amino acid sequence of HGTNLED (SEQ ID NO: 14); and (c) a light chain variable region CDR3 comprising the amino acid sequence of VHYAQFPYT (SEQ ID NO: 15). In certain embodiments, the anti-OX40 antibody comprises the VH and VL sequences
EVQLVQSGAE VKKPGASVKV SCKASGYAFT NYLIEWVRQA PGQGLEWIGV INPGSGDTYY SEKFKGRVTI TRDTSTSTAY LELSSLRSED TAVYYCARDR LDYWGQGTLV TVSS (SEQ ID NO: 16)
and
DIQMTQSPSS LSASVGDRVT ITCHASQDIS SYIVWYQQKP GKAPKLLIYH GTNLEDGVPS RFSGSGSGTD FTLTISSLQP EDFATYYCVH YAQFPYTFGQ GTKVEIK (SEQ ID NO: 17), respectively, including post-translational modifications of those sequences.

Further details regarding anti-OX40 antibodies are provided in WO 2015/153513, which is incorporated herein by reference in its entirety.

In certain embodiments, an antibody produced by the cells and methods disclosed herein is capable of binding to influenza virus B hemagglutinin, i.e., “fluB” (e.g., an antibody that binds hemagglutinin from the Yamagata lineage of influenza B viruses, binds hemagglutinin from the Victoria lineage of influenza B viruses, binds hemagglutinin from ancestral lineages of influenza B virus, or binds hemagglutinin from the Yamagata lineage, the Victoria lineage, and ancestral lineages of influenza B virus, in vitro and/or in vivo). Further details regarding anti-FluB antibodies are described in WO 2015/148806, which is incorporated herein by reference in its entirety.

In certain embodiments, an antibody produced by the cells and methods disclosed herein is capable of binding to low density lipoprotein receptor-related protein (LRP)-1 or LRP-8 or transferrin receptor, and at least one target selected from the group consisting of beta-secretase (BACE1 or BACE2), alpha-secretase, gamma-secretase, tau-secretase, amyloid precursor protein (APP), death receptor 6 (DR6), amyloid beta peptide, alpha-synuclein, Parkin, Huntingtin, p75 NTR, CD40 and caspase-6.

In certain embodiments, an antibody produced by the cells and methods disclosed herein is a human IgG2 antibody against CD40. In certain embodiments, the anti-CD40 antibody is RG7876.

In certain embodiments, the cells and methods of the present disclosure can be used to product a polypeptide. For example, but not by way of limitation, the polypeptide is a targeted immunocytokine. In certain embodiments, the targeted immunocytokine is a CEA-IL2v immunocytokine. In certain embodiments, the CEA-IL2v immunocytokine is RG7813. In certain embodiments, the targeted immunocytokine is a FAP-IL2v immunocytokine. In certain embodiments, the FAP-IL2v immunocytokine is RG7461.

In certain embodiments, the multispecific antibody (such as a bispecific antibody) produced by the cells or methods provided herein is capable of binding to CEA and at least one additional target molecule. In certain embodiments, the multispecific antibody (such as a bispecific antibody) produced according to methods provided herein is capable of binding to a tumor targeted cytokine and at least one additional target molecule. In certain embodiments, the multispecific antibody (such as a bispecific antibody) produced according to methods provided herein is fused to IL2v (i.e., an interleukin 2 variant) and binds an IL1-based immunocytokine and at least one additional target molecule. In certain embodiments, the multispecific antibody (such as a bispecific antibody) produced according to methods provided herein is a T-cell bispecific antibody (i.e., a bispecific T-cell engager or BiTE).

In certain embodiments, the multispecific antibody (such as a bispecific antibody) produced according to methods provided herein is capable of binding to at least two target molecules selected from: IL-1 alpha and IL-1 beta, IL-12 and IL-1S; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-~; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL17F, CEA and CD3, CD3 and CD19, CD138 and CD20; CD138 and CD40; CD19 and CD20; CD20 and CD3; CD3S and CD13S; CD3S and CD20; CD3S and CD40; CD40 and CD20; CD-S and IL-6; CD20 and BR3, TNF alpha and TGF-beta, TNF alpha and IL-1 beta; TNF alpha and IL-2, TNF alpha and IL-3, TNF alpha and IL-4, TNF alpha and IL-5, TNF alpha and IL6, TNF alpha and IL8, TNF alpha and IL-9, TNF alpha and IL-10, TNF alpha and IL-11, TNF alpha and IL-12, TNF alpha and IL-13, TNF alpha and IL-14, TNF alpha and IL-15, TNF alpha and IL-16, TNF alpha and IL-17, TNF alpha and IL-18, TNF alpha and IL-19, TNF alpha and IL-20, TNF alpha and IL-23, TNF alpha and IFN alpha, TNF alpha and CD4, TNF alpha and VEGF, TNF alpha and MIF, TNF alpha and ICAM-1, TNF alpha and PGE4, TNF alpha and PEG2, TNF alpha and RANK ligand, TNF alpha and Te38, TNF alpha and BAFF, TNF alpha and CD22, TNF alpha and CTLA-4, TNF alpha and GP130, TNF a and IL-12p40, VEGF and Angiopoietin, VEGF and HER2, VEGF-A and HER2, VEGF-A and PDGF, HER1 and HER2, VEGFA and ANG2, VEGF-A and VEGF-C, VEGF-C and VEGF-D, HER2 and DR5, VEGF and IL-8, VEGF and MET, VEGFR and MET receptor, EGFR and MET, VEGFR and EGFR, HER2 and CD64, HER2 and CD3, HER2 and CD16, HER2 and HER3; EGFR (HER1) and HER2, EGFR and HER3, EGFR and HER4, IL-14 and IL-13, IL-13 and CD40L, IL4 and CD40L, TNFR1 and IL-1 R, TNFR1 and IL-6R and TNFR1 and IL-18R, EpCAM and CD3, MAPG and CD28, EGFR and CD64, CSPGs and RGM A; CTLA-4 and BTN02; IGF1 and IGF2; IGF1/2 and Erb2B; MAG and RGM A; NgR and RGM A; NogoA and RGM A; OMGp and RGM A; POL-1 and CTLA-4; and RGM A and RGM B.

In certain embodiments, the multispecific antibody (such as a bispecific antibody) produced according to methods provided herein is an anti-CEA/anti-CD3 bispecific antibody. In certain embodiments, the anti-CEA/anti-CD3 bispecific antibody is RG7802. In certain embodiments, the anti-CEA/anti-CD3 bispecific antibody comprises the amino acid sequences set forth in SEQ ID NOs: 18-21 are provided below:

(SEQ ID NO: 18)

DIQMTQSPSS LSASVGDRVT ITCKASAAVG TYVAWYQQKP
GKAPKLLIYS ASYRKRGVPS RFSGSGSGTD FTLTISSLQP
EDFATYYCHQ YYTYPLFTFG QGTKLEIKRT VAAPSVFIFP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC (SEQ ID NO: 19)

QAVVTQEPSL TVSPGGTVTL TCGSSTGAVT TSNYANWVQE
KPGQAFRGLI GGTNKRAPGT PARFSGSLLG GKAALTLSGA
QPEDEAEYYC ALWYSNLWVF GGGTKLTVLS SASTKGPSVF
PLAPSSKSTS GGTAALGCLV KDYFPEPVTV SWNSGALTSG
VHTFPAVLQS SGLYSLSSVV TVPSSSLGTQ TYICNVNHKP
SNTKVDKKVE PKSC (SEQ ID NO: 20)

QVQLVQSGAE VKKPGASVKV SCKASGYTFT EFGMNWVRQA
PGQGLEWMGW INTKTGEATY VEEFKGRVTF TTDTSTSTAY
MELRSLRSDD TAVYYCARWD FAYYVEAMDY WGQGTTVTVS
SASTKGPSVF PLAPSSKSTS GGTAALGCLV KDYFPEPVTV
SWNSGALTSG VHTFPAVLQS SGLYSLSSVV TVPSSSLGTQ
TYICNVNHKP SNTKVDKKVE PKSCDGGGGS GGGGSEVQLL
ESGGGLVQPG GSLRLSCAAS GFTFSTYAMN WVRQAPGKGL
EWVSRIRSKY NNYATYYADS VKGRFTISRD DSKNTLYLQM
NSLRAEDTAV YYCVRHGNFG NSYVSWFAYW GQGTLVTVSS
ASVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGECDKT HTCPPCPAPE
AAGGPSVFLF PPKPKDTLMI SRTPEVTCVV VDVSHEDPEV
KFNWYVDGVE VHNAKTKPRE EQYNSTYRVV SVLTVLHQDW
LNGKEYKCKV SNKALGAPIE KTISKAKGQP REPQVYTLPP
CRDELTKNQV SLWCLVKGFY PSDIAVEWES NGQPENNYKT
TPPVLDSDGS FFLYSKLTVD KSRWQQGNVF SCSVMHEALH
NHYTQKSLSL SPGK (SEQ ID NO: 21)

QVQLVQSGAE VKKPGASVKV SCKASGYTFT EFGMNWVRQA
PGQGLEWMG WINTKTGEATY VEEFKGRVTF TTDTSTSTAY
MELRSLRSDD TAVYYCARWD FAYYVEAMD YWGQGTTVTVS
SASTKGPSVF PLAPSSKSTS GGTAALGCLV KDYFPEPVTV
SWNSGALTS GVHTFPAVLQS SGLYSLSSVV TVPSSSLGTQ
TYICNVNHKP SNTKVDKKVE PKSCDKTHT CPPCPAPEAAG

-continued

GPSVFLFPPK PKDTLMISRT PEVTCVVVDV SHEDPEVKFN
WYVDGVEVH NAKTKPREEQY NSTYRVVSVL TVLHQDWLNG
KEYKCKVSNK ALGAPIEKTI SKAKGQPRE PQVCTLPPSRD
ELTKNQVSLS CAVKGFYPSD IAVEWESNGQ PENNYKTTPP
VLDSDGSFF LVSKLTVDKSR WQQGNVFSCS VMHEALHNHY
TQKSLSLSPG K

Further details regarding anti-CEA/anti-CD3 bispecific antibodies are provided in WO 2014/121712, which is incorporated herein by reference in its entirety.

In certain embodiments, a multispecific antibody (such as a bispecific antibody) produced by the cells and methods disclosed herein is an anti-VEGF/anti-angiopoietin bispecific antibody. In certain embodiments, the anti-VEGF/anti-angiopoietin bispecific antibody bispecific antibody is a Crossmab. In certain embodiments, the anti-VEGF/anti-angiopoietin bispecific antibody is RG7716. In certain embodiments, the anti-CEA/anti-CD3 bispecific antibody comprises the amino acid sequences set forth in SEQ ID NOs: 22-25 are provided below:

(SEQ ID NO: 22)

EVQLVESGGG LVQPGGSLRL SCAASGYDFT HYGMNWVRQA
PGKGLEWVGW INTYTGEPTY AADFKRRFTF SLDTSKSTAY
LQMNSLRAED TAVYYCAKYP YYYGTSHWYF DVWGQGTLVT
VSSASTKGPS VFPLAPSSKS TSGGTAALGC LVKDYFPEPV
TVSWNSGALT SGVHTFPAVL QSSGLYSLSS VVTVPSSSLG
TQTYICNVNH KPSNTKVDKK VEPKSCDKTH TCPPCPAPEA
AGGPSVFLFP PKPKDTLMAS RTPEVTCVVV DVSHEDPEVK
FNWYVDGVEV HNAKTKPREE QYNSTYRVVS VLTVLAQDWL
NGKEYKCKVS NKALGAPIEK TISKAKGQPR EPQVYTLPPC
RDELTKNQVS LWCLVKGFYP SDIAVEWESN GQPENNYKTT
PPVLDSDGSF FLYSKLTVDK SRWQQGNVFS CSVMHEALHN
AYTQKSLSLS PGK (SEQ ID NO: 23)

QVQLVQSGAE VKKPGASVKV SCKASGYTFT GYYMHWVRQA
PGQGLEWMGW INPNSGGTNY AQKFQGRVTM TRDTSISTAY
MELSRLRSDD TAVYYCARSP NPYYYDSSGY YYPGAFDIWG
QGTMVTVSSA SVAAPSVFIF PPSDEQLKSG TASVVCLLNN
FYPREAKVQW KVDNALQSGN SQESVTEQDS KDSTYSLSST
LTLSKADYEK HKVYACEVTH QGLSSPVTKS FNRGECDKTH
TCPPCPAPEA AGGPSVFLFP PKPKDTLMAS RTPEVTCVVV
DVSHEDPEVK FNWYVDGVEV HNAKTKPREE QYNSTYRVVS
VLTVLAQDWL NGKEYKCKVS NKALGAPIEK TISKAKGQPR
EPQVCTLPPS RDELTKNQVS LSCAVKGFYP SDIAVEWESN
GQPENNYKTT PPVLDSDGSF FLVSKLTVDK SRWQQGNVFS
CSVMHEALHN AYTQKSLSLS PGK

-continued (SEQ ID NO: 24)

```
DIQLTQSPSS LSASVGDRVT ITCSASQDIS NYLNWYQQKP
GKAPKVLIYF TSSLHSGVPS RFSGSGSGTD FTLTISSLQP
EDFATYYCQQ YSTVPWTFGQ GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

(SEQ ID NO: 25)

```
SYVLTQPPSV SVAPGQTARI TCGGNNIGSK SVHWYQQKPG
QAPVLVVYDD SDRPSGIPER FSGSNSGNTA TLTISRVEAG
DEADYYCQVW DSSSDHWVFG GGTKLTVLSS ASTKGPSVFP
LAPSSKSTSG GTAALGCLVK DYFPEPVTVS WNSGALTSGV
HTFPAVLQSS GLYSLSSVVT VPSSSLGTQT YICNVNHKPS
NTKVDKKVEP KSC
```

In certain embodiments, the multispecific antibody (such as a bispecific antibody) produced by methods disclosed herein is an anti-Ang2/anti-VEGF bispecific antibody. In certain embodiments, the anti-Ang2/anti-VEGF bispecific antibody is RG7221. In certain embodiments, the anti-Ang2/anti-VEGF bispecific antibody is CAS Number 1448221-05-3.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or can be cells which have been transformed by recombinant techniques to express the transmembrane molecule. Other antigens and forms thereof useful for preparing antibodies will be apparent to those in the art.

In certain embodiments, the polypeptide (e.g., antibodies) produced by the cells and methods disclosed herein is capable of binding to can be further conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). An immunoconjugate comprising an antibody or bispecific antibody produced using the methods described herein can contain the cytotoxic agent conjugated to a constant region of only one of the heavy chains or only one of the light chains.

5.5.6 Antibody Variants

In certain aspects, amino acid sequence variants of the antibodies provided herein are contemplated, e.g., the antibodies provided in Section 5.5.5. For example, it can be desirable to alter the binding affinity and/or other biological properties of the antibody. Amino acid sequence variants of an antibody can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

5.5.6.1 Substitution, Insertion, and Deletion Variants

In certain aspects, antibody variants having one or more amino acid substitutions are provided. Sites of interest for substitutional mutagenesis include the CDRs and FRs. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions can be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids can be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which can be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) can be made in CDRs, e.g., to improve antibody affinity. Such alterations can be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding can be specifically identified, e.g., using alanine scanning mutagenesis or modeling. CDR-H3 and CDR-L3 in particular are often targeted.

In certain aspects, substitutions, insertions, or deletions can occur within one or more CDRs so long as such alterations do not substantially reduce the ability of the antibody to bind antigen. For example, conservative alterations (e.g., conservative substitutions as provided herein) that do not substantially reduce binding affinity can be made in the CDRs. Such alterations can, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that can be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions can be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues can be targeted or eliminated as candidates for substitution. Variants can be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

5.5.6.2 Glycosylation Variants

In certain aspects, an antibody provided herein is altered to increase or decrease the extent to which the antibody is glycosylated. Addition or deletion of glycosylation sites to an antibody can be conveniently accomplished by altering the amino acid sequence such that one or more glycosylation sites is created or removed.

Where the antibody comprises an Fc region, the oligosaccharide attached thereto can be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide can include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the disclosure can be made in order to create antibody variants with certain improved properties.

In one aspect, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one aspect, antibody variants are provided having an increased proportion of non-fucosylated oligosaccharides in the Fc region as compared to a native or parent antibody. For example, the proportion of non-fucosylated oligosaccharides can be at least about 20%, at least about 40%, at least about 60%, at least about 80%, or even about 100% (i.e., no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 can also be located about ±3 amino acids upstream or downstream of position 297, i.e., between positions 294 and 300, due to minor sequence variations in antibodies. Such antibodies having an increased proportion of non-fucosylated oligosaccharides in the Fc region can have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO 2003/085107), or cells with reduced or abolished activity of a GDP-fucose synthesis or transporter protein (see, e.g., US2004259150, US2005031613, US2004132140, US2004110282).

In a further aspect, antibody variants are provided with bisected oligosaccharides, e.g., in which a biantennary oligosaccharide attached to the Fc region of the antibody is bisected by GlcNAc. Such antibody variants can have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants can have improved CDC function. Such antibody variants are described, e.g., in WO 1997/30087; WO 1998/58964; and WO 1999/22764.

5.5.6.3 Fc Region Variants

In certain aspects, one or more amino acid modifications can be introduced into the Fc region of an antibody provided herein, thereby generating an Fc region variant. The Fc region variant can comprise a human Fc region sequence (e.g., a human $IgG_1$, $IgG_2$, $IgG_3$ or $IgG_4$ Fc region) comprising an amino acid modification (e.g., a substitution) at one or more amino acid positions.

In certain aspects, the present disclosure contemplates an antibody variant that possesses some but not all effector functions, which make it a desirable candidate for applications in which the half life of the antibody in vivo is important yet certain effector functions (such as complement-dependent cytotoxicity (CDC) and antibody-dependent cell-mediated cytotoxicity (ADCC)) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods can be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. *Proc. Nat'l Acad. Sci. USA* 95:652-656 (1998). C1q binding assays can also be carried out to confirm that the antibody is unable to bind C1q and hence lacks CDC activity. See, e.g., C1q and C3c binding ELISA in WO 2006/029879 and WO 2005/100402. To assess complement activation, a CDC assay can be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006); WO 2013/120929 A1).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain aspects, an antibody variant comprises an Fc region with one or more amino acid substitutions which improve ADCC, e.g., substitutions at positions 298, 333, and/or 334 of the Fc region (EU numbering of residues).

In certain aspects, an antibody variant comprises an Fc region with one or more amino acid substitutions which diminish FcγR binding, e.g., substitutions at positions 234 and 235 of the Fc region (EU numbering of residues). In one aspect, the substitutions are L234A and L235A (LALA). In certain aspects, the antibody variant further comprises D265A and/or P329G in an Fc region derived from a human $IgG_1$ Fc region. In one aspect, the substitutions are L234A, L235A and P329G (LALA-PG) in an Fc region derived from a human $IgG_1$ Fc region. (See, e.g., WO 2012/130831). In another aspect, the substitutions are L234A, L235A and D265A (LALA-DA) in an Fc region derived from a human $IgG_1$ Fc region.

In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (See, e.g., U.S. Pat. No. 7,371,826; Dall'Acqua, W. F., et al. J. Biol. Chem. 281 (2006) 23514-23524).

Fc region residues critical to the mouse Fc-mouse FcRn interaction have been identified by site-directed mutagenesis (see e.g. Dall'Acqua, W. F., et al. J. Immunol 169 (2002) 5171-5180). Residues 1253, H310, H433, N434, and H435 (EU index numbering) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1994) 542). Residues 1253, H310, and H435 were found to be critical for the interaction of human Fc with murine FcRn (Kim, J. K., et al., Eur. J. Immunol. 29 (1999) 2819). Studies of the human Fc-human FcRn complex have shown that residues 1253, 5254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In certain aspects, an antibody variant comprises an Fc region with one or more amino acid substitutions, which reduce FcRn binding, e.g., substitutions at positions 253, and/or 310, and/or 435 of the Fc-region (EU numbering of residues). In certain aspects, the antibody variant comprises an Fc region with the amino acid substitutions at positions 253, 310 and 435. In one aspect, the substitutions are I253A, H310A and H435A in an Fc region derived from a human IgG1 Fc-region. See, e.g., Grevys, A., et al., J. Immunol. 194 (2015) 5497-5508.

In certain aspects, an antibody variant comprises an Fc region with one or more amino acid substitutions, which reduce FcRn binding, e.g., substitutions at positions 310, and/or 433, and/or 436 of the Fc region (EU numbering of residues). In certain aspects, the antibody variant comprises an Fc region with the amino acid substitutions at positions 310, 433 and 436. In one aspect, the substitutions are H310A, H433A and Y436A in an Fc region derived from a human $IgG_1$ Fc-region. (See, e.g., WO 2014/177460 A1).

In certain aspects, an antibody variant comprises an Fc region with one or more amino acid substitutions which increase FcRn binding, e.g., substitutions at positions 252, and/or 254, and/or 256 of the Fc region (EU numbering of residues). In certain aspects, the antibody variant comprises an Fc region with amino acid substitutions at positions 252, 254, and 256. In one aspect, the substitutions are M252Y, S254T and T256E in an Fc region derived from a human $IgG_1$ Fc-region. See also Duncan & Winter, Nature 322:738-40 (1988); U.S. Pat. Nos. 5,648,260; 5,624,821; and WO 94/29351 concerning other examples of Fc region variants.

The C-terminus of the heavy chain of the antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, an antibody comprising a heavy chain including a C-terminal CH3 domain as specified herein, comprises the C-terminal glycine-lysine dipeptide (G446 and K447, EU index numbering of amino acid positions). In one aspect of all aspects as reported herein, an antibody comprising a heavy chain including a C-terminal CH3 domain, as specified herein, comprises a C-terminal glycine residue (G446, EU index numbering of amino acid positions).

5.5.6.4 Cysteine Engineered Antibody Variants

In certain aspects, it can be desirable to create cysteine engineered antibodies, e.g., THIOMAB™ antibodies, in which one or more residues of an antibody are substituted with cysteine residues. In particular aspects, the substituted residues occur at accessible sites of the antibody. By substituting those residues with cysteine, reactive thiol groups are thereby positioned at accessible sites of the antibody and can be used to conjugate the antibody to other moieties, such as drug moieties or linker-drug moieties, to create an immunoconjugate, as described further herein. Cysteine engineered antibodies can be generated as described, e.g., in U.S. Pat. Nos. 7,521,541, 8,30,930, 7,855,275, 9,000,130, or WO 2016040856.

5.5.6.5 Antibody Derivatives

In certain aspects, an antibody provided herein can be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water. The polymer can be of any molecular weight, and can be branched or unbranched. The number of polymers attached to the antibody can vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

5.5.7 Immunoconjugates

The present disclosure also provides immunoconjugates comprising an antibody disclosed herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another aspect, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another aspect, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it can comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent can be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) can be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl sulfone)benzoate) which are commercially available (e.g., from Pierce Biotechnology, Inc., Rockford, IL., U.S.A).

5.6 Exemplary Embodiments

A. In certain non-limiting embodiments, the presently disclosed subject matter provides for a mammalian cell having reduced or eliminated lactogenic activity, wherein the expression of a pyruvate kinase muscle (PKM) polypeptide isoform is knocked down or knocked out, and wherein the PKM polypeptide isoform comprises a PKM-1 polypeptide isoform.

A1. The foregoing mammalian cell of A, wherein the expression of the PKM-2 polypeptide isoform is knocked down or knocked out.

A2. The foregoing mammalian cell of A or A1, wherein the cell is a CHO cell.

A3. The foregoing mammalian cell of any one of A-A2, comprising a nucleic acid sequence encoding a product of interest.

A4. The foregoing mammalian cell of A3, wherein the product of interest comprises a protein.

A5. The foregoing mammalian cell of A3 or A4, wherein the product of interest comprises a recombinant protein.

A6. The foregoing mammalian cell of any one of A3-A5, wherein the product of interest comprises an antibody or an antigen-binding fragment thereof.

A7. The foregoing mammalian cell of A6, wherein the antibody is a multispecific antibody or an antigen-binding fragment thereof.

A8. The foregoing mammalian cell of A6, wherein the antibody consists of a single heavy chain sequence and a single light chain sequence or antigen-binding fragments thereof.

A9. The foregoing mammalian cell of any one of A6-A8, wherein the antibody comprises a chimeric antibody, a human antibody or a humanized antibody.

A10. The foregoing mammalian cell of any one of A6-A9, wherein the antibody comprises a monoclonal antibody.

A11. The foregoing mammalian cell of any one of A3-A10, wherein the nucleic acid sequence is integrated in the cellular genome of the mammalian cell at a targeted location.

A12. The foregoing mammalian cell of A11, further comprising a nucleic acid encoding the product of interest that is randomly integrated in the cellular genome of the mammalian cell.

A13. The foregoing mammalian cell of any one of A-A12, wherein the lactogenic activity of the mammalian cells is less than about 50% of the lactogenic activity of a reference cell.

A14. The foregoing mammalian cell of A13, wherein the lactogenic activity of the mammalian cells is less than about 20% of the lactogenic activity of a reference cell.

A15. The foregoing mammalian cell of A13 or A14, wherein the reference cell is a cell that comprises wild-type alleles of the PKM gene.

A16. The foregoing mammalian cell of any one of A-A15, wherein the lactogenic activity of the mammalian cell is determined at day 14 or day 15 of a production phase.

A17. The foregoing mammalian cell of any one of A-A16, wherein the mammalian cell produces less than about 2.0 g/L of lactate during a production phase.

A18. The foregoing mammalian cell of any one of A-A16, wherein the mammalian cell produces less than about 2.0 g/L of lactate during a production phase in a shake flask.

A19. The foregoing mammalian cell of any one of A-A16, wherein the mammalian cell produces less than about 2.0 g/L of lactate during a production phase in a bioreactor.

B. In certain non-limiting embodiments, the presently disclosed subject matter provides for a mammalian cell comprising an allele of a PKM gene that comprises a nucleotide sequence selected from the group consisting of SEQ ID NOs: 39-41, or the nucleotide sequences set forth in SEQ ID NOs: 37 and 38.

C. In certain non-limiting embodiments, the presently disclosed subject matter provides for a composition comprising a mammalian cell of any of the foregoing mammalian cell of A-A19.

D. In certain non-limiting embodiments, the presently disclosed subject matter provides for a method for reducing or eliminating lactogenic activity in a cell, comprising knocking down or knocking out the expression of a pyruvate kinase muscle (PKM) polypeptide isoform.

E. In certain non-limiting embodiments, the presently disclosed subject matter provides for a method for reducing or eliminating lactogenic activity in a cell, comprising administering to the cell a genetic engineering system, wherein the genetic engineering system knocks down or knocks out the expression of a pyruvate kinase muscle (PKM) polypeptide isoform.

E1. The foregoing method of E, wherein the genetic engineering system is selected from the group consisting of a CRISPR/Cas system, a zinc-finger nuclease (ZFN) system, a transcription activator-like effector nuclease (TALEN) system and a combination thereof.

E2. The foregoing method of E or E1, wherein the genetic engineering system is a CRISPR/Cas9 system.

E3. The foregoing method of E2, wherein the CRISPR/Cas9 system comprises:

(a) a Cas9 molecule, and (b) one or more guide RNAs (gRNAs) comprising a targeting sequence that is complementary to a target sequence in a PKM gene.

E4. The foregoing method of E3, wherein the target sequence is selected from the group consisting of: a portion of the PKM gene, a region within exon 1, a 5' region flanking exon 2, a region within exon 2, a 5' intron region flanking exon 9 of the PKM gene, a 3' intron region flanking exon 9 of the PKM gene, a 3' intron region flanking exon 10 of the PKM gene, a region within exon 1 of the PKM gene, a region within exon 12 of the PKM gene and combinations thereof.

E5. The foregoing method of any one of E3-E4, wherein the one or more gRNAs comprises a sequence selected from the group consisting of SEQ ID NOs: 33-34 and 42-43 and a combination thereof.

E6. The foregoing method of E3 or E4, wherein the one or more gRNAs comprises (1) a first gRNA comprising a target sequence that is complementary to a 5' intron region flanking exon 9 of the PKM gene; and (2) a second gRNA comprising a target domain that is complementary to a 3' intron region flanking exon 9 of the PKM gene.

E7. The foregoing method of any one of E3-E6, wherein the one or more gRNAs comprises a sequence selected from the group consisting of SEQ ID NOs: 33-34 and a combination thereof.

E8. The foregoing method of E3 or E4, wherein the one or more gRNAs comprises (1) a first gRNA comprising a target sequence that is complementary to a region within exon 2 of the PKM gene; and (2) a second gRNA comprising a target domain that is complementary to region within exon 12 of the PKM gene.

E9. The foregoing method of any one of E3-E5 and E8, wherein the one or more gRNAs comprises a sequence selected from the group consisting of SEQ ID NOs: 42-43 and a combination thereof.

E10. The foregoing method of any one of D and E-E9, wherein the expression of the PKM polypeptide isoform is knocked out, and the lactogenic activity in the cell is eliminated or reduced compared to the lactogenic activity of a reference cell.

E11. The foregoing method of any one of D and E-E9, wherein the expression of the PKM polypeptide isoform is knocked down, and the lactogenic activity in the cell is reduced compared to the lactogenic activity of a reference cell.

E12. The foregoing method of E10 or E11, wherein the lactogenic activity of the cell is less than about 50% of the lactogenic activity of the reference cell.

E13. The foregoing method of E10 or E11, wherein the lactogenic activity of the cell is less than about 20% of the lactogenic activity of the reference cell.

E14. The foregoing method of any one of D and E-E13, wherein the lactogenic activity of the cell is determined at day 14 or day 15 of a production phase.

E15. The foregoing method of any one of D and E-E14, wherein the cell produces less than about 2.0 g/L of lactate during a production phase.

E16. The foregoing method of any one of D and E-E14, wherein the cell produces less than about 2.0 g/L of lactate during a production phase in a shake flask.

E17. The foregoing method of any one of D and E-E14, wherein the cell produces less than about 2.0 g/L of lactate during a production phase in a bioreactor.

E18. The foregoing method of any one of E11-E17, wherein the reference cell is a cell that comprises wild-type alleles of the PKM gene.

E19. The foregoing method of any one of D and E-E18, wherein the PKM polypeptide isoform is the PKM-1 polypeptide isoform.

E20. The foregoing method of any one of D and E-E19, wherein the PKM polypeptide isoform is the PKM-1 polypeptide isoform and the PKM-2 polypeptide isoform.

E21. The foregoing method of E, wherein the genetic engineering system comprises an RNA selected from the group consisting of: a short hairpin RNA (shRNA), a small interference RNA (siRNA), and a microRNA (miRNA), wherein the RNA is complementary to a portion of an mRNA expressed by the PKM gene.

E22. The foregoing method of E21, wherein the mRNA expressed by the PKM gene encodes a PKM-1 polypeptide isoform.

E23. The foregoing method of E22, wherein the expression of the PKM-1 polypeptide isoform is knocked out or knocked down and the lactogenic activity of the cell is reduced as compared to the lactogenic activity of a reference cell.

E24. The foregoing method of any one of E21-E23, wherein the genetic engineering system further comprises a second RNA selected from the group consisting of: shRNA, an siRNA, and a microRNA miRNA, wherein the second RNA is complementary to a portion of an mRNA expressed by the PKM gene that encodes a PKM-2 polypeptide isoform.

E25. The foregoing method of E24, wherein the expression of the PKM-1 and PKM-2 polypeptide isoforms are knocked out or knocked down, and the lactogenic activity of the cell is reduced.

E26. The foregoing method of E, wherein the genetic engineering system is a zinc-finger nuclease (ZFN) system or a transcription activator-like effector nuclease (TALEN) system.

E27. The foregoing method of D and E-E26, wherein the cell is a mammalian cell.

E28. The foregoing method of E27, wherein the mammalian cell is a CHO cell.

E29. The foregoing method of D and E-E28, wherein the cell expresses a product of interest.

E30. The foregoing method of E29, wherein the product of interest expressed by the cells is encoded by a nucleic acid sequence.

E31. The foregoing method of E30, wherein the nucleic acid sequence is integrated in the cellular genome of the cell at a targeted location.

E32. The foregoing method of any one of E26-E31, wherein the product of interest expressed by the cells is further encoded by a nucleic acid sequence that is randomly integrated in the cellular genome of the mammalian cell.

E33. The foregoing method of E26-E31, wherein the product of interest comprises a protein.

E34. The foregoing method of E33, wherein the product of interest comprises a recombinant protein.

E35. The foregoing method of any one of E26-E33, wherein the product of interest comprises an antibody or an antigen-binding fragment thereof.

E36. The foregoing method of E35, wherein the antibody is a multispecific antibody or an antigen-binding fragment thereof.

E37. The foregoing method of E35, wherein the antibody consists of a single heavy chain sequence and a single light chain sequence or antigen-binding fragments thereof.

E38. The foregoing method of any one of E35-E37, wherein the antibody is a chimeric antibody, a human antibody or a humanized antibody.

E39. The foregoing method of any one of E35-E38, wherein the antibody is a monoclonal antibody.

F. In certain non-limiting embodiments, the presently disclosed subject matter provides a method of producing a product of interest comprising culturing mammalian cells expressing the product of interest, wherein the mammalian cells express the product of interest and have reduced or eliminated lactogenic activity.

G. In certain non-limiting embodiments, the presently disclosed subject matter provides a method of culturing a population of mammalian cells expressing a product of interest, wherein the mammalian cells have reduced or eliminated lactogenic activity.

G1. The foregoing method of F or G, wherein the reduction or elimination of lactogenic activity results from the knock out or knock down of the expression of a pyruvate kinase muscle (PKM) polypeptide isoform in the mammalian cells.

G2. The foregoing method of G1, wherein the PKM polypeptide isoform is the PKM-1 polypeptide isoform.

G3. The foregoing method of G1, wherein the PKM polypeptide isoform is the PKM-1 polypeptide isoform and the PKM-2 polypeptide isoform.

G4. The foregoing method of any one of F and G-G3, wherein the lactogenic activity of the mammalian cells is less than about 50% of the lactogenic activity of a reference cell.

G5. The foregoing method of any one of F and G-G3, wherein the lactogenic activity of the mammalian cells is less than about 20% of the lactogenic activity of a reference cell.

G6. The foregoing method of any one of F and G-G5, wherein the lactogenic activity of the mammalian cells is determined at day 14 or day 15 of a production phase.

G7. The foregoing method of any one of F and G-G6, wherein the mammalian cells produce less than about 2.0 g/L of lactate during a production phase.

G8. The foregoing method of any one of F and G-G6, wherein the mammalian cells produce less than about 2.0 g/L of lactate during a production phase in a shake flask.

G9. The foregoing method of any one of F and G-G6, wherein the mammalian cells produce less than about 2.0 g/L of lactate during a production phase in a bioreactor.

G10. The foregoing method of any one of F and G-G9, wherein the reference cell is a cell that comprises at least one or both wild-type alleles of the PKM gene.

G11. The foregoing method of any one of F and G-10, wherein the mammalian cells are CHO cells.

G12. The foregoing method of any one of F and G-G11, wherein the product of interest expressed by the mammalian cells is encoded by a nucleic acid sequence.

G13. The foregoing method of G12, wherein the nucleic acid sequence is integrated in the cellular genome of the mammalian cells at a targeted location.

G14. The foregoing method of any one of F and G-G13, wherein the product of interest expressed by the cells is further encoded by a nucleic acid sequence that is randomly integrated in the cellular genome of the mammalian cells.

G15. The foregoing method of any one of F and G-G14, wherein the product of interest comprises a protein.

G16. The foregoing method of any one of F and G-G15, wherein the product of interest comprises a recombinant protein.

G17. The foregoing method of any one of F and G-G16, wherein the product of interest comprises an antibody or an antigen-binding fragment thereof.

G18. The foregoing method of G17, wherein antibody is a multispecific antibody or an antigen-binding fragment thereof.

G19. The foregoing method of G17, wherein the antibody consists of a single heavy chain sequence and a single light chain sequence or antigen-binding fragments thereof.

G20. The foregoing method of any one of G17-G19, wherein the antibody is a chimeric antibody, a human antibody or a humanized antibody.

G21. The foregoing method of any one of G17-G20, wherein the antibody is a monoclonal antibody.

G22. The foregoing method of any one of F and G-G21, further comprising harvesting the product of interest.

EXAMPLES

The following examples are merely illustrative of the presently disclosed subject matter and should not be considered as limitations in any way.

Example 1: PKM-1 Expression Drove Lactogenic Behavior in CHO Cell Lines, Triggering Lower Viability and Productivity In the process of cell line development (CLD), two lactogenic cell lines expressing different antibody molecules were identified. The lactogenic behaviors of these cell lines could be differentially mitigated through optimization of either nutrient feeds or culture pH, depending on the cell line. Analysis of various proteins involved in the glycolysis pathway revealed a direct correlation between the pyruvate kinase muscle-1 (PKM-1) isoform levels and lactogenic behavior.

CRISPR/Cas9 was used for targeted deletion of exon-9 to knockout PKM-1 expression. Knocking out PKM-1 expression completely abolished lactogenic behavior in the selected two cell lines, eliminating the needs for mitigation strategies. A single cell line was identified in which expression of both PKM-1 and PKM-2 genes were fully disrupted without any adverse effects on growth and viability. Further analysis of paternal and CHO cell lines revealed that they all expressed both PKL and PKR versions of pyruvate kinase, which, without being bound by theory, could enable them to tolerate complete lack of PKM expression. The unique mitigation strategies used to control the lactogenic behavior of these cell lines shifted their metabolic pathways, altering the pattern of PKM-1 transcription and expression, preventing or delaying the lactogenic behavior. PKM gene is knocked out entirely in order to analyze the behavior of the resulting cell lines in culture and in bioreactors.

In summary, the present disclosure delineates a direct correlation between lactogenic behavior and high PKM-1 levels in production cultures. Furthermore, elimination of PKM-1 expression was tolerated and reversed the lactogenic behavior in the selected CHO cell lines. Hence, permanent deletion of PKM-1, or the entire PKM gene for that matter, in CHO cells can be beneficial in reducing occurrences of lactogenic behavior during production in bioreactors.

Materials and Methods

Cell Lines

Cell lines secreting recombinant monoclonal antibody mAb-1 or mAb-2 were derived from a CHO-K1 host utilizing a glutamine synthetase (GS) selection marker. Seed trains were maintained in a proprietary DMEM/F12-based medium containing methionine sulfoximine (MSX) as a selection agent at 150 rpm shaking speed, 37° C., and 5% $CO_2$. Cells were passaged every 3 or 4 days.

2-L Bioreactor Production

2-L bioreactor production was performed in glass stirred-tank bioreactors (Applikon, Foster City, CA) with Finesse controllers (Applikon, Foster City, CA). All production cultures utilized a single inoculum train stage (N-1) for 3 days in the bioreactors before inoculating the production stage (N), lasting 14 days. The N-1 inoculation cultures were inoculated between 1.5 and 1.7 L of working volume to a target packed cell volume (PCV) of 0.17%. They were operated at 37° C., a pH set point of 7.0, a dissolved oxygen (DO) set point of 30%, and an agitation of 275 rpm. After three days, cells were transferred to inoculate the production (N) bioreactors to a volume between 1.4 and 1.7 L at a target PCV of 0.25%. All bioreactors were operated at 37° C. with a temperature shift to 35° C. at 72 hours. Cultures were run at a pH of 7.00 with a dead band of 0.03 using CO2 as acid control and 1 M sodium carbonate as the base control. The only exception to this pH operation was the mAb-2 pH level that was operated at a constant pH of 6.80 with the same dead band of 0.03. All cultures were set to operate at 350 rpm and a DO of 30% utilizing a combination of air and oxygen gas flows to keep DO constant. For the control process cultures of mAb-1, feeds occurred on day 3 of production (72 hours) and were 20% of the total volume of the culture at that time. For the enhanced feed process, feeds occurred on day 3 (72 hours) and on day 6 (144 hours) at 15% of the total volume culture for each feed.

AMBR15 Operation

Production cultures in the AMBR15 system (Sartorius, Goettingen Germany) were operated at set points of a temperature of 37° C., a DO of 30%, a pH of 7.0, and an agitation rate of 1400 rpm. The N-1 inoculation trains were run for 4 days and then the production (N) stage was inoculated at 1 million cells/mL with a total volume of 13 mL with a temperature of 37° C., a DO of 30%, a pH of 7.0, and an agitation rate of 1400 rpm. For these cultures, a scaled down process of 2-L bioreactor was performed.

Off-Line Sample Analyses

Supernatant and cell pellet samples were collected for submission to assays or Western blotting analysis. Samples were analyzed for viable cell concentration (VCC) and viability using the Vi-Cell XR (Beckman Coulter), and for $pO_2$, pH, $pCO_2$, $Na^+$, glucose, and lactate using the Bioprofile 400 (Nova Biomedical). All samples from 2-L and AMBR bioreactors were analyzed on the BioProfile 400 within a few minutes after sampling to minimize off-gassing. The same Vi-Cell XR, BioProfile 400, and osmometer (Model 2020, Advanced Instruments) were used for all samples to eliminate instrument-to-instrument variability. Antibody titer was measured using high pressure liquid chromatography (HPLC) with a protein A column. Antibody product quality assays were conducted using cell culture supernatant samples purified by PhyTip (PhyNexus, San Jose, CA) protein A column. Antibody molecular size distribution was analyzed by size-exclusion chromatography (SEC). Protein charge heterogeneity was measured using imaged capillary isoelectric focusing (icIEF), and all charge heterogeneity samples were pretreated with carboxypeptidase B. All protein product quality assays were developed in-house, and detailed protocols have been published (Hopp et al., 2009, Biotechnol. Prog. 25(5):1427-32).

Immunoblotting

Cell pellets were lysed in lysis buffer (10 mM Tris pH 8.0, 0.5% NP40, 150 mM NaCl, 5 mM $MgCl_2$, with protease inhibitors) and incubated on ice for 20 minutes. Samples were then spun down at 13,000 rpm for 10 minutes and the supernatant was transferred to a new tube to determine protein concentration using a Nanodrop 2000 (Thermo Scientific, Wilmington Del.) using the absorbance at 280 nm. 15 μL of the lysate was combined with 5 μL of 4× running buffer (400 μL of 2× Invitrogen loading buffer+400 μL of 50% glycerol+200 μL of 20% SDS+100 μL beta-mercaptoethanol) and heated at 90° C. for 5 minutes. Equivalent amounts of protein were then loaded onto a 12 well 4-20% Tris-Glycine gel and run for 1.5 hours at 150 V using SDS running buffer. Afterward the proteins were transferred to nitrocellulose membrane using the iBlot2 from Thermo Fisher. After washing with 1×TBST buffer, blots were blocked in of 5% milk solution for a minimum of 1 hour followed by incubation with the primary antibodies overnight. The blots were then washed and incubated in the secondary antibody for a minimum of one hour and washed with TBST buffer again. ECL reagents were used followed by imaging of the blots using Bio-Rad imaging machine (Bio-Rad, Hercules, CA).

PKM-1 Knockout

To knock out PKM-1, guide RNAs (gRNAs) targeting to both the 5' and the 3' intron regions flanking the exon 9 of PKM gene were cloned into a Genentech gRNA-expression vector. This construct was then co-transfected with Cas9 expression plasmid into mAb-2 expressing cells. Transfected cells were single cell cloned and deletion of exon 9 was confirmed by genomic DNA PCR. The following gRNA oligoes were most effective in deleting exon-9 (PKM-1) and the pools targeted with these oligoes were used to isolate PKM-1 knockout mAb-2 cell lines:

```
5' gRNA:
                                    (SEQ ID NO: 33)
GTCCTTTGGGCAGAGACAG

3' gRNA:
                                    (SEQ ID NO: 34)
GACCAGAGTACTCCCTCGT
```

Sequence of Genomic DNA PCR Primers:

```
5'-primer:
                                    (SEQ ID NO: 35)
CCAGATTTGGTGAGGACGAT

3'-primer:
                                    (SEQ ID NO: 36)
AGCTGTGTTGTGAGGCATTG
```

Results

Figure 1B:
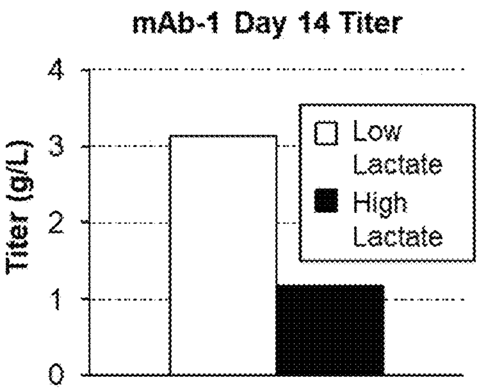
Figure 1C:
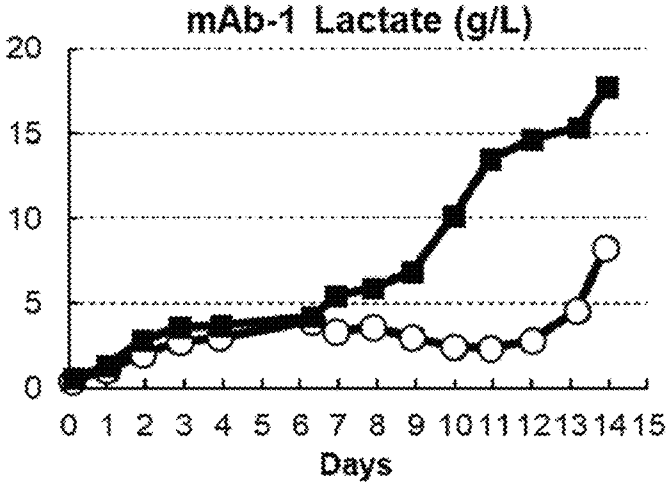

Increase in PKM-1 levels during production correlates with CHO cells lactogenic behavior A cultured seed train of the mAb-1 expressing cell line was used to source production cultures in bioreactors using standard or enhanced feeding strategies. Standard feeding triggered lactogenic behavior in mAb-1 cell line while an enhanced feeding strategy mitigated the lactogenic behavior. The high lactate conditions triggered a drop of cell viability after day 10 in the production culture (FIG. 1A), resulting in lower day 14 titers compared to low lactate conditions (FIG. 1B). While both culture conditions had comparable levels of lactate till day 7, the high lactate conditions showed a sharp increase in lactate accumulation from day 7 in production culture, reaching upwards of 15 g/L on day 14. For low lactate conditions, a delay of 3-4 days was observed before lactate levels started to trend higher (between days 12 to 14) reaching only 8 g/L by day 14 (FIG. 1C).

Figure 1D:
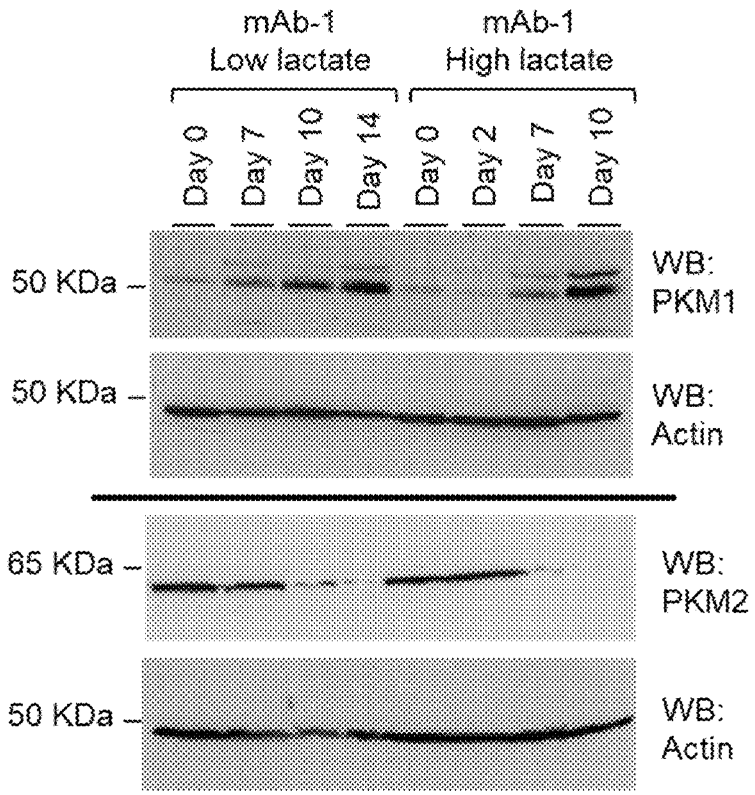
Figure 1E:
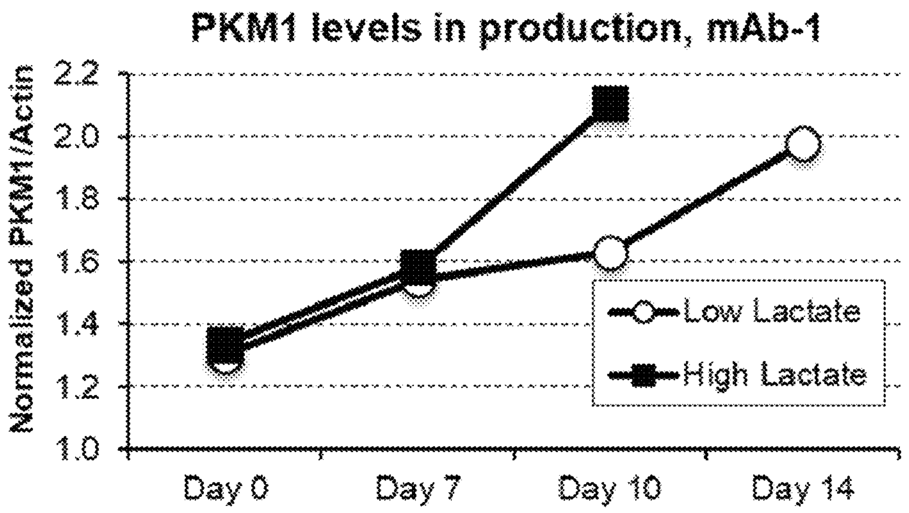
Figure 1F:
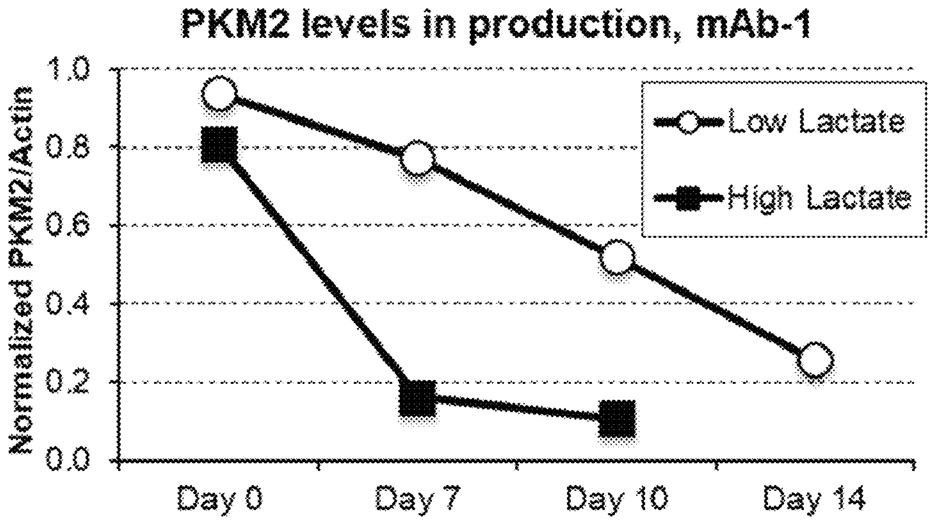

To identify enzyme(s) that might correlate with the observed lactogenic behavior, Western blot analysis was performed on a variety of proteins involved in cell growth signaling and glycolysis pathways. Since in high lactate conditions cell viability dropped sharply after day 10, samples from days 0, 2, 7 and 10 of this set were compared to samples from days 0, 7, 10, and 14 of the low lactate condition (FIGS. 1D-1F). Among all the different proteins analyzed (data not shown), only PKM-1 levels showed a direct correlation with lactogenic behavior of the mAb-1 expressing cell line. FIG. 1D-1F showed PKM-1 and PKM-2 protein levels in cell pellets. PKM-1 expression levels in high lactate samples started to divergently increase after day 7 in production culture relative to the low lactate samples. Interestingly, the increase in PKM-1 levels tightly trended with the increase in lactate accumulation since even under low lactate conditions the increase in PKM-1 levels towards the end of production culture (FIG. 1E, between days 10 and 14) trended with the higher lactate levels in culture (FIG. 1C). The levels of PKM-2, however, correlated inversely with lactogenic behavior in mAb-1 expressing cell line (FIG. 1F).

Figure 2A:
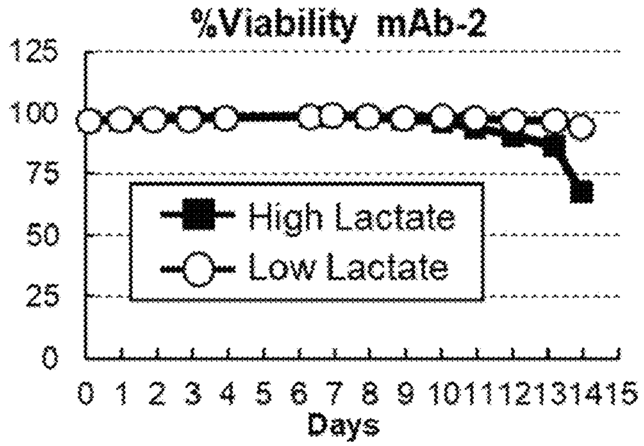
Figure 2B:
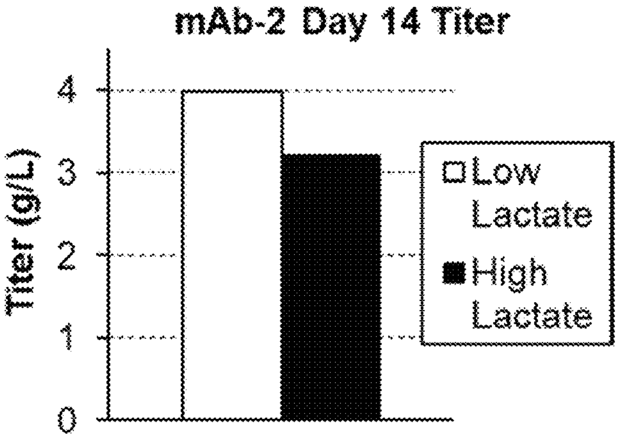
Figure 2C:
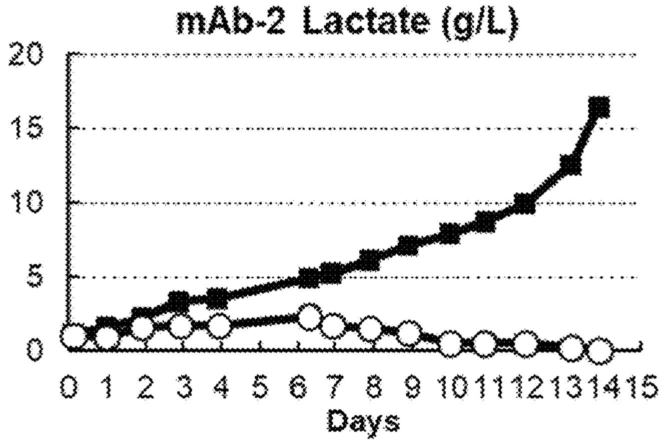
Figure 2D:
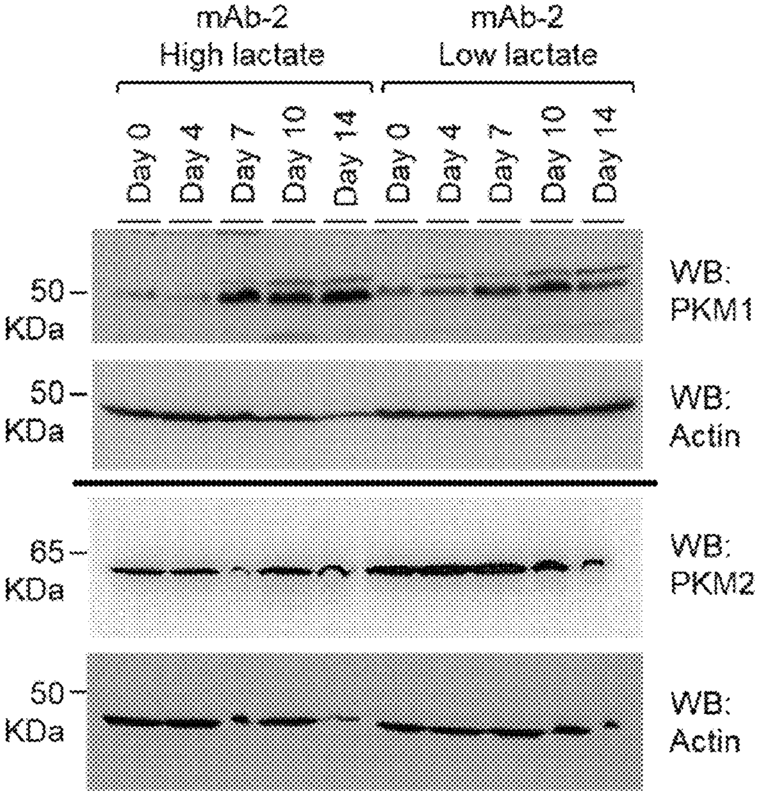
Figure 2E:
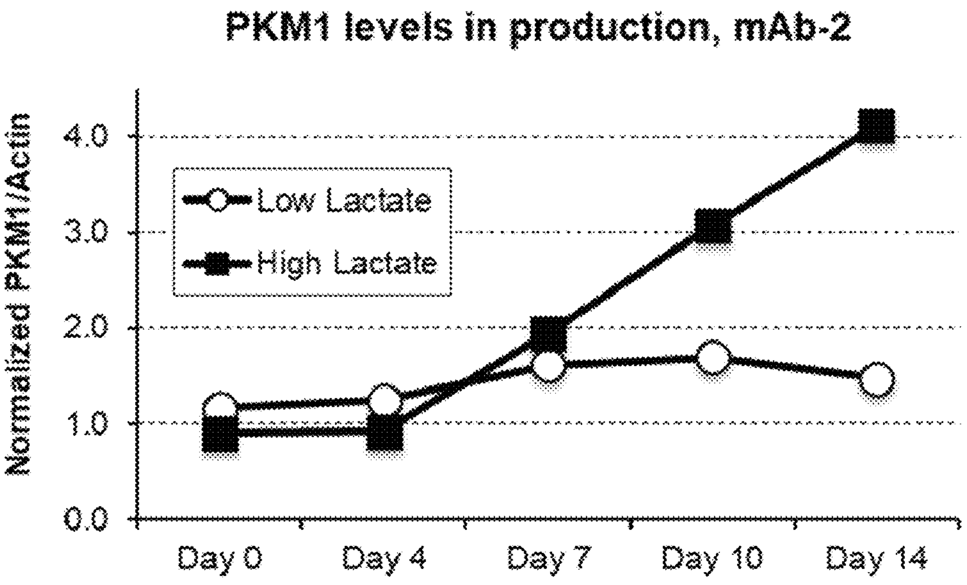
Figure 2F:
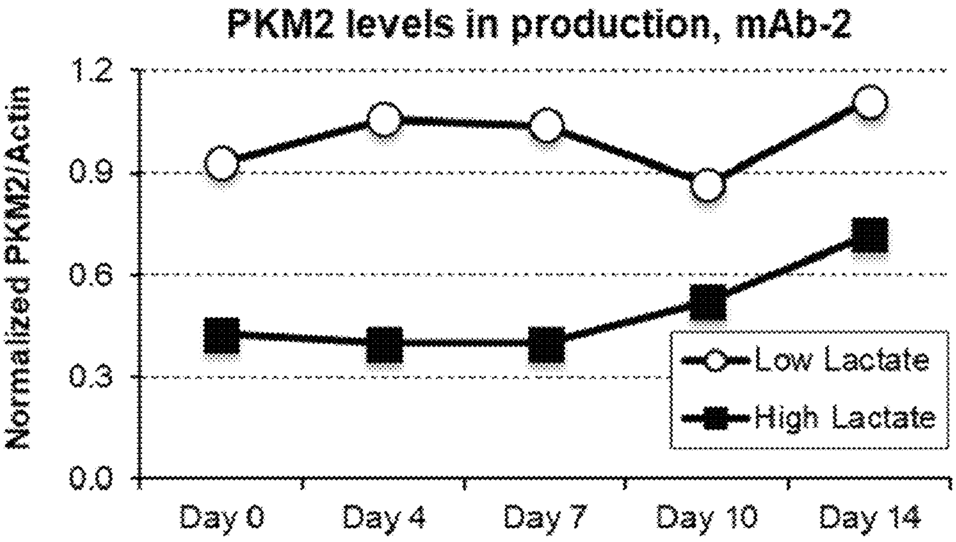

Similar bioreactor experiments were conducted for the mAb-2 expressing cell line. Such cell line was cultured in production media with conditions promoting lactogenic or non-lactogenic behaviors. Cell viability for mAb-2 cell line was comparable between high and low lactate conditions until days 13 and 14 of the production culture (FIG. 2A). This resulted in a titer reduction of approximately 25% for the high lactate compared to the low lactate condition (FIG. 2B). Throughout the production process, lactate accumulation in the media was low for the low lactate control arm of mAb-2 cell line experiment. However, under the high lactate conditions lactate levels started to diverge from day 7, reaching upwards of 15 g/L by day 14 of the production culture (FIG. 2C). Western blot analysis revealed that PKM-1 protein levels started to increase in the high lactate samples, relative to the low lactate ones, around day 7 in production and linearly increased until the end of the production culture (FIGS. 2D and 2E). This increase in PKM-1 levels correlated tightly with the increase in accumulated lactate (FIGS. 2C and 2E). Similar to mAb-1, overall levels of PKM-2 in low lactate mAb-2 samples were higher than those of high lactate samples as illustrated in FIG. 2D (lower panels) and FIG. 2F. Taken together, these data suggest a direct correlation between lactogenic behavior in mAb-1 and mAb-2 expressing cells and the PKM-1 levels in these cells.

Figure 3A:
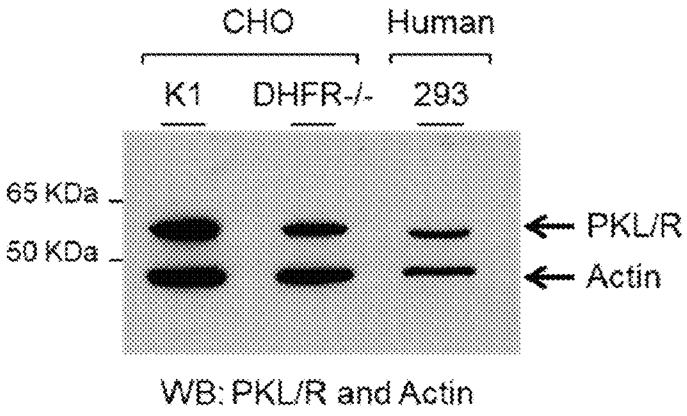
Figure 3B:
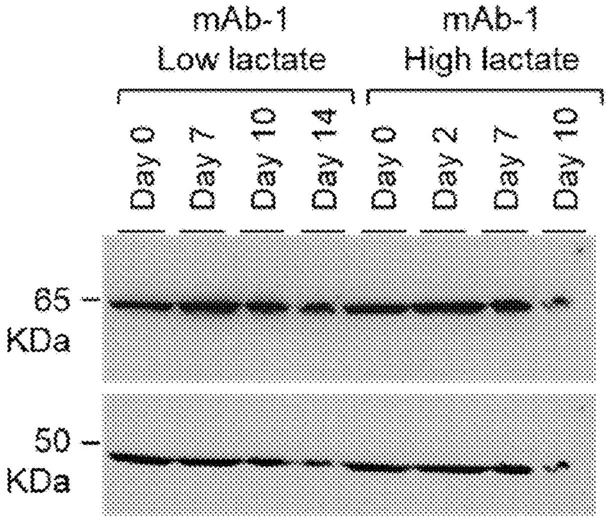
Figure 3C:
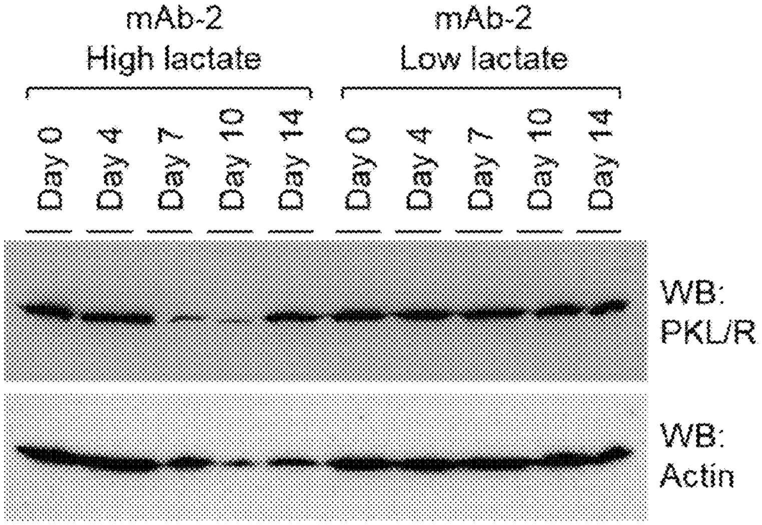
Figure 3D:
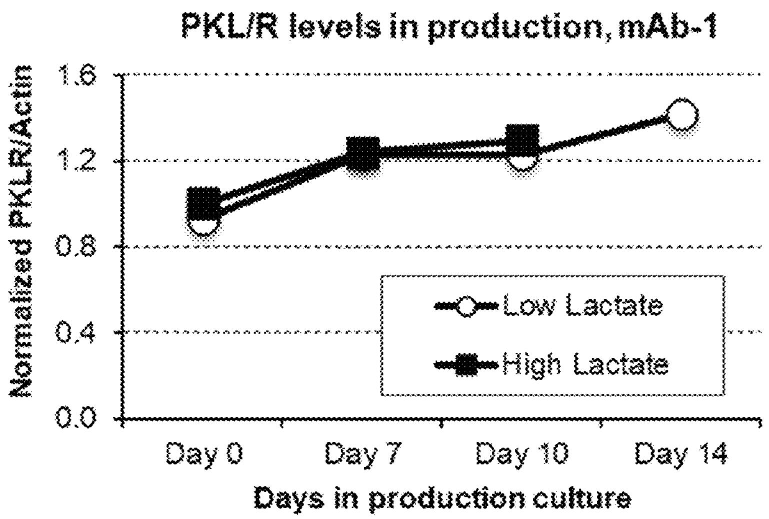
Figure 3E:
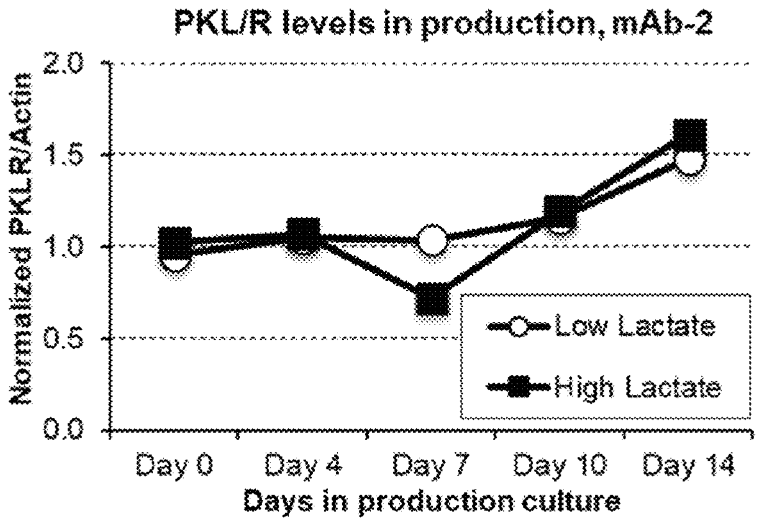

PKL/R Proteins are Expressed in CHO Cells but do not Correlate with Lactogenic Behavior To evaluate whether other forms of PK (other than PKM) are expressed in the proprietary CHO host cells, two different CHO host cell lines (CHO-K1 and DHFR−/−) and a human (HEK 293) cell line were analyzed for expression of PKL and PKR (PKL/R) proteins. Both CHO cell lines as well as the control HEK 293 cell line showed expression of PKL/R enzyme (FIG. 3A), indicating that all isoforms of PK genes (including PKM-1, PKM-2, and PKL/R) are expressed in the selected CHO hosts. Whether expression of PKL/R was differentially regulated when comparing high versus low lactate conditions in mAb-1 and/or mAb-2 expressing cell lines was evaluated next. PKL/R expression levels were comparable (once the protein levels were normalized against actin as internal control) between high and low lactate conditions in both mAb-1 and mAb-2 cell lines, showing no correlation with lactogenic behavior in these cell lines (FIGS. 3B-3D). The lower levels of PKL/R in mAb-2 high lactate samples for days 7 and 10 in FIG. 3C, was due to lower overall protein loading as reflected by lower levels of actin (as loading control) in the same lanes. Besides PK isoforms, expression of several different proteins involved in the cell growth signaling and glycolysis pathways were also analyzed. However, no clear correlation between the expression of these proteins and the lactogenic behavior observed in mAb-1 or mAb-2 expressing cell lines was observed (data not shown). The fact that different PK isoforms were expressed in selected CHO host cells suggested that these cell lines might be able to tolerate targeted deletion of one or more isoforms of PK. The observed direct correlation between lactogenic behaviors of mAb-1 and mAb-2 cell lines with PKM-1 levels during production phase made this enzyme a good candidate for targeted deletion.

CRISPR/Cas9 Mediated Targeted Deletion of Exon-9 in PKM Gene

The PKM gene is responsible for expression of both PKM-1 and PKM-2 enzymes, which differ only in alternative inclusion of exon 9 or exon 10, respectively. Since the selected CHO cell lines were not sequenced and annotated, no information regarding PKM allele types, gene copy numbers, or sequence were available. Therefore, to disrupt expression of PKM-1 gene, guide RNA constructs targeting intron regions flanking exon 9 using available CHO sequences in the public databases were designed (Kent et al. 2002, Genome Res. 12(6):996-1006). The 5' screening PCR primer(s) was designed to match the intron region between exons 8 and 9, and the 3' screening PCR primer was designed to matched exon 10 (FIG. 4A). Exon sequence information was obtained based on amplifying and sequencing PKM cDNA from the selected CHO hosts' mRNAs. The mAb-2 expressing cell line was transfected with Cas9 and various gRNA constructs. After initial screening, the pool showing the most efficient targeting of exon 9 was subjected to single cell cloning. Twenty cell lines from this pool were screened for targeted deletion of exon-9, and two heterozygous (HET-3 and HET-18) and two knockout (KO-2 and KO-15) cell lines were identified for which the targeted allele's deletion were fully confirmed by PCR and sequencing (FIGS. 4B and 4C). Cultures for these cell lines were then expanded for further evaluation in bioreactors. Sequencing of the targeted allele(s) confirmed deletion of exon 9 in all selected cell lines (FIG. 4C). Three cell lines (KO-2, HET-3, and HET-18) had the deletion of exon 9 exactly at the 5' and 3' gRNA targeting sites (FIG. 4C). For KO-15 cell line, the PCR size of targeted allele(s) was smaller than those observed for other cell lines (FIG. 4B). Sequencing analysis confirmed that 122 base pairs (bp) upstream of 5' gRNA was deleted in the KO-15 cell line and partially replaced with an unrelated insertion (FIG. 4C and data not shown). Deletion in this region could affect the integrity of the intron between exons 8 and 9. Irrespective of this, exon 9 was fully deleted in all selected cell lines according to the sequencing analysis.

Blocking or Decreasing PKM-1 Expression Averted or Reduced Lactogenic Behavior in mAb-2 Cell Line, Respectively.

Figure 5A:
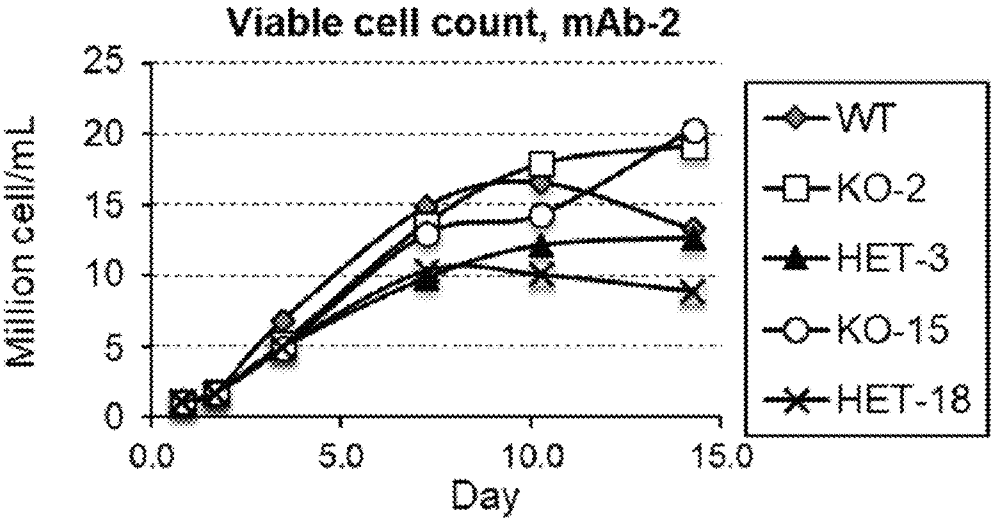
Figure 5B:
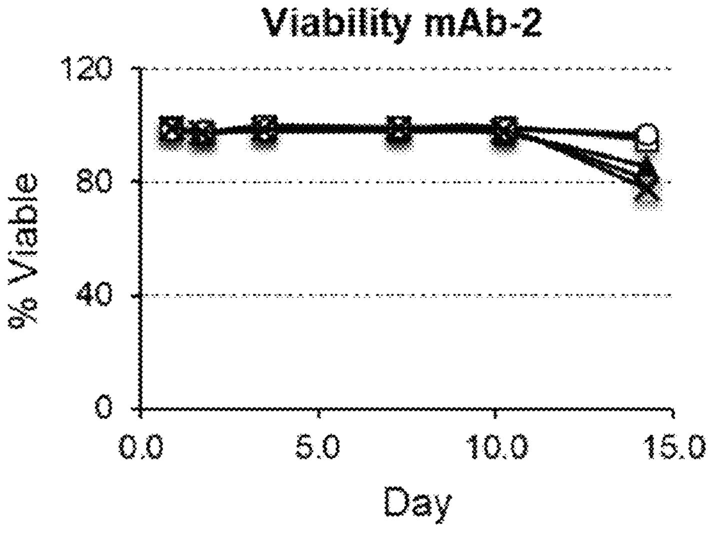
Figure 5C:
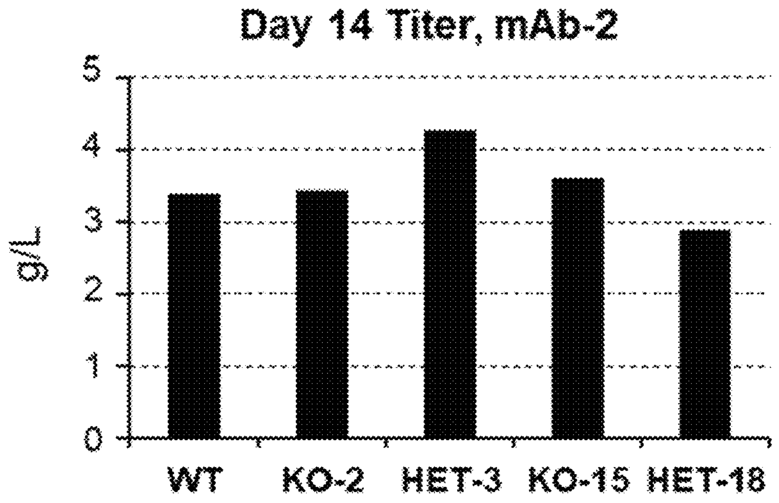
Figure 5D:
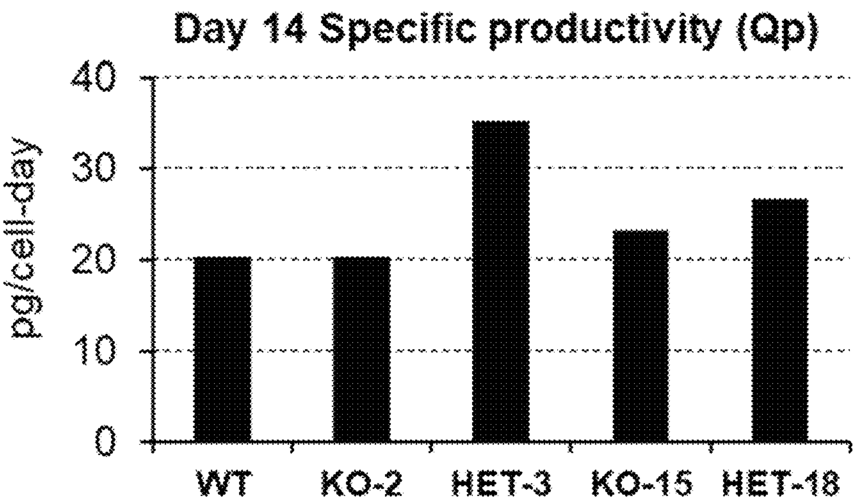
Figure 5E:
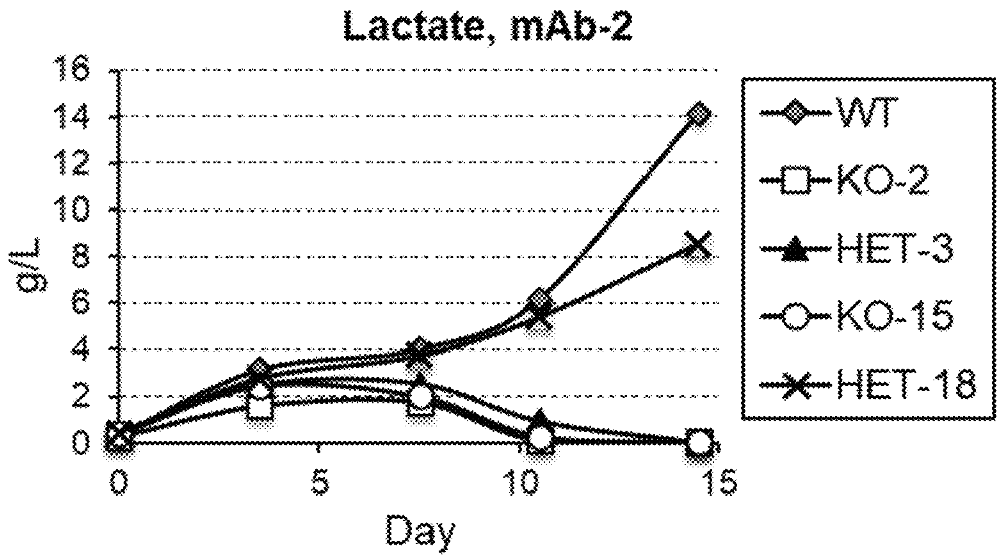

The four mAb-2 cell lines with deletion of exon-9 in some (HET) or all (KO) alleles and the WT mAb-2 line were all sourced to set up a 14-day production culture in AMBR bioreactors. Growth and viability of PKM-1 KO, HET and WT cell lines were shown in FIGS. 5A and 5B. The PKM-1 HET or KO mAb-2 lines had relatively similar titers and specific productivities to that of WT mAb-2 cell line (FIGS. 5C and 5D). PKM-1 KO (KO-2 and KO-15) and one of the HET mAB-2 cell lines (HET-3) had very low lactate levels compared to the WT mAb-2 cell line (FIG. 5E) when cultured under control (lactogenic) condition. The RET-18 line on the other hand displayed similar lactogenic behavior compared to the WT mAb-2 till day 10. After day 10 the rate of lactate accumulation in the WT mAb-2 line increased, approximately doubled relative to the HET-18 line by day 14 (FIG. 5E).

Figure 5F:
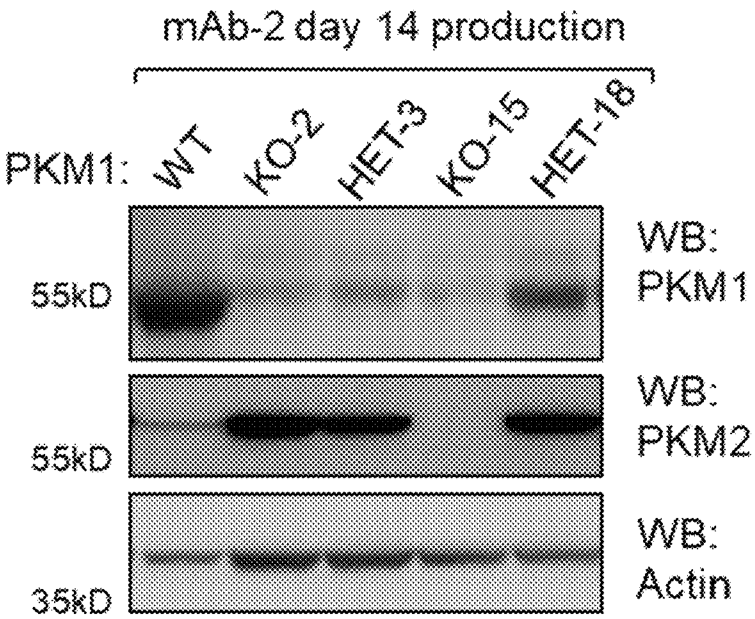
Figure 5G:
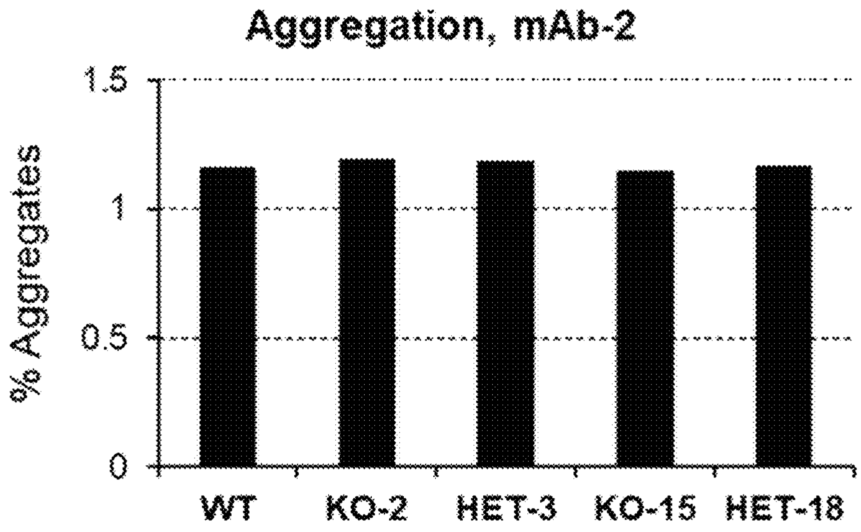
Figure 5H:
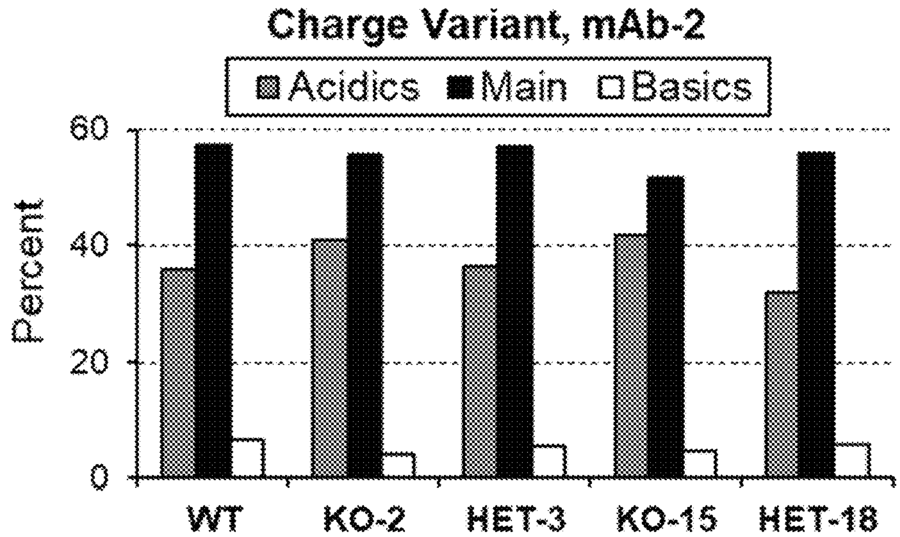

Western blot analysis of these cell lines showed that KO-2 and KO-15 lines were fully deficient in expression of PKM-1, and HET-3 cell line had lower PKM-1 expression compared to the HET-18 cell line (FIG. 5F). The fact that lactogenic behavior of PKM-1 HET and KO cell lines directly correlated with the PKM-1 protein expression in several cell lines suggested that the observed change in lactogenic behavior is not due only to other clonal differences. Since a band corresponding to the full length WT allele could be amplified from the genomic DNA of the HET cell lines (FIG. 4B), possible explanations for these observations could include, but not be limited to: differential expression of PKM-1 from different CHO PKM allele(s); targeting of the WT PKM allele(s) by only one gRNA construct, resulting in disruption of proper exon splicing; inversion of the gRNA targeted region, or 4-homogenitization mediated by allele recombination.

PKM-2 levels were low for the WT mAb-2 cell line (the relative difference was considered with the caveat that actin loading control was also lower for this sample), while it was higher for the HET-3, HET-18, and KO-2 cell lines (FIG. 5F). Interestingly, the KO-15 mAb-2 cell line was completely deficient in the expression of PKM-2 in addition to PKM-1 (FIG. 5F). This was likely due to the larger deletion(s) observed upstream of 5' gRNA targeted region of the PKM allele(s), possibly affecting functionality of intron region between exons 8 and 9 (FIG. 4C). This suggested that the selected CHO cells could tolerate complete lack of both PKM-1 and PKM-2 enzymes, perhaps due to their ability to express PKL/R enzyme(s) (FIG. 3A).

Product quality attributes such as high molecular weight (aggregates) and charge variant species between WT and PKM-1 KO and HET mAb2 expressing cell lines were investigated. Although no significant differences in product aggregation levels between WT and PKM-1 KO and HET cell lines were observed (FIG. 5G), some variations were observed for mAb-2 product charge variant (FIG. 5H) profiles. Since there were no clear trends or correlations between lactate levels and product quality attributes (FIGS. 5G and 511), the observed differences could be due to normal variations that could occur during cell line derivation. Additionally, the media and feed used in these experiments were optimized for the WT mAb-2 cell line, not the PKM-1 KO or HET cell lines. Since altering PKM levels could affect the overall metabolic profile of these cell lines, fine-tuning media and feed could be required in order to explore their full effects and influence on product quality attributes.

Figure 6A:
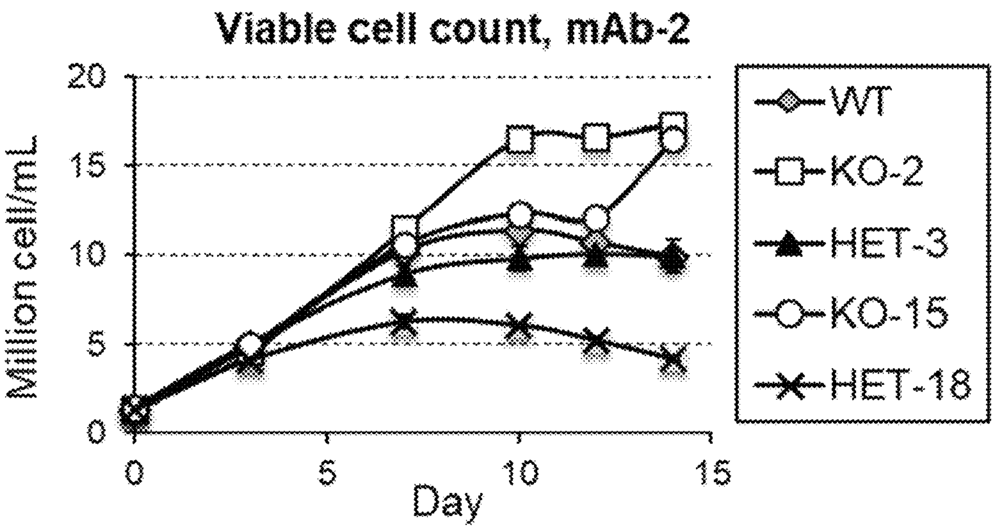
Figure 6B:
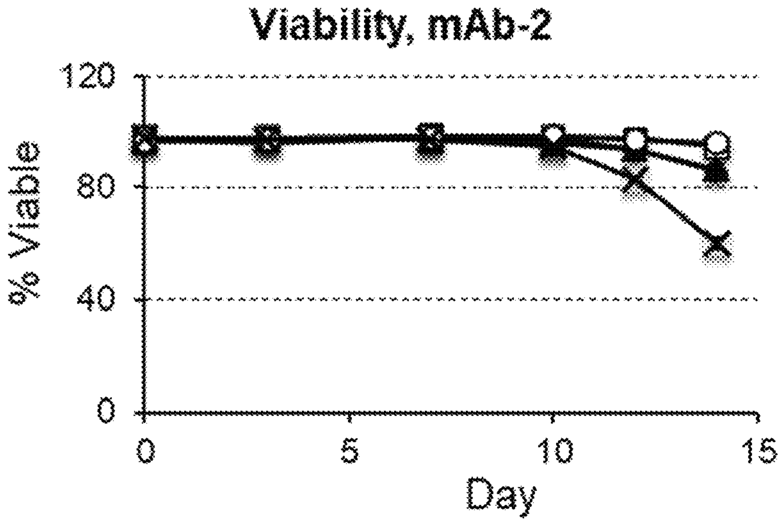
Figure 6C:
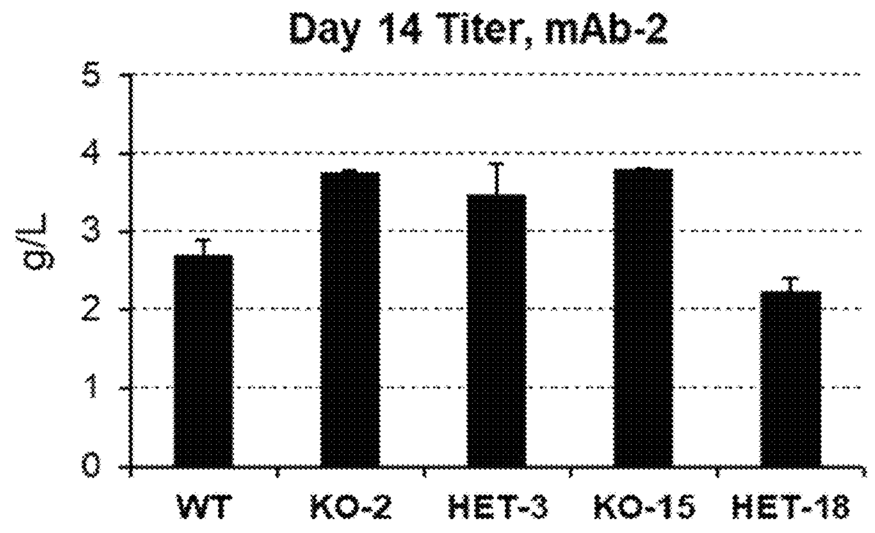
Figure 6D:
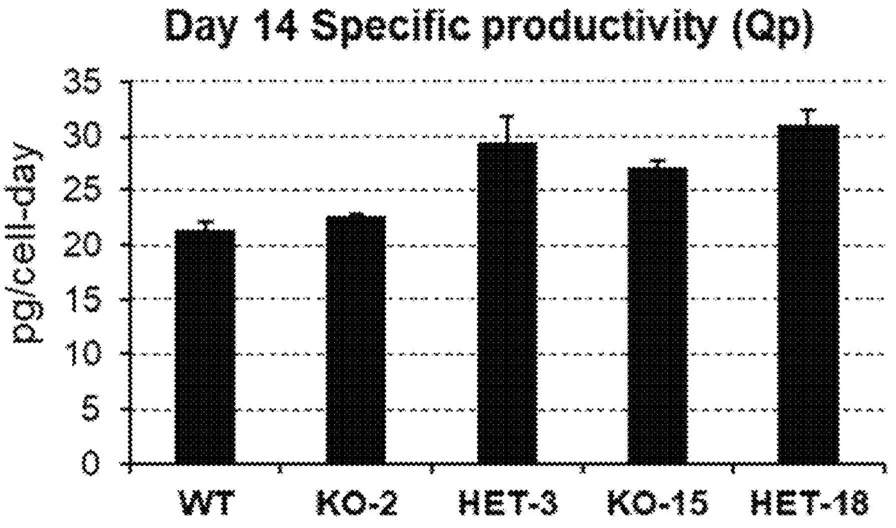
Figure 6E:
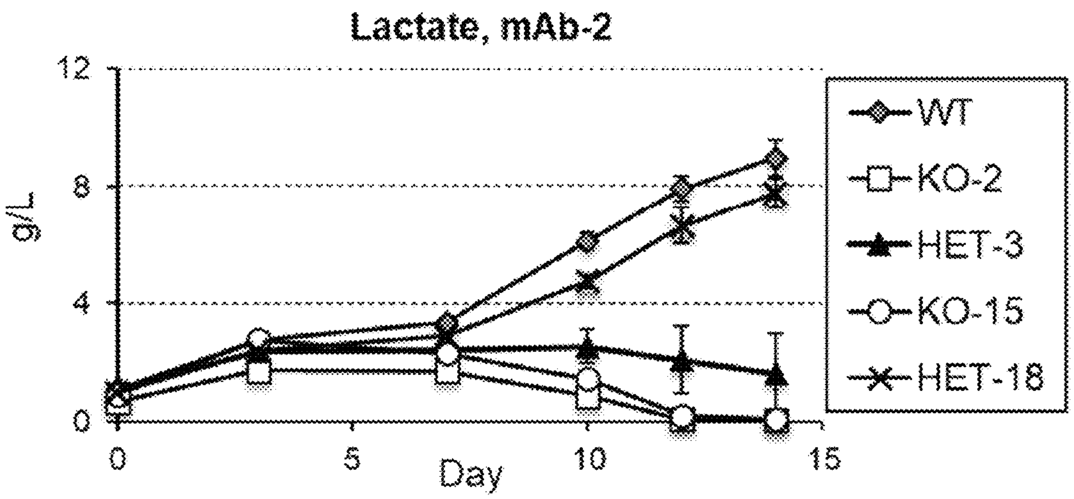
Figure 6F:
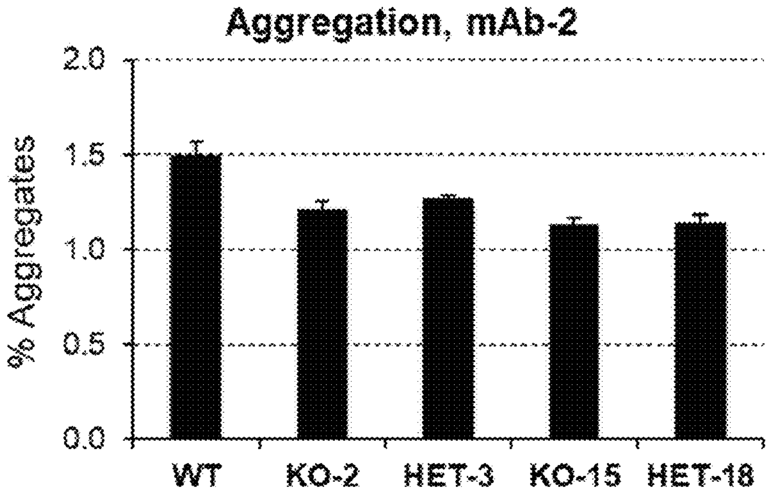
Figure 6G:
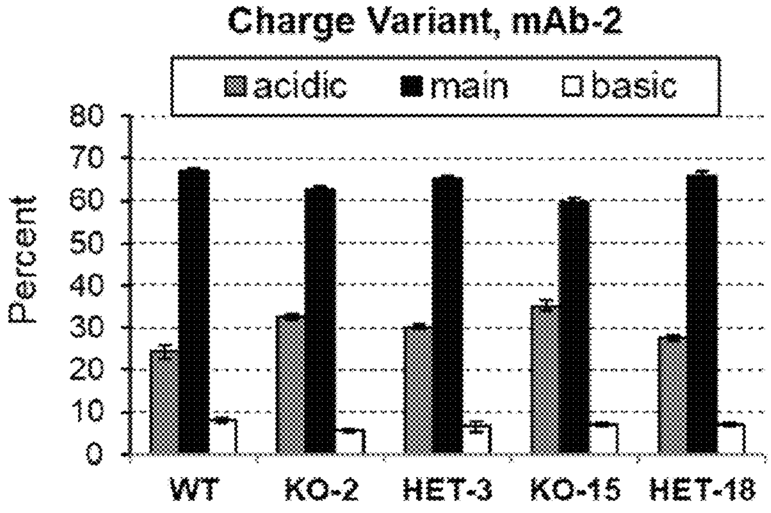

Since it is important to analyze the behavior of any cell line post cell banking and thaw, the PKM-1 KO and HET mAb-2 cell lines were banked and then thawed and maintained in culture for 2.5 weeks, along with the WT cell line as control. These cells were then sourced to set up production cultures, in quadruplet, for each cell line, in order to evaluate their performance post-thaw. The data showed that growth, viability, titer, specific productivity, and lactogenic profiles of PKM-1 KO and HET cell lines were comparable prior to, and post cell banking (FIGS. 5A-5D and 6A-6D). As was previously observed (data not shown), the freshly thawed WT mAb-2 cells were less lactogenic (10 g/L, FIG. 6E) relative to the older cells (15 g/L, FIG. 5E). However, this behavior was unique to the WT mAb-2 cell line, since cell age had no significant effects on the lactogenic behavior of mAb-2 PKM-1 KO and HET cell lines (FIGS. 5E and 6E). Note that for all the cell lines a gradual accumulation of lactate in the media was observed by day 7 of the production culture, after which PKM-1 KO and HET-3 cell lines consumed the lactate while a lactate run-away profile was observed for both WT and HET-18 cell lines (FIG. 6E). Although it was observed that all the younger cell lines (post-thaw) had relatively lower % acidic peaks (FIG. 6G) compared to the older cell lines (FIG. 5G), a trait that was perhaps related to the cell age, there were no major differences with regards to product quality between lactogenic (WT or PKM-1 HET-18) and non-lactogenic (PKM-1 KO or HET-3) cell lines (FIGS. 6F-6G).

Discussion

Lactogenic behavior in CHO cell cultures could trigger culture acidification and high osmolarity as the result of base addition to control the culture pH, negatively impacting viability, VCC, and eventually production titer (Li et al., 2010, MAbs 2(5):466-79). Lactate generation results from aerobic glycolysis, a behavior that is commonly known as the Warburg effect (Warburg, 1956, Science 123(3191):309-14) and it is observed in many cultured and cancer cells. These cells utilize the glycolysis process to generate energy and regulate this process in response to various energy and metabolic fluxes (Mulukutla et al., 2014, PLoS One 9(6): e98756; Mulukutla et al. 2010, Trends Biotechnol. 28(9): 476-84; Luo et al., 2012, Biotechnol. Bioeng. 109(1):146-56; Ahn and Antoniewicz, 2012, Biotechnol. J. 7(1):61-74). Although some lactogenic behaviors could be curbed by process engineering (Luo et al., 2012, Biotechnol. Bioeng. 109(1):146-56; Gagnon et al., 2011, Biotechnol. Bioeng. 108(6):1328-37), these approaches however did not reveal the root cause of the observed behavior. To have a better understanding of lactogenic behavior in CHO host, two lactogenic cell lines expressing mAb-1 or mAb-2 were identified for which lactogenic behavior could be curbed by either modifying feeding strategy or culture pH. These independently derived cell lines were utilized as tools where we analyzed a panel of proteins and enzymes involved in cell growth signaling or glycolysis pathways, in order to delineate their possible correlation with lactogenic behavior. These findings revealed a direct correlation between PKM-1 expression and lactogenic behavior in both mAb-1 and mAb-2 cell lines (FIGS. 1D-1F and 2D-2F).

The detected levels of PKM-1 in both mAb-1 and mAb-2 production cultures were low at early time points during production and increased in a manner correlated with increase in lactate levels in the culture. PKM-2 levels were inversely correlated with lactogenic behavior in these cell lines (FIGS. 1D-1F and 2D-2F). This could be due to the function of proteins involved in alternative splicing of PKM-1 or PKM-2 transcripts from PKM gene (Chaneton and Gottlieb, 2012, Trends Biochem. Sci. 37(8):309-16; Israelsen and Vander Heiden, 2015, Semin. Cell Dev. Biol. 43:43-51; Mazurek, 2011, Int. J. Biochem. Cell Biol. 43(7): 969-80; Harada et al., 1978, Biochim. Biophys. Acta. 524 (2):327-39; Noguchi et al., 1986, J. Biol. Chem. 261(29): 13807-12; Noguchi et al., 1987, J. Biol. Chem. 262(29): 14366-71). Of the two isoforms of PKM gene, PKM-2 is reported to act as a central switch for altering metabolic pathways, allowing cancer cells to survive and thrive under physiologically unfavorable conditions such as within a tumor environment (Christofk et al., 2008, Nature 452 (7184):230-3; Chaneton and Gottlieb, 2012, Trends Biochem. Sci. 37(8):309-16; Israelsen and Vander Heiden, 2015, Semin. Cell Dev. Biol. 43:43-51). On the other hand, PKM-1 isoform is constitutively active once expressed. Without wishing to be bound by theory, the correlation of PKM-1 level with lactogenic behavior late in the production culture could be due to uncontrollable conversion of PEP to pyruvate by this enzyme, followed by LDH mediated conversion of pyruvate to lactate.

CRISPR mediated deletion of exon-9 and hence PKM-1 in the mAb-2 expressing cell line resulted in complete reversal of lactogenic behavior in PKM-1 KO cells under conditions where WT mAb-2 expressing cells displayed lactogenic behavior (FIG. 5E). The two PKM-1 HET mAb-2 cell lines displayed distinct behaviors. While the HET-3 KO cell line produced very little lactate (only a little more than its PKM-1 KO counterparts), the HET-18 cell line was lactogenic and generated approximately ⅔ as much lactate as the WT mAb-2 cells (FIG. 5E). A direct correlation between the lactogenic behavior of these PKM-1 HET cell lines and the higher levels of PKM-1 in these cells was also observed (FIG. 5F). Differences in PKM-1 levels observed in HET-18 compared to HET-3 cell lines could be due to: differential expression of PKM-1 from different PKM alleles, or partial targeting of PKM allele(s) by a gRNA construct(s) in HET-3 cell line, or inversion of targeted region within the targeted PKM allele(s).

A PKM-1 knockout cell line (KO-15) that was unable to express PKM-2 protein (FIG. 5F) was identified. The cell line has a 122-bp deletion and insertion of random bases at the intron upstream of 5' gRNA targeting region (FIG. 3C). The KO-15 cell line can tolerate loss of both PKM-1 and PKM-2 enzymes because the CHO cell lines also express PKL/R (FIG. 3A), which can compensate for lack of PKM expression. The expression of PKL/R protein(s) in the WT and all the PKM-1 HET and KO cell lines were confirmed via Western blot analysis (data not shown). Nevertheless, lack of or reduced PKM-1 expression resulted in lower lactate generation in all the PKM-1 KO or HET cell lines, respectively, without an effect on titer or specific productivity (FIGS. 5C-5D and 6C-6D). Absence or attenuation of lactogenic behavior in these cell lines were reproducible and consistent in post-thaw younger cell ages and among all replicates (FIGS. 5A-5E and 6A-6E).

Controlling lactogenic behavior during production culture is important for obtaining optimal titer and product quality from manufacturing runs, therefore, knocking out PKM-1 expression from hosts can be advantageous in dealing with lactogenic behavior of CHO cells. It is important to confirm and monitor the expression of other PK enzymes in CHO cells prior to targeting PKM-1 or the entire PKM gene for deletion, because PKL/R enzymes can compensate PKM ablation. Knocking out of the entire PKM gene can be tolerated in CHO hosts, and the PKM KO CHO hosts are capable of expressing antibodies or products of interest with comparable titer and product quality to that of WT host. These PKM KO hosts can reduce lactogenic behavior and have a better growth profile than the WT host as observed in KO-2 and KO-15 cell lines (FIGS. 5A and 6A).

Example 2: Production of mAb-3 in PKM Knockout and PKM-1 Knockout CHO Cell Lines The PKM gene or PKM-1 gene was knocked out in a CHO-K1M cell line, generating one PKM KO host cell line and four PKM-1 KO host cell lines. A transgene encoding mAb-3 was introduced into the WT CHO-K1M, PKM KO, and PKM-1 KO host cell lines by target integration, generating three mAb-3 expressing WT pools from the same host cell line, three mAb-3 expressing PKM KO pools from the same host cell line, and four mAb-3 expressing PKM-1 KO pools from four different host cell lines.

The following experiments were performed as disclosed in Example 1 except that the gRNAs for generating the PKM KO host are different and provided below. The gRNAs used to generate the PKM-1 KO host cells are the same as used in Example 1.

The gRNAs for generating the PKM KO host cells had the following sequences:

```
5'-gRNA:
CCCATCACGGCCCGCAACAC
(SEQ ID NO: 42, targeting a region
within exon 2 of the PKM gene)

3'-gRNA:
CTTCTTCAAGACGGGGGATG
(SEQ ID NO: 43, targeting a region
within exon 12 of the PKM gene)
```

MAb-3 producing pools derived from PKM and PKM-1 KO host cell lines had comparable or higher Qp and titers than WT pools, but lower growth (represented by integral viable cell concentration (IVCC)) in shake flask production (FIG. 7). MAb-3 producing pools derived from PKM and PKM1 KO host cell lines also generated lower lactate than WT host cell lines (FIG. 8A), but consumed more glucose (FIG. 8B) in shake flask production. As shown in FIG. 8A, WT host cells produced about 1.0 g/L of lactate by day 15 of production in a shake flask. During shake flask production, a lactate concentration between 1-2.5 g/L is considered high. In contrast, the PKM-1 KO host cells produced very little lactate and the PKM KO host cells produced less than 0.2 g/L of lactate by day 15, resulting in a reduction in the production of lactate of greater than an 80% when PKM-1 or both PKM-1 and PKM-2 are knocked out.

MAb-3 producing pools derived from PKM/PKM-1 KO host cell lines had different amino acid synthesis/consumption rates in shake flask production (FIG. 9A and FIG. 10). For example, PKM KO host cell lines accumulated 3-phosphoglycerate, which led to the increased production of serine and glycine as compared to WT and PKM-1 host cells (FIG. 9B). WT host cell lines accumulated pyruvate compared to PKM KO and PKM-1 host cells (FIG. 9C). Without being limited to a particular theory, the accumulation of pyruvate in WT host cells can lead to the accumulation of lactate and increased production of alanine (FIG. 10). PKM-1 KO host cell lines accumulated TCA cycle products such as oxaloacetate, which led to the accumulation of aspartic acid and asparagine (FIG. 9D), and alpha-ketoglutarate (a-KG), which led to the accumulation of glutamic acid, arginine and glutamine (FIG. 9E). Without being limited to a particular theory, these results suggest that PKM-1 and PKM-2 can function to regulate the level of pyruvate production so pyruvate preferentially enters the TCA cycle. A summary of the above findings is shown in FIG. 10. Based on these data, the cell culture media and conditions used to culture the PKM-1 and PKM KO cells can be adjusted to compensate for the amount of glucose that is consumed and/or the amount of amino acids that is consumed or synthesized.

MAb-3 producing pools derived from PKM/PKM1 KO host cell lines had different glycosylation profiles in shake flask production. PKM KO host had decreased galactosylation, and PKM KO and PKM-1 KO host cell lines had slightly decreased fucosylation (FIG. 11). Without being limited to a particular theory, these changes in glycosylation will likely not affect the activity of the antibody generated.

The contents of all figures and all references, patents and published patent applications and Accession numbers cited throughout this application are expressly incorporated herein by reference.

What is claimed is:

1. A mammalian cell having reduced or eliminated lactogenic activity, wherein the cell comprises an exogenous nucleic acid sequence encoding a product of interest, wherein the expression of a pyruvate kinase muscle (PKM) polypeptide isoform in the cell is knocked down or knocked out, and wherein the PKM polypeptide isoform comprises a PKM-1 polypeptide isoform or a PKM-2 polypeptide isoform; wherein the cell is a CHO cell.

2. The mammalian cell of claim 1, wherein the PKM polypeptide isoform comprises a PKM-2 polypeptide isoform, wherein the expression of the PKM-2 polypeptide isoform is knocked down or knocked out.

3. The mammalian cell of claim 1, wherein the product of interest is a recombinant protein.

4. The mammalian cell of claim 3, wherein the recombinant protein is an antibody or an antigen-binding fragment thereof.

5. The mammalian cell of claim 4, wherein (i) the antibody is a multispecific antibody or an antigen-binding fragment thereof; or (ii) the antibody consists of a single heavy chain sequence and a single light chain sequence or antigen-binding fragments thereof.

6. The mammalian cell of claim 1, wherein the exogenous nucleic acid sequence is integrated in the cellular genome of the mammalian cell at a targeted location.

7. The mammalian cell of claim 1, wherein the lactogenic activity of the mammalian cell is less than about 50% or less than about 20% of the lactogenic activity of a reference cell.

8. The mammalian cell of claim 1, wherein the mammalian cell produces less than about 2.0 g/L of lactate during a production phase.

9. A composition comprising the mammalian cell of claim 1.

10. A method of producing a product of interest, comprising culturing the mammalian cell of claim 1, wherein the mammalian cell expresses the product of interest.

11. A method of culturing a population of mammalian cells having reduced or eliminated lactogenic activity, comprising culturing one or more mammalian cells of claim 1.

12. A mammalian cell comprising:

(a) an allele of a PKM gene that comprises a nucleotide sequence selected from the group consisting of SEQ ID NOs: 37-41; and (b) an exogenous nucleic acid sequence encoding a product of interest.

13. A composition comprising a mammalian cell of claim 12.

14. A method of producing a product of interest, comprising culturing the mammalian cell of claim 12, wherein the mammalian cell expresses the product of interest.

15. A method of culturing a population of mammalian cells having reduced or eliminated lactogenic activity, comprising culturing one or more mammalian cells of claim 12.

16. The method of claim 3, wherein the recombinant protein is a fusion protein.

17. The mammalian cell of claim 12, wherein the product of interest is a recombinant protein.

18. The mammalian cell of claim 17, wherein the product of interest comprises an antibody or an antigen-binding fragment thereof.

19. The mammalian cell of claim 17, wherein the product of interest comprises a fusion protein.

* * * * *